US012590307B2

(12) United States Patent
Liang et al.

(10) Patent No.: US 12,590,307 B2
(45) Date of Patent: Mar. 31, 2026

(54) TRANSLATION ENHANCING NUCLEIC ACID COMPOUNDS: ASO COUPLED TRANSLATION-UPREGULATION 1 (ACT-UP1) AND USES THEREOF

(71) Applicant: Arnatar Therapeutics, Inc, San Diego, CA (US)

(72) Inventors: Xuehai Liang, San Diego, CA (US); Lingdi Zhang, San Diego, CA (US)

(73) Assignee: ARNATAR THERAPEUTICS, INC, San Diego, CA (US)

( * ) Notice: Subject to any disclaimer, the term of this patent is extended or adjusted under 35 U.S.C. 154(b) by 0 days.

(21) Appl. No.: 19/054,728

(22) Filed: Feb. 14, 2025

(65) Prior Publication Data

US 2025/0250570 A1      Aug. 7, 2025

Related U.S. Application Data

(63) Continuation of application No. PCT/US2025/013612, filed on Jan. 29, 2025.

(60) Provisional application No. 63/727,989, filed on Dec. 4, 2024, provisional application No. 63/677,274, filed on Jul. 30, 2024, provisional application No. 63/558,080, filed on Feb. 26, 2024, provisional application No. 63/626,347, filed on Jan. 29, 2024.

(51) Int. Cl.

| | |
|---|---|
| *C12N 15/113* | (2010.01) |
| *A61K 9/00* | (2006.01) |
| *A61K 38/17* | (2006.01) |
| *A61P 1/16* | (2006.01) |
| *C12N 15/67* | (2006.01) |

(52) U.S. Cl.
CPC .......... *C12N 15/113* (2013.01); *A61K 9/0019* (2013.01); *A61K 38/1709* (2013.01); *A61P 1/16* (2018.01); *C12N 15/67* (2013.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/3519* (2013.01)

(58) Field of Classification Search
CPC .. C12N 15/113; C12N 15/67; C12N 2310/11; C12N 2310/315; C12N 2310/321; C12N 2310/322; C12N 2310/3231; C12N 2310/3341; C12N 2310/3519; A61K 9/0019; A61K 38/1709; A61P 1/16
See application file for complete search history.

(56) References Cited

U.S. PATENT DOCUMENTS

| | | |
|---|---|---|
| 5,869,282 A | 2/1999 | Ish-Horowicz et al. |
| 5,916,808 A | 6/1999 | Kole et al. |
| 7,888,497 B2 | 2/2011 | Bentwich et al. |
| 8,877,721 B2 | 11/2014 | Li et al. |
| 9,018,368 B2 | 4/2015 | Wilton et al. |
| 9,297,008 B2 | 3/2016 | Li et al. |
| 10,822,369 B2 | 11/2020 | Crooke et al. |
| 11,096,956 B2 | 8/2021 | Aznarez et al. |
| 2006/0003322 A1* | 1/2006 | Bentwich ............... G16B 15/10 |
| | | 435/6.16 |
| 2006/0166922 A1 | 7/2006 | Eichler et al. |
| 2007/0042380 A1 | 2/2007 | Bentwich et al. |
| 2011/0046200 A1 | 2/2011 | Howard et al. |
| 2013/0309246 A1 | 11/2013 | Kang et al. |
| 2015/0329918 A1 | 11/2015 | Kang et al. |
| 2019/0275170 A1 | 9/2019 | Benenato et al. |
| 2022/0118000 A1 | 4/2022 | Aznarez et al. |
| 2022/0127621 A1 | 4/2022 | Yeo et al. |
| 2022/0204978 A1 | 6/2022 | Yeo et al. |
| 2023/0090706 A1 | 3/2023 | Dickinson et al. |

FOREIGN PATENT DOCUMENTS

| | | |
|---|---|---|
| WO | WO2013/173635 | 11/2013 |
| WO | WO2016/061509 | 4/2016 |
| WO | WO2016/170348 | 10/2016 |
| WO | WO2017/201342 | 11/2017 |
| WO | WO2023049707 | 3/2023 |
| WO | WO2023/230167 | 11/2023 |
| WO | WO2023212687 | 11/2023 |
| WO | WO2023240254 | 12/2023 |
| WO | WO2004/0483225 | 6/2024 |
| WO | WO2024/137543 | 6/2024 |
| WO | WO2024/137545 | 6/2024 |
| WO | WO2024/259134 | 12/2024 |

OTHER PUBLICATIONS

Watts et al. ("Silencing disease genes in the laboratory and the clinic." The Journal of pathology 226.2 (2012): 365-379).*
Watts J Pathol 2012; 226: 365-379.*
Wang, J., et al., 2023a Engineered mRNA Delivery Systems for Biomedical Applications. Adv Mater: e2308029).
Li, L. C., 2017, Small RNA-Guided Transcriptional Gene Activation (RNAa) in Mammalian Cells. Adv Exp Med Biol 983: 1-20.
Watts, J. K., et al., 2010, Effect of chemical modifications on modulation of gene expression by duplex antigene RNAs that are complementary to non-coding transcripts at gene promoters. Nucleic Acids Res 38: 5242-5259.
Sergeeva, O. V., E. Y. Sheberbinina, N. Shomron and T. S. Zatsepin, 2022, Modulation of RNA Splicing by Oligonucleotides: Mechanisms of Action and Therapeutic Implications, Nucleic Acid Ther 32: 123-138).

(Continued)

*Primary Examiner* — Kimberly Chong
(74) *Attorney, Agent, or Firm* — ADRIANO & ASSOCIATES

(57) ABSTRACT

Disclosed herein are methods and compounds for enhancing gene expression by ACT-UP1 compounds. Such methods and compounds are useful for increasing expression of certain genes, many of which are associated with a variety of diseases and disorders.

21 Claims, 33 Drawing Sheets

Specification includes a Sequence Listing.

(56)　　　　References Cited

OTHER PUBLICATIONS

Nomakuchi, T. T., F. Rigo, I. Aznarez and A. R. Krainer, 2016 Antisense oligonucleotide-directed inhibition of nonsense-mediated mRNA decay. Nat Biotechnol 34: 164-166.

Samad, A. F. A., and M. F. Kamaroddin, 2023 Innovative approaches in transforming microRNAs into therapeutic tools. Wiley Interdiscip Rev RNA 14: e1768.

Liang et al., Antisense Oligonucleotides Targeting Translation Inhibitory Elements in 5'UTRs Can Selectively Increase Protein Levels, Nucleic Acids Res, 2017, 45(16): 9528-9546.

Liang et al., Translation Efficiency of mRNAs Is Increased by Antisense Oligonucleotides Targeting Upstream Open Reading Frames, Nature Biotechnology, 2016, 34(8):875-880.

Li et al., Targeting 3' and 5' Untranslated Regions with Antisense Oligonucleotides to Stabilize Frataxin mRNA and Increase Protein Expression, Nucleic Acids Res, 2021, 49(20):11560-11574.

Torkzaban et al. Development of a Tethered mRNA Amplifier to Increase Protein Expression, Biotechnol. J., Oct. 2022, 17(10):e2200214.

Nadim Majdalani et al., Regulation of RpoS by a novel small RNA: the characterization of RprA, Molecular Microbiology (2001) 39(5). 1382 1394.

Roslyn M. Ray et. al., Long Non-coding RNAs Mechanisms of Action in HIV-1 Modulation and the Identification of Novel Therapeutic Targets, Non-coding RNA 2020, 6,12, 1-17.

Candra S. Bathula et al., 2021, ZFP36L1 Regulates Fgf21 mRNA Turnover and Modulates Alcoholic Hepatic Steatosis and Inflammation in Mice. Biomarkers, Genomics, Protcomics, and Gene Regulation: 209-225.

Hong-Hsi Chen and Woan-Yuh Tarn, uORF-mediated translational control: recently elucidated mechanisms and implications in cancer. RNA Biology: 1327-1338).

Claudia Fritsch et al., 2017, Genome-wide search for novel human uORFs and N-terminal protein extensions using ribosomal footprinting. Genomne Research 22: 2208-2218.

Xiangwei Gao et al., 2015, Quantitative profiling of initiating ribosomes in vivo. Nat Methods 12:147-153.

Xiulin Jiang et al., 2021, The role of m6A modification in the biological functions and diseases. Signal Transduction and Targeting Therapy 6: 1-16.

Xue-Hai Liang et al., Translation Efficiency of mRNAs Is Increased by Antisense Oligonucleotides Targeting Upstream Open Reading Frames, Nature Biotechnology, 2016, 34(8):875-880.

Xue-Hai Liang et al., 2017, Specific Increase of Protein Levels by Enhancing Translation Using Antisense Oligonucleotides Targeting Upstream Open Frames. Springer Nature Singapore, 2017:12-146.

Silva et al., 2019 Upstream open reading frames (uORFs) as translational regulators in human disease. Atlas of Science another view on science: 1-2.

Pieter Spealman et al., 2023. Conserved non-AUG uORFs revealed by a novel regression analysis of ribosome profiling data. Genome Res. 2018 28: 214-222.

Yvette Stallwood et al., 2006 Small Interfering RNA-Mediated Knockdown of Notch Ligands in Primary CD4$^+$ T Cells and Dendritic Cells Enhances Cytokine Production, J Immunol, 2006 177:885-895.

Ann B. Zimrin et al., 1996, An Antisense Oligonucleotide to the Notch Ligand Jagged Enhances Fibroblast Growth Factor-induced Angiogenesis in Vitro. The Journal of Biological Chemistry, vol. 271: 32499-32502.

Zhang et al., 2020, uORFs: Important Cis-Regulatory Elements in Plants. International Journal of Molecular Sciences, 21: 1-14.

Bon Carlotta et al: "SINEUP non-coding RNAs rescue defective frataxin expression and activity in a cellular model of Friedreich's Ataxia", Nucleic Acids Research, vol. 47, No. 20, Nov. 18, 2019 (Nov. 18, 2019), pp. 10728-10743.

Pierattini Bianca et al: "SINEUP non-coding RNA activity depends on specific N6-methyladenosine nucleotides", Molecular Therapy-Nucleic Acids, vol. 32, Apr. 7, 2023 (Apr. 7, 2023), pp. 402-414.

Espinoza Stefano et al: "SINEUP Non-coding RNA Targeting GDNF Rescues Motor Deficits and Neurodegeneration in a Mouse Model of Parkinson's Disease", Molecular Therapy, vol. 28, No. 2, Feb. 1, 2020 (Feb. 1, 2020), pp. 642-652.

Cao Yang et al: "RNA-based translation activators for targeted gene upregulation", Nature Communications, vol. 14, No. 1, Oct. 26, 2023 (Oct. 26, 2023).

S Zucchelli et al: "SINEUPs; A new class of natural and synthetic antisense long non-coding RNAs that activate translation", RNA Biology, vol. 12, No. 8, Aug. 3, 2015 (Aug. 3, 2015), pp. 771-779.

Sandahl Alexander F. et al: "On-demand synthesis of phosphoramidites", Nature Communications, vol. 12, No. 1, May 12, 2021 (May 12, 2021).

International Search Report for Application No. PCT/US2025/013612.

Written Opinion for Application No. PCT/US2025/013612.

* cited by examiner

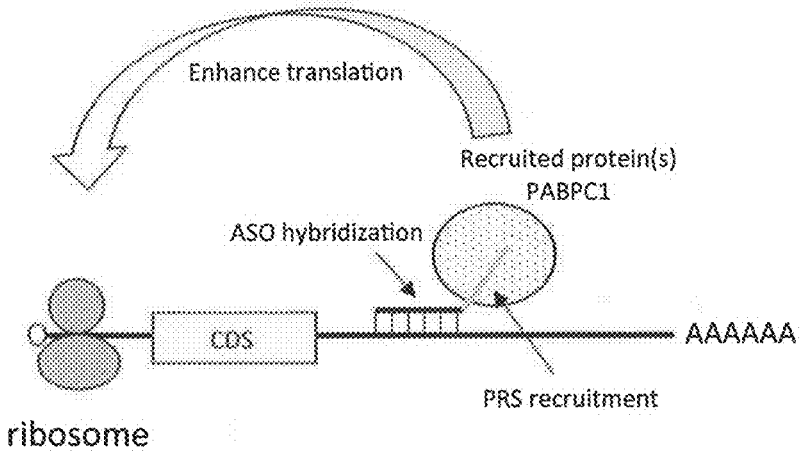
Figure 1: Schematic Diagram of Proposed ACT-UP1 Mechanism

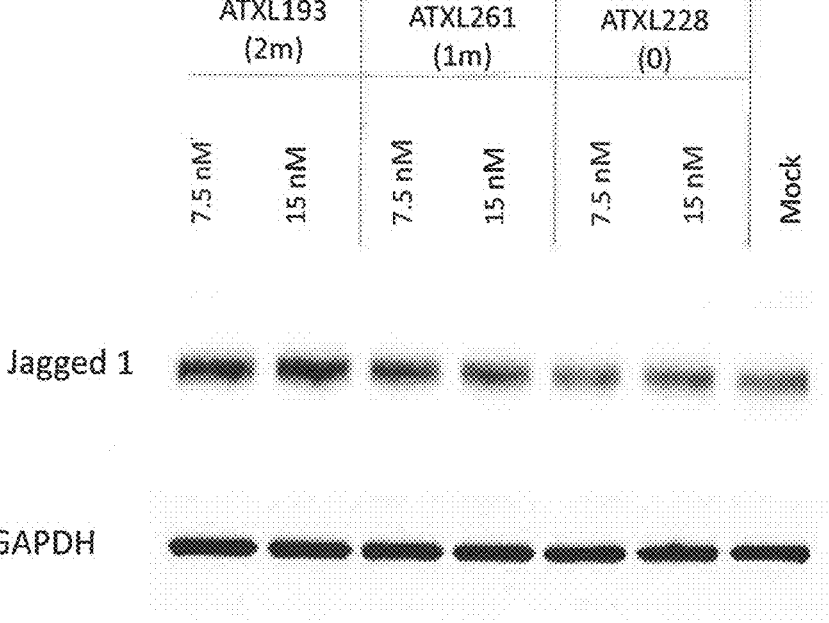
Figure 2. Jagged 1 Protein in HeLa Cells Transfected with ACT-UP1 Compounds

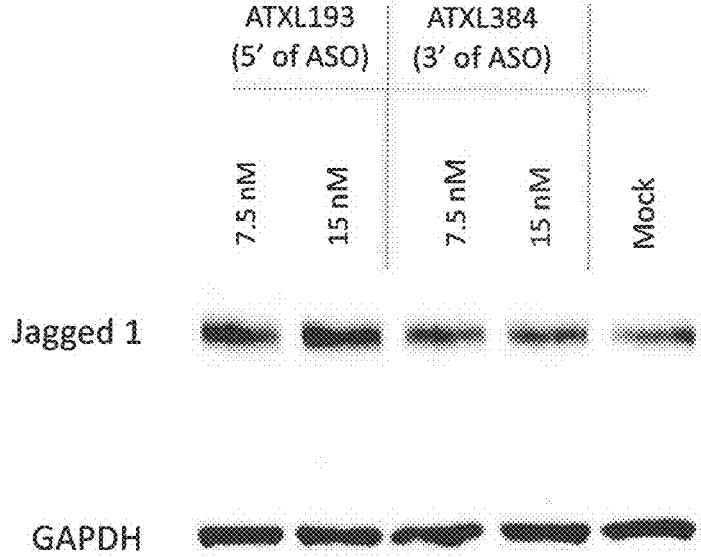
Figure 3. PRS Position in the ACT-UP1 Compound is Important for Increasing Protein Levels

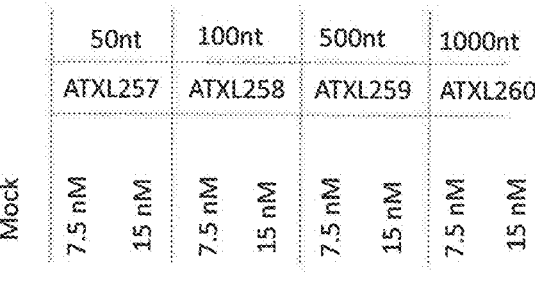
Position from stop codon
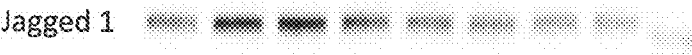
Jagged 1
GAPDH
Figure 4. Jagged 1 Protein in HeLa Cells Transfected with Different ACT-UP1 Compounds Targeting Different Positions within the 3′ UTR of JAG1 mRNA

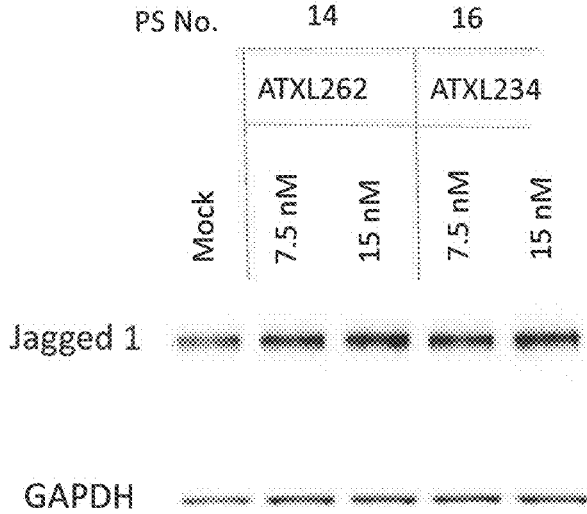
Figure 5. Jagged 1 Protein in HeLa Cells Transfected with Different ACT-UP1 Compounds Containing Different Numbers of PS linkages

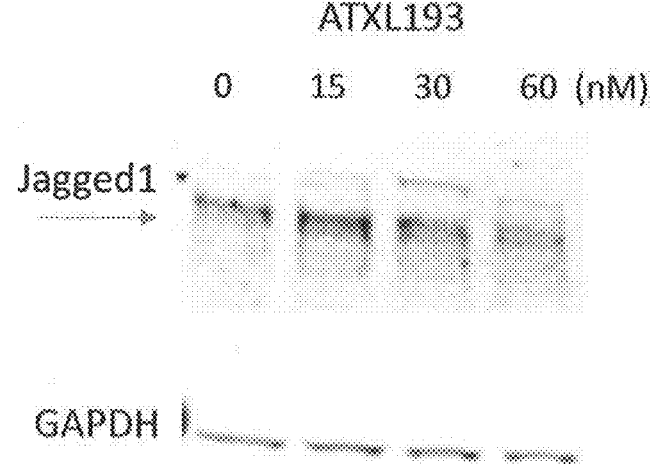
Figure 6. Jagged 1 Protein Levels in HEK293 Cells Transfected with Different Concentrations of ATXL193

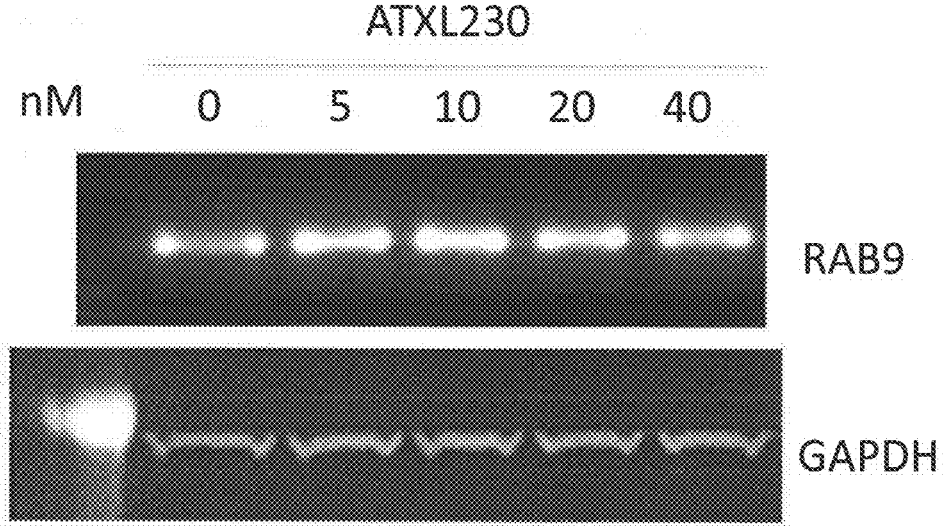
Figure 7. Rab9 Protein Levels in HeLa Cells Transfected with
Different Concentrations of ATXL230

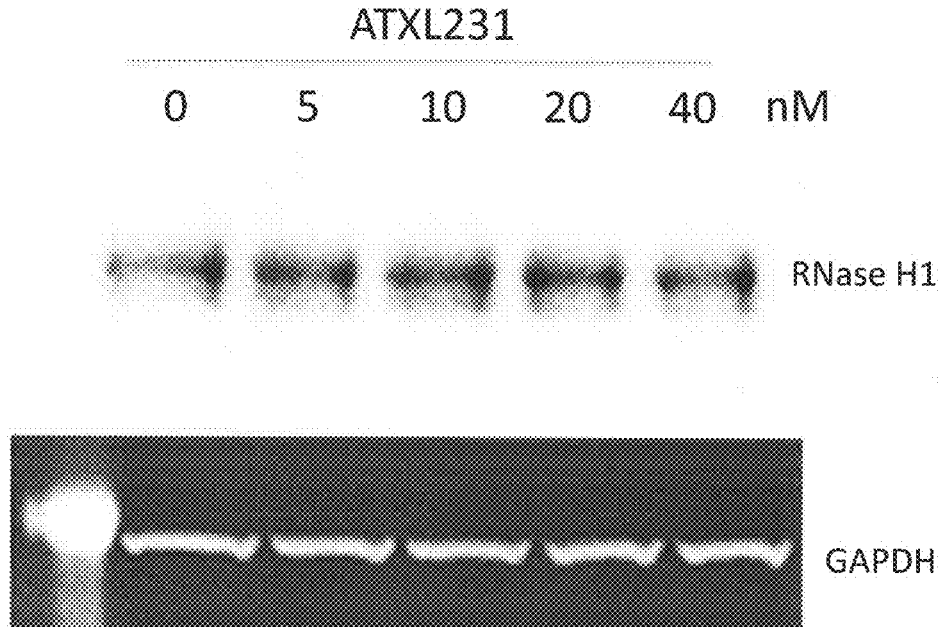
Figure 8. RNase H1 Protein in HeLa Cells Transfected with Different Concentrations of ATXL231

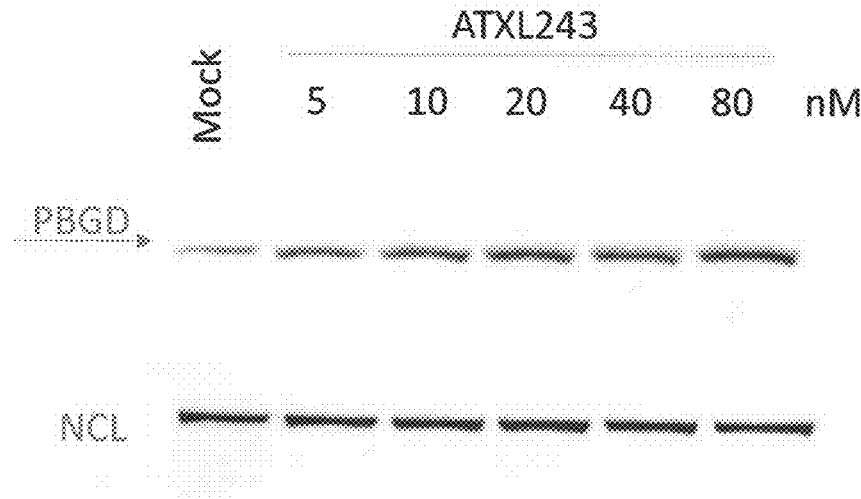
Figure 9. PBGD Protein in HeLa Cells Transfected with Different Concentrations of ATXL243

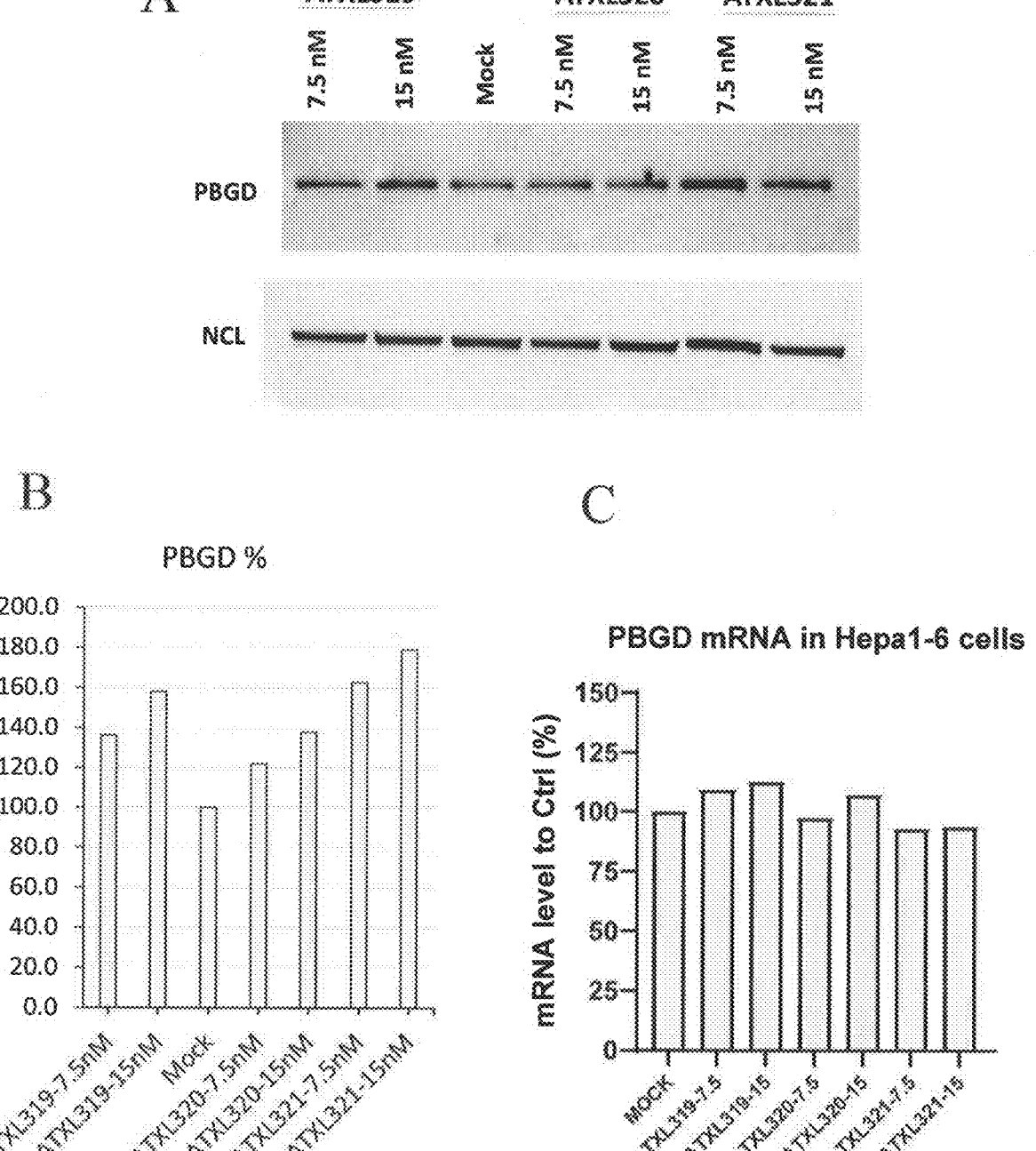
Figure 10. PBGD Protein (A and B) and mRNA (C) Levels in Murine Hepa1-6 Cells Transfected with Different ACT-UP1 Compounds

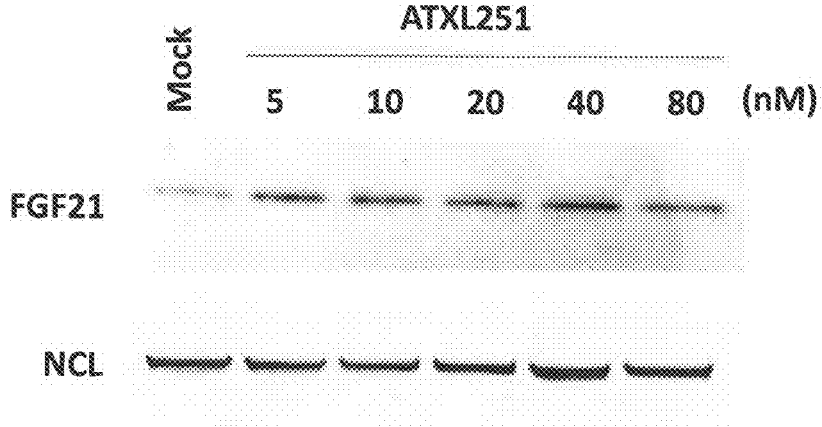
Figure 11. FGF21 Protein in Hep3B cells Transfected with Different Concentrations of ACT-UP1 Compound ATXL251

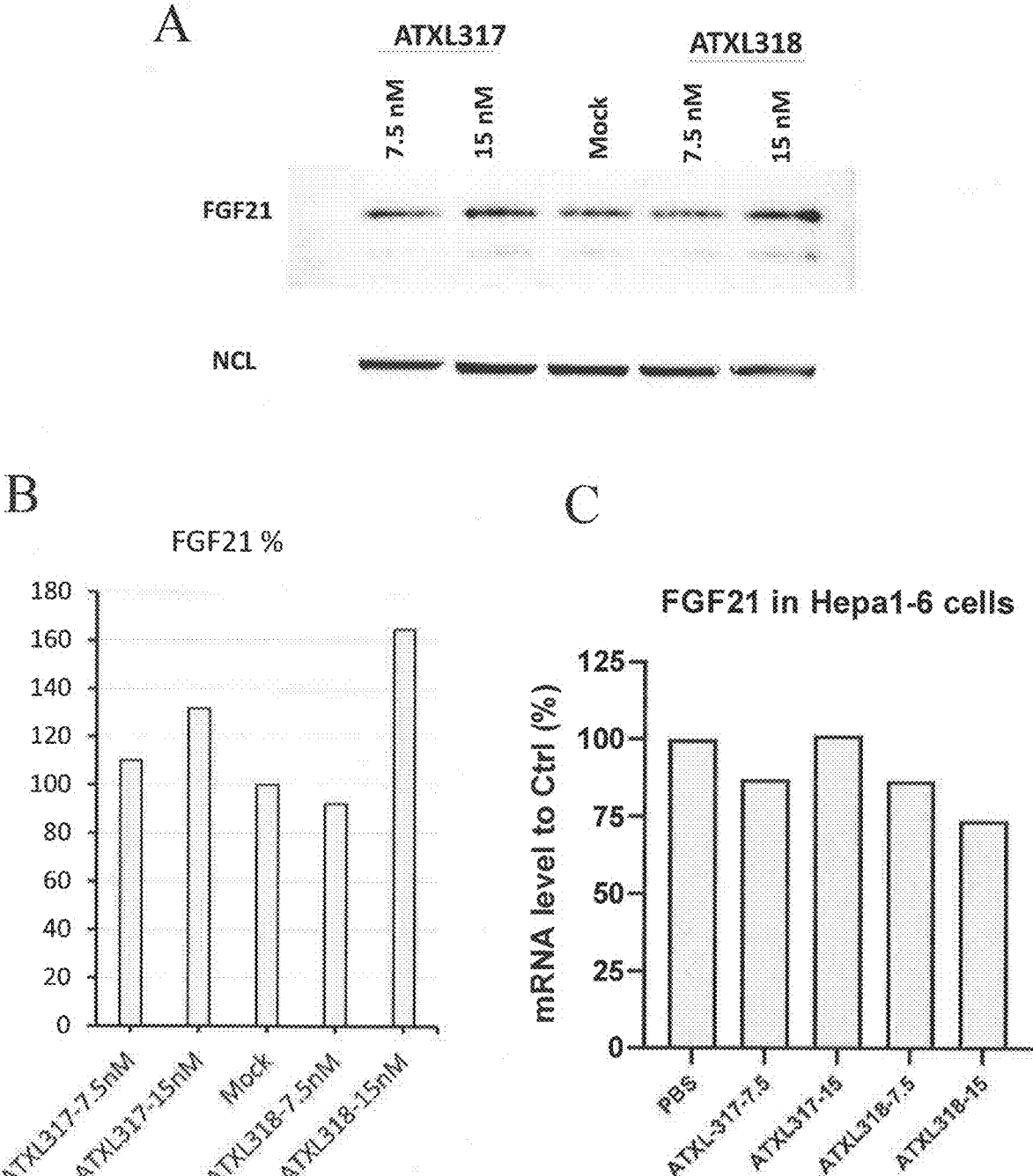
Figure 12. FGF21 Protein in Hepa1-6 Cells Transfected with
Varying Concentrations of ACT-UP1 Compounds A
Affinity selection of ACT-UP1 ASO-binding protein(s)
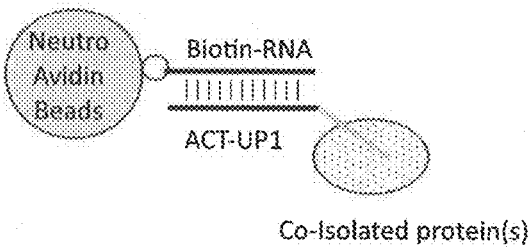
B
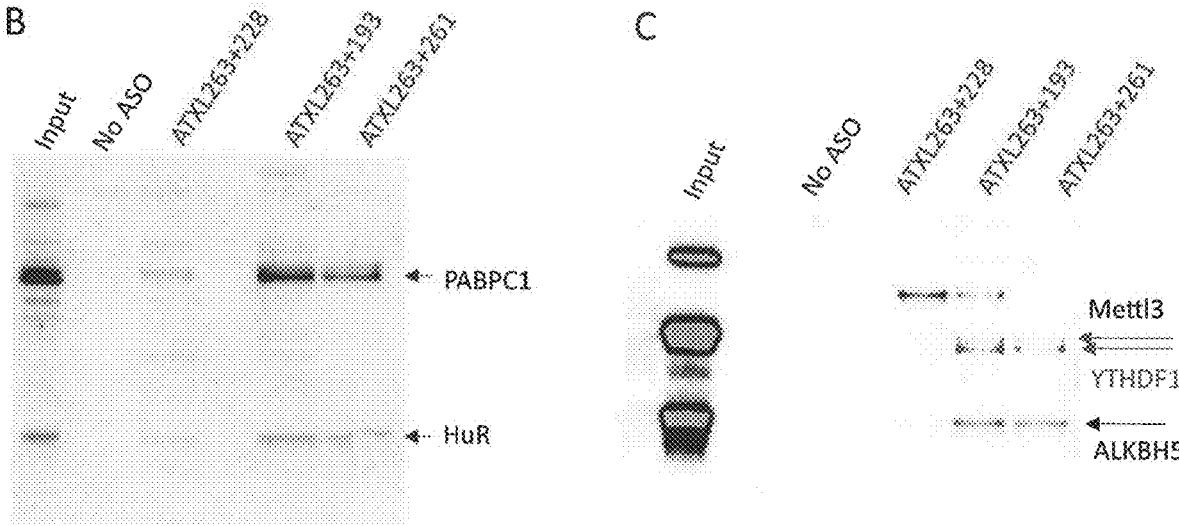
C
Figure 13. Translation Related Proteins Can Be
Recruited to the Duplex by ACT-UP1 Compounds

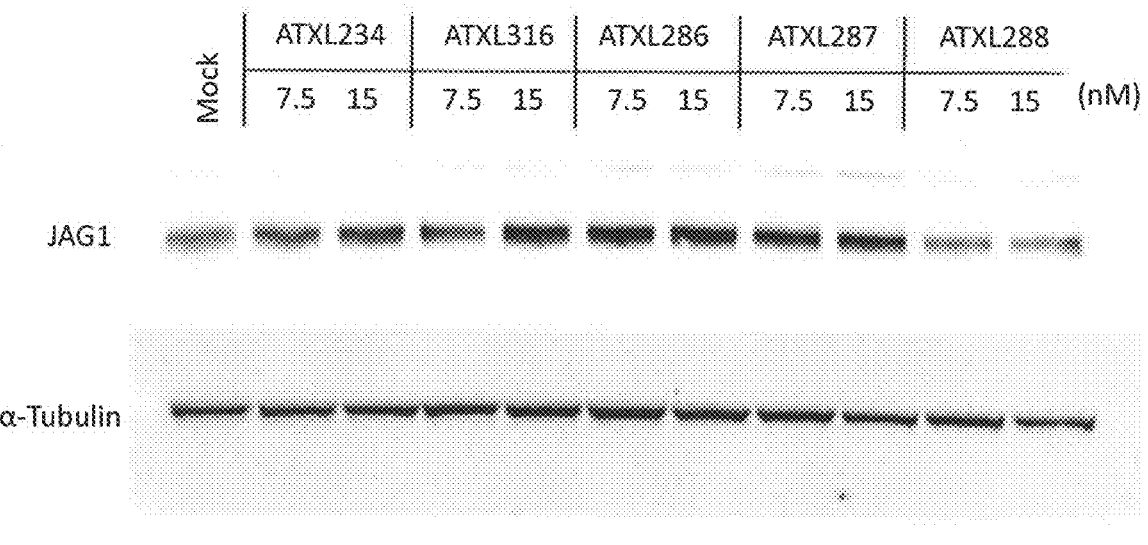
Figure 14. Different ACT-UP1 PRSs Can Increase Target Protein Levels in HeLa Cells

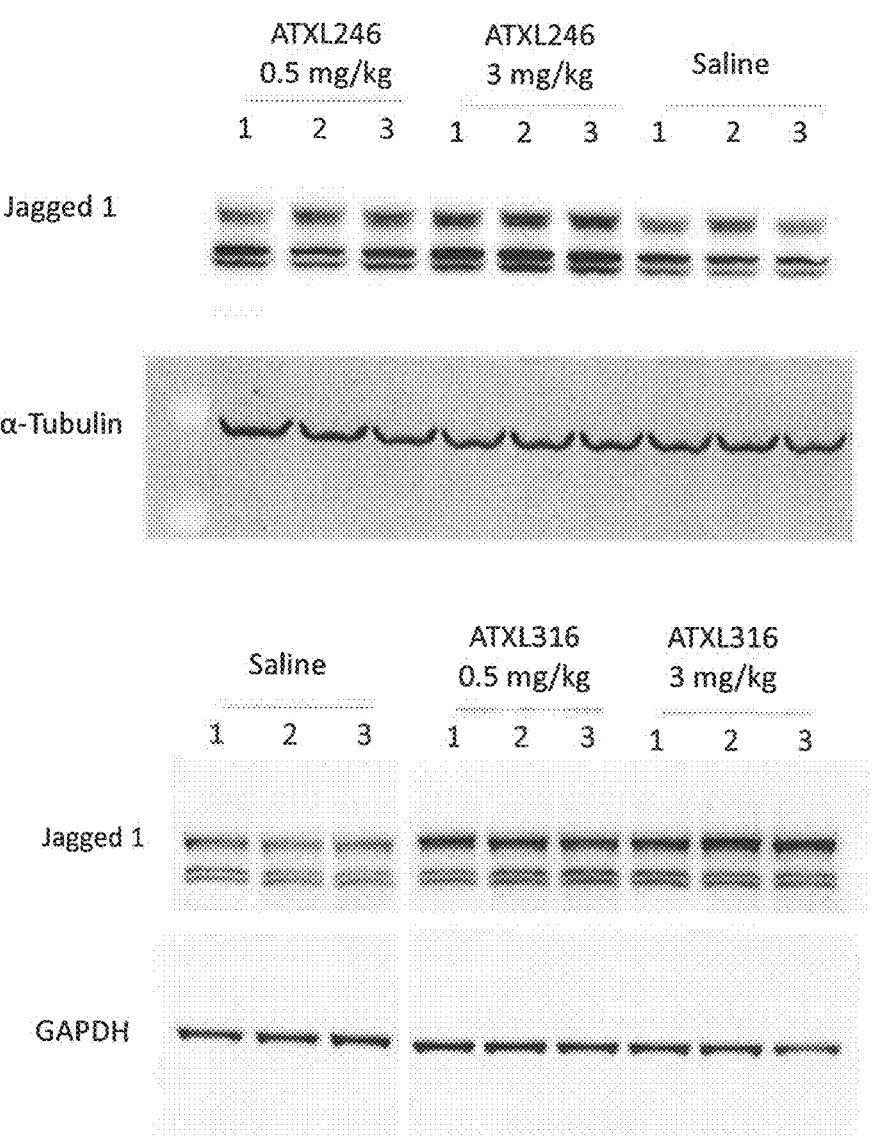
Figure 15. Jagged 1 Protein is Increased in the Liver of Animals Treated with ACT-UP1 Compounds ATXL246 and ATXL316

A
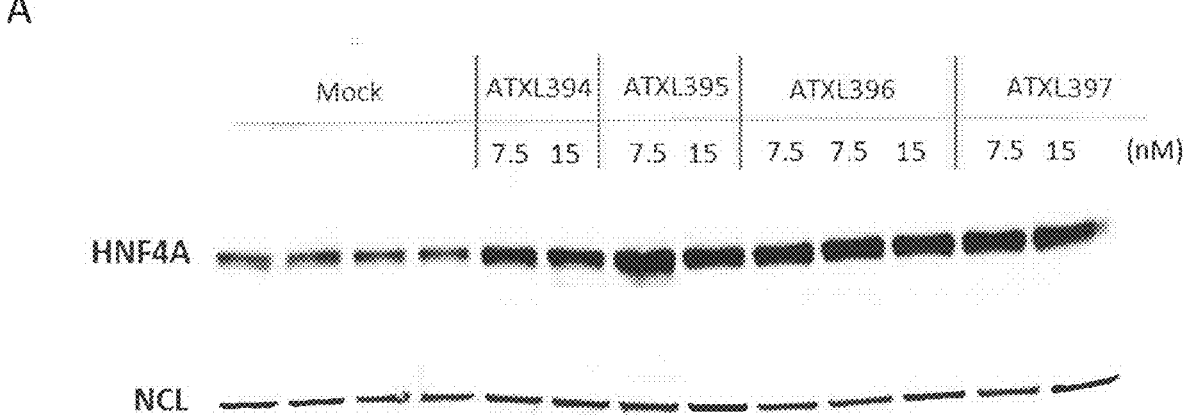
B
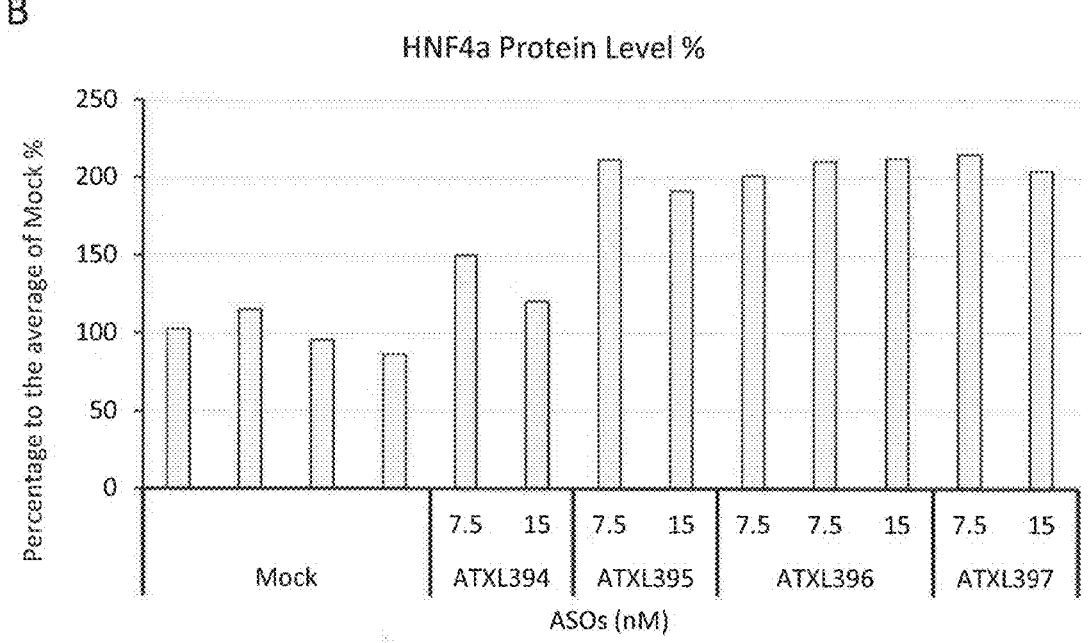
Figure 16. Human HNF4A Protein is Increased Using Different ACT-UP1 Compounds After Transfection in Hep3B cells.

A
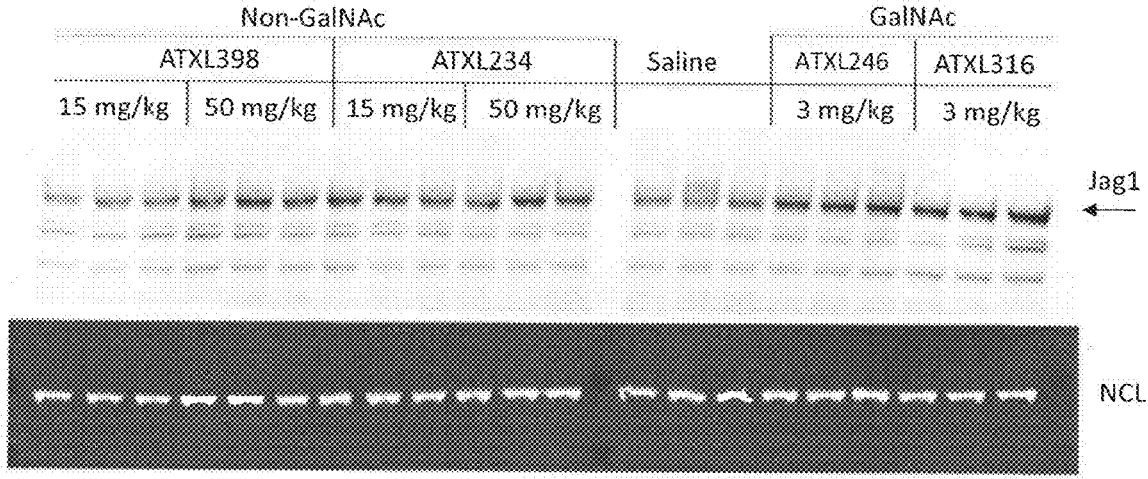
B
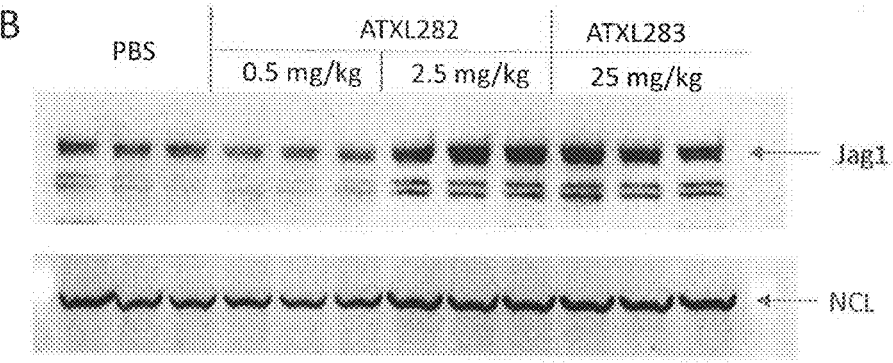
Figure 17. JAG1 Protein Levels in Mice Dosed with Different ACT-UP1 Compounds

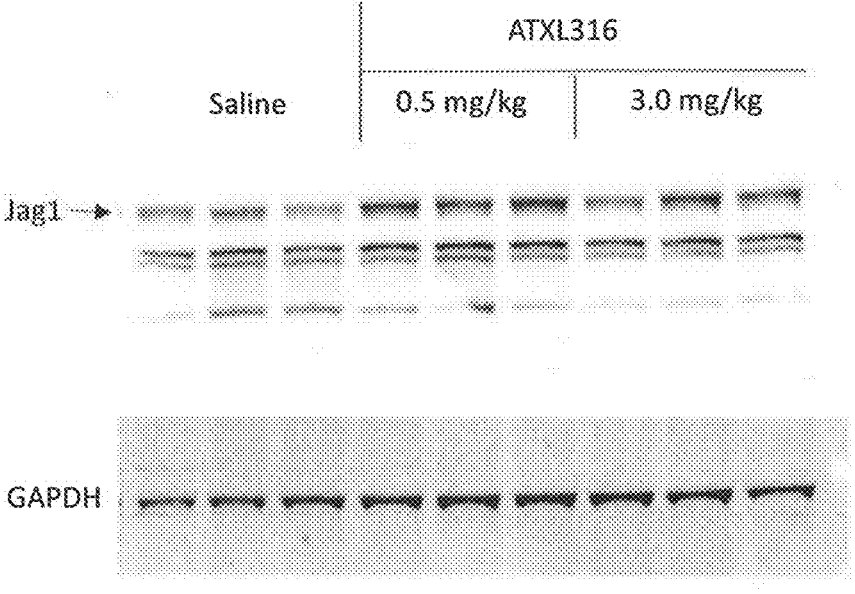
Figure 18. JAG1 Protein Levels in Mice 4 Weeks After Dosing with ACT-UP1 Compound ATXL316

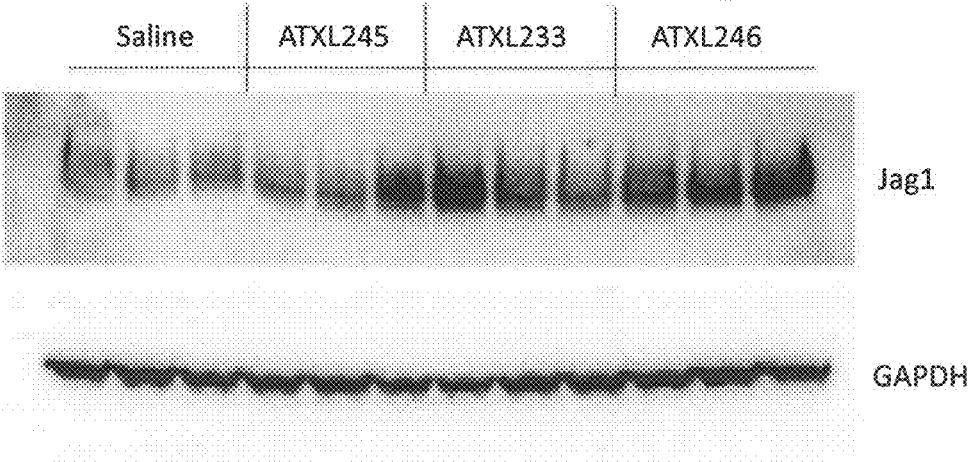
Figure 19. JAG1 Protein Levels in Male JAG1$^{+/-}$ Mice After 2 Doses

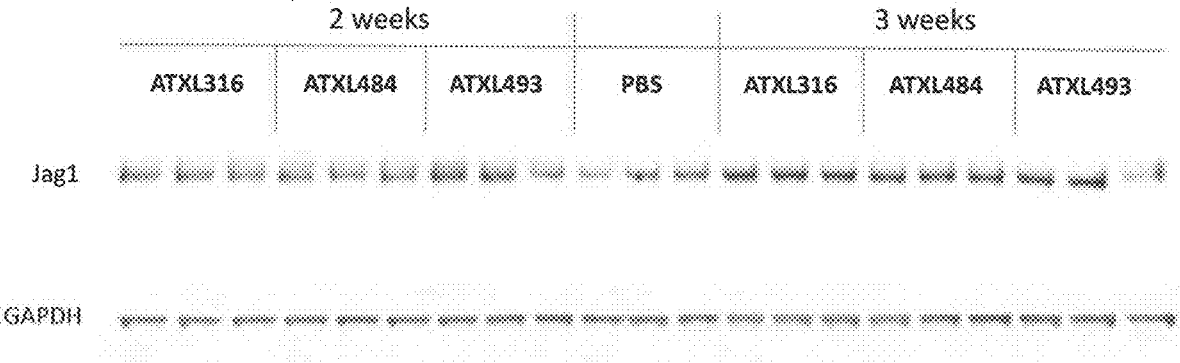
Figure 20. JAG1 Protein Levels in Mice at 2- and 3-Weeks After Dosing with ACT-UP1 Compounds

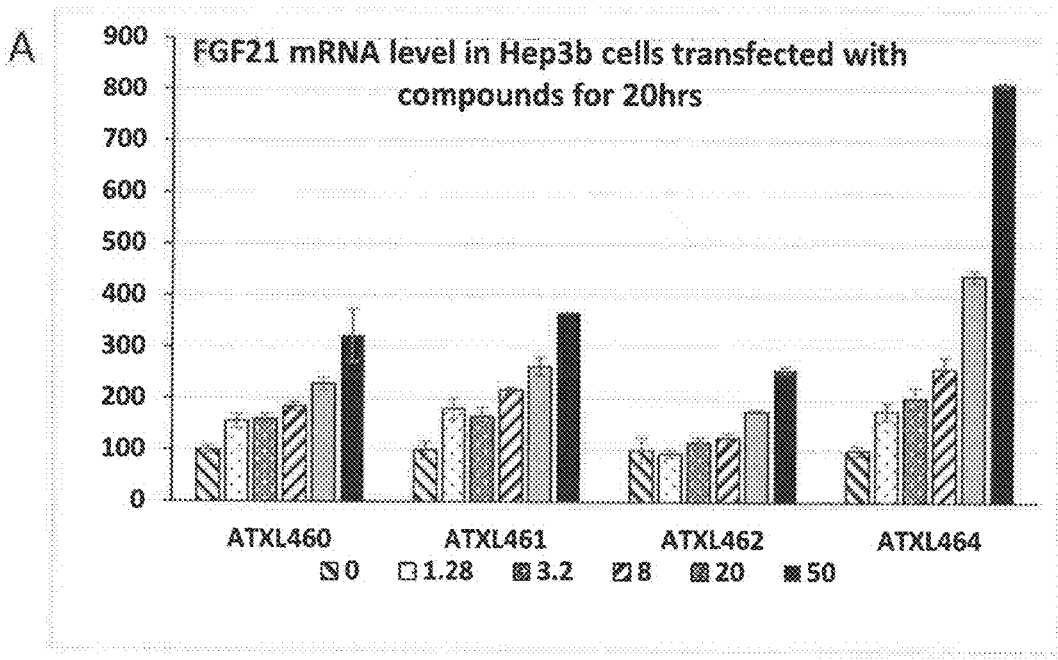
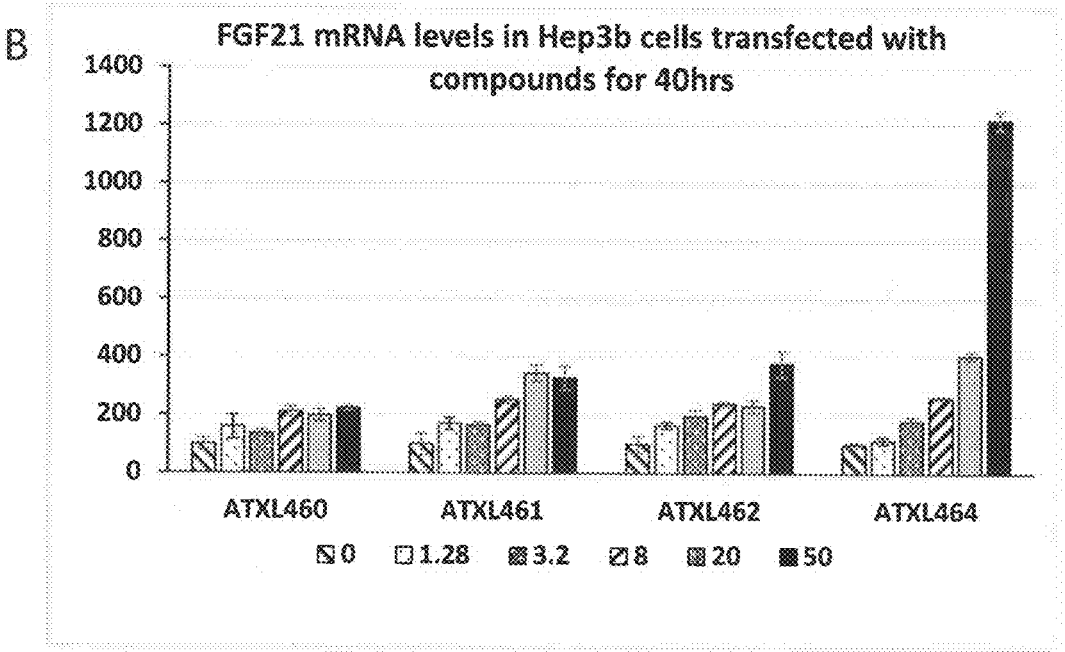
Figure 21. FGF21 mRNA Levels in Hep3B Cells Transfected with Compounds for 20 (A) or 40 (B) Hours

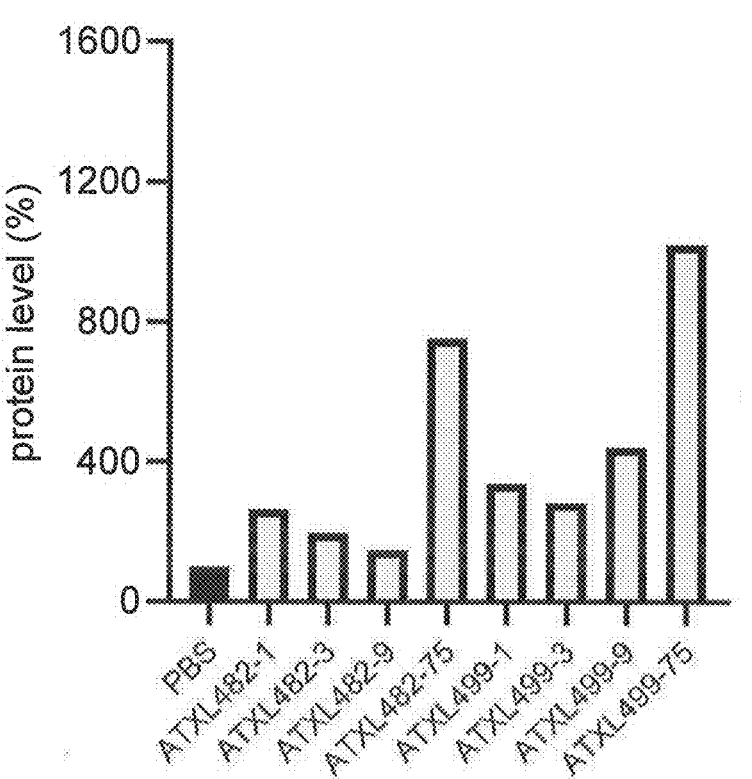
Figure 22. FGF21 Protein Levels in Mice Treated Two Times with Compounds 72 hrs Apart

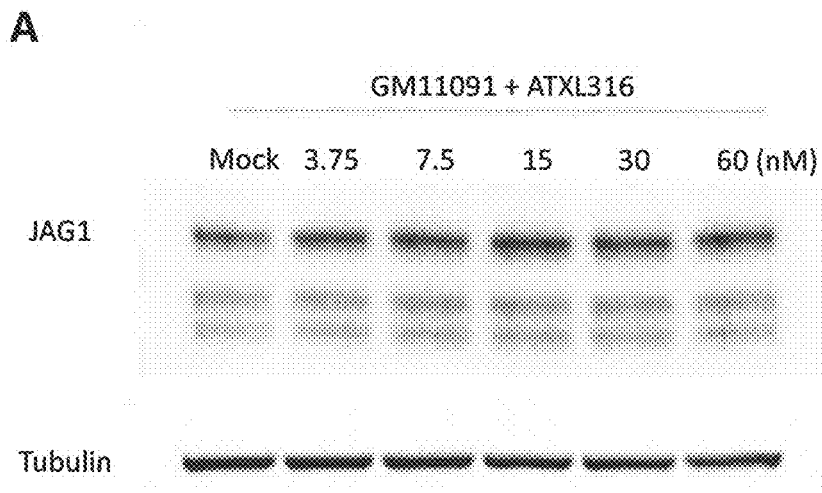
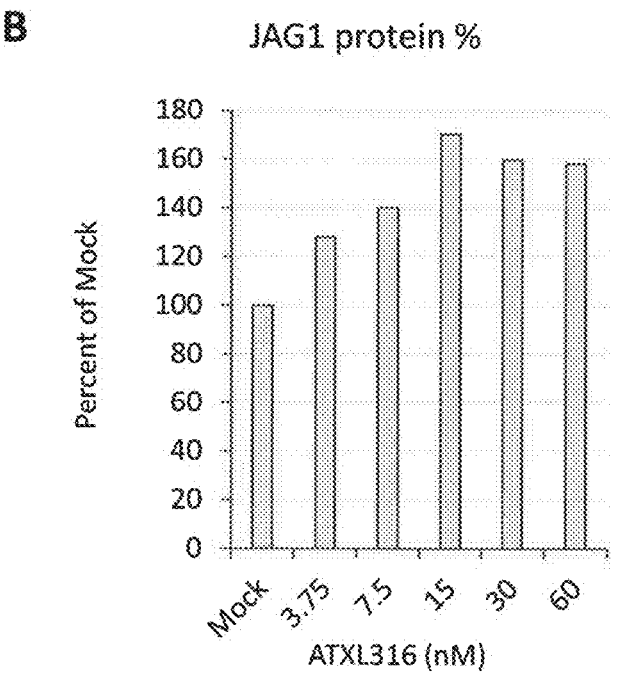
Figure 23. ATXL316 Increased JAG1 Protein in Patient GM11091 Cells at 24 Hrs A
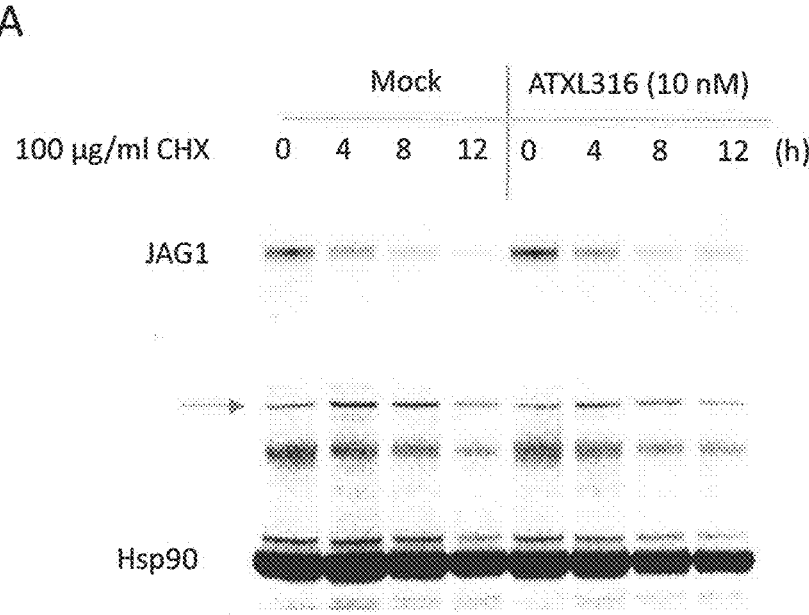
B
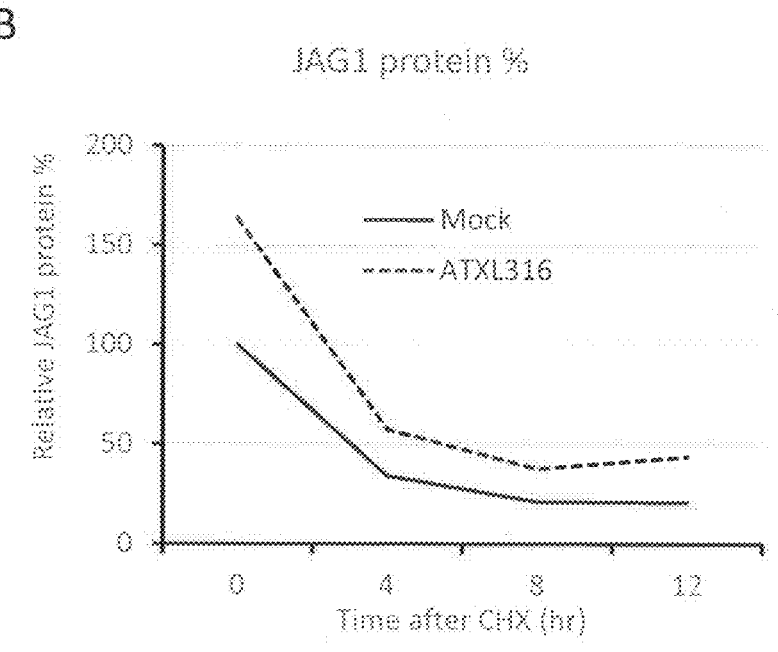
Figure 24. ATXL316 Does Not Affect JAG1 Protein Stability

Figure 25 (1/3). ACT-UP1 Compounds with Different PRSs Targeting JAG1 Can Increase Protein Levels

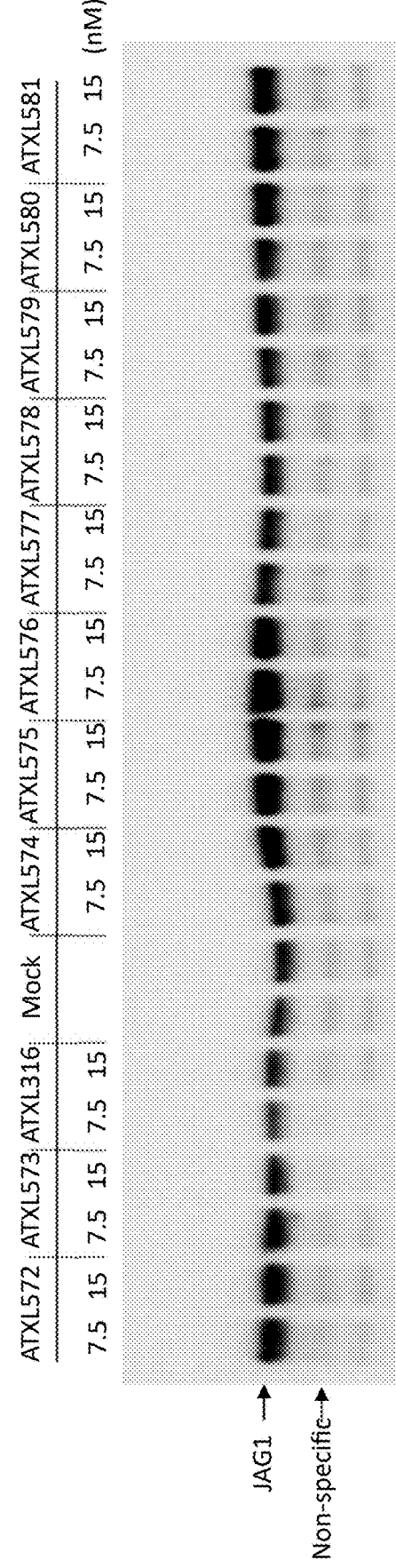
B
JAG1
Non-specific
Figure 25 (2/3). ACT-UP1 Compounds with Different PRSs Targeting JAG1 Can Increase Protein Levels C
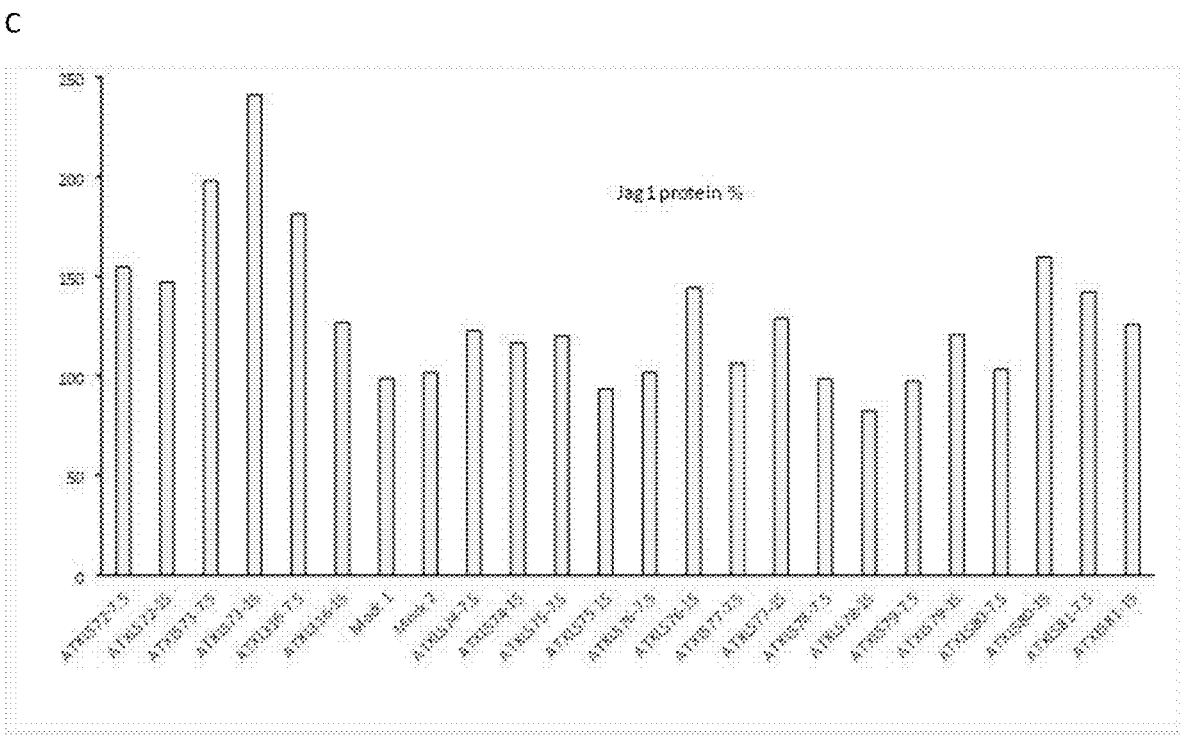
Figure 25 (3/3). ACT-UP1 Compounds with Different PRSs Targeting JAG1 Can Increase Protein Level

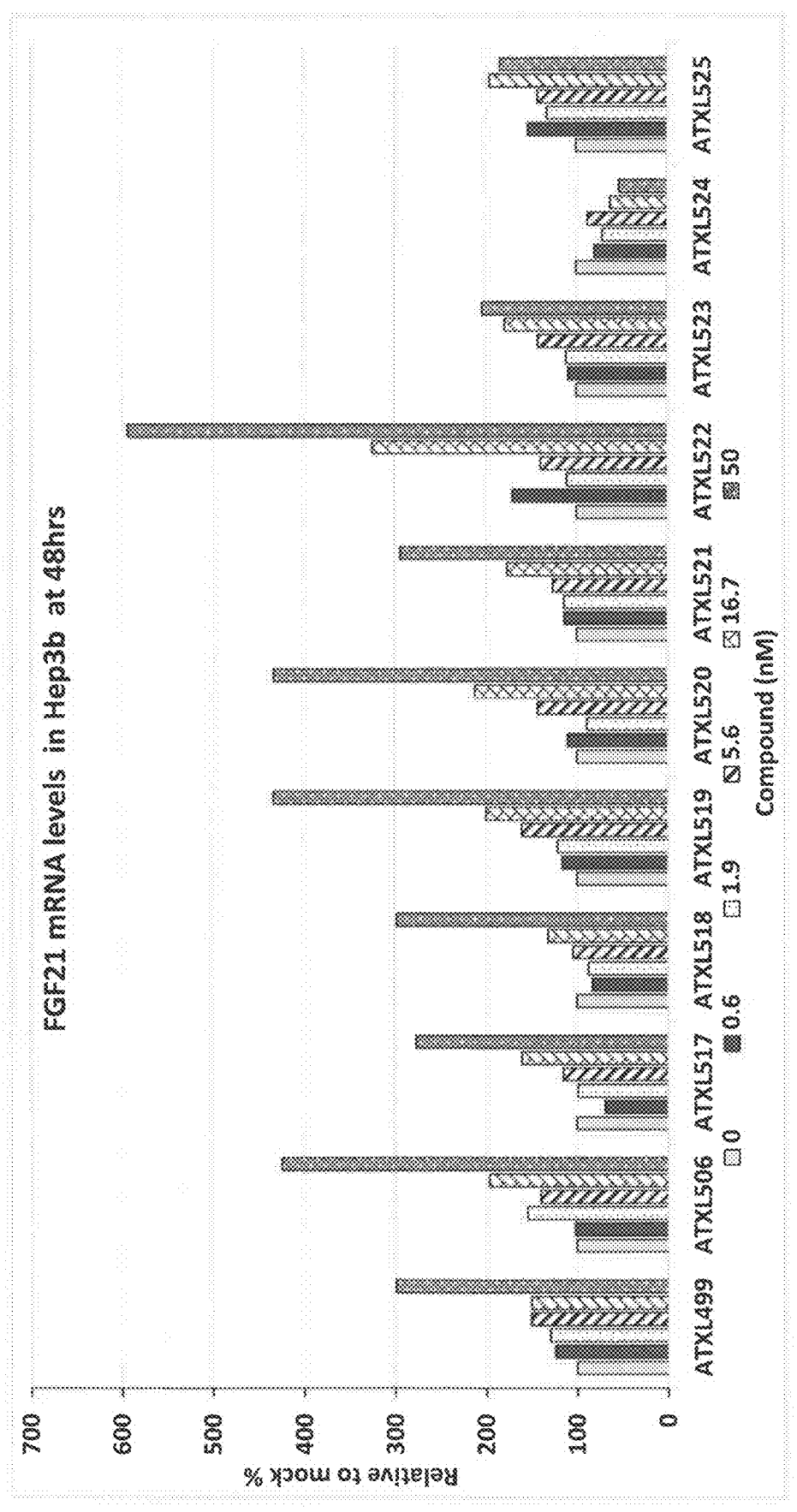
Figure 26. Different Dual Functional Compounds Can Increase FGF21 mRNA Levels in Human Hep3b Cells

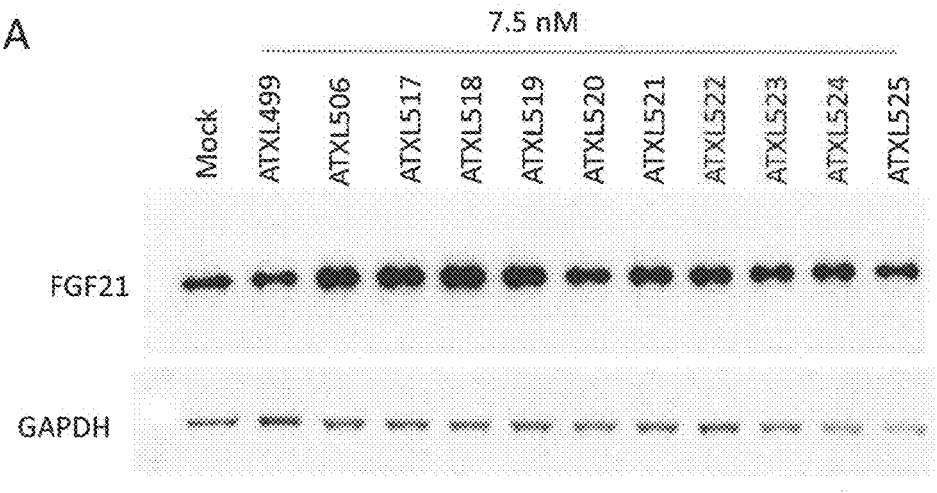
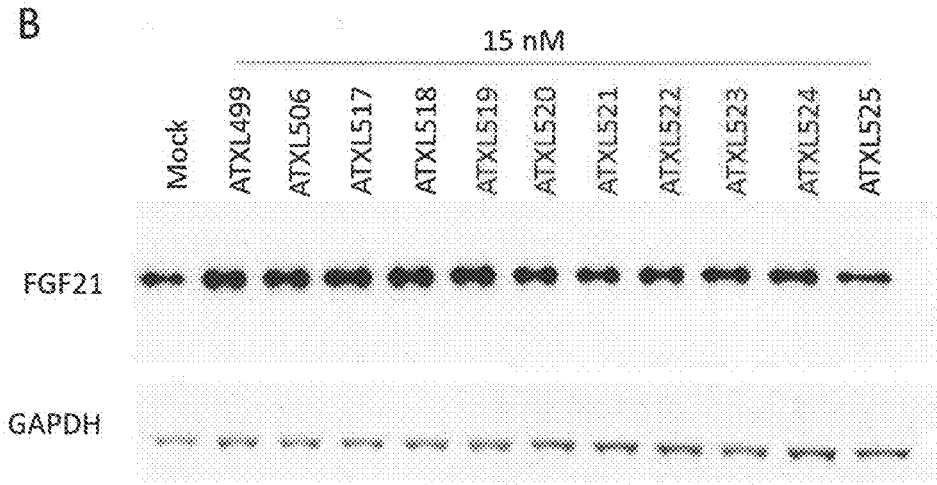
Figure 27. Different Dual Functional ACT-UP1 Compounds Can Increase FGF21 Protein Levels in Human HepG2 Cells

A
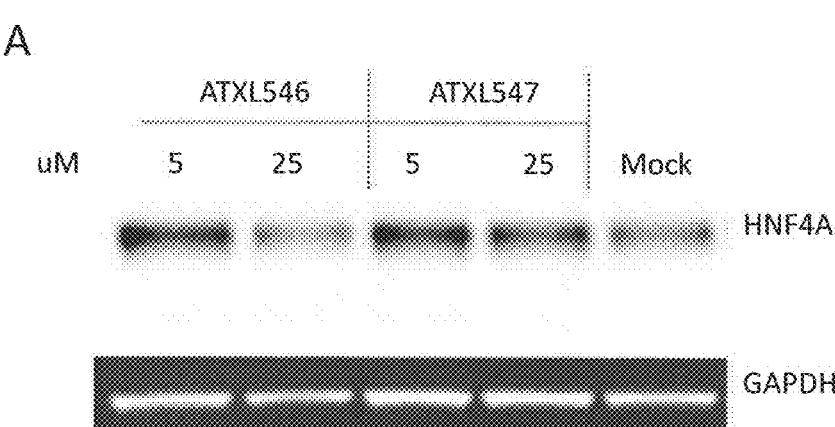
B
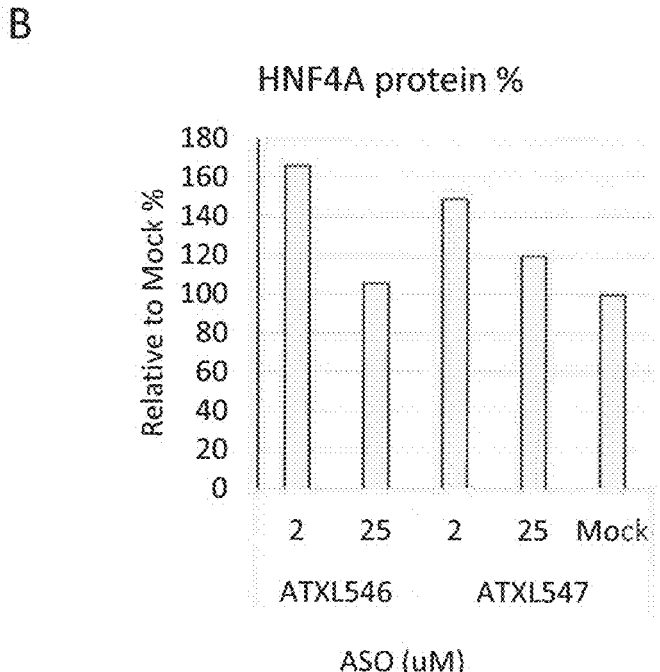
Figure 28. Western Analysis of HNF4A Protein Levels in Human Primary
Hepatocytes Treated with ACT-UP1 Compounds by Free Uptake for 66 Hrs

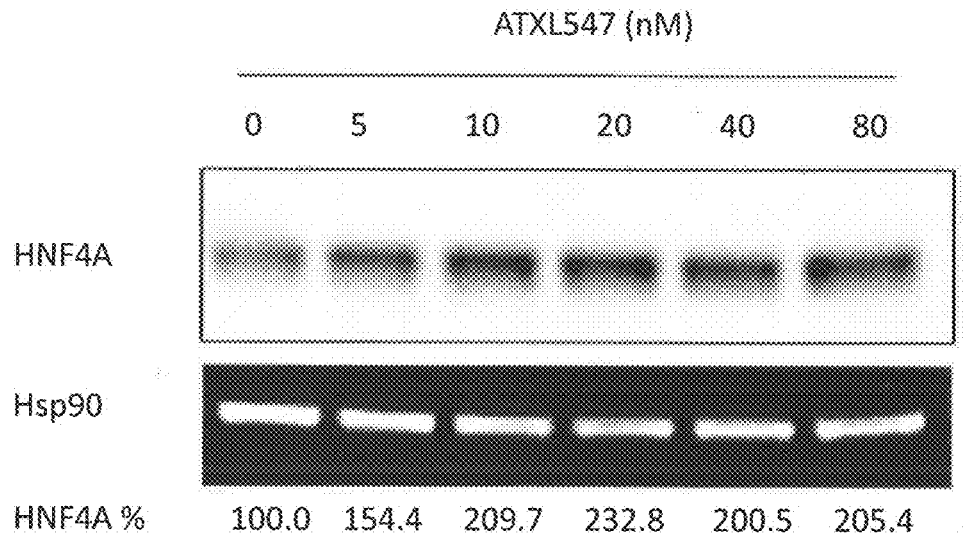
Figure 29. ACT-UP1 Compound Increased HNF4A Protein in Mouse Hepa1-6 Cells within a Broad Dose Range

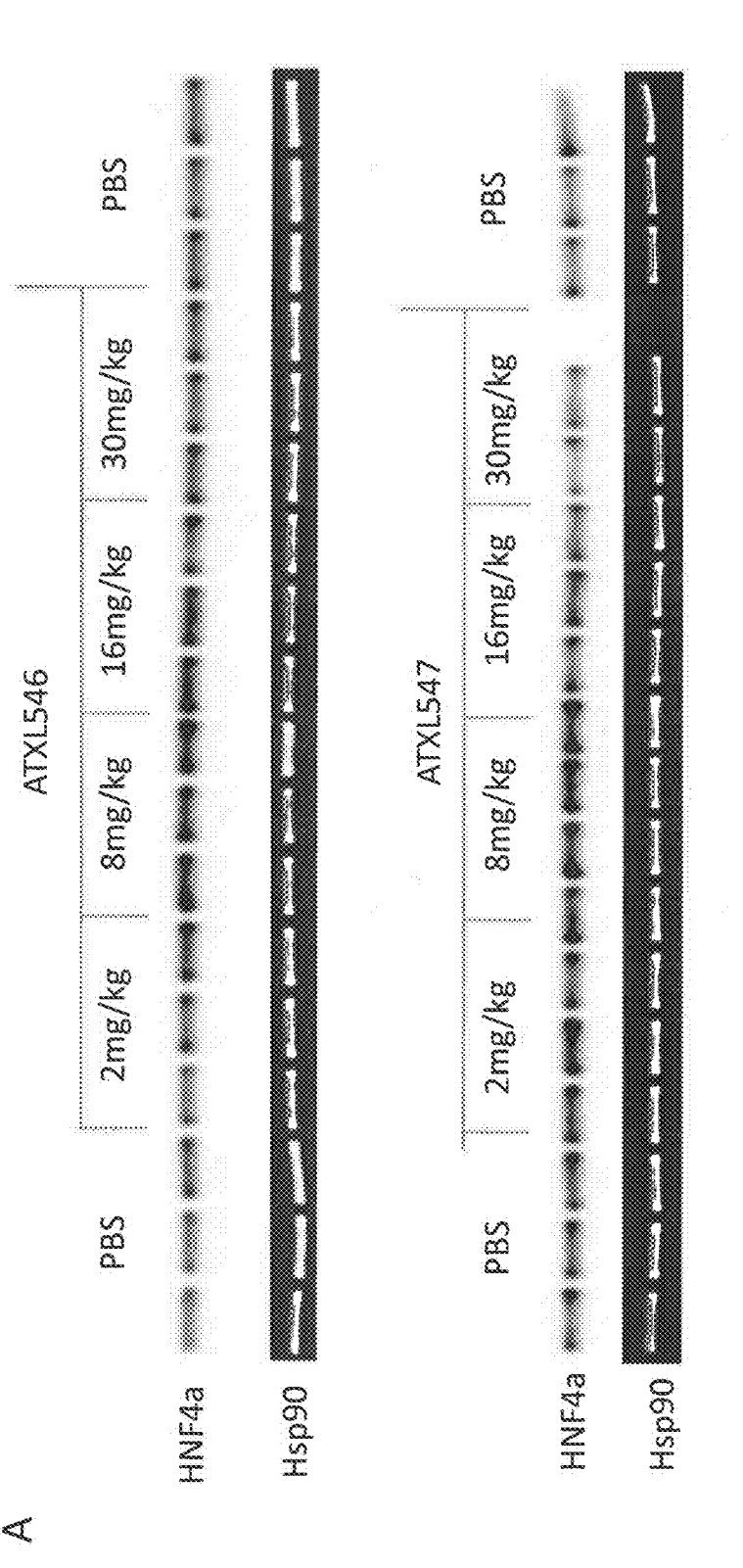
Figure 30 (1/2). Western Analysis for HNF4A Protein Levels in Mouse Liver Treated with ACT-UP1 Compounds

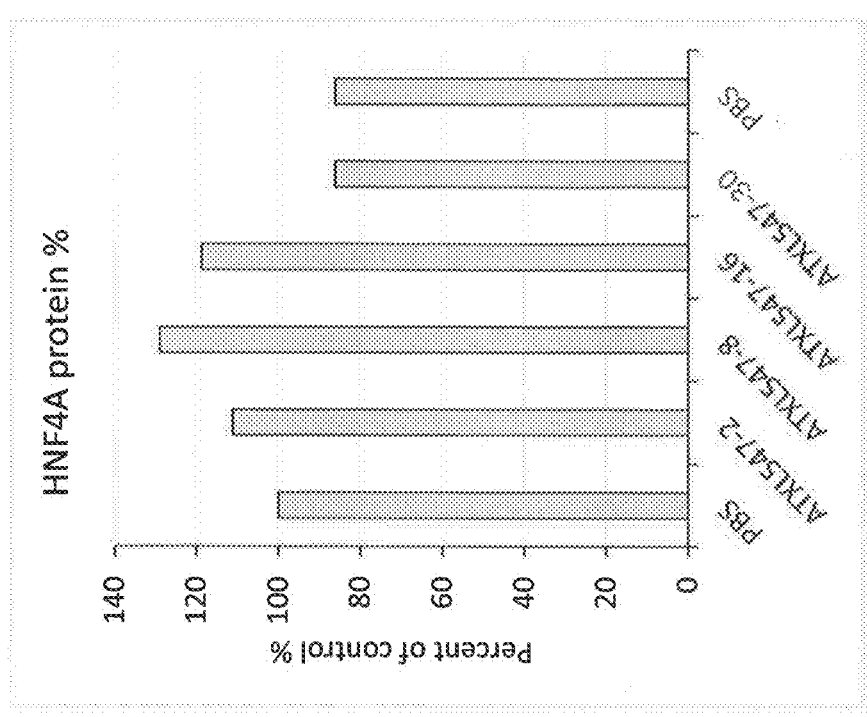
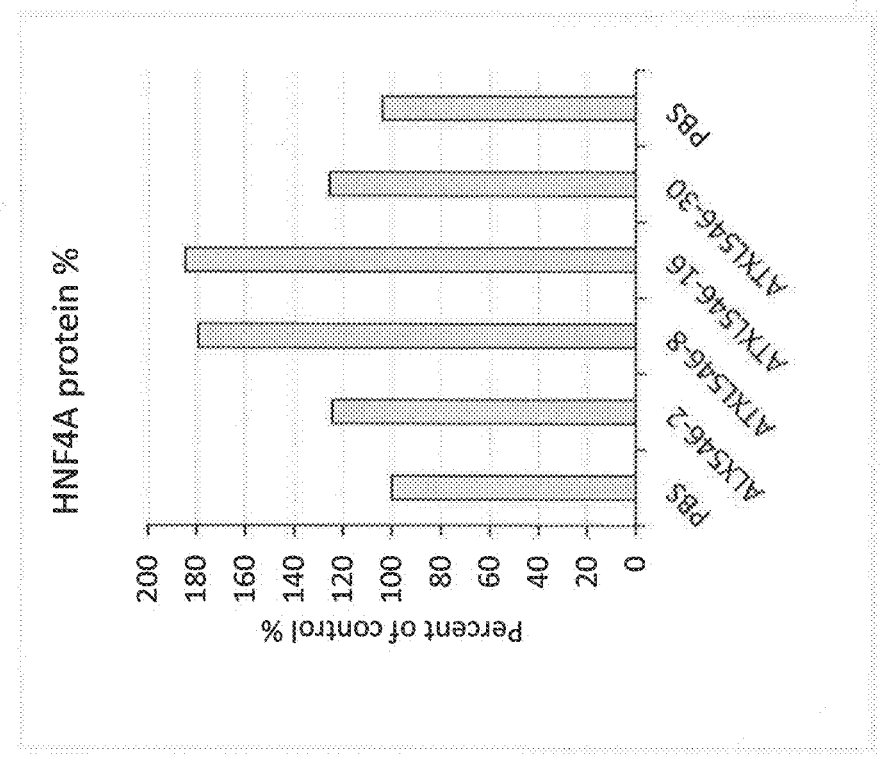
Figure 30 (2/2). Western Analysis for HNF4A Protein Levels in Mouse Liver Treated with ACT-UP1 Compounds

TRANSLATION ENHANCING NUCLEIC ACID COMPOUNDS: ASO COUPLED TRANSLATION-UPREGULATION 1 (ACT-UP1) AND USES THEREOF

CROSS-REFERENCE TO RELATED APPLICATIONS

This subject application claims priority under 35 U.S.C. § 111(A) to PCT Application No. PCT/US25/13612 filed Jan. 29, 2025, which application claims the benefit of U.S. Provisional Applications Nos. 63/626,347, filed Jan. 29, 2024; 63/558,080, filed Feb. 26, 2024; 63/677,274, Jul. 30, 2024; and 63/727,989, filed Dec. 4, 2024, the contents of which are incorporated herein in their entireties by this reference.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: the text file named "2025_01_29_Seq_List_Act_Up" _(1236 KB), which was created on Jan. 28, 2025.

Throughout this application various publications are referenced. All publications, gene transcript identifiers, patents, and patent applications mentioned in this specification are herein incorporated by reference to the same extent as if each individual publication, gene transcript identifiers, patent, or patent application was specifically and individually indicated to be incorporated by reference.

FIELD

Certain embodiments are directed to compounds for enhancing gene expression and methods of using the compounds. Such methods and compounds are useful for increasing expression of certain genes, many of which are associated with a variety of diseases and disorders.

BACKGROUND

Many diseases are caused by insufficient levels of functional proteins that normally perform important biological roles in ensuring cellular activities. Protein deficiency has many causes, including, for example, by mutations in the corresponding protein encoding genes, down-regulation of gene expression by altered upstream proteins or processes, and other reasons, Increasing the levels of the under-expressed, disease-related proteins can be a desired approach to treat diseases.

Various approaches have been assessed to restore the expression of proteins through different mechanisms. These approaches include, but, are not limited to: delivery of DNA/mRNA molecules using virus or LNPs to introduce wild type protein expressing DNA or RNA (Samulski, R. J., and N. Muzyczka, 2014 AAV-Mediated Gene Therapy for Research and Therapeutic Purposes. Annu Rev Virol 1: 427-451; Wang, J., et al., 2023a Engineered mRNA Delivery Systems for Biomedical Applications. Adv Mater: e2308029); enhancing transcription using small activation RNAs (saRNA) or oligonucleotides by targeting the promoter regions (Li, L. C., 2017, Small RNA-Guided Transcriptional Gene Activation (RNAa) in Mammalian Cells. Adv Exp Med Biol 983: 1-20; Watts, J. K., et al., 2010, Effect of chemical modifications on modulation of gene expression by duplex antigene RNAs that are complementary to non-coding transcripts at gene promoters. Nucleic Acids Res 38: 5242-5259); modulating pre-mRNA splicing to generate more stable mRNA isoforms which in turn express more proteins (Sergeeva, O. V., E. Y. Shcherbinina, N. Shomron and T. S. Zatsepin, 2022, Modulation of RNA Splicing by Oligonucleotides: Mechanisms of Action and Therapeutic Implications. Nucleic Acid Ther 32: 123-138); increasing mRNA stability using oligonucleotides or small molecules that inhibit mRNA degradation through the nonsense mediated decay (NMD) pathway (Nomakuchi, T. T., F. Rigo, I. Aznarez and A. R. Krainer, 2016 Antisense oligonucleotide-directed inhibition of nonsense-mediated mRNA decay. Nat Biotechnol 34: 164-166); inhibiting miRNA function to de-repress gene expression using antisense oligonucleotides (ASOs) targeting either miRNA itself (anti-miRs) or targeting miRNA-binding sites in the mRNA sequences (Samad, A. F. A., and M. F. Kamaroddin, 2023 Innovative approaches in transforming microRNAs into therapeutic tools. Wiley Interdiscip Rev RNA 14: e1768); antisense oligonucleotides (ASOs) targeting inhibitory elements in the 5' UTR of mRNA, such as uORFs or TIEs to enhance translation (U.S. Pat. No. 10,822,369; Liang et al., Antisense Oligonucleotides Targeting Translation Inhibitory Elements in 5'UTRs Can Selectively Increase Protein Levels, Nucleic Acids Res, 2017, 45(16): 9528-9546; Liang et al., Translation Efficiency of mRNAs is Increased by Antisense Oligonucleotides Targeting Upstream Open Reading Frames, Nature Biotechnology, 2016, 34(8):875-880); and, enhancing translation using a chimeric oligonucleotide compound coupling a guide RNA (gRNA) with an internal ribosome entry site (IRES) (US Publication US20230090706). Additional examples of methodologies to upregulate gene expression have been described by Li et al., (Targeting 3' and 5' Untranslated Regions with Antisense Oligonucleotides to Stabilize Frataxin mRNA and Increase Protein Expression, Nucleic Acids Res, 2021, 49(20):11560-11574); Torkzaban et al. (Development of a Tethered mRNA Amplifier to Increase Protein Expression, Biotechnol. J., 2022 October, 17(10):e2200214); U.S. Pat. Nos. 5,916,808; 9,018,368; 5,916,808; 9,297,008; US Publication US20110046200; US Publication US20220204978; US Publication US20190275170; and US Publication US20220127621.

Upregulation of protein expression is an area of therapeutic interest for the treatment of disease and several companies are developing nucleic acid-based therapeutics to increase expression of protein. For example, Sarepta Therapeutics is using a phosphorodiamidate morpholino oligomer (PMO) to facilitate exon skipping to treat diseases such as Duchenne Muscular Dystrophy (eteplirsen) (US Publication US20190275072). Ionis developed nusinersen which modulates alternative splicing to increase protein expression (U.S. Pat. No. 10,436,802). Stoke Therapeutics is developing antisense oligonucleotides (ASOs) to increase protein levels in haploinsufficient patients by affecting intron retention by splicing to increase protein expression (U.S. Pat. No. 11,096, 956).

These approaches described above have specific advantages and may be applicable in certain situations. However, each approach has its own challenges that limit their application. For example, efficient and safe delivery of large molecules including mRNAs or DNAs into cells and nuclei remain challenging (Wang, Y. S., et al., 2023b mRNA-based vaccines and therapeutics: an in-depth survey of current and upcoming clinical applications. J Biomed Sci 30: 84). ASOs targeting miRNAs to enhance a particular gene expression may not be specific to a desired target since each miRNA may modulate the expression of hundreds of genes (Chen, P. Y., and G. Meister, 2005, microRNA-guided posttranscriptional gene regulation. Biol Chem 386: 1205-1218). The approaches of using ASOs targeting other elements, such as 5' UTR uORFs, TIEs, splice sites, or 3' UTR miRNA binding sites, require the presence of such elements in the target mRNAs, thus limiting the application of such approaches to the genes that must have such elements.

Although significant progress has been made in the field of oligomeric compound technology, there remains a need in the art for new efficient ways to increase protein expression and treat a subject in need thereof, e.g., a subject with deficient protein expression and/or a subject having a disease described herein. Disclosed herein is a novel approach, antisense oligonucleotide (ASO) Coupled Translation-Upregulation 1 (ACT-UP1), that increases protein levels without the need of existing elements in the target mRNAs, therefore, in theory, it can increase the protein levels of any gene.

SUMMARY OF THE INVENTION

Several embodiments provided herein relate to the discovery of certain modifications to antisense compounds that can enhance their effectiveness in modulating gene expression. In certain embodiments, the antisense compounds enhance gene expression.

In certain embodiments, the invention is directed to an antisense compound which is an antisense oligonucleotide (ASO) Coupled Translation-Upregulation 1 (ACT-UP1) compound. The ACT-UP1 compound comprises an ASO component joined to a protein recruiting sequence (PRS) component, wherein the ASO component hybridizes to a target mRNA, the PRS recruits translation related proteins, and wherein the ACT-UP1 compound enhances expression of a target protein. The ACT-UP1 compound may further comprise a conjugate. In accordance with the practice of the invention, the ASO component may be joined to the PRS directly or indirectly.

In certain embodiments, an ACT-UP1 compound may be of about 17 to 45 linked nucleosides in length. The ACT-UP1 compound comprises an ASO component of about 12 to 25 linked nucleosides in length joined to a protein recruiting sequence (PRS) component of about 5 to 20 linked nucleosides in length. The ASO component hybridizes to a target mRNA, the PRS recruits translation-related proteins, and wherein the ACT-UP1 compound enhances protein expression.

In certain embodiments, an ACT-UP1 compound may be of about 22 to 35 linked nucleosides in length. The ACT-UP1 compound comprises an ASO component 12 to 25 linked nucleosides in length joined to a protein recruiting sequence (PRS) component comprising GGACUGGACU (SEQ ID NO: 11) or AAACUAAACU (SEQ ID NO: 13). The ASO component hybridizes to a target mRNA, the PRS recruits translation-related proteins, and wherein the ACT-UP1 compound enhances protein expression.

In further aspects, an ACT-UP1 compound may be anywhere from about 17 to 45 linked nucleosides in length, the ASO is about 12 to 25 linked nucleosides in length and the PRS is about to 20 linked nucleosides in length; includes at least one modified sugar, such as a bicyclic sugar, a 2'-O-(2-methoxyethyl) group, a 2'-O-methyl group, and/or a 4'-CH(CH₃)—O-2' (cEt) group; includes at least one modified internucleoside linkage, such as a phosphorothioate internucleoside linkage; and/or includes at least one modified nucleobase, such as a 5-methylcytidine.

Certain embodiments provide kits and methods of using the compounds disclosed herein and processes to manufacture the compounds.

BRIEF DESCRIPTION OF TIE DRAWINGS

FIG. 1: A schematic diagram that shows a potential ACT-UP1 mechanism. The ACT-UP1 compound comprises an antisense oligonucleotide (ASO) joined to a protein recruiting sequence (PRS). The ASO specifically hybridizes to a target mRNA sequence, bringing the PRS into close proximity to the target mRNA. The PRS, a short sequence of linked nucleosides, recruits translation related proteins, e.g., PABPC1, close to the target mRNA thereby increasing translation of the targeted mRNA.

FIG. 2: A Western Blot that shows Jagged 1 protein levels after HeLa cell transfection with ACT-UP1 compounds comprising different PRSs, namely, ATXL193, ATXL261 and ATXL228. The ACT-UP1 compounds with PRS enhance Jagged 1 protein expression.

FIG. 3: A Western Blot that shows Jagged 1 protein levels after HeLa cell transfection with ACT-UP1 compounds. The data show that a PRS positioned 5' to the ASO in an ACT-UP1 compound is more effective at increasing protein levels than a PRS positioned 3' to the ASO in an ACT-UP1 compound.

FIG. 4: A Western Blot that shows Jagged 1 protein levels after HeLa cell transfection with ACT-UP1 compounds. The data show that ASO binding positions on the target mRNA affect the ability of the ACT-UP1 compounds to increase protein expression. To certain degree, the closer the binding position to the transcript's stop codon, the more protein expressed.

FIG. 5: A Western Blot that shows Jagged 1 protein levels after HeLa cell transfection with ACT-UP1 compounds containing different amounts of phosphorothioate (PS) linkages.

FIG. 6: A Western Blot that shows Jagged 1 protein levels in a Western Blot after HEK293 cell transfection with an ACT-UP1 compound. The data shows that the ACT-UP1 compound can increase protein expression in cell lines other than HeLa.

FIG. 7: A Western Blot that shows RAB9 protein levels after HeLa cell transfection with an ACT-UP1 compound. The data shows that the ACT-UP1 compound can increase protein expression of gene transcripts other than Jagged 1.

FIG. 8: A Western Blot that shows RNase H1 protein levels after HeLa cell transfection with an ACT-UP1 compound. The data shows that the ACT-UP1 compound can increase protein expression of gene transcripts other than Jagged 1.

FIG. 9: A Western Blot that shows PBGD protein levels after HeLa cell transfection with an ACT-UP1 compound. The data shows that the ACT-UP compound can increase protein expression of gene transcripts other than Jagged 1.

FIG. 10A-C: A) A Western Blot that shows PBGD protein levels after murine Hepa1-6 cell transfection with ACT-UP1 compounds; and, B) a bar graph summarizing the PBGD protein levels; and, C) a bar graph summarizing mRNA levels in murine Hepa1-6 cells transfected with different PBGD ACT-UP1 compounds. The data indicate that ACT-UP1 compounds increase PBGD protein levels, but, do not increase PBGD mRNA levels significantly.

FIG. 11: A Western Blot that shows FGF21 protein levels after Hep3B cell transfection with an ACT-UP1 compound.

The data indicates that the ACT-UP1 compound can increase protein expression of other gene transcripts besides Jagged 1 and in cells other than HeLa.

FIG. 12A-C: A) Western Blot that shows FGF21 protein levels after murine Hepa1-6 cell transfection with ACT-UP1 compounds; B) a bar graph summarizing the FGF21 protein levels; and, C) a bar graph summarizing mRNA levels in murine Hepa1-6 cells transfected with different FGF21 ACT-UP1 compounds. The data indicates that ACT-UP1 compounds increase FGF21 protein levels, but, do not increase FGF21 mRNA levels.

FIG. 13A-C: A) A schematic of the ACT-UP1 affinity selection assay, B) and C) Western Blots showing that translation related proteins were recruited by ACT-UP1 compounds.

FIG. 14: A Western Blot that shows Jagged 1 protein levels after HeLa cell transfection with ACT-UP1 compounds containing different PRS components.

FIG. 15: Western Blots that show Jagged 1 protein levels after in vivo treatment of mice with ACT-UP1 compounds.

FIG. 16A-B: A) Western Blot that shows HNF4A protein levels after human Hep3B cell transfection with ACT-UP1 compounds; and, B) a bar graph summarizing the HNF4A protein levels. The data indicates that human HNF4A protein is increased using different ACT-UP1 compounds in Hep3B cells.

FIG. 17A-B: A) Western blot that shows Jagged 1 protein levels after in vivo treatment of mice with ACT-UP1 compounds with or without GalNAc conjugate; and, B) Western blot that shows Jagged 1 protein levels after in vivo treatment of mice with ACT-UP1 compounds with (ATXL282) or without (ATXL283) GalNAc conjugate.

FIG. 18: Western blot that shows Jagged 1 protein levels four weeks after in vivo treatment of mice with an ACT-UP1 compound.

FIG. 19: Western blot that shows Jagged 1 protein levels after in vivo treatment of Jag1$^{+/-}$ mice with ACT-UP1 compounds.

FIG. 20: Western blot that shows Jagged 1 protein levels in mice at 2- and 3-weeks After dosing with ACT-UP1 compounds.

FIG. 21A-B: Bar graphs with qRT-PCR results that show the FGF21 mRNA levels in Hep3B cells treated with different ACT-UP1 compounds for 20 hr (Panel A) or 40 hr (Panel B).

FIG. 22: A bar graph with ELISA results that show the plasma FGF21 protein levels in mice treated with different ACT-UP1 compounds.

FIG. 23A-B: A) A Western Blot that shows JAG1 protein levels in GM11091 cells after transfection with ATXL316 ASO at 24 hr; and, B) a bar graph summarizing the JAG1 protein levels from the Western Blot with JAG1 protein normalized to Tubulin protein. The data indicates that ATXL316 increased JAG1 protein in patient GM11091 cells at 24 hrs.

FIG. 24A-B: A) Western Blot that shows JAG1 protein levels in HeLa cells after transfection with 10 nM ATXL316, followed by 100 µg/ml CHX treatment at different times as indicated above the lanes; and, B) a graph plotting the JAG1 protein levels from the Western Blot with and JAG1 protein levels normalized to a CHX-insensitive protein detected by Hsp90 antibody. The data indicates ATXL316 ASO does not affect JAG1 protein stability.

Figure 25:
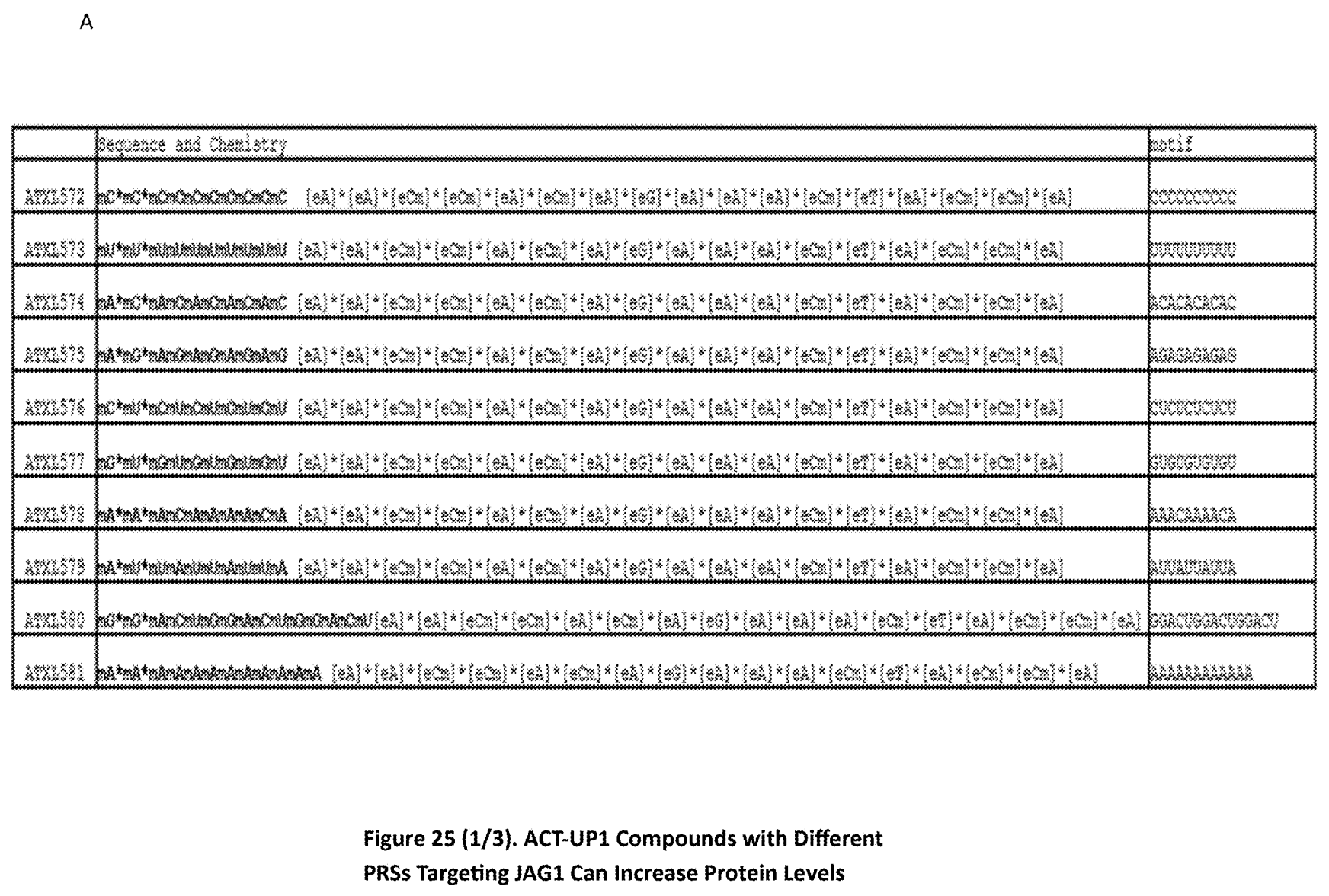

FIG. 25A-C: A) A table listing sequence, chemistry, and PRSs of ACT-UP1 compounds targeting JAG1, B) A Western Blot that shows JAG1 protein levels in HeLa cells after transfection with the ACT-UP1 compounds; and, C) a bar graph summarizing the JAG1 protein levels from the Western Blot with JAG1 protein normalized to a non-specific protein. The data indicates ACT-UP1 compounds with different PRSs can increase protein levels at 24 hrs.

FIG. 26: A bar graph showing that different dual functional ASOs can increase FGF21 mRNA levels in human Hep3b cells.

FIG. 27A-B: Western Blot analysis of FGF21 protein levels in human HepG2 cells after transfection with different ASOs at different concentrations. The data indicates that different dual functional ACT-UP1 compounds can increase FGF21 protein levels in human HepG2 cells.

FIG. 28A-B: A) A Western Blot of HNF4A protein levels in human primary hepatocytes (HPH) treated with ACT-UP1 compounds by free uptake; and, B) a bar graph summarizing the HNF4A protein levels from the Western Blot with HNF4A protein normalized to GAPDH protein. The data indicates that ACT-UP1 compounds can increase protein levels at 66 hrs.

FIG. 29: Western Blot analysis of HNF4A protein levels in murine Hepa1-6 cells after transfection with an ASO at different concentrations. The data indicates that the ACT-UP1 compound increased HNF4A protein in Hepa1-6 mouse cells within a broad dose range.

FIG. 30A-B: A) Western Blots of HNF4A protein levels in mouse liver after treatment with ACT-UP1 compounds; and, B) bar graphs summarizing the HNF4A protein levels from the Western Blots with HNF4A protein normalized to Hsp90 protein. The data indicates that ACT-UP1 compounds can increase HNF4A protein levels in vivo.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated-by-reference for the portions of the document discussed herein, as well as in their entirety.

Unless otherwise indicated, the following terms have the following meanings:

"2'-O-(2-methoxyethyl)" (also 2'-MOE and 2'-O(CH$_2$)$_2$—OCH$_3$) refers to an 2-methoxyethyl modification at the 2' position at the 0 of a furanose ring. A 2'-O-(2-methoxyethyl) modified sugar is a modified sugar.

"2'-MOE nucleoside" (also 2'-O-(2-methoxyethyl) nucleoside) means a nucleoside comprising a 2'-MOE modi-fied sugar moiety. "2'-MOE nucleotide" (also 2'-O-(2-methoxyethyl) nucleotide) means a nucleotide comprising a 2'-MOE modified sugar moiety.

"2'-O-methyl" (also 2'-OCH$_3$ and 2'-OMe) refers to an methyl modification at the 2' position at the 0 of a furanose ring. A 2'-O-methyl modified sugar is a modified sugar.

"2'-OMe nucleoside" (also 2'-O-methyl nucleoside) means a nucleoside comprising a 2'-OMe modified sugar moiety. "2'-OMe nucleotide" (also 2'-O-methyl nucleotide) means a nucleotide comprising a 2'-OMe modified sugar moiety.

"2'-substituted nucleoside" means a nucleoside compris-ing a substituent, i.e., a modification, at the 2'-position of the furanosyl ring other than H or OH. In certain embodiments, 2' substituted nucleosides include nucleosides with a fluoro (2'-F), O-methyl (2'-OMe), O-(2-methoxyethyl) (2'-MOE) or bicyclic sugar modifications. A 2'-substituted nucleoside is a modified nucleoside.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5 position. A 5-methylcytosine is a modified nucleobase and is part of a modified nucleo-side. "5-methylcytidine" is the name of the nucleoside when the 5 methyl modified nucleobase is combined with a modified or unmodified sugar.

"About" as used herein means within ±7% of a measur-able value. For example, if it is stated, "the compounds affected at least about 70% inhibition of mRNA", it is implied that the mRNA levels are inhibited within a range of 63% and 77%. The term "about" as used herein when referring to an amount of a compound or agent of this invention, dose, time, temperature, and the like, is meant to encompass variations of ±10%, ±5%, ±1%, ±0.5%, or even ±0.1% of the specified amount. For sequence identity, "about" as used for percent sequence identity encompasses variations of ±5%. Unless otherwise indicated, all numbers expressing quantities of ingredients, properties such as reac-tion conditions, and so forth used in the specification and claims are to be understood as being modified in all instances by the term "about."

"Average" as used herein may be mean, mode or medium for a group of measurements.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art.

"ACT-UP1" or "ASO Coupled Translation-Upregulation 1" refers to an antisense oligonucleotide (ASO) joined to a protein recruiting sequence (PRS). The ASO specifically hybridizes to a target mRNA sequence, bringing the PRS into close proximity to the target mRNA. The PRS, a short sequence of linked nucleosides, attracts translation regula-tory proteins close to the target mRNA thereby increasing translation of the targeted mRNA. As used herein, the protein recruiting sequence (PRS), although it comprises a short linkage of nucleosides, is not an antisense oligonucle-otide (ASO) as it does not hybridize with a target nucleic acid (i.e., the protein recruiting sequence is not antisense to a target nucleic acid). The ASO can be joined directly to the PRS or they can be joined by a linker. In some preferred aspects the PRS is joined to the 5' end of the ASO. In some aspects the PRS is joined to the 3' end of the ASO. Joined=covalently linked; It is to be understood that the ACT-UP1 compound may comprise additional sequences in addition to the ASO and PRS. For example, in some embodi-ments, the ACT-UP1 comprises an ASO and PRS and a linker for joining the ASO and PRS.

"ACT-UP1 activity" means any detectable or measurable activity attributable to the hybridization of an ACT-UP1 compound to its target nucleic acid. In certain embodiments, ACT-UP1 activity is an increase (i.e., up-regulation) in the amount of a target nucleic acid and/or expression of the protein encoded by such target nucleic acid.

"ACT-UP1 upregulation" or "ACT-UP1 enhancement" means increasing target protein levels in the presence of an ACT-UP1 compound compared to target protein levels in the absence of the ACT-UP1 compound.

"Animal" refers to a human or non-human animal, includ-ing, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fe region.

"Antisense compound" means an oligomeric compound that is capable of undergoing hybridization to a target nucleic acid through hydrogen bonding. Examples of anti-sense compounds include single-stranded and double-stranded compounds, such as, antisense oligonucleotides (ASOs), siRNAs, shRNAs, snoRNAs, miRNAs, and satel-lite repeats. It is to be understood that antisense compounds include ACT-UP1 compounds which comprise an antisense oligonucleotide (ASO) joined to a protein recruiting sequence (PRS).

"Antisense oligonucleotide" or "ASO" means a single-stranded oligonucleotide having a nucleobase sequence that permits hybridization to a corresponding region or segment of a target nucleic acid. In certain embodiments, the ASO comprises one or more modified nucleosides. In certain embodiments, the ASO comprises part of an ACT-UP1 compound. As used herein, ASO does not refer to the protein recruiting sequence (PRS) in ACT-UP1 compounds.

"Base complementarity" refers to the capacity for the base pairing of nucleobases of an oligonucleotide with corre-sponding nucleobases in a target nucleic acid (i.e., hybrid-ization), and is mediated by Watson-Crick, Hoogsteen or reversed Hoogsteen hydrogen binding between correspond-ing nucleobases. Base complementarity also refers to canonical (e.g., A:U, A:T, or C:G) or non-canonical base pairings (e.g., A:G, A:U, G:U, I:U, I:A, or I:C).

"Bicyclic sugar" means a furanose ring modified by the bridging of two non-geminal carbon atoms. A bicyclic sugar is a modified sugar.

"Cap structure" or "terminal cap moiety" means chemical modifications, which have been incorporated at either terminus of an antisense compound.

"cEt" or "constrained ethyl" means a bicyclic sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemical modification" means modification of molecular structure or element from naturally occurred molecules. For example, antisense oligonucleotides are composed of linked deoxyribonucleosides (also sometimes referred to herein as DNA nucleoside), therefore, substitution of a 2'-MOE nucleoside for a DNA nucleoside is considered a chemical modification of the antisense oligonucleotide. Examples of other chemical modification may be found hereinbelow.

"Chemically distinct region" refers to a region of an antisense compound that is in some way chemically different than another region of the same antisense compound. For example, a region having 2'-O-(2-methoxyethyl) nucleotides is chemically distinct from a region having nucleotides without 2'-O-(2-methoxyethyl) modifications.

"Complementarity" means the capacity for pairing between nucleobases of a first nucleic acid and a second nucleic acid.

"Comply" means the adherence with a recommended therapy by an individual.

"Comprise," "comprises" and "comprising" will be understood to imply the inclusion of a stated step or element or group of steps or elements but not the exclusion of any other step or element or group of steps or elements.

"Contiguous nucleobases" means nucleobases immediately adjacent to each other.

"Deoxyribonucleoside" means a nucleoside having a hydrogen at the 2' position of the sugar portion of the nucleoside. A deoxyribonucleoside is sometimes referred to as DNA nucleoside, "D" or "d" herein. Deoxyribonucleosides may be modified with any of a variety of substituents and may be connected by covalent linkages other than naturally occurring phosphodiester such as phosphorothioate.

"Deoxyribonucleotide" means a nucleotide having a hydrogen at the 2' position of the sugar portion of the nucleotide. A deoxyribonucleotide is sometimes referred to as DNA nucleotide, "D" or "d" herein. Deoxyribonucleotides may be modified with any of a variety of substituents and may be connected by covalent linkages other than naturally occurring phosphodiester such as phosphorothioate.

"Derivative" of a protein recruiting sequence (PRS) refers to selecting a sequence and then modifying the sequence for use as a PRS. For example, GGACU (SEQ ID NO: 8), a m$^6$A methylation target sequence found in mRNA, can be the basis to make GGACU derivatives that are not used as a methylation target and are not found in mRNA (e.g., the GGACU sequence has been derivatized to be used as a PRS). Derivatives useful as PRS components of ACT-UP1 can also be made with additional nucleobases added to the original sequence (e.g., ACGGACUUGGACU, SEQ ID NO: 12), repeats of the original sequence linked together (e.g., GGACUGGACU, SEQ ID NO: 11), partial repeats of the original sequence linked together (GGACUGGAC, SEQ ID NO: 10), or a combination of modifications. In some examples, a derivative comprises one or more repeats or partial repeats of a specified sequence. Merely by way of example, modifications may be any of insertions, additions, deletions, or substitutions of particular nucleosides into a sequence (for example, GAACU (SEQ ID NO: 42), AGACU (SEQ ID NO: 43) or GGACA (SEQ ID NO:44) is a substitution of A into GGACU) as well as chemical modifications. For example, in the PRS, a modification includes at least one substitution. In other embodiments, a modifications includes at least two substitutions.

"Dual functional compound" or "dual functional ACT-UP1 compound" refers to a compound with an ACT-UP1 design plus a design for a second function or mechanism that is not ACT-UP1. For example, a dual functional compound has an ACT-UP1 design (e.g., binds to the 3'UTR of a target transcript and has a PRS) and an AU rich element (ARE) targeting sequence. This dual functional compound would increase protein levels by both increasing mRNA levels (via blocking ARE binding) and also increasing protein translation (via ACT-UP1).

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Fully modified" or "Fully chemically modified" refers to an antisense compound comprising a contiguous sequence of nucleosides wherein essentially each nucleoside has a chemical modification.

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Immediately adjacent" means there are no intervening elements between the immediately adjacent elements.

"Individual" means a human or non-human animal selected for treatment or therapy.

"Induce", "inhibit", "potentiate", "elevate", "increase", "decrease", "enhance" or the like, generally denote quantitative differences between two states.

"Inhibiting the expression or activity" refers to a reduction, or blockade of the expression or activity and does not necessarily indicate a total elimination of expression or activity.

"Internucleoside linkage" or "linkage" refers to the chemical bond between nucleosides.

The 3' position of a nucleoside is hereby linked to a 5' position of a subsequent nucleoside via the internucleoside linkage.

"Isolated" means a state following one or more purifying steps but does not require absolute purity.

"Joined" ASO and PRS components of ACT-UP1 compound means that the ASO and PRS components are covalently linked to form the ACT-UP1 compound. It is to be understood that the ACT-UP1 compound may comprise additional sequences joined to the ASO and/or PRS. For example, in some embodiments, the ACT-UP1 comprises the ASO and PRS components and a linker for joining the ASO and PRS.

"Linked deoxynucleoside" means a nucleic acid base (A, G, C, T, U) substituted by deoxyribose linked by a phosphate ester to form a nucleotide.

"Linked nucleosides" means adjacent nucleosides (e.g., A, G, C, T, or U) linked together by an internucleoside linkage. Examples of linked nucleosides include deoxyribonucleosides (sometimes referred to as DNA nucleosides herein) or ribonucleosides (sometimes referred to as RNA nucleosides herein).

"Linker" means a molecule that functions as a spacer between two components, e.g., between the ACT-UP1 compound and a GalNAc conjugate moiety, and/or between a PRS and ASO within the ACT-UP1 compound. Examples of linkers include one or more of a fatty acid, polyethylene glycol (PEG), or amino acid.

"Mismatch" or "non-complementary nucleobase" refers to the case when a nucleobase of a first nucleic acid is not capable of pairing with the corresponding nucleobase of a second or target nucleic acid through Watson-Crick base-pairing (e.g., A:T, A:U, or C:G).

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U). In certain embodiments, an RNA nucleoside is considered modified when a DNA nucleoside is substituted for the RNA nucleoside. In certain embodiments, a DNA nucleoside is considered modified when an RNA nucleoside is substituted for the DNA nucleoside.

"Modified nucleoside" means a nucleoside having, independently, a modified sugar moiety and/or modified nucleobase.

"Modified nucleotide" means a nucleotide having, independently, a modified sugar moiety, modified internucleoside linkage, and/or a modified nucleobase.

"Modified oligonucleotide" means an oligonucleotide comprising at least one modified internucleoside linkage, a modified sugar, and/or a modified nucleobase.

"Modified sugar" means substitution and/or any change from a natural sugar moiety.

"Moiety" means one of the portions into which something is divided i.e., a part or component of something. For example, a sugar moiety of a nucleotide is the sugar component of the nucleotide.

"Monomer" refers to a single unit of an oligomer. Monomers include, but are not limited to, nucleosides and nucleotides, whether naturally occurring or modified.

"Motif" means the pattern of unmodified and modified nucleosides in an antisense compound. Antisense compounds comprise motifs with various modified nucleobases, modified sugars and/or internucleoside linkages in order to improve, among other characteristics, delivery, stability, specificity, safety and potency of the antisense compounds. The motif is independent of the nucleobase sequence of the antisense compound and identifies only the pattern of modifications.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA e.g., mRNA), deoxyribonucleic acids (DNA), single-stranded nucleic acids (e.g., antisense oligonucleotides (ASOs) and microRNAs (miRNA)), double-stranded nucleic acids (e.g., small interfering ribonucleic acids (siRNAs) and short hairpin RNAs (shRNAs).

"Nucleobase" means a heterocyclic moiety capable of pairing with a base of another nucleic acid.

"Nucleobase complementarity" refers to a nucleobase that is capable of base pairing (also known as being complementary) with another nucleobase. If a nucleobase at a certain position of an oligomeric compound is capable of hydrogen bonding with a nucleobase at a certain position of a target nucleic acid, then the position of hydrogen bonding between the oligomeric compound and the target nucleic acid is considered to be complementary at that nucleobase pair. For example, in DNA, adenine (A) is complementary to thymine (T); in RNA, adenine (A) is complementary to uracil (U); and, Guanine (G) is complementary to cytosine (C) in both DNA and RNA. Base pairs, or complementary nucleobases, are usually canonical Watson-Crick base pairs (e.g., C:G, A:U, or A:T), but, non-canonical base pairs such as Hoogsteen base pairs (e.g., A:G, or A:U), Wobble base pairs (e.g., G:U, I:U, I:A, or I:C, wherein I is hypoxanthine) and the like are also included. Nucleobase complementarity facilitates hybridization of the oligomeric compounds described herein to their target nucleic acids.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a linkage group (e.g., a phosphate (p) or phosphorothioate (PS) group) covalently linked to the sugar portion of the nucleoside. Nucleotides include ribonucleotides and deoxyribonucleotides. Ribonucleotides are the linked nucleotide units forming RNA. Deoxyribonucleotides are the linked nucleotide units forming DNA.

"Off-target effect" refers to an unwanted or deleterious biological effect associated with modulation of RNA or protein expression of a gene other than the intended target nucleic acid.

"Oligomeric compound" means a sequence of linked monomeric subunits that is capable of undergoing hybridization to at least a region of a target nucleic acid through hydrogen bonding. The monomeric subunits can be modified or unmodified nucleotides or nucleosides. Examples of oligomeric compounds include antisense compounds (e.g., antisense oligonucleotides (ASOs) or ACT-UP1 compounds comprising antisense oligonucleotides).

"Oligonucleotide" as used herein means a polymer of linked nucleosides each of which can be modified or unmodified, independent one from another. Oligonucleotides can have a linking group other than a phosphate group (e.g., a phosphorothioate=thiophosphate group) used as a linking moiety between nucleosides.

"Substantially modified" or "substantially chemically modified" refers to an antisense compound comprising a contiguous sequence of nucleosides wherein the nucleosides are mostly, but, not fully, chemically modified. For example, the compound includes not more than about 5, 4, 3, 2, or 1 unmodified nucleoside.

"Phosphorothioate linkage" or "PS" means a linkage between nucleosides where the phosphodiester bond is modified by replacing one of the non-bridging oxygen atoms with a sulfur atom. A phosphorothioate (=thiophosphate or also known as thiophosphate) linkage is a modified internucleoside linkage.

"Protein recruiting sequence" or "PRS" is a short sequence of linked nucleosides that attracts and/or binds translation regulatory proteins. Merely by way of example, a translation regulatory protein can be an RNA binding protein (RBP) that regulates translation of mRNA into protein which is well known in the art (see Example 12). The PRS is the component of the ACT-UP1 compound that interacts with RNA binding proteins while the ASO is the component of the ACT-UP1 compound that hybridizes with a target nucleic acid; together, the ASO and PRS components of the ACT-UP1 compound enhance translation of a mRNA target. The protein recruiting sequence, although it comprises a short linkage of nucleosides, is not an antisense oligonucleotide (ASO) as it does not hybridize with a target nucleic acid (i.e., the protein recruiting sequence is not antisense to a target nucleic acid). The PRS component of ACT-UP1 may be a sequence derived from a naturally occurring sequence. For example, the PRS may be a sequence located in the 3'UTR of an mRNA transcript and derived to be a trans-acting PRS component of an ACT-UP1 compound. The derivative forming the PRS can be optionally modified with additional nucleobase(s), deletion of nucleobase(s), substitution of nucleobase(s), repetition of nucleobases, and the like.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Region" is defined as a portion of the target nucleic acid having at least one identifiable structure, function, or characteristic.

"RNA" or "ribonucleic acid" consists of ribose nucleotides or ribonucleotides (nitrogenous bases attached to a ribose sugar) linked by phosphodiester bonds, forming strands of varying lengths. The nitrogenous bases in RNA are adenine, guanine, cytosine, and uracil. The ribose sugar of RNA is a cyclical structure of five carbons and one oxygen.

"Ribonucleoside" means a nucleoside having a hydroxy at the 2' position of the sugar portion of the nucleoside. A ribonucleoside is sometimes referred to as RNA nucleoside, "R" or "r" herein.

"Ribonucleotide" means a nucleotide having a hydroxy at the 2' position of the sugar portion of the nucleotide. A ribonucleotide is sometimes referred to as RNA nucleotide, "R" or "r" herein.

"Segments" are defined as smaller or sub-portions of regions within a target nucleic acid.

"Sites," as used herein, are defined as unique nucleobase positions within a target nucleic acid.

"Specifically hybridizable" refers to an antisense compound having a sufficient degree of complementarity between an antisense compound (e.g., ASO) and a target nucleic acid to induce a desired effect, while exhibiting minimal or no effects on non-target nucleic acids under conditions in which specific binding is desired, i.e., under physiological conditions in the case of in vivo assays and therapeutic treatments. Examples of sufficient degrees of complementarity are disclosed herein.

"Stringent hybridization conditions" or "stringent conditions" refer to conditions under which an antisense compound will hybridize to its target sequence, but to a minimal number of other sequences.

"Subject" means a human or non-human animal selected for treatment or therapy.

"Target" refers to a protein or nucleic acid sequence (e.g., mRNA), the modulation of which is desired. In certain embodiments, the modulation is an increase in expression of the target nucleic acid. In certain embodiments, the modulation is a decrease in expression of the target nucleic acid.

"Target gene" refers to a gene encoding a target.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment. In an embodiment, a target segment is at least a 12-nucleobase portion (i.e., at least 12 consecutive nucleobases) of a target region to which an antisense compound is targeted.

"Therapeutic efficacy" refers to the effectiveness of a therapeutic compound such as an antisense compound. Therapeutic efficacy can be increased by improvements in delivery, stability, specificity, safety and potency of the therapeutic compound.

"Unmodified" RNA nucleoside mean the purines adenine (A) and guanine (G), and the pyrimidines cytosine (C) and uracil (U). "Unmodified" DNA nucleoside mean the purines adenine (A) and guanine (G), and the pyrimidines thymine (T) and cytosine (C). In certain embodiments, an unmodified RNA nucleoside is considered modified when a DNA nucleoside is substituted for the RNA nucleoside. In certain embodiments, an unmodified DNA nucleoside is considered modified when an RNA nucleoside is substituted for the DNA nucleoside.

"Unmodified nucleoside" means a nucleoside composed of commonly and naturally occurring nucleobases and sugar moieties. For example, an unmodified nucleoside is a DNA nucleoside if used in a DNA sequence, however, in such DNA sequence, any other nucleoside (e.g., RNA nucleoside, 2'-OMe, 2'-MOE, or 2'-F) is considered a modified nucleoside.

"Unmodified nucleotide" means a nucleotide composed of commonly and naturally occurring nucleobases, sugar moieties, and internucleoside linkages. For example, an unmodified nucleotide is a DNA nucleotide if used in a DNA sequence, however, in such DNA sequence, any other nucleotide (e.g., RNA nucleotide, 2'-OMe, 2'-MOE or 2'-F) is considered a modified nucleotide.

"Validated target segment" is defined as at least an 8-nucleobase portion (i.e. 8 consecutive nucleobases) of a target region to which an antisense compound is targeted.

"Wing segment" means a plurality of nucleosides at the 3' and/or 5' end of an antisense oligonucleotide, wherein the nucleosides are modified to impart to the antisense oligonucleotide properties such as, for example, enhanced activity, increased binding affinity for a target nucleic acid, and/or resistance to degradation by in vivo nucleases.

Disclosed herein are antisense compounds that enhance target protein expression. In certain embodiments, the antisense compound comprises an antisense oligonucleotide (ASO) Coupled Translation-Upregulation 1 (ACT-UP1) compound. The ACT-UP1 compound comprises an ASO component joined to a protein recruiting sequence (PRS) component, wherein the ASO component hybridizes to a target mRNA, the PRS recruits translation related proteins, and wherein the ACT-UP1 compound enhances expression of a target protein. In some preferred aspects, the PRS is joined to the 5' end of the ASO. In some aspects the PRS is joined to the 3' end of the ASO.

In certain embodiments, the ACT-UP1 compound comprises about 17 to 45, 17 to 44, 17 to 43, 17 to 42, 17 to 41, 17 to 40, 17 to 39, 17 to 38, 17 to 37, 17 to 36, 17 to 35, 17 to 34, 17 to 33, 17 to 32, 17 to 31, 17 to 30, 17 to 29, 17 to 28, 17 to 27, 17 to 26, 17 to 25, 19 to 45, 19 to 40, 19 to 35, 19 to 34, 19 to 33, 19 to 32, 19 to 31, 19 to 30, 19 to 29, 19 to 28, 19 to 27, 19 to 26, 19 to 25, 22 to 45, 22 to 40, 22 to 35, 22 to 34, 22 to 33, 22 to 32, 22 to 31, 22 to 30, 22 to 29, 22 to 28, 22 to 27, 22 to 26, 22 to 25, 25 to 45, 25 to 40, 25 to 35, 25 to 34, 25 to 33, 25 to 32, 25 to 31, to 30, 25 to 29, 25 to 28, or 25 to 27 linked subunits.

In certain embodiments, the ASO component of the ACT-UP1 compound comprises about 12 to 25, 12 to 24, 12 to 23, 12 to 22, 12 to 21, 12 to 20, 12 to 19, 12 to 18, 12 to 17, 12 to 16, 12 to 15, or 12 to 14 linked nucleosides in length.

In certain embodiments, the PRS component of the ACT-UP1 compound comprises about to 20, 5 to 19, 5 to 18, 5 to 17, 5 to 16, 5 to 15, 5 to 14, 5 to 13, 5 to 12, 5 to 11, 5 to 10, 5 to 9, to 8, 5 to 7, or 5 to 6 linked nucleosides in length.

In certain embodiments, an ACT-UP1 compound may be about 17 to 45 linked nucleosides in length. The ACT-UP1 compound may comprise an ASO component of about 12 to 25 linked nucleosides in length joined to a protein recruiting sequence (PRS) component 5 to 20 linked nucleosides in length. In accordance with the invention, in some embodiments, the ASO component hybridizes to a target mRNA, the PRS recruits translation-related proteins, so that the ACT-UP1 compound enhances protein expression. In some preferred aspects, the PRS is joined to the 5' end of the ASO. In some aspects the PRS is joined to the 3' end of the ASO.

In certain embodiments, the PRS comprises a derivative of a DRACH consensus sequence. In certain embodiments, the derivative of the DRACH consensus sequence comprises GGACU (SEQ ID NO: 8), GGAUU (SEQ ID NO: 9), GAACU (SEQ ID NO: 41), AGACU (SEQ ID NO: 42), AAACU (SEQ ID NO: 43), GGACA (SEQ ID NO: 44), AAACA (SEQ ID NO: 154) or a derivative thereof.

In certain embodiments, the PRS comprises a derivative of a RRANN consensus sequence. In certain embodiments, the derivative of the RRANN consensus sequence comprises GGACU (SEQ ID NO: 8), GGAUU (SEQ ID NO: 9), GAACU (SEQ ID NO: 41), AGACU (SEQ ID NO: 42), AAACU (SEQ ID NO: 43) or GGACA (SEQ ID NO: 44) or a derivative thereof.

In certain embodiments, the PRS comprises a derivative of an RRAWN consensus sequence. In certain embodiments, the derivative of the RRAWN consensus sequence comprises GGACU (SEQ ID NO: 8), GGAUU (SEQ ID NO: 9), GAACU (SEQ ID NO: 41), AGACU (SEQ ID NO: 42), AAACU (SEQ ID NO: 43) or GGACA (SEQ ID NO: 44) or a derivative thereof.

In certain embodiments, the PRS comprises a derivative of a GGACU sequence (SEQ ID NO: 8). In certain embodiments, the GGACU derivative is selected from any of GGACU (SEQ I) NO: 8), GGACUGGAC (SEQ ID NO: 10), GGACUGGACU (SEQ ID NO: 11), GGACUGGACUGGACU (SEQ ID NO: 101), and ACGGACUUGGACU (SEQ ID NO: 12).

In certain embodiments, the PRS comprises two to four repeats of derivative sequences GGACU (SEQ ID NO: 8), GGAUU (SEQ ID NO: 9), GAACU (SEQ ID NO: 41), AGACU (SEQ ID NO: 42), AAACU (SEQ ID NO: 43) or GGACA (SEQ ID NO: 44), or mixed combinations of the derivative sequences (e.g., GGACUGGACU (SEQ II) NO: 11) or AAACUAAACU (SEQ ID NO: 13)).

In certain embodiments, the PRS comprises a derivative of a poly(A) sequence in the 3'UTR of a mRNA. In certain embodiments, the derivative of the poly(A) sequence is AAACUAAACU (SEQ ID NO: 13), AAAAAAAAAAAA (SEQ ID NO: 102), or AAAAAAAAAA (SEQ ID NO: 15).

In certain embodiments, the PRS comprises a derivative of a poly(C) sequence in the 3'UTR of a mRNA. In certain embodiments, the derivative of the poly(C) sequence is CCCCCCCCCC (SEQ ID NO: 93).

In certain embodiments, the PRS comprises a derivative of a poly(G) sequence in the 3'UTR of a mRNA. In certain embodiments, the derivative of the poly(G) sequence is GGGGGGGGGG (SEQ ID NO: 152).

In certain embodiments, the PRS comprises a derivative of a poly(T) sequence in the 3'UTR of a mRNA. In certain embodiments, the derivative of the poly(T) sequence is TTTTTTTTTT (SEQ ID NO: 153).

In certain embodiments, the PRS comprises a derivative of a poly(U) sequence in the 3'UTR of a mRNA. In certain embodiments, the derivative of the poly(U) sequence is UUUUUUUUUU (SEQ ID NO: 94).

Additional examples of PRSs are found in the Tables herein.

In certain embodiments, the ACT-UP1 compound is about 22 to 35 linked nucleosides in length. The ACT-UP1 compound comprises an ASO component having about 12 to 25 linked nucleosides in length joined to a PRS component comprising GGACUGGACU (SEQ ID NO: 11) or AAAC-UAAACU (SEQ ID NO: 13). In accordance with the invention, in some embodiments, the ASO component hybridizes to a target mRNA, the PRS recruits translation-related proteins so that the ACT-UP1 compound enhances protein expression. In some preferred aspects, the PRS is joined to the 5' end of the ASO. In some aspects, the PRS is joined to the 3' end of the ASO.

In certain embodiments, the ACT-UP1 compound is a trans-acting protein enhancer. In certain embodiments, the ACT-UP1 trans-acting protein enhancer targets an mRNA transcript and recruits endogenous translation-related proteins to increase translation of a target protein.

In certain embodiments, the ACT-UP1 compound targets a eukaryotic or prokaryotic mRNA. In certain embodiments, the ACT-UP1 compound targets a mammalian mRNA, a plant mRNA, a yeast mRNA, or a bacteria mRNA. In certain embodiments, the mammalian mRNA targeted encodes any of a Delta/Serrate/Lag-2 (DSL) protein such as JAG1, a RAB family of small GTPases such as RAB9, a porpho-bilinogen deaminase (PBGD), a RNase H family protein such as RNase H1, a nuclear transcription factor such as HNF4A, or a fibroblast growth factor such as FGF21.

In certain embodiments, the ACT-UP1 compound targets a region about 20 to 50, 40 to 70, 60 to 90, 80 to 110, 100 to 130, 120 to 150, 140 to 170, 160 to 190, 180 to 210, 200 to 230, 220 to 250, 240 to 300, or 280 to 500 nucleotides downstream of a stop codon on a targeted mRNA.

In certain embodiments, the ACT-UP1 compound further comprises an agent (e.g., a delivery, therapeutic, or diagnostic agent) so as to form a conjugated compound. In certain embodiments, the conjugate agent (also known as a conjugate moiety) can be selected from cholesterols, lipids, carbohydrates, phospholipids, biotin, phenazine, folate, phenanthridine, anthraquinone, acridine, fluoresceins, rhodamines, coumarins, peptides, antibodies, dyes, and tocopherol. In certain embodiments, the conjugate agent is a N-Acetylgalactosamine (GalNAc). In certain embodiments, the GalNAc is a GalNAc described in Sharma et al. (2018, Bioconjugate Chem, 29:2478-2488) or as described in WO2024137545).

In certain embodiments, the ACT-UP1 compound comprises at least one chemical modification. In certain embodiments, the ACT-UP1 compound is partially, substantially, or fully chemically modified. In certain embodiments, the ACT-UP1 compound is chemically modified such that the chemical modification is selected from one or more of 2'-O-methyl (2'-OMe), 2'-O-(2-methoxyethyl) (2'-MOE), 2'-fluoro (2'-F), constrained ethyl (cEt), unlocked nucleic acid (UNA), locked nucleic acid (LNA), 2'-MOE modified T, and/or 5-methylcytosine base. In certain embodiments, the ASO and PRS of the ACT-UP1 compound comprise the same or different chemical modifications. In certain embodiments, the PRS chemical modification is 2'-OMe and/or 2'-MOE. In a preferred embodiment, the nucleosides of the PRS are 2'-OMe modified, and the nucleosides of the ASO are 2'-MOE modified. In another preferred embodiment, the nucleosides of the PRS are 2'-OMe modified, and the nucleosides of the ASO comprise cEt, LNA and/or 2'-MOE modified adenosines (eA), thymidines (eT), uridines (eU), and guanosines (eG), cytodines (eC), and 2'-MOE modified 5-methylcytidines (eCm). In an embodiment, the PRS comprises ribonucleosides or deoxyribonucleosides. In an embodiment, the ASO comprises ribonucleosides or deoxyribonucleosides. In a preferred embodiment, the PRS and ASO comprises modified ribonucleosides wherein the modification can be a substitution of a DNA nucleoside for an RNA nucleoside.

In certain embodiments, the ACT-UP1 compound comprises at least one modified internucleoside linkage. In certain embodiments, the at least one modified internucleoside linkage is a phosphorothioate internucleotide (PS) linkage. In one embodiment, the PS linkage is placed/situated between the first and second nucleosides (counting from the 5' to 3' direction) in the PRS of the ACT-UP1 compound. In another embodiment, the PS linkage is between the second and third nucleosides in the PRS of the ACT-UP1 compound. In an embodiment, the PS linkage is between two or more nucleosides in the ASO of the ACT-UP1 compound. In an embodiment, the ASO of the ACT-UP1 compound is substantially modified with internucleoside PS linkages. In an embodiment, the ASO of the ACT-UP1 compound comprises PS linkages at the 3' and 5' end of the ASO and phosphate (PO) linkages in the middle of the ASO. In an embodiment, the ASO of the ACT-UP1 compound comprises PS linkages between at least 2, at least 3, at least 4, or at least 5 nucleosides at the 3' end of the ASO, PS linkages between at least 2, at least 3, at least 4, or at least 5 nucleosides at the 5' end of the ASO, and phosphate (PO) linkages in the middle of the ASO. In an embodiment, the PS linkage is between each nucleoside in the ASO of the ACT-UP1 compound. In a preferred embodiment, the PS linkages are between the first, second and third nucleosides of the PRS and between each nucleoside of the ASO. In certain embodiments, the PS linkages are placed between nucleosides adjacent to the PRS and ASO junction. In one embodiment, the PS linkages are placed in the PRS between at least 2, at least 3, at least 4, or at least 5 nucleosides immediately adjacent to the ASO, In one embodiment, the PS linkages are placed in the ASO between at least 2, at least 3, at least 4, or at least 5 nucleosides immediately adjacent to the PRS. In another embodiment, the ACT-UP1 compound comprises PS linkages: a) in the PRS between the first, second and third nucleosides, b) in the PRS between at least 2, at least 3, at least 4, or at least 5 nucleosides immediately adjacent to the ASO, c) in the ASO between at least 2, at least 3, at least 4, at least 5, at least 6, at least 7, at least 8, at least 9, or at least 10 nucleosides immediately adjacent to the PRS, and/or d) in the ASO between at least 2, at least 3, at least 4, or at least 5 nucleosides from the 3' end of the ASO. In certain embodiments, the ACT-UP1 compound comprises a linker between the PRS and ASO portions of the ACT-UP1 compound. In another embodiment, the ACT-UP1 compound comprises a linker between the PRS and ASO and further comprises RS linkages: a) in the PRS between the first, second and third nucleosides, b) in the PRS between at least 2, at least 3, at least 4, or at least 5 nucleosides immediately adjacent to the linker, c) in the ASO between at least 2, at least 3, at least 4, at least 5, at least 6, at least 7, at least 8, at least 9, or at least 10 nucleosides immediately adjacent to the linker, and d) in the ASO between at least 2, at least 3, at least 4, or at least 5 nucleosides from the 3' end of the ASO.

In certain embodiments, the ACT-UP1 compound is about 17 to 45 linked nucleosides in length, the ASO is about 12 to 25 linked nucleosides in length and the PRS is about 5 to 20 linked nucleosides in length; includes at least one modified sugar, such as a bicyclic sugar, a 2'-O-(2-methoxyethyl) group (2'-MOE), a 2'-O-methyl group (2'-OMe), and/or a 4'-CH(CH$_3$)—O-2' constrained ethyl (cEt) group; includes at least one modified internucleoside linkage, such as a phosphorothioate (PS) internucleoside linkage; and/or includes at least one modified nucleobase, such as a 5-methylcytidine.

In certain embodiments, the ACT-UP1 compound is about 22 to 35 linked nucleosides in length. The ACT-UP1 compound comprises an ASO component which is about 12 to 25 linked nucleosides in length joined to a PRS component comprising GGACUGGACU (SEQ ID NO: 11) or AAAC- UAAACU (SEQ ID NO: 13); includes at least one modified sugar, such as a bicyclic sugar, a 2'-O-(2-methoxyethyl) group (2'-MOE), a 2'-O-methyl group (2'-OMe), and/or a 4'-CH(CH₃)—O-2' (cEt) group; includes at least one modified internucleoside linkage, such as a phosphorothioate (PS) internucleoside linkage; and/or includes at least one modified nucleobase, such as a 5-methylcytidine. Further, in some embodiments, the ASO component hybridizes to a target mRNA, the PRS recruits translation-related proteins so that the ACT-UP1 compound enhances protein expression.

In certain embodiments, the ACT-UP1 compound increases expression of a protein in a cell by at least about 10%, 15%, 20%, 25%, 30%, 35%, 40%, 45%, 50%, 55%, 60%, 65%, 70%, 75%, 80%, 85%, 90%, 95%, 100%, 150%, 200%, or 300%.

Certain embodiments disclosed herein provide a pharmaceutical composition comprising the ACT-UP1 compound of described herein, alone or in combination with a pharmaceutically acceptable carrier or excipient.

Certain embodiments disclosed herein provide a method for increasing translation of a target mRNA in a cell comprising administering an ACT-UP1 compound to a cell, in an amount sufficient to increase translation of the target mRNA. The ACT-UP1 compound increases translation of the target mRNA by at least about 10%, 15%, 20%, 25%, 30%, 35%, 40%, 45%, 50%, 55%, 60%, 65%, 70%, 75%, 80%, 85%, 90%, 95%, 100%, 150%, 200%, or 300%.

Certain embodiments disclosed herein provide a method for increasing translation of a target mRNA in a subject comprising administering an ACT-UP1 compound to the subject, in an amount sufficient to increase translation of the target mRNA. The ACT-UP1 compound increases translation of the target mRNA by at least about 10%, 15%, 20%, 25%, 30%, 35%, 40%, 45%, 50%, 55%, 60%, 65%, 70%, 75%, 80%, 85%, 90%, 95%, 100%, 150%, 200%, or 300%.

Certain embodiments disclosed herein provide a method for treating a haploinsufficiency disorder in a subject comprising administering an ACT-UP1 compound to the subject, in an amount sufficient to treat the haploinsufficiency disorder in the subject. The ACT-UP1 compound increases expression of a protein by at least about 10%, 15%, 20%, 25%, 30%, 35%, 40%, 45%, 50%, 55%, 60%, 65%, 70%, 75%, 80%, 85%, 90%, 95%, 100%, 150%, 200%, or 300% in order to treat the haploinsufficiency disorder in the subject.

In certain embodiments, an ACT-UP1 compound can be administered subcutaneously, intrathecally or intravenously to a subject.

Certain embodiments disclosed herein provide a process or methods for making an ACT-UP1 compound of the invention comprising synthesizing an oligonucleotide on a solid support using phosphoramidite chemistry thereby making the ACT-UP1 compound.

In one embodiment, a process for preparing an ACT-UP1 compound of the invention is provided, wherein the process comprises the steps of: a) preparing the compound by sequential coupling of modified and/or unmodified nucleotides and/or linkers via the phosphoramiditc oligonucleotide synthesis on a conjugate modified or unmodified solid support; b) optionally, coupling a conjugate moiety to the compound on the solid support via the phosphoramidite oligonucleotide synthesis; c) detaching the compound from the solid support and removing the solid support; d) optionally, adding a conjugate post cleavage, and e) optionally, further purifying the compound, optionally using chromatography.

Certain embodiments disclosed herein provide an ACT-UP1 compound for enhancing expression of JAG1 in a cell, wherein the compound comprises any of the antisense oligomeric sequences targeting JAG1 in Table 52D. Certain embodiments disclosed herein provide an ACT-UP1 compound for enhancing expression of JAG1 in a cell, wherein the compound comprises any of the modified antisense oligomeric sequences targeting JAG1 in Table 52C. In a preferred embodiment, the compound comprises the sequence of ATXL316 (SEQ ID NO: 11) or the chemistry and sequence of ATXL316 (SEQ ID NO: 36). In another preferred embodiment, the compound comprises the chemical structure of ATXL316:

-continued
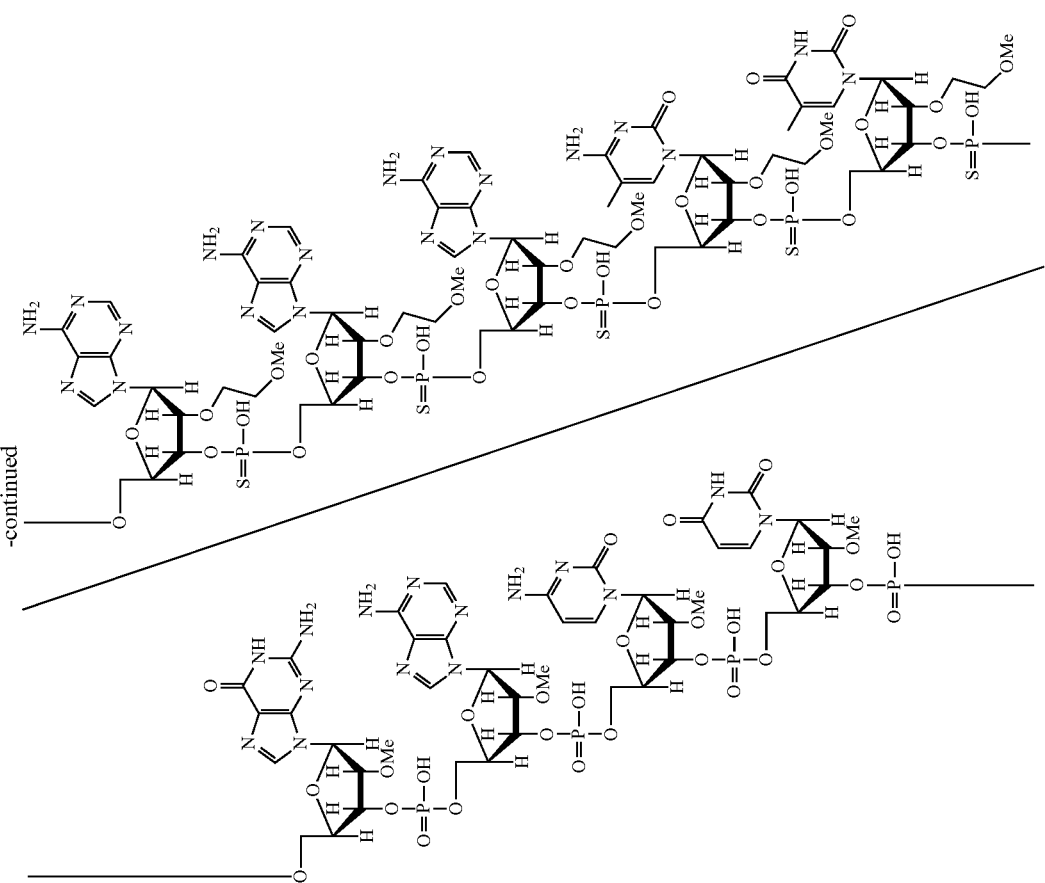

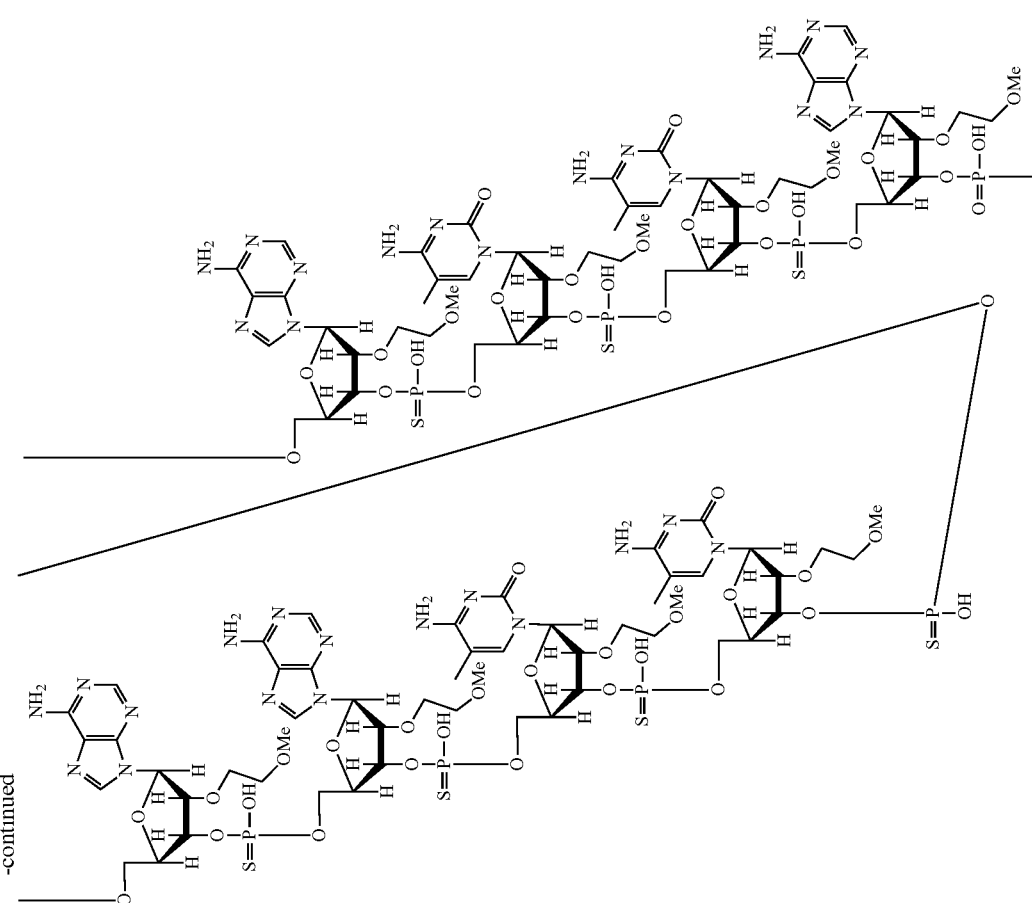
-continued

-continued

In one embodiment, a pharmaceutical composition comprises an antisense oligomeric compound for enhancing expression of JAG1 in a cell, alone or in combination with a pharmaceutically acceptable carrier and/or excipient. In a preferred embodiment, the pharmaceutical composition comprises ATXL316, alone or in combination with a pharmaceutically acceptable carrier and/or excipient.

Certain embodiments provide a process or method for enhancing expression of JAG1 mRNA in a cell comprising administering an antisense oligomeric compound for increasing translation of JAG1, or a pharmaceutical composition comprising the antisense oligomeric compound for increasing translation of JAG1, to the cell, in an amount sufficient to increase translation of JAG1 mRNA. In one embodiment, the antisense oligomeric compound, or pharmaceutical composition thereof, increases translation of JAG1 protein by at least about 10%, 15%, 20%, 25%, 30%, 35%, 40%, 45%, 50%, 55%, 60%, 65%, 70%, 75%, 80%, 85%, 90%, 95%, 100%, 150%, 200%, 250%, or 300%. In a preferred embodiment, the antisense oligomeric compound for increasing translation of JAG1 is ATXL316.

Certain embodiments provide a method for treating Alagille Syndrome in a subject comprising administering an antisense oligomeric, or pharmaceutical composition thereof, to increase JAG1 expression to the subject, in an amount sufficient to increase JAG1 in the subject. In a preferred embodiment, the compound or pharmaceutical composition comprises ATXL316. In certain embodiments, the compound or the compound or pharmaceutical composition is administered subcutaneously, intrathecally or intravenously to the subject.

Certain embodiments provide a process for preparing ATXL316, wherein the process comprises the steps of: a) preparing the compound by sequential coupling of modified and/or unmodified nucleotides and/or linkers via the phosphoramidite oligonucleotide synthesis on a conjugate modified or unmodified solid support; b) optionally, coupling a conjugate moiety to the compound on the solid support via the phosphoramidite oligonucleotide synthesis; c) detaching the compound from the solid support and removing the solid support; and d) optionally, adding a conjugate post cleavage; and/or e) optionally, further purifying the compound, optionally using chromatography.

Certain embodiments disclosed herein provide an ACT-UP1 compound for enhancing expression of FGF21 in a cell, wherein the compound comprises any of the antisense oligomeric sequences targeting FGF21 in Table 52D. Certain embodiments disclosed herein provide an ACT-UP1 compound for enhancing expression of FGF21 in a cell, wherein the compound comprises any of the modified antisense oligomeric sequences targeting FGF21 in Table 52C. In a preferred embodiment, the compound comprises the sequence of ATXL506 (SEQ ID NO: 136) or the chemistry and sequence of ATXL506 (SEQ ID NO: 81). In another preferred embodiment, the compound comprises the chemical structure of ATXL506:

-continued
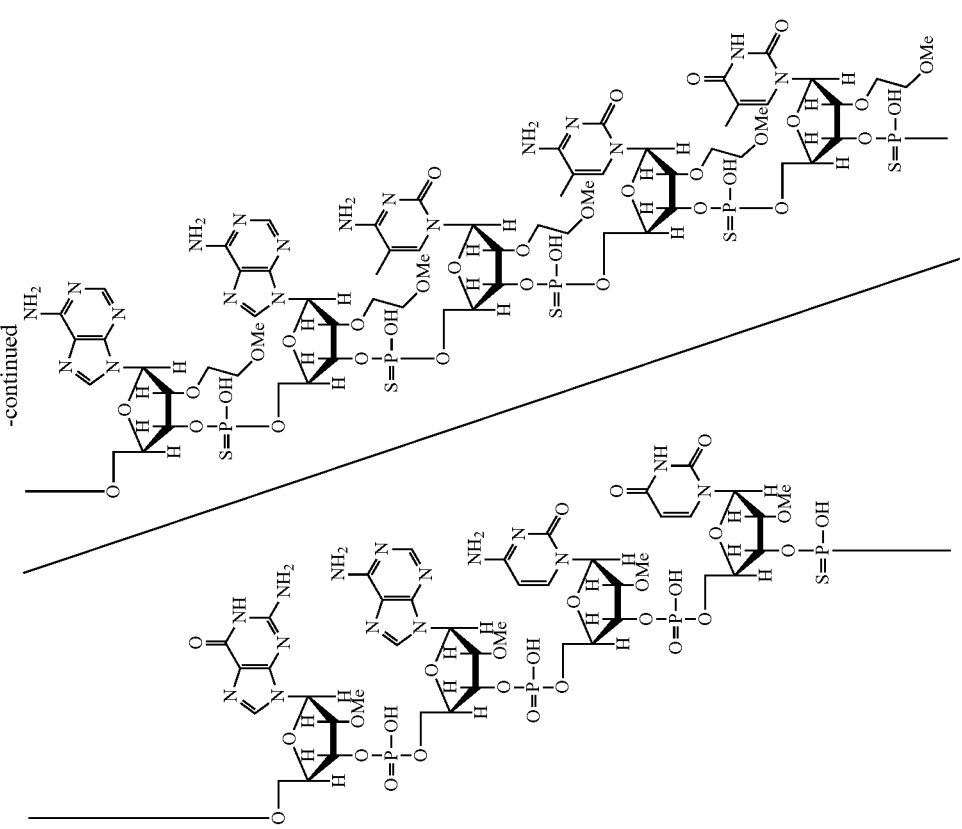

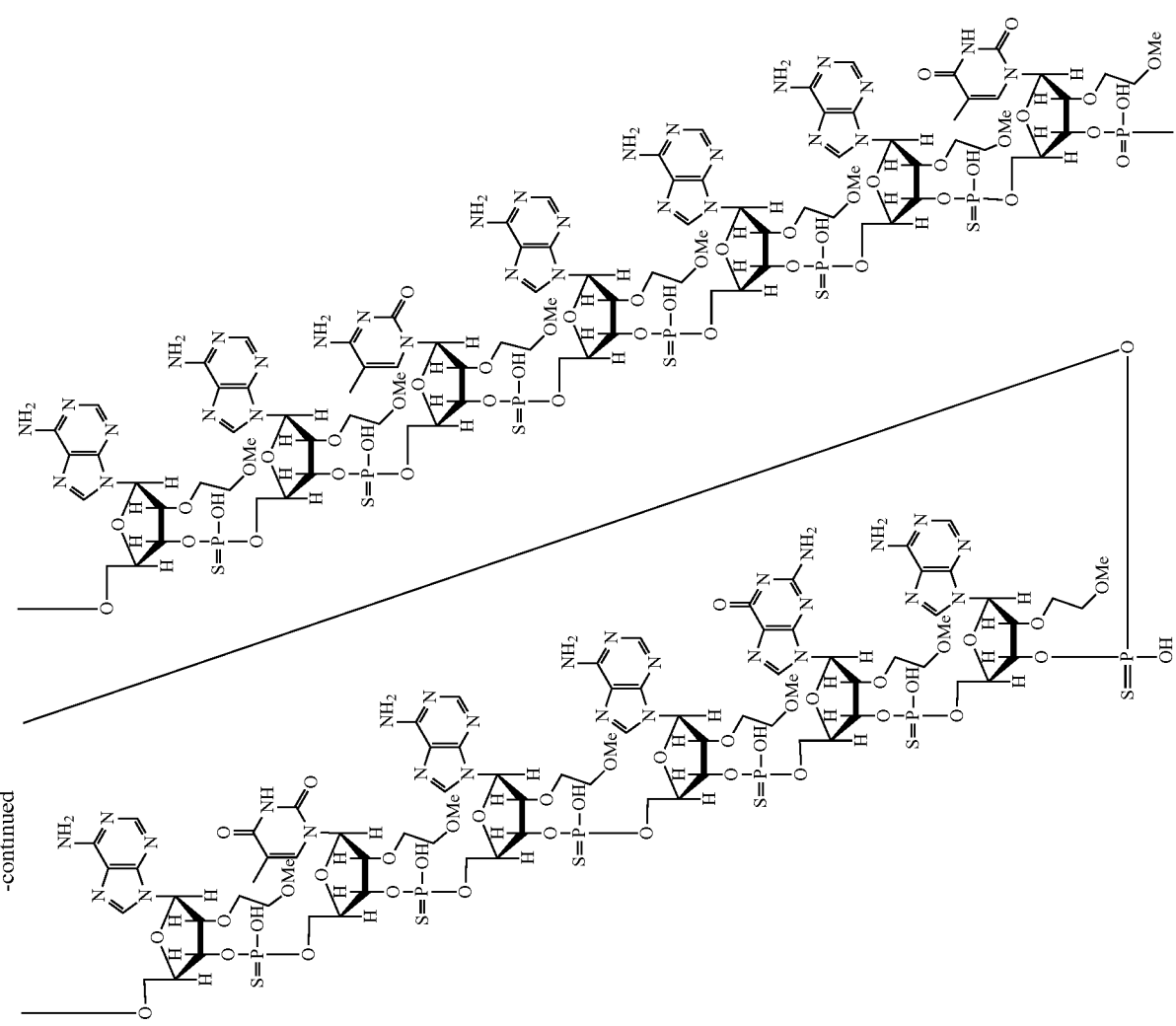
-continued

In one embodiment, a pharmaceutical composition comprises an antisense oligomeric compound for enhancing expression of FGF21 in a cell, alone or in combination with a pharmaceutically acceptable carrier and/or excipient. In a preferred embodiment, the pharmaceutical composition comprises ATXL506, alone or in combination with a pharmaceutically acceptable carrier and/or excipient.

Certain embodiments provide a process or method for enhancing expression of FGF21 mRNA in a cell comprising administering an antisense oligomeric compound for increasing translation of FGF21, or a pharmaceutical composition comprising the antisense oligomeric compound for increasing translation of FGF21, to the cell, in an amount sufficient to increase translation of FGF21 mRNA. In one embodiment, the antisense oligomeric compound, or pharmaceutical composition thereof, increases translation of FGF21 protein by at least about 10%, 15%, 20%, 25%, 30%, 35%, 40%, 45%, 50%, 55%, 60%, 65%, 70%, 75%, 80%, 85%, 90%, 95%, 100%, 150%, 200%, 250%, or 300%. In a preferred embodiment, the antisense oligomeric compound for increasing translation of FGF21 is ATXL506.

Certain embodiments provide a method for treating an inflammatory disease, disorder or condition in a subject comprising administering an antisense oligomeric compound, or pharmaceutical composition thereof, to the subject, in an amount sufficient to increase FGF21 in the subject. In certain embodiments, the inflammatory disease, disorder or condition is a metabolic disease, disorder or condition, a cardiovascular disease, disorder or condition and/or a dyslipidemia. In certain embodiments, the dyslipidemia is hyperlipidemia, hypercholesterolemia and/or hypertriglyceridemia. In certain embodiments, the hypertriglyceridemia is severe hypertriglyceridemia (SHTG). In certain embodiments, the metabolic disease, disorder or condition is glucose intolerance (e.g., peripheral glucose intolerance), steatosis, obesity, diabetes, non-alcoholic fatty liver disease (NAFLD) and/or metabolic dysfunction-associated steatohepatitis (MASH) (previously known as non-alcohol related steatohepatitis (NASH)).

In a preferred embodiment, the compound or pharmaceutical composition comprises ATXL506. In certain embodiments, the compound or the compound or pharmaceutical composition is administered subcutaneously, intrathecally or intravenously to the subject.

Certain embodiments provide a process for preparing ATXL506, wherein the process comprises the steps of: a) preparing the compound by sequential coupling of modified and/or unmodified nucleotides and/or linkers via the phosphoramidite oligonucleotide synthesis on a conjugate modified or unmodified solid support; b) optionally, coupling a conjugate moiety to the compound on the solid support via the phosphoramidite oligonucleotide synthesis; c) detaching the compound from the solid support and removing the solid support; and d) optionally, adding a conjugate post cleavage; and/or e) optionally, further purifying the compound, optionally using chromatography.

Certain embodiments disclosed herein provide an ACT-UP1 compound for enhancing expression of HNF4A in a cell, wherein the compound comprises any of the antisense oligomeric sequences targeting HNF4A in Table 52D. Certain embodiments disclosed herein provide an ACT-UP1 compound for enhancing expression of HNF4A in a cell, wherein the compound comprises any of the modified antisense oligomeric sequences targeting HNF4A in Table 52C. In a preferred embodiment, the compound comprises the sequence of ATXL546 (SEQ ID NO: 150) or the chemistry and sequence of ATXL546 (SEQ ID NO: 91). In another preferred embodiment, the compound comprises the chemical structure of ATXL546:

-continued
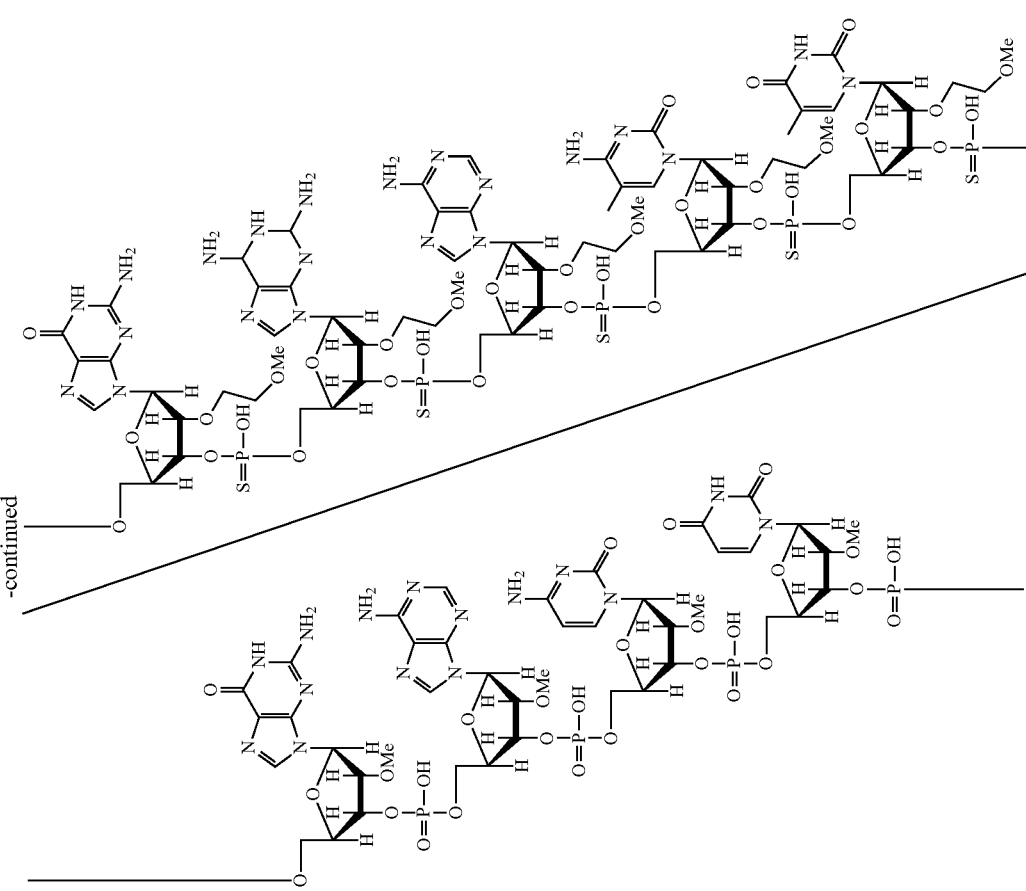

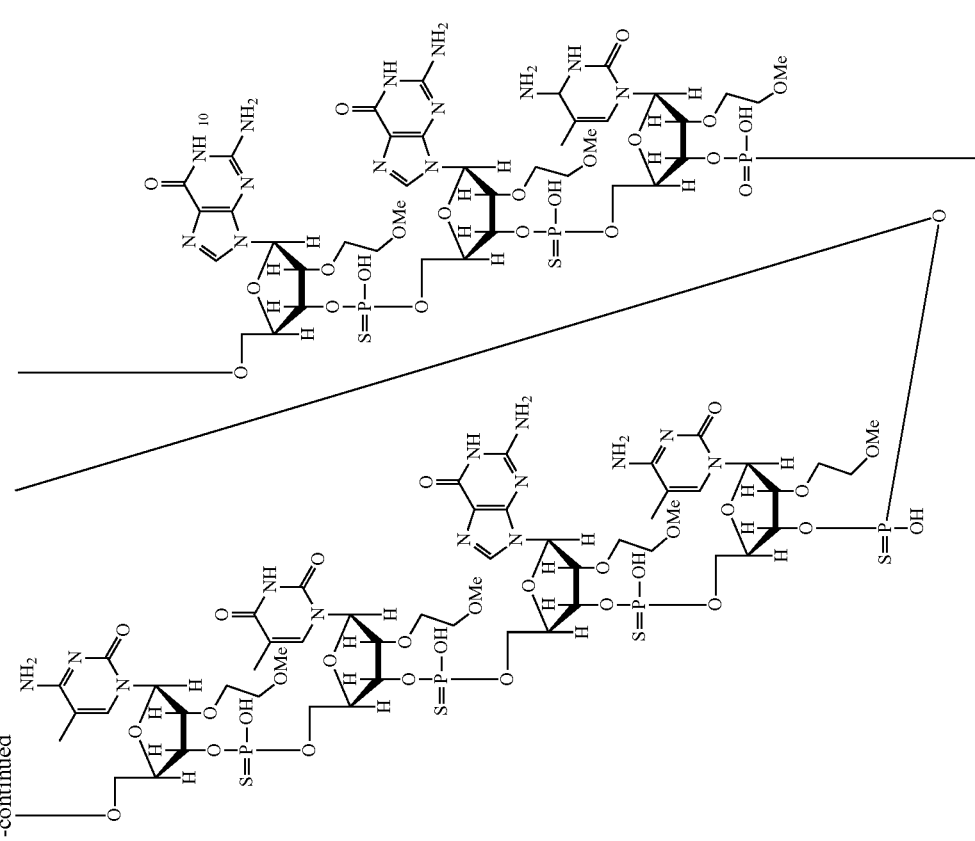
-continued

-continued

In a preferred embodiment, the compound comprises the sequence of ATXL547 (SEQ ID NO: 151) or the chemistry and sequence of ATXL547 (SEQ ID NO: 92). In another preferred embodiment, the compound comprises the chemical structure of ATXL547:

-continued
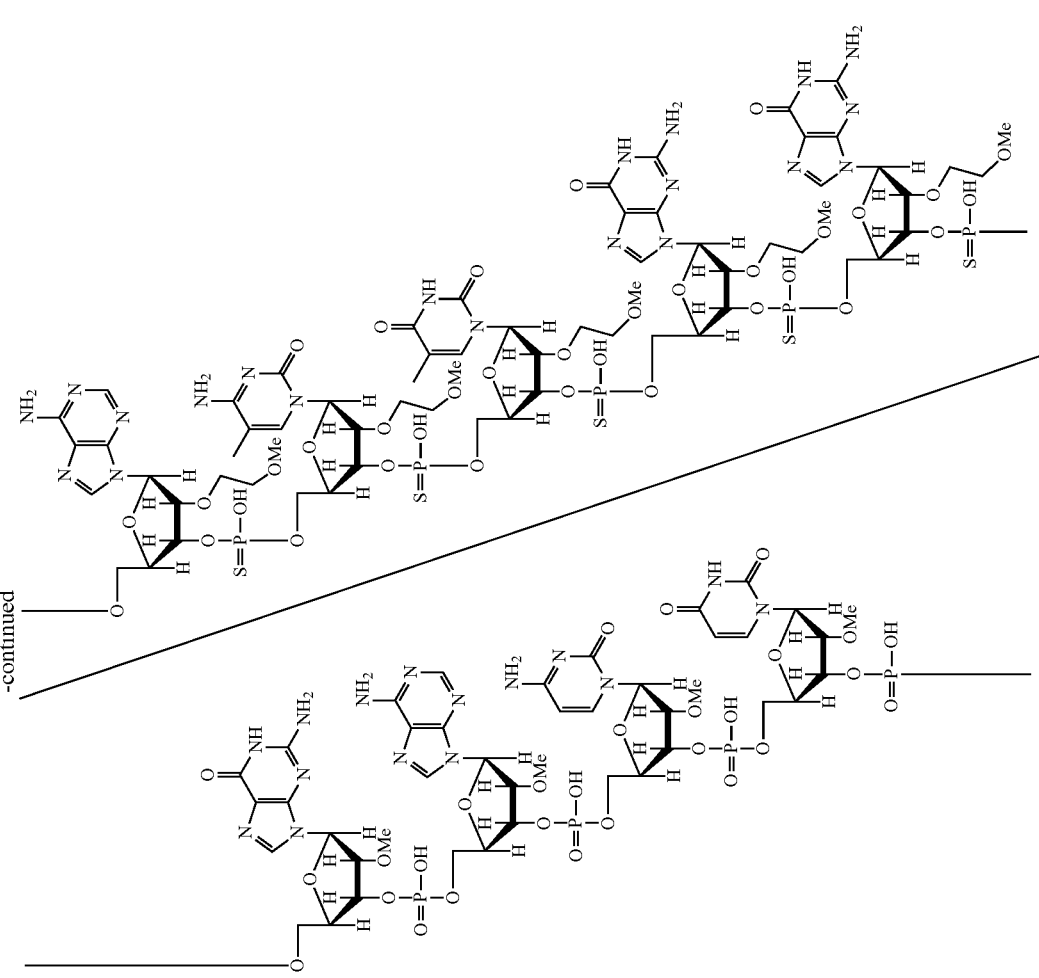

-continued
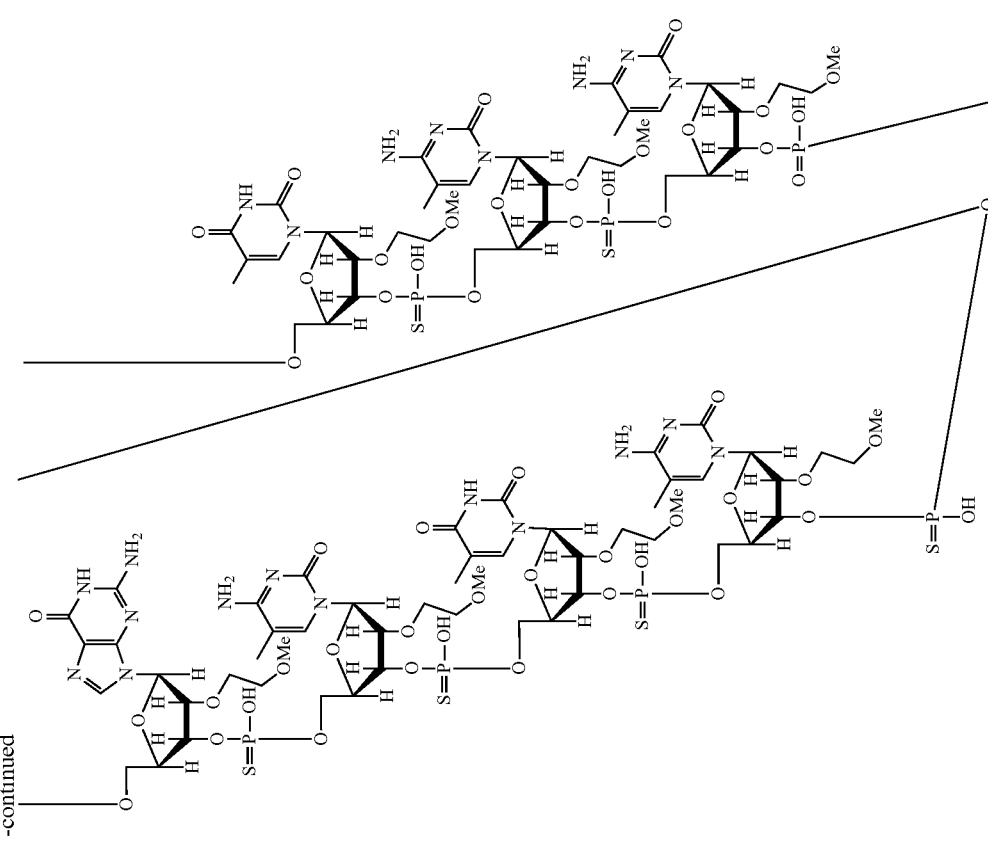

In one embodiment, a pharmaceutical composition comprises an antisense oligomeric compound for enhancing expression of HNF4A in a cell, alone or in combination with a pharmaceutically acceptable carrier and/or excipient. In a preferred embodiment, the pharmaceutical composition comprises ATXL546, alone or in combination with a pharmaceutically acceptable carrier and/or excipient. In a preferred embodiment, the pharmaceutical composition comprises ATXL547, alone or in combination with a pharmaceutically acceptable carrier and/or excipient.

Certain embodiments provide a process or method for enhancing expression of HNF4A mRNA in a cell comprising administering an antisense oligomeric compound for increasing translation of HNF4A, or a pharmaceutical composition comprising the antisense oligomeric compound for increasing translation of HNF4A, to the cell, in an amount sufficient to increase translation of HNF4A mRNA. In one embodiment, the antisense oligomeric compound, or pharmaceutical composition thereof, increases translation of HNF4A protein by at least about 10%, 15%, 20%, 25%, 30%, 35%, 40%, 45%, 50%, 55%, 60%, 65%, 70%, 75%, 80%, 85%, 90%, 95%, 100%, 150%, 200%, 250%, or 300%. In a preferred embodiment, the antisense oligomeric compound for increasing translation of HNF4A is ATXL546. In a preferred embodiment, the antisense oligomeric compound for increasing translation of HNF4A is ATXL547.

Certain embodiments provide a method for treating fibrosis, cirrhosis, cancer and/or diabetes in a subject comprising administering an antisense oligomeric compound, or pharmaceutical composition thereof, to the subject, in an amount sufficient to increase HNF4A in the subject. In certain embodiments, the fibrosis is liver fibrosis. In certain embodiments, the cancer is hepatocellular carcinoma (HCC). In certain embodiments, the diabetes is maturity-onset diabetes of the young (MODY1). Certain embodiments provide a method for treating diseases of the liver in a subject comprising administering an antisense oligomeric compound, or pharmaceutical composition thereof, to the subject, in an amount sufficient to increase HNF4A in the subject. In a preferred embodiment, the compound or pharmaceutical composition comprises ATXL546. In another preferred embodiment, the compound or pharmaceutical composition comprises ATXL547. In certain embodiments, the antisense oligomeric compound or pharmaceutical composition can be administered subcutaneously, intrathecally or intravenously to the subject.

Certain embodiments provide a process for preparing ATXL546 or ATXL547, wherein the process comprises the steps of: a) preparing the compound by sequential coupling of modified and/or unmodified nucleotides and/or linkers via the phosphoramidite oligonucleotide synthesis on a conjugate modified or unmodified solid support; b) optionally, coupling a conjugate moiety to the compound on the solid support via the phosphoramidite oligonucleotide synthesis; c) detaching the compound from the solid support and removing the solid support; and d) optionally, adding a conjugate post cleavage; and/or e) optionally, further purifying the compound, optionally using chromatography.

Embodiment 1 provides an antisense oligonucleotide (ASO) Coupled Translation-Upregulation 1 (ACT-UP1) compound, wherein the ACT-UP1 compound comprises an ASO component joined to a protein recruiting sequence (PRS) component, wherein the ASO component is capable of hybridizing to a target mRNA, wherein the PRS is capable of recruiting translation related proteins, and wherein the ACT-UP1 compound is capable of enhancing protein expression. In one embodiment, the ASO component is joined to the PRS directly or indirectly.

In Embodiment 2 provides the ACT-UP1 compound of Embodiment 1, wherein the PRS is 5 to 20, 5 to 19, 5 to 18, 5 to 17, 5 to 16, 5 to 15, 5 to 14, 5 to 13, 5 to 12, 5 to 11, 5 to 10, 5 to 9, 5 to 8, 5 to 7, or 5 to 6 linked nucleosides in length.

Embodiment 3 provides the ACT-UP1 compound of Embodiment 1, wherein the PRS is a derivative of a DRACH consensus sequence or a sequence comprising (a) a DRACH consensus sequence and (b) additional sequence comprising one or more repeats or partial repeats of a DRACH consensus sequence wherein D is adenine (A), guanine (G) or thymine (T); R is adenine (A) or guanine (G); A is adenine (A); C is cytosine (C); H is adenine (A), cytosine (C) or uracil (U). In one embodiment, the DRACH consensus sequence is GGACU (SEQ ID NO: 8), GAACU (SEQ ID NO: 41), AGACU (SEQ ID NO: 42), AAACU (SEQ ID NO: 43), GGACA (SEQ ID NO: 44), or AAACA (SEQ ID NO: 154), or a derivative thereof.

Embodiment 4 provides the ACT-UP1 compound of Embodiment 1, wherein the PRS is an RRANN consensus sequence or a sequence comprising (a) an RRANN consensus sequence and (b) additional sequence comprising one or more repeats or partial repeats of an RRANN consensus sequence, wherein R is adenine (A) or guanine (G); and N is adenine (A), guanine (G), cytosine (C), thymine (T) or uracil (U). In one embodiment, the RRANN consensus sequence is GGACU (SEQ ID NO: 8), GGAUU (SEQ ID NO: 9), GAACU (SEQ ID NO: 41), AGACU (SEQ ID NO: 42), AAACU (SEQ ID NO: 43), GGACA (SEQ ID NO: 44), AAACA (SEQ ID NO: 154), or a derivative thereof. In certain embodiments, the N at the 3' end of the RRANN consensus sequence is a T.

Embodiment 5 provides the ACT-UP1 compound of Embodiment 1, wherein the PRS is an RRAWN consensus sequence or a sequence comprising (a) an RRAWN consensus sequence and (b) additional sequence comprising one or more repeats or partial repeats of an RRANN consensus sequence, wherein R is adenine (A) or guanine (G); W is adenine (A) or cytosine (C); and N is adenine (A), guanine (G), cytosine (C), thymine (T) or uracil (U). In one embodiment, the DRACH consensus sequence is GGACU (SEQ ID NO: 8), GAACU (SEQ ID NO: 41), AGACU (SEQ ID NO: 42), AAACU (SEQ ID NO: 43), GGACA (SEQ ID NO: 44), AAACA (SEQ ID NO: 154), or a derivative thereof. In certain embodiments, the N in the RRAWN consensus sequence is a T.

Embodiment 6 provides the ACT-UP1 compound of Embodiments 3, 4 or 5, wherein the GGACU or its derivative is selected from one of GGACU (SEQ ID NO: 8), GGACUGGAC (SEQ ID NO: 10), GGACUGGACU (SEQ ID NO: 11) and ACGGACUUGGACU (SEQ ID NO: 12).

Embodiment 7 provides the ACT-UP1 compound of Embodiment 1, wherein the PRS is a derivative of a poly(A), poly(C), poly(G), poly(T), or poly(U) sequence in the 3'UTR of a mRNA. Embodiment 7 further provides a PRS with the sequence of GUGUGUGUGU (SEQ ID NO: 76) or CUCUCUCUCU (SEQ ID NO: 75).

Embodiment 8 provides the ACT-UP1 compound of Embodiment 7, wherein the derivative of the poly(A) tail is AAACUAAACU (SEQ ID NO: 13), AAAAAAAAAA (SEQ ID NO: 15), AAACAAAACA (SEQ ID NO:99), AAAAAAAAAAAA (SEQ ID NO: 102); the poly(C) sequence is CCCCCCCCCC (SEQ ID NO: 93); the poly(U) sequence is UUUUUUUUUU (SEQ ID NO: 94).

Embodiment 9 provides the ACT-UP1 compound of Embodiment 1, wherein the PRS supports binding of an RNA-binding protein and its associated complexes. In one embodiment, the RNA-binding protein and its associated complexes are translation-related proteins. In another embodiment, the translation-related protein(s) is selected from the group consisting of PABPC1, YTHDF1, ALKBH5, METTL3, and METTL14, and combination thereof.

Embodiment 10 provides the ACT-UP1 compound of Embodiment 1, wherein the compound comprises 17 to 45, 17 to 44, 17 to 43, 17 to 42, 17 to 41, 17 to 40, 17 to 39, 17 to 38, 17 to 37, 17 to 36, 17 to 35, 17 to 34, 17 to 33, 17 to 32, 17 to 31, 17 to 30, 17 to 29, 17 to 28, 17 to 27, 17 to 26, 17 to 25, 19 to 45, 19 to 40, 19 to 35, 19 to 34, 19 to 33, 19 to 32, 19 to 31, 19 to 30, 19 to 29, 19 to 28, 19 to 27, 19 to 26, 19 to 25, 22 to 45, 22 to 40, 22 to 35, 22 to 34, 22 to 33, 22 to 32, 22 to 31, 22 to 30, 22 to 29, 22 to 28, 22 to 27, 22 to 26, 22 to 25, 25 to 45, 25 to 40, 25 to 35, 25 to 34, 25 to 33, 25 to 32, 25 to 31, 25 to 30, 25 to 29, 25 to 28, or 25 to 27 linked subunits.

Embodiment 11 provides the ACT-UP1 compound of Embodiment 1, wherein the ASO is 12 to 25, 12 to 24, 12 to 23, 12 to 22, 12 to 21, 12 to 20, 12 to 19, 12 to 18, 12 to 17, 12 to 16, 12 to 15, or 12 to 14 linked nucleosides in length.

Embodiment 12 provides the ACT-UP1 compound of Embodiment 1, wherein the ASO binds to a sequence in the 3' UTR of the target mRNA. In one embodiment, the ASO binds to a sequence between the stop codon and the polyadenylation signal of the 3'-UTR of the target mRNA. In one embodiment, the polyadenylation signal is AAUAAA.

Embodiment 13 provides the ACT-UP1 compound of Embodiment 1, wherein the ACT-UP1 compound comprises a dual function ASO. This dual functional compound may work via two mechanisms of action to enhance protein expression: (1) ACT-UP1 recruitment of translation proteins to increase protein expression, and (2) blocking a cis element in the target mRNA in order to stabilize or prevent degradation of the mRNA. In one embodiment, the cis element is an AU rich element (ARE) of the mRNA transcript. In one embodiment, the dual functional ACT-UP1 compound binds to the 3'UTR of a target transcript and comprises an AU rich element (ARE) targeting sequence, wherein the ARE-targeting sequence of the ACT-UP1 compound blocks the binding of cellular proteins to the ARE of a transcript and inhibits target mRNA degradation. In one embodiment, inhibiting target mRNA degradation increases target mRNA and protein expression. In one embodiment, the dual function ASO can increase FGF21 mRNA levels and FGF21 protein expression. In one embodiment, the dual functions of the ACT-UP1 compound are additive or synergistic in increasing protein expression of a target gene.

Embodiment 14 provides the ACT-UP1 compound of Embodiment 1, wherein the ASO sequence is not a reverse complement of the PRS sequence.

Embodiment 15 provides the ACT-UP1 compound of Embodiment 1, wherein the PRS is not an internal ribosome entry site (IRES) sequence.

Embodiment 16 provides the ACT-UP1 compound of Embodiment 1, wherein the ACT-UP1 compound is a trans-acting protein enhancer. In one embodiment, the trans-acting protein enhancer recruits translation-related proteins to the target mRNA. In one embodiment, the translation-related protein is selected from the group consisting of PABPC1, YTHDF1, ALKBH5, METTLE3, and METTL14, and combination thereof.

Embodiment 17 provides the ACT-UP1 compound of Embodiment 1, wherein the target mRNA is a mammalian mRNA, a plant mRNA, a yeast mRNA, or a bacteria mRNA.

Embodiment 18 provides the ACT-UP1 compound of Embodiment 17, wherein the target mRNA is mammalian JAG1, RAB9, PBGD, RNase H I, HNF4A, or FGF21.

Embodiment 19 provides the ACT-UP1 compound of Embodiment 1, wherein the ACT-UP1 compound targets a region about 20 to 50, 40 to 70, 60 to 90, 80 to 110, 100 to 130, 120 to 150, 140 to 170, 160 to 190, 180 to 210, 200 to 230, 220 to 250, 240 to 300, or 280 to 500 nucleotides downstream of a stop codon on the mRNA.

Embodiment 20 provides the ACT-UP1 compound of Embodiment 1, further comprising a conjugate. In one embodiment, the conjugate can be selected from cholesterols, lipids, carbohydrates, phospholipids, biotin, phenazine, folate, phenanthridine, anthraquinone, acridine, fluoresceins, rhodamines, coumarins, peptides, antibodies, dyes, and tocopherol. In one embodiment, the conjugate is an N-acetylgalactosamine (GalNAc)-containing compound.

Embodiment 21 provides the ACT-UP1 compound of Embodiment 1, wherein the compound comprises at least one chemical modification. In one embodiment, the compound is fully chemically modified. In one embodiment, the ASO and PRS comprise the same chemical modification. In one embodiment, the ASO and PRS comprise different chemical modifications. In one embodiment, the chemical modification can be selected from 2'-O-methyl (2'-OMe), 2'-O-(2-methoxyethyl) (2'-MOE), 2'-fluoro (2'-F), constrained ethyl (cEt), unlocked nucleic acid (UNA), locked nucleic acid (LNA), 2'-MOE modified T, and/or 5-methylcytosine base. In one embodiment, the PRS chemical modification is 2'-O-methyl (2'-OMe). In one embodiment, the ASO chemical modification is cEt and/or 2'-O-MOE modified 5-methylcytidines (eCm).

Embodiment 22 provides the ACT-UP1 compound of Embodiment 1, wherein the compound comprises at least one modified internucleoside linkage. In one embodiment, the at least one modified internucleoside linkage is a phosphorothioate internucleotide (PS) linkage.

Embodiment 23 provides the ACT-UP1 compound of Embodiment 1, comprising 17 to 45 linked nucleosides in length, wherein the ACT-UP1 compound comprises an ASO component comprising 12 to 25 linked nucleosides in length joined to a protein recruiting sequence (PRS) component comprising 5 to 20 linked nucleosides in length.

Embodiment 24 provides the ACT-UP1 compound of Embodiment 1, comprising 22 to 35 linked nucleosides in length, wherein the ACT-UP1 compound comprises an ASO component comprising 12 to 25 linked nucleosides in length joined to a protein recruiting sequence (PRS) component comprising the sequence GGACUGGACU (SEQ ID NO: 11) or the sequence AAACUAAACU (SEQ ID NO: 13).

Embodiment 25 provides the ACT-UP1 compound of any preceding embodiment, wherein the compound increases expression of a protein by at least about 10%, 15%, 20%, 25%, 30%, 35%, 40%, 45%, 50%, 55%, 60%, 65%, 70%, 75%, 80%, 85%, 90%, 95%, 100%, 150%, 200%, 250%, or 300%.

Embodiment 26 provides a pharmaceutical composition comprising the ACT-UP1 compound of any preceding embodiment, alone or in combination with a pharmaceutically acceptable carrier and/or excipient.

Embodiment 27 provides a method for increasing translation of a target mRNA in a cell comprising administering the ACT-UP1 compound of any of embodiments 1 to 25 or the pharmaceutical composition of embodiment 26 to the cell, in an amount sufficient to increase translation of the target mRNA. In one embodiment, the ACT-UP1 compound or the pharmaceutical composition can be administered subcutaneously, intrathecally or intravenously to the subject.

Embodiment 28 provides a method for treating a haplo-insufficiency disorder in a subject comprising administering the ACT-UP1 compound of any of embodiments 1 to 25 or the pharmaceutical composition of embodiment 26 to the subject, in an amount sufficient to treat the haploinsufficiency disorder in the subject. In one embodiment, the ACT-UP1 compound or the pharmaceutical composition can be administered subcutaneously, intrathecally or intravenously to the subject.

Embodiment 29 provides a process for preparing the compound of any one of preceding embodiments, wherein the process comprises the steps of:

a) preparing the compound by sequential coupling of modified and/or unmodified nucleotides and/or linkers via the phosphoramidite oligonucleotide synthesis on a conjugate modified or unmodified solid support;

b) optionally, coupling a conjugate moiety to the compound on the solid support via the phosphoramidite oligonucleotide synthesis;

c) detaching the compound from the solid support and removing the solid support; and d) optionally, adding a conjugate post cleavage.

e) optionally, further purifying the compound, optionally using chromatography.

Antisense Compounds

Antisense compounds include antisense oligonucleotides (ASOs) and compounds that comprise ASOs such as ASO Coupled Translation-Upregulation 1 (ACT-UP1) compounds. An antisense compound is "antisense" to a target nucleic acid, meaning that it is capable of undergoing hybridization to a target nucleic acid through hydrogen bonding.

In certain embodiments, an antisense oligonucleotide comprises a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, the antisense compound comprises an ACT-UP1 compound which in turn comprises an antisense oligonucleotide (ASO) component and a protein recruiting sequence (PRS) component.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 to 20 subunits in length.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 to 19 subunits in length.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 to 18 subunits in length.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 to 17 subunits in length.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 to 16 subunits in length.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 to 15 subunits in length.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 to 14 subunits in length.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 to 13 subunits in length.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 to 12 subunits in length.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 to 11 subunits in length.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 to 10 subunits in length.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 to 9 subunits in length.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 to 8 subunits in length.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 to 7 subunits in length.

In certain embodiments, an antisense compound is about 17 to 45 subunits in length. In certain embodiments, an antisense compound comprises an ACT-UP1 compound which in turn comprises an antisense oligonucleotide about 12 to 25 subunits in length and a protein recruiting sequence about 5 or 6 subunits in length.

In other embodiments, an antisense compound is about 17 to 45, 17 to 44, 17 to 43, 17 to 42, 17 to 41, 17 to 40, 17 to 39, 17 to 38, 17 to 37, 17 to 36, 17 to 35, 17 to 34, 17 to 33, 17 to 32, 17 to 31, 17 to 30, 17 to 29, 17 to 28, 17 to 27, 17 to 26, 17 to 25, 19 to 45, 19 to 40, 19 to 35, 19 to 34, 19 to 33, 19 to 32, 19 to 31, 19 to 30, 19 to 29, 19 to 28, 19 to 27, 19 to 26, 19 to 25, 22 to 45, 22 to 40, 22 to 35, 22 to 34, 22 to 33, 22 to 32, 22 to 31, 22 to 30, 22 to 29, 22 to 28, 22 to 27, 22 to 26, 22 to 25, 25 to 45, 25 to 40, 25 to 35, 25 to 34, 25 to 33, 25 to 32, 25 to 31, 25 to 30, 25 to 29, 25 to 28, or 25 to 27 linked subunits. In certain such embodiments, antisense compounds are about 17, 18, 19, 20, 21, 22, 23, 24, 25, 26, 27, 28, 29, 30, 31, 32, 33, 34, 35, 36, 37, 38, 39, 40, 41, 42, 43, 44, or 45 linked subunits in length, or a range defined by any two of the above values.

In certain embodiments, an antisense oligonucleotide (ASO) is about 12 to 25, 12 to 24, 12 to 23, 12 to 22, 12 to 21, 12 to 20, 12 to 19, 12 to 18, 12 to 17, 12 to 16, 12 to 15, or 12 to 14 linked subunits in length. In certain embodiments, an antisense oligonucleotide is about 13 to 25, 13 to 24, 13 to 23, 13 to 22, 13 to 21, 13 to 20, 13 to 19, 13 to 18, 13 to 17, 13 to 16, 13 to 15, or 13 to 14 linked subunits in length. In certain embodiments, an antisense oligonucleotide is about 14 to 25, 14 to 24, 14 to 23, 14 to 22, 14 to 21, 14 to 20, 14 to 19, 14 to 18, 14 to 17, 14 to 16, or 14 to linked subunits in length. In certain embodiments, an antisense oligonucleotide is about 15 to 25, 15 to 24, 15 to 23, 15 to 22, 15 to 21, 15 to 20, 15 to 19, 15 to 18, 15 to 17, or 15 to 16 linked subunits in length. In certain embodiments, an antisense oligonucleotide is about 12, 13, 14, 15, 16, 17, 18, 19, 20, 21, 22, 23, 24 or 25 linked subunits in length, or a range defined by any two of the above values.

In certain embodiments, a protein recruiting sequence (PRS) is about 5 to 20, 5 to 19, 5 to 18, 5 to 17, 5 to 16, 5 to 15, 5 to 14, 5 to 13, 5 to 12, 5 to 11, 5 to 10, 5 to 9, 5 to 8, 5 to 7 or 5 to 6 linked subunits in length. In certain embodiments, a protein recruiting sequence is about 5, 6, 7, 8, 9, 10, 11, 12, 13, 14, 15, 16, 17, 18, 19, or 20 linked subunits in length, or a range defined by any two of the above values.

It is possible to increase or decrease the length of an antisense compound, such as an antisense oligonucleotide, and/or introduce base mismatch(s) with the target without eliminating activity (U.S. Pat. No. 7,772,203, incorporated-by-reference herein). For example, it is possible to introduce non-canonical base pairings (e.g., A:G, A:C, G:U, I:U, I:A, or I:C) into an antisense oligonucleotide without eliminating activity. In certain embodiments, designing an antisense oligonucleotide with one or more non-canonical base pairings, i.e., mismatch(s), enhances the activity of the antisense compound.

Antisense Oligonucleotide Motifs

A motif refers to a pattern of modification of an antisense oligonucleotide. Various motifs have been described in the art and are incorporated-by-reference herein (e.g., U.S. Pat. Nos. 11,203,755; 10,870,849; EP Patent 1,532,248; U.S. Pat. Nos. 11,406,716; 10,668,170; 9,796,974; 8,754,201; 10,837,013; 7,732,593; 7,015,315; 7,750,144; 8,420,799; 8,809,516; 8,796,436; 8,859,749; 9,708,615; 10,233,448; 10,273,477; 10,612,024; 10,612,027; 10,669,544; 11,401,517;

9,260,471; 9,970,005; 11,193,126; U.S. Pat. No. 8,604,183; 9,150,605; 9,708,610; USSN 2020/0031862; and USSN 2016/0272970).

In certain embodiments, antisense oligonucleotides disclosed herein have chemically modified subunits arranged into motifs or patterns (i.e., chemical modification motifs/patterns) to confer on to the antisense oligonucleotides beneficial properties including, but not limited to: enhanced activity to increase potency; increased binding affinity to increase specificity for a target nucleic acid, thereby limiting off-target effects and increasing safety; or enhanced resistance to degradation by in vivo nucleases thereby increasing stability and durability.

Target mRNAs and Associated Gene Expression

Several embodiments are directed to methods of upregulating a target mRNA and/or upregulation of a target gene expression by an ACT-UP1 compound.

In certain embodiments, the target mRNA is a transcript of JAG1. In some embodiments, the JAG1 mRNA sequence is SEQ ID NO: 1 (GENBANK Accession No. NM_000214.3) or a sequence comprising at least 90%, 91%, 92%, 93%, 94%, 95%, 96%, 97%, 98%, or 99% sequence identity thereto.

In certain embodiments, the target mRNA is a transcript of RAB9A. In some embodiments, the RAB9A mRNA sequence is SEQ ID NO: 2 (GENBANK Accession No. NM_004251.5) or a sequence comprising at least 90%, 91%, 92%, 93%, 94%, 95%, 96%, 97%, 98%, or 99% sequence identity thereto. In certain embodiments, the target mRNA is a transcript of RNase H1. In some embodiments, the RNase H1 mRNA sequence is SEQ ID NO: 3 (GENBANK Accession No. NM_001286834.3) or a sequence comprising at least 90%, 91%, 92%, 93%, 94%, 95%, 96%, 97%, 98%, or 99% sequence identity thereto.

In certain embodiments, the target mRNA is a transcript of PBGD. In some embodiments, the PBGD mRNA sequence is SEQ ID NO: 4 (GENBANK Accession No. NM_000190.4) or a sequence comprising at least 90%, 91%, 92%, 93%, 94%, 95%, 96%, 97%, 98%, or 99% sequence identity thereto.

In certain embodiments, the target mRNA is a transcript of FGF21. In some embodiments, the FGF21 mRNA sequence is SEQ ID NO: 5 (GENBANK Accession No. NM_019113.4) or a sequence comprising at least 90%, 91%, 92%, 93%, 94%, 95%, 96%, 97%, 98%, or 99% sequence identity thereto.

In certain embodiments, the target mRNA is a transcript of HNF4A. In some embodiments, the HNF4A mRNA sequence is SEQ ID NO: 45 (GENBANK Accession No. NM_178849.3) or a sequence comprising at least 90%, 91%, 92%, 93%, 94%, 95%, 96%, 97%, 98%, or 99% sequence identity thereto.

In certain embodiments, the target mRNA is a transcript of klotho (KL). In some embodiments, the KL mRNA sequence is SEQ ID NO: 46 (GENBANK Accession No. NM_004795.4) or a sequence comprising at least 90%, 91%, 92%, 93%, 94%, 95%, 96%, 97%, 98%, or 99% sequence identity thereto.

In certain embodiments, the target mRNA is a transcript of OPA1. In some embodiments, the OPA1 mRNA sequence is SEQ ID NO: 47 (GENBANK Accession No. NM_015560.3) or a sequence comprising at least 90%, 91%, 92%, 93%, 94%, 95%, 96%, 97%, 98%, or 99% sequence identity thereto.

In certain embodiments, the target mRNA is a transcript of PKD1. In some embodiments, the PKD1 mRNA sequence is SEQ ID NO: 48 (GENBANK Accession No.

NM_001009944.3) or a sequence comprising at least 90%, 91%, 92%, 93%, 94%, 95%, 96%, 97%, 98%, or 99% sequence identity thereto.

In certain embodiments, the target mRNA is a transcript of PKD2. In some embodiments, the PKD2 mRNA sequence is SEQ ID NO: 49 (GENBANK Accession No. NM_000297.4) or a sequence comprising at least 90%, 91%, 92%, 93%, 94%, 95%, 96%, 97%, 98%, or 99% sequence identity thereto.

In certain embodiments, the target mRNA is a transcript of HBB. In some embodiments, the HBB mRNA sequence is SEQ ID NO: 50 (GENBANK Accession No. NM_000518.5) or a sequence comprising at least 90%, 91%, 92%, 93%, 94%, 95%, 96%, 97%, 98%, or 99% sequence identity thereto.

In certain embodiments, the target mRNA is a transcript of GRN. In some embodiments, the GRN mRNA sequence is SEQ ID NO: 51 (GENBANK Accession No. NM_002087.4) or a sequence comprising at least 90%, 91%, 92%, 93%, 94%, 95%, 96%, 97%, 98%, or 99% sequence identity thereto.

In certain embodiments, the target mRNA is a transcript of SCN1A. In some embodiments, the SCN1A mRNA sequence is SEQ ID NO: 52 (GENBANK Accession No. NM_001165963.4) or a sequence comprising at least 90%, 91%, 92%, 93%, 94%, 95%, 96%, 97%, 98%, or 99% sequence identity thereto.

In certain embodiments, the ACT-UP1 compounds of the invention target a sequence no farther than about 500 nucleotides, about 300 nucleotides, about 280 nucleotides, about 250 nucleotides, about 240 nucleotides, about 210 nucleotides, about 200 nucleotides, about 190 nucleotides, about 180 nucleotides, about 170 nucleotides, about 160 nucleotides, about 150 nucleotides, about 140 nucleotides, about 130 nucleotides, about 120 nucleotides, about 110 nucleotides, about 100 nucleotides, about 95 nucleotides, about 90 nucleotides, about 80 nucleotides, about 70 nucleotides, about 60 nucleotides, about 50 nucleotides or about 40 nucleotides downstream of a stop codon on a mRNA transcript. In certain embodiments, the ACT-UP1 compounds target a region of about 20 nucleotides to about 50 nucleotides, about 40 nucleotides to about 70 nucleotides, about 60 nucleotides to about 90 nucleotides, about 80 nucleotides to about 110 nucleotides, about 100 nucleotides to about 130 nucleotides, about 120 nucleotides to about 150 nucleotides, about 140 nucleotides to about 170 nucleotides, about 160 nucleotides to about 190 nucleotides, about 70 nucleotide to about 240 nucleotides, or about 180 nucleotides to about 210 nucleotides downstream of a stop codon on a mRNA transcript. In certain embodiments, the ACT-UP1 compounds target a sequence of about 50 nucleotides, about 70 nucleotides, about 80 nucleotides, about 90 nucleotides, about 100 nucleotides, about 150 nucleotides, about 160 nucleotides or about 190 nucleotides downstream of a stop codon on a mRNA transcript. In certain embodiments, the ACT-UP1 compounds target a region of about 20 to 50, about 40 to 70, about 60 to 90, about 80 to 110, about 100 to 130, about 120 to 150, about 140 to 170, about 160 to 190, about 180 to 210, about 200 to 230, about 220 to 250, about 240 to 300, or about 280 to 500 nucleotides downstream of a stop codon on a mRNA transcript. In certain embodiments, the targeted region on the mRNA is about 12, 13, 14, 15, 16, 17, 18, 19, 20, 21, 22, 23, 24, 25, 26, 27, 28, 29, or 30 nucleotides in length. In certain embodiments, the targeted region on the mRNA is in the 3'UTR. In certain embodiments, the targeted region on the mRNA is the 3' UTR but not the poly(A) tail.

In some preferred embodiments of the invention, the ACT-UP1 compounds of the invention target a sequence no farther than about 240 nucleotides, about 210 nucleotides, about 200 nucleotides, about 190 nucleotides, about 180 nucleotides, about 170 nucleotides, about 160 nucleotides, about 150 nucleotides, about 140 nucleotides, about 130 nucleotides, about 120 nucleotides, about 110 nucleotides, about 100 nucleotides, about 95 nucleotides, about 90 nucleotides, about 80 nucleotides, about 70 nucleotides, about 60 nucleotides, about 50 nucleotides or about 40 nucleotides downstream of a stop codon on a mRNA transcript. In a preferred embodiment, the target sequence is from about 50 nucleotides to about 240 nucleotides downstream of a stop codon on a mRNA transcript. In another preferred embodiment, the target sequence is from about 70 nucleotides to about 240 nucleotides downstream of a stop codon on a mRNA transcript. In yet another preferred embodiment, the target sequence is from about 95 nucleotides to about 240 nucleotides downstream of a stop codon on a mRNA transcript. In a further preferred embodiment, the target sequence is from about 140 nucleotides to about 240 nucleotides downstream of a stop codon on a mRNA transcript.

In certain embodiments, the target mRNA is present in a eukaryotic cell or a prokaryotic cell. In certain embodiments, the target protein is expressed in a eukaryotic cell or a prokaryotic cell. In certain embodiments, the eukaryotic cell or a prokaryotic cell is a mammalian cell, a plant cell, a yeast cell or a bacteria cell. In some embodiments, the mammalian cell includes cells from mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perissodactyla, including Equines (horses). In some aspects, the mammals are of the order Primates, Ceboids, or Simoids (monkeys) or of the order Anthropoids (humans and apes). In a preferred aspect, the mammalian cell is a human cell. In certain embodiments, the cell is in the form of a cultured cell line. In certain embodiments, the cell line is a primary cell line.

Hybridization

In some embodiments, hybridization occurs between an antisense compound disclosed herein and a mRNA. The most common mechanism of hybridization involves hydrogen bonding (e.g., Watson-Crick, Hoogsteen or reversed Hoogsteen hydrogen bonding) between complementary nucleobases of the nucleic acid molecules.

In Watson-Crick canonical base pairings, adenine (A) is complementary to thymine (T) in DNA, adenine (A) is complementary to uracil (U) in RNA, and Guanine (G) is complementary to cytosine (C) in both DNA and RNA. Base pairs, or complementary nucleobases, are usually Watson-Crick base pairs (e.g., C:G, A:U, or A:T), but, non-canonical base pairs such as Hoogsteen base pairs (e.g., A:G or A:U), Wobble base pairs (e.g., G:U, I:U, I:A, or I:C, wherein I is hypoxanthine) and the like are also permitted during hybridization of the antisense compound to a target nucleic acid or target region. Wobble base pairs in RNAi agents have previously been described (see e.g., U.S. Pat. Nos. 7,732, 593 and 7,750,144).

Nucleobase complementarity facilitates hybridization of the antisense compounds described herein to their target nucleic acids with the stronger the pairing (e.g., the more base pairs and/or the stronger the hydrogen bond), the stronger the hybridization of the antisense compound to the target. Hybridization can occur under varying conditions.

Stringent conditions are sequence-dependent and are determined by the nature and composition of the antisense compound to be hybridized.

Methods of determining whether a sequence is specifically hybridizable to a target nucleic acid are well known in the art. In certain embodiments, the antisense compounds provided herein are specifically hybridizable with a target mRNA with little to no off-target binding.

Complementarity

An antisense compound comprising an antisense oligonucleotide is "complementary", a "complement", or has "complementarity" to a target nucleic acid when a sufficient number of nucleobases of the antisense oligonucleotide can hydrogen bond with the corresponding nucleobases of the target nucleic acid, such that a desired effect will occur (e.g., ACT-UP1 upregulation of a target nucleic acid such as an mRNA nucleic acid).

Non-complementary nucleobases between an antisense oligonucleotide and an mRNA nucleic acid may be tolerated provided that the antisense oligonucleotide remains able to specifically hybridize to a target nucleic acid. Moreover, an antisense oligonucleotide may hybridize over one or more segments of an mRNA nucleic acid such that intervening or adjacent segments are not involved in the hybridization event (e.g., a loop structure, mismatch or hairpin structure).

In certain embodiments, for antisense compounds which comprise an antisense oligonucleotide, the antisense oligonucleotide portion, are, or are at least, about 70%, 80%, 85%, 86%, 87%, 88%, 89%, 90%, 91%, 92%, 93%, 94%, 95%, 96%, 97%, 98%, 99%, or 100% complementary to an mRNA nucleic acid, a target region, target segment, or specified portion thereof. Percent complementarity of an antisense oligonucleotide with a target nucleic acid can be determined using routine methods.

For example, an antisense compound in which about 18 out of 20 nucleobases of the antisense oligonucleotide are complementary to a target region, and would therefore specifically hybridize to the target, would represent 90 percent complementarity. In this example, the remaining noncomplementary nucleobases of the antisense oligonucleotide may be clustered or interspersed with complementary nucleobases and need not be contiguous to each other or to complementary nucleobases. As such, an antisense oligonucleotide which is 18 nucleobases in length having four noncomplementary nucleobases which are flanked by two regions of complete complementarity with the target nucleic acid would have 77.8% overall complementarity with the target nucleic acid and would thus fall within the scope of the present invention. Percent complementarity of an antisense oligonucleotide with a region of a target nucleic acid can be determined routinely using BLAST programs (basic local alignment search tools) and PowerBLAST programs known in the art (Altschul et al., *J. Mol. Biol.,* 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense oligonucleotides provided herein, or specified portions thereof, are fully complementary (i.e., 100% complementary) to a target nucleic acid, or specified portion thereof. For example, an antisense oligonucleotide may be fully complementary to an mRNA nucleic acid, or a target region, or a target segment or target sequence thereof. As used herein, "fully complementary" means each nucleobase of an antisense oligonucleotide is capable of precise base pairing with the corresponding nucleobases of a target nucleic acid. For example, a 20 nucleobase antisense oligonucleotide is fully complementary to a target sequence that is 400 nucleobases long, so long as there is a corresponding 20 nucleobase portion of the target nucleic acid that is fully complementary to the antisense oligonucleotide. Fully complementary can also be used in reference to a specified portion of the first and/or the second nucleic acid. For example, a 20 nucleobase portion of a 30 nucleobase antisense oligonucleotide can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense oligonucleotide. At the same time, the entire 30 nucleobase antisense oligonucleotide may or may not be fully complementary to the target sequence, depending on whether the remaining 10 nucleobases of the antisense oligonucleotide are also complementary to the target sequence.

The location of a non-complementary nucleobase may be at the 5' end or 3' end of the antisense oligonucleotide. Alternatively, the non-complementary nucleobase or nucleobases may be at an internal position of the antisense oligonucleotide. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense oligonucleotide that are, or are up to about 14, 15, 16, 17, 18, 19, or 20 nucleobases in length comprise no more than 4, no more than 3, no more than 2, or no more than one (1) non-complementary nucleobase(s) relative to a target nucleic acid, such as an mRNA nucleic acid, or specified portion thereof.

In certain embodiments, antisense oligonucleotide that are, or are up to about 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an mRNA nucleic acid, or specified portion thereof.

The antisense oligonucleotides provided also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense oligonucleotide. In certain embodiments, the antisense oligonucleotides are complementary to at least a 10 nucleobase portion of a target segment. In certain embodiments, the antisense oligonucleotides are complementary to at least an 11 nucleobase portion of a target segment. In certain embodiments, the antisense oligonucleotides are complementary to at least a 12 nucleobase portion of a target segment. In certain embodiments, the antisense oligonucleotides are complementary to at least a 13 nucleobase portion of a target segment. In certain embodiments, the antisense oligonucleotides are complementary to at least a 14 nucleobase portion of a target segment. In certain embodiments, the antisense oligonucleotides are complementary to at least a 15 nucleobase portion of a target segment. Also contemplated are antisense oligonucleotides that are complementary to at least an about 12, 13, 14, 15, 16, 17, 18, 19, 20, or more nucleobase portion of a target segment, or a range defined by any two of these values.

Identity

The antisense oligonucleotides provided herein may also have a defined percent identity to a particular nucleotide sequence, SEQ ID NO, or compound represented by a specific identity number, or portion thereof. As used herein, an antisense oligonucleotide is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense oligonucleotide described herein as well as oligonucleotides having non-identical bases relative to the antisense oligonucleotides provided herein also are contemplated. The non-identical bases may be adjacent to each other or dispersed throughout the antisense oligonucleotide. Percent identity of an antisense oligonucleotide is calculated according to the number of bases that have identical base pairing relative to the sequence to which it is being compared.

In certain embodiments, the antisense oligonucleotides, or portions thereof, are at least about 70%, 75%, 80%, 85%, 90%, 95%, 96%, 97%, 98%, 99% or 100% identical to one or more of the antisense oligonucleotides or SEQ ID NOs, or a portion thereof, disclosed herein.

In certain embodiments, a portion of the antisense oligonucleotide is compared to an equal length portion of the target nucleic acid. In certain embodiments, an about 10, 11, 12, 13, 14, 15, 16, 17, 18, 19, 20, 21, 22, 23, 24, or 25 nucleobase portion is compared to an equal length portion of the target nucleic acid.

Chemical Modifications

A nucleoside is a base-sugar combination. The nucleobase (also known as base) portion of the nucleoside is normally a heterocyclic base moiety. Nucleotides are nucleosides that further include a covalent linkage (e.g., phosphate group or a chemically modified linkage as described infra) to the sugar portion of the nucleoside. Oligonucleotides are formed through the covalent linkage of adjacent nucleotides to one another, to form a linear polymeric oligonucleotide. Within the oligonucleotide structure, the linkage groups are commonly referred to as forming the internucleoside linkages of the oligonucleotide.

Antisense compounds include antisense oligonucleotides (ASOs) and compounds that comprise ASOs such as ASO Coupled Translation-Upregulation 1 (ACT-UP1) compounds.

Modifications to antisense compounds encompass substitutions or changes to nucleobases, internucleoside linkages or sugar moieties. Modified antisense compounds are often preferred over native or unmodified forms because of desirable properties such as, for example, enhanced delivery (e.g., increased cellular uptake), enhanced specificity or affinity for a nucleic acid target, increased stability in the presence of nucleases, enhanced safety (e.g., fewer side effects after administration of the compound to a subject) or increased potency (e.g., increased activity).

Internucleoside Linkage Modifications

The naturally occurring internucleoside linkage of RNA and DNA is a 3' to 5' phosphodiester linkage. For nucleosides that include a pentofuranosyl sugar, the phosphate group can be linked to the 2', 3' or 5' hydroxyl moiety of the sugar. Oligomeric compounds having one or more modified, i.e. non-naturally occurring, internucleoside linkages are often selected over oligomeric compounds having naturally occurring internucleoside linkages because of desirable properties such as, for example, enhanced cellular uptake, enhanced affinity for target nucleic acids, decreased toxicity, increased stability and durability, decreased degradation and other desirable features for an oligomeric compound. Modified internucleoside linkages and their advantages are well known in the art (Crooke, S. T., et al., 2021a Antisense technology: an overview and prospectus. Nat Rev Drug Discov 20: 427-453; Crooke, S. T., et al., 2021b Antisense technology: A review. J Biol Chem 296: 100416).

Oligomeric compounds having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates (e.g., 5'-methylphosphonate (5'-MP)), phosphoramidate, phosphorothioates (e.g., phosphorodithioate Rp isomer (PS, Rp), phosphorodithioate Rp isomer (PS, Sp), or 5'-phosphorothioate (5'-PS)), methoxypropylphosphonate, (S)-5'-C-methyl with Phosphate, and 5'-(E)-vinylphosphonate. In certain aspects, the internucleoside linkage may be replaced with a peptide nucleic acid (PNA) linkage.

In certain embodiments, oligomeric compounds targeted to a nucleic acid comprise one or more modified internucleoside linkages. In certain embodiments, the modified internucleoside linkages are phosphorothioate (PS) linkages. In certain embodiments, one or more internucleoside linkage of an oligomeric compound is a phosphorothioate internucleoside linkage. In certain embodiments, each internucleoside linkage of an oligomeric compound is a phosphorothioate internucleoside linkage. In certain embodiments, each internucleoside linkage of an oligonucleotide is a phosphorothioate internucleoside linkage.

Sugar Modifications

Oligomeric compounds provided herein can contain one or more nucleosides wherein the sugar group has been modified. Such sugar modified nucleosides may impart desirable features such as increased stability, increased durability (e.g., increased half-life), increased binding affinity, decreased off-target effects, decreased immunogenicity, decreased toxicity, increased potency, or some other beneficial biological property to the oligomeric compounds. Sugar modifications and their advantages are known in the art (Faria, M., and H. Ulrich, 2008 Sugar boost: when ribose modifications improve oligonucleotide performance. Curr Opin Mol Ther 10: 168-175; Crooke, S. T., et al., 2021b Antisense technology: A review. J Biol Chem 296: 100416; Egli, M., and M. Manoharan, 2023 Chemistry, structure and function of approved oligonucleotide therapeutics. Nucleic Acids Res 51: 2529-2573).

In certain embodiments, nucleosides comprise a chemically modified ribofuranose ring moiety. Examples of chemically modified ribofuranose rings can include, without limitation, addition of substituent groups (e.g., 5' sugar modifications, or 2' sugar modifications); bridging of non-geminal ring atoms to form bicyclic nucleic acids (BNA); replacement of the ribosyl ring oxygen atom with S, N(R), or C(R1)(R)2 (R=H, $C_1$-$C_{12}$ alkyl or a protecting group); nucleoside mimetic; and combinations thereof.

Examples of chemically modified sugars include, 2'-F-5'-methyl substituted nucleoside (see, e.g., PCT Publication WO2008101157 for other disclosed 5', 2'-bis substituted nucleosides), replacement of the ribosyl ring oxygen atom with S with further substitution at the 2'-position (see, e.g., U.S. Publication US20050130923), or, alternatively, 5'-substitution of a BNA (see, PCT Publication WO2007134181 wherein LNA is substituted with, for example, a 5'-methyl or a 5'-vinyl group).

A 2'-modified sugar refers to a furanosyl sugar modified at the 2' position. A 2'-modified nucleoside refers to a nucleoside comprising a sugar modified at the 2' position of a furanose ring. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nONH_2$, $OCH_2C(=O)N(H)CH_3$, and $O(CH_2)_nON$ $[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, and a group for improving the pharmacodynamic properties of an oligomeric compound, and other substituents having similar properties.

Further examples of nucleosides having modified sugar moieties include, without limitation, nucleosides comprising 5'-vinyl, 5'-methyl (R or S), 2'-F-5'-methyl, 4'-S, 2'-deoxy-2'-fluoro (2'-F), 2'-$OCH_3$ (2'-O-methyl, 2'-OMe), 2'-$O(CH_2)_2OCH_3$ (2'-O-(2-methoxyethyl), 2'-O-MOE, 2'-MOE), 2'-O-methyl-4-pyridine, phosphorodiamidate morpholino (PMO), tricyclo-DNA (tcDNA), 2'-arabino-fluoro, 2'-O-benzyl, glycol nucleic acid (GNA), and/or unlocked nucleic acid (UNA) substituent groups. The substituent at the 2' position can also be selected from allyl, amino, azido, thio, O-allyl, O—$C_1$-$C_{10}$ alkyl, $OCF_3$, $O(CH_2)_2SCH_3$, $O(CH_2)_2$—O—N(Rm)(Rn), and O—$CH_2$—C(=O)—N(Rm)(Rn), where each Rm and Rn is, independently, H or substituted or unsubstituted $C_1$-$C_{10}$ alkyl. 2'-OMe or 2'-$OCH_3$ or 2'-O-methyl each refers to a nucleoside comprising a sugar comprising an —$OCH_3$ group at the 2' position of the sugar ring. 2'-F refers to a sugar comprising a fluoro group at the 2' position. 2'-O-(2-methoxyethyl) or 2'-O-MOE or 2'-MOE each refers to a nucleoside comprising a sugar comprising an —$O(CH_2)_2OCH_3$ group at the 2' position of the sugar ring.

BNAs refer to modified nucleosides comprising a bicyclic sugar moiety wherein a bridge connecting two carbon atoms of the sugar ring connects the 2' carbon and another carbon of the sugar ring. Examples of bicyclic nucleosides include, without limitation, nucleosides comprising a bridge between the 4' and the 2' ribosyl ring atoms such as in locked nucleic acid (LNA). In certain embodiments, oligomeric compounds provided herein include one or more bicyclic nucleosides wherein the bridge comprises a 4' to 2' bicyclic nucleoside. LNAs and UNAs have been described by Campbell and Wengel (Chem Soc Rev, 2011, 40(12):5680-9) and are incorporated-by-reference herein.

In certain embodiments, oligomeric compounds comprise one or more nucleotides having modified sugar moieties. In certain embodiments, the modified sugar moiety is 2'-MOE. In certain embodiments, the modified sugar moiety has a 2'-OMe modification. In certain embodiments, the modified sugar moiety has a 2'-F modification. In certain embodiments, the modified sugar moiety is a cEt.

Nucleobase Modifications

An ACT-UP1 compound can also include nucleobase (often referred to in the art simply as "base") modifications or substitutions. As used herein, "natural" nucleobases include the purine bases adenine (A) and guanine (G), and the pyrimidine bases thymine (1'), cytosine (C), and uracil (U). Modified nucleobases include other synthetic and natural nucleobases such as substitution of a ribonucleoside for a deoxyribonucleoside in a DNA oligomeric compound (e.g., substituting U in place of T in an RNA strand), substitution of a deoxyribonucleoside for a ribonucleoside in an RNA oligomeric compound (e.g., substituting T in place of U in an RNA strand), universal pairing nucleosides such as 3-formylidole and/or 5-Nitroindole (T. S. Zatsepin, D. A. Stetsenko, M. J. Gait and T. S. Oretskaya, Bioconjugate Chemistry, 16, 471-489, 2005; A. Okamoto, K. Tainaka and I. Saito, Tetrahedron Lett., 43,4581-4583,2002; D. Loakes, Nucleic Acids Research, 29,2437-2447, 2001; F. H. Martin, M. M. Castro, F. Aboul-ela and I. Tinoco, Jr, Nucleic Acids Research, 13, 8927-8938, 1985; S. C. Case-Green, E. M. Southern, Nucleic Acids Research, 22, 131-136, 1994; R. Eritja, D. M. Horowitz, P. A. Walker, J. P. Ziehler-Martin, M. S. Boosalis, M. F. Goodman, K. Itakura and B. E. Kaplan, Nucleic Acids Research, 14, 8135-8153, 1986; D. Picken and V. Gault, Nucleosides, Nucleotides and Nucleic Acids, 16, 937-939, 1997)

Modified nucleobases can further include deoxythymidine (dT), 5-methylcytosine (also known as 5-me-C or mC), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L. ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications. Representative U.S. Patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540;

5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

Oligomeric Compound Delivery Systems

Oligomeric compounds require entry into target cells to become active. A variety of modalities have been used to traffic oligomeric compounds into target cells including viral delivery vectors, lipid-based delivery, polymer-based delivery, and conjugate-based delivery (Paunovska et al., Drug Delivery Systems for RNA Therapeutics, 2022, Nature Reviews Genetics, 23(5):265-280; Chen et al., 2022, Molecular Therapy, Nucleic Acids, 29:150-160).

Lipid-based particles can form specific structures such as micelles, liposomes and lipid nanoparticles (LPNs) to carry oligomeric compounds into cells. To form these particles, LPNs can include one or more of a cationic or ionizable lipid (e.g., DLin-MC3-DMA, SM-102, or ALC-0315), cholesterol, a helper lipid, 1,2-distearoyl-sn-glycero-3-phosphocholine (DSPC), poly(ethylene glycol) (PEG) modified lipid (e.g., PEG-2000-C-DMG, PEG-2000-DMG, or ALC-0159), C12-200, cKK-E12 and the like. Different combinations of lipids can be formulated to affect the delivery of the oligomeric compound to different types of cells. In one example, therapeutic siRNA patisiran was formulated in cationic ionizable lipid DLin-MC3-DMA, cholesterol, polar phospholipid DSPC, and PEG-2000-C-DMG for delivery to hepatocytes.

Polymer-based particles are also used in oligomeric compound delivery systems. Such polymers include poly(lactic-co-glycolic acid) (PLGA), polyethylenimine (PEI), poly(l-lysine) (PLL), poly(beta-amino ester) (PBAE), dendrimers (e.g., poly(amidoamine) (PAMAM) or PLL), and other polymers or modified polymers thereof. The polymer composition can be varied depending on the traits desired for delivery of the oligomeric compound.

The oligomeric compounds disclosed herein may be covalently linked to one or more moieties or conjugate agents which enhance the activity, cellular distribution or cellular uptake of the resulting compound. Conjugate agents can include cholesterols, lipids, carbohydrates, phospholipids, biotin, phenazine, folate, phenanthridine, anthraquinone, acridine, fluoresceins, rhodamines, coumarins, peptides, antibodies, dyes, tocopherol (Nishina et al., 2008, Molecular Therapy, 16(4):734-740), etc. Conjugate-based delivery can actively deliver oligomeric compounds to specific cell types.

In an example, N-Acetylgalactosamine (GalNAc) is conjugated to an oligomeric compound and delivered into hepatocytes. Various GalNAc conjugate agents can be found in several publications including the following, all of which are incorporated-by-reference herein: Sharma et al., 2018, Bioconjugate Chem, 29:2478-2488; Nair et al., J. Am. Chem. Soc. 2014, 136(49):16958-16961; Keam, 20; 2, Drugs, 82:1419-1425; U.S. Pat. No. 10,087,208; Prakash et al., 2014, Nucleic Acids Res, 42(13):8796-807; Debacker et al., 2020, Molecular Therapy, 28(8):1759-1771; U.S. Pat. Nos. 11,110,174; 9,796,756; 9,181,549; 10,344,275; 10,570, 169; 9,506,030; 7,582,744; and, WO2024137545.

Oligomeric Compound Synthesis

Oligomeric compounds were designed, synthesized, and prepared using methods known in the art.

Solid phase syntheses of oligonucleotides were done on a MerMade$^T$M 48× synthesizer (BioAutomation, LGC, Biosearch Technologies, Hoddesdon, UK), which can make up to 48 1 μMole or 5 μMole scale oligonucleotides per run using standard phosphoramidite chemistry. Phosphoramidite synthesis of oligonucleotides on a solid support is well known in the art (e.g., Beaucage and Caruthers, 1981, Tetrahedron Letters, 22(20): 1859-1862; Roy and Caruthers, 2013, Molecules, 18:14268-14284; and Roy and Caruthers et al., 2021, Nature Communications, 12:2760). Solid support is controlled pore glass (500-1400 A) loaded with universal linkers or loaded with 3'-GalNAc conjugates (AM Chemicals, Vista, CA, USA; Primetech ALC, Minsk, Belarus; Gene Link, Elmsford, NY, USA; or any GalNAc conjugate disclosed herein) or universal solid support (AM Chemicals, Vista, CA, USA). Ancillary synthesis reagents and standard 2'-cyanoethyl phosphoramidite monomers (2'-fluoro nucleosides, 2'-O-methyl nucleosides, RNA nucleosides, DNA nucleosides) were obtained from various sources (Hongene Biotech, Shanghai, China; Sigma-Aldrich, St. Louis, MO, USA; Glen Research, Sterling, VA, USA; ThermoFisher Scientific, Waltham, MA, USA; LGC Biosearch Technologies, Hoddesdon, UK). Phosphoramidite mixtures were prepared in anhydrous acetonitrile or 30% DMF:acetonitrile and were coupled using 0.25M 4,5-dicyanoimidazole (DCI)(Sigma-Aldrich, St. Louis, MO, USA) with coupling times ranging from 120-360 seconds. Standard phosphodiester linkages were achieved using 0.02M iodine mixture in Tetrahydrofuran (THF), pyridine and water. Phosphorothiate linkages were generated using 0.05M sulfurizing Reagent II (3-((Dimethylamino-methylidene)amino)-3H-1,2,4-dithiazole-3-thione, DDTT) (40:60, Pyridine/Acetonitrile) (LGC Biosearch Technologies, Hoddesdon, UK) with an oxidation time of 6 minutes. All sequences were synthesized with Dimethoxy Trityl (DMT) protecting group removed.

Upon completion of solid phase synthesis, the oligonucleotides were cleaved from the solid support, and deprotection of base labile groups performed by incubation in ammonium hydroxide at 55° C. for 6 hours. Ammonium hydroxide was removed using a centrifugal vacuum concentrator to dryness at room temperature. For sequences containing natural ribonucleotides (2'-OH) protected with tert-butyl dimethyl silyl (TBDMS), a second deprotection was performed using triethylamine; trihydrofluoride (TEA:3HF). To each TBDMS protected oligonucleotide, 100 μL DMSO and 125 μL TEA:3HF were added and incubated at 65'C for 2.5 hours. After incubation, 25 μL of 3M sodium acetate was added to the solution which was subsequently precipitated in butanol at −20° C. for 30 minutes. The cloudy solution was centrifuged to a cake at which time the supernatant was carefully decanted with a pipette. The standard precipitation process was then completed with 75% ethanol:water then 100% ethanol as supernatant solutions. The oligonucleotide cake was dried for 30 minutes in a centrifugal vacuum concentrator.

Desalting without HPLC purification was performed after precipitation with 3M sodium acetate with a follow on G25 Sephadex® column (Sigma-Aldrich, St. Louis, MO, USA) elution. Purification of oligonucleotides was afforded by anion exchange chromatography on a Gilson GX271 prep HPLC system (Middleton, WI, USA) using BioWorks Q40 resin (Uppsala, Sweden). Final desalt was performed by Sephadex® G25 column. All oligonucleotides were analyzed by ion pairing reverse phase HPLC for purity on an Agilent 1200 analytical HPLC (Santa Clara, CA, USA), negative ion mass spectrometry for intact mass on an Agilent 6130 single quad mass spectrometer (Santa Clara, CA, USA), and A260 quantification by UV/Vis on a Tecan Infinite® M Plex plate reader (Zurich, Switzerland).

In Vitro Testing of Oligomeric Compounds

Described herein are methods for the treatment of cells with oligomeric compounds such as ACT-UP1 compounds.

Cells may be treated with oligomeric compounds when the cells reach approximately 60-80% confluency in culture.

Reagents commonly used to introduce oligomeric compounds into cultured cells include the cationic lipid transfection reagent Oligofectamine™ 2000 or Lipofectamine™ 2000 (ThermoFisher Scientific, Waltham, MA). In one example, oligomeric compounds may be mixed with Oligofectamine™ 2000 in OPTI-MEM 1 (ThermoFisher Scientific, Waltham, MA) to achieve the desired final concentration of oligomeric compounds that may range from 0.001 to 300 nM oligomeric compounds in culture medium. Transfection procedures are done according to the manufacturer's recommended protocols.

Another technique used to introduce oligomeric compounds into cultured cells includes electroporation.

Oligomeric compounds conjugated with GalNAc can be introduced to cells through incubation of the conjugated compounds with cells without transfection reagents, referenced herein as "free uptake". The oligo-GalNAc conjugates are transported into asialoglycoprotein receptor (ASGR) positive cells, such as hepatocytes, via endocytosis.

Cells are treated with oligonieric compounds by routine methods. Cells may be harvested 4-144 hours after oligomeric compounds treatment, at which time mRNA (harvested at 4-144 hrs) or protein levels (extracted at 24-96 hrs) of target nucleic acids are measured by methods known in the art and described herein. In general, treatments are performed in multiple replicates, and the data are presented as the average (e.g., mean value) of the replicate treatments plus the standard deviation.

The concentration of oligomeric compounds used varies from cell line to cell line and target to target. Methods to determine the optimal oligomeric compound concentration for a particular target in a particular cell line are well known in the art. In general, cells are treated with oligomeric compounds in a dose-dependent manner to allow for the calculation of the half-maximal inhibitory concentration value (IC50). Oligomeric compounds are typically used at concentrations ranging from 0.001 nM to 300 nM when transfected with Oligofectamine™ 2000 or Lipofectamine™ 2000. Oligomeric compounds are used at higher concentrations ranging from 7.5 to 20,000 nM when transfected using electroporation or free uptake.

In Vivo Testing of Oligomeric Compounds

The oligomeric compounds of the invention, for example, ACT-UP1 compounds, are tested in animals to assess their ability to modulate expression of a target protein and produce phenotypic changes such as a change in one or more markers affected by the target nucleic acid. Also, the phenotypic change can be a decrease in a disease, disorder, condition, or symptom related to the target nucleic acid. Testing may be performed in normal animals, or in experimental disease models. For administration to animals, oligomeric compounds are formulated in a pharmaceutically acceptable diluent, such as phosphate-buffered saline (PBS). Administration includes parenteral routes of administration, such as intraperitoneal, intravenous, and subcutaneous. Calculation of dosage and dosing frequency depends upon factors such as route of administration and animal body weight. In one embodiment, following a period of treatment with oligomeric compounds of the invention, RNA encoding the target nucleic acid is isolated from liver tissue and changes in the target nucleic acid expression are measured. Changes in protein levels expressed by the target nucleic acid can also be measured.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Thermo Fisher Scientific, Waltham, MA), Qiagen RNeasy kit (Qiagen, Hilden, Germany), or AcroPrep Advance 96-well Filter Plates (Pall Corporation, Port Washington, New York) using Qiagen's RLT, RW1 and RPE buffers. RNA extraction procedures are done according to the manufacturer's recommended protocols.

Protein Isolation

Protein analysis can be conducted on total cell extracts or tissue lysates. Methods of cell extracts or tissue lysates are well known in the art. Cellular proteins are prepared using methods well known in the art, for example, using RIPA buffer (ThermoFisher Scientific, Waltham, MA) or other appropriate buffers. Tissue lysates are prepared in RIPA buffer, with tissue homogenizer. Levels of proteins can be analyzed using Western blotting, ELISA, or other approaches.

Compositions and Methods for Formulating Pharmaceutical Compositions

The oligomeric compounds of the invention, such as ACT-UP1 compounds described herein, can be combined with pharmaceutically acceptable active or inert substances, such as a diluent, excipient or carrier, for the preparation of pharmaceutical compositions or formulations.

Compositions and methods for the formulation of pharmaceutical compositions are dependent upon a number of criteria, including, but not limited to, route of administration, extent of disease, or dose to be administered.

In certain embodiments, the pharmaceutical carrier or excipient is a pharmaceutically acceptable solvent, suspending agent, or any other pharmacologically inert vehicle for delivering one or more oligomeric compounds to an animal. The excipient can be liquid or solid and can be selected, with the planned manner of administration in mind, so as to provide for the desired bulk, consistency, etc., when combined with nucleic acid and the other components of a given pharmaceutical composition. Typical pharmaceutical carriers include, but are not limited to, binding agents (e.g., pregelatinized maize starch, polyvinylpyrrolidone and/or hydroxypropyl methylcellulose, etc.); fillers (e.g., lactose and other sugars, microcrystalline cellulose, pectin, gelatin, calcium sulfate, ethyl cellulose, polyacrylates and/or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, and/or sodium acetate, etc.); disintegrants (e.g., starch, and/or sodium starch glycolate, etc.); and wetting agents (e.g., sodium lauryl sulfate, etc.).

Pharmaceutically acceptable organic or inorganic excipients, which do not deleteriously react with nucleic acid compounds, suitable for parenteral or non-parenteral administration can also be used to formulate the compositions of the present invention. Suitable pharmaceutically acceptable carriers include, but are not limited to, water, salt solutions, alcohols, polyethylene glycols, gelatin, lactose, amylose, magnesium stearate, tale, silicic acid, viscous paraffin, hydroxymethylcellulose, polyvinylpyrrolidone and the like. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an oligomeric compound and a pharmaceutically acceptable diluent. In certain embodiments, the pharmaceutically acceptable diluent is PBS. In certain embodiments, the oligomeric compound is an ACT-UP1 compound.

Pharmaceutical compositions comprising oligomeric compounds such as ACT-UP1 compounds can encompass any pharmaceutically acceptable salts, esters, or salts of such esters, which, upon administration to an animal, including a human, is capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts.

In certain embodiments, a pharmaceutical composition is prepared for administration by injection (e.g., intravenous, subcutaneous, and/or intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer (e.g., PBS). In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers.

Dosages

For purposes of the disclosure, the amount or dose of the active agent (i.e., oligomeric compound of the invention) administered should be sufficient to e.g., modulate the expression of a target protein in an animal. In the animal (e.g., human), dose will be determined by the efficacy of the particular active agent and the condition of the animal, as well as the body weight of the animal to be treated.

Many assays for determining an administered dose are known in the art.

The dose of the active agent of the present disclosure also will be determined by the existence, nature and extent of any adverse side effects that might accompany the administration of a particular active agent of the present disclosure. Typically, the attending physician will decide the dosage of the active agent of the present disclosure with which to treat each individual patient, taking into consideration a variety of factors, such as age, body weight, general health, diet, sex, active agent of the present disclosure to be administered, route of administration, and the severity of the condition being treated.

Dosing

In certain embodiments, pharmaceutical compositions are administered according to a dosing regimen (e.g., dose, dose frequency, and duration) wherein the dosing regimen can be selected to achieve a desired effect. The desired effect can be, for example, reduction of a target nucleic acid or the prevention, reduction, amelioration or slowing the progression of a disease, disorder and/or condition, or symptom thereof, associated with the target nucleic acid. In certain embodiments, the variables of the dosing regimen are adjusted to result in a desired concentration of pharmaceutical composition in a subject. "Concentration of pharmaceutical composition" as used with regard to dose regimen can refer to the oligomeric compound or active ingredient of the pharmaceutical composition. For example, in certain embodiments, dose and dose frequency are adjusted to provide a tissue concentration or plasma concentration of a pharmaceutical composition at an amount sufficient to achieve a desired effect.

Dosing is dependent on severity and responsiveness of the disease state to be treated, with the course of treatment lasting from several days to several months, or until a cure is effected or a diminution of the disease state is achieved. Dosing is also dependent on drug potency and metabolism. In certain embodiments, dosage is from about 0.01 µg to 50 mg per kg of body weight, 0.01 µg to 100 mg per kg of body weight, or within a range of about 0.001 mg to 1000 mg dosing, and may be given once or more daily, weekly, monthly, quarterly or yearly, or even once every 2 to 20 years. Following successful treatment, it may be desirable to have the patient undergo maintenance therapy to prevent the recurrence of the disease state, wherein the oligomeric compound is administered in maintenance doses, ranging from about 0.01 µg to 100 mg per kg of body weight, once or more daily, once or more weekly, once or more monthly, once or more quarterly, once or more yearly, to once every 20 years or ranging from about 0.001 mg to 1000 mg dosing. In certain embodiments, it may be desirable to administer the oligomeric compound from at most once daily, once weekly, once monthly, once quarterly, once yearly, once every two years, once every three years, once every four years, once every five years, once every ten years, to once every 20 years.

In certain embodiments, the range of dosing is between any of about 1 mg-1500 mg, 100 mg-1400 mg, 100 mg-1300 mg, 100 mg-1200 mg, 100 mg-1100 mg, 100 mg-1000 mg, 100 mg-900 mg, 200 mg-800 mg, 300 mg-700 mg, 400 mg-600 mg, 100 mg-400 mg, 200 mg-500 mg, 300 mg-600 mg, and 400 mg-700 mg. In certain embodiments, a dose is about 100 mg, 150 mg, 200 mg, 250 mg, 300 mg, 350 mg, 400 mg, 450 mg, 500 mg, 550 mg, 600 mg, 650 mg, 700 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, or 1500 mg.

In certain embodiments, the oligomeric compound is dosed at any of about 150 mg, 200 mg, 300 mg, 400 mg, 500 mg, 600 mg, 700 mg, 800 mg, or 900 mg twice a year. In certain embodiments, the oligomeric compound is dosed at about 100 mg, 150 mg, 200 mg, 300 mg, 400 mg, 500 mg, 600 mg, 700 mg, 800 mg, or 900 mg quarterly. In certain embodiments, the oligomeric compound is dosed at about 50 mg, 100 mg, 150 mg, 200 mg, 300 mg, 400 mg, 500 mg, 600 mg, 700 mg, 800 mg, or 900 mg once monthly or every two months. In certain embodiments, the oligomeric compound is dosed at about 10 mg, 15 mg, 20 mg 25 mg, 50 mg, 100 mg, 150 mg, 200 mg, 300 mg, 400 mg, 500 mg, 600 mg, 700 mg, 800 mg, or 900 mg weekly or every two weeks.

Administration

The oligomeric compounds, such as ACT-UP1, or pharmaceutical compositions of the present invention can be administered in a number of ways depending upon whether local or systemic treatment is desired and upon the area to be treated. Administration can be oral, inhaled or parenteral.

In certain embodiments, the compounds and compositions as described herein are administered parenterally. Parenteral administration includes intravenous, intra-arterial, subcutaneous, intraperitoneal or intramuscular injection or infusion; or intracranial, e.g., intrathecal or intraventricular, administration. In certain embodiments, parenteral administration is by infusion. Infusion can be chronic or continuous or short or intermittent. In certain embodiments, infused pharmaceutical agents are delivered with a pump.

In certain embodiments, parenteral administration is by injection. The injection can be delivered with a syringe or a pump. In certain embodiments, the injection is a bolus injection. In certain embodiments, the injection is administered directly to a tissue or organ.

In certain embodiments, formulations for parenteral, intrathecal or intraventricular administration can include sterile aqueous solutions which can also contain buffers, diluents and other suitable additives such as, but not limited to, penetration enhancers, carrier compounds and other pharmaceutically acceptable carriers or excipients.

In certain embodiments, formulations for oral administration of the compounds or compositions can include, but is not limited to, pharmaceutical carriers, excipients, powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In certain embodiments, oral formulations are those in which compounds provided herein are administered in conjunction with one or more penetration enhancers, surfactants and chelators.

Kits of the Invention

According to another aspect of the invention, kits are provided. Kits according to the invention include package(s) comprising any of the compositions of the invention or oligomeric compound of the invention. In various aspects, the kit comprises any of the compositions of the invention as a unit dose. For purposes herein "unit dose" refers to a discrete amount dispersed in a suitable carrier.

The phrase "package" means any vessel containing compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes (including pre-filled syringes), bottles, and any packaging material suitable for a selected formulation and intended mode of administration and treatment.

The kit can also contain items that are not contained within the package but are attached to the outside of the package, for example, pipettes.

Kits may optionally contain instructions for administering compositions of the present invention to a subject having a condition in need of treatment. Kits may also comprise instructions for approved uses of components of the composition herein by regulatory agencies, such as the United States Food and Drug Administration. Kits may optionally contain labeling or product inserts for the present compositions. The package(s) and/or any product insert(s) may themselves be approved by regulatory agencies. The kits can include compositions in the solid phase or in a liquid phase (such as buffers provided) in a package. The kits also can include buffers for preparing solutions for conducting the methods, and pipettes for transferring liquids from one container to another.

The kit may optionally also contain one or more other compositions for use in combination therapies as described herein. In certain embodiments, the package(s) is a container for any of the means for administration such as intravitreal delivery, intraocular delivery, intratumoral delivery, peritumoral delivery, intraperitoneal delivery, intrathecal delivery, intramuscular injection, subcutaneous injection, intravenous delivery, intra-arterial delivery, intraventricular delivery, intrasternal delivery, intracranial delivery, or intradermal injection.

Methods of Use

The invention provides methods for enhancing the expression of a target protein in a subject comprising administering an effective amount of an oligomeric compound of the invention or a pharmaceutical composition of the invention, so as to increase the expression of a target protein in the subject. In certain embodiments, the oligomeric compound is an ACT-UP1 compound. In some preferred aspects, in the ACT-UP1 compound, the PRS is joined to the 5' end of the ASO. In some aspects the PRS is joined to the 3' end of the ASO.

The invention provides methods for enhancing the expression of a target protein in a eukaryotic cell or a prokaryotic cell comprising administering an effective amount of an oligomeric compound of the invention or a pharmaceutical composition of the invention, so as to increase the expression of a target protein in the subject. In certain embodiments, the oligomeric compound is an ACT-UP1 compound. In certain embodiments, eukaryotic cell or a prokaryotic cell is a mammalian cell, a plant cell, a yeast cell or a bacteria cell.

In certain embodiments, a method of enhancing a target gene expression in a cell comprises administering to the cell an oligomeric compound targeted to an mRNA transcript. In an embodiment, the oligomeric compound is an ACT-UP1 compound. In some preferred aspects, in the ACT-UP1 compound, the PRS is joined to the 5' end of the ASO. In some aspects the PRS is joined to the 3' end of the ASO.

In certain embodiments, an oligomeric compound of the invention increases expression of a protein by at least about 10%, 15%, 20%, 25%, 30%, 35%, 40%, 45%, 50%, 55%, 60%, 65%, 70%, 75%, 80%, 85%, 90%, 95%, or 100%. In an embodiment, the oligomeric compound is an ACT-UP1 compound.

In certain embodiments, a method of enhancing Jagged 1 (JAG1) gene expression in a cell comprises administering to the cell an oligomeric compound targeted to a human JAG1 mRNA transcript (GenBank No: NM_000214.3, SEQ ID NO: 1) is provided. In an embodiment, the oligomeric compound is an ACT-UP1 compound targeting JAG1. In certain embodiments, enhancing JAG1 gene expression in a cell treats a subject suffering from a JAG1 related disease. In certain embodiments, the JAG1 related disease is related to a decreased level of JAG1 protein. In a preferred embodiment, the oligomeric compound is an ACT-UP1 compound targeting JAG1.

In certain embodiments, a method of enhancing RAB9A gene expression in a cell comprises administering to the cell an oligomeric compound targeted to a human RAB9A mRNA transcript (GenBank No: NM_004251.5, SEQ ID NO: 2) is provided. In an embodiment, the oligomeric compound is an ACT-UP1 compound targeting RAB9A. In certain embodiments, enhancing RAB9A gene expression in a cell treats a subject suffering from a RAB9 related disease. In certain embodiments, the RAB9A related disease is related to a decreased level of RAB9A protein. In a preferred embodiment, the oligomeric compound is an ACT-UP1 compound targeting RAB9A.

In certain embodiments, a method of enhancing RNase H1 gene expression in a cell comprises administering to the cell an oligomeric compound targeted to a human RNase H1 mRNA transcript (GenBank No: NM_001286834.3, SEQ ID NO: 3) is provided. In certain embodiments, enhancing RNase H1 gene expression in a cell treats a subject suffering from a RNase H1 related disease. In certain embodiments, the RNase H1 related disease is related to a decreased level of RNase H1 protein. In a preferred embodiment, the oligomeric compound is an ACT-UP1 compound targeting RNase H1.

In certain embodiments, a method of enhancing PBGD gene expression in a cell comprises administering to the cell an oligomeric compound targeted to a human PBGD (also known as HMBS) mRNA transcript (GenBank No: NM_000190.4, SEQ ID NO: 4) is provided. In certain embodiments, a method of enhancing PBGD gene expression in a cell comprises administering to the cell an oligomeric compound targeted to a murine PBGD mRNA (GenBank No: NM_013551.2, SEQ ID NO: 6) is provided. In certain embodiments, enhancing PBGD gene expression in a cell treats a subject suffering from a PBGD related disease. In certain embodiments, the PBGD related disease is related to a decreased level of PBGD protein. In a preferred embodiment, the oligomeric compound is an ACT-UP1 compound targeting PBGD.

In certain embodiments, a method of enhancing FGF21 gene expression in a cell comprises administering to the cell an oligomeric compound targeted to a human FGF21 mRNA transcript (GenBank No: NM_019113.4, SEQ ID NO: 5) is provided. In certain embodiments, a method of enhancing FGF21 gene expression in a cell comprises administering to the cell an oligomeric compound targeted to a murine FGF21 mRNA (GenBank No: NM_020013.4, SEQ ID NO: 7) is provided. In certain embodiments, enhancing FGF21 gene expression in a cell treats a subject suffering from a FGF21 related disease. In certain embodiments, the FGF21 related disease is related to a decreased level of FGF21 protein production and/or secretion. In a preferred embodiment, the oligomeric compound is an ACT-UP1 compound targeting FGF21.

In certain embodiments, a method of enhancing HNF4alpha (HNF4A) gene expression in a cell comprises administering to the cell an oligomeric compound targeted to a HNF4alpha mRNA transcript (GenBank No: NM_178849.3, SEQ ID NO: 45). In certain embodiments, enhancing HNF4alpha gene expression in a cell treats a subject suffering from a HNF4alpha related disease. In certain embodiments, the HNF4alpha related disease is related to a decreased level of HNF4alpha protein. In a preferred embodiment, the oligomeric compound is an ACT-UP1 compound targeting HNF4alpha.

In certain embodiments, a method of enhancing klotho (KL) gene expression in a cell comprises administering to the cell an oligomeric compound targeted to a mRNA transcript (GenBank No: NM_004795.4, SEQ ID NO: 46). In certain embodiments, enhancing KL gene expression in a cell treats a subject suffering from a KL related disease. In certain embodiments, the KL related disease is related to a decreased level of klotho protein. In a preferred embodiment, the oligomeric compound is an ACT-UP1 compound targeting KL.

In certain embodiments, a method of enhancing OPA1 gene expression in a cell comprises administering to the cell an oligomeric compound targeted to an OPA1 mRNA transcript (GenBank No: NM_015560.3, SEQ ID NO: 47). In certain embodiments, enhancing OPA1 gene expression in a cell treats a subject suffering from an OPA1 related disease. In certain embodiments, the OPA1 related disease is related to a decreased level of OPA1 protein. In a preferred embodiment, the oligomeric compound is an ACT-UP1 compound targeting OPA1.

In certain embodiments, a method of enhancing PKD1 gene expression in a cell comprises administering to the cell an oligomeric compound targeted to a PKD1 mRNA transcript (GenBank No: NM_001009944.3, SEQ ID NO: 48). In certain embodiments, enhancing PKD1 gene expression in a cell treats a subject suffering from a PKD1 related disease. In certain embodiments, the PKD1 related disease is related to a decreased level of PKD1 protein. In a preferred embodiment, the oligomeric compound is an ACT-UP1 compound targeting PKD1.

In certain embodiments, a method of enhancing PKD2 gene expression in a cell comprises administering to the cell an oligomeric compound targeted to a PKD2 mRNA transcript (GenBank No: NM_000297.4, SEQ ID NO: 49). In certain embodiments, enhancing PKD2 gene expression in a cell treats a subject suffering from a PKD2 related disease. In certain embodiments, the PKD2 related disease is related to a decreased level of PKD2 protein. In a preferred embodiment, the oligomeric compound is an ACT-UP1 compound targeting PKD2.

In certain embodiments, a method of enhancing HBB gene expression in a cell comprises administering to the cell an oligomeric compound targeted to an HBB mRNA transcript (GenBank No: NM_000518.5, SEQ ID NO: 50). In certain embodiments, enhancing HBB gene expression in a cell treats a subject suffering from an HBB related disease. In certain embodiments, the HBB related disease is related to a decreased level of HBB protein. In a preferred embodiment, the oligomeric compound is an ACT-UP1 compound targeting HBB.

In certain embodiments, a method of enhancing GRN gene expression in a cell comprises administering to the cell an oligomeric compound targeted to a GRN mRNA transcript (GenBank No: NM_002087.4, SEQ ID NO: 51). In certain embodiments, enhancing GRN gene expression in a cell treats a subject suffering from a GRN related disease. In a preferred embodiment, the oligomeric compound is an ACT-UP1 compound targeting GRN.

In certain embodiments, a method of enhancing SCN1A gene expression in a cell comprises administering to the cell an oligomeric compound targeted to a SCN1A mRNA transcript (GenBank No: NM_001165963.4, SEQ ID NO: 52). In certain embodiments, enhancing SCN1A gene expression in a cell treats a subject suffering from a SCN1A related disease. In certain embodiments, the SCN1A related disease is related to a decreased level of SCN1A protein. In a preferred embodiment, the oligomeric compound is an ACT-UP1 compound targeting SCN1A.

In some embodiments of the present disclosure, the subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perissodactyla, including Equines (horses). In some aspects, the mammals are of the order Primates, Ceboids, or Simoids (monkeys) or of the order Anthropoids (humans and apes). In a preferred aspect, the mammal is a human.

In Vivo Testing of ACT-UP1 Compounds

In some embodiments of the present disclosure, ACT-UP1 compounds can be tested in subjects to assess their ability to enhance expression of a protein. In certain embodiments, ACT-UP1 compounds can be tested in subjects to assess their ability to increase mRNA translation in order to increase protein production and/or produce phenotypic changes related to that protein. In certain embodiments, ACT-UP1 compounds can be tested in subjects to assess their ability to treat a disease associated with the protein. Testing may be performed in normal subjects, or in experimental disease models. For administration to subjects, ACT-UP1 compounds are formulated in a pharmaceutically acceptable diluent, such as phosphate-buffered saline. Administration includes parenteral routes of administration, such as intraperitoneal, intravenous, and subcutaneous. Calculation of ACT-UP1 dosage and dosing frequency depends upon factors such as route of administration and subject's body weight. In one embodiment, following a period of treatment with an ACT-UP1 compound, the protein is isolated from a tissue and changes in protein expression are measured.

In Vitro Assay to Identify ACT-UP1 Compounds for Enhancing Protein Expression

In some embodiments of the present disclosure, in vitro assays to identify ACT-UP1 compounds for enhancing target protein expression are provided.

In one example, a test mRNA is chosen as a target to upregulate its protein expression. Cells in culture (e.g., HeLa, Hepa1-6, or HEK293), are seeded and grown in one day to ~70% confluency. The cells are then transfected with the ACT-UP1 compounds of interest at about 7.5 nM or 15 nM final concentrations using Lipofectamine™ 2000 Transfection Reagent (ThermoFisher Scientific, Waltham, MA), or are mock transfected as a control. Twenty-four (24) hr after transfection, cells are harvested and lysed, then the protein is extracted using RIPA Lysis and Extraction Buffer (ThermoFisher Scientific, Waltham, MA). The level of target protein can be determined by Western Blot or chemiluminescence, using a target protein specific antibody and optionally, a secondary antibody conjugated to either alkaline phosphatase or horse radish peroxidase. Western Blot images can be quantified using ImageJ (an open source software for processing and analyzing scientific images), and the results are quantified as percent protein levels relative to mock transfected cells following normalization to a loading control protein such as GAPDH or nucleolin (NCL). As the control protein is not targeted by the ACT-UP1 compounds tested in the assay, the level of the control protein is not affected, showing the specificity of the ACT-UP1 compounds in modulating target protein levels.

Advantages of the Invention

Many biological steps are involved in protein expression, e.g., RNA transcription, pre-mRNA splicing, mRNA stability, translation, and protein stability. Difficulties at any of these steps can lead to a decrease in protein expression or the production of nonfunctional protein, e.g., missense or nonsense mutations can lead to haploinsufficiency.

Antisense compounds are maturing for use in therapeutic methods with several now commercially available for treatment of various diseases (Crooke, S. T., et al., 2021c, Antisense drug discovery and development technology considered in a pharmacological context. Biochem Pharmacol 189: 114196). As disclosed herein, antisense oligonucleotide (ASO) Coupled Translation-Upregulation 1 (also known as ACT-UP1) is a novel method to enhance protein expression. Also disclosed herein, a new class of antisense compounds, ACT-UP1 compounds, was developed for the novel approach to increase protein levels without the need of existing inhibitory elements in the target mRNAs. These ACT-UP1 compounds have been shown herein to increase the protein levels of multiple genes.

The ACT-UP1 compound comprises an antisense oligonucleotide (ASO) joined to a protein recruiting sequence (PRS). Without being bound by any particular theory, the ASO component of the ACT-UP1 compound specifically hybridizes to a mRNA sequence of interest, bringing the PRS component of the ACT-UP1 compound into close proximity to the target mRNA. The PRS component attracts translation regulatory proteins to the target mRNA, facilitating the interaction of the translation-related proteins with the mRNA of interest, thereby increasing translation of the targeted mRNA.

The PRS is a short single-strand sequence of linked nucleosides that can interact and/or bind with regulatory proteins. Single-stranded RNA can bind more proteins than double-stranded RNA (Liang, X. H., et al., 2015, Identification and characterization of intracellular proteins that bind oligonucleotides with phosphorothioate linkages. Nucleic Acids Res 43: 2927-2945). Thus, single-strand sequences were assessed for their protein recruiting ability as the PRS component of ACT-UP1.

$m^6A$ RNA methylation plays an important role in the regulation of gene expression (He and He, $m^6A$ RNA Methylation: From Mechanisms to Therapeutic Potential, EMBO, 2021 Feb. 1, 40(3):e105977), where specific proteins involved in the $m^6A$ RNA methylation such as METTL3, an RNA methyltransferase, enhance mRNA translation through interaction with the cellular translation initiation machinery (Lin et al., METTL3 Promotes Translation in Human Cancer Cells, Mol Cell. 2016, 62(3):335-345; Choe et al., mRNA Circularization by METTL3-eIF3h Enhances Translation and Promotes Oncogenesis), Among the many components in the $m^6A$ methyltransferase complex, METTL3 forms a heterodimer with METTL14 to mediate adenine (A) to $N^6$-methyl-adenosine ($m^6A$) conversion in mRNA. The METTL3-METTL14 complex identifies a consensus sequence, DRACH (D is adenine (A), guanine (G) or thymine (T); R is adenine (A) or guanine (G); A is adenine (A); C is cytosine (C); H is adenine (A), cytosine (C) or uracil (U)) (He and He, EMBO, 2021 Feb. 1, 40(3):e105977). Examples of DRACH include, but are not limited to, the sequence GGACU (SEQ ID NO: 8) that can mediate $N^6$-methyl-adenosine ($m^6A$) conversion (Liu et al., A METTL3-METTL14 Complex Mediates Mammalian Nuclear RNA $N^6$-Adenosine Methylation, Nat Chem Biol, 2014, 10(2):93-95). Sequences derived from GGACU sequence in mRNA (e.g., GGACU (SEQ ID NO: 8), GGAUU (SEQ ID NO: 9), GGACUGGAC (SEQ ID NO: 10), GGACUGGACU (SEQ ID NO: 11), ACGGACUUGGACU (SEQ ID NO: 12)), and GGACUGGACUGGACU (SEQ ID NO: 101)), were designed as the PRS component in ACT-UP1 compounds and tested in the examples hereinbelow.

Other sequences derived from the DRACH consensus sequence are also contemplated for the PRS component of ACT-UP1 (e.g., AAACAAAACA (SEQ ID NO: 99). Also contemplated are PRS components derived from the RRANN consensus sequence (R is an Adenine or Guanine; A is an Adenine; and N is an Adenine, Guanine, Cytosine, Thymine or Uracil) or RRAWN consensus sequences (R is an Adenine or Guanine; A is an Adenine; W is an Adenine or Cytosine; and N is an Adenine, Guanine, Cytosine, Thymine or Uracil) in mRNA. PRS sequences derived from DRACH, RRANN or RRAWN consensus sequences include, but are not limited to, any of the following: 5 to 20 linked nucleosides comprising the sequences of GGACU (SEQ ID NO: 8), GGAUU (SEQ ID NO: 9), GAACU (SEQ ID NO: 41), AGACU (SEQ ID NO: 42), AAACU (SEQ ID NO: 43), GGACA (SEQ ID NO: 44), AAACA (SEQ ID NO: 154), or combinations thereof. For example, the PRS can comprise two to four repeats of sequence elements GGACU, GAACU, AGACU, AAACU or GGACA, or combinations thereof.

The 3UTR of mRNAs play important roles in modulating translation through interactions with miRNAs or proteins (Hong, D., and S. Jeong, 2023, 3'UTR Diversity: Expanding Repertoire of RNA Alterations in Human mRNAs. Mol Cells 46: 48-56). For example, it has been known that poly(A) binding proteins (PABPs) that interact with 3' UTR poly(A) tail are required for translation. Sequences derived from the poly(A) tail in mRNA (e.g., AAACUAAACU (SEQ ID NO: 13), AAAAAAAA (poly(A)s) (SEQ ID NO: 14), AAAAAAAAAA (poly(A)$_{10}$ (SEQ II) NO: 15), AAACAAAACA (SEQ ID NO: 99), or AAAAAAAAAAAA (poly(A)$_{12}$ (SEQ ID NO: 102)) were designed as the PRS component in ACT-UP1 compounds and tested in the examples hereinbelow.

Although some methylation target sites and poly(A) tails have been associated with proteins related to translation as discussed above, the idea of using these RNA sequences outside of their natural mRNA environment to attract and recruit translation related proteins is a novel and inventive concept. In other words, naturally occurring cis-elements in mRNAs (e.g., DRACH consensus sequence, GGACU (SEQ ID NO: 8) and/or poly(A) tail) were transformed into trans-elements (i.e., the PRS) for use in ACT-UP1 compounds that can be administered to a subject to modulate gene expression. These PRSs were further transformed to make novel new PRSs as disclosed herein by chemically modifying the sequences to stabilize them, adding nucleobases to the sequences and/or changing the nucleobase sequences in order to improve the protein recruiting function of these PRSs.

Unexpectedly, ACT-UP1 compounds coupling short PRSs with ASOs were shown to be effective in enhancing protein expression. As shown in the examples, hereinbelow, ACT-UP1 compounds were effective in upregulating gene expression of multiple targets and ACT-UP1 mediated protein upregulation was achieved both in vitro and in vivo. Thus, the ACT-UP1 approach has the potential to dramatically increase the number of targetable genes and extends potential therapeutic treatment to broader disease areas in subjects who need enhanced protein expression e.g., haploinsufficient patients.

The ACT-UP1 approach and compound have several advantages as follows.

As antisense compounds, ACT-UP1 compounds have the mature delivery, chemistry and stability of antisense compounds. The tolerability of different chemical modifications in supporting the specificity and activity of antisense compounds allows longer duration and less frequent dosing.

ACT-UP1 compounds comprise a short PRS. The short length of the PRS element contributes to the short length of the ACT-UP1 compound allowing easier and shorter synthesis of the compound and use of less materials for synthesis of the compound. Short ACT-UP1 compounds make for easier entry into cells or tissue, an important requirement for safe and effective application of therapeutic agents.

ACT-UP1 compounds can theoretically be used to upregulate any protein of interest as the ASO element of the ACT-UP1 compound can be designed to target any mRNA transcript and the PRS element enhances protein expression irrespective of target.

ACT-UP1 compounds do not require co-delivery of exogenous proteins. Instead, the ACT-UP1 compound upon administration to subject is complete in and of itself to enhance target protein expression as it recruits a cell's endogenous translation proteins to the target mRNA. Therefore, ACT-UP1 compounds can be applied as therapeutic agents with relative ease.

ACT-UP1 compounds acting mainly by increasing translation without affecting stability of target mRNA may be more suitable as a treatment option for haplo-insufficient patients wherein return to normality of a target protein may be no more than 2-fold or about 2-fold of the protein level observed in the haplo-insufficient patients avoiding massive overexpression of the target protein.

ACT-UP1 compounds comprise modular components, accommodating additional elements to be added to the compounds. For example, when significantly high protein expression levels are desired. ACT-UP1 compounds may incorporate an ARE-targeting sequence to further stabilize the target mRNA. With both a higher steady state level of mRNA and increased translation of any single target mRNA due to the PRS, significantly high protein level is achieved as shown for the dual functional ACT-UP1 compound targeting FGF21 mRNA, as shown infra.

ACT-UP1 compounds permit versatility of adjusting or fine-tuning protein expression level of a target mRNA in a cell based on the design of the ACT-UP compounds by choice of ACT-UP1 binding site location in a target mRNA, modification of the ACT-UP1 sequence, length of PRS, type of PRS, location of the PRS in relation to the ASO, presence of an existing element (e.g., an ARE-target sequence), and dose of ACT-UP1 compounds.

EXAMPLES

Non-Limiting Disclosure and Incorporation-by-Reference

While certain compounds, compositions and methods described herein have been described with specificity in accordance with certain embodiments, the following examples serve only to illustrate the compounds described herein and are not intended to limit the same. Each of the references recited in the present application is herein incorporated-by-reference in its entirety.

The following applies to all modified sequences disclosed herein.

A notation is made before or after each nucleoside indicating the type of chemical modification, if any, made to the nucleoside. If no modification notation is made before or after a letter designating a nucleoside, the nucleoside is a deoxyribonucleoside. Notations for the chemical modifications to the compounds can be found as follows:

"(5p)" before a nucleoside refers to a 5'-phosphate

"r" before a nucleoside refers to a ribonucleoside (ribonucleoside which has been substituted for a deoxyribonucleoside)

"d" (or no notation made before or after a nucleoside) before a nucleoside refers to a deoxyribonucleoside "f" before a nucleoside refers to a 2'-fluoro (2'-F) sugar modification "m" before a nucleoside refers to a 2'-OCH$_3$ (also known as 2'-O-methyl, 2'-OMe) modification "e" before a nucleoside refers to a 2'-O(CH$_2$)OCIH3 (also known as 2'-O-(2-methoxyethyl), 2'-O-MOE, 2'-MOE) modification "eCm" refers to a 2'-O-MOE modified 5-methylcytidine "*" refers to a phosphorothioate (PS) linkage which has been substituted for a phosphate (PO) linkage "gna" before a nucleoside refers to a glycol nucleic acid modification "L" after a nucleoside refers to a locked nucleic acid (LNA) modification of the nucleoside "GL-GalNAc" is a GalNAc moiety described by Sharma et al. (2018, Bioconjugate Chem, 29:2478-2488)

"AN-GalNAc" is a GalNAc moiety described in WO2024137545.

If more than one sequence is disclosed in one row of the tables, the SEQ ID NO applies to the modified sequence ("Sequence+Chemistry"). Bolded and underlined sequences denote the PRS of an ACT-UP1 compound.

Example 1: ACT-UP1 Compounds Increase Jagged 1 Protein Levels

Alagille syndrome (ALGS) is a rare genetic disease mainly caused by a haploinsufficiency mutation(s) of the JAG1 gene (i.e., one allele of JAG1 remains wild type, whereas the other allele contains a mutation(s) that disrupts the normal production and/or function of the Jagged 1 protein) (Kohut, T. J., et al., 2021, Alagille Syndrome: A Focused Review on Clinical Features, Genetics, and Treatment. Semin Liver Dis 41:525-537). Such mutation(s) leads to insufficient levels of functional Jagged 1 protein, resulting in impaired development of the bile ducts in the liver. The impaired bile ducts lead to accumulation of bile acids in liver and blood, thus causing liver and other tissue damage. Therefore, restoration of the expression of functional Jagged 1 protein is expected to have therapeutic potential for ALGS.

ACT-UP1 compounds targeting human JAG1 mRNA (GenBank NM_000214.3; SEQ ID NO: 1) were designed to assess whether they can increase JAG1 expression. The ACT-UP1 compounds comprise 2 elements coupled together: (1) an antisense oligonucleotide targeting JAG1 mRNA (JAG1 ASO), and (2) a protein recruiting sequence (PRS).

The ASO element of the ACT-UP1 compounds was designed to bind to the 3'UTR of JAG1 mRNA (SEQ ID NO: 1) approximately 160 nucleotides downstream from the stop codon.

The PRS elements of the ACT-UP1 compounds were designed as a single stranded sequence with one GGACU (SEQ ID NO: 8) sequence frequently found as m6A modification sites in mRNAs (Linder, B., et al., 2015, Single-nucleotide-resolution mapping of m6A and m6Am throughout the transcriptome. Nat Methods 12: 767-772) or with an incomplete repeat of the GGACU sequence i.e., GGACUGGAC (SEQ ID NO: 10). The GGACU sequence may recruit cellular proteins to modify the adenosine nucleotide and may modulate translation (Meyer, K. D., 2019, m(6)A-mediated translation regulation. Biochim Biophys Acta Gene Regul Mech 1862: 301-309). The PRS elements in the ACT-UP1 compounds are shown as the bolded and underlined sequences in Table 1.

A compound only comprising the JAG1 ASO, ATXL228, targeting the same JAG1 mRNA sequence as the ACT-UP1 compounds was used as a control.

To protect the compounds from nuclease degradation, the compounds were modified with 2'-O-methyl (also known as 2'-OMe) which was noted as "m" in front of the nucleotides modified as shown in Table 1.

TABLE 1

| Sequence and Chemistry of Compounds | | | |
|---|---|---|---|
| Compound | Sequence and Chemistry (5' to 3') | Sequence (5' to 3') | SEQ ID NO |
| ATXL228 (JAG1 ASO) | mAmAmCmCmAmCmAmGm AmAmAmCmUmAmCmCmA | AACCACAGA AACUACCA | 16 |
| ATXL261 (PRS + JAG1 ASO) | mGmGmAmCmU mAmAmCmCmAmCmAmGm AmAmAmCmUmAmCmCmA | GGACUAACC ACAGAAACU ACCA | 17 |
| ATXL193 (PRS + JAG1 ASO) | mGmGmAmCmUmGmGmAmC mAmAmCmCmAmCmAmGmA mAmAmCmUmAmCmCmA | GGACUGGAC AACCACAGA AACUACCA | 18 |

In Vitro Assay

HeLa cells, seeded and grown in one day to ~70% confluency, were transfected with the compounds listed in Table 1 at 7.5 nM or 15 nM final concentrations using Lipofectamine 2000 Transfection Reagent (ThermoFisher Scientific, Waltham, MA), or were mock transfected as a control. Twenty-four (24) hr after transfection, cells were harvested and lysed, then the protein was extracted using RIPA Lysis and Extraction Buffer (ThermoFisher Scientific, Waltham, MA). The level of Jagged 1 protein was determined by Western Blot, using a Jagged 1 specific antibody (ab109536 from Abcam, Waltham, MA). The Western result is shown in FIG. 2. The Western Blot image was quantified using ImageJ, and the results are shown in Table 2 as percent protein levels relative to mock transfected cells following normalization to a loading control protein, GAPDH. GAPDH was not targeted by the assay compounds and the level of GAPDH was not affected, suggesting the specificity of the compounds in modulating the target protein levels.

TABLE 2

| Jagged 1 Protein Levels in Cells Treated with Different Compounds | | | | | | |
|---|---|---|---|---|---|---|
| Compound | Mock (no treatment) | ATXL193 | | ATXL261 | | ATXL228 |
| Concen-tration (nM) | n/a | 7.5 | 15 | 7.5 | 15 | 7.5 | 15 |
| Jagged 1 protein level % | 100 | 135.8 | 144.7 | 120.4 | 111.6 | 89.9 | 100.5 |

The results show that the ACT-UP1 compounds, ATXL193 and ATXL261, can increase the targeted Jagged 1 protein levels. The results also show that increasing the length of the PRS (ATXL193) increased expression of the Jagged 1 protein more than a shorter PRS (ATXL261). On the other hand, control JAG1 ASO ATXL228 that lacks the PRS but has the same mRNA binding sequence as the two ACT-UP1 compounds did not increase Jagged1 protein level, indicating the importance of the presence of the PRS in upregulating JAG1 expression.

Example 2. The Position of the Protein Recruiting Sequence (PRS) Affects Activity The above ACT-UP1 compounds tested contain the protein recruiting sequence (PRS) at the 5' end of the ACT-UP1 compounds. To determine if ACT-UP1 compounds with 3' PRSs can also increase protein levels, an ACT-UP1 compound, ATXL384, was designed and synthesized. ATXL384 has the same mRNA binding domain as previously described for ATXL193 in Example 1, supra, and in Table 3, infra, but the PRS is placed at the 3' end of the ACT-UP1 compound instead of the 5' end of the JAG1 ASO. The PRSs tested are shown as the bolded and underlined sequences in Table 3. The sequence and chemistry of ATXL384 are listed in Table 3.

TABLE 3

Sequence and Chemistry of ATXL193 and ATXL384

| Compound | Sequence and Chemistry (5' to 3') | Sequence (5' to 3') | SEQ ID NO. |
|---|---|---|---|
| ATXL193 (PRS + JAG1 ASO) | mGmGmAmCmUmGmGmAmC mAmAmCmCmAmCmAmGmA mAmAmCmUmAmCmCmA | GGACUGGAC AACCACAGA AACUACCA | 18 |
| ATXL384 (JAG1 ASO + PRS) | mAmAmCmCmAmCmAmGmA mAmAmCmUmAmCmCmAm GmGmAmCmUmGmGmAmC | AACCACAGA AACUACCAG GACUGGAC | 19 |

In Vitro Assay

HeLa cells, seeded and grown in one day to ~70% confluency, were transfected with the compounds listed in Table 3 at 7.5 nM or 15 nM final concentrations using Lipofectamine™ 2000 Transfection Reagent (ThermoFisher Scientific, Waltham, MA), or were mock transfected as a control. Twenty-four (24) hr after transfection, cells were harvested and lysed, then the protein was extracted using RIPA Lysis and Extraction Buffer (ThermoFisher Scientific, Waltham, MA). The level of Jagged 1 protein was determined by Western Blot, using a Jagged 1 specific antibody (ab109536 from Abcam, Waltham, MA). The Western result is shown in FIG. 3. The Western Blot was quantified using Image J, and the results are shown in Table 4 as percent protein levels relative to mock transfected cells following normalization to a loading control protein, GAPDH. GAPDH was not targeted by the assay compounds and the level of GAPDH was not affected, suggesting the specificity of the compounds in modulating the target protein levels.

TABLE 4

Jagged 1 Protein Levels in HeLa Cells

| Compound | Mock (no treatment) | ATXL193 | | ATXL384 | |
|---|---|---|---|---|---|
| Concentration (nM) | n/a | 7.5 | 15 | 7.5 | 15 |
| Jagged 1 protein level % | 100 | 167.1 | 185.9 | 122.4 | 113.9 |

The results show that ACT-UP1 compound ATXL384 with a 3' PRS failed to substantially increase Jagged 1 protein level, whereas under the same experimental conditions, the ACT-UP1 compound ATXL193 that contains a 5' PRS again successfully increased Jagged1 protein level, indicating the importance of the position of the PRS in the ACT-UP1 compound.

Example 3. The ASO Binding Position in the mRNA can Affect ACT-UP1 Activity

To determine whether ASO binding position within the 3' UTR of a target mRNA affects an ACT-UP1 compound's activity in increasing protein levels, ACT-UP1 compounds were designed to bind to approximately 50 (ATXL257), 100 (ATXL258), 500 (ATXL259), and 1000 (ATXL260) nucleotides downstream from the stop codon of JAG1 mRNA. These ACT-UP1 compounds contained the same PRSs (bolded and underlined sequences) at the 5' end of the JAG1 ASOs as shown in Table 5.

To protect the compounds from nuclease degradation, the compounds were modified with 2'-O-methyl (also known as 2'-OMe) which was noted as "m" in front of the nucleosides modified as shown in Table 5. To further enhance stability of the compounds, two phosphorothioate (PS) modifications were introduced next to the first two nucleosides and denoted by "*" in Table 5.

TABLE 5

Sequence and Chemistry of JAGI ACT-UP1 Compounds Targeting Different Positions within the 3' UTR of JAG1 mRNA

| Compound | Sequence and Chemistry (5' to 3') | Sequence (5' to 3') | SEQ ID NO |
|---|---|---|---|
| ATXL257 (PRS + JAG1 ASO) | mG*mG*mAmCmUmGmGmAmCmU mGmUmUmUmAmAmGmAmAmC mUmAmCmAmAmGmCmC | GGACUGGACUGUUUA AAGAACUACAAGCC | 20 |
| ATXL258 (PRS + JAG1 ASO) | mG*mG*mAmCmUmGmGmAmCmU mGmGmAmUmUmCmUmAmAmGmU mCmAmGmCmAmA | GGACUGGACUGGAUU CUAAGUCAGCAA | 21 |
| ATXL259 (PRS + JAG1 ASO) | mG*mG*mAmCmUmGmGmAmCmU mUmGmCmUmGmUmGmGmUmUmC mUmGmAmGmCmUmG | GGACUGGACUUGCUG UGGUUCUGAGCUG | 22 |
| ATXL260 (PRS + JAG1 ASO) | mG*mG*mAmCmUmGmGmAmCmU mCmUmGmCmAmGmCmAmGmAmU mCmAmCmCmUmGmC | GGACUGGACUCUGCA GCAGAUCACCUGC | 23 |

In Vitro Assay

HeLa cells, seeded and grown in one day to ~70% confluency, were transfected with the compounds listed in Table 5 at 7.5 nM or 15 nM final concentrations using Lipofectamine™ 2000 Transfection Reagent (ThermoFisher Scientific, Waltham, MA), or were mock transfected as a control. Twenty-four (24) hr after transfection, cells were harvested and lysed, then the protein was extracted using RIPA Lysis and Extraction Buffer (ThermoFisher Scientific, Waltham, MA). The level of Jagged 1 protein was determined by Western Blot, using a Jagged 1 specific antibody (ab109536 from Abcam, Waltham, MA). The Western result is shown in FIG. 4. The Western Blot was quantified using Image J, and the results are shown in Table 6 as percent protein levels relative to mock transfected cells following normalization to a loading control protein, GAPDH. GAPDH was not targeted by the assay compounds and the level of GAPDH was not affected, suggesting the specificity of the compounds in modulating the target protein levels.

compounds are listed in Table 7. PS was denoted by "*", 2'-OMe was denoted as "m", and 2'-MOE was denoted by "e", and 2'-MOE modified 5-methylcytidine was denoted as "eCm" in Table 7.

The ACT-UP1 compounds contained the same PRSs (bolded and underlined sequences) at the 5' end of the JAG1 ASOs as shown in Table 7.

TABLE 7

Sequence and Chemistry of Jagged 1 ACT-UP1 Compounds with Varying PS Numbers

| Compound | Sequence and Chemistry (5' to 3') | Sequence (5' to 3') | SEQ ID NO |
|---|---|---|---|
| ATXL234 (PRS + JAG1 ASO) | mG*mG*mAmCmUmGmGmAmCmU eA*eA*eCm*eCm*eA*eCm* eA*eG*eA*eA*eA*eCm* eT*A*cCm*eCm*eA | GGACUGGACUA ACCACAGAAAC TACCA | 24 |

TABLE 6

Jagged 1 Protein Levels in Cells Treated with ACT-UP1 Compounds Targeting Different Positions within the 3' UTR of JAG1 mRNA

| Compound | Mock (no treatment) | ATXL257 | | ATXL258 | | ATXL259 | | ATXL260 | |
|---|---|---|---|---|---|---|---|---|---|
| Concentration (nM) | n/a | 7.5 | 15 | 7.5 | 15 | 7.5 | 15 | 7.5 | 15 |
| Jagged 1 protein % | 100 | 153.3 | 187.9 | 138.1 | 132.8 | 107.6 | 102.8 | 64.1 | 57.4 |

The results showed that ACT-UP1 compounds with ASOs targeting different positions within the 3' UTR had different activity in increasing protein levels. ASO binding to positions closer to the stop codon had better activity. These results further suggest that positions closer to stop codon may be preferentially targeted.

Example 4. ACT-UP1 Compounds Containing PS and 2'-MOE Modifications

For antisense oligonucleotides (ASOs) previously described in the art, phosphorothioate (PS) backbone modification is commonly used to increase nuclease resistance, enhance cellular uptake, and improve ASO drug performance. Thus, ACT-UP1 compounds were designed with PS backbone modifications.

Different numbers of PS backbone modifications were introduced into an ACT-UP1 compound similar to ATXL193 (previously described, supra), generating alternative ACT-UP1 compounds ATXL234 and ATXL262. In addition, since 2'-O-(2-methoxyethyl) (also known as 2'-O-MOE, 2'-MOE or MOE) modifications have been successfully used in ASO drugs with excellent safety benefits (Crooke, S. T., et al., 2021a, Antisense technology: an overview and prospectus. Nat Rev Drug Discov 20: 427-453), 2'-MOE modifications were introduced into the ASO portion of an ACT-UP1 compound, where the ASO hybridizes with the target JAG1 mRNA sequence. To avoid potential effects of 2'-MOE on protein binding to the protein recruiting sequence (PRS) due to the bulky size of 2'-MOE, PRS was modified with 2'-OMe. The sequence and chemistry of these ACT-UP1

TABLE 7-continued

Sequence and Chemistry of Jagged 1 ACT-UP1 Compounds with Varying PS Numbers

| Compound | Sequence and Chemistry (5' to 3') | Sequence (5' to 3') | SEQ ID NO |
|---|---|---|---|
| ATXL262 (PRS + JAG1 ASO) | mG*mG*mAmCmUmGmGmAmCmU eAeAeCm*eCm*eA*eCm*eA* eG*eA*eA*eA*eCm*eT*eA* eCm*eCm*eA | GGACUGGACUA ACCACAGAAAC TACCA | 25 |

In Vitro Assay

HeLa cells, seeded and grown in one day to ~70% confluency, were transfected with the compounds listed in Table 7 at 7.5 nM or 15 nM final concentrations using Lipofectamine™ 2000 Transfection Reagent (ThermoFisher Scientific, Waltham, MA), or were mock transfected as a control. Twenty-four (24) hr after transfection, cells were harvested and lysed, then the protein was extracted using RIPA Lysis and Extraction Buffer (ThermoFisher Scientific, Waltham, MA). The level of Jagged 1 protein was determined by Western Blot, using a Jagged 1 specific antibody (ab109536 from Abcam, Waltham, MA). The Western result is shown in FIG. 5. The Western Blot was quantified using Image J, and the results are shown in Table 8 as percent protein levels relative to mock transfected cells following normalization to a loading control protein, GAPDH. GAPDH was not targeted by the assay compounds and the level of GAPDH was not affected, suggesting the specificity of the compounds in modulating the target protein levels.

TABLE 8

Jagged 1 Protein Levels in Cells Treated with
ACT-UP1 compounds with Different Numbers of PS

| Compound | Mock (no treatment) | ATXL234 | | ATXL262 | |
|---|---|---|---|---|---|
| Concentration (nM) | n/a | 7.5 | 15 | 7.5 | 15 |
| Jagged 1 protein level % | 100 | 113.7 | 140.6 | 12.7.4 | 139.3 |

The results indicate that ACT-UP1 compounds with multiple PS and 2'-MOE modifications can also increase Jagged 1 protein levels, and that 14 or 16 PS modifications in the ACT-UP1 compound do not show significant differences in ACT-UP1 activity.

Example 5. ACT-UP1 Compound can Increase Jagged 1 Protein Levels in a Different Cell Type The effect of the above-described ACT-UP1 compound ATXL193 was also assessed in HEK293 cells. Cells were transfected with ATXL193 at different concentrations using Lipofectamine™ 2000 Transfection Reagent (ThermoFisher Scientific, Waltham, MA), or were mock transfected as a control. Twenty-four (24) hr after transfection, cells were harvested and lysed, then the protein was extracted using RIPA Lysis and Extraction Buffer (ThermoFisher Scientific, Waltham, MA). The level of Jagged 1 protein was determined by Western Blot, using a Jagged 1 specific antibody (ab109536 from Abcam, Waltham, MA). The Western result is shown in FIG. 6. The Western Blot was quantified using Image J, and the results are shown in Table 9 as percent protein levels relative to mock transfected cells following normalization to a loading control protein, GAPDH. GAPDH was not targeted by the assay compounds and the level of GAPDH was not affected, suggesting the specificity of the compounds in modulating the target protein levels.

TABLE 9

Jagged 1 Protein Levels in HEK293 Cells Treated with ATXL193

| Compound | Mock (no treatment) | ATXL193 | | |
|---|---|---|---|---|
| Concentration (nM) | n/a | 15 | 30 | 60 |
| Jagged 1 protein level % | 100 | 140.7 | 126.5 | 93.6 |

The result indicates that Jagged 1 protein levels can also be increased in HEK293 cells using an ACT-UP1 compound, suggesting that this upregulation phenotype is not unique to a specific cell type.

Example 6. Rab9 Protein Level can be Increased Using an ACT-UP1 Compound

To determine whether ACT-UP1 compounds can increase other protein levels besides Jagged 1, an ACT-UP1 compound was designed to target RAB9 which encodes a protein involved in the endolysosomal system. The ACT-UP1 compound was designed to bind an 18 nucleotide region of the RAB9 mRNA approximately 90 nt downstream from the stop codon of human RAB9A mRNA (GenBank No: NM_004251.5, SEQ ID NO: 2). To determine if altering the length and position of the ACT-UP1 PRS can affect protein level increases, two additional nucleosides were added to the 5' end of the PRS and one nucleoside was introduced into the middle of the two GGACU sequences. The sequence and chemistry are shown in Table 10. PS was denoted by "*" and 2'-OMe was denoted as "m" in Table 10. The PRS of the ACT-UP1 compound is the bolded and underlined sequence at the 5' end of the RAB9 ASO as shown in Table 10.

TABLE 10

Sequence and Chemistry of ATXL230

| Compound | Sequence and Chemistry (5' to 3') | Sequence (5' to 3') | SEQ ID NO |
|---|---|---|---|
| ATXL230 (PRS + RAB1 ASO) | mA*mC*mGmGmAmCmUmUm GmGmAmCmUmCmUmGmCmU mGmCmAmAmAmCmGmCmU* mA*mA | ACGGACUUGG ACUCUGCUGC AAACGCUAA | 26 |

In Vitro Assay

HeLa cells, seeded and grown in one day to ~70% confluency, were transfected with the ACT-UP1 compound ATXL230 at 5 nM, 10 nM, 20 nM, and 40 nM final concentrations using Lipofectamine™ 2000 Transfection Reagent (ThermoFisher Scientific, Waltham, MA), or were mock transfected as a control. Twenty-four (24) hr after transfection, cells were harvested and lysed, then the protein was extracted using RIPA Lysis and Extraction Buffer (ThermoFisher Scientific, Waltham, MA). The level of RAB9 protein was determined by Western Blot, using a RAB9 specific antibody (ab2810 from Abcam, Waltham, MA). The Western result is shown in FIG. 7. The Western Blot was quantified using Image J, and the results are shown in Table 11 as percent protein levels relative to mock transfected cells following normalization to a loading control protein, GAPDH. GAPDH was not targeted by the assay compounds and the level of GAPDH was not affected, suggesting the specificity of the compounds in modulating the target protein levels.

TABLE 11

Rab9 Protein Level in HeLa Cells Treated with ATXL230

| Compound | Mock (no treatment) | ATXL230 | | | |
|---|---|---|---|---|---|
| Concentration (nM) | n/a | 5 | 10 | 20 | 40 |
| Rab9 protein level % | 100 | 112.7 | 125.5 | 113.6 | 100.7 |

The results indicate that Rab9 protein can also be increased using an ACT-UP1 compound, despite the compound containing a PRS (13 nt) lengthened with additional nucleotides.

Example 7. RNase H1 Protein can be Increased Using an ACT-UP1 Compound

RNase H1 protein is an endonuclease involved in R-loop solving and genome integrity (Cerritelli, S. M., and R. J. Crouch, 2019 RNases H: Multiple roles in maintaining genome integrity. DNA Repair (Amst) 84: 102742). Increasing the level of this protein has a potential benefit to treating Myelodysplastic Syndrome (Chen, L., et al., 2018, The Augmented R-Loop Is a Unifying Mechanism for Myelodysplastic Syndromes Induced by High-Risk Splicing Factor Mutations. Mol Cell 69: 412-425 e416). An ACT-UP1 compound, ATXL231, was designed to bind to the 3'UTR of human RNase 1-11 with 18 nucleosides hybridizing to RNase H mRNA approximately 80 nucleotides downstream from the stop codon of human RNase H mRNA (GenBank No: NM_001286834.3, SEQ ID NO: 3). ATXL231 targeting RNase H1 was designed with the same PRS as previously described for ATXL230 targeting RAB9. The sequence and chemistry for ATXL231 are shown in Table 12. PS was denoted by "*" and 2'-OMe was denoted as "m" in Table 12. The PRS of the ACT-UP1 compound is the bolded and underlined sequence at the 5' end of the RNase H1 ASO, as shown in Table 12.

TABLE 12

Sequence and Chemistry of ATXL231

| Compound | Sequence and Chemistry (5' to 3') | Sequence (5' to 3') | SEQ ID NO |
|---|---|---|---|
| ATXL231 (PRS + RNase H1 ASO) | mA*mC*mGmGmAmCm UmUmGmGmAmCmUm CmAmAmUmGmGmUm CmCmUmAmCmCmU* mG*mC | ACGGACUUGG ACUCAAUGGU CCUACCUGC | 27 |

In Vitro Assay

HeLa cells, seeded and grown in one day to ~70% confluency, were transfected with the ACT-UP1 compound ATXL231 at 5 nM, 10 nM, 20 nM, and 40 nM final concentrations using Lipofectamine™ 2000 Transfection Reagent (ThermoFisher Scientific, Waltham, MA), or were mock transfected as a control. Twenty-four (24) hr after transfection, cells were harvested and lysed, then the protein was extracted using RIPA Lysis and Extraction Buffer (ThermoFisher Scientific, Waltham, MA). The level of RNase H1 protein was determined by Western Blot, using an RNase H1 specific antibody (15606-1-AP from Proteintech®, Rosemont, IL). The Western result is shown in FIG. 8. The Western Blot was quantified using Image J, and the results are shown in Table 13 as percent protein levels relative to mock transfected cells following normalization to a loading control protein, GAPDH. GAPDH was not targeted by the assay compounds and the level of GAPDH was not affected, suggesting the specificity of the compounds in modulating the target protein levels.

TABLE 13

RNase H1 Protein Level in HeLa Cells Treated with ATXL231

| Compound | Mock (no treatment) | ATXL231 | | | |
|---|---|---|---|---|---|
| Concentration (nM) | n/a | 5 | 10 | 20 | 40 |
| RNase H1 protein level % | 100 | 123.4 | 139.0 | 138.1 | 119.0 |

The results indicate a significant increase in the levels of RNase H1 protein using the ACT-UP1 compound, suggesting that different target proteins can be increased using this technique, and that active ACT-UP I compounds can contain different lengths or sequences.

Example 8. PBGD Protein can be Increased Using an ACT-UP1 Compound

Acute Intermittent *Porphyria* (AIP) is a severe genetic disease that is caused by haploinsufficient mutation(s) of the Porphobilinogen Deaminase gene (PBGD, also known as hydroxymethylbilane synthase (HMBS)), a protein required for the heme biosynthesis pathway. An insufficient level of PBGD in a subject can cause accumulation of heme synthesis intermediates. Thus, increasing PBGD in a subject can potentially restore normal function in heme biosynthesis and treat the disease in the subject.

An ACT-UP1 compound, ATXL243, was designed to bind to the 3'UTR of PBGD with at a sequence conserved between human, monkey, and mouse PBGD mRNA approximately 190 nucleotides downstream from the stop codon of human PBGD mRNA (GenBank No: NM_000190.4, SEQ ID NO: 4). The sequence and chemistry for ATXL243 is shown in Table 14. PS was denoted by "*" and 2'-OMe was denoted as "m" in Table 14. The PRS of the ACT-UP1 compound is the bolded and underlined sequence at the 5' end of the PBGD ASO, as shown in Table 14.

TABLE 14

Sequence and Chemistry of ATXL243 Targeting PBGD mRNA

| Compound | Sequence and Chemistry (5' to 3') | Sequence (5' to 3') | SEQ ID NO |
|---|---|---|---|
| ATXL243 (PRS + PBGD ASO) | mG*mG*mAmCmUmGmGmAm CmU*mC*mU*mA*mA*mA* mG*mA*mG*mA*mU*mG* mA*mA*mG*mC*mC | GGACUGGACUC UAAAGAGAUGA AGCC | 28 |

In Vitro Assay

HeLa cells, seeded and grown in one day to ~70% confluency, were transfected with the ACT-UP1 compound ATXL231 at 5 nM, 10 nM, 20 nM, 40 nM, and 80 nM final concentrations using Lipofectamine™ 2000 Transfection Reagent (ThermoFisher Scientific, Waltham, MA), or were mock transfected as a control. Twenty-four (24) hr after transfection, cells were harvested and lysed, and then the protein was extracted using RIPA Lysis and Extraction Buffer (ThermoFisher Scientific, Waltham, MA). The level of PBGD protein was determined by Western Blot, using a PBGD specific antibody (ab129092 from Abeam, Waltham, MA). The Western result is shown in FIG. 9. The Western Blot was quantified using Image J, and the results are shown in Table 15 as percent protein levels relative to mock transfected cells following normalization to a loading control protein, nucleolin (NCL). NCL was not targeted by the assay compounds, and the level of NCL was not affected, suggesting the specificity of the compounds in modulating the target protein levels.

TABLE 15

PBGD Protein Level in HeLa Cells Transfected with ATXL243

| Compound | Mock (no treatment) | ATXL243 | | | | |
|---|---|---|---|---|---|---|
| Concentration (nM) | n/a | 5 | 10 | 20 | 40 | 80 |
| PBGD protein level % | 100 | 126.1 | 128.2 | 147.1 | 142.2 | 173.9 |

The results indicate that an ACT-UP1 compound can also increase PBGD protein levels, suggesting again that the ACT-UP1 upregulation approach described herein can be applied to upregulate expression of different target nucleic acids.

Example 9. ACT-UP1 Compounds can Increase PBGD Protein in Mouse Hepa1-6 Cells To determine if ACT-UP1 mediated protein increase of PBGD in human HeLa cells can also be observed in a different species, ACT-UP1 compounds were designed to target mouse PBGD mRNA.

harvested and lysed, then the protein was extracted using RIPA Lysis and Extraction Buffer (ThermoFisher Scientific, Waltham, MA). The level of PBGD protein was determined by Western Blot, using a PBGD specific antibody (ab129092 from Abcam, Waltham, MA). The Western result is shown in FIG. 10A, and a chart graphing the results is shown in FIG. 10B. The Western Blot was quantified using Image J, and the results are shown in Table 17 as percent protein levels relative to mock transfected cells following normalization to a loading control protein, NCL. NCL was not targeted by the assay compounds and the level of NCL was not affected, suggesting the specificity of the compounds in modulating the target protein levels.

TABLE 17

| | | | PBGD Protein Levels in Mouse Hepa1-6 Cells Transfected with ACT-UP1 Compounds | | | | |
|---|---|---|---|---|---|---|---|
| | Mock | ATXL319 7.5 nM | ATXL319 15 nM | ATXL320 7.5 nM | ATXL320 15 nM | ATXL321 7.5 nM | ATXL321 15 nM |
| PBGD Protein % | 100 | 136.2 | 158.1 | 122.0 | 137.9 | 162.7 | 179.1 |

ACT-UP1 compound ATXL319 was designed to target approximately 150 nt downstream of the stop codon of murine PBGD mRNA (GenBank No: NM_013551.2, SEQ ID NO: 6). To increase binding affinity, ATXL319 contains 3 locked nucleic acid (LNA) modified nucleotides at the 3' end of the compound. ATXL320 and ATXL321 were designed to target a site 5 nucleotide upstream from the ATXL319 target site, but with different lengths of ASO hybridization regions. The sequence and chemistry of the compounds are listed in Table 16. PS was denoted by "*", 2'-OMe was denoted as "m" in front of the modified nucleoside and LNA was denoted as "L" after the modified nucleoside in Table 16. "*[mCL]" specifically denotes an LNA 5-methyl cytidine 5'-thiophosphate. The PRS of the ACT-UP1 compound is the bolded and underlined sequence at the 5' end of the PBGD ASO as shown in Table 16. Each compound further comprised a GalNAc conjugate as described in WO20241,37545 and designated "AN-Gal-NAc".

In general, all three ACT-UP1 compounds were able to increase the protein level, with the higher dose showing more protein increase. Though different compounds may vary in increasing the PBGD protein level, the results indicate that PBGD protein levels can be increased using ACT-UP1 compounds in mouse cells, suggesting that the ACT-UP1 approach described herein is not unique to a particular species.

In Vitro Assay—mRNA Assessment

To determine if the ACT-UP1 compounds that were shown to increase protein levels also affect PBGD mRNA levels, total RNA was collected from cells as described above, and the level of PBGD mRNA was determined using quantitative real-time PCR (qRT-PCR), using mouse PBGD specific TaqMan primer probe sets (Mm01143545_m1 from ThermoFisher Scientific, Waltham, MA). qRT-PCR was performed using AgPath-ID™ One-Step RT-PCR Reagents

TABLE 16

Sequence and Chemistry of mouse PGBD targeting ACT-UP1 Compounds

| Compound | Sequence and Chemistry (5' to 3') | Sequence (5' to 3') | SEQ ID NO |
|---|---|---|---|
| ATXL319 (PRS + PBGD ASO) | mG*mG*mAmCmUmGmGmAmCmUmA*mG*mG* C*mC*mC*mC*mA*mA*mG*mG*mU*[GL]*mA* [GL]*mG*[mCL]-[AN-GalNAc] | GGACUGGACUAG CCCCAAGGUGAG GC | 29 |
| ATXL320 (PRS + PBGD ASO) | mG*mG*mAmCmUmGmGmAmCmUmC*mC*mC* A*mA*mG*mG*mU*mG*mA*mG*mG*mC*mA* mU*mA*mU*mC-[AN-GalNAc] | GGACUGGACUCC CAAGGUGAGGCA UAUC | 30 |
| ATXL321 (PRS + PBGD ASO) | mG*mG*mAmCmUmGmGmAmCmUmC*mA*mA* G*mG*mU*mG*mA*mG*mG*mC*mA*mU*mA* mU*mC-[AN-GalNAc] | GGACUGGACUCA AGGUGAGGCAUA UC | 31 |

In Vitro Assay—Protein Assessment

Hepa1-6 cells, seeded and grown in one day to ~70% confluency, were transfected with the ACT-UP1 compounds 7.5 nM or 15 nM final concentrations using Lipofectamine™ 2000 Transfection Reagent (ThermoFisher Scientific, Waltham, MA), or were mock transfected as a control. Twenty-four (24) hr after transfection, cells were in QS3 real-time PCR system (ThermoFisher Scientific, Waltham, MA). The target PBGD mRNA levels detected in qRT-PCR assay were normalized to total RNA levels measured with Ribogreen™ (ThermoFisher Scientific, Waltham, MA) detected in the aliquots of the corresponding RNA samples. The mRNA levels are shown in FIG. 10C and Table 18.

TABLE 18

| | The PBGD mRNA Levels in Cells Treated with Various ACT-UP1 Compounds | | | | | | |
|---|---|---|---|---|---|---|---|
| Compound | Mock (no treatment) | ATXL319 7.5 nM | ATXL319 15 nM | ATXL320 7.5 nM | ATXL320 15 nM | ATXL321 7.5 nM | ATXL321 15 nM |
| PBGD mRNA % | 100.0 | 109.5 | 112.7 | 97.4 | 107.3 | 92.9 | 93.8 |

The results indicate that ACT-UP1 compounds increased PBGD protein levels, but, did not substantially affect PBGD mRNA levels. The results suggest that ACT-UP1 compounds may increase protein levels by enhancing translation, and not by increasing the mRNA levels.

Example 10. FGF21 Protein can be Increased Using ACT-UP1 Compound

Fibroblast growth factor 21 (FGF21) is a hormone that regulates important metabolic pathways, including the regulation of energy balance and glucose and lipid homeostasis. Administration of FGF21 to rodents or non-human primates causes considerable pharmacological benefits on a cluster of obesity-related metabolic complications, including a reduction in fat mass and alleviation of hyperglycemia, insulin resistance, dyslipidemia, cardiovascular disorders and non-alcoholic steatohepatitis (NASH). Currently, FGF21 and its analogues have been tested in clinical trials. However, due to the relative short half-life and potential immune responses of artificial FGF21, it is attractive to increase the expression of endogenous FGF21 protein for the treatment of chronic metabolic diseases.

ACT-UP1 compound ATXL251 was designed to bind to the 3'UTR of FGF21 mRNA, approximately 90 nucleotides downstream of the stop codon of human FGF21 mRNA (GenBank No: NM_019113.4, SEQ ID NO: 5). The sequence and chemistry of ATXL251 are listed in Table 19. PS was denoted by "*", 2'-OMe was denoted as "m" in front of the modified nucleoside (e.g., mG), 2'-MOE was denoted by "e" in front to the modified nucleoside (e.g., eG), and 2'-MOE modified 5-methylcytidine was denoted as "eCm" in Table 19. The PRS of ATXL251 is the bolded and underlined sequence at the 5' end of the FGF21 ASO as shown in Table 19.

TABLE 19

| | Sequence and Chemistry of ATXL251 | | |
|---|---|---|---|
| Compound | Sequence and Chemistry (5' to 3') | Sequence (5' to 3') | SEQ ID NO |
| ATXL251 (PRS + FGF21 ASO) | mG*mG*mAmCmUm GmGmAmCmUeA* eCm*eT*eCm*eT *eT*eT*eA*eT* eT*eA*eT*eCm* eT*eCm*eA*eA* eG | GGACUGGACU ACTCTTTATT ATCTCAAG | 32 |

In Vitro Assay

Hep3B cells express FGF21 at relatively high levels based on the database of Protein Atlas (www.proteinatlas.com). The Hep3B cells, seeded and grown in one day to ~70% confluency, were transfected with the ACT-UP1 compound at 5, 10, 20, 40, or 80 nM final concentrations using Lipofectamine™ 2000 Transfection Reagent (ThermoFisher Scientific, Waltham, MA), or were mock transfected as a control. Twenty-four (24) hr after transfection, cells were harvested and lysed, then the protein was extracted using RIPA Lysis and Extraction Buffer (ThermoFisher Scientific, Waltham, MA). The level of FGF21 protein was determined by Western Blot, using a FGF21 specific antibody (ab171941 from Abcam, Waltham, MA). The Western result is shown in FIG. 11. The Western Blot was quantified using Image J, and the results are shown in Table 20 as percent protein levels relative to mock transfected cells following normalization to a loading control protein, NCL. NCL was not targeted by the assay compounds and the level of NCL was not affected, suggesting the specificity of the compounds in modulating the target protein levels.

TABLE 20

| | FGF21 Protein Level in Hep3B Cells Transfected with ATXL251 | | | | | |
|---|---|---|---|---|---|---|
| Compound | Mock (no treatment) | ATXL243 | | | | |
| Concentration (nM) | n/a | 5 | 10 | 20 | 40 | 80 |
| FGF21 protein level % | 100 | 220.6 | 209.8 | 192.9 | 205.7 | 160.1 |

The results indicate that ATXL251 can increase FGF21 protein levels, further confirming that the ACT-UP1 approach described herein can be applied to increase protein levels of different genes.

Example 11. FGF21 Protein can be Increased in Mouse Cells Using ACT-UP1 Compounds To determine if ACT-UP1 mediated protein increase of FGF21 in human HeLa cells can also be observed in a different species, ACT-UP1 compounds were designed to target the 3'UTR of mouse FGF21 mRNA.

An ACT-UP1 compound was designed to target approximately 70 nt (ATXL318) downstream of the stop codon of murine FGF21 mRNA (GenBank No: NM_020013.4, SEQ ID NO: 7). This sequence is conserved between human, monkey, and mouse. In addition, ATXL317, which is derived from ATXL251 but with GalNAc conjugate (as described in WO2024137545), was also synthesized. ATXL317 has two mismatches with the mouse FGF21 mRNA. The sequence and chemistry of the compounds are listed in Table 21. PS was denoted by "*", 2'-OMe was denoted as "m" in front of the modified nucleoside (e.g., mG), 2'-MOE was denoted by "e" in front of the modified nucleoside (e.g., eG), and 2'-MOE modified 5-methylcytidine was denoted as "eCm" in Table 21. The PRS of the ACT-UP1 compounds is shown as the bolded and underlined sequences at the 5' end of the FGF21 ASOs in Table 21. Each compound further comprised a GalNAc conjugate as described in WO2024137545 and designated AN-GalNAc.

TABLE 21

| | Sequence and Chemistry of ACT-UP1 Compounds Targeting Mouse FGF21 mRNA | | |
|---|---|---|---|
| Compound | Sequence and Chemistry (5' to 3') | Sequence (5' to 3') | SEQ ID NO |
| ATXL317 (PRS + FGF21 ASO) | mG*mG*mAmCmUmGmGmAmCm UeA*eCm*eT*eCm*eT*eT* eT*eA*eT*eT*eA*eT*eT* eCm*eCm*eA*eA*eG- [AN-GalNAc] | GGACUGGACUACTCTTTATTATTCCAAG | 33 |
| ATXL318 (PRS + FGF21 ASO) | mG*mG*mAmCmUmGmGmAmC mUeA*eA*eA*eT*eA*eA* eA*eT*eA*eA*eG*eA*eT* eA*eA*eA*eT*eA- [AN-GalNAc] | GGACUGGACUAAATAAATAAGATAAATA | 34 |

In Vitro Assay—Protein Assessment

Hepa1-6 cells, seeded and grown in one day to ~70% confluency, were transfected with the ACT-UP1 compounds 7.5 nM or 15 nM final concentrations using Lipo-fectamine™ 2000 Transfection Reagent (ThermoFisher Scientific, Waltham, MA), or were mock transfected as a control. Twenty-four (24) hr after transfection, cells were harvested and lysed, then the protein was extracted using RIPA Lysis and Extraction Buffer (ThermoFisher Scientific, Waltham, MA).

The level of FGF21 protein was determined by Western Blot, using a FGF21 specific antibody (ab171941 from Abcam, Waltham, MA). The Western result is shown in FIG. 12A and a chart graphing the results is shown in FIG. 12B. The Western Blot was quantified using Image J, and the results are shown in Table 22 as percent protein levels relative to mock transfected cells following normalization to a loading control protein, NCL. NCL was not targeted by the assay compounds and the level of NCL was not affected, suggesting the specificity of the compounds in modulating the target protein levels.

TABLE 22

| | FGF21 Protein Level in Mouse Hepal-6 Cells Transfected with ACT-UP1 Compounds | | | | |
|---|---|---|---|---|---|
| Compound | Mock (no treatment) | ATXL317 7.5 nM | ATXL317 15M | ATXL318 7.5 nM | ATXL318 15M |
| FGF21 protein % | 100.0 | 110.1 | 131.9 | 92.2 | 164.5 |

In general, the ACT-UP1 compounds assessed were able to increase FGF21 protein level, with a higher dose showing more protein increase than a lower dose. Consistent with what was observed with Jagged 1 ASO in a previous example, supra, the FGF21 ACT-UP1 compound, ATXL318, that hybridizes closer to the stop codon appears to increase expression of more FGF21 protein than ATXL317 which hybridizes farther from the stop codon and with 2 mismatches. Together, the results indicate that FGF21 protein levels can be increased using ACT-UP1 compounds in mouse cells, again suggesting that the ACT-UP1 approach described herein is not unique to a particular species.

In Vitro Assay—mRNA Assessment

To determine if the ACT-UP1 compounds that were shown to increase protein levels also affect FGF21 mRNA levels, total RNA was collected from cells as described above, and the level of FGF21 mRNA was determined using quantitative real-time PCR (qRT-PCR), using mouse FGF21 specific TaqMan prime probe sets (Mm07297622_g1 from ThermoFisher Scientific, Waltham, MA). qRT-PCR was performed using AgPath-ID™ One-Step RT-PCR Reagents in QS3 real-time PCR system (ThermoFisher Scientific, Waltham, MA). The target FGF21 mRNA levels detected in qRT-PCR assay were normalized to either total RNA levels measured with Ribogreen™ (ThermoFisher Scientific, Waltham, MA) detected in the aliquots of RNA samples. The mRNA levels are shown in FIG. 12C and Table 23.

TABLE 23

| | FGF21 mRNA Levels in Hepal-6 Cells Treated with ACT-UP1 Compounds | | | | |
|---|---|---|---|---|---|
| Compound | Mock (no treatment) | ATXL317 7.5 nM | ATXL317 15 nM | ATXL318 7.5 nM | ATXL318 15 nM |
| FGF21 mRNA % | 100.00 | 87.17 | 101.35 | 86.56 | 73.81 |

The results indicate that ACT-UP1 compounds increased FGF21 protein levels, but, did not increase FGF21 mRNA levels. The results suggest that ACT-UP1 compounds may increase protein levels by enhancing translation, and not by increasing the mRNA levels.

Example 12. ACT-UP1 can Recruit Cellular Proteins Potentially Involved in Translation "ASO Coupled Translation-Upregulation 1" or "ACT-UP1" refers to an antisense oligonucleotide (ASO) joined to a protein recruiting sequence (PRS).

The ASO specifically hybridizes to a target mRNA sequence, bringing the PRS into close proximity to the target mRNA as shown in the previous examples which targeted specific nucleic acids and were able to increase protein expression of the specific targets.

The PRS, a short sequence of linked nucleosides, is not an antisense oligonucleotide (ASO) as it does not hybridize with a target nucleic acid (i.e., the protein recruiting sequence is not antisense to a target nucleic acid nor does it specifically base pair with a sequence of the target nucleic acid).

Without being bound to any particular theory, it is thought that the PRS element of an ACT-UP1 compound attracts translation regulatory proteins close to the target mRNA bound by the ASO element of the ACT-UP1 compound, thereby increasing translation of the targeted mRNA.

To evaluate this hypothesis, a 17-nucleobase long oligo-nucleotide (ATXL263) was designed and synthesized. ATXL263 contains a 5' biotin and sequence derived from the 3'UTR of JAG1 mRNA (SEQ ID NO: 1). The sequence and chemistry of ATXL263 are shown in Table 24. 2'-OMe was denoted as "m" in Table 24.

TABLE 24

| | Sequence and Chemistry (5' to 3') | Sequence (5' to 3') | SEQ ID NO |
|---|---|---|---|
| Compound | | | |
| ATXL263 | Biotin-mUmGmGmUm AmGmUmUmUmCmUmG mUmGmGmUmU | UGGUAGUUUCUG UGGUU | 35 |

ATXL263 can form 17 base-pair long duplexes with previously described compounds ATXL228, ATXL261, and ATXL193 (see Table 1). Also, as shown in Table 1, ATXL228 has no PRS component and is purely an ASO. ATXL261 is an example of an ACT-UP1 compound with a 5-nucleoside long PRS, and ATXL193 is an ACT-UP1 compound with a 9-nucleoside long PRS.

ATXL263 is added to solutions of each of the other 3 compounds in 1× phosphate-buffered saline, and the duplexes were formed at 30 μM by heating the solutions at 94° C. for 4 mins in a block heater, followed by removal of the heating block containing the solution from the block heater and allowing it to gradually cool down to room temperature over a time course of 1 hr.

NeutroAvidin Resin (Thermofisher Scientific, Waltham, MA) was prewashed with W100 buffer (50 mM Tris-HCl (pH7.5), 100 mM NaCl, 5 mM EDTA and 0.1% NP40), then incubated with duplex at 30 μM. The duplexes were attached to NeutroAvidin beads (schematic shown in FIG. 13A). After washing with W100 buffer twice to get rid of excess duplex, the resin was blocked with blocking buffer (W100 with 10 mg/ml BAS, 1.2 mg/ml glycogen and 0.2 mg/ml transfer RNA) for 1 hr. Then, after twice washing by W100, 2.5 mg total protein prepared from HeLa cells was incubated with the duplex-coated beads for 2 hours. Proteins that were associated with the duplex were washed, and eluted from the beads by boiling in 2×SDS-loading buffer (ThermoFisher Scientific, Waltham, MA).

The isolated proteins were analyzed on SDS-PAGE, and the presence of several proteins that potentially modulate translation was assessed: PABPC1 and m6A-recognization proteins (e.g., Mett13, YTHDF1, and ALKB15).

PABPC1

It has been recently shown that through a guide RNA-Cas13-PABPC1 fusion system the fusion protein can be recruited to the 3'UTR of target mRNAs to increase the levels of target proteins (Torkzaban et al., Biotechnol. J., 2022 October, 17(10):e2200214). PABPC1 is an abundant cytoplasmic Poly(A) binding protein that is required for translation (Lemay, J. F., et al., 2010 Crossing the borders: poly(A)-binding proteins working on both sides of the fence. RNA Biol 7: 291-295). Therefore, co-isolation of PABPC1 with the ACT-UP1 compounds was evaluated by Western Blot using a specific PABPC1 antibody (10970-1-AP, from Proteintech®, Rosemont, IL, USA). The results, shown in FIG. 13B, indicate significant co-isolation of PABPC1 with the ACT-UP1 compounds, in a PRS length dependent manner; higher levels of PABPC1 protein were found co-isolated with ACT-UP1 compound ATXL193 which had a longer PRS than ATXL261 which had a shorter PRS. This is consistent with previous findings that the length of the RNA can affect the binding affinity of PABPC1 (Sachs, A. B., et al., 1987, A single domain of yeast poly(A)-binding protein is necessary and sufficient for RNA binding and cell viability. Mol Cell Biol 7: 3268-3276).

As a control, another RNA binding protein, HuR (antibody ab200342 from Abcam, Cambridge, UK), did not show substantial PRS-dependent binding to the compounds (FIG. 13B). These results suggest that an ACT-UP1 compound can recruit RNA binding protein PABPC1 with its PRS component, which may enhance translation of the target mRNA.

Additionally, a few proteins involved in the m6A modification pathway were also evaluated for binding to ACT-UP1 compounds. m6A is a nucleotide modification that is present in many mRNAs and may modulate translation through binding to m6A-recognization proteins (He, P. C., and C. He, 2021, m(6) A RNA methylation: from mechanisms to therapeutic potential. EMBO J 40: e105977; Meyer, K. D., 2019, m(6)A-mediated translation regulation. Biochim Biophys Acta Gene Regul Mech 1862: 301-309). The proteins assessed include Mett13 (antibody ab195352 from Abcam, Waltham, MA), a m6A writer protein; YTHDF1 (antibody ab252346 from Abcam, Waltham, MA), a m6A reader protein; and ALKBH5 (antibody ab195377 from Abcam, Waltham, MA), a m6A eraser protein (Huang, H., et al., 2020, The Biogenesis and Precise Control of RNA m(6)A Methylation. Trends Genet 36: 44-52). Western Blot results are shown in FIG. 13C.

The data indicate that the ACT-UP1 compounds can significantly recruit YTHDF1, ALKBH5, and to a lesser extent, Mett13 proteins. As a control, the ASO ATXL228 without a PRS showed very weak binding to these proteins. Similar to PABPC1, these proteins also bind more to the ACT-UP1 compound with the longer PRS (ATXL193) than the ACT-UP1 compound with the shorter PRS (ATXL261). This trend of protein binding is consistent with the observation that ATXL193 caused a higher Jagged 1 protein increase compared with ATXL261, whereas ATXL228 (no PRS) did not increase the protein level (see Example 1, supra). These results together imply that an ACT-UP1 compound may recruit cellular RNA binding proteins including Mett13, YTHDF1, and ALKBH5, to the target mRNA, enhancing translation.

Example 13. Different PRS can Increase Target Protein Levels

The above-described protein recruiting sequences (PRSs) were derived from a consensus sequence GGACU (SEQ ID NO: 8) present in mRNAs that are preferentially modified for m6A (Linder, B., et al., 2015, Single-nucleotide-resolution mapping of m6A and m6Am throughout the transcriptome. Nat Methods 12: 767-772). The previous example showed that PABPC1 can be recruited to the GGACU derived PRS.

Next, we assess the ability of other sequences for their ability to act as protein recruiting sequences (PRSs) in ACT-UP1 compounds.

ACT-UP1 compounds were designed based on Jagged 1 targeting ACT-UP1 compound ATXL234 using the same ASO sequence, but, with different PRSs. The PRS components of the ACT-UP1 compounds were designed as derivatives of Poly(A) sequences because PABP protein has been shown to preferentially bind a poly(A) sequence (Lemay, J. F., et al., 2010 Crossing the borders: poly(A)-binding proteins working on both sides of the fence. RNA Biol 7: 291-295). The sequence and chemical modifications of the compounds are shown in Table 25. PS was denoted by "*", 2'-OMe was denoted as "m" in front of the modified nucleosides, and 2'-MOE was denoted by "e" in front of the modified nucleosides (e.g., eG), and 2'-MOE modified 5-methylcytidine was denoted as "eCm", as shown in Table 25. The PRS of the ACT-UP1 compounds is shown as the bolded and underlined sequences at the 5' end of the JAG1 ASOs in Table 25. Each newly designed compound further comprised a GalNAc conjugate as described in WO2024137545 and designated AN-GalNAc). ATXL316 is the same sequence and sequence modification as ATXL234, but, additionally has a GalNAc conjugate attached. ATXL234 was previously described, supra.

reducing the Poly(A) length to 8 nt abolished the PRS function in the ACT-UP1 compound. The data suggest that the PRS length is an important factor affecting the activity of ACT-UP1 compounds, likely due to influence on recruitment of important proteins regulating translation including PABPC1. Together, these results suggest that different PRSs can be employed to increase protein levels.

TABLE 25

Sequence and Chemistry of ACT-UP1 Compounds Containing Different PRSs

| Compound | Sequence and Chemistry (5' to 3') | Sequence (5' to 3') | SEQ ID NO |
|---|---|---|---|
| ATXL316 | mG*mG*mAmCmUmGmGmAmCmU eA*eA*eCm*eCm*eA*eCm*eA*eG*eA*eA*eA*eCm *eT*eA*eCm*eCm*eA-[AN-GalNAc] | GGACUGGACUA ACCACAGAAACT ACCA | 36 |
| ATXL286 | mA*mA*mAmCmUmAmAmAmCmU eA*eA*eCm*eCm*eA*eCm*eA*eG*eA*eA*eA*eCm *eT*eA*eCm*eCm*eA-[AN-GalNAc] | AAACUAAACUA ACCACAGAAACT ACCA | 37 |
| ATXL287 | mA*mA*mAmAmAmAmAmAmAmA eA*eA*eCm*eCm*eA*eCm*eA*eG*eA*eA*eA*eCm *eT*eA*eCm*eCm*eA-[AN-GalNAc] | AAAAAAAAAAA ACCACAGAAACT ACCA | 38 |
| ATXL288 | mA*mA*mAmAmAmAmAmA eA*eA*eCm*eCm*eA*eCm*eA*eG*eA*eA*eA*eCm *eT*eA*eCm*eCm*eA-[AN-GalNAc] | AAAAAAAAAC CACAGAAACTAC CA | 39 |

In Vitro Assay

HeLa cells, seeded and grown in one day to ~70% confluency, were transfected with the ACT-UP1 compounds 7.5 nM or 15 nM final concentrations using Lipofectamine™ 2000 Transfection Reagent (ThermoFisher Scientific, Waltham, MA), or were mock transfected as a control. Twenty-four (24) hr after transfection, cells were harvested and lysed, then the protein was extracted using RIPA Lysis and Extraction Buffer (ThermoFisher Scientific, Waltham, MA). The level of Jagged 1 protein was determined by Western Blot, using a Jagged 1 specific antibody (ab109536 from Abcam, Waltham, MA). The Western result is shown in FIG. 14. The Western Blot was quantified using Image J, and the results are shown in Table 26 as percent protein levels relative to mock transfected cells following normalization to a loading control protein, NCL. NCL was not targeted by the assay compounds and the level of NCL was not affected, suggesting the specificity of the compounds in modulating the target protein levels.

Example 14. Jagged 1 Protein is Increased in Mouse Liver Using ACT-UP1 Compound

To determine if the ACT-UP1 compounds that increased protein levels in vitro can also increase protein levels in vivo, a new ACT-UP1 compound, ATXL246, was designed and synthesized. ATXL246 was derived from ACT-UP1 compound ATXL234 but removed 3 nucleotides near 3' end of the ASO region to determine if shorter base-pairing can still increase protein levels. In addition, ATXL246 contains a GalNAc conjugate (as described in WO2024137545) designated AN-GalNAc to facilitate liver delivery. The sequence and chemistry of ASO ATXL246 are listed in Table 27. PS was denoted by "*", 2'-OMe was denoted as "m" in front of the modified nucleoside (e.g., mG), 2'-MOE was denoted by "e" in front of the modified nucleoside (e.g., eG),

TABLE 26

Jagged 1 Protein Levels in HeLa Cells Transfected with ACT-UP1 Compounds Containing Different PRSs

| Compound | Mock (no treatment) | ATXL234 | | ATXL316 | | ATXL286 | | ATXL287 | | ATXL288 | |
|---|---|---|---|---|---|---|---|---|---|---|---|
| Concentration (nM) | n/a | 7.5 | 15 | 7.5 | 15 | 7.5 | 15 | 7.5 | 15 | 7.5 | 15 |
| Jagged 1 protein % | 100.0 | 120.4 | 125.1 | 95.8 | 134.3 | 135.3 | 138.2 | 132.6 | 151.6 | 78.7 | 95.4 |

The results indicate that other short linked nucleoside sequences (e.g., AAACUAAACU or AAAAAAAAAA) can also function as a PRS in an ACT-UP1 compound and increase target Jagged 1 protein level. However, it seems and 2'-MOE modified 5-methylcytidine was denoted as "eCm" in Table 27. ATXL316 was previously described in Table 25, supra. AN-GalNAc is a GalNAc conjugate described in WO2024137545.

TABLE 27

Sequence and Chemistry of ATXL246

| Compound | Sequence and Chemistry (5' to 3') | Sequence (5' to 3') | SEQ ID NO |
|---|---|---|---|
| ATXL246 | mG*mG*mAmCmUmGmGmAmCmU eA*eA*eCm*eCm*eA*eCm* eA*eG*eA*eA*eA*eCm* eCm*eA-[AN-GalNAc] | GGACUGGAC-UAACCACAGAAACCA | 40 |

Three animals per group of 7- to 8-week-old male Balb/C mice were injected subcutaneously with 0.5 mg/kg or 3 mg/kg of ATXL246 or ATXL316. Phosphate buffered saline was injected as a control. Post dosing 96 hr, the mice were dosed a second time, and then after another 96 hr, the mice were sacrificed, and organs harvested for analysis. Total protein from mouse liver was prepared and subjected to Western analysis. Jagged 1 protein was detected using antibody (ab109536 from Abeam, Waltham, MA). The Western result is shown in FIG. 15. The Western Blot was quantified using Image J, and the results are shown in Table 28 as percent protein levels relative to PBS-treated control mice following normalization to a loading control protein, alpha-tubulin.

TABLE 28

Jagged 1 Protein Level in Mice Treated with ATXL246 and ATXL316

| | PBS | ATXL246 0.5 mg/kg | ATXL246 3 mg/kg | ATXL316 0.5 mg/kg | ATXL316 3 mg/kg |
|---|---|---|---|---|---|
| Jagged 1 protein % | 100 | 134.4 | 170.3 | 160.7 | 210.2 |

The results indicate that the ACT-UP1 compounds ATXL246 and ATXL316 can increase Jagged 1 protein levels in animals, consistent with what was observed in vitro.

Example 15. HNF4A Protein can be Increased in Cells Using ACT-UP1 Compounds

HNF4A is a transcription factor important for the metabolic pathway in the liver. The protein level tends to be reduced along with the progression of metabolic diseases (Baciu et al., 2017, PLoS ONE 12(12): e0189223; Lu et al., 2022, Lipids Health Dis., 21(1):46). Increasing the HNF4A protein level in liver using either mRNA delivery or saRNA leads to beneficial effects for disease phenotypes including NASH and obesity (Yang et al., 2021, J Hepatol., 75(6): 1420-1433; Huang et al., 2020, Mol Ther Nucleic Acids, 19:361-370). To determine if HNF4A protein can be increased using ACT-UP1 mechanism, ACT-UP1 compounds were designed to target the 3'UTR of human HNF4A mRNA.

Four ACT-UP1 compounds were designed to target approximately 70 nt (ATXL394), 95 nt (ATXL395), 140 nt (ATXL396), and 240 nt (ATXL397) downstream of the stop codon of human HNF4A mRNA (GenBank No: NM_178849.3, SEQ ID NO: 45). These sequences are conserved between human and monkey. The ATXL395 is also conserved in mice. The sequence and chemistry of the compounds are listed in Table 29. PS was denoted by "*", 2'-OMe was denoted as "m" in front of the nucleosides modified, as shown in Table 29. The PRS of the ACT-UP1 compounds is shown as the bolded and underlined sequences at the 5' end of the HNF4A ASOs in Table 29.

TABLE 29

Sequence and Chemistry of ACT-UP1 Compounds Targeting Human HNF4A mRNA

| Compound | Sequence and Chemistry (5' to 3') | Sequence (5' to 3') | SEQ ID NO |
|---|---|---|---|
| ATXL394 | mG*mG*mAmCmUmGmGmAmCmU mCmCmUmUmUmGmCmCmGmUm GmAmCmCmAmC*mG*mU | GGACUGGACUCCUUUGCCGUGACCACGU | 53 |
| ATXL395 | mG*mG*mAmCmUmGmGmAmCmU mCmUmGmCmUmCmUmGmGmGmA mCmUmGmGmU*mC*mC | GGACUGGACUCUGCUCUGGGACUGGUCC | 54 |
| ATXL396 | mG*mG*mAmCmUmGmGmAmCmU mCmCmUmUmAmGmGmCmCmAmU mGmGmUmCmU*mC*mG | GGACUGGACUCCUUAGGCCAUGUUCUCG | 55 |
| ATXL397 | mG*mG*mAmCmUmGmGmAmCmU mGmGmUmGmGmCmUmUmCmAmAmC mAmUmGmA*mG*mA | GGACUGGACUGUGGCUUCAACAUGAGA | 56 |

In Vitro Assay—Protein Assessment

Hep3B cells, seeded and grown for one day to ~70% confluency, were transfected with the ACT-UP1 compounds at 7.5 nM or 15 nM final concentrations using Lipofectamine™ 2000 Transfection Reagent (ThermoFisher Scientific, Waltham, MA), or were mock transfected as a control. Twenty-four (24) hr after transfection, cells were harvested and lysed, then the protein was extracted using RIPA Lysis and Extraction Buffer (ThermoFisher Scientific, Waltham, MA). The level of HNF4A protein was determined by Western Blot, using a HNF4A specific antibody (ab181604 from Abcam, Waltham, MA). The Western Blot result is shown in FIG. 16A and a bar graph quantifying the results is shown in FIG. 16B. The Western Blot was quantified using Image J, and the results are shown in Table 30 as percent protein levels relative to the average of four mock transfected cell samples following normalization to a loading control protein, NCL. NCL was not targeted by the assay compounds and the level of NCL was not affected, suggesting the specificity of the compounds in modulating the target protein levels.

TABLE 30

HNF4A Protein Level in Human Hep3B Cells Transfected with ACT-UP1 Compounds

| Compound | Mock | | | | ATXL394 | | ATXL395 | | ATXL396 | | | ATXL397 | |
|---|---|---|---|---|---|---|---|---|---|---|---|---|---|
| Concentration (nM) | 0 | 0 | 0 | 0 | 7.5 | 15 | 7.5 | 15 | 7.5 | 7.5 | 15 | 7.5 | 15 |
| HNF4A protein level % | 103 | 115 | 96 | 87 | 150 | 121 | 212 | 191 | 201 | 210 | 212 | 215 | 204 |

In general, the ACT-UP1 compounds assessed were able to increase HNF4A protein levels. Together, the results indicate that HNF4A protein levels can be increased using ACT-UP1 compounds in human cells, again suggesting that the ACT-UP1 approach described herein can be applied to different genes.

Example 16. GalNAc-Conjugated ACT-UP1 Compounds Show Better Activity Increasing JAG1 Protein Levels To determine if ACT-UP1 compounds without GalNAc conjugation can also increase protein levels, several ACT-UP1 compounds were designed and assessed. Compound ATXL398 has the same sequence and sequence modifications as previously described ATXL246 but lacks the Gal-NAc conjugate of ATXL246. Compound ATXL282 targets a different position of the 3' UTR of Jagged 1 mRNA than ATXL398. Compound ATXL283 has the same sequence and sequence modifications as ATXL282 but lacks GalNAc conjugation. The sequence and chemistry of these compounds are listed in Table 31. The GalNAc conjugate is designated AN-GalNAc and is described in WO2024137545.

TABLE 31

| | Sequence and Chemistry of ASOs | | |
|---|---|---|---|
| Compound | Sequence and Chemistry (5' to 3') | Sequence (5' to 3') | SEQ ID NO |
| ATXL398 | mG*mG*mAmCmUmGmGmAm CmUeA*eA*eCm*eCm*eA* eCm*eA*eG*eA*eA*eA* eCm*eCm*eA | GGACUGGACU AACCACAGAA ACCA | 57 |
| ATXL282 | mG*mG*mAmCmUmGmGmAm CmUeG*eT*eT*eT*eA*eA *eA*eG*eA*eA*eCm*eT* eA*eCm*eA*eA*eG*eCm* eCm-[AN-GalNAc] | GGACUGGACU GTTTAAAGAA CTACAAGCC | 58 |
| ATXL283 | mG*mG*mAmCmUmGmGmAm CmUeG*eT*eT*eT*eA*eA *eA*eG*eA*eA*eCm*eT *eA*eCm*eA*eA*eG* eCm*eCm | GGACUGGACU GTTTAAAGAA CTACAAGCC | 59 |

Three animals per group of 7- to 8-week-old male Balb/C mice were injected subcutaneously with 0.5 mg/kg or 3 mg/kg of GalNAc-conjugated compounds ATXL246 or ATXL316. In addition, the corresponding non-GalNAc-conjugated counterparts, ATXL398 and ATXL234, were dosed at 15 and 50 mg/kg. Non-GalNAc-conjugated compounds are dosed at higher concentrations because their efficiency in entering cells is lower than GalNAc-conjugated compounds.

In another study, ATXL282 was dosed at 0.5 mg/kg or 2.5 mg/kg; whereas the ATXL283 compound was dosed at 25 mg/kg. Phosphate buffered saline (PBS) was injected as a control in each case. After dosing 96 hr, the mice were dosed a second time and then after another 96 hr, the mice were sacrificed, and organs were harvested for analysis. Total protein from mouse liver was prepared and subjected to Western analysis. Jagged 1 protein was detected using antibody (ab109536 from Abcam, Cambridge, UK). The Western result is shown in FIG. 17A and FIG. 17B. The Western Blot was quantified using Image J, and the results are shown in Tables 32A-B as percent protein levels relative PBS-treated control mice following normalization to a loading control protein, NCL (ab22758 from Abcam, Cambridge, UK).

TABLE 32A

| | Jagged 1 Protein Level in the Livers of Mice Treated with Different Compounds | | | | | | |
|---|---|---|---|---|---|---|---|
| | | ATXL398 | | ATXL234 | | ATXL246 | ATXL316 |
| | PBS | 15 mg/kg | 50 mg/kg | 15 mg/kg | 50 mg/kg | 3 mg/kg | 3 mg/kg |
| Jagged 1 protein level % | 100.0 | 150.4 | 219.2 | 171.8 | 159.6 | 176.4 | 233.0 |

TABLE 32B

| | Jagged 1 Protein Level in the Livers of Mice Treated with Different Compounds | | | |
|---|---|---|---|---|
| | | ATXL282 | | ATXL283 |
| | PBS | 0.5 mg/kg | 2.5 mg/kg | 25 mg/kg |
| Jagged 1 protein level % | 100.0 | 81.0 | 179.7 | 164.3 |

The results indicate that the ACT-UP1 compounds without GalNAc conjugation can also increase the protein levels, whereas the compounds with GalNAc can increase the protein levels at low doses, consistent with the observations that GalNAc conjugation facilitates compound uptake by liver hepatocytes.

Example 17. ACT-UP1 Compounds Increase JAG1 Protein Levels at 4 Weeks after Dosing in Mice To determine whether the activity of ACT-UP1 compounds is durable in mice after dosing, three animals per cohort of 7- to 8-week-old male Balb/C mice were injected subcutaneously with 0.5 mg/kg or 3 mg/kg of GalNAc-conjugated ATXL316. Post dosing 96 hr, the mice were dosed a second time. The mice were sacrificed 4 weeks after initial dosing, and organs were harvested for analysis. Total protein from mouse liver was prepared and subjected to Western analysis. Jagged 1 protein was detected using antibody (ab109536 from Abcam, Cambridge, UK). The Western Blot result is shown in FIG. 18. The Western Blot was quantified using Image J, and the results are shown in Table 33, as percent protein levels relative to PBS control treated mice following normalization to a loading control protein, NCL (ab22758 from Abcam, Cambridge, UK).

TABLE 33

Jagged 1 Protein Level in Mice Treated with ATXL316

|  | PBS | ATXL316 (0.5 mg/kg) | ATXL316 (3 mg/kg) |
|---|---|---|---|
| Jagged 1 protein % | 100.0 | 142.5 | 135.2 |

The results showed that the ACT-UP1 compound can increase Jagged 1 protein levels even at 4 weeks after dosing, suggesting a long lasting effect.

Example 18. ACT-UP1 Compound Increases JAG1 Protein Levels in JAG1 Heterozygous Mice A mouse model that carries a JAG1 heterozygous deletion (JAG+/−) (pr139410, The Jackson Laboratory, Bar Harbor, Maine, USA) was used to assess upregulation of JAG1 by ACT-UP1 compounds.

The compounds assessed in the JAG+/− model were 2 newly designed control compounds which do not contain a PRS element (ATXL245 and ATXL233) and previously described ACT-UP1 compound ATXL246. ATXL245 does not target JAG1. ATXL233 targets the 5' UTR of the JAG1 mRNA transcript. The sequence and chemistry of the new compounds are listed in Table 34. GL-GalNAc is a GalNAc conjugate described by Sharma et al. (2018, Bioconjugate Chem, 29:2478-2488). AN-GalNAc is a GalNAc conjugate described in WO2024137545.

TABLE 34

Sequence and Chemistry of ASOs

| Compound | Sequence and Chemistry (5' to 3') | Sequence (5' to 3') | SEQ ID NO |
|---|---|---|---|
| ATXL245 | eT*eG*eCm*eA*eCm*eT* eG*eA*eCm*eG*eG*eA* eA*eT*eA*eCm*eA*eA- [GL-GalNAc] | TGCACT GACGGA ATACAA | 60 |
| ATXL233 | eT*eG*eCm*eA*eCm*eG* eA*eCm*eT*eG*eG*eA* eA*eA*eA*eCm*eA*eA- [AN-GalNAc] | TGCACG ACTGGA AAACAA | 61 |

6-8 week old male JAG1+/− mice were dosed two times with 3 mg/kg compound, 96 hrs apart between the two doses. Mice were sacrificed at 96 hrs after last dosing, and organs were harvested for analysis. Total protein from mouse liver was prepared and subjected to Western Blot analysis. JAG1 protein was detected using antibody (ab109536 from Abcam, Cambridge, UK). The Western Blot result is shown in FIG. 19. The Western Blot was quantified using Image J, and the results are shown in Table 35, as percent protein levels relative to PBS control treated mice following normalization to loading control protein GAPDH (G8795 from Sigma-Aldrich, St. Louis, MO, USA).

TABLE 35

Jagged 1 Protein Level in Jag1$^{+/-}$ Mice

|  | PBS | ATXL245 | ATXL233 | ATXL246 |
|---|---|---|---|---|
| Jag1 protein % | 100.0 | 133.5 | 183.7 | 186.5 |

The results showed that the ACT-UP1 compound ATXL246 significantly increased the JAG1 protein level in JAG1+/− mice. In addition, another compound, ATXL233, which targets a uORF region within the 5' UTR of JAG1 mRNA, also substantially increased the protein level. However, no statistically significant increase of JAG1 protein was seen by the non-JAG1-targeting control compound ATXL245.

Example 19. ACT-UP1 Compounds with Varying PS Linkage Amounts Increase JAG1 Protein Levels in Animals Several ACT-UP1 compounds described above, such as ATXL316, contain a PRS that has two PS linked nucleosides at the 5' end of the compound to protect the PRS from being degraded, and contain eight 2'-modified nucleosides linked with phosphodiester (PO) backbone to reduce non-specific protein binding. To determine whether the amounts of PS linkages in ACT-UP1 compounds can increase protein binding levels, two new compounds were designed based on the ATXL316 sequence with additional PS linkages between the PRS nucleosides. The new compounds, containing varying PS linkage amounts in the PRS (bolded and underlined in the table), are listed in Table 36. AN-GalNAc is a GalNAc conjugate described in WO2024137545.

TABLE 36

Sequence and Chemistry of Jag1 ACT-UP1 Compounds

| Compound | Sequence and Chemistry (5' to 3') | Sequence (5' to 3') | SEQ ID NO |
|---|---|---|---|
| ATXL484 | mG*mG*mA*mC*mU*mG*mG *mA*mC*mU*eA*eA*eCm* eCm*eA*eCm*eA*eG*eA* eA*eA*eCm*eT*eA*eCm* eCm*eA-[AN-GalNAc] | GGACUGGACU AACCACAGAA ACTACCA | 62 |
| ATXL493 | mG*mG*mAmCmUmG*mG* mAmCmU*eA*eA*eCm* eCm*eA*eCm*eA*eG*A* eA*eA*eCm*eT*eA*eCm* eCm*eA-[AN-GalNAc] | GGACUGGACU AACCACAGAA ACTACCA | 63 |

In Vivo Assay

The new compounds, together with ATXL316, were tested in animals to evaluate their activity and duration. Three animals per group of 7- to 8-week-old male Balb/C mice were injected subcutaneously with 3 mg/kg of Gal-NAc-conjugated compounds. Phosphate buffered saline (PBS) was injected as a control. Post dosing 96 hr, the mice were dosed a second time, the mice were sacrificed at 2 weeks or 3 weeks after the second dosing, and organs were harvested for analysis. Total protein from mouse liver was prepared and subjected to Western Blot analysis. Jagged 1 protein was detected using antibody (70109T from Cell Signaling Technology, Danvers, MA, USA). The Western Blot result is shown in FIG. 20. The Western Blot was quantified using Image J, and the results are shown in Table 37 as percent protein levels relative to saline control treated mice following normalization to a loading control protein, GAPDH (G8795 from Sigma-Aldrich, St. Louis, MO, USA).

TABLE 37

JAG1 Protein Levels in the Livers of
Mice Treated with ACT-UP1 Compounds

|  | | PBS | ATXL316 | ATXL484 | ATXL493 |
|---|---|---|---|---|---|
| JAG1 protein | 2 week | 100 | 142.9 | 140.8 | 143.8 |
| levels % | 3 week | 100 | 161.5 | 134.2 | 128.7 |

The results showed that ACT-UP1 compounds with different numbers of PS can also increase the target JAG1 protein levels, and a substantial increase can be observed for ATXL316 at 3 weeks after compound dosing.

Example 20. A Dual Functional ACT-UP1 Compound Increases FGF21 mRNA Levels In Vitro In order to further increase FGF21 levels, a dual functional ACT-UP1 compound, ATXL464, was designed. Without being bound by any particular theory, this dual functional compound may work via two mechanisms of action: (1) ACT-UP1 recruitment of translation proteins to increase protein expression, and (2) blocking the binding of cellular proteins to an AU rich element (ARE) of a transcript, thereby, inhibiting mRNA degradation. As a comparison to the dual functional ACT-UP1 compound, four additional compounds were designed to work solely via the ARE mechanism and target an ARE of FGF21 mRNA: ATXL460-ATXL463. ATXL464 has the same sequence and chemistry as ATXL461 plus a PRS, thus, it is a dual functional ACT-UP1+ARE targeting compound. The sequence and chemistry of the compounds are listed in Table 38. PS was denoted by "*", 2'-OMe was denoted as "m" in front of the modified nucleosides, LNA was denoted as "L" after the modified nucleoside, 2'-MOE was denoted by "e" in front of the modified nucleoside, and 2'-MOE modified 5-methylcytidine was denoted as "eCm". The PRS is bolded and underlined in the table.

TABLE 38

Sequence and Chemistry of FGF21 Compounds

| Compound | Sequence and Chemistry (5' to 3') | Sequence (5' to 3') | SEQ ID NO |
|---|---|---|---|
| ATXL460 | eA*eT*eA*eA*eG*eA*eT*eA*eA*eA*eT*eA*eA*eCm*eCm*eT*eA*AL*eT*AL*eA*AL*eT | ATAAGATAAATAACCTAATAAAT | 64 |
| ATXL461 | eA*eT*eAeAeGeAeTeAeAeAeTeAeA[eCm][eCm]eTeAeAeTeA*eA*eA*eT | ATAAGATAAATAACCTAATAAAT | 65 |
| ATXL462 | eT*eA*eA*eGeAeTeAeAeAeTeAeA[eCm][eCm]eTeAeAeAT*eA*eA*eA | TAAGATAAATAACCTAATAAA | 66 |
| ATXL463 | eA*eA*eT*eAeAeAeTeAeAeGeAeTeAeAeAeTeA*eA*eCm*eCm | AATAAATAAGATAAATAACC | 67 |

TABLE 38-continued

Sequence and Chemistry of FGF21 Compounds

| Compound | Sequence and Chemistry (5' to 3') | Sequence (5' to 3') | SEQ ID NO |
|---|---|---|---|
| ATXL464 | mG*mG*mAmCmUmGm GmAmCmUeA*eT*eAe AeGeAeTeAeAeAeTe AeA[eCm][Cm]eTeA eAeTeA*eA*eA*eT | GGACUGGACUAT AAGATAAATAAC CTAATAAAT | 68 |

In Vitro Assay

Hep3B cells, seeded and grown in one day to ~70% confluency, were transfected with the compounds at 5 different concentrations using Lipofectamine™ 2000 Transfection Reagent (ThermoFisher Scientific, Waltham, MA), or were mock transfected as a control. At 20 hr or 40 hr after transfection, cells were harvested and total RNA was prepared using Qiagen's RNeasy kit (Qiagen, Hilden, Germany) and the level of FGF21 mRNA was determined using quantitative real-time PCR (qRT-PCR), using human FGF21 specific TaqMan primer probe sets (Assay ID: Hs00173927_m1, ThermoFisher Scientific, Waltham, MA). qRT-PCR was performed using AgPath-ID™ One-Step RT-PCR Reagents in QS3 real-time PCR system (ThermoFisher Scientific, Waltham, MA). The FGF21 mRNA levels detected in qRT-PCR assay were normalized to total RNA levels measured with Ribogreen™ (ThermoFisher Scientific, Waltham, MA) detected in the aliquots of the corresponding RNA samples. The mRNA levels are shown in FIG. 21 and Table 39.

TABLE 39

FGF21 mRNA Levels in Hep3B Cells After Transfection

| Time | Concentration (nM) | 0.0 | 1.3 | 3.2 | 8.0 | 20.0 | 50.0 |
|---|---|---|---|---|---|---|---|
| 20 hr | ATXL460 | 100.0 | 155.2 | 160.1 | 184.3 | 228.4 | 323.5 |
|  | ATXL461 | 100.0 | 179.5 | 164.8 | 216.4 | 263.0 | 367.6 |
|  | ATXL462 | 100.0 | 93.5 | 115.2 | 124.9 | 176.0 | 258.3 |
|  | ATXL464 | 100.0 | 176.6 | 201.9 | 259.5 | 439.7 | 811.6 |
| 40 hr | ATXL460 | 100.0 | 159.0 | 137.1 | 210.9 | 198.3 | 222.1 |
|  | ATXL461 | 100.0 | 170.9 | 165.6 | 252.1 | 345.0 | 328.4 |
|  | ATXL462 | 100.0 | 165.1 | 196.2 | 239.5 | 231.0 | 378.6 |
|  | ATXL464 | 100.0 | 114.9 | 180.4 | 261.4 | 406.3 | 1220.1 |

The results indicate that the three compounds only targeting ARE increased FGF21 mRNA levels in a dose-dependent manner at two different time points. The dual functional ARE targeting plus ACT-UP1 compound (ATXL464) increased FGF21 mRNA levels substantially more than the compound only targeting ARE (ATXL461), especially at high doses.

Example 21. The Dual Functional FGF21 ACT-UP1 Compound Increased FGF21 Protein Levels in Mouse Plasma To determine if a dual functional FGF21 ACT-UP1 compound can increase plasma FGF21 protein levels, new compounds ATXL482 and ATXL499 were designed based on previously described compounds ATXL461 and ATXL464 sequences, respectively, but with phosphorothioate linkages in the ARE binding region. Additionally, these compounds are also GalNAc conjugated to facilitate delivery to liver hepatocytes. The sequence and chemistry of the compounds are listed in Table 40. AN-GalNAc is a GalNAc conjugate described in WO2024137545. Bolded and underlined sequence is the PRS.

TABLE 40

| | Sequence and Chemistry (5' to 3') | Sequence (5' to 3') | SEQ ID NO |
|---|---|---|---|
| Compound | | | |
| ATXL482 | eA*eT*eA*eA*eG*<br>eA*eT*eA*eA*eA*<br>eT*eA*eA*eCm*eCm*<br>eT*eA*eA*eT*eA*<br>eA*eA*eT-[AN-<br>GalNAc] | ATAAGATAAAT<br>AACCTAATAAA<br>T | 69 |
| ATXL499 | mG*mG*mAmCmUmGm<br>GmAmCmUeA*eT*eA*<br>eA*eG*eA*eT*eA*<br>eA*eA*eT*eA*eA*<br>eCm*eCm*eT*eA*<br>eA*eT*eA*eA*eA*<br>eT-[AN-GalNAc] | GGACUGGACUA<br>TAAGATAAATA<br>ACCTAATAAAT | 70 |

Title header: Sequence and Chemistry of FGF21 ASOs

To determine the activity of the new FGF21 dual functional ACT-UP1 compound in mice, three animals per group of 7- to 8-week-old male Balb/C mice were injected subcutaneously with 1, 3, 9, or 75 mg/kg of the GalNAc-conjugated compounds ATXL482 and ATXL499. Post dosing 72 hr, the mice were dosed a second time. The mice were sacrificed 72 hrs after the second dose, and blood samples were collected from mice using tubes coated with lithium heparin as an anticoagulant, and plasma was prepared by centrifugation of the blood samples at 2000×g for 10 min at 4° C. Plasma FGF21 protein levels were then determined using an ELISA kit specific to murine FGF21 (KE10042, Proteintech®, Rosemont, IL, USA). The FGF21 protein levels relative to saline control treated mice are shown in FIG. 22 and in Table 41.

TABLE 41

Relative Plasma FGF21 Protein Levels in Mice Treated with ASOs

| mg/kg | PBS | ATXL482 | | | | ATXL499 | | | |
|---|---|---|---|---|---|---|---|---|---|
| | | 1 | 3 | 9 | 75 | 1 | 3 | 9 | 75 |
| FGF21 protein % | 100.0 | 265.8 | 197.9 | 148.2 | 754.0 | 339.5 | 285.2 | 442.8 | 1022.2 |

The results indicate that the dual functional ACT-UP1 compound ATXL499 caused more protein increase than the ARE targeting compound ATXL482, with around 4-fold increase at 9 mg/kg, and over 10-fold increase at 75 mg/kg, relative to saline treated group.

Example 22. ACT-UP1 Compound can Increase Jagged 1 Protein Levels in ALGS Patient Derived Fibroblast Cells To evaluate if an ACT-UP1 compound can increase the target protein in a disease setting, the effect of the above-described ACT-UP1 compound ATXL316 was also assessed in GM11091 cells. This cell line was derived from an ALGS patient, and contains a heterozygous mutation in the JAG1 gene (Brooks B. M., et al., 2021, Stem Cell Res: 54:102447).

GM11091 cells, grown to about 70% confluency, were transfected with ATXL316 at different concentrations using Lipofectamine™ 2000 Transfection Reagent (ThermoFisher Scientific, Waltham, MA), or were mock transfected as a control. Twenty-four (24) hr after transfection, cells were harvested and lysed, then the protein was extracted using RIPA Lysis and Extraction Buffer (ThermoFisher Scientific, Waltham, MA). The level of Jagged 1 protein was determined by Western Blot, using a JAG1 specific antibody (ab109536 from Abcam, Waltham, MA). The Western Blot result is shown in FIG. 23. The Western Blot was quantified using Image J, and the results are shown in Table 42 as percent protein levels relative to mock transfected cells following normalization to a loading control protein, alpha-tubulin (ab7291 from Abcam, Waltham, MA).

TABLE 42

| JAG1 Protein Levels in GM11091 Cells Treated with ATXL316 | | | | | | |
|---|---|---|---|---|---|---|
| Compound | Mock (no treatment) | ATXL316 | | | | |
| Concentration (nM) | n/a | 3.75 | 7.5 | 15 | 30 | 60 |
| JAG1 protein level % | 100 | 127.9 | 140.1 | 170.2 | 159.6 | 158.3 |

The results indicate that Jagged 1 protein levels can also be increased in GM11091 patient cells using the ATXL316 ACT-UP1 compound, suggesting that this upregulation approach may increase JAG1 protein levels in patients.

Example 23. ACT-UP1 Compound ATXL316 can Increase Jagged 1 Protein Levels but Not Protein Stability As shown in previous examples, ATXL316 can increase JAG1 protein levels in cells. Without being bound by any particular theory, the increase in JAG1 protein levels may be due to increased JAG1 translation. However, the increase in JAG1 protein levels may also be the result of increased JAG1 protein stability. To assess this possibility, JAG1 protein stability in HeLa cells treated with or without ATXL316 was evaluated using cycloheximide (CHX), a potent translation inhibitor that stops the synthesis of new protein products.

HeLa cells, seeded and grown in one day to ~70% confluency, were mock transfected or transfected with 20 nM ATXL316 using Lipofectamine™ 2000 Transfection Reagent (ThermoFisher Scientific, Waltham, MA). Twelve (12) hours after transfection, the cells were treated with 100 μg/ml CHX for 0, 4, 8, or 12 hr to stop translation. Cells were then harvested and lysed, and the protein was extracted using RIPA Lysis and Extraction Buffer (ThermoFisher Scientific, Waltham, MA). JAG1 protein levels were determined by Western Blot using a JAG1 specific antibody (ab109536 from Abcam, Waltham, MA) as shown in FIG. 24A. JAG1 protein levels in the Western Blot were quantified using ImageJ, and the results are shown in Table 43 as percent protein levels relative to mock transfected cells at time point 0 following normalization to a loading control protein detected by an Hsp90 antibody (ProteinTech, Rosemont, IL, USA; Catalog #13171-1-AP).

TABLE 43

| JAG1 Protein Levels in HeLa Cells after Cycloheximide Treatment | | |
|---|---|---|
| | JAG1 protein % | |
| CHX treatment (hr) | Mock Treated | ATXL316 Treated |
| 0 | 100.00 | 163.92 |
| 4 | 34.10 | 57.65 |

TABLE 43-continued

| JAG1 Protein Levels in HeLa Cells after Cycloheximide Treatment | | |
|---|---|---|
| | JAG1 protein % | |
| CHX treatment (hr) | Mock Treated | ATXL316 Treated |
| 8 | 21.20 | 37.81 |
| 12 | 20.89 | 43.84 |

The results indicate that ATXL316 increased JAG1 protein level by approximately 63% before CHX treatment (time point 0). The JAG1 protein degradation rate is comparable in ATXL316 or mock treated cells, indicating that ATXL316 does not affect JAG1 protein stability. CHX treatment reduced the protein levels over time by inhibiting new JAG1 production, reflecting the pre-existing protein stability. These results suggest that ACT-UP1 compound ATXL316 increases protein translation.

Example 24. Different PRS of ACT-UP1 Compound Targeting Jagged 1 can Increase Protein Levels In Example 13, it was shown that several different protein recruiting sequences (PRSs) in ACT-UP1 compounds can increase target protein levels. To evaluate the influence of additional ACT-UP1 PRSs on their ability to increase protein levels, 10 ACT-UP1 compounds with the same JAG1 mRNA binding sequence as ATXL316, but, with different PRSs (bolded and underlined in table) were designed, as shown in FIG. 25A and Table 44A. These ACT-UP1 compounds were assessed in HeLa cells.

HeLa cells, seeded and grown in one day to ~70% confluency, were transfected with the ACT-UP1 compounds at 7.5 nM or 15 nM final concentrations using Lipofectamine™ 2000 Transfection Reagent (ThermoFisher Scientific, Waltham, MA), or were mock transfected as a control. Twenty-four (24) hours after transfection, cells were harvested and lysed, then the protein was extracted using RIPA Lysis and Extraction Buffer (ThermoFisher Scientific, Waltham, MA). The level of JAG1 protein was determined by Western Blot, using a JAG1 specific antibody (ab109536 from Abcam, Waltham, MA). The Western Blot result is shown in FIG. 25B. The Western Blot was quantified using ImageJ, and the results are shown in Table 44B and FIG. 25C as percent protein levels relative to mock transfected cells following normalization to a non-specific protein band detected by the same antibody.

TABLE 44A

Sequence and Chemistry of ASOs with New PRSs

| Compound | Sequence and Chemistry (5' to 3') | Sequence (5' to 3') | SEQ ID NO |
|---|---|---|---|
| ATXL572 | mC*mC*mCmCmCmCmCmCmC [eA]*[eA]*[eCm]*[eA]*[eCm]*[eA]*[eG]* [eA]*[eA]*[eA]*[eCm]*[eT]*[eA]*[eCm]*[eCm]* [eA] | CCCCCCCCCAACCACAGAAACTACCA | 71 |
| ATXL573 | mU*mU*mUmUmUmUmUmUmUmU [eA]*[eA]*[eCm]*[eA]*[eCm]*[eA]*[eG]* [eA]*[eA]*[eA]*[eCm]*[eT]*[eA]*[eCm]*[eCm]* [eA] | UUUUUUUUUAACCACAGAAACTACCA | 72 |
| ATXL574 | mA*mC*mAmCmAmCmAmCmAmC [eA]*[eA]*[eCm]*[eA]*[eCm]*[eA]*[eG]* [eA]*[eA]*[eA]*[eCm]*[eT]*[eA]*[eCm]*[eCm]* [eA] | ACACACACACAACCACAGAAACTACCA | 73 |
| ATXL575 | mA*mG*mAmGmAmGmAmGmAmG [eA]*[eA]*[eCm]*[eA]*[eCm]*[eA]*[eG]* [eA]*[eA]*[eA]*[eCm]*[eT]*[eA]*[eCm]*[eCm]* [eA] | AGAGAGAGAACCACAGAAACTACCA | 74 |
| ATXL576 | mC*mU*mCmUmCmUmCmUmCmU [eA]*[eA]*[eCm]*[eCm]*[eA]*[eA]*[eG]* [eA]*[eA]*[eA]*[eCm]*[eT]*[eA]*[eCm]*[eCm]* [eA] | CUCUCUCUCUAACCACAGAAACTACCA | 75 |

TABLE 44A-continued

Sequence and Chemistry of ASOs with New PRSs

| Compound | Sequence and Chemistry (5' to 3') | Sequence (5' to 3') | SEQ ID NO |
|---|---|---|---|
| ATXL577 | mG*mU*mGmUmGmUmGmUmGmU [eA]*[eA]*[eCm]*[eCm]*[eA]*[eCm]*[eA]*[eG]* [eA]*[eA]*[eA]*[eCm]*[eT]*[eA]*[eCm]*[eCm]* [eA] | GUGUGUGUAAC CACAGAAACTACCA | 76 |
| ATXL578 | mA*mA*mAmCmAmAmAmAmAmCmA [eA]*[eA]*[eCm]*[eCm]*[eA]*[eCm]*[eA]*[eG]* [eA]*[eA]*[eA]*[eCm]*[eT]*[eA]*[eCm]*[eCm]* [eA] | AAACAAAACAAACC ACAGAAACTACCA | 77 |
| ATXL579 | mA*mU*mUmAmUmUmAmUmUmA [eA]*[eA]*[eCm]*[eCm]*[eA]*[eCm]*[eA]*[eG]* [eA]*[eA]*[eA]*[eCm]*[eT]*[eA]*[eCm]*[eCm]* [eA] | AUUAUUAUUAAACC ACAGAAACTACCA | 78 |
| ATXL580 | mG*mG*mAmCmUmGmGmAmCmUmGmGmAmCmU [eA]*[eA]*[eCm]*[eCm]*[eA]*[eCm]*[eA]*[eG]* [eA]*[eA]*[eA]*[eCm]*[eT]*[eA]*[eCm]*[eCm]* [eA] | GGACUGGACUGGA CUAACCACAGAAAC TACCA | 79 |
| ATXL581 | mA*mA*mAmAmAmAmAmAmAmAmA [eA]*[eA]*[eCm]*[eCm]*[eA]*[eCm]*[eA]*[eG]* [eA]*[eA]*[eA]*[eCm]*[eT]*[eA]*[eCm]*[eCm]* [eA] | AAAAAAAAAAAA ACCACAGAAACTAC CA | 80 |

TABLE 44B

JAG1 Protein Levels in HeLa Cells Transfected with
ACT-UP1 Compounds Containing Different PRSs

| ASO | JAG1 protein % |
|---|---|
| ATXL572-7.5 | 154.8 |
| ATXL572-15 | 147.1 |
| ATXL573-7.5 | 197.9 |
| ATXL573-15 | 240.9 |
| ATXL316-7.5 | 181.2 |
| ATXL316-15 | 127.0 |
| Mock 1 | 98.6 |
| Mock 2 | 101.4 |
| ATXL574-7.5 | 122.8 |
| ATXL574-15 | 116.7 |
| ATXL575-7.5 | 120.0 |
| ATXL575-15 | 93.2 |
| ATXL576-7.5 | 101.5 |
| ATXL576-15 | 144.2 |
| ATXL577-7.5 | 106.5 |
| ATXL577-15 | 129.0 |
| ATXL578-7.5 | 98.5 |
| ATXL578-15 | 82.1 |
| ATXL579-7.5 | 97.2 |
| ATXL579-15 | 120.8 |
| ATXL580-7.5 | 103.2 |
| ATXL580-15 | 159.6 |

TABLE 44B-continued

JAG1 Protein Levels in HeLa Cells Transfected with
ACT-UP1 Compounds Containing Different PRSs

| ASO | JAG1 protein % |
|---|---|
| ATXL581-7.5 | 142.2 |
| ATXL581-15 | 125.8 |

The results, together with results from Example 13, showed that many of the tested PRSs can increase JAG1 protein levels, to different extents, suggesting that the ACT-UP1 PRS region can tolerate sequence variations in enhancing protein levels.

Example 25. Different Dual-Functional ACT-UP1 Compounds Targeting FGF21 mRNA Can Increase FGF21 mRNA Levels in Hep3B Cells To evaluate the effects of different chemistry and sequence on increasing FGF21 mRNA levels, several compounds were designed around the dual functional ACT-UP1 compound ATXL499 (previously described in Example 21) with different chemistry, sequence, and/or PRSs. Examples of these compounds are listed in Table 45.

TABLE 45

Sequence and Chemistry of ACT-UP1 Compounds Targeting FGF21

| Compound | Sequence and Chemistry (5' to 3') | Sequence (5' to 3') | SEQ ID NO |
|---|---|---|---|
| ATXL506 | mG*mG*mAmCmUmGmGmAmCmU*[eA]*[eT]*[eA]*[eA]*[eG]*[eA]*[eT]*[eA]*[eA]*[eA]*[eT]*[eA]*[eA]*[eCm]*[eCm]*[eT]*[eA]*[eA]*[eT]*[eA]*[eA]*[eA]*[eA]*[eT][AN-GalNAc] | GGACUGGACUAT AAGATAAATAAC CTAATAAAT | 81 |
| ATXLS17 | mG*mG*mAmCmUmG*mG*mAmCmU*[eA]*[eT]*[eA]*[eA]*[eG]*[eA]*[eT]*[eA]*[eA]*[eA]*[eT]*[eA]*[eA]*[eCm]*[eCm]*[eT]*[eA]*[eA]*[eT]*[eA]*[eA]*[eA]*[eA]*[eT][AN-GalNAc] | GGACUGGACUAT AAGATAAATAAC CTAATAAAT | 82 |
| ATXL518 | mG*mG*mAmCmUmUmG*mG*mAmCmU*[eA]*[eT]*[eA]*[eA]*[eG]*[eA]*[eT]*[eA]*[eA]*[eA]*[eT]*[eA]*[eA]*[eCm]*[eCm]*[eT]*[eA]*[eA]*[eT]*[eA]*[eA]*[eA]*[eA]*[eT][AN-GalNAc] | GGACUGGACUAT AAGATAAATAAC CTAATAAAT | 83 |
| ATXL519 | mG*mG*mAmCmUmUmG*mGmA*mC*mU*[eA]*[eT]*[eA]*[eA]*[eG]*[eA]*[eT]*[eA]*[eA]*[eA]*[eT]*[eA]*[eA]*[eCm]*[eCm]*[eT]*[eA]*[eA]*[eT]*[eA]*[eA]*[eA]*[eA]*[eT][AN-GalNAc] | GGACUGGACUAT AAGATAAATAAC CTAATAAAT | 84 |
| ATXL520 | mG*mG*mAmCmUmUmG*mG*mA*mC*mU*[eA]*[eT]*[eA]*[eA]*[eG]*[eA]*[eT]*[eA]*[eA]*[eA]*[eT]*[eA]*[eA]*[eCm]*[eCm]*[eT]*[eA]*[eA]*[eT]*[eA]*[eA]*[eA]*[eA]*[eT][AN-GalNAc] | GGACUGGACUAT AAGATAAATAAC CTAATAAAT | 85 |
| ATXLS21 | mG*mG*mAmCmUmUmG*mGmA*mC*[eA]*[eT]*[eA]*[eA]*[eG]*[eA]*[eT]*[eA]*[eA]*[eA]*[eT]*[eA]*[eA]*[eCm]*[eCm]*[eT]*[eA]*[eA]*[eT]*[eA]*[eA]*[eA]*[eA]*[eT][AN-GalNAc] | GGACUGGACATA AGATAAATAACC TAATAAAT | 86 |

TABLE 45-continued

| | Sequence and Chemistry (5' to 3') | Sequence (5' to 3') | SEQ ID NO |
|---|---|---|---|
| Compound | | | |
| ATXLS22 | mG*mG*mAmCmUmGmGmAmCmUmA*mU*mA *mA*mG*mA*mU*mA*mA*mA*mU*mA*mA*m C*mC*mU*mA*mA*mU*mA*mA*mA*mU[AN-GalNAc] | GGACUGGACUA UAAGAUAAAUAA CCUAAUAAAU | 87 |
| ATXL523 | mG*mG*mA*mC*mU* [eA]*[eT]*[eA]*[eA]*[eG]*[eA]* [eT]*[eA]*[eA]*[eA]*[eT]*[eA]* [eA]*[eCm]*[eCm]*[eT]*[eA]* [eA]*[eT]*[eA]*[eA]*[eA] *[eA]*[eT][AN-GalNAc] | GGACUATAAGAT AAATAACCTAAT AAAT | 88 |
| ATXL524 | mG*mG*mAmCmU* [eA]*[eT]*[eA]*[eA]*[eG]*[eA]* [eT]*[eA]*[eA]*[eA]*[eT]*[eA]* [eA]*[eCm]*[eCm]*[eT]*[eA]* [eA]*[eT]*[eA]*[eA]*[eA] *[eA]*[eT][AN-GalNAc] | GGACUATAAGAT AAATAACCTAAT AAAT | 89 |
| ATXL525 | mG*mG*mAmCmU [eA]*[eT]*[eA]*[eA]*[eG]*[eA]* [eT]*[eA]*[eA]*[eA]*[eT]*[eA]* [eA]*[eCm]*[eCm]*[eT]*[eA]* [eA]*[eT]*[eA]*[eA]*[eA] *[eA]*[eT][AN-GalNAc] | GGACUATAAGAT AAATAACCTAAT AAAT | 90 |

In Vitro Assay for FGF21 mRNA Levels in Hep3B Cells

Hep3B (human hepatoma) cells, seeded and grown in one day to ~70% confluency, were transfected with the compounds at five different concentrations using Lipofectamine™ 2000 Transfection Reagent (ThermoFisher Scientific, Waltham, MA), or were mock transfected as a control. 48 hr after transfection, cells were harvested, and total RNA was prepared using Qiagen's RNeasy mini kit (Qiagen, Hilden, Germany) and the level of FGF21 mRNA was determined using quantitative real-time PCR (qRT-PCR), using human FGF21 specific TaqMan primer probe sets (Assay ID: Hs00173927_m1, ThermoFisher Scientific, Waltham, MA). qRT-PCR was performed using AgPath-ID™ One-Step RT-PCR Reagents in QS3 real-time PCR system (ThermoFisher Scientific, Waltham, MA). The FGF21 mRNA levels detected by the qRT-PCR assay were normalized to total RNA levels measured with Ribogreen™ (ThermoFisher Scientific, Waltham, MA) detected in the aliquots of the corresponding RNA samples. The mRNA levels are shown in FIG. 26 and Table 46.

The results showed that these compounds with different chemistry, sequences and/or PRSs can increase FGF21 mRNA levels in Hep3B cells, especially those with longer PRSs (e.g., GGACUGGACU). The shorter PRS-containing compounds (ATXL523, ATXL524, and ATXL525) appear less active than those with longer PRSs.

In Vitro Assay for FGF21 mRNA Levels in HepG2 Cells

HepG2 cells, derived from liver and express FGF21 protein, were seeded and grown in one day to ~70% confluency, then transfected with the compounds listed in Table 45 at 7.5 nM or 15 nM final concentrations using Lipofectamine™ 2000 Transfection Reagent (ThermoFisher Scientific, Waltham, MA), or were mock transfected as a control. Twenty-four (24) hr after transfection, cells were harvested and lysed, then the protein was extracted using RIPA Lysis and Extraction Buffer (ThermoFisher Scientific, Waltham, MA). The level of FGF21 protein was determined by Western Blot, using a FGF21 specific antibody (ab171941 from Abcam, Waltham, MA). The Western Blot results of the 7.5 and 15 nM samples are shown in FIG. 27,

TABLE 46

FGF21 mRNA Levels in Hep3B Cells Transfected with Different Compounds

| Name (nM) | ATXL499 | ATXL506 | ATXL517 | ATXL518 | ATXL519 | ATXL520 | ATXL521 | ATXL522 | ATXL523 | ATXL524 | ATXL525 |
|---|---|---|---|---|---|---|---|---|---|---|---|
| 0 | 100 | 100 | 100 | 100 | 100 | 100 | 100 | 100 | 100 | 100 | 100 |
| 0.6 | 124.1 | 102.0 | 69.1 | 82.8 | 116.1 | 110.2 | 113.4 | 170.6 | 108.8 | 80.0 | 153.6 |
| 1.9 | 129.7 | 154.8 | 98.7 | 87.0 | 121.2 | 88.6 | 114.1 | 110.5 | 111.1 | 71.1 | 132.4 |
| 5.6 | 150.7 | 140.2 | 115.3 | 104.1 | 161.0 | 143.0 | 126.2 | 139.4 | 142.7 | 87.4 | 142.9 |
| 16.7 | 150.5 | 196.2 | 160.8 | 132.2 | 200.2 | 212.1 | 176.5 | 324.5 | 179.1 | 62.6 | 195.7 |
| 50 | 299.1 | 424.2 | 277.4 | 298.6 | 433.7 | 433.5 | 293.9 | 592.7 | 204.0 | 53.2 | 184.3 | panels A and B, respectively. The Western Blot image was quantified using ImageJ, normalization to a loading control protein, GAPDH, and the percentages of protein levels relative to mock-transfected cells were calculated and are shown in Table 47.

In Vitro Assay—Protein Assessment

The two GalNAc-conjugated compounds were evaluated in human primary hepatocytes (HPH) through free uptake, i.e., compounds were incubated with cells in the absence of

TABLE 47

| | | | | | FGF21 Protein Levels in HepG2 Cells Transfected with 7.5 nM of Compounds | | | | | | |
|---|---|---|---|---|---|---|---|---|---|---|---|
| Name (nM) | Mock | ATXL499 | ATXL506 | ATXL517 | ATXL518 | ATXL519 | ATXL520 | ATXL521 | ATXL522 | ATXL523 | ATXL524 | ATXL525 |
| 7.5 nM | 100 | 85 | 239 | 260 | 314 | 249 | 162 | 185 | 165 | 172 | 221 | 196 |
| 15 nM | 100 | 175 | 156 | 179 | 163 | 156 | 111 | 80 | 89 | 99 | 82 | 43 |

The results indicate that these different ACT-UP1 compounds could increase FGF21 protein levels in HepG2 cells, although compounds with short PRS (e.g., ATXL525) showed lower activity than longer PRS-containing compounds, especially at higher compound concentrations.

Example 26. HNF4A Protein can be Increased in Human Primary Hepatocytes Using Newly Designed ACT-UP1 Compounds To further evaluate the activity of ACT-UP1 compounds in increasing HNF4A protein levels, two new compounds were designed around previously described ATXL395 (see Example 15), with different sequences and chemistry, but, the same PRS. The new compounds contain a phosphorothioate (PS) backbone and 2'-MOE sugar modifications in the mRNA binding region to improve in vivo stability and GalNAc conjugate agents for delivery into hepatocytes. These compounds are listed in Table 48 with the PRS of the ACT-UP1 compounds shown as the bolded and underlined sequences at the 5' end of the HNF4A antisense oligonucleotide sequence.

transfection reagents and entered cells through endocytosis via the GalNAc conjugate and ASGR receptor interactions.

HPH cells were grown to ~70% confluence, then compounds were delivered at 5 and 25 μM final concentrations in OptiCulture media (XenoTech, Kansas City, KS, USA, K8300) to the cells. Cells were incubated in OptiCulture media with the compounds or water for 66 hrs, harvested and lysed, then the protein was extracted using RIPA Lysis and Extraction Buffer (ThermoFisher Scientific, Waltham, MA). The level of HNF4A protein was determined by Western Blot, using a HNF4A specific antibody (ab181604 from Abcam, Waltham, MA). The Western Blot result is shown in FIG. 28A and a bar graph quantifying the results is shown in FIG. 28B. The Western Blot was quantified using ImageJ, and the results are shown in Table 49 as percent protein levels relative to the average of four mock (PBS) cell samples following normalization to a loading control protein, GAPDH, detected using a GAPDH specific antibody (G8795 from Sigma-Aldrich, St. Louis, MO, USA).

TABLE 48

Sequence and Chemistry of New ACT-UP1
Compounds Targeting Human HNF4A mRNA

| Compound | Sequence and Chemistry (5' to 3') | Sequence (5' to 3') | SEQ ID NO |
|---|---|---|---|
| ATXL546 | mG*mG*mAmCmUmGmGmAmCmU [eCm]*[eT]*[eG]*[eCm]* [eT]*[eCm]*[eT]*[eG]* [eG]*[eG]*[eA]*[eCm]* [eT]*[eG]*[eG]*[eT] [AN-GalNAc] | GGACUGG ACUCTGC TCTGGGA CTGGT | 91 |
| ATXL547 | mG*mG*mAmCmUmGmGmAmCmU [eG]*[eCm]*[eT]*[eCm]* [eT]*[eG]*[eG]*[eG]* [eA]*[eCm]*[eT]*[eG] *[eG]*[eT]*[eCm]* [eCm][AN-GalNAc] | GGACUGG ACUGCTC TGGGACT GGTCC | 92 |

TABLE 49

HNF4A Protein Level in HPH Incubated
with ACT-UP1 Compounds

|  | Compound (μM) | HNF4A protein % |
|---|---|---|
| ATXL546 | 2 | 165.77 |
|  | 25 | 105.54 |
| ATXL547 | 2 | 148.96 |
|  | 25 | 119.76 |
| Mock |  | 100.00 |

The results show that the GalNAc-conjugated compounds derived from ATXL395 are able to increase HNF4A protein levels in human primary hepatocytes.

Example 27. Dose-Response Study of ACT-UP1 Compound ATXL547 in Mouse Cells

To evaluate the dose-response relationship, the activity of ATXL547 (previously described in Example 26) was tested in mouse Hepa1-6 cells by transfection. Cells, seeded and grown for one day to ~70% confluency, were transfected with ATXL547 at 5, 10, 20, 40, and 80 nM final concentrations using Lipofectamine™ 2000 Transfection Reagent (ThermoFisher Scientific, Waltham, MA), or were mock transfected as a control. Twenty-four (24) hr after transfection, cells were harvested and lysed, then the protein was extracted using RIPA Lysis and Extraction Buffer (ThermoFisher Scientific, Waltham, MA). The level of HNF4A protein was determined by Western Blot, using a HNF4A specific antibody (R&D Systems, Minneapolis, MN, USA; Catalog #PP-1-11415-OC). The Western Blot result is shown in FIG. 29. The Western Blot was quantified using ImageJ, and the results are shown in Table 50 as percent protein levels relative to the average of four mock transfected cell samples following normalization to a loading control protein detected by an Hsp90 antibody (ProteinTech, Rosemont, IL, USA; Catalog #13171-1-AP).

TABLE 50

HNF4A Protein Level in Mouse Hepa1-6
Cells Transfected with ATXL547

| | ATXL547 (nM) | | | | |
|---|---|---|---|---|---|
| | 0 | 5 | 10 | 20 | 40 | 80 |
| HNF4a protein % | 100.0 | 154.4 | 209.7 | 232.8 | 200.5 | 205.4 |

The results indicate that HNF4A protein levels can be increased using ATXL547 at a broad dose range from 5 to 80 nM, and the protein level remains controlled without super high over expression.

Example 28. ACT-UP1 Compounds Increase HNF4A Protein Levels In Vivo

To assess the activity of HNF4A ACT-UP1 compounds in vivo, mice were treated with the compounds and HNF4A protein levels were determined.

Three animals per cohort of 7- to 8-week-old male Balb/C mice were injected subcutaneously with 2.0, 8.0, 16.0, or 30.0 mg/kg of GalNAc-conjugated ATXL546 or ATXL547. Phosphate buffered saline (PBS) was injected as a control. Post dosing 96 hr, the mice were dosed a second time with the same dose. The mice were sacrificed 4 days after the second dose and organs were harvested for analysis. Total protein from mouse liver was prepared and subjected to Western analysis. HNF4A protein was detected using antibody (R&D Systems, Minneapolis, MN, USA; Catalog #PP-H1415-OC). The Western Blot results are shown in FIG. 30. The Western Blots were quantified using ImageJ, and the results are shown in Table 51, as percent protein levels relative to PBS control treated mice following normalization to a loading control protein, Hsp90, detected using antibody (ProteinTech, Rosemont, IL, USA; Catalog #13171-1-AP).

TABLE 51

HNF4A Protein Level in Mice Treated with ACT-UP1 Compounds

| Compound or PBS | HNF4A protein % | Compound or PBS | HNF4A protein % |
|---|---|---|---|
| PBS | 100.00 | PBS | 100.00 |
| ATXL546-2 | 124.35 | ATXL547-2 | 111.01 |
| ATXL546-8 | 179.17 | ATXL547-8 | 129.00 |
| ATXL546-16 | 184.64 | ATXL547-16 | 118.76 |
| ATXL546-30 | 125.48 | ATXL547-30 | 86.15 |
| PBS | 103.87 | PBS | 86.14 |

The results show that the ACT-UP1 compounds can increase HNF4A protein levels in vivo, consistent with what was observed in vitro.

TABLE 52A

Sequence Listing of GenBank Sequences

| SEQ ID NO | Sequence | Name/Description |
|---|---|---|
| 1 | agacgggctctccgggtccttctccgagagccgggcgggcacgcgtca ttgtgttacctgcggccggcccgcgagctaggctggttttttttttc tccctccctcccccttttccatgcagctgatctaaaagggaataa aaggctgcgcataatcataataataaaagaaggggagcgcgagagaag gaaagaaagccgggaggtggaagaggaggggagcgtctcaaagaagc gatcagaataataaaaggaggccgggctctttgccttctggaacgggc cgctcttgaaagggcttttgaaaagtggtgttgttttccagtcgtgca tgctccaatcggcggagtatattagagccgggacgcggcggccgcagg ggcagcggcgacggcagcaccggcggcagcaccagcgcgaacagcagc ggcggcgtcccgagtgcccgcggcgcgcggcgcagcgatgcgttcccc acggacgcgcggccggtccgggcgcccccctaagcctcctgctcgccct gctctgtgccctgcgagccaaggtgtgtgggcctcgggtcagttcga gttggagatcctgtccatgcagaacgtgaacggggagctgcagaacgg | Human JAG1 mRNA GENBANK Accession No. NM_000214.3 https://www.ncbi. nlm.nih.gov/nuc core/NM_000214.3 |

TABLE 52A-continued

| Sequence Listing of GenBank Sequences | |
|---|---|
| SEQ ID NO Sequence | Name/Description |
| gaactgctgcggcggcgcccggaacccgggagaccgcaagtgcacccg<br>cgacgagtgtgacacatacttcaaagtgtgcctcaaggagtatcagtc<br>ccgcgtcacggccgggggggccctgcagcttcggctcagggtccacgcc<br>tgtcatcggggggcaacaccttcaacctcaaggccagccgcggcaacga<br>ccgcaaccgcatcgtgctgcctttcagtttcgcctggccgaggtccta<br>tacgttgcttgtggaggcgtgggattccagtaatgacaccgttcaacc<br>tgacagtattattgaaaaggcttctcactcgggcatgatcaacccccag<br>ccggcagtggcagacgctgaagcagaacacgggcgttgcccactttga<br>gtatcagatccgcgtgacctgtgatgactactactatggctttggctg<br>caataagttctgccgccccagagatgacttctttggacactatgcctg<br>tgaccagaatggcaacaaaacttgcatggaaggctggatgggcccccga<br>atgtaacagagctatttgccgacaaggctgcagtcctaagcatgggtc<br>ttgcaaactcccaggtgactgcaggtgccagtacggctggcaaggcct<br>gtactgtgataagtgcatcccacacccgggatgcgtccacggcatctg<br>taatgagccctggcagtgcctctgtgagaccaactggggcggccagct<br>ctgtgacaaagatctcaattactgtgggactcatcagccgtgtctcaa<br>cgggggaacttgtagcaacacaggccctgacaaatatcagtgttcctg<br>ccctgaggggtattcaggacccaactgtgaaattgctgagcacgcctg<br>cctctctgatccctgtcacaacagaggcagctgtaaggagacctccct<br>gggctttgagtgtgagtgttccccaggctggaccggccccacatgctc<br>tacaaacattgatgactgttctcctaataactgttcccacggggggcac<br>ctgccaggacctggttaacgggatttaagtgtgtgtgccccccacagtg<br>gactgggaaaacgtgccagttagatgcaaatgaatgtgaggccaaacc<br>ttgtgtaaacgccaaatcctgtaagaatctcattgccagctactactg<br>cgactgtcttcccggctggatgggtcagaattgtgacataaatattaa<br>tgactgccttggccagtgtcagaatgacgcctcctgtcgggatttggt<br>taatggttatcgctgtatctgtccacctggctatgcaggcgatcactg<br>tgagagagacatcgatgaatgtgccagcaacccctgtttgaatggggg<br>tcactgtcagaatgaaatcaacagattccagtgtctgtgtcccactgg<br>tttctctggaaacctctgtcagctggacatcgattattgtgagcctaa<br>tccctgccagaacggtgcccagtgctacaaccgtgccagtgactattt<br>ctgcaagtgcccccgaggactatgagggcaagaactgctcacacctgaa<br>agaccactgccgcacgaccccctgtgaagtgattgacagctgcacagt<br>ggccatggcttccaacgacacacctgaaggggtgcggtatatttcctc<br>attcacctgtgactgtaacaaaggcttcacgggaacatactgccatga<br>caacgtctgtggtcctcacgggaagtgcaagagtcagtcgggaggcaa<br>aaatattaatgactgtgagagcaacccttgtagaaacggtggcacttg<br>catcgatggtgtcaactcctacaagtgcatctgtagtgacggctgggga<br>gggggcctactgtgaaaccaatattaatgactgcagccagaacccctg<br>ccacaatgggggcacgtgtcgcgacctggtcaatgacttctactgtga<br>ctgtaaaaatgggtggaaaggaaagacctgccactcacgtgacagtca<br>gtgtgatgaggccacgtgcaacaacggtggcacctgctatgatgaggg<br>ggatgcttttaagtgcatgtgtcctggcggctgggaaggaacaacctg<br>taacatagcccgaaacagtagctgcctgcccaacccctgccataatgg<br>gggcacatgtgtggtcaacggcgagtcctttacgtgcgtctgcaagga<br>aggctgggagggggcccatctgtgctcagaataccaatgactgcagccc<br>tcatccctgttacaacagcggcacctgtgtggatggagacaactggta<br>ccggtgcgaatgtgccccgggtttttgctgggcccgactgcagaataaa<br>catcaatgaatgccagtcttcaccttgtgcctttggagcgacctgtgt<br>ggatgagatcaatggctaccggtgtgtctgccctccagggcacagtgg<br>tgccaagtgccaggaagtttcagggagaccttgcatcaccatgggggag<br>Egtgataccagatggggccaaatgggatgatgactgtaataccgcca<br>gtgcctgaatggacggatcgcctgctcaaaggtctggtgtggccctcg<br>accttgcctgctccacaaagggcacagcgagtgccccagcgggcagag<br>ctgcatcccatcctggacgaccagtgcttcgtccacccctgcactgg<br>tgtgggcgagtgtcggtcttccagtctccagccggtgaagacaaagtg<br>cacctctgactcctattaccaggataactgtgcgaacatcacatttac<br>ctttaacaaggagatgatgtcaccaggtcttactacggagcacatttg<br>cagtgaattgaggaatttgaatattttgaagaatgtttccgctgaata<br>ttcaatctacatcgcttgcgagccttccccttcagcgaacaatgaaat<br>acatgtggccatttctgctgaagatatacgggatgatgggaacccgat<br>caaggaaatcactgacaaaataatcgatcttgttagtaaacgtgatgg<br>aaacagctcgctgattgctgccgttgcagaagtaagagttcagaggcg<br>gcctctgaagaacagaacagatttccttgttcccttgctgagctctgt<br>cttaactgtggcttggatctgttgcttggtgacggccttctactggtg<br>cctgcggaagcggcggaagccgggcagccacacacactcagcctctga<br>ggacaacaccaccaacaacgtgcgggagcagctgaaccagatcaaaaa<br>ccccattgagaaacatggggccaacacggtccccatcaaggattatga<br>gaacaagaactccaaaatgtctaaaataaggacacacaattctgaagt<br>agaagaggacgacatggacaaacaccagcagaaagcccggtttgccaa<br>gcagccggccgtacacgctggtagacagagaagagaagcccccccaacgg<br>cacgccgacaaaacacccaaactggacasacaaacaggacaacagaga<br>cttggaaagtgcccagagcttaaaccgaatggagtacatcgtatagca<br>gaccgcgggcactgccgccgctaggtagagtctgagggcttgtagttc<br>tttaaactgtcgtgtcatactcgagtctgaggccgttgctgacttaga<br>atccctgtgttaatttaagttttgacaagctggcttacactggcaatg | |

TABLE 52A-continued

Sequence Listing of GenBank Sequences

| SEQ ID NO | Sequence | Name/Description |
|---|---|---|
| | gtagtttctgtggttggctgggaaatcgagtgccgcatctcacagcta<br>tgcaaaaagctagtcaacagtaccctggttgtgtgtcccccttgcagcc<br>gacacggtctcggatcaggctcccaggagcctgcccagcccctggtc<br>tttgagctcccacttctgccagatgtcctaatggtgatgcagtcttag<br>atcatagttttatttatatttattgactcttgagttgttttttgtatat<br>tggttttatgatgacgtacaagtagttctgtatttgaaagtgcctttg<br>cagctcagaaccacagcaacgatcacaaatgactttattatttatttt<br>ttttaattgtattttttgttgttgggggagggggagactttgatgtcagc<br>agttgctggtaaaatgaagaatttaaagaaaaaaatgtcaaaagtaga<br>actttgtatagttatgtaaataattctttttttattaatcactgtgtat<br>atttgatttattaacttaataatcaagagcctaaaacatcattcctt<br>tttatttatatgtatgtgtttagaattgaaggttttttgatagcattgt<br>aagcgtatggctttatttttttgaactcttctcattacttcttgccta<br>taagccaadattaaggtgtttgaaaatagtttattttaaaacaatagg<br>atgggcttctgtgcccagaatactgatggaatttttttgtacgacgtc<br>agatgtttaaaacaccttctatagcatcacttaaaacacgttttaagg<br>actgactgaggcagtttgaggattagtttagaacaggtttttttgttt<br>gtttgttttttgttttctgctttagacttgaaaagagacaggcaggt<br>gatctgctgcagagcagtaagggaacaagttgagctatgacttaacat<br>agccaaaatgtgagtggttgaatatgattaaaaatatcaaattaattg<br>tgtgaacttggaagcacaccaatcttactttgtaaattctgatttctt<br>ttcaccattcgtacataatactgaaccacttgtagatttgattttttt<br>ttttaatctactgcatttagggagtattctaataagctagttgaatac<br>ttgaaccataaaatgtccagtaagatcactgtttagatttgccataga<br>gtacactgcctgccttaagtgaggaaatcaaagtgctattacgaagtt<br>caagatcaaaaaggcttataaaacagagtaatcttgttggttcaccat<br>tgagaccgtgaagatactttgtattgtcctattagtgttatatgaaca<br>tacaaatgcatctttgatgtgttgttcttggcaataaattttgaaaag<br>taatatttattaaattttttttgtatgaaaacatggaacagtgtggcct<br>cttctgagcttacgtagttctaccggctttgccatgtgcttctgccac<br>cctgctgagtctcttctggtaatcggggtataataggctctgcctgac<br>agagggatggaggaagaactgaaaggcttttcaaccacaaaactcatc<br>tggagttctcaaagacctggggctgctgtgaagctggaactgcgggag<br>ccccatctaggggagccttgattcccttgttattcaacagcaagtgtg<br>aatactgcttgaataaacaccactggattaatggcc | |
| 2 | atgttgttccctccgcgctggacgggagcagctggagcgggagcctgg<br>ctgcgctaccgcggctgcctcctgctgtgcaggtccccgaccctctct<br>ctgtcctcattgcgcccagacgggccggcccagagctcccgggtcgtc<br>tttcgtgtggccgcgagacactcttgcactcctgtaatgagcctggca<br>ctgtgatgaaacacttttcccgtgtcgtttgagtgcatcttctcaaca<br>accctaggagggttcttgaagcttttgagattaacaatggcaggaaaa<br>tcatcacttttttaaagtaattctccttggagatggtggagttgggaag<br>agttcacttatgaacagatatgtaactaataagtttgatacccagctc<br>ttccatacaataggtgtggaattttttaaataaagatttggaagtggat<br>ggacattttgttaccatgcagatttgggacacggcaggtcaggagcga<br>ttccgaagcctgaggacaccattttacagaggttctgactgctgcctg<br>cttacttttagtgtcgatgattcacaaagcttccagaacttaagtaac<br>tggaagaaagaattcatatattatgcagatgtgaaagagcctgagagc<br>tttccttttgtgattctgggtaacaagattgacataagcgaacggcag<br>gtgtctacagaagaagcccaagcttggtgcagggacaacggcgactat<br>ccttattttgaaacaagtgcaaaagatgccacaaatgtggcagcagcc<br>tttgaggaagcggttcgaagagttcttgctaccgaggataggtcagat<br>catttgattcagacagacacagtcaatcttcaccgaaagcccaagcct<br>agctcatcttgctgttgattgttagattgttgatgcattctaaccaac<br>tcacacatatacacaaaatcaacatggggatggagaagagaattagcg<br>tttgcagcagtgtatcatctactaataaaattaaactaatgttgctgc<br>ttcattagttggtgggagaagggacacatccactcttggaggaatata<br>tttactcaataatggcaccttacatttataaattgtaacagttgtcta<br>ataacgtttctttaatttaaatatgtaagttgcagagctaataaatga<br>aatgaccaagactttaattataataaaaaataagaaacttgactattct<br>agaagttatacttggatttttttcctgggaaaatgggagaactacttttt<br>atatgtgtatgtttttatgcaattagcattgtattcttggttcaggga<br>aatactttcctaaagcaataatgttagatattaaagattaaaatctaa<br>tgtatttgcaatgcattgttaatttacttcttcattctcttcaaaatg<br>atttaaccattcctgttttcattctacatactagaattactctcacta<br>gtaattactcatcatttgtgtgccattcatgcaccccccaccccaaa<br>atcatgttccacagtctcaggcggagggtgggccccagtggtacaag<br>agttgcttcatacagtctgtaatacatccagctaaattcaagttgtct<br>atgaatggaaagcctttccatagatagagttcagtttttaagaaaaagg<br>ctaactactgaacttggagaacagacaaatgtgcatttgataactgat<br>gtaataattacaatgtactgtgtggaagatacaaaattacaattcgat<br>taatggactaaatattttttgttactttcttgacccttggggaaagttt<br>cttaattgaagttaaaacattcctttataacacaagacacaagctgac<br>tttatcactctcagaagaaatactaagaaggattgtactttgtgagag<br>ggtaaacgaagacatctttattcggcaatgtatttacttagtgtcttc | Human RAB9A mRNA<br>GENBANK<br>Accession No.<br>NM_004251.5<br>https://www.ncbi.<br>nlm.nih.gov/nuc<br>core/NM_004251.5 |

TABLE 52A-continued

| Sequence Listing of GenBank Sequences | |
|---|---|
| SEQ ID NO Sequence | Name/Description |
|     tctattactgaacatttagtgatttgctctcaaggagattttttgtta<br>gaaaaagacttgttgcagtgatcagacttgataaagcaaattgtggtc<br>ttttgtggatgaagttca | |
| 3    ggtgttgagcgccggcggctcgcgcccacgctgggccgggagtcgaaa<br>tgcttcccggtgccgggagtgagcgatgagctggcttctgttcctggc<br>ccacagagtcgccttggccgccttgccctgccgccgcggctctcgcgg<br>gttcgggatgttctatgccgtgaggaggggccgcaagaccggggtctt<br>tctgacctggaatgagtgcagagcacaggtggaccggtttcctgctgc<br>cagatttaagaagtttgccacagaggatgaggcctgggcctttgtcag<br>gaaatctgcaagcccggaagtttcagaagggcatgaaaatcaacatgg<br>acaagaatcggaggcgaaagccagcaagcgactccgtgagccactgga<br>tggagatggacatgaaagcgcagagccgtatgcaaagcacatgaagcc<br>gagcgtggagccggcgcctccagttagcagagacacgttttcctacat<br>gggagacttcgtcgtcgtctacactgatggctgctgctccagtaatgg<br>gcgtagaaggccgcgagcaggaatcggcgtttactgggggccaggcca<br>tcctttaaatgtaggcattagacttcctgggcggcagacaaaccaaag<br>agcggaaattcatgcagcctgcaaagccattgaacaagcaaagactca<br>aaacatcaataaactggttctgtatacagacagtatgtttacgataaa<br>tggtataactaactgggttcaaggttggaagaaaaatgggtggaagac<br>aagtgcaggaaagaggtgatcaacaaagaggactttgtggcactgga<br>gaggcttacccaggggatggacattcagtggatgcatgttcctggtca<br>ttcgggatttataggcaatgaagaagctgacagattagccagagaagg<br>agctaaacaatcggaagactgagccatgtgactttagtccttgggaga<br>acttgagccagcggctgtcttgctgcctgtacttactggtgtggaaaa<br>tagcctgcaggtaggaccattgcagtgatgggcagatgcgtctttcac<br>acggaatcaggcacagtggccttctgtgacatgtgtttataaaaaatg<br>gttaagtatataataaattgaacatctttgagattggagaattatgtg<br>agatttccacattatgtttactgggttcaatactgtccttgcttgttt<br>tattgcaggcaagcaaggcaaatggcctaaaatgctgtggcttatatt<br>ttgataagaaatcaaaaaaccattggttaaaagatgcaactcagaagt<br>ctggaagtattctgaaagcatccatttaccgtccagttgacaggtttg<br>agtctcctgcttgtataggtgacttgtgcccatgggtacattaaagga<br>acatgctgcccaggggcctgggcggacagctcagtgggcaggatgtgtg<br>ctgggtctcagccccatgtgcctgcttgctgggcagttagtatagggc<br>aaagcctgcctgcggcgaccctggctgctaggccattctctaggaaca<br>gctgcgactcataaagaccaagaagcataaataaactttcaaaaattt<br>atttggctctttcgttaaaaactgtgcaaattaaaaaaaaaaaaaaaa<br>aagtaagacaccggctgggcacagtggctcacttctgtaatcctagca<br>ctttgggaggccaaggcgggcagatcacttgaggtcaggagtttgaga<br>ccagcttggccaacatgacgaaaccctgtctctactaaaattacaaaa<br>attatccaggtgtggtggcacgggcttgtagtcccagctacttgggag<br>gctgaggcacaagaatcacttgaacccaggcggcagaggttgcagtga<br>gccaagattgcaccactgcactccatcctgggcaacagagtgagactc<br>tgtctcaaaaaaaaaaaaaagtagtaaaagtttgacatgattatttat<br>ttagtttttaaaccttttttattataaaaacatacaggaagtgacacaaa<br>acaaatgtatagcttattgaatgattatgattgtaaggtgaataacct<br>ttgtgtccaccacctggtgaagaaatagtactttgccagatacccag<br>gaggctctcccaagtgcccctccagccacagccctcttcttctccccc<br>tccttgccccaacaagtaatcctgacttttacagaaatgactttcttg<br>gtttttgatggcagtttagtcttgtctgcttttttttgtttattttt<br>ttatctacttcagtgtccatttgcagtcccgtcggcctcactgttttc<br>cctgccgtttatctgttgaagagcctgggctgtttgtcccatggcttc<br>ccacagtgtagattttgctgacccacgtggtcatggtgtagttcagcat<br>ggtcctctatgtttcctgcacattggcagctgggtccagaggcttgat<br>gagcctcaaatttgatccctttggcaggagaacaggcggttaggagct<br>ttcctcaggaaagtaccatgttgacggcagctgatgctcagtgccaag<br>atccattaattatttggggttgcaaaatggtggtattctcattctgtc<br>gttttgcttgcctttattagctggaatggttttctaagaaagtgtttt<br>cttttttatacttatctggttacccagtggtacagttcatataggaag<br>ggcaggataaatgcttgattctttgctcttgtacactaagttttttaag<br>ataatgcattagttgtctgtcaaggaaggtgagtggtgaagggtttt<br>acatatatacaagaattcatgggctgggcatggtgtcttatgcctgta<br>atcccagcactttgggaggctgaggctggaggatcacatgaacccagg<br>agtttgagactagtctgggcaacatagtgacaccctgtctctacagaa<br>aattaaaataaaatcaggtgggtgtggtagtgcctgcctgttgtccca<br>gctattctggaggctgagatgggaggatcgcttgggcccaggaggtcg<br>aggatgcgtgagctgtgaccatgccaccacattccagcctgggcgaca<br>gcaagtccttgtcttaaaaaaaaaaaagaatttgtggagttaagcata<br>cttggtgggtttcaatccgttgtgattttttatctttatttagctcaga<br>ctagcttattcggtcagtgagagggagcctcttcagcttggctcttgc<br>tttcttttgataagtgtgcacatgtgtgcatacatgtgtgcacagacc<br>acacgcacagtcattgatagctccctgcagcctggcatgtcaagatgc<br>tctaggcccaatttatagagcttctgctccaaacctgtcttaaaagaa<br>aaactttagacaagttagcagtttaattgagcagaaaatagtttcttc<br>agctgggtagcactcaggaccaaaagtggttcagaacgttctcctgtg | Human RNase H1 mRNA<br>GENBANK<br>Accession No.<br>NM_001286834.3<br>https://www.ncbi.<br>nlm.nih.gov/nuc<br>core/NM_001286834.3 |

TABLE 52A-continued

<u>Sequence Listing of GenBank Sequences</u>

| SEQ ID NO | Sequence | Name/Description |
|---|---|---|
| | cgttgtgtgcaggctgtatttatttatagccacaggaagggaaagaca<br>catgtacatggccagactgactgcaggtcagcctccacctcacatagg<br>catgttttgggagccttcagcatgtgattggtgagactctgctgcttg<br>ttacagaagtgtactctcaagtcaggtcccagtttgcttatacattaa<br>gtgaggttataagtcactatgtacagaggcagttttaggccaaactta<br>attccgtttaacacttggaatccattattttttcccagagtctctggta<br>gagatggtatttcagatccagtttaggatgctcattgctattgcgttg<br>gtcattatttctagattttttggacggagctttaaaaaaatacaaacat<br>tgcacacacatatttaaaggaagaatattttctgagcctatattgata<br>ttcccaatacaaattcagggtcctggggcctttacatagcctcctcta<br>tatgatgtctgtgtctcctgcactcggaatcctgcttctcaagacaca<br>ggacaatggcatggaatatccatcccttaatcactcacttgttttatt<br>cctctttagcatttagcatttaaaaaaaatactaataccatagcatta<br>attgtgatgatgaaaacagcactgtgtctacgttgtcagaaaaattgc<br>tccttttttaccaccattgactcatttctgtgtgttcaggtctcataac<br>cagtctatagtcagtgtcatcttggggacagtattccttgagtttctg<br>atgttgaattcagtttttgctggatacgaaattcttggcccagatttttc<br>tttgagtatcttgtttttattctgtttttcttccagcataaagtgatgca<br>tgaaaagcctgatgaatcttgtttttcttcccctgacagtcatatgctg<br>tttttccttagatgcccaaaggattttttttcctttttctgtcaagtcgg<br>ccgtttttattcgaatgtgtcatgtgttggtattggttgtcctggtcca<br>tatttgcaagcgtatggtgtgctctttctatgtgtacttcatatctgt<br>tattttaagaagatttgcttgaactggagtttagtgttacatttttct<br>tgctttggctttttttctgtgggatccctgttatctgtatgttgaaat<br>ctaaattggctgttctcagtgtttgccactgtctcttgaatctctttt<br>atctctttctttgtttcttttttgagttttaaaagttgttattgtacca<br>cttttgttttgtttttgttatttaaaataggaacagtgtctcactgtgt<br>tgcccaggctggtcttaaactcctggcctcaagcgatcctccttcctt<br>ggcctcccaaagtgctgggattacaggtgtgagccaccaaagccggcc<br>ccaccttgctttttaaaacagctctgttgaggtgtaactgacaggtaa<br>tgaactgcacatacgtgaagtgaccgatgcatttgcctgtgaagctgt<br>cgccagaacatgtccatcaccaccaacagcagtttcacaccccggtct<br>aaaccgtccctcgtgtcctccatgttcaggcaaccactggtctgctcc<br>ctctcactaaaggttaatttatatattctagaattttatctgagtgga<br>atcgcagagcaagtactgtggggggaggtgcttctactcagcataatt<br>attttggcattcacccattttgtgtacatcaataatccacattttgta<br>ttgcatggatataccacagtttatttatttacctgttgaccgatattt<br>cgattatttccaatttctaaataaaaataaagcaaataaagctgccgt<br>gaacattta |  |
| 4 | aagtgacgcgaggctctgcggagaccaggagtcagactgtaggacgac<br>ctcgggtcccacgtgtccccgggtactcgccggccggagcccccggctt<br>cccgggggccgggggaccttagcggcacccacacacagcctactttcca<br>agcggagccatgtctggtaacggcaatgcggctgcaacggcggaagaa<br>aacagcccaaagatgagagtgattcgcgtgggtacccgcaagagccag<br>cttgctcgcatacagacggacagtgtggtggcaacattgaaagcctcg<br>taccctggcctgcagtttgaaatcattgctatgtccaccacaggggac<br>aagattcttgatactgcactctctaagattggagagaaaagcctgttt<br>accaaggagcttgaacatgccctggagaagaatgaagtggacctggtt<br>gttcactccttgaaggacctgcccactgtgcttcctcctggcttcacc<br>atcggagccatctgcaagcgggaaaaccctcatgatgctgttgtcttt<br>cacccaaaatttgttgggaagaccctagaaaccctgccagagaagagt<br>gtggtgggaaccagctccctgcgaagagcagcccagctgcagagaaag<br>ttcccgcatctggagttcaggagtattcggggaaacctcaacacccgg<br>cttcggaagctggacgagcagcaggagttcagtgccatcatcctggca<br>acagctggcctgcagcgcatgggctggcacaaccgggtggggcagatc<br>ctgcaccctgaggaatgcatgtatgctgtgggccaggggggccttgggc<br>gtggaagtgcgagccaaggaccaggacatcttggatctggtgggtgtg<br>ctgcacgatcccgagactctgcttcgctcgctcatcgctgaaagggcttc<br>ctgaggcacctggaaggaggctgcagtgtgccagtagccgtgcataca<br>gctatgaaggatgggcaactgtacctgactggaggagtctggagtcta<br>gacggctcagatagcatacaagagaccatgcaggctaccatccatgtc<br>cctgcccagcatgaagatggccctgaggatgacccacagttggtaggc<br>atcactgctcgtaacattccacgagggcccccagttggctgcccagaac<br>ttgggcatcagcctggccaacttgttgctgagcaaaggagccaaaaac<br>atcctggatgttgcacggcagcttaacgatgcccattaactggtttgt<br>ggggcacagatgcctgggttgctgctgtccagtgcctacatcccgggc<br>ctcagtgccccattctcactgctatctggggagtgattaccccgggag<br>actgaactgcagggttcaagccttccagggatttgcctcaccttgggg<br>ccttgatgactgccttgcctcctcagtatgtgggggcttcatctcttt<br>agagaagtccaagcaacagcctttgaatgtaaccaatcctactaataa<br>accagttctgaaggtgt | Human PBGD (also<br>known as HMBS) mRNA<br>GENBANK<br>Accession No.<br>NM_000190.4<br>https://www.ncbi.<br>nlm.nih.gov/nuc<br>core/NM_000190.4 |

TABLE 52A-continued

Sequence Listing of GenBank Sequences

| SEQ ID NO | Sequence | Name/Description |
|---|---|---|
| 5 | acagatgaggttgaggttggcccacggccaggtgagaggcttccaagg caggatacttgtgtctcagatgcggtcgcttctttcatacagcaattg ccgccttgctgaggatcaaggaacctcagtgtcagatcacgccctccc cccaaacttagaaattcagatggggcgcagaaatttctcttgttctgc gtgatctgcatagatggtccaagaggtggtttttccaggagcccagca cccctcctccctccgactcagacccaggagtctggccctccattgaaa ggaccccaggttacatcatccattcaggctgcccttgccacgatggaa ttctgtagctcctgccaaatgggtcaaatatcatggttcaggcgcagg gagggtgattgggcgggcctgtctgggtataaattctggagcttctgc atctatcccaaaaaacaagggtgttctgtcagctgaggatccagccga aagaggagccaggcactcaggccacctgagtctactcacctggacaac tggaatctggcaccaattctaaaccactcagcttctccgagctcacac cccggagatcacctgaggacccgagccattgatggactcggacgagac cgggttcgagcactcaggactgtgggtttctgtgctggctggtcttct gctgggagcctgccaggcacacccatccctgactccagtcctctcct gcaattcggggggccaagtccggcagcggtacctctacacagatgatgc ccagcagacagaagcccacctggagatcagggaggatgggacggtggg gggcgctgctgaccagagccccgaaagtctcctgcagctgaaagcctt gaagccgggagttattcaaatcttgggagtcaagacatccaggttcct gtgccagcggcagatggggccctgtatggatcgctccactttgaccc tgaggcctgcagcttccgggagctgcttcttgaggacggatacaatgt ttaccagtccgaagcccacggcctcccgctgcacctgccagggaacaa gtccccacaccgggaccctgcaccccgaggaccagctcgcttcctgcc actaccaggcctgccccccgcactcccggagccacccggaatcctggc ccccagcccccgatgtgggctcctcggaccctctgagcatggtggg accttcccagggccgaagccccagctacgcttcctgaagccagaggct gtttactatgacatctcctctttatttattaggttatttatcttattt attttttattttttcttacttgagataataaagagttccagaggagga taa | Human FGF21 mRNA GENBANK Accession No. NM_019113.4 https://www.ncbi. nlm.nih.gov/nuc core/NM_019113.4 |
| 6 | gaggaaggcaccgccccgttgagggagggcagcggacgtgacgcagag ctcagcaggtcctgcagccggagtgaagtgcgggctcgggccccatgt gccttcagtcccggccggcccaggtcgccggcttctgcagacaccagg ggaccgcagcggcactgccgcgcctgcgccctgggcggagtcatgtcc ggtaacggcggcgcggccacaaccgcggaagaaaacggctcaaagatg agggtgattcgagtgggcacccgtaagagccagctggctcgcatacag accgacactgtggtggcgatgctgaaagccttgtaccctggcatacag tttgaaatcattgctatgtccaccacgggagacaagattcttgatact gcactctctaagattggagagaagagcctgtttaccaaggagctagaa aacgccctggaaaaaaacgaagtggacctggtcgttcactccctgaag gatgtgcctaccatactacctcctggctttactattggagccatctgc aaacgggaaaacccttgtgatgctgttgtctttcacccaaagtttatt ggaaagaccctggaaaccttgccagagaaaagtgccgtgggaaccagc tctctgaggagagtggctcagctacagagaaagttcccccacctggaa ttcaagagtattcggggaaacctcaacacccgcctccggaagctggat gagctgcaggaattcagtgccatcgtcctggctgtggctggcctacag cgcatgggctggcagaaccgggtgggccagatttttgcacccagaagaa tgcatgtatgctgtgggtcagggagccctagccgtggaagtccgagcc aaggaccaggatatcttggacctagtgagtgtgttgcacgatcctgaa actctgcttcgctgcattgctgaaagggcttttctgaggcacctggaa ggaggctgcagcgtgcccgtagcagtgcatacagtgatgaaagatggg caactgtacctgactggtggagtctggagtctagatggctcagatagc atgcaagagactatgcaggccaccatccaggtccctgttcagcaagaa gatggtccagaagatgacccacaactggttggaatcactgcccgtaac attccaagaggagcccagctagctgctgagaacctgggcatcagcctg gccagcttgctgctcaacaaaggagccaagaacatcctggatcttgca cggcagcttaatgatgtgcgctaactggtctgtagggcacaggaaccc tggctgccactccactgcctacttctggcttccaagtgccctgtgctc catccctagggatgtgattatcccaggaaattgaaccacggggttgtt gagacttccactttggaagatatgcctcaccttggggcctccatatct gcctttccctcagtagttgggggcttcatctctttagagaaagtccat gccaatctttgaatgtaaccaataccactaataaaccagtttagaatg tggttcttctgatagagttggggaagatatgaataaacccaaagccct tttaaacttgaaaaaaaaaaaaaaaa | Murine PBGD (also known as HMBS) mRNA GenBank No: NM_013551.2 https://www.ncbi. nlm.nih.gov/nuc core/NM_013551.2 |
| 7 | agacagccttagtgtcttctcagctggggattcaacacaggagaaaca gccattcactttgcctgagccccagtctgaacctgacccatccctgct gggcaccggagtcagaacacaattccagctgccttggctcctcagccg ctcgcttgccaggggctctcccgaacggagcgcagccctgatggaatg gatgagatctagagttgggaccctgggactgtgggtccgactgctgct ggctgtcttcctgctgggggtctaccaagcataccccatccctgactc cagcccctcctccagtttggggggtcaagtccggcagaggtacctcta cacagatgacgaccaagacactgaagcccacctggagatcagggagga tggaacagtggtaggcgcagcacaccgcagtccagaaagtctcctgga gctcaaagccttgaagccaggggtcattcaaatcctgggtgtcaaagc ctctaggtttctttgccaacagccagatggagctctctatggatcgcc | Murine FGF21 mRNA GENBANK No: NM_020013.4 https://www.ncbi. nlm.nih.gov/nuc core/NM_020013.4 |

TABLE 52A-continued

Sequence Listing of GenBank Sequences

| SEQ ID NO | Sequence | Name/Description |
|---|---|---|
| | tcactttgatcctgaggcctgcagcttcagagaactgctgctggagga cggttacaatgtgtaccagtctgaagcccatggcctgcccctgcgtct gcctcagaaggactccccaaaccaggatgcaacatcctggggacctgt gcgcttcctgcccatgccaggcctgctccacgagccccaagaccaagc aggattcctgcccccagagcccccagatgtgggctcctctgaccccct gagcatggtagagcctttacagggccgaagccccagctatgcgtcctg actcttcctgaatctagggctgtttctttttgggtttccacttattta ttacgggtatttatcttatttattttagtttttttttcttactt ggaataataaagagtctgaaagaaaaatgtgtgtt | |
| 45 | agatcttcccagaggacggttttgaaaggaaggcagagagggcactggg aggaggcagtgggaggggggaggggggggggccttcggggtgggcgccc agggtagggcaggtggccgcgcgtggaggcagggagaatgcgactct ccaaaaccctcgtcgacatggacatggccgactacagtgctgcactgg acccagcctacaccaccctggaatttgagaatgtgcaggtgttgacga tgggcaatgacacgtcccctcagaaggcaccaacctcaacgcgccca acagcctgggtgtcagcgccctgtgtgccatctgcggggaccgggcca cgggcaaacactacggtgcctcgagctgtgacggctgcaagggcttct tccgggaggagcgtgcggaagaaccacatgtactcctgcagatttagcc ggcagtgcgtggtggacaaagacaagaggaaccagtgccgctactgca ggctcaagaaatgcttccgggctggcatgaagaaggaagccgtccaga atgagcgggaccggatcagcactcgaaggtcaagctatgaggacagca gcctgccctccatcaatgcgctcctgcaggcggaggtcctgtcccgac agatcacctcccccgtctccgggatcaacggcgacattcgggcgaaga agattgccagcatcgcagatgtgtgtgagtccatgaaggagcagctgc tggttctcgttgagtgggcaagtacatcccagctttctgcgagctcc ccctggacgaccaggtggccctgctcagagcccatgctggcgagcacc tgctgctcggagccaccaagagatccatggtgttcaaggacgtgctgc tcctaggcaatgactacattgtccctcggcactgcccggagctggcgg agatgagccgggtgtccatacgcatccttgacgagctggtgctgccct tccaggagctgcagatcgatgacaatgagtatgcctacctcaaagcca tcatcttctttgacccagatgccaaggggctgagcgatccagggaaga tcaagcggctgcgttcccaggtgcaggtgagcttggaggactacatca acgaccgccagtatgactcgcgtggccgctttggagagctgctgctgc tgctgcccaccttgcagagcatcacctggcagatgatcgagcagatcc agttcatcaagctcttcggcatggccaagattgacaacctgttgcagg agatgctgctgggagggtcccccagcgatgcaccccatgcccaccacc ccctgcaccctcacctgatgcaggaacatatgggaaccaacgtcatcg ttgccaacacaatgcccactcacctcagcaacggacagatgtccaccc ctgagacccacagccctcaccgccaggtggctcagggtctgagccct ataagctcctgccgggagccgtcgccacaatcgtcaagcccctctctg ccatcccccagccgaccatcaccaagcaggaagttatctagcaagccg ctggggcttgggggctccactggctcccccagcccccctaagagagca cctggtgatcacgtggtcacggcaaaggaagacgtgatgccaggacca gtcccagagcaggaatgggaaggatgaagggcccgagaacatggccta agggccacatcccactgccacccttgacgccctgctctggataacaag actttgacttggggagacctctactgccttggacaacttttctcatgt tgaagccactgccttcaccttcaccttcatccatgtccaaccccgac ttcatcccaaaggacagccgcctggagatgacttgaggccttacttaa acccagctcccttcttccctagcctggtgcttctcctctcctagcccc tgtcatggtgtccagacagagccctgtgaggctgggtccaattgtggc acttggggcaccttgctcctccttctgctgctgcccccacctctgctg cctccctctgctgtcaccttgctcagccatcccgtcttctccaacacc acctctccagaggccaaggaggccttggaaacgattcccccagtcatt ctgggaacatgttgtaagcactgactgggaccaggcaccaggcagggt ctagaaggctgtggtgagggaagacgcctttctcctccaacccaacct catcctccttcttcagggacttgggtgggtacttgggtgaggatccct gaaggccttcaacccgagaaaacaaacccaggttggcgactgcaacag gaacttggagtggagaggaaaagcatcagaaagaggcagaccatccac caggcctttgagaaagggtagaattctggctggtagagcaggtgagat gggacattccaaagaacagcctgagccaaggcctagtggtagtaagaa tctagcaagaattgaggaagaatggtgtgggagagggatgatgaagag agagagggcctgctggagagcatagggtctggaacaccaggctgaggt cctgatcagcttcaaggagtatgcagggagctgggcttccagaaaatg aacacagcagttctgcagaggacgggaggctggaagctggaggtcag gtggggtggatgatataatgcgggtgagagtaatgaggcttggggctg gagaggacaagatgggtaaaccctcacatcagagtgacatccaggagg aataagctcccagggcctgtctcaagctcttccttactcccaggcact gtcttaaggcatctgacatgcatcatctcatttaatcctcccttcctc cctattaacctagagattgttttgttttttattctcctcctccctcc ccgccctcacccgcccactccctcctaacctagagattgttacagaa gctgaaattgcgttctaagaggtgaagtgatttttttttctgaaactca cacaactaggaagtggctgagtcaggacttgaacccaggtctccctgg atcagaacaggagctcttaactacagtggctgaatagcttctccaaag gctccctgtgttctcaccgtgatcaagttgaggggcttccggctccct tctacagcctcagaaaccagactcgttcttctgggaacccctgcccact | Human HNF4A mRNA GENBANK Accession No. NM_178849.3 https://www.ncbi. nlm.nih.gov/nuc core/NM_178849.3 |

TABLE 52A-continued

Sequence Listing of GenBank Sequences

| SEQ ID NO Sequence | Name/Description |
|---|---|
| cccaggaccaagattggcctgaggctgcactaaaattcacttagggtc<br>gagcatcctgtttgctgataaatattaaggagaattcatgactcttga<br>cagcttttctctcttcactccccaagtcaaggggaggggtggcagggg<br>tctgtttcctggaagtcaggctcatctggcctgttggcatgggggtgg<br>gacagtgtgcacagtgtgggggcaggggagggctaagcaggcctgggt<br>ttgagggctgctccggagaccgtcactccaggtgcattctggaagcat<br>tagaccccaggatggagcgaccagcatgtcatccatgtggaatcttgg<br>tggctttgaggacattctggaaaatgccactgaccagtgtgaacaaaa<br>gggatgtgttatggggctggaggtgtgattaggtaggagggaaactgt<br>tggaccgactcctgccccctgctcaacactgacccctctgagtggttg<br>gaggcagtgccccagtgcccagaaatcccaccattagtgattgttttt<br>tatgagaaagaggcgtggagaagtattggggcaatgtgtcagggagga<br>atcaccacatccctacggcagtcccagccaagcccccaatcccagcgg<br>agactgtgccctgctcagagctcccaagccttcccccaccacctcact<br>caagtgcccctgaaatccctgccagacggctcagcctggtctgcggta<br>aggcagggaggctggaaccatttctgggcattgtggtcattcccactg<br>tgttcctccacctcctccctccagcgttgctcagacctctgtcttggg<br>agaaaggttgagataagaatgtcccatggagtgccgtgggcaacagtg<br>gcccttcatgggaacaatctgttggagcaggggtcagttctctgctg<br>ggaatctacccctttctggaggagaaacccattccaccttaataactt<br>tattgtaatgtgagaaacacaaaacaaagtttacttttttgactctaa<br>gctgacatgatattagaaaatctctcgctctcttttttttttttttttt<br>ttttttttggctacttgagttgtggtcctaaaacataaaatctgatgg<br>acaaacagagggttgctgggggggacaagcgtgggcacaatttccccac<br>caagacaccctgatcttcaggcgggtctcaggagcttctaaaaatccg<br>catggctctcctgagagtggacagaggagaggagagggtcagaaatga<br>acgctcttctatttcttgtcattaccaagccaattacttttgccaaat<br>ttttctgtgatctgccctgattaagatgaattgtgaaatttacatcaa<br>gcaattatcaaagcgggctgggtcccatcagaacgacccacatctttc<br>tgtgggtgtgaatgtcattaggtcttgcgctgacccctgagcccccat<br>cactgccgcctgatggggcaaagaaacaaaaaacatttcttactcttc<br>tgtgttttaacaaaagtttataaaacaaaataaatggcgcatatgttt<br>tctaagtccttggataagtatcttttctttcaggtatcagaaataaga<br>ctgaatcttctggttctacttgggggttaaaaaattttttttaaagga<br>agaatgagaatagttttatagttctttgtgatgtgcagaatgtttttg<br>tgtccattataattttttcagtcttcacatcaagaggtaagcagttaga<br>catgattactcccactttccagatgaggagactgaggcttgggggaag<br>tgacttctcttggaaggcagaggtggacatctaaccctggtctcttga<br>ttccaagtacttagtatatcgagagagtgaaagttgatcccccttctt<br>gaagaggggagtgatgaggggagagtgcaatggcaagatctggaagaa<br>tggcaagagggtccaagggtctgtcatcctccaccaaggttcaagaca<br>gaaccttttgctgggtcacctcaatctgccagcaatggaagatgagta<br>gctgtgggggacatttcataaaagcaagtggtttttttttgttttgttttg<br>ttttgttttttgtttttttttctagaacaaggctgtgcacagtggctc<br>acctctgtaatcccagcactttgggaggctgaggcgggaggatcactt<br>gagctcaggagttcgagaccagccagagcaatataaggagaccccatc<br>tctacaaaaaatttaaaaattagccaggtatagtggtgtgtgcctata<br>gtaccagctactctgaaggctgaggtgggaagattgcttcagcccagg<br>agttcgaggatgcagtgagctatgaatgcaacactgcactacagcctg<br>gatgaaagaacaagactctgtctcaaaacataaataataagtaaaaag<br>aataaaagcaagagatgcacttgagaatctccagccagatctgtagcc<br>actgggcttctctccaaggctaaactattacaggagggtggccttgtg<br>tctcggtcaccacagaccacagcgttccattcactcggggttgtgctg<br>gagctggcttgtgagaactgactgttagcttctcttcccaactccatg<br>tttgccagtgccacactgatagcttgaaattggttattgccggagtgt<br>ttacaccacaaggactagcaaactctacaaatccgggcttttgttcct<br>ggagagcccgttgttaacattcaccagcacaccacagcattcggcaat<br>ggctggaccatgggatgcctacatatggggacatcctccttggggatg<br>agggtagagcagggcgatcctttcacctcttccttaagggaggggaca<br>aaagttctggtctgggaagcacacgttttgctgatcagcgtaaccttg<br>ggcaggtcactccaccactccgagcctcatctgtaaagtgggaatgat<br>atctccctccagggcagatgtcaggattcaatggaatgagatcacagt<br>aactgtgagagctcccgttacatgaggagtacaagtgaactcttcatg<br>cgcccctttttagcgagaagttaaccattaaactctccaggcttcaga<br>gcacccattcgctgtctacctgatccctagggccgctcccgccttccc<br>ctgtgccttccctccactagtcagcaccaggaaatgttttcgataacg<br>ttgcaacggaggccttgttcatgctgccgccatcggggacaagcgcgg<br>ggggggggggggtggaggccagaggagactatttcagtcctaaattgtg<br>cttaataaacccatatcaaaaccataaa | |

TABLE 52A-continued

Sequence Listing of GenBank Sequences

| SEQ ID NO | Sequence | Name/Description |
|---|---|---|
| 46 | gcctggctcccgcgcagcatgcccgccagcgccccgccgcgccgcccg<br>cggccgccgccgccgtcgctgtcgctgctgctggtgctgctgggcctg<br>ggcggccgccgcctgcgtgcggagccgggcgacggcgcgcagacctgg<br>gcccgtttctcgcggcctcctgcccccgaggccgcgggcctcttccag<br>ggcaccttccccgacggcttcctctgggccgtgggcagcgccgcctac<br>cagaccgagggcggctggcagcagcacggcaagggtgcgtccatctgg<br>gatacgttcacccaccacccctggcaccccgggagactcccggaac<br>gccagtctgccgttgggcgccccgtcgccgctgcagcccgccaccggg<br>gacgtagccagcgacagctacaacaacgtcttccgcgacacggaggcg<br>ctgcgcgagctcggggtcactcactaccgcttctccatctcgtgggcg<br>cgagtgctccccaatggcagcgcgggcgtccccaaccgcgaggggctg<br>cgctactaccggcgcctgctggagcggctgcgggagctgggcgtgcag<br>cccgtggtcaccctgtaccactgggacctgcccagcgcctgcaggac<br>gcctacggcggctgggccaaccgcgccctggccgaccacttcagggat<br>tacgcggagctctgcttccgccacttcggcggtcaggtcaagtactgg<br>atcaccatcgacaacccctacgtggtggcctggcacggctacgccacc<br>gggcgcctggcccccg.gcatccggggcagcccgcgggtcgggtacctg<br>gtggcgcacaacctcctcctggctcatgccaaagtctggcatctctac<br>aatacttctttccgtcccactcagggaggtcaggtgtccattgcccta<br>agctctcactggatcaatcctcgaagaatgaccgaccacagcatcaaa<br>gaatgtcaaaaatctctggactttgtactaggttggtttgccaaaccc<br>gtatttattgatggtgactatcccgagagcatgaagaataacctttca<br>tctattctgcctgattttactgaatctgagaaaaagttcatcaaagga<br>actgctgactttttttgctctttgctttggacccaccttgagttttcaa<br>cttttggaccctcacatgaagttccgccaattggaatctcccaacctg<br>aggcaactgctttcctggattgaccttgaatttaaccatcctcaaata<br>tttattgtggaaaatggctggtttgtctcagggaccaccaagagagat<br>gatgccaaatatatgtattacctcaaaaagttcatcatggaaacctta<br>aaagccatcaagctggatggggtggatgtcatcgggtataccgcatgg<br>tccctcatggatggtttcgagtggcacagaggttacagcatcaggcgt<br>ggactcttctatgttgactttctaagccaggacaagatgttgttgcca<br>aagtcttcagccttgttctaccaaaagctgatagagaaaaatggcttc<br>cctcctttacctgaaaatcagcccctagaagggacatttccctgtgac<br>tttgcttggggagttgttgacaactacattcaagtagataccactctg<br>tctcagtttaccgacctgaatgtttacctgtgggatgtccaccacagt<br>aaaaggcttattaaagtggatggggttgtgaccaagaagaggaaatcc<br>tactgtgttgactttgctgccatccagccccagatcgctttactccag<br>gaaatgcacgttacacattttcgcttctccctggactgggccctgatt<br>ctccctctgggtaaccagtcccaggtgaaccacaccatcctgcagtac<br>tatcgctgcatggccagcgagcttgtccgtgtcaacatcaccccagtg<br>gtggccctgtggcagcctatggccccgaaccaaggactgccgcgcctc<br>ctggccaggcagggcgcctgggagaacccctacactgccctggccttt<br>gcagagtatgcccgactgtgctttcaagagctcggccatcacgtcaag<br>ctttggataacgatgaatgagccgtatacaaggaatatgacatacagt<br>gctggccacaaccttctgaaggcccatgccctggcttggcatgtgtac<br>aatgaaaagtttaggcatgctcagaatgggaaaatatccatagccttg<br>caggctgattggatagaacctgcctgcccttctcccaaaaggacaaa<br>gaggtggctgagagagtttttggaatttgacattggctggctggctgag<br>cccatttcggctctggagattatccatgggtgatgagggactggctg<br>aaccaaagaaacaatttctttcttccttatttcactgaagatgaaaaa<br>aagctaatccagggtacctttgacttttttggctttaagccattatacc<br>accatccttgtagactcagaaaaagaagatccaataaaatacaatgat<br>tacctagaagtgcaagaaatgaccgacatcacgtggctcaactccccc<br>agtcaggtggcggtagtgccctggggggttgcgcaaagtgctgaactgg<br>ctgaagttcaagtacggagacctccccatgtacataatatccaatgga<br>atcgatgacgggctgcatgctgaggacgaccagctgagggtgtattat<br>atgcagaattacataaacgaagctctcaaagcccacatactggatggt<br>atcaatctttgcggatactttgcttattcgtttaacgaccgcacagct<br>ccgaggtttggcctctatcgttatgctgcagatcagtttgagcccaag<br>gcatccatgaaacattacaggaaaattattgacagcaatggtttcccg<br>ggcccagaaactctggaaagattttgtccagaagaattcaccgtgtgt<br>actgagtgcagtttttttcacacccgaaagtctttactggctttcata<br>gcttttctatttttttgcttctattatttctctctcccttatattttac<br>tactcgaagaaaggcagaagaagttacaaatagttctgaacatttttc<br>tattcattcattttgaaataattatgcagacacatcagctgttaacca<br>tttgcacctctaagtgttgtgaaactgtaaatttcatacatttgactt<br>ctagaaaacatttttgtggcttatgacagaggttttgaaatgggcata<br>ggtgatcgtaaaatattgaataatgcgaatagtgcctgaatttgttct<br>cttttttgggtgattaaaaaactgacaggcactataatttctgtaacac<br>actaacaaaagcatgaaaaataggaaccacaccaatgcaacatttgtg<br>cagaaatttgaatgacaagattaggaatattttcttctgcacccactt<br>ctaaatttaatgttttttctggaagtagtaattgcaagagttcgaatag<br>aaagttatgtaccaagtaaccatttctcagctgccataataatgccta<br>agatacaggagagacgacagagggtcctaggctggaatgttcctttcg<br>gtggcttcccctctgtcaaatctagtttcctatggaaaagaagatggc<br>atgacatacttggagagcaaattatggaaatgtgtattttatatgatt | Human KL mRNA<br>GENBANK<br>Accession No.<br>NM_004795.4<br>https://www.ncbi.<br>nlm.nih.gov/nuc<br>core/NM_004795.4 |

TABLE 52A-continued

Sequence Listing of GenBank Sequences

| SEQ ID NO | Sequence | Name/Description |
|---|---|---|

```
           aaagcaatgcttctatcaaatactagtattaatttatgtatctggtta
           gcatcttgttgagggccttgcacataggaaacttttgataagtatctg
           tttgaggtcctgtctaaaccctgtgtccctgagggatctgtctcactg
           cggaaaaacaaacatgaatcctgtgatattgggctcttcaggaagcat
           aaagcaattgtgaaatacagtataccgcagtggctctaggtggaggaa
           aggaggaaaaagtgcttattatgtgcaacattatgattaatctgatta
           tacaccatttttgagcagatcttggaatgaatgacatgacctttccct
           tttctattctttagctgtactgtaatttctttgagttgatagtttac
           agagaataaggatgaaataatcactcattctatgaacagtgacactac
           aaattcttaataggttcaaaagcaatctggtctgaataacactggatt
           tgtttctgtgatctctgaggtctattttatgttttttgctgctacttct
           gtggaagtagctttgaactagtttttactttgaactttcacgctgaaac
           atgctagtgatatctagaaagggctaattaggtctcatcctttaatgc
           cccttaaataagtcttgctgattttcagacagggaagtctctctatta
           cactggagctgttttatagataagtcaatattgtatcaggcaagataa
           accaatgtcataacaggcattgccaacctcactgacacagggtcatag
           attttttcatgaaagataagctttggtaatattcattttaaagtgga
           tgtataataatatactgtactatataatatatcatctttagaggtatg
           cttattaaaattggatgctagagaatcaagtttattttatgtatatat
           ttttctgattataagagtaatatatgttcattgtaaaaattttttaaaa
           Cacagaaactatatgcaaagaaaaaataaaaattatctataatctcag
           aacccagaaatagccactattaacatttcctacgtattttatttttaca
           tagatcatattgtatatagttagtatctttattaattttttattatgaa
           actttcctttgtcattattagtcttcaaaagcatgattttttaatagtt
           gttgagtattccaccacaggaatgtatcacaacttaaccgttcccgtt
           tgttagactagtttcttattaatgttgatgaatgttgtttaaaaataa
           ttttgttgctacatttactttaatttccttgactgtaaagagaagtaa
           ttttgctccttgataaagtattatattaataataaatctgcctgcaac
           tttttgccttctttcataatca
```

47 |
```
           aggctcttgcggaagtccatgcgccattgggagggcctcggccgcggc
           tctgtgcccttgctgctgagggccacttcctgggtcattcctggaccg
           ggagccgggctggggctcacacgggggctcccgcgtggccgtctcggc
           gcctgcgtgacctccccgccgggcgggatgtggcgactacgtcgggccg
           ctgtggcctgtgaggtctgccagtctttagtgaaacacagctctggaa
           taaaaggaagtttaccactacaaaaactacatctggtttcacgaagca
           tttatcattcacatcatcctaccttaaagcttcaacgaccccaattaa
           ggacatcctttcagcagttctcttctctgacaaaccttcctttacgta
           aactgaaattctctccaattaaatatggctaccagcctcgcaggaatt
           tttggccagcaagattagctacgagactcttaaaacttcgctatctca
           tactaggatcggctgttggggggtggctacacagccaaaaagacttttg
           atcagtggaaagatatgataccggaccttagtgaatataaatggattg
           tgcctgacattgtgtgggaaattgatgagtatatcgattttgagaaaa
           ttagaaaagcccttcctagttcagaagaccttgtaaagttagcaccag
           actttgacaagattgttgaaagccttagcttattgaaggactttttta
           cctcaggttctccggaagaaacggcgtttagagcaacagatcgtggat
           ctgaaagtgacaagcattttagaaaggtgtcagacaaagagaaaattg
           accaacttcaggaagaacttctgcacactcagttgaagtatcagagaa
           tcttggaacgattagaaaaggagaacaaagaattgagaaaattagtat
           tgcagaaagatgacaaaggcattcatcatagaaagcttaagaaatctt
           tgattgacatgtattctgaagttcttgatgttctctctgattatgatg
           ccagttataatacgcaagatcatctgccacggggttgttgtggttggag
           atcagagtgctggaaagactagtgtgttggaaatgattgcccaagctc
           gaatattcccaagaggatctggggagatgatgacacgttctccagtta
           aggtgactctgagtgaaggtcctcaccatgtggccctatttaaagata
           gttctcgggagtttgatcttaccaaagaagaagatcttgcagcattaa
           gacatgaaatagaacttcgaatgaggaaaaatgtgaaagaaggctgta
           ccgttagccctgagaccatatccttaaatgtaaaaggccctggactac
           agaggatggtgcttgttgacttaccaggtgtgattaatactgtgacat
           caggcatggctcctgacacaaaggaaactattttcagtatcagcaaag
           cttacatgcagaatcctaatgccatcatactgtgtattcaagatggat
           ctgtggatgctgaacgcagtattgttacagacttggtcagtcaaatgg
           accctcatggaaggagaaccatattcgttttgaccaaagtagacctgg
           cagagaaaaatgtagccagtccaagcaggattcagcagataattgaag
           gaaagctcttcccaatgaaagctttaggttattttgctgttgtaacag
           gaaaagggaacagctctgaaagcattgaagctataagagaatatgaag
           aagagttttttcagaattcaaagctcctaaagacaagcatgcctaaagg
           cacaccaagtgactacaagaaatttaagccttgcagtatcagactgct
           tttggaaaatggtacgagagtctgttgaacaacaggctgatagtttca
           aagcaacacgttttaaccttgaaactgaatggaagaataactatcctc
           gcctgcgggaacttgaccggaatgaactatttgaaaaagctaaaaatg
           aaatccttgatgaagttatcagtctgagccaggttacaccaaaacatt
           gggaggaaatccttcaacaatctttgtgggaaagagtatcaactcatg
           tgattgaaaacatctaccttccagctgcgcagaccatgaattcaggaa
           cttttaacaccacagtggatatcaagcttaaacagtggactgataaac
           aacttcctaataaagcagtagaggttgcttgggagaccctacaagaag
```
| Human OPA1 mRNA GENBANK Accession No. NM_015560.3 https://www.ncbi.nlm.nih.gov/nuccore/NM_015560.3 |

TABLE 52A-continued

Sequence Listing of GenBank Sequences

| SEQ ID NO Sequence | Name/Description |
|---|---|
| aattttcccgctttatgacagaaccgaaagggaaagagcatgatgaca<br>tatttgataaacttaaagaggctgttaaggaagaaagtattaaacgac<br>acaagtggaatgactttgcggaggacagcttgagggttattcaacaca<br>atgctttggaagaccgatccatatctgataaacagcaatgggatgcag<br>ctatttattttatggaagaggctctgcaggctcgtctcaaggatactg<br>aaaatgcaattgaaaacatggtgggtccagactggaaaaagaggtggt<br>tatactggaagaatcggacccaagaacagtgtgttcacaatgaaacca<br>agaatgaattggagaagatgttgaaatgtaatgaggagcacccagctt<br>atcttgcaagtgatgaaataaccacagtccggaagaaccttgaatccc<br>gaggagtagaagtagatccaagcttgattaaggatacttggcatcaag<br>tttatagaagacattttttaaaaacagctctaaaccattgtaaccttt<br>gtcgaagaggttttattactaccaaaggcattttgtagattctgagt<br>tggaatgcaatgatgtggtcttgttttggcgtatacagcgcatgcttg<br>ctatcaccgcaaatactttaaggcaacaacttacaaatactgaagtta<br>ggcgattagagaaaaatgttasagaggtattggaagattttgctgaag<br>atggtgagaagaagattaaattgcttactggtaaacgcgttcaactgg<br>cggaagacctcaagaaagttagagaaattcaagaaaaacttgatgctt<br>tcattgaagctcttcatcaggagaaataaattaaaatcgtactcataa<br>tcagctctgcatacatctgaagaacaaaaacatcaacgtcttttgtcc<br>agcctcttttcttctgctgttccacctttctaaacatacaataaagt<br>catgggataaaaataatcgatgtatgttacgggcgctttaaccatcag<br>ctgcctctcgaatggaagaacagtggtaatggattaacatcctatttt<br>gttgtactaaagtgacaaatcggaataatataattggtatggccatta<br>ggttcagtccttgaagataagaaacttgttctctgtttgttgtcttat<br>ttgtggtggcactcgtttaatggattaactgaggttgctcaatgttca<br>gtttcttttccagaaatacaatgctaggtgttttgaaataaaacttat<br>atagcaattgtttaaagttatcaattgtatataaaatcacagtagcct<br>gctaaatcattgtatgtgtctgtagtattctattcccagaaactattt<br>gaccatgataattcagtttatattcacccacatgaaagaaaaatgggta<br>acagaagaaccccttaaaacaggttaatttggattgtaacgttcagtga<br>aagaaatttcaacccttcatagccagcgaagaaatttgccttggaagc<br>caagtcagtaccagcttacctatttgattcagttgctgttttctcact<br>ctctatatccatttgaaattgatttattttagatgttgtatacttacg<br>ttaggctttctgttaatagtggtttttctcctgttgacagagccaccg<br>gattatgacacaggatgaggaagattaaggataatcaattgactaatt<br>tcatttagaatattatcaaacatttcaactaggtatcagaaaaaggct<br>ttctttcataagactattttaaatagaaattatttcaacaattaaagt<br>aatgttgaccatcccccctctcagctgaataaagaaaaatttagttcaa<br>tttattgcaatttaattacaatactaccttcacaacattttcatgtgt<br>tttaaataaatattttttaattggctaaaggacattcaagcaaagaaa<br>tgctttctttacttaaaatgtctatctcatttgctgcctttttcactaa<br>gcctttactttgttaataaaagtgtccattgtgtgatgttttttgattt<br>tacagtttgctaaatcttattttcttggagttgcttttttggtaacagc<br>cccattgctactccccattttattgtttacatcaatgcatgcttcgt<br>tgtgatccctcaagatgtaacacttggtatgctcggttgaggatatga<br>aaaaatacttccgaaaccaggaattcaatgtatgtttgtttttatactg<br>tttgataagaaaagtaggtccagccttaagcagcacagatgcgctggt<br>agatgcatagtcaggaactttttttatttcttttaggtctagggacag<br>gagtgaatagaaagggaggagagctctattatgttctatacacagatt<br>aggagatgaccttactgggtacacccctctaaccagtgcttacaggtt<br>aatgcatgttaatgaatattttttgcagttgtaaagcataacaattaca<br>actacacatctatttctaaagaataaaacaggaccatatttatttact<br>tctgtcaactatagaaagaaagaccttcagctgtatttccacagattt<br>ctcccaaggaaaaggctaatattagtcactactgttatcacatccctt<br>tgtataagttttaaaaagagatggagggagatcttcatttctttgagg<br>agatcagtattgtaacgtatgtgaatagatgataacaattaatattac<br>taaaagtcccacatgagagtcctgacgccctctccatgccccacagta<br>atgtggcttcttttcatgggttttttttttcttcttttttagctgatctca<br>tcctaagcatgctttattttttccttgaaagctaggtatttatcaactg<br>cagatgttattgaaagaaaataaaattcagtctcaagagtaaaccctg<br>tgtcttgtgtctgtagttcaaaagtcagaaatgattctaatttaaaca<br>aaaagatactaaatatacagaagttaaattcgaactagccacagaatc<br>atttgtttttatgtcagaatttgcaaagagtggagtggacaaagctct<br>gtatggaagactgaacaactgtaaatagatgatatccaaacttaattt<br>ggctaggacttcaattttaaaaatcagtgtacctaggcagtgcacagc<br>acgaaataagtggcccttgcagcttccccgtttaacccactgtgctat<br>agttgcgggtggaacagtcaacctttctagtagtttatgatattgccc<br>tctttgtattcccattttctacagttttttccgcagacttctttctgc<br>aaattattcagcctccaaatgcaaatgaatgatataaaaataagtagg<br>gaacatggcagagagtggtgcttcccagcctcacaatgtgggaatttg<br>acataggatgagagtcagagtataggtttaaaagataaaatctttagt<br>taataattttgtatttatttattctagatgtatgtatctgaggaaaga<br>aatctggtattttttgctttccaataaaggggggatcaaagtaatggtttt<br>tctctcagttctctaagctggtctatgttatagctctagcagtatgga<br>aatgtgctttaaaatatgcttaccttttgaatgatcatggctatatgt<br>tgttgagatatttgaaacttaccttgttttcacttgtgcactgtgaat | |

TABLE 52A-continued

Sequence Listing of GenBank Sequences

| SEQ ID NO | Sequence | Name/Description |
|---|---|---|
| | gaactttgtattatttttttaaaaccttcacattacgtgtagatatta<br>ttgcaacttatattttgcctgagcttgatcaaaggtcatttgtgtaga<br>tgagtaattaaaaaatatttaaatcacattataattctattattggag<br>agcatcttttaaatttttttctgttttaacgagggaaagagaaacctg<br>tatacctagggtcattatttgaccccatagtataaccagattcatggt<br>ctaacaagctctcagtgtggcttttctctgaatgcttgaatttcacat<br>gccttgcatttcacagttgtactccatggtcaaccggtgctttttttc<br>acatcgtggtacttgtcaaaacatttttgttattttccttggtaaaata<br>tataaaaaaggtttctaatttca | |
| 48 | gcactgcagcgccagcgtccgagcgggcggccgagctcccggagcggc<br>ctggccccgagccccgagcgggcgtcgctcagcagcaggtcgcggccg<br>cagccccatccagccccgcgcccgccatgccgtccgcggggccccgcct<br>gagctgcggcctccgcgcgcgggcgggcctggggacggcggggccatg<br>cgcgcgctgccctaacgatgccgcccgccgcgcccgcccgcctggcgc<br>tggccctgggcctgggcctgtggctcggggcgctggcggggggccccg<br>ggcggggctgcgggccctgcgagcccccctgcctctgcggcccagcgc<br>ccggcgccgcctgccgcgtcaactgctcgggccgcgggctgcggacgc<br>tcggtcccgcgctgcgcatccccgcggacgccacagcgctagacgtct<br>cccacaacctgctccgggcgctggacgttgggctcctggcgaacctct<br>cggcgctggcagagctggatataagcaacaacaagatttctacgttag<br>aagaaggaatatttgctaatttatttaatttaagtgaaataaacctga<br>gtgggaacccgtttgagtgtgactgtggcctggcgtggctgccgcgat<br>gggcggaggagcagcaggtgcgggtggtgcagcccgaggcagccacgt<br>gtgctgggcctggctccctggctggccagcctctgcttggcatcccct<br>tgctggacagtggctgtggtgaggagtatgtcgcctgcctccctgaca<br>acagctcaggcaccgtggcagcagtgtccttttcagctgcccacgaag<br>gcctgcttcagccagaggcctgcagcgccttctgcttctccaccggcc<br>agggcctcgcagccctctcggagcagggctggtgcctgtgtggggcgg<br>cccagccctccagtgcctcctttgcctgcctgtccctctgctccggcc<br>ccccgccacctcctgcccccacctgtaggggccccaccctcctccagc<br>acgtcttccctgcctccccaggggccaccctggtggggccccacggac<br>ctctggcctctggccagctagcagccttccacatcgctgccccgctcc<br>ctgtcactgccacacgctgggacttcggagacggctccgccgaggtgg<br>atgccgctgggccggctgcctcgcatcgctatgtgctgcctgggcgct<br>atcacgtgacggccgtgctggccctgggggccggctcagccctgctgg<br>ggacagacgtgcaggtggaagcggcacctgccgccctggagctcgtgt<br>gcccgtcctcggtgcagagtgacgagagcctcgacctcagcatccaga<br>accgcggtggttcaggcctggaggccgcctacagcatcgtggccctgg<br>gcgaggagccggccccgagcggtgcacccgctctgcccctcggacacgg<br>agatcttccctggcaacgggcactgctaccgcctggtggtggagaagg<br>cggcctggctgcaggcgcaggagcagtgtcaggcctgggccgggggccg<br>ccctggcaatggtggacagtcccgccgtgcagcgcgcttcctggtctccc<br>gggtcaccaggagcctagacgtgtggatcggcttctcgactgtgcagg<br>gggtggaggtgggcccagcgccgcagggcgaggccttcagcctggaga<br>gctgccagaactggctgcccggggagccacacccagccacagccgagc<br>actgcgtccggctcgggcccaccgggtggtgtaacaccgacctgtgct<br>cagcgccgcacagctacgtctgcgagctgcagcccggaggcccagtgc<br>aggatgccgagaacctcctcgtgggagcgcccagtggggacctgcagg<br>gacccctgacgcctctggcacagcaggacggcctctcagccccgcacg<br>agcccgtggaggtcatggtattcccggggcctgcgtctgagccgtgaag<br>ccttcctcaccacggccgaatttgggacccaggagctccggcggcccg<br>cccagctgcggctgcaggtgtaccggctcctcagcacagcagggaccc<br>cggagaacggcagcgagcctgagagcaggtccccggacaacaggaccc<br>agctggccccgcgtgcatgccaggggggacgctggtgccctggagcca<br>acatctgcttgccgctggacgcctcctgccacccccaggcctgcgcca<br>atggctgcacgtcagggccagggctacccggggcccctatgcgctat<br>ggagagagttcctcttctccgttcccgcgggcccccgcgcagtact<br>cggtcaccctccacggccaggatgtcctcatgctccctggtgacctcg<br>ttggcttgcagcacgacgctggccctggcgcctcctgcactgctcgc<br>cggctcccggccaccctggtccccgggccccgtacctctccgccaacg<br>cctcgtcatggctgccccacttgccagcccagctggagggcacttggg<br>cctgccctgcctgtgccctgcggctgcttgcagccacggaacagctca<br>ccgtgctgctgggcttgaggcccaaccctggactgcggctgcctgggc<br>gctatgaggtccgggcagaggtgggcaatggcgtgtccaggcacaacc<br>tctcctgcagctttgacgtggtctccccagtggctgggctgcgggtca<br>tctaccctgcccccgcgacgccgcctctacgtgcccaccaaacggct<br>cagccttggtgctccaggtggactctggtgccaacgccacggccacgg<br>ctcgctggcctgggggcagtgtcagcgcccgctttgagaatgtctgcc<br>ctgccctggtggccaccttcgtgcccggctgccctgggagaccaacg<br>ataccctgttctcagtggtagcactgccgtggctcagtgaggggggagc<br>acgtggtggacgtggtggtggaaaacagcgccagccgggccaacctca<br>gcctgcgggtgacggcggaggagcccatctgtggcctccgcgccacgc<br>ccagccccgaggcccgtgtactgcagggagtcctagtgaggtacagcc<br>ccgtggtggaggccggctcggacatggtcttccggtggaccatcaacg<br>acaagcagtccctgaccttccagaacgtggtcttcaatgtcatttatc | Human PKD1 mRNA<br>GENBANK<br>Accession No.<br>NM_001009944.3<br>https://www.ncbi.<br>nlm.nih.gov/nuc<br>core/NM_001009944.3 |

TABLE 52A-continued

| Sequence Listing of GenBank Sequences | |
|---|---|
| SEQ ID NO Sequence | Name/Description | agagcgcggcggtcttcaagctctcactgacggcctccaaccacgtga
gcaacgtcaccgtgaactacaacgtaaccgtggagcggatgaacagga
tgcagggtctgcaggtctccacagtgccggccgtgctgtcccccaatg
ccacgctagcactgacggcgggcgtgctggtggactcggccgtggagg
tggccttcctgtgggacctttggggatggggagcaggccctccaccagt
tccagcctccgtacaacgagtccttccccggttccagacccctcggtgg
cccaggtgctggtggagcacaatgtcatgcacacctacgctgccccag
gtgagtacctcctgaccgtgctggcatctaatgccttcgagaacctga
cgcagcaggtgcctgtgagcgtgcgcgcctccctgccctccgtggctg
tgggtgtgagtgacggcgtcctggtggccggccggcccgtcaccttct
acccgcacccgctgccctcgcctgggggtgttctttacacgtgggact
tcggggacggctccctgtcctgacccagagccagccggctgccaacc
acacctatgcctcgaggggcacctaccacgtgcgcctggaggtcaaca
acacggtgagcggtgcggcggcccaggcggatgtgcgcgtctttgagg
agctccgcggactcagcgtggacatgagcctggccgtggagcagggcg
cccccgtggtggtcagcgccgcggtgcagacgggcgacaacatcacgt
ggaccttcgacatgggggacggcaccgtgctgtcgggcccggaggcaa
cagtggagcatgtgtacctgcgggcacagaactgcacagtgaccgtgg
gtgcggccagccccgccggccacctggcccggagcctgcacgtgctgg
tcttcgtcctggaggtgctgcgcgttgaacccgccgcctgcatcccca
cgcagcctgacgcgcggctcacggcctacgtcaccgggaacccggccc
actacctcttcgactggaccttcggggatggctcctccaacacgaccg
tgcgggggtgcccgacggtgacacacaacttcacgcggagcggcacgt
tcccctggcgctggtgctgtccagccgcgtgaacagggcgcattact
tcaccagcatctgcgtggagccagaggtgggcaacgtcaccctgcagc
cagagaggcagtttgtgcagctcggggacgaggcctggctggtggcat
gtgcctggcccccgttcccctaccgctacacctgggactttggcaccg
aggaagccgcccccacccgtgccaggggccctgaggtgacgttcatct
accgagacccaggctcctatcttgtgacagtcaccgcgtccaacaaca
tctctgctgccaatgactcagccctggtggaggtgcaggagcccgtgc
tggtcaccagcatcaaggtcaatggctcccttgggctggagctgcagc
agccgtacctgttctctgctgtggggccgtgggcgccccgccagctacc
tgtgggatctggggggacggtgggtggctcgagggtccggaggtcaccc
acgcttacaacagcacaggtgacttcacccttagggtggccggctgga
atgaggtgagccgcagcgaggcctggctcaatgtgacggtgaagcggc
gcgtgcgggggctcgtcgtcaatgcaagccgcacggtggtgcccctga
atgggagcgtgagcttcagcacgtcgctggaggccggcagtgatgtgc
gctattcctgggtgctctgtgaccgctgcacgcccatccctgggggtc
ctaccatctcttacaccttccgctccgtgggcaccttcaatatcatcg
tcacggctgagaacgaggtgggctccgcccaggacagcatcttcgtct
atgtcctgcagctcatagaggggctgcaggtggtgggcggtggccgct
acttccccaccaaccacacggtacagctgcaggccgtggttagggatg
gcaccaacgtctcctacagctggactgcctggagggacaggggcccgg
ccctggccggcagcggcaaaggcttctcgctcaccgtgctcgaggccg
gcacctaccatgtgcagctgcgggccaccaacatgctgggcagcgcct
gggccgactgcaccatggacttcgtggagcctgtggggtggctgatgg
tggccgcctccccgaacccagctgccgtcaacacaagcgtcaccctca
gtgccgagctggctggtggcagtggtgtcgtatacacttggtccttgg
aggaggggctgagctgggagacctccgagccatttaccacccatagct
tccccacacccggcctgcacttggtcaccatgacggcagggaacccgc
tgggctcagccaacgccaccgtggaagtggatgtgcaggtgcctgtga
gtggcctcagcatcagggccagcgagcccggaggcagcttcgtggcgg
ccgggtcctctgtgcccttttgggggcagctggccacgggcaccaatg
tgagctggtgctgggctgtgcccggcggcagcagcaagcgtggccctc
atgtcaccatggtcttcccggatgctggcaccttctctccatccggctca
atgcctccaacgcagtcagctgggtctcagccacgtacaacctcacgg
cggaggagcccatcgtgggcctggtgctgtgggccagcagcaaggtgg
tggcgcccgggcagctggtccatttttcagatcctgctggctgccggct
cagctgtcaccttccgcctgcaggtcggcggggccaacccccgaggtgc
tccccgggcccgtttctcccacagcttccccgcgcgtcggagaccacg
tggtgagcgtgcggggcaaaaaccacgtgagctgggcccaggcgcagg
tgcgcatcgtggtgctggaggccgtgagtgggctgcaggtgcccaact
gctgcgagcctggcatcgccacgggcactgagaggaacttcacagccc
gcgtgcagcgcggctctcgggtcgcctacgcctggtacttctcgctgc
agaaggtccagggcgactcgctggtcatcctgtcgggccgcgacgtca
cctacacgcccgtggccgcggggctgttggagatccaggtgcgcgcct
tcaacgccctgggcagtgagaaccgcacgctggtgctggaggttcagg
acgccgtccagtatgtggccctgcagagcggcccctgcttcaccaacc
cctaccactgggactttggggatgggtcgccagggcaggacacagatg
gctcggcgcagtttgaggccgccaccagccccagcccccggcgtgtgg
agcccagggccgagcactcctacctgaggcctggggactaccgcgtgg
aggtgaacgcctccaacctggtgagcttcttcgtggcgcaggccacgg
tgaccgtccaggtgctggcctgccggggagccggaggtggacgtggtcc
tgcccctgcaggtgctgatgcggcgatcacagcgcaactacttggagg
cccacgttgacctgcgcgactgcgtcacctaccagactgagtaccgct
gggaggtgtatcgcaccgccagctgccagcggccggggcgcccagcgc TABLE 52A-continued Sequence Listing of GenBank Sequences

| SEQ ID NO Sequence | Name/Description |
| --- | --- |
| gtgtggccctgcccggcgtggacgtgagccggcctcggctggtgctgc | |
| cgcggctggcgctgcctgtggggcactactgctttgtgtttgtcgtgt | |
| catttggggacacgccactgacacagagcatccaggccaatgtgacgg | |
| tggcccccgagcgcctggtgcccatcattgagggtggctcataccgcg | |
| tgtggtcagacacacgggacctggtgctggatgggagcgagtcctacg | |
| accccaacctggaggacggcgaccagacgccgctcagtttccactggg | |
| cctgtgtggcttcgacacagagggaggctggcgggtgtgcgctgaact | |
| ttgggcccgcgggagcagcacggtcaccattccacgggagcggctgg | |
| cggctggcgtggagtacaccttcagcctgaccgtgtggaaggccggcc | |
| gcaaggaggaggccaccaaccagacggtgctgatccggagtggccggg | |
| tgcccattgtgtccttggagtgtgtgtcctgcaaggcacaggccgtgt | |
| acgaagtgagccgcagctcctacgtgtacttggagggccgctgcctca | |
| attgcagcagcggctccaagcgagggcggtgggctgcacgtacgttca | |
| gcaacaagacgctggtgctggatgagaccaccacatccacgggcagtg | |
| caggcatgcgactggtgctgcggcggggcgtgctgcgggacggcgagg | |
| gatacaccttcacgctcacggtgctgggccgctctggcgaggaggagg | |
| gctgcgcctccatccgcctgtcccccaaccgcccgccgctgggggggct | |
| cttgccgcctcttcccactgggggctgtgcacgccctcaccaccaagg | |
| tgcacttcgaatgcacgggctggcatgacgcggaggatgctggcgccc | |
| cgctggtgtacgccctgctgctgcggcgctgtcgccagggccactgcg | |
| aggagttctgtgtgtctacaagggcagcctctccagctacggagccgtgc | |
| tgcccccgggtttcaggccacacttcgaggtgggcctggccgtggtgg | |
| tgcaggaccagctgggagccgctgtggtcgccctcaacaggtctttgg | |
| ccatcaccctcccagagcccaacggcagcgcaacggggctcacagtct | |
| ggctgcacgggctcaccgctagtgtgctcccagggctgctgcggcagg | |
| ccgatcccagcacgtcatcgagtactcgttggccctggtcaccgtgc | |
| tgaacgagtacgagcgggccctggacgtggcggcagagcccaagcacg | |
| agcggcagcaccgagcccagatacgcaagaacatcacggagactctgg | |
| tgtccctgagggtccacactgtggatgacatccagcagatcgctgctg | |
| cgctggcccagtgcatggggcccagcagggagctcgtatgccgctcgt | |
| gcctgaagcagacgctgcacaagctggaggccatgatgctcatcctgc | |
| aggcagagaccaccgcgggcaccgtgacgcccaccgccatcggagaca | |
| gcatcctcaacatcacaggagacctcatccacctggccagctcggacg | |
| tgcgggcaccacagccctcagagctgggagccgagtcaccatctcgga | |
| tggtggcgtcccaggcctacaacctgacctctgccctcatgcgcatcc | |
| tcatgcgctcccgcgtgctcaacgaggagcccctgacgctggcgggcg | |
| aggagatcgtggcccagggcaagcgctcggacccgcggagcctgctgt | |
| gctatggcggcgccccagggcctggctgccacttctccatccccgagg | |
| ctttcagcggggccctggccaacctcagtgacgtggtgcagctcatct | |
| ttctggtggactccaatcccttctcctttggctatatcagcaactaca | |
| ccgtctccaccaaggtggcctcgatggcattccagacacaggccggcg | |
| cccagatccccatcgagcggctggcctcagagcgcgccatcaccgtga | |
| aggtgcccaacaactcggactgggctgcccggggccaccgcagctccg | |
| ccaactccgccaactccgttgtggtccagccccaggcctccgtcggtg | |
| ctgtggtcaccctggacagcagcaaccctgcggccgggctgcatctgc | |
| agctcaactatacgctgctggacggccactacctgtctgaggaacctg | |
| agccctacctggcagtctacctacactcggagccccggcccaatgagc | |
| acaactgctcggctagcaggaggatccgcccagagtcactccagggtg | |
| ctgaccaccggccctacaccttcttcatttccccgggggagcagagacc | |
| cagcggggagttaccatctgaacctctccagccacttccgctggtcgg | |
| cgctgcaggtgtccgtgggcctgtacacgtccctgtgccagtacttca | |
| gcgaggaggacatggtgtggcggacagagggggctgctgcccctggagg | |
| agacctcgccccgccaggccgtctgcctcacccgccacctcaccgcct | |
| tcggcgccagcctcttcgtgccccaagccatgtccgctttgtgtttc | |
| ctgagccgacagcggatgtaaactacatcgtcatgctgacatgtgctg | |
| tgtgcctggtgacctacatggtcatggccgccatcctgcacaagctgg | |
| accagttggatgccagccggggccgcgccatcccctttctgtgggcagc | |
| ggggccgcttcaagtacgagatcctcgtcaagacaggctggggccggg | |
| gctcaggtaccacggcccacgtgggcatcatgctgtatggggtggaca | |
| gccggagcggccaccggcacctggacggcgacagagccttccaccgca | |
| acagcctggacatcttccggatcgccacccccgcacagcctgggtagcg | |
| tgtggaagatccgagtgtggcacgacaacaaagggctcagccctgcct | |
| ggttcctgcagcacgtcatcgtcagggacctgcagacggcacgcagcg | |
| ccttcttcctggtcaatgactggctttcggtggagacggaggccaacg | |
| ggggcctggtggagaaggaggctgctggccgcgagcgacgcagcccttt | |
| tgcgcttccggcgcctgctggtggctgagctgcagcgtggcttctttg | |
| acaagcacatctggctctccatatgggaccggccgcccctcgtagccgtt | |
| tcactcgcatccagagggccacctgctgcgttctcctcatctgcctct | |
| tcctgggcgccaacgccgtgtggtacggggctgttggcgactctgcct | |
| acagcacggggcatgtgtccaggctgagcccgctgagcgtcgacacag | |
| tcgctgttggcctggtgtccagcgtggttgtctatcccgtctacctgg | |
| ccatcctttttctcttccggatgtcccgggagcaaggtggctgggagcc | |
| cgagccccacacctgccgggcagcaggctggacatcgacagctgcc | |
| tcgactcgtccgtgctggacagctccttcctcacgttctctcaggcctcc | |
| acgctgagcaggcctttgttggacagatgaagagtgacttgtttctgg | |
| atgattctaagagtctggtgtgctggccctccggcgagcgagggaacgctca | |

TABLE 52A-continued

| Sequence Listing of GenBank Sequences | |
|---|---|
| SEQ ID NO Sequence | Name/Description |

```
gttggccggacctgctcagtgacccgtccattgtgggtagcaatctgc
ggcagctggcacggggccaggcgggccatgggctgggcccagaggagg
acggcttctccctggccagcccctactcgcctgccaaatccttctcag
catcagatgaagacctgatccagcaggtccttgccgagggggtcagca
gcccagcccctacccaagacacccacatggaaacggacctgctcagca
gcctgtccagcactcctggggagaagacagagacgctggcgctgcaga
ggctgggggagctggggccacccagcccaggcctgaactgggaacagc
cccaggcagcgaggctgtccaggacaggactggtggagggtctgcgga
agcgcctgctgccggcctggtgtgcctccctggcccacgggctcagcc
tgctcctggtggctgtggctgtggctgtctcagggtgggtgggtgcga
gcttccccccgggcgtgagtgttgcgtggctcctgtccagcagcgcca
gcttcctggcctcattcctcggctgggagccactgaaggtcttgctgg
aagccctgtacttctcactggtggccaagcggctgcacccggatgaag
atgacacctggtagagagcccggctgtgacgcctgtgagcgcacgtg
tgccccgcgtacggccaccccacggctttgcactcttcctggccaagg
aagaagcccgcaaggtcaagaggctacatggcatgctgcggagcctcc
tggtgtacatgcttttttctgctggtgaccctgctggccagctatgggg
atgcctcatgccatgggcacgcctaccgtctgcaaagcgccatcaagc
aggagctgcacagccgggccttcctggccatcacgcggtctgaggagc
tctggccatggatggcccacgtgctgctgccctacgtccacgggaacc
agtccagcccagagctggggcccccacggctgcggcaggtgcggctgc
aggaagcactctacccagaccctcccggccccagggtccacacgtgct
cggccgcaggaggcttcagcaccagcgattacgacgttggctgggaga
gtcctcacaatggctcggggacgtgggcctattcagcgccggatctgc
tgggggcatggtcctggggctcctgtgccgtgtatgacagcgggggct
acgtgcaggagctgggcctgagcctggaggagagccgcgaccggctgc
gcttcctgcagctgcacaactggctggacaacaggagccgcgctgtgt
tcctggagctcacgcgctacagccccggccgtggggctgcacgccgccg
tcacgctgcgcctcgagttcccggcggccggccgcgccctggccgccc
tcagcgtccgcccctttgcgctgcgccgcctcagcgcgggcctctcgc
tgcctctgctcacctcggtgtgcctgctgctgttcgccgtgcacttcg
Ccgtggccgaggcccgtacttggcacagggaagggcgctggcgcgtgc
tgcggctcggagcctgggcgcggtggctgctggtggcgctgacggcgg
ccacggcactggtacgcctcgcccagctgggtgccgctgaccgccagt
ggacccgtttcgtgcgcggccgcccgcgccgcttcactagcttcgacc
aggtggcgcagctgagctccgcagcccgtggcctggcggcctcgctgc
tcttcctgcttttggtcaaggctgcccagcagctacgcttcgtgcgcc
agtggtccgtctttggcaagacattatgccgagctctgccagagctcc
tgggggtcaccttgggcctggtggtgctcggggtagcctacgcccagc
tggccatcctgctcgtgtcttcctgtgtggactccctctggagcgtgg
cccaggccctgttggtgctgtgccctgggactgggctctctaccctgt
gtcctgccgagtcctggcacctgtcacccctgctgtgtgtggggctct
gggcactgcggctgtggggcgccctacggctgggggctgttattctcc
gctggcgctaccacgccttgcgtggagagctgtaccggccggcctggg
agccccaggactacgagatggtggagttgttcctgcgcaggctgcgcc
tctggatgggcctcagcaaggtcaaggagttccgccacaaagtccgct
ttgaagggatggagccgctgccctctcgctcctccaggggctccaagg
tatccccggatgtgcccccacccagcgctggctccgatgcctcgcacc
cctccacctcctccagccagctggatgggctgagcgtgagcctgggcc
ggctggggacaaggtgtgagcctgagccctcccgcctccaagccgtgt
tcgaggccctgctcacccagtttgaccgactcaaccaggccacagagg
acgtctaccagctggagcagcagctgcacagcctgcaaggccgcagga
gcagccgggcgcccgccggatcttcccgtggcccatccccgggcctgc
ggccagcactgcccagccgcctgcccgggccagtcggggtgtggacc
tggccactggccccagcaggacacccccttcgggccaagaacaaggtcc
accccagcagcacttagtcctccttcctggcggggggtgggccgtggag
tcggagtggacaccgctcagtattactttctgccgctgtcaaggccga
gggccaggcagaatggctgcacgtaggttccccagagagcaggcaggg
gcatctgtctgtctgtgggcttcagcactttaaagaggctgtgtggcc
aaccaggacccagggtcccctccccagctcccttgggaaggacacagc
agtattggacggtttctagcctctgagatgctaatttatttccccgag
tcctcaggtacagcgggctgtgcccggccccaccccctgggcagatgt
cccccactgctaaggctgctggcttcagggagggttagcctgcaccgc
cgccaccctgcccctaagttattacctctccagttcctaccgtactcc
ctgcaccgtctcactgtgtgtctcgtgtcagtaatttatatggtgtta
aaatgtgtatattttgtatgtcactattttcactagggctgaggggc
ctgcgcccagagctggcctcccccaacacctgctgcgcttggtaggtg
tggtggcgttatggcagcccggctgctgcttggatgcgagcttggcct
tgggccggtgctgggggcacagctgtctgccaggcactctcatcaccc
cagaggccttgtcatcctcccttgccccaggccaggtagcaagagagc
agcgcccaggcctgctggcatcaggtctgggcaagtagcaggactagg
```

TABLE 52A-continued

Sequence Listing of GenBank Sequences

| SEQ ID NO | Sequence | Name/Description |
|---|---|---| catgtcagaggacccccagggtggttagaggaaaagactcctcctggg
gctggctcccagggtggaggaaggtgactgtgtgtgtgtgtgtgtgcg
cgcgcgcacgcgcgagtgtgctgtatggcccaggcagcctcaaggccc
tcggagctggctgtgcctgcttctgtgtaccacttctgtgggcatggc
cgcttctagagcctcgacacccccccaacccccgcaccaagcagacaa
agtcaataaaagagctgtctgactgcaa

| 49 | aggcggcggcgggcgccgggaagaaaggaacatggctcctgaggcgca | Human PKD2 mRNA |
|---|---|---|
| | cagcgccgagcgcggcgccgcgcaccgcgcgcggacgccagtgacc | GENBANK |
| | gcgatggtgaactccagtcgcgtgcagcctcagcagcccggggacgcc | Accession No. |
| | aagcggccgcccgcgccccgcgcgccggacccgggccggctgatggct | NM_000297.4 |
| | ggctgcgcggccgtgggcgccagcctcgccgccccggcggcctctgc | https://www.ncbi. |
| | gagcagcggggcctggagatcgagatgcagcgcatccggcaggcggcc | nlm.nih.gov/nuc |
| | gcgcgggaccccccggccggagccgcggcctcccttctcctccgctc | core/NM_000297.4 |
| | tcgtcgtgctcccggcaggcgtggagccgcgataaccccggcttcgag | |
| | gccgaggaggaggaggaggaggtggaaggggaagaaggcggaatggtg | |
| | gtggagatggacgtagagtggcgcccgggcagccggaggtcggccgcc | |
| | tcctcggccgtgagctccgtgggcgcgcggagccgggggcttgggggc | |
| | taccacggcgcgggccacccgagcgggaggcggcgccggcgagaggac | |
| | cagggccgccgtgccccagcccagtcggcggcggggacccgctgcat | |
| | cgccacctcccctggaagggcagccgccccgagtggcctgggcggag | |
| | aggctggttcgcgggctgcgaggtctctggggaacaagactcatggag | |
| | gaaagcagcactaaccgagagaaataccttaaaagtgttttacgggaa | |
| | ctggtcacatacctcctttttctcatagtcttgtgcatcttgacctac | |
| | ggcatgatgagctccaatgtgtactactacacccggatgatgtcacag | |
| | ctcttcctagacacccccgtgtccaaaacggagaaaactaactttaaa | |
| | actctgtcttccatggaagacttctgtgaagttcacagaaggctcctta | |
| | ttggatgggctgtactggaagatgcagcccagcaaccagactgaagct | |
| | gacaaccgaagtttcatcttctatgagaacctgctgttaggggttcca | |
| | cgaatacggcaactccgagtcagaaatggatcctgctctatcccccag | |
| | gacttgagagatgaaattaaagagtgctatgatgtctactctgtcagt | |
| | agtgaagatagggctccctttgggccccgaaatggaaccgcttggatc | |
| | tacacaagtgaaaaagacttgaatggtagtagccactggggaatcatt | |
| | gcaacttatagtggagctggctattatctggatttgtcaagaacaaga | |
| | gaggaaacagctgcacaagttgctagcctcaagaaaaatgtctggctg | |
| | gaccgaggaaccagggcaacttttattgacttctcagtgtacaacgcc | |
| | aacattaacctgttctgtgtggtcaggttattggttgaattcccagca | |
| | acaggtggtgtgattccatcttggcaatttcagccttaaagctgatc | |
| | cgatatgtcacaacttttgatttcttcctggcagcctgtgagattatc | |
| | ttttgtttctttatctttttactatgtggtggaagagatattggaaatt | |
| | cgcattcacaaactacactatttcaggagtttctggaattgtctggat | |
| | gttgtgatcgttgtgctgtcagtggtagctataggaattaacatatac | |
| | agaacatcaaatgtggaggtgctactacagtttctggaagatcaaaat | |
| | actttccccaactttgagcatctggcatattggcagatacagttcaac | |
| | aatatagctgctgtcacagtattttttgtctggattaagctcttcaaa | |
| | ttcatcaattttaacaggaccatgagccagctctcgacaaccatgtct | |
| | cgatgtgccaaagacctgtttggctttgctattatgttcttcattatt | |
| | ttcctagcgtatgctcagttggcataccttgtctttggcactcaggtc | |
| | gatgacttcagtactttccaagagtgtatcttcactcaattccgtatc | |
| | attttgggcgatatcaactttgcagagattgaggaagctaatcgagtt | |
| | ttgggaccaatttatttcactacatttgtgttctttatgttcttcatt | |
| | cttttgaatatgttttttggctatcatcaatgatacttactctgaagtg | |
| | asatctgacttggcacagcagaaagctgaaatggaactctcagatctt | |
| | atcagaaagggctaccataaagctttggtcaaactaaaactgaaaaaa | |
| | aataccgtggatgacatttcagagagtctgcggcaaggaggaggcaag | |
| | ttaaactttgacgaacttcgacaagatctcaaagggaagggccatact | |
| | gatgcagagattgaggcaatattcacaaagtacgaccaagatggagac | |
| | caagaactgaccgaacatgaacatcagcagatgagagacgacttggag | |
| | aaagagagggaggacctggatttggatcacagttctttaccacgtccc | |
| | atgagcagccgaagtttccctcgaagcctggatgactctgaggaggat | |
| | gacgatgaagatagcggacatagctccagaaggagggaagcatttct | |
| | agtggcgtttcttacgaagagtttcaagtcctggtgagacgagtggac | |
| | cggatggagcattccatcggcagcatagtgtccaagattgacgccgtg | |
| | atcgtgaagctagagattatggagcgagccaaactgaagaggagggag | |
| | gtgctgggaaggctgttggatggggtggccgaggatgaaaggctgggt | |
| | cgtgacagtgaaatccataggga acagatggaacggctagtacgtgaa | |
| | gagttggaacgctgggaatccgatgatgcagcttcccagatcagtcat | |
| | ggtttaggcacgccagtgggactaaatggtcaacctcgccccagaagc | |
| | tcccgcccatcttcctcccaatctacagaaggcatggaaggtgcaggt | |
| | ggaaatgggagttctaatgtccacgtatgatatgtgtgtttcagtatg | |
| | tgtgtttctaataagtgaggaagtggctgtcctgaattgctgtaacaa | |
| | gcacactatttatatgccctgaccaccataggatgctagtctttgtga | |
| | ccgattgctaatcttctgcactttaatttattttatataaactttacc | |
| | catggttcaaagatttttttttttcttttttctcatataagaaatctaggt | |
| | gtaaatattgagtacagaaaaaaatcttcatgatgtgtattgagcgg | |
| | tacgcccagttgccaccatgactgagtcttctcagttgacaatgaagt | |

TABLE 52A-continued

| Sequence Listing of GenBank Sequences | | |
|---|---|---|
| SEQ ID NO | Sequence | Name/Description |
| | agccttttaaagctagaaaactgtcaaagggcttctgagtttcatttc<br>cagtcacaaaaatcagtattgttatttttttccaagagtgtgaaggaa<br>aatggggcattcctttccactctggcatagttcatgagcttaatacat<br>agctttcttttaagaaaggagcctttttttttcaactagcttcctgggg<br>taaacttttctaaaagataaaatggaaaggaactccaaactatgatag<br>aatctgtgtgaatggttaagatgaatgttaaatactatgcttttttgt<br>aagttgatcgtatctgatgtctgtgggactaactgtatcacttaattt<br>ttaccttattttggctctaatttgaataagctgagtaaaaccaccaaa<br>gatcagttataggataaaatggcatctctaaccataaacacaggagaat<br>tggaaggagccctaagttgtcactcagtttaattctttaatggtta<br>gtttagcctaaagatttatctgcatattcttttcccatgtggctcta<br>ctcatttgcaactgaatttaatgttataactcatctagtgagaccaac<br>ttactaaatttttagtatgcactgaaagtttttatccaacaattatgt<br>tcattttaagcaaaattttaagaaagtttttgaaattcataaagcattt<br>ggttttaaactattttaagaatatagtactcggtcaggtatgacggct<br>cacgcctglaatcccagcactttgggaggccgaaacaggcgaatcact<br>tgagcccaggagttcaagaccaacatgggcaatgtggcgaaactccat<br>ctctacaaaaaatgcaaaaataaaaaatatagtactcaagtattcttg<br>atcctgtgtttcaaaactagaatttgtaatgcaaatggagctcagtct<br>aataaaaaagaggtttttggtattaaaagttcatacattagacagtatc<br>agccaaaatttgagttagcaacactgttttctttacgagagggtctca<br>cccaaatttatggggagaaatctatttctcaaaaaaaaaaaatcttctt<br>ttacagaaatgttgagtaaggtgacattttgagcgctaataagcaaaa<br>gagcatgcagtgctgttgaataaccctcacttggagaaccaagagaat<br>cctgtcgtttaatgctatattttaatttcacaagttgttcatttaact<br>ggtagaatgtcagtccaatctccaatgagaacatgagcaaatagacct<br>ttccaggttgaaagtgaaacatactgggtttctgtaagttttccctca<br>tggcttcatctctatctttactttctcttgaatatgctacacaaagtt<br>ctttattactacatactaaagtttgcattccagggatattgactgtac<br>atatttatgtatatgtaccatgttgttacatgtaaacaaacttcaatt<br>tgaagtgcagctattatgtggtatccatgtgtatcgaccatgtgccat<br>atatcaattatggtcactagaaagtctctttatgatacttttttattgt<br>actgtttttcatttcacttgcaaaattttgcagaattcctcctttcta<br>Cccataaattacatatatttttcttcttagtcatggagaactccccc<br>cctcatctcttccctattatctttccctgtgtactggtattattaaaa<br>agacattacatacgcaagtctttctcgacaatcaagaatgttattaat<br>gtgtaatactgagcactttacttcttaataaaaacttgatatagtagc<br>a | |
| 50 | acatttgcttctgacacaactgtgttcactagcaacctcaaacagaca<br>ccatggtgcatctgactcctgaggagaagtctgccgttactgccctgt<br>ggggcaaggtgaacgtggatgaagttggtggtgaggccctgggcaggc<br>tgctggtggtctacccttggacccagaggttctttgagtcctttgggg<br>atctgtccactcctgatgctgttatgggcaaccctaaggtgaaggctc<br>atggcaagaaagtgctcggtgcctttagtgatggcctggctcacctgg<br>acaacctcaagggcacctttgccacactgagtgagctgcactgtgaca<br>agctgcacgtggatcctgagaacttcaggctcctgggcaacgtgctgg<br>tctgtgtgctggcccatcactttggcaaagaattcaccccaccagtgc<br>aggctgcctatcagaaagtggtggctggtgtggctaatgccctggccc<br>acaagtatcactaagctcgctttcttgctgtccaatttctattaaagg<br>ttcctttgttccctaagtccaactactaaactgggggatattatgaag<br>ggccttgagcatctggattctgcctaataaaaaacatttattttcatt<br>gcaa | Human HBB mRNA<br>GenBank<br>Accession No.<br>NM_000518.5<br>https://www.ncbi.<br>nlm.nih.gov/nuc<br>core/NM_000518.3 |
| 51 | gctgctgcccaaggaccgcggagtcggacgcaggcagaccatgtggac<br>cctggtgagctgggtggccttaacagcagggctggtggctggaacgcg<br>gtgcccagatggtcagttctgccctgtggcctgctgcctggaccccgg<br>aggagccagctacagctgctgccgtcccccttctggacaaatggccac<br>aacactgagcgaggcatctgggtggcccctgccaggttgatgccccactg<br>ctctgccggccactcctgcatctttaccgtctcagggacttccagttg<br>ctgccccttcccagaggccgtggcatgcggggatggccatcactgctg<br>cccacgggggcttccactgcagtgcagacgggcgatcctgcttccaaag<br>atcaggtaacaactccgtgggtgccatccagtgccctgatagtcagtt<br>cgaatgcccggacttctccacgtgctgtgttatggtcgatggctcctg<br>ggggtgctgccccatgccccaggcttcctgctgtgaagacagggtgca<br>ctgctgtccgcacggtgccttctgcgacctggttcacacccgctgcat<br>cacacccacgggcacccacccctggcaaagaagctccctgcccagag<br>gactaacagggcagtggccttgtccagctcggtcatgtgtccggacgc<br>acggtcccggtgccctgatggttctacctgctgtgagctgcccagtgg<br>gaagtatggctgctgcccaatgcccaacgccacctgctgctccgatca<br>cctgcactgctgccccccaagacactgtgtgtgacctgatccagagtaa<br>gtgcctctccaaggagaacgctaccacggacctcctcactaagctgcc<br>tgcgcacacagtgggggatgtgaaatgtgacatggaggtgagctgccc<br>agatggctatacctgctgccgtctacagtcggggggcctgggctgctg<br>cccttttacccaggctgtgtgctgtgaggaccacatacactgctgtcc<br>cgcggggtttacgtgtgacacgcagaagggtacctgtgaacaggggcc | Human GRN mRNA<br>GENBANK<br>Accession No.<br>NM_002087.4<br>https://www.ncbi.<br>nlm.nih.gov/nuc<br>core/NM_002087.4 |

TABLE 52A-continued

Sequence Listing of GenBank Sequences

| SEQ ID NO | Sequence | Name/Description |
|---|---|---|
| | ccaccaggtgccctggatggagaaggccccagctcacctcagcctgcc agacccacaagccttgaagagagatgtcccctgtgataatgtcagcag ctgtccctcctccgatacctgctgccaactcacgtctggggagtgggg ctgctgtccaatcccagaggctgtctgctgctcggaccaccagcactg ctgccccagggctacacgtgtgtagctgaggggcagtgtcagcgagg aagcgagatcgtggctggactggagaagatgcctgcccgccgggcttc cttatcccaccccagagacatcggctgtgaccagcacaccagctgccc ggtggggcagacctgctgcccgagcctgggtgggagctgggcctgctg ccagttgccccatgctgtgtgctgcgaggatcgccagcactgctgccc ggctggctacacctgcaacgtgaaggctcgatcctgcgagaaggaagt ggtctctgcccagcctgccaccttcctggcccgtagccctcacgtggg tgtgaaggacgtggagtgtggggaaggacacttctgccatgataacca gacctgctgccgagacaaccgacagggctgggcctgctgtccctaccg ccagggcgtctgttgtgctgatcggcgccactgctgtcctgctggctt ccgctgcgcagccaggggtaccaagtgtttgcgcagggaggccccgcg ctgggacgcccctttgagggacccagccttgagacagctgctgtgagg gacagtactgaagactctgcagccctcgggacccccactcggagggtgc cctctgctcaggcctccctagcacctcccctaaccaaattctccctg gaccccattctgagctccccatcaccatgggaggtggggcctcaatct aaggccttccctgtcagaaggggggttgtggcaaaagccacattacaag ctgccatcccctccccgtttcagtggaccctgtggccaggtgcttttc cctatccacagggggtttgtgtgtgtgcgcgtgtgcgtttcaataaa gtttgtacactttcttaa | |
| 52 | accatagagtgaggcgaggatgaagccgagaggatactgcagaggtct ctggtgcatgtgtgtatgtgtgcgtttgtgtgtgtttgtgtgtctgtg tgttctgccccagtgagactgcagcccttgtaaatactttgacacctt ttgcaagaaggaatctgaacaattgcaactgaaggcacattgttatca tctcgtctttgggtgatgctgttcctcactgcagatggataattttcc ttttaatcagaacagcataagaattatttctgagtggaggtgaggctt gtccaaatgtctttgctatcatggatttcctgactcctacctgtttga ggtttgggcaattatgaataaggctgctgtatacatccgtgtgcagga ttttgtgtggacataagttttcaactcctttggttaaatcctaaggaa tttcatatgcagaataaatggtaattaaaatgtgcaggatgacaagat ggagcaaacagtgcttgtaccaccaggacctgacagcttcaacttctt caccagagaatctcttgcggctattgaaagacgcattgcagaagaaaa ggcaaagaatcccaaaccagacaaaaaagatgacgacgaaaatggccc aaagccaaatagtgacttggaagctggadagaaccttccatttattta tggagacattcctccagagatggtgtcagagcccctggaggacctgga cccctactatatcaataagaaaacttttatagtattgaataaagggaa ggccatcttccggttcagtgccacctctgccctgtacattttaactcc cttcaatcctcttaggaaaatagctattaagattttggtacattcatt attcagcatgctaattatgtgcactattttgacaaactgtgtgtttat gacaatgagtaaccctcctgattggacaaagaatgtagaatacacctt cacaggaatatatacttttgaatcacttataaaaattattgcaagggg attctgtttagaagattttactttccttcgggatccatggaactggct cgatttcactgtcattacatttgcgtacgtcacagagtttgtggacct gggcaatgtctcggcattgagaacattcagagttctccgagcattgaa gacgatttcagtcattccaggcctgaaaaccattgtgggagccctgat ccagtctgtgaagaagctctcagatgtaatgatcctgactgtgttctg tctgagcgtatttgctctaattgggctgcagctgttcatgggcaacct gaggaataaatgtatacaatggcctcccaccaatgcttccttggagga acatagtatagaaaagaatataactgtgaattataatggtacacttat aaatgaaactgtctttgagtttgactggaagtcatatattcaagattc aagatatcattatttcctggaggggttttttagatgcactactatgtgg aaatagctctgatgcaggccaatgtccagagggatatatgtgtgtgaa agctggtagaaatcccaattatggctacacaagctttgataccttcag ttgggcttttttgtccttgtttcgactaatgactcaggacttctggga aaatctttatcaactgacattacgtgctgctgggaaaacgtacatgat attttttgtattggtcattttcttgggctcattctacctaataaattt gatcctggctgtggtggccatggcctacgaggaacagaatcaggccac cttggaagaagcagaacagaaagaggccgaatttcagcagatgattga acagcttaaaaagcaacaggaggcagctcagcaggcagcaacggcaac tgcctcagaacattccagagagcccagtgcagcaggcaggctctcaga cagctcatctgaagcctctaagttgagttccaagagtgctaaggaaag aagaaatcggaggaagaaaagaaaacagaaagagcagtctggtgggga agagaaagatgaggatgaattccaaaaatctgaatctgaggacagcat caggaggaaaggtttttcgcttctccattgaagggaaccgattgacata tgaaaagaggtactcctccccacaccagtctttgttgagcatccgtgg ctccctattttcaccaaggcgaaatagcagaacaagccttttcagctt tagagggcgagcaaaggatgtgggatctgagaacgacttcgcagatga tgagcacagcacctttgaggataacgagagccgtagagattccttgtt tgtgccccgacgacacggagagagacgcaacagcaacctgagtcagac cagtaggtcatcccggatgctggcagtgtttccagcgaatgggaagat gcacagcactgtggattgcaatggtgtggtttccttggttggtggacc ttcagttcctacatcgcctgttggacagcttctgccagaggtgataat | Human SCN1A mRNA GENBANK Accession No. NM_001165963.4 https://www.ncbi. nlm.nih.gov/nuc core/NM_001165963.4 |

TABLE 52A-continued

Sequence Listing of GenBank Sequences

| SEQ ID NO Sequence | Name/Description |
|---|---|
| agataagccagctactgatgacaatggaacaaccactgaaactgaaat | | agataagccagctactgatgacaatggaacaaccactgaaactgaaat
gagaaagagaaggtcaagttctttccacgtttccatggactttctaga
agatccttcccaaaggcaacgagcaatgagtatagccagcattctaac
aaatacagtagaagaacttgaagaatccaggcagaaatgcccaccctg
ttggtataaattttccaacatattcttaatctgggactgttctccata
ttggttaaaagtgaaacatgttgtcaacctggttgtgatggacccatt
tgttgacctggccatcaccatctgtattgtcttaaatactcttttcat
ggccatggagcactatccaatgacggaccatttcaataatgtgcttac
agtaggaaacttggttttcactgggatctttacagcagaaatgtttct
gaaaattattgccatggatccttactattatttccaagaaggctggaa
tatctttgacggttttattgtgacgcttagcctggtagaacttggact
cgccaatgtggaaggattatctgttctccgttcatttcgattgctgcg
agttttcaagttggcaaaatcttggccaacgttaaatatgctaataaa
gatcatcggcaattccgtgggggctctgggaaatttaaccctcgtctt
ggccatcatcgtcttcatttttgccgtggtcggcatgcagctctttgg
taaaagctacaaagattgtgtctgcaagatcgccagtgattgtcaact
cccacgctggcacatgaatgacttcttccactccttcctgattgtgtt
ccgcgtgctgtgtggggagtggatagagaccatgtgggactgtatgga
ggttgctggtcaagccatgtgccttactgtcttcatgatggtcatggt
gattggaaacctagtggtcctgaatctctttctggccttgcttctgag
ctcatttagtgcagacaaccttgcagccactgatgatgataatgaaat
gaataatctccaaattgctgtggataggatgcacaaaggagtagctta
tgtgaaaagaaaaatatatgaatttattcaacagtccttcattaggaa
acaaaagattttagatgaaattaaaccacttgatgatctaaacaacaa
gaaagacagttgtatgtccaatcatacagcagaaattgggaaagatct
tgactatcttaaagatgtaaatggaactacaagtggtataggaactgg
cagcagtgttgaaaaatacattattgatgaaagtgattacatgtcatt
cataaacaaccccagtcttactgtgactgtaccaattgctgtaggaga
atctgactttgaaaatttaaacacggaagactttagtagtgaatcgga
tctggaagaaagcaaagagaaactgaatgaaagcagtagctcatcaga
aggtagcactgtggacatcggcgcacctgtagaagaacagcccgtagt
ggaacctgaagaaactcttgaaccagaagcttgtttcactgaaggctg
tgtacaaagattcaagtgttgtcaaatcaatgtggaagaaggcagagg
aaaacaatggtggaacctgagaaggacgtgtttccgaatagttgaaca
taactggtttgagaccttcattgttttcatgattctccttagtagtgg
tgctctggcatttgaagatatatatattgatcagcgaaagacgattaa
gacgatgttggaatatgctgacaaggttttcacttacattttcattct
ggaaatgcttctaaaatgggtggcatatggctatcaaacatatttcac
caatgcctggtgttggctggacttcttaattgttgatgtttcattggt
cagtttaacagcaaatgccttgggttactcagaacttggagccatcaa
atctctcaggacactaagagctctgagacctctaagagccttatctcg
atttgaagggatgagggtggttgtgaatgcccttttaggagcaattcc
atccatcatgaatgtgcttctggtttgtcttatattctggctaatttt
cagcatcatgggcgtaaatttgtttgctggcaaattctaccactgtat
taacaccacaactggtgacaggtttgacatcgaagacgtgaataatca
tactgattgcctaaaactaatagaaagaaatgagactgctcgatggaa
aaatgtgaaagtaaactttgataatgtaggatttgggtatctctcttt
gcttcaagttgccacattcaaaggatggatggatataatgtatgcagc
agttgattccagaaatgtggaactccagcctaagtatgaagaaagtct
gtacatgtatctttactttgttattttcatcatctttgggtccttctt
caccttgaacctgtttattggtgtcatcatagataatttcaaccagca
gaaaaagaagtttggaggtcaagacatctttatgacagaagaacagaa
gaaatactataatgcaatgaaaaaattaggatcgaaaaaaccgcaaaa
gcctatacctcgaccaggaaacaaatttcaaggaatggtctttgactt
cgtaaccagacaagttttgacataagcatcatgattctcatctgtct
taacatggtcacaatgatggtggaaacagatgaccagagtgaatatgt
gactaccattttgtcacgcatcaatctggtgttcattgtgctatttac
tggagagtgtgtactgaaactcatctctctacgccattattattttac
cattggatggaatattttgatttttgtggttgtcattctctccattgt
aggtatgtttcttgccgagctgatagaaaagtatttcgtgtcccctac
cctgttccgagtgatccgtcttgctaggattggccgaatcctacgtct
gatcaaaggagcaaaggggatccgcacgctgctctttgctttgatgat
gtcccttcctgcgttgtttaacatcggcctcctactcttcctagtcat
gttcatctacgccatctttgggatgtccaactttgcctatgttaagag
ggaagttgggatcgatgacatgttcaactttgagaccctttggcaacag
catgatctgcctattccaaattacaacctctgctggctcggatggatt
gctagcacccattctcaacagtaagccacccgactgtgaccctaataa
agttaaccctggaagctcagttaagggagactgtgggaacccatctgt
tggaattttcttttttgtcagttacatcatcatatccttcctggttgt
ggtgaacatgtacatcgcggtcatcctggagaacttcagtgttgctac
tgaagaaagtgcagagcctctgagtgaggatgactttgagatgttcta
tgaggtttgggagaagtttgatcccgatgcaactcagttcatggaatt
tgaaaaattatctcagtttgcagctgcgcttgaaccgcctctcaatct
gccacaaccaaacaaactccagctcattgccatggatttgcccatggt
gagtggtgaccggatccactgtcttgatatcttatttgcttttacaaa
gcgggttctaggagagagtgggagagatggatgctctacgaatacagat TABLE 52A-continued Sequence Listing of GenBank Sequences

| SEQ ID NO Sequence | Name/Description |
|---|---|

```
ggaagagcgattcatggcttccaatccttccaaggtctcctatcagcc
aatcactactacttttaaaacgaaaacaagaggaagtatctgctgtcat
tattcagcgtgcttacagacgccaccttttaaagcgaactgtaaaaca
agcttcctttacgtacaataaaaacaaaatcaaaggtggggctaatct
tcttataaaagaagacatgataattgacagaataaatgaaaactctat
tacagaaaaaactgatctgaccatgtccactgcagcttgtccaccttc
ctatgaccgggtgacaaagccaattgtggaaaaacatgagcaagaagg
casagatgaaaaagccaaagggaaataaatgaaaataaataaaaataa
ttgggtgacaaattgtttacagcctgtgaaggtgatgtatttttatca
acaggactcctttaggaggtcaatgccaaactgactgttttacacaa
atctccttaaggtcagtgcctacaataagacagtgaccccttgtcagc
aaactgtgactctgtgtaaaggggagatgaccttgacaggaggttact
gttctcactaccagctgacactgctgaagataagatgcacaatggcta
gtcagactgtagggaccagtttcaaggggtgcaaacctgtgattttgg
ggttgtttaacatgaaacactttagtgtagtaattgtatccactgttt
gcatttcaactgccacatttgtcacatttttatggaatctgttagtgg
attcatcttttttgttaatccatgtgtttattatatgtgactatttttg
taaacgaagtttctgttgagaaataggctaaggacctctataacaggt
atgccacctgggggggtatggcaaccacatggccctcccagctacacaa
agtcgtggtttgcatgagggcatgctgcacttagagatcatgcatgag
aaaaagtcacaagaaaaacaaattcttaaatttcaccatatttctggg
aggggtaattgggtgataagtggaggtgcttgttgatcttgttttgc
gaaatccagcccctagaccaagtagattatttgtgggtaggccagtaa
atcttagcaggtgcaaacttcattcaaatgtttggagtcataaatgtt
atgtttcttttttgttgtattaaaaaaaaaacctgaatagtgaatattg
cccctcaccctccaccgccagaagactgaattgaccaaaattactctt
tataaatttctgctttttcctgcactttgtttagccatcttcggctct
cagcaaggttgacactgtatatgttaatgaaatgctatttattatgta
aatagtcattttaccctgtggtgcacgtttgagcaaacaastaatgac
ctaagcacagtatttattgcatcaaatatgtaccacaagaaagtaga
gtgcaagctttacacaggtaataaaatgtattctgtaccatttataga
tagtttggatgctatcaatgcatgtttatattaccatgctgctgtatc
tggtttctctcactgctcagaatctcatttatgagaaaccatatgtca
gtggtaaagtcaaggaaattgttcaacagatctcatttatttaagtca
ttaagcaatagtttgcagcactttaacagcttttggttattttttaca
ttttaagtggataacatatggtatatagccagactgtacagacatgtL
taaaaaaacacactgcttaacctattaaatatgtgtttagaattttat
aagcaaatataaatactgtaaaaagtcactttattttatttttcagca
ttatgtacataaatatgaagaggaaattatcttcaggttgatatcaca
atcacttttcttactttctgtccatagtacttttttcatgaaagaaatt
tgctaaataagacatgaaaacaagactgggtagttgtagatttctgct
ttttaaattacatttgctaattttagattatttcacaattttaaggag
caaaataggttcacgattcatatccaaattatgctttgcaattggaaa
agggtttaaaattttatttatatttctggtagtacctgcactaactga
attgaaggtagtgcttatgttatttttgttctttttttctgacttcgg
tttatgttttcatttctttggagtaatgctgctctagattgttctaaa
tagaatgtgggcttcataattttttttttccacaaaaacagagtagtca
acttatatagtcaattacatcaggacattttgtgtttcttacagaagc
aaaccataggctcctcttttccttaaaactacttagataaactgtatt
cgtgaactgcatgctggaaaatgctactattatgctaaataatgctaa
ccaacatttaaaatgtgcaaaactaataaagattacattttttatttt
attgtttgcccagtcacttttttgttaacagaatattctaatgatatgg
agattttttacattacaaattggggagaaggggagcgcgcgcgcaca
cacacacacacacacacacacacacacacagaggcataccca
cgttgacaacaaaacctagggtagatatgtcactggaggtaggggggta
atgacctcccagaattacaagcagcaggtgtgttctctgttaggagga
agaactggtgtcagaggatagctagtgattctaggaggaagagaagta
tggaagccagagtgatggtggatgacccccttgagctatgaaaagaaac
ccttaaatcatcatttaaaaatttagaattgccatgtgtgtaggatac
tgtgtttgctcctccagagccactctctctgcttctgcatcattctgt
gtgtcccagaagggtgacttctacacattgcaaaaatgggctctccta
cctttgagctcccaattggtttggccaatgagaagcaccagtgggaaa
gcaccagagagagaagattgacataggaatatttcttctccaattcct
tctttgctgggttggcactggactcattcctccccgaaaagtcatact
ccaatcagactgcccctcatacaactgaagctactttctctggggtca
ggtaatcactcctccccttgctccttcaggtctgctgctgcattgaga
gtgctttttgtattccttgtagctttctcctaacattgctgacactttt
gtaaatgtccccttcatgaaattcttctatatgcctcatttcagcatg
ccatctgtctcctgcctggctgacacaaggtgattcaacagctcatga
aagtcagcaggaagcaaagatgtgccttgcttcagcttggggtcttaa
tcttgctaacttttgcagataaagaaaaacagtaactgggggaaccac
agtgaagtccagtgcagaattcacagatatcatggaaaggttactcgg
gtggtccagatagtaaaattaacagtctaaattaatctatctaaattt
ctgaggaacgagaagccttcccttgtcatcaggtgaagccagaagagg
gaatatagcctcaaccagaaaagggacagtaattaaaaggctttccc
atccttgtacaatggactgactttgcctcttcataacatcacaatcct
```

TABLE 52A-continued

Sequence Listing of GenBank Sequences

| SEQ ID NO Sequence | Name/Description |
|---|---|
| aaagcaacacaacaattaattctgatatattagtagctgaaaaaaatt<br>cccatttccaactaaggtaggtcagaattataggatataaaccctgcaga<br>ctttttatactacccatccacgccattactcactgttacctttccaaa<br>tacaaagagaagaactggtaaaacataatcatatataaatctccatattc<br>attttgaaatatttggcatgatattttctgtgctaaaaagtaattatt<br>cttcaaagaatgatgaggtcatgtcagtaagacacaggaaccaactag<br>aaggggcttcccactggccaaatctggggcaagttgagcatcaaaata<br>aatgatagtaaaagattataattcattgaataagaatcagcaaataca<br>tactgatgtaagtaaataaggaaaagtacaaatctgtttcttgcagtt<br>gaatgttaattaacaattgtagaagaaataacggagttagaaaaatca<br>ctatttggcaatcaccctaatgacaattgattcatacaagaatcatca<br>atgagtattaaaactcatgggtgaaagtttgatgaggaatagggtatt<br>tatagcatcttaaagtatctcttctctattaagtagaaaatttaaaca<br>gaagaaagtatactttggagaaatacagcagacaataccttcaaagat<br>atcatcaattatgagaccaactgatactatgtgcctcctgataagata<br>tactgaaagggccacattacttcttggtacacagtcaaaattttaaaa<br>ccagaatctaactacaaggaaaatcaaattgaggacactctataaaat<br>aagtggactgaactccttaaaaatgtcaatgtcatgaaagacaaagaa<br>aggctaaagaattccatgaggtcaaagaactatgacaactaaacacaa<br>ttctggatggaatatcaaattaaaaaataacagatataataatattatt<br>gggaaagttgaataaatttgaatatggactgtttattagttattagta<br>ttataatagtgttaattttcctaattttgttaagactagtgtgcctgt<br>tccatgaaaatagaaaatgttcttattctctgaaaatgcatgctaaag<br>tatttaggggtgaatgcaacaatgtctgcagctcattcttgaatcagt<br>tcaaagaaaaatgagttacatttatatatatatgtatgtatgtaaaca<br>gacatagataaaagtatagatgtgtgtgtgtctttagaaaggggagga<br>ttttttttttttttttgctgtgtgttactgaagtgcctatgtctgcgt<br>gttcacactatcatattttgtatgccctggactttataatttctacct<br>tcaaaattagatctactgttggtaattaattcaatatatactggtttt<br>ttaactactattctcatttcctagcagtaatcttcctgaaaagtcaca<br>gaaatgattacattccttgttcttcataataatcactgtttaattaaa<br>ataagaatattttagaaaagatctgcggcatagtggttaagacccccag<br>tatttgatgctaaacagatctgatttggataacagaaggtggcacttt<br>gctgtttaagctgggggaccagacactgtgggtataaaatagtaattcca<br>aacacagctccacagagcagcaccccttatgacaaggttttcatatgtc<br>tatagttaagccagaaaattaagaataatgccataaatatttataaag<br>ctgaacatatccaagttaaagacctttatcctgaaattgtatcttttta<br>gattattttctaaagactaataccatttaatgtttaaatgttctttgg<br>aaatgatggtgagaatacgtgataatgggtcattggttttaatatttt<br>atttagccaagtggaaaattggcaacctggtgtcggtcctcccatttg<br>tattttactggtgcatgaaatccaaaagtctagtaaccattgggacag<br>acaactctactgcataagtttgtatgtttgtatatctgtatcacaaag<br>cccagacactcgaactatataaacttgtcgcactaaagacagcaaata<br>tgtctggtaattgcatattcttcatgtgtgcactggaatttcttatta<br>tataagaaaataaatgtgtttctaaaccaccatgaa | |

| TABLE 52B | | | | TABLE 52B-continued | | |
|---|---|---|---|---|---|---|
| Sequence Listing of PRSs | | | | Sequence Listing of PRSs | | |
| SEQ ID NO | Sequence | Name/Description | | SEQ ID NO | Sequence | Name/Description |
| 8 | GGACU | PRS GGACU derivative | | 43 | AAACU | PRS GGACU derivative |
| 9 | GGAUU | PRS GGAUU derivative | | 44 | GGACA | PRS GGACU derivative |
| 10 | GGACUGGAC | PRS GGACU derivative | | 93 | CCCCCCCCCC | PRS |
| 11 | GGACUGGACU | PRS GGACU derivative | | 94 | UUUUUUUUUU | PRS |
| 12 | ACGGACUUGGACU | PRS GGACU derivative | | 95 | ACACACACAC | PRS |
| 13 | AAACUAAACU | PRS Poly(A) derivative | | 96 | AGAGAGAGAG | PRS |
| 14 | AAAAAAAA | PRS Poly(A) derivative | | 97 | CUCUCUCUCU | PRS |
| 15 | AAAAAAAAAA | PRS Poly(A) derivative | | 98 | GUGUGUGUGU | PRS |
| 41 | GAACU | PRS GGACU derivative | | 99 | AAACAAAACA | PRS Poly(A) derivative |
| 42 | AGACU | PRS GGACU derivative | | 100 | AUUAUUAUUA | PRS |

TABLE 52B-continued

| Sequence Listing of PRSs | | |
|---|---|---|
| SEQ ID NO | Sequence | Name/Description |
| 101 | GGACUGGACUGGACU | PRS GGACU derivative |
| 102 | AAAAAAAAAAAA | PRS Poly(A) derivative |
| 152 | GGGGGGGGGG | PRS |

TABLE 52B-continued

| Sequence Listing of PRSs | | |
|---|---|---|
| SEQ ID NO | Sequence | Name/Description |
| 153 | TTTTTTTTTT | PRS |
| 154 | AAACA | PRS Poly(A) derivative |

TABLE 52C

| Sequence Listing of Compound Sequence with Chemistry | | |
|---|---|---|
| SEQ ID NO | Sequence + Chemistry | Name/Description |
| 16 | mAmAmCmCmAmCmAmGmAmAmAmCmUmAmCmCmA | ATXL228 (JAG1 ASO) |
| 17 | mGmGmAmCmUmAmAmCmCmAmCmAmGmAmAmAmCmUmAmCmCmA | ATXL261 (PRS + JAG1 ASO) |
| 18 | mGmGmAmCmUmGmGmAmCmAmAmCmCmAmCmAmGmAmAmAmCmUmAmCmCmA | ATXL193 (PRS + JAG1 ASO) |
| 19 | mAmAmCmCmAmCmAmGmAmAmAmCmUmAmCmCmAmGmGmAmCmUmGmGmAmC | ATXL384 (JAG1 ASO + PRS) |
| 20 | mGmGmAmCmUmGmGmAmCmUmGmUmUmAmAmAmGmAmAmCmUmAmCmAmAmGmCmC | ATXL257 (PRS + JAG1 ASO) |
| 21 | mGmGmAmCmUmGmGmAmCmUmGmGmAmUmUmCmUmAmAmOmUmCmAmGmCmAmA | ATXL258 (PRS + JAG1 ASO) |
| 22 | mGmGmAmCmUmGmGmAmCmUmUmGmCmUmGmUmGmGmUmUmCmUmGmAmGmCmUmG | ATXL259 (PRS + JAG1 ASO) |
| 23 | mGmGmAmCmUmGmGmAmCmUmCmUmGmCmAmGmCmAmGmAmUmCmAmCmCmUmGmC | ATXL260 (PRS + JAG1 ASO) |
| 24 | mG*mG*mAmCmUmGmGmAmCmUeA*eA*eCm*eCm*eA*eCm*eA*eG*eA*eA*eA*eCm*eT*eA*eCm*eCm*eA | ATXL234 (PRS + JAG1 ASO) |
| 25 | mG*mG*mAmCmUmGmGmAmCmUeAeAeCm*eCm*eA*eCm*eA*eG*eA*eA*eA*eCm*eT*eA*eCm*eCm*eA | ATXL262 (PRS + JAG1 ASO) |
| 26 | mA*mC*mGmGmAmCmUmUmGmGmAmCmUmCmUmGmCmUmG mCmAmAmAmCmGmCmU*mA*mA | ATXL230 (PRS + RAB1 ASO) |
| 27 | mA*mC*mGmGmAmCmUmUmGmGmAmCmUmCmAmAmUmGmG mUmCmCmUmAmCmCmU*mG*mC | ATXL231 (PRS + RNase H1 ASO) |
| 28 | mG*mG*mAmCmUmGmGmAmCmU*mC*mU*mA*mA*mA*mG*mA*mG*mA*mU*mG*mA*mA*mG*mC*mC | ATXL243 (PRS + PBGD ASO) |
| 29 | mG*mG*mAmCmUmGmGmAmCmUmA*mG*mG*mC*mC*mC*mC*mA*mA*mG*mG*mU*[GL]*mA*[GL]*mG*[mCL]-[AN-GalNAc] | ATXL319 (PRS + PBGD ASO) Murine |
| 30 | mG*mG*mAmCmUmGmGmAmCmUmC*mC*mC*mA*mA*mG*mG**U*mG*mA*mG*mG*mC*mA*mU*mA*mU*mC-[AN-GalNAc] | ATXL320 (PRS + PBGD ASO) Marine |
| 31 | mG*mG*mAmCmUmGmGmAmCmUmC*mA*mA*mG*mG*mU*mG*mA*mG*mG*mC*mA*mU*mA*mU*mC-[AN-GalNAc] | ATXL321 (PRS + PBGD ASO) Murine |
| 32 | mG*mG*mAmCmUmGmGmAmCmUeA*eCm*eT*eCm*eT*eT*eA*eT*eT**A*eT*eCm*eT*eCm*eA*eA*eG | ATXL251 (PRS + FGF21 ASO) |
| 33 | mG*mG*mAmCmUmGmGmAmCmUeA*eCm*eT*eCm*eT*eT*eA*eT*eT*eA*eT*eT*eCm*eCm*A*eA*eG-[AN-GalNAc] | ATXL317 (PRS + FGF21 ASO) Marine |
| 34 | mG*mG*mAmCmUmGmGmAmCmUeA*eA**A*eT*eA*eA*eA*eT*eA*eA*eG*eA*eT*eA*eT*CA-[AN-GalNAc] | ATXL318 (PRS + FGF21 ASO) Murine |

TABLE 52C-continued

Sequence Listing of Compound Sequence with Chemistry

| SEQ ID NO | Sequence + Chemistry | Name/Description |
|---|---|---|
| 35 | Biotin-mUmGmGmUmAmGmUmUmUmCmUmGmUmGmGmUmU | ATXL263 + biotin |
| 36 | mG*mG*mAmCmUmGmGmAmCmUeA*eA*eCm*eCm*eA*eCm*eA *eG*cA*eA*cA*eCm*eT*eA*eCm*eCm*eA-[AN-GalNAc] | ATXL316 |
| 37 | mA*mA*mAmCmUmAmAmAmCmUeA + eA*eCm*eCm*eA*eCm*eA *eG*eA*cA*eA**cCm*eT*eA*eCm*eCm*eA-[AN-GalNAc] | ATXL286 |
| 38 | mA*mA*mAmAmAmAmAmAmAeA*eA*eCm*eCm*eA*eCm*e A*eG*A*eA*cA*eCm*eT*eA*eCm*eCm*eA-[AN-GalNAc] | ATXL287 |
| 39 | mA*mA*mAmAmAmAmAmAeA*eA*eCm*eCm*eA*eCm*cA*eG*e A*eA*eA*cCm*eT*eA*eCm*eCm*eA-[AN-GalNAc] | ATXL288 |
| 40 | mG*mG*mAmCmUmGmGmAmCmUeA*eA*eCm*eCm*eA*cCm*eA *G*eA*cA*cA*cCm*eCm*eA-[AN-GalNAc] | ATXL246 |
| 53 | mG*mG*mAmCmUmGmGmAmCmUmCmCmUmUmGmCmCmG mUmOmAmCmCmAmC*mG*mU | ATXL394 (PRS + HNF4A ASO) |
| 54 | mG*mG*mAmCmUmGmGmAmCmUmCmUmGmCmUmCmUmGmG mGmAmCmUmGmGmU*mC*mC | ATXL395 (PRS + HNF4A ASO) |
| 55 | mG*mG*mAmCmUmGmGmAmCmUmCmCmUmUmAmGmGmCmC mAmUmGmUmUmCmU*mC*mG | ATXL396 (PRS + HNF4A ASO) |
| 56 | mG*mG*mAmCmUmGmGmAmCmUmGmUmGmGmCmUmUmCmA mAmCmAmUmGmA*mG*mA | ATXL397 (PRS + HNF4A ASO) |
| 57 | mG*mG*mAmCmUmGmGmAmCmUeA*eA*eCm*eCm*eA*eCm*eA *eG*eA*eA*eA*eCm*eCm*eA | ATXL398 |
| 58 | mG*mG*mAmCmUmGmGmAmCmUeGTT*cT*eA*eA*eA*eG* eA*eA*eCm*eT*eA*cCm*eA*eA*eG*eCm*eCm-[AN-GalNAc] | ATXL282 |
| 59 | mG*mG*mAmCmUmGmGmAmCmUeG*eT*eT**T*eA*eA*eA*eG* eA*eA*eCm*eT*eA*eCm*eA*cA*eG*eCm*eCm | ATXL283 |
| 60 | eTeG*eCm*eA*eCm*eT*eG*eA*eCm*eG*eG*eA*eA*eT*eA*eCm* eA*eA-[GL-GalNAc] | ATXL245 |
| 61 | eT*eG*eCm*eA*eCm*eG*eA*eCm*eT*eG*eG*cA*eA*cA*eA*eCm *eA*eA-[AN-GalNAc] | ATXL233 |
| 62 | mG*mG*mA*mC*mU*mG*mG*mA*mC*mU**A*eA*eCm*eCm*eA *eCm*eA*eG*eA*eA*eA*eCm*eT*eA*eCm*eCm*eA-[AN-GalNAc] | ATXL484 |
| 63 | mG*mG*mAmCmUmG*mG*mAmCmU**A*cA*eCm*eCm*eA*eCm *eA*eG*eA*cA*eA*eCm*eT*eA*eCm*eCm*eA-[AN-GalNAc] | ATXL493 |
| 64 | eA*eT*eA*eA*eG*eA*eT*eA*eA*cA*eT*eA*cA*eCm*eCm*eT*eA *AL*T*AL*eA*AL*eT | ATXL460 |
| 65 | eA*eT*eAeAeGeAeTeAeAcAeTeAeA[eCm][eCm]eTeAeAeTeA*eA*e A*ET | ATXL461 |
| 66 | eT*eA*eA*eGeAeTeAcAcAeTeAcA[eCm][eCm]eTeAeAeT*eA*eA*eA | ATXL462 |
| 67 | eA*eA*eT*eAeAcAeTeAeAeGeAeTeAceAeAeTeA*eA*eCm*eCm | ATXL463 |
| 68 | mG*mG*mAmCmUmGmGmAmCmUeA*eT*eAeAeGeAeTeAeAeAe TeAcA[eCm][eCm]eTeAeAeTeA*eA*eA*eT | ATXL464 |
| 69 | eA*eT*eA*eA*eG*eA*eT**A*cA*eA*eT*eA*eA*eCm*eCm*eT*eA *cA*eT*eA*eA*eA*eT-[AN-GalNAc] | ATXL482 |
| 70 | mG*mG*mAmCmUmGmGmAmCmUeA*eT*eA*eA*eG*eA*eT*eA* cA*eA*eT*cA*eA*eCm*eCm*eT*eA*eA*eT*eA*eA*eA*eT-[AN-GalNAc] | ATXL499 |
| 71 | mC*mC*mCmCmCmCmCmCmCmC[eA]*[eA]*[eCm]*[eCm]*[eA]* [eCm]*[eA]*[eG]*[eA]*[eA]*[eA]*[eCm]*[eT]*[eA]*[eCm]*[eCm]*[eA] | ATXL572 |
| 72 | mU*mU*mUmUmUmUmUmUmUmU[eA]*[eA]*[eCm]*[eCm]*[eA]* [eCm]*[eA]*[eG]*[eA]*[eA]*[eA]*[eCm[*[eT]*[eA]*[eCm]*[eCm]*[eA] | ATXL573 |

TABLE 52C-continued

Sequence Listing of Compound Sequence with Chemistry

| SEQ ID NO | Sequence + Chemistry | Name/Description |
|---|---|---|
| 73 | mA*mC*mAmCmAmCmAmCmAmC[eA]*[eA]*[eCm]*[eCm]*[eA]*[eCm]*[eA]*[eG]*[eA]*[eA]*[eA]*[eCm]*[eT]*[eA]*[eCm]*[eCm]*[eA] | ATXL574 |
| 74 | mA*mG&mAmGmAmGmAmGmAmG[eA]*[eA]*[eCm]*[eCm]*[eA]*[eCm]*[eA]*[eG]*[eA]*[eA]*[eA]*[eCm]*[eT]*[eA]*[eCm]*[eCm]*[eA] | ATXL575 |
| 75 | mCmUmCmUmCmUmCmUmCmU[eA]*[eA]*[eCm]*[eCm]*[eA]*[eCm]*[eA]*[eG]*[eA]*[eA]*[eA]*[eCm]*[eT]*[eA]*[eCm]*[eCm]*[eA] | ATXL576 |
| 76 | mG*mU*mGmUmGmUmGmUmGmU[eA]*[eA]*[eCm]*[eCm]*[eA]*[eCm]*[eA]*[eG]*[eA]*[eA]*[eA]*[eCm]*[eT]*[eA]*[eCm]*[eCm]*[eA] | ATXL577 |
| 77 | mA*mA*mAmCmAmAmAmAmCmA[eA]*[eA]*[eCm]*[eCm]*[eA]*[eCm]*[eA]*[eG]*[eA]*[eA]*[eA]*[eCm]*[eT]*[eA]*[eCm]*[eCm]*[eA] | ATXL578 |
| 78 | mA*mU*mUmAmUmUmAmUmUmA[eA]*[eA]*[eCm]*[eCm]*[eA]*[eCm]*[eA]*[eG]*[eA]*[eA]*[eA]*[eCm]*[eT]*[eA]*[eCm]*[eCm]*[eA] | ATXL579 |
| 79 | mG*mG*mAmCmUmGmGmAmCmUmGmGmAmCmU[eA]*[eA]*[eCm]*[eCm]*[eA]*[eCm]*[eA]*[eG]*[eA]*[eA]*[eA]*[eCm]*[eT]*[eA]*[eCm]*[eCm]*[eA] | ATXL580 |
| 80 | mA*mA*mAmAmAmAmAmAmA[eA]*[eA]*[eCm]*[eCm]*[eA][eCm][eA][eG]*[eA]*[eA]*[eA]*[eCm]*[eT]*[eA]*[eCm]*[eCm]*[eA] | ATXL581 |
| 81 | mG*mG*mAmCmUmGmGmAmCmU*[eA]*[eT]*[eA]*[eA]*[eG]*[eA]*[eT]*[eA]*[eA]*[eA]*[eT]*[eA]*[eA]*[eCm]*[eCm]*[eT]*[eA]*[eA]*[eT]*[eA]*[eA]*[eA]*[eT][AN-GalNAc] | ATXL506 |
| 82 | mG*mG*mAmCmUmG*mG*mAmCmU*[eA]*[eT]*[eA]*[eA]*[eG]*[eA]*[eT]*[eA]*[eA]*[eA]*[eT]*[eA]*[eA]*[eCm]*[eCm]*[eT]*[eA]*[eA]*[eT]*[eA]*[eA]*[eA]*[eT][AN-GalNAc] | ATXL517 |
| 83 | mG*mG*mAmCmUmG*mG*mAmCmU[eA]*[eT]*[eA]*[eA]*[eG]*[eA]*[eT]*[eA]*[eA]*[eA]*[eT]*[eA]*[eA]*[eCm]*[eCm]*[eT]*[eA]*[eA]*[eT]*[eA]*[eA]*[eA]*[eT[AN-GalNAc] | ATXL518 |
| 84 | mG*mG*mAmCmUmG*mGmA*mC*mU*[eA]*[eT]*[eA]*[eA]*[eG]*[eA]*[eT]*[eA]*[eA]*[eA]*[eT]*[eA]*[eA]*[eCm]*[eCm]*[eT]*[eA]*[eA]*[eT]*[eA]*[eA]*[eA]*[eT][AN-GalNAc] | ATXL519 |
| 85 | mG*mG*mAmCmUmG*mG*mA*mC*mU*[eA]*[eT]*[eA]*[eA]*[eG]*[eA]*[eT]([eA]*[eA]*[eA]*[eT]*[eA]*[eA]*[eCm]*[eCm]*[eT]*[eA]*[eA]*[eT]*[eA]*[eA]*[eA]*[eT][AN-GalNAc] | ATXL520 |
| 86 | mG*mG*mAmCmUmG*mGmA*mC*[eA]*[eT]*[eA]*[eA]*[eG]*[eA]*[eT]*[eA]*[eA]*[eA]*[eT]*[eA]*[eA]*[eC]*[me]*[Cm]*[eT]*[eA]*[eA]*[eT][eA]*[eA]*[eA]*[eT][AN-GalNAc] | ATXL521 |
| 87 | mG*mG*mAmCmUmGmGmAmCmUmA*mU*mA*mA*mG*mA*mU*mA*mA*mA*mU*mA*mA*mC*mC*mU*mA*mA*mU*mA*mA*mA*mU[AN-GalNAc] | ATXL522 |
| 88 | mG*mG*mA*mC*mU*[eA][eT]*[eA]*[eA]*[eG]*[eA]*[eT]*[eA]*[eA]*[eA]*[eT]*[eA]*[eA]*[eC]*[me]*[Cm]*[eT]*[eA]*[eA]*[eT]*[eA]*[eA]*[eA]*[eT][AN-GalNAc] | ATXL523 |
| 89 | mG*mG*mAmCmU*[eA]*[eT]*[eA]*[eA]*[eG]*[eA]*[eT]*[eA]*[eA]*[eA]*[eT]*[eA]*[eA]*[eCm]*[eCm]*[eT]*[eA]*[eA]*[eT]*[eA]*[eA]*[eA][eT][AN-GalNAc] | ATXL524 |
| 90 | mG*mG*mAmCmU[eA]*[eT]*[eA]*[eA]*[eG]*[eA]*[eT]*[eA]*[eA]*[eA]*[eT]*[eA]*[eA]*[eCm]*[eCm]*[eT]*[eA]*[eA]*[eT]*[eA]*[eA]*[eA]*[eT][AN-GalNAc] | ATXL525 |
| 91 | mG*mG*mAmCmUmGmGmAmCmU[eCm][eT]*[eG]*[eG]*[eCm]*[eT]*[eCm]*[eT]*[eG]*[eG]*[eG]*[eA]*[eCm]*[eT]*[eG]*[eG]*[eT][AN-GalNAc] | ATXL546 |
| 92 | mG*mG*mAmCmUmGmGmAmCmU[eG]*[eCm]*[eT]*[eCm*][eT]*[eG]*[eG]*[eG]*[eA]*[eCm]*[eT]*[eG]*[eG]*[eT]*[eCm]*[eCm][AN-GalNAc] | ATXL547 |

TABLE 52D

| SEQ ID NO | Sequence | Name/Description |
|-----------|----------|------------------|
| Sequence Listing of Compound Sequence without Chemistry | | |
| 103 | AACCACAGAAACUACCA | ATXL228 (JAG1 ASO) |
| 104 | GGACUAACCACAGAAACUACCA | ATXL261 (PRS + JAG1 ASO) |
| 105 | GGACUGGACAACCACAGAAACUACCA | ATXL193 (PRS + JAG1 ASO) |
| 106 | AACCACAGAAACUACCAGGACUGGAC | ATXL384 (JAG1 ASO + PRS) |
| 107 | GGACUGGACUGUUUAAAGAACUACAAGCC | ATXL257 (PRS + JAG1 ASO) |
| 108 | GGACUGGACUGGAUUCUAAGUCAGCAA | ATXL258 (PRS + JAG1 ASO) |
| 109 | GGACUGGACUUGCUGUGGUUCUGAGCUG | ATXL259 (PRS + JAG1 ASO) |
| 110 | GGACUGGACUCUGCAGCAGAUCACCUGC | ATXL260 (PRS + JAG1 ASO) |
| 111 | GGACUGGACUAACCACAGAAACTACCA | ATXL234 (PRS + JAG1 ASO) ATXL262 (PRS + JAG1 ASO) ATXL316 ATXL484 ATXL493 |
| 112 | ACGGACUUGGACUCUGCUGCAAACGCUAA | ATXL230 (PRS + RAB1 ASO) |
| 113 | ACGGACUUGGACUCAAUGGUCCUACCUGC | ATXL231 (PRS + RNase H1 ASO) |
| 114 | GGACUGGACUCUAAAGAGAUGAAGCC | ATXL243 (PRS + PBGD ASO) |
| 115 | OGACUGGACUAGGCCCCAAGGUGAGGC | ATXL319 (PRS + PBGD ASO) |
| 116 | GGACUGGACUCCCAAGGUGAGGCAUAUC | ATXL320 (PRS + PBGD ASO) |
| 117 | GGACUGGACUCAAGGUGAGGCAUAUC | ATXL321 (PRS + PBGD ASO) |
| 118 | GGACUGGACUACTCTTTATTATCTCAAG | ATXL251 (PRS + FGF21 ASO) |
| 119 | GGACUGGACUACTCTTTATTATTCCAAG | ATXL317 (PRS + FGF21 ASO) |
| 120 | GGACUGGACUAAATAAATAAGATAAATA | ATXL318 (PRS + FGF21 ASO) |
| 121 | UGGUAGUUUCUGUGGUU | ATXL263 |
| 122 | AAACUAAACUAACCACAGAAACTACCA | ATXL286 |
| 123 | AAAAAAAAAAAACCACAGAAACTACCA | ATXL287 |
| 124 | AAAAAAAAAACCACAGAAACTACCA | ATXL288 |
| 125 | GGACUGGACUAACCACAGAAACCA | ATXL246 ATXL398 |
| 126 | GGACUGGACUCCUUUGCCGUGACCACGU | ATXL394 |
| 127 | GGACUGGACUCUGCUCUGGGACUGGUCC | ATXL395 |
| 128 | GGACUGGACUCCUUAGGCCAUGUUCUCG | ATXL396 |

TABLE 52D-continued

| Sequence Listing of Compound Sequence without Chemistry | | |
|---|---|---|
| SEQ ID NO | Sequence | Name/Description |
| 129 | GGACUGGACUGUGGCUUCAACAUGAGA | ATXL397 |
| 130 | GGACUGGACUGTTTAAAGAACTACAAGCC | ATXL282 ATXL283 |
| 131 | TGCACTGACGGAATACAA | ATXL245 |
| 132 | TGCACGACTGGAAAACAA | ATXL233 |
| 133 | ATAAGATAAATAACCTAATAAAT | ATXL460 ATXL461 ATXL482 |
| 134 | TAAGATAAATAACCTAATAAA | ATXL462 |
| 135 | AATAAATAAGATAAATAACC | ATXL463 |
| 136 | GGACUGGACUATAAGATAAATAACCTAATAAAT | ATXL464 ATXL499 ATXL506 ATXL517 ATXL518 ATXL519 ATXL520 |
| 137 | CCCCCCCCCCAACCACAGAAACTACCA | ATXL572 |
| 138 | UUUUUUUUUUAACCACAGAAACTACCA | ATXL573 |
| 139 | ACACACACACAACCACAGAAACTACCA | ATXL574 |
| 140 | AGAGAGAGAGAACCACAGAAACTACCA | ATXL575 |
| 141 | CUCUCUCUCUAACCACAGAAACTACCA | ATXL576 |
| 142 | GUGUGUGUGUAACCACAGAAACTACCA | ATXL577 |
| 143 | AAACAAAACAAACCACAGAAACTACCA | ATXL578 |
| 144 | AUUAUUAUUAAACCACAGAAACTACCA | ATXL579 |
| 145 | GGACUGGACUGGACUAACCACAGAAACTACCA | ATXL580 |
| 146 | AAAAAAAAAAAACCACAGAAACTACCA | ATXL581 |
| 147 | GGACUGGACATAAGATAAATAACCTAATAAAT | ATXL521 |
| 148 | GGACUGGACUAUAAGAUAAAUAACCUAAUAAAU | ATXL522 |
| 149 | GGACUAUAAGATAAATAACCTAATAAAT | ATXL523 ATXL524 ATXL525 |
| 150 | GGACUGGACUCTGCTCTGGGACTGGT | ATXL546 |
| 151 | GGACUGGACUGCTCTGGGACTGGTCC | ATXL547 |

What is claimed is:

1. A compound comprising an oligonucleotide for enhancing expression of JAG1 in a cell or salt thereof, wherein the oligonucleotide comprises at least a 20 nucleobase portion of the sequence of SEQ ID NO: 111, or a sequence thereof which differs up to 2 positions of SEQ ID NO: 111, wherein the compound further comprises a conjugate.

2. The compound of claim 1, wherein the conjugate is an N-Acetyl galactosamine (GalNAc) moiety.

3. A compound comprising an oligonucleotide for enhancing expression of JAG1 in a cell or salt thereof, wherein the oligonucleotide comprises at least a 20 nucleobase portion of the sequence of SEQ ID NO: 111, or a sequence thereof which differs up to 2 positions of SEQ ID NO: 111, wherein the compound comprises at least one chemical modification.

4. The compound of claim 3, wherein the at least one chemical modification can be selected from 2'-O-methyl (2'-OMe), 2'-O-(2-methoxyethyl) (2'-MOE), 2'-fluoro (2'-F), constrained ethyl (cEt), unlocked nucleic acid (UNA), locked nucleic acid (LNA), 2'-MOE modified T, and/or 5-methylcytosine base.

5. A compound comprising an oligonucleotide for enhancing expression of JAG1 in a cell or salt thereof, wherein the oligonucleotide comprises at least a 20 nucleobase portion of the sequence of SEQ ID NO: 111, or a sequence thereof which differs up to 2 positions of SEQ ID NO: 111, wherein the compound is fully chemically modified.

6. The compound of claim 5, wherein the chemical modifications can be selected from 2'-O-methyl (2'-OMe), 2'-O-(2-methoxyethyl) (2'-MOE), 2'-fluoro (2'-F), constrained ethyl (cEt), unlocked nucleic acid (UNA), locked nucleic acid (LNA), 2'-MOE modified T, and/or 5-methylcytosine base.

7. A compound comprising an oligonucleotide for enhancing expression of JAG1 in a cell or salt thereof, wherein the oligonucleotide comprises at least a 20 nucleobase portion of the sequence of SEQ ID NO: 111, or a sequence thereof which differs up to 2 positions of SEQ ID NO: 111, wherein the compound comprises at least one modified internucleoside linkage.

8. The compound of claim 7, wherein the at least one modified internucleoside linkage is a phosphorothioate (PS) internucleoside linkage.

9. A method for enhancing JAG1 expression in a cell, comprising administering to the cell the compound of claim 1, 3, 5 or 7 in an amount sufficient to enhance expression of JAG1, thereby enhancing expression of JAG1 in the cell.

10. The method of claim 9, wherein expression of JAG1 in a cell is increased by at least about 10%, 15%, 20%, 25%, 30%, 35%, 40%, 45%, 50%, 55%, 60%, 65%, 70%, 75%, 80%, 85%, 90%, 95%, 100%, 150%, 200%, 250%, or 300%.

11. A pharmaceutical composition for enhancing expression of JAG1 comprising the compound of claim 1, or salt thereof, alone or in combination with a pharmaceutically acceptable carrier and/or excipient.

12. A kit comprising the pharmaceutical composition of claim 11, and a label.

13. The compound of claim 3, e for enhancing expression of JAG1 in a cell, wherein the compound comprises the sequence and chemistry of ATXL316 (SEQ ID NO: 36) as shown in the chemical structure:

-continued
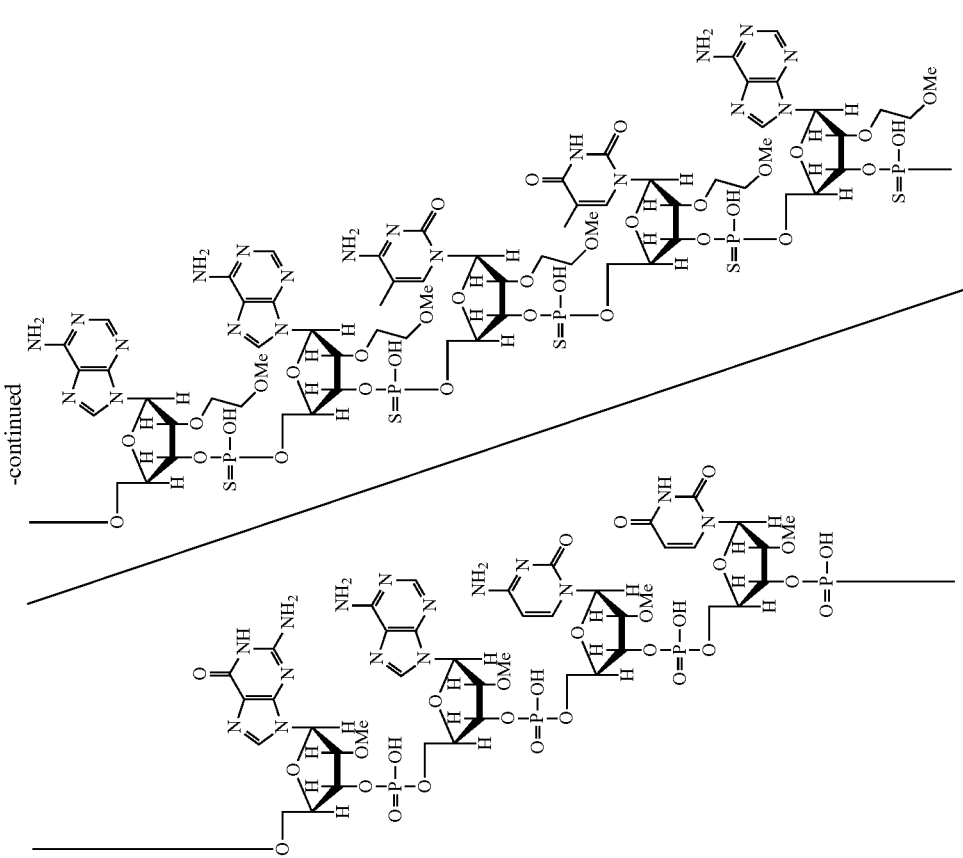

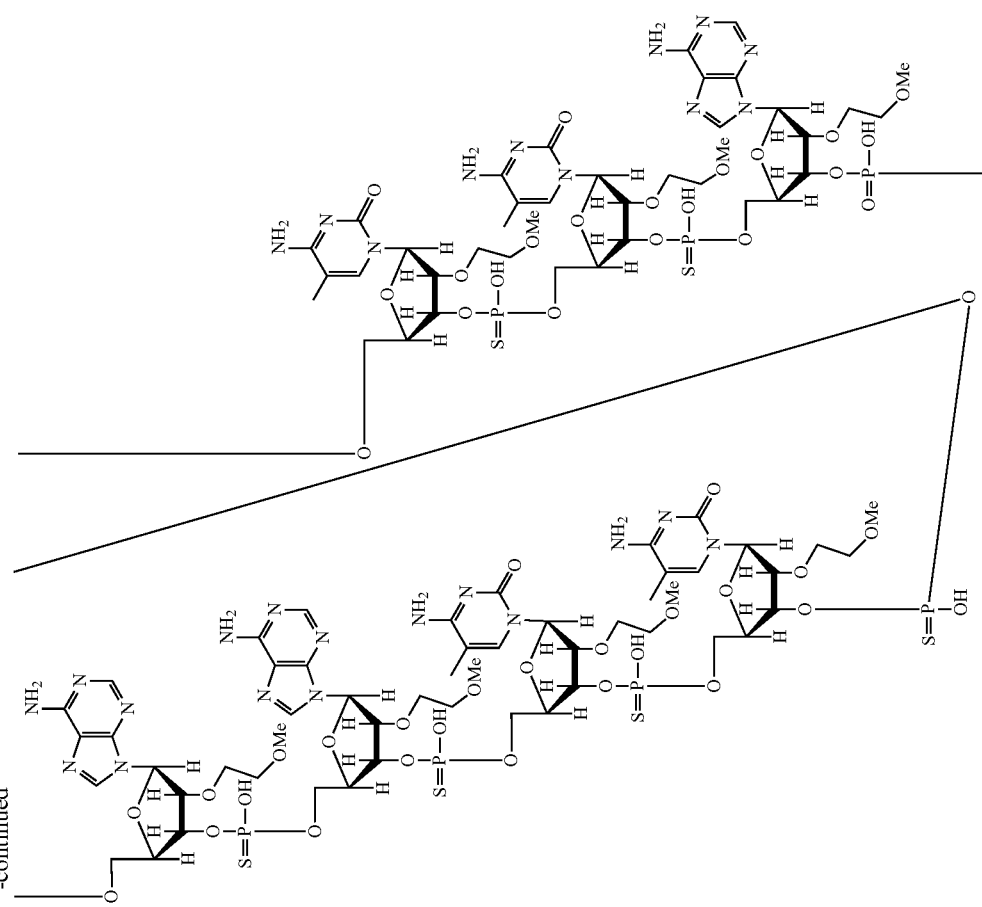
-continued

-continued
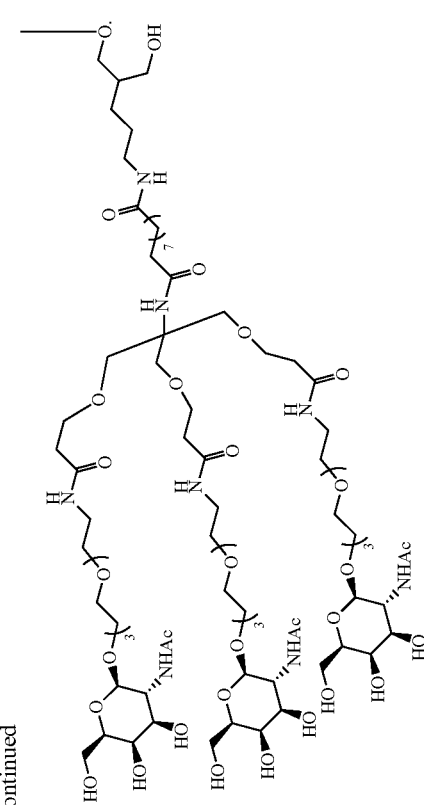

14. A pharmaceutical composition for enhancing the expression of JAG1 comprising the compound of claim 13, or a salt thereof, alone or in combination with a pharmaceutically acceptable carrier and/or excipient.

15. A kit comprising the pharmaceutical composition of claim 14, and a label.

16. A pharmaceutical composition for enhancing the expression of JAG1 comprising the compound of claim 3, or salt thereof, alone or in combination with a pharmaceutically acceptable carrier and/or excipient.

17. A pharmaceutical composition for enhancing the expression of JAG1 comprising the compound of claim 5, or salt thereof, alone or in combination with a pharmaceutically acceptable carrier and/or excipient.

18. A pharmaceutical composition for enhancing the expression of JAG1 comprising the compound of claim 7, or salt thereof, alone or in combination with a pharmaceutically acceptable carrier and/or excipient.

19. A kit comprising the pharmaceutical composition of claim 16, and a label.

20. A kit comprising the pharmaceutical composition of claim 17, and a label.

21. A kit comprising the pharmaceutical composition of claim 18, and a label.

* * * * *

SEQUENCE LISTING

Sequence total quantity: 154
SEQ ID NO: 1          moltype = DNA  length = 5940
FEATURE               Location/Qualifiers
source                1..5940
                      mol_type = other DNA
                      organism = Homo sapiens
SEQUENCE: 1
agacgggctc tccgggtcct tctccgagag ccgggcgggc acgcgtcatt gtgttacctg    60
cggccggccc gcgagctagg ctggtttttt tttttctccc ctccctcccc ccttttttcca   120
tgcagctgat ctaaaaggga ataaaaggct gcgcataatc ataataataa aagaaggggga   180
gcgcgagaga aggaaagaaa gccgggaggt ggaagaggag ggggagcgtc tcaaagaagc    240
gatcagaata ataaaaggag gccgggctct ttgccttctg gaacgggccg ctcttgaaag    300

-continued

```
ggcttttgaa aagtggtgtt gttttccagt cgtgcatgct ccaatcggcg gagtatatta    360
gagccgggac gcggcggccg caggggcagc ggcgacggca gcaccggcgg cagcaccagc    420
gcgaacagca gcggcggcgt cccgagtgcc cgcggcgcgc ggcgcagcga tgcgttcccc    480
acggacgcgc ggccggtccg ggcgcccct aagcctcctg ctcgccctgc tctgtgccct    540
gcgagccaag gtgtgtgggg cctcgagtca gttcgagttg gagatcctgt ccatgcagaa    600
cgtgaacggg gagctgcaga acgggaactg ctgcggcggc gcccggaacc cgggagaccg    660
caagtgcacc cgcgacgagt gtgacacata cttcaaagtg tgcctcaagg agtatcagtc    720
ccgcgtcacg gccggggggc cctgcagctt cggctcaggg tccacgcctg tcatcggggg    780
caacaccttc aacctcaagg ccagccgcgg caacgaccgc aaccgcatcg tgctgccttt    840
cagtttcgcc tggccgaggt cctatacgtt gcttgtggag gcgtgggatt ccagtaatga    900
caccgttcaa cctgacagta ttattgaaaa ggcttctcac tcgggcatga tcaaccccag    960
ccggcagtgg cagacgctga agcagaacac gggcgttgcc cactttgagt atcagatccg   1020
cgtgacctgt gatgactact actatggctt tggctgcaat aagttctgcc gccccagaga   1080
tgacttcttt ggacactatg cctgtgacca gaatggcaac aaaacttgca tggaaggctg   1140
gatgggcccc gaatgtaaca gagctatttg ccgacaaggc tgcagtccta agcatgggtc   1200
ttgcaaactc ccaggtgact gcaggtgcca gtacggctgg caaggcctgt actgtgataa   1260
gtgcatccca cacccgggat gcgtccacgg catctgtaat gagccctggc agtgcctctg   1320
tgagaccaac tggggcggcc agctctgtga caaagatctc aattactgtg ggactcatca   1380
gccgtgtctc aacgggggaa cttgtagcaa cacaggccct gacaaatatc agtgttcctg   1440
ccctgagggg tattcaggac ccaactgtga aattgctgag cacgcctgcc tctctgatcc   1500
ctgtcacaac agaggcagct gtaaggagac ctccctgggc tttgagtgtg agtgttcccc   1560
aggctggacc ggcccacat gctcacaaa cattgatgac tgttctccta ataactgttc   1620
ccacgggggc acctgccagg acctggttaa cggatttaag tgtgtgtgcc ccccacagtg   1680
gactgggaaa acgtgccagt tagatgcaaa tgaatgtgag gccaaacctt gtgtaaacgc   1740
caaatcctgt aagaatctca ttgccagcta ctactgcgac tgtcttcccg gctggatggg   1800
tcagaattgt gacataaata ttaatgactg ccttggccaa tgtcagaatg acgcctcctg   1860
tcgggatttg gttaatggtt atcgctgtat ctgtccacct ggctatgcag gcgatcactg   1920
tgagagagac atcgatggaa tgtgccagca acccctgtttg aatgggggtc actgtcagaa   1980
tgaaatcaac agattccagt gtctgtgtcc cactggtttc tctggaaacc tctgtcagct   2040
ggacatcgat tattgtgagc ctaatccctg ccagaacggc gcccagtgct acaaccgtgc   2100
cagtgactat ttctgcaagt gccccgagga ctatgagggc aagaactgct cacacctgaa   2160
agaccactgc cgcacgaccc cctgtgaagt gattgacagc tgcacagtgg ccatggcttc   2220
caacgacaca cctgaagggg tgcggtatat ttcctccaac gtctgtgtgtc ctcacgggaa   2280
gtgcaagagt cagtcgggag gcaaattcac ctgtgactgt aacaaaggct tcacgggaac   2340
atactgccat gaaaatatta atgactgtga gagcaaccct tgtagaaacg gtggcacttg   2400
catcgatggt gtcaactcct acaagtgcat ctgtagtgac ggctgggagg gggcctactg   2460
tgaaaccaat attaatgact gcagccagaa ccccctgccac aatgggggca cgtgtcgcga   2520
cctggtcaat gacttctact gtgactgtaa aaatgggtgg aaaggaaaga cctgccactc   2580
acgtgacagt cagtgtgatg aggccacgtg caacaacggt caacctgct atgatgaggg   2640
ggatgctttt aagtgcatgt gtcctggcgg ctgggaagga acaacctgta acatagcccg   2700
aaacagtagc tgcctgccca accccctgcca taatggggc acatgtgtgg tcaacggcga   2760
gtcctttacg tgcgtctgca aggaaggctg ggaggggccc atctgtgctc agaataccaa   2820
tgactgcagc cctcatccct gttacaacag cggcacctgt gtggatggag acaactggta   2880
ccggtgcgaa tgtgcccgg gttttgctgg gcccgactgc agaataaaca tcaatgaatg   2940
ccagtcttca ccttgtgcct ttggagcgac ctgtgtggat gagatcaatg ctaccggtg   3000
tgtctgccct ccagggcaca gtggtgccaa gtgccaggaa gtttcaggga gaccttgcat   3060
caccatgggg agtgtgatac cagatggggc caaatggcat gatgactgta atacctgcca   3120
gtgcctgaat ggacggatcg cctgctcaaa ggtctggtgt ggccctcgac cttgcctgct   3180
ccacaaaggg cacagcgagt gccccagcgg gcagagctgc atcccatcc tggacgacca   3240
gtgcttcgtc caccctgca ctggtgtggg cgagtgtcgg tcttccagtc tccagccggt   3300
gaagacaaag tgcacctctg actcctatta ccaggatcac tgtgcgaaca tcacatttac   3360
ctttaacaag gagatgatgt caccaggtct tactacggag cacatttgca gtgaattgag   3420
gaatttgaat attttgaaga atgtttccgc tgaatattca atctacatcg cttgcgagcc   3480
ttcccttca gcgaacaatg aaatacatgt ggccatttct gctgaagata tacgggatga   3540
tgggaacccg atcaaggaaa tcactgacaa aataatcgat cttgttagta aacgtgatgg   3600
aaacagctcg ctgattgctg ccgttgcaga agtaagagtt cagaggcggc ctctgaagaa   3660
cagaacagat ttccttgttc ccttgctgag ctctgtctta actgtggctt ggatctgttg   3720
cttggtgacg gccttctact ggtgcctgcg gaagcggcgg aagccgggca gccacacaca   3780
ctcagcctct gaggacaaca ccaccaacaa cgtgcgggag cagctgaacc agatcaaaaa   3840
ccccattgag aaacatgggg ccaacacggt ccccatcaag gattatgaga acaagaactc   3900
caaaatgtct aaaataagga cacacaattc tgaagtagaa gaggacgaca tggacaaaca   3960
ccagcagaaa gcccggtttg ccaagcagcc ggcgtacacg ctggtagaca gagaagagaa   4020
gccccccaac ggcacgccga caaaacaccc aaactggaca aacaaacagg acaacagaga   4080
cttggaaagt gcccagatct aaaaccgaat ggagtacatc gtatagcaca ccgcgggcac   4140
tgccgccgct aggtagagtc tgagggcttg tagttcttta aactgtcgtg tcatactcga   4200
gtctgaggcc gttgctgact tagaatccct gtgttaattt aagttttgac aagctggctt   4260
acactggcaa tggtagtttc tgtggttggc tgggaaatcg agtgccgcat ctcacagcta   4320
tgcaaaaagc tagtcaacag taccctggtt gtgtgtcccc ttgcagccga cacggtctcg   4380
gatcaggctc ccaggagcct gcccagcccc ctggtcttta agctcccact tctgccagat   4440
gtcctaatgg tgatgcagtc ttagatcata gttttatttta tatttattga ctcttgagtt   4500
gttttttgtat attggttttta tgatgacgta caagtagttc tgtatttgaa agtgcctttg   4560
cagctcagaa ccacagcaac gatcacaaat gactttatta tttattttt ttaattgtat   4620
ttttgttgtt ggggaggggg agactttgat gtcagcagtt gctggtaaaa tgaagaattt   4680
aaagaaaaaa atgtcaaaag tagaactttg tatagttatg taaataattc tttttattta   4740
atcactgtgt atatttgatt tattaactta ataatcaaga gccttaaaac atcattcctt   4800
tttatttata tgtatgtgtt tagaattgaa ggtttttgat agcattgtaa gcgtatggct   4860
ttattttttt gaactcttct cattacttgt tgcctataag ccaaaattaa ggtgtttgaa   4920
aatagttat tttaaaacaa taggatgggc ttctgtgccc agaatactga tggaattttt   4980
ttgtacgacg tcagatgttt aaaacacctt ctatagcatc acttaaaaca cgttttaagg   5040
```

```
actgactgag gcagtttgag gattagttta gaacaggttt tttttgtttgt ttgtttttttg   5100
tttttctgct ttagacttga aaagagacag gcaggtgatc tgctgcagag cagtaaggga   5160
acaagttgag ctatgactta acatagccaa aatgtgagtg gttgaatatg attaaaaata   5220
tcaaattaat tgtgtgaact tggaagcaca ccaatcttac tttgtaaatt ctgatttctt   5280
ttcaccattc gtacataata ctgaaccact tgtagatttg atttttttttt ttaatctact   5340
gcatttaggg agtattctaa taagctagtt gaatacttga accataaaat gtccagtaag   5400
atcactgttt agatttgcca tagagtacac tgcctgcctt aagtgaggaa atcaaagtgc   5460
tattacgaag ttcaagatca aaaaggctta taaaacagag taatcttgtt ggttcaccat   5520
tgagaccgtg aagatacttt gtattgtcct attagtgtta tatgaacata caaatgcatc   5580
tttgatgtgt tgttcttggc aataaatttt gaaaagtaat atttattaaa tttttttgta   5640
tgaaaacatg gaacagtgtg gcctcttctg agcttacgta gttctaccgg ctttgccatg   5700
tgcttctgcc accctgctga gtctgttctg gtaatcgggg tataataggc tctgcctgac   5760
agagggatgg aggaagaact gaaaggcttt tcaaccacaa aactcatctg gagttctcaa   5820
agacctgggg ctgctgtgaa gctggaactg cgggagcccc atctagggga gccttgattc   5880
ccttgttatt caacagcaag tgtgaatact gcttgaataa acaccactgg attaatggcc   5940
```

```
SEQ ID NO: 2              moltype = DNA  length = 2034
FEATURE                   Location/Qualifiers
source                    1..2034
                          mol_type = other DNA
                          organism = Homo sapiens
SEQUENCE: 2
atgttgttcc ctccgcgctg gacgggagca gctggagcgg gagcctggct gcgctaccgc   60
ggctgcctcc tgctgtgcag gtccccgacc ctctctctgt cctcattgcg cccagacggg   120
ccggcccaga gctcccgggt cgtctttcgt gtggccgcga gacactcttg cactcctgta   180
atgagcctgg cactgtgatg aaacactttt cccgtgtcgt ttgagtgcat cttctcaaca   240
accctaggag ggttcttgaa gcttttgaga ttaacaatgg caggaaaatc atcacttttt   300
aaagtaattc tccttggaga tggtggagtt gggaagagtt cacttatgaa cagatatgta   360
actaataagt ttgatacccca gctcttccat acaataggtg tggaattttt aaataaagat   420
ttggaagtgg atggacattt tgttaccatg cagatttggg acacggcagg tcaggagcga   480
ttccgaagcc tgaggacacc attttacaga ggtctgact gctgcctgct tactttttagt   540
gtcgatgatt cacaaagctt ccagaactta agtaactgga agaaagaatt catatattat   600
gcagatgtga aagagcctga gagctttcct tttgtgattc tgggtaacaa gattgacata   660
agcgaacggc aggtgtctac agaagaagcc caagcttggt gcagggacaa cggcgactat   720
ccttatttttg aaacaagtgc aaaagatgcc acaaatgtgg cagcagcctt tgaggaagcg   780
gttcgaagag ttcttgctac cgaggatagg tcagatcatt tgattcagac agacacagtc   840
aatcttcacc gaaagcccaa gcctagctca tcttgctgtt gattgttaga ttgttgatgc   900
attctaacca actcacacat atacacaaaa tcaacatggg gatggagaag agaattagcg   960
tttgcagcag tgtatcatct actaataaaa ttaaactaat gttgctgctt cattagttg   1020
tgggagaagg gacacatcca ctcttggagg aatatattta ctcaataatg gcaccttaca   1080
tttataaatt gtaacagttg tctaataacg tttcttttaat ttaaatatgt aagttgcaga   1140
gctaataaat gaaatgacca agactttaat tataataaaa ataagaaact tgactattct   1200
agaagttata cttggatttt ttcctgggaa aatggagaac tactttttat atgtgtatgt   1260
ttttatgcaa ttagcattgt attcttggtt cagggaaata ctttcctaaa gcaataatgt   1320
tagatattaa agattaaaat ctaatgtatt tgcaatgcat tgttaattta cttcttcatt   1380
ctcttcaaaa tgatttaacc attcctgttt tcattctaca tactagaatt actctcacta   1440
gtaattactc atcatttgtg tgccattcat gcacccccac ccccataaat catgttccac   1500
agtctcaggc ggagggtggg cccccagtgg tacaagagtg gcttcataca gtctgtaata   1560
catccagcta aattcaagtt gtctatgaat ggaaagcctt tccatagata gagttcagtt   1620
ttaagaaaaa ggctaactac tgaacttgga gaacagacaa atgtgcattt gataactgat   1680
gtaataatta caatgtactg tgtggaagat acaaaattac aattcgatta atggactaaa   1740
tatttttgtt actttcttga cccttgggga aagtttctta attgaagtta aaacattcct   1800
ttataacaca agacacaagc tgactttatc actctcagaa gaaatactaa gaaggattgt   1860
actttgtgag agggtaaacg aagacatctt tattcggcaa tgtatttact tagtgtcttc   1920
tctattactg aacatttagt gatttgctct caaggagatt ttttgttaga aaaagacttg   1980
ttgcagtgat cagacttgat aaagcaaatt gtggtctttt gtggatgaag ttca         2034
```

```
SEQ ID NO: 3              moltype = DNA  length = 5289
FEATURE                   Location/Qualifiers
source                    1..5289
                          mol_type = other DNA
                          organism = Homo sapiens
SEQUENCE: 3
ggtgttgagc gccggcggct cgcgcccacg ctgggccggg agtcgaaatg cttcccggtg   60
ccgggagtga gcgatgagct ggcttctgtt cctggcccac agagtcgcct tggccgcctt   120
gccctgccgc cgcggctctc gcgggttcgg gatgttctat gccgtgagga ggggccgcaa   180
gaccggggtc tttctgacct ggaatgagtg cagagcacag gtggaccggt ttcctgctgc   240
cagatttaag aagtttgcca cagaggatga ggcctgggcc tttgtcagga aatctgcaag   300
cccggaagtt tcagaagggc atgaaaatca acatgacaaa gaatcggagg cgaaagccag   360
caagcgactc cgtgagccac tggatgggaga tggacatgaa agcgcagagc cgtatgcaaa   420
gcacatgaag ccgagcgtgg agccggcgcc tccagttagc agagacacgt tttcctacat   480
gggagacttc gtcgtcgtct acactgatgg ctgctgctcc agtaatgggc gtagaaggc   540
gcgagcagga atcggcgttt actggggggcc aggccatcct ttaaatgtag gcattagact   600
tcctgggcgg cagacaaacc aaagagcgga aattcatgca gcctgcaaag ccattgaaca   660
agcaaagact caaaacatca ataaactggt tctgtataca gacagtatgt ttacgataaa   720
tggtataact aactgggttc aaggttggaa gaaaaatggg tggaagacaa gtgcaggaa   780
agaggtgatc aacaaagagg actttgtggc actggagagg cttacccagg ggatggacat   840
tcagtggatg catgttcctg gtcattcggg atttataggc aatgaagaag ctgacagatt   900
agccagagaa ggagctaaac aatcggaaga ctgagccatg tgacttagt ccttgggaga   960
```

-continued

```
acttgagcca gcggctgtct tgctgcctgt acttactggt gtggaaaata gcctgcaggt   1020
aggaccattg cagtgatggg cagatgcgtc tttcacacgg aatcaggcac agtggccttc   1080
tgtgacatgt gtttataaaa aatggttaag tatataataa attgaacatc tttgagattg   1140
gagaattatg tgagatttcc acattatgtt tactgggttc aatactgtcc ttgcttgttt   1200
tattgcaggc aagcaaggca aatggcctaa aatgctgtgt cttatatttt gataagaaat   1260
caaaaaacca ttggttaaaa gatgcaactc agaagtctgg aagtattctg aaagcatcca   1320
tttaccgtcc agttgacagg tttgagtctc ctgcttgtat aggtgacttg tgcccatggg   1380
tacattaaag gaacatgctg cccagggcct gggcggacag ctcagtgggc aggatgtgtg   1440
ctgggtctca gccccatgtg cctgcttgct gggcagttag tatagggcaa agcctgcctg   1500
cggcgaccct ggctgctagg ccattctcta ggaacagctg cgactcataa agaccaagaa   1560
gcataaataa actttcaaaa atttatttgg ctctttcgtt aaaaactgtg caaattaaaa   1620
aaaaaaaaaa aaaagtaaga caccggctgg gcacagtggc tcacttctgt aatcctagca   1680
ctttgggagg ccaaggcggg cagatcactt gaggtcagga gtttgagacc agcttggcca   1740
acatgacgaa accctgtctc tactaaaatt acaaaaatta tccaggtgtg gtggcacggg   1800
cttgtagtcc cagctacttg ggaggctgag gcacaagaat cacttgaacc caggcggcag   1860
aggttgcagt gagccaagat tgcaccactg cactccatcc tgggcaacag agtgagactc   1920
tgtctcaaaa aaaaaaaaa gtagtaaaag tttgacatga ttatttattt agttttaaac   1980
cttttatta taaaaacata caggaagtga cacaaaacaa atgtatagct tattgaatga   2040
ttatgattgt aaggtgaata acctttgtgt ccaccacctg gtgaagaaat agtactttgc   2100
cagatacccc aggaggctct cccaagtgcc cctccagcca cagccctctt cttctccccc   2160
tccttgcccc aacaagtaat cctgactttt acagaaatga ctttcttggt tttttgatgg   2220
cagtttagtc ttgtctgctt ttttttgttt attttttat ctacttcagt gtccatttgc   2280
agtcccgtcg gcctcactgt tttccctgcc gtttatctgt tgaagagcct gggctgtttg   2340
tcccatggct tcccacagtg tagattttgc tgaccacgtg gtcatggtgt agttcagcat   2400
ggtcctctat gtttcctgca cattggcagc tgggtccaga ggcttgatga gcctcaaatt   2460
tgatcccttt ggcaggagaa caggcggtta ggagctttcc tcaggaaagt accatgttga   2520
cggcagctga tgctcagtgc caagatccat taattatttg gggttgcaaa atggtggtat   2580
tctcattctg tcgttttgct tgcctttatt agctggaatg gttttctaag aaagtgtttt   2640
cttttttata cttatctggt tacccagtgg tacagttcat ataggaaggg caggatataaat   2700
gcttgattct ttgctcttgt acactaagtt tttaagataa tgcattagtt gtctgtcaaga   2760
gaaggtgagt ggtgaagggt ttttacatat atacaagaat tcatgggctg ggcatggtgt   2820
cttatgcctg taatcccagc actttgggag gctgaggctg gaggatcaca tgaacccagg   2880
agtttgagac tagtctgggc aacatagtga caccctgtct ctacagaaaa ttaaaataaa   2940
atcaggtggg tgtggtagtg cctgcctgtt gtcccagcta ttctggaggc tgagatggga   3000
ggatcgcttg ggcccaggag gtcgaggatg cgtgagctgt gaccatgcca ccacattcca   3060
gcctgggcga cagcaagtcc ttgtcttaaa aaaaaaaaag aatttgtgga gttaagcata   3120
cttggtgggt ttcaatccgt tgtgattttt atctttattt agctcagact agcttattcg   3180
gtcagtgaga gggagcctct tcagcttggc tcttgctttc ttttgataag tgtgcacatg   3240
tgtgcataca tgtgtgcaca gaccacacgc acagtcattg atagctccct gcagcctggc   3300
atgtcaagat gctctaggcc caatttatg agcttctgct ccaaacctgt cttaaaagaa   3360
aaactttaga caagttagca gtttaattga gcagaaaata gtttcttcag ctgggtagca   3420
ctcaggacca aaagtggttc agaacgttct cctgtgcgtt gtgtgcaggc tgtatttatt   3480
tatagccaca ggaagggaaa gacacatgta catggccaga ctgactgcag gtcagcctcc   3540
acctcacata ggcatgtttt gggagccttc agcatgtgat tggtgagact ctgctgcttg   3600
ttacagaagt gtactctcaa gtcaggtccc agtttgctta tacattaagt gaggttataa   3660
gtcactatgt acagaggcag ttttaggcca aacttaattc cgtttaacac ttggaatcca   3720
ttatttttcc cagagtctct ggtagagatg gtatttcaga tccagtttag gatgctcatt   3780
gctattgcgt tggtcattat ttctagattt ttggacggag cttttaaaaaa atacaaacat   3840
tgcacacaca tatttaaagg aagaatattt tctgagccta tattgatatt cccaatacaa   3900
attcagggtc ctggggcctt tacatagcct cctctatatg atgtctgtgt ctcctgcact   3960
cggaatcctg cttctcaaga cacaggacaa tggcatggaa tatccatccc ttaatcactc   4020
acttgtttta ttcctctta gcatttagca tttaaaaaaa atactaatac catagcatta   4080
attgtgatga tgaaaacagc actgtgtcta cgttgtcaga aaaattgctc cttttttacca   4140
ccattgactc atttctgtgt gttcaggtct cataaccagt ctatagtcag tgtcatcttg   4200
gggacagtat tccttgagtt tctgatgttg aattcagttt tgctggatac gaaattcttg   4260
gcccagattt tctttgagta tcttgtttta ttctgttttc ttccagcata aagtgatgca   4320
tgaaaagcct gatgaatctt gttttcttcc cctgacagtc atatgctgtt tttccttaga   4380
tgcccaaagg attttttcct ttttctgtca agtcggccgt tttattcgaa tgtgtcatgt   4440
gttggtattg gttgtcctgg tccatatttg caagcgtatg gtgtgctctt tctatgtgta   4500
cttcatatct gttattttaa gaagatttgc ttgaactgga gtttagtgtt acatttttct   4560
tgctttggct tttttctgtg gggatccctg ttatctgtat gttgaaatct aaattggctg   4620
ttctcagtgt ttgccactgt ctcttgaatc tcttttatct ctttctttgt ttctttttga   4680
gttttaaaag ttgttattgt accacttttg ttttgttttg ttatttaaaa taggaacagt   4740
gtctcactgt gttgcccagg ctggtcttaa actcctggcc tcaagcgatc ctccttcctt   4800
ggcctcccaa agtgctggga ttacaggtgt gagccaccaa agccggcccc accttgcttt   4860
ttaaaacagc tctgttgagg tgtaactgac aggtaatgaa ctgcacatac gtgaagtgac   4920
cgatgcattt gcctgtgaag ctgtcgccag aacatgtcca tcaccaccaa cagcagtttc   4980
acaccccggt ctaaaccgtc cctcgtgtcc tccatgttca ggcaaccact ggtctgctcc   5040
ctctcactaa aggttaattt atatattcta gaattttatc tgagtggaat cgcagagcaa   5100
gtactgtggg gggaggtgct tctactcagc ataattattt tggcattcac ccattttgtg   5160
tacatcaata atccacattt tgtattgcat ggatatacca cagtttattt atttacctgt   5220
tgaccgatat ttcgattatt tccaatttct aaataaaaat aaagcaaata aagctgccgt   5280
gaacattta                                                           5289

SEQ ID NO: 4          moltype = DNA   length = 1505
FEATURE               Location/Qualifiers
source                1..1505
                      mol_type = other DNA
                      organism = Homo sapiens
```

```
SEQUENCE: 4
aagtgacgcg aggctctgcg gagaccagga gtcagactgt aggacgacct cgggtcccac   60
gtgtccccgg tactcgccgg ccggagcccc cggcttcccg gggccggggg accttagcgg  120
cacccacaca cagcctactt tccaagcgga gccatgtctg gtaacggcaa tgcggctgca  180
acggcggaag aaaacagccc aaagatgaga gtgattcgcg tgggtacccg caagagccag  240
cttgctcgca tacagacgga cagtgtggtg gcaacattga aagcctcgta ccctggcctg  300
cagtttgaaa tcattgctat gtccaccaca ggggacaaga ttcttgatac tgcactctct  360
aagattggag agaaaagcct gtttaccaag gagcttgaac atgccctgga gaagaatgaa  420
gtggacctgg ttgttcactc cttgaaggac ctgcccactg tgcttcctcc tggcttcacc  480
atcggagcca tctgcaagcg ggaaaaccct catgatgctg ttgtctttca cccaaaattt  540
gttgggaaga ccctagaaac cctgccagag aagagtgtgg tgggaaccag ctccctgcga  600
agagcagccc agctgcagag aaagttcccg catctggagt tcaggagtat tcggggaaac  660
ctcaacaccc ggcttcggaa gctggacgag cagcaggagt tcagtgccat catcctggca  720
acagctggcc tgcagcgcat gggctggcac aaccgggtgg ggcagatcct gcaccctgag  780
gaatgcatgt atgctgtggg ccaggggggc ttgggcgtgg aagtgcgagc caaggaccag  840
gacatcttgg atctggtggg tgtgctgcac gatcccgaga ctctgcttcg ctgcatcgct  900
gaaagggcct tcctgaggca cctggaagga ggctgcagtg tgccagtagc cgtgcataca  960
gctatgaagg atgggcaact gtacctgact ggaggagtct ggagtctaga cgagctcagat 1020
agcatacaag agaccatgca ggctaccatc catgtccctg cccagcatga agatggccct 1080
gaggatgacc cacagttggt aggcatcact gctcgtaaca ttccacgagg gccccagttg 1140
gctgcccaga acttgggcat cagcctggcc aacttgttgc tgagcaaagg agccaaaaac 1200
atcctggatg ttgcacggca gcttaacgat gcccattaac tggtttgttgg ggcacagatg 1260
cctgggttgc tgctgtccag tgcctacatc ccgggcctca gtgccccatt ctcactgcta 1320
tctgggagt  gattacccecg ggagactgaa ctgcagggtt caagccttcc agggatttgc 1380
ctcaccttgg ggccttgatg actgccttgc ctcctcagta tgtgggggct tcatctcttt 1440
agagaagtcc aagcaacagc ctttgaatgt aaccaatcct actaataaac cagttctgaa 1500
ggtgt                                                               1505

SEQ ID NO: 5            moltype = DNA  length = 1347
FEATURE                 Location/Qualifiers
source                  1..1347
                        mol_type = other DNA
                        organism = Homo sapiens
SEQUENCE: 5
acagatgagg ttgaggttgg cccacggcca ggtgagaggc ttccaaggca ggatacttgt   60
gtctcagatg cggtcgcttc tttcatacag caattgccgc cttgctgagg atcaaggaac  120
ctcagtgtca gatcacgccc tccccccaaa cttagaaatt cagatggggc gcagaaattt  180
ctcttgttct gcgtgatctg catagatggt ccaagaggtg gttttccag gagcccagca  240
ccctcctcc  ctccgactca gacccaggag tctggccctc cattgaaagg accccaggtt  300
acatcatcca ttcaggctgc ccttgccacg atggaattct gtagctcctg ccaaatgggt  360
caaatatcat ggttcaggcg cagggaaggt gattgggcgg gcctgtctgg gtataaattc  420
tggagcttct gcatctatcc caaaaaacaa gggtgttctg tcagctgagg atccagccga  480
aagaggagcc aggcactcag gccacctgag tctactcacc tggacaactg gaatctggca  540
ccaattctaa accactcagc ttctccgagc tcacaccccg gagatcacct gaggacccga  600
gccattgatg gactcggacg agaccgggtt cgagcactca ggactgtggg tttctgtgct  660
ggctggtctt ctgctgggag cctgccaggc acacccatc cctgactcca gtcctctcct  720
gcaattcggg ggccaagtcc ggcagcggta cctctacaca gatgatgccc agcagacaga  780
agcccacctg gagatcaggg aggatgggac ggtggggggc gctgctgacc agagccccga  840
aagtctcctg cagctgaaag ccttgaagcc gggagttatt caaatcttgg gagtcaagac  900
atccaggttc ctgtgccagc ggccagatgg ggccctgtat ggatcgctcc actttgaccc  960
tgaggcctgg agcttccggg agctgcttct tgaggacgga tacaatgttt accagtccga 1020
agcccacggc ctcccgctgc acctgccagg gaacaagtcc ccacaccggg accctgcacc 1080
ccgaggacca gctcgcttcc tgccactacc aggcctgccc cccgcactcc cggagccacc 1140
cggaatcctg gccccccagc cccccgatgt gggctcctcg gacctctga gcatggtggg 1200
accttcccag ggccgaagcc ccagctacgc ttcctgaagc cagaggctgt ttactatgac 1260
atctcctctt tatttattag gttatttatc ttatttattt ttttatttt cttacttgag 1320
ataataaaga gttccagagg aggataa                                     1347

SEQ ID NO: 6            moltype = DNA  length = 1611
FEATURE                 Location/Qualifiers
source                  1..1611
                        mol_type = other DNA
                        organism = Mus musculus
SEQUENCE: 6
gaggaaggca ccgccccgtt gagggagggc agcggacgtg acgcagagct cagcaggtcc   60
tgcagccgga gtgaagtgcg ggctcgggcc ccatgtgcct tcagtcccgg ccggcccagg  120
tcgccggctt ctgcagacac caggggaccg cagcggcact gccgcgcctg cgccctgggc  180
ggagtcatgt ccggtaacgg cggcgcggcc acaaccgcgg aagaaacagg ctcaaagatg  240
agggtgattc gagtgggcac ccgtaagagc cagctgtgcc gcatacagac cgacactgtg  300
gtggcgatgc tgaaagcctt gtaccctggc atacagtttg aaatcattgc tatgtccacc  360
acgggagaca agattcttga tactgcactc tctaagattg gagagaagag cctgtttacc  420
aaggagctag aaaacgccct ggaaaaaaac gaagtggacc tggtcgttca ctccctgaag  480
gatgtgccta ccatactacc tcctggcttt actattggag ccatctgcaa acgggaaaac  540
ccttgtgatg ctgttgtctt tcacccaaag tttattggaa agaccctgga aaccttgcca  600
gagaaaagtc ccgtgggaac cagctctctg aggagagtgg ctcagctaca gagaaagttc  660
ccccacctgg aattcaagag tattcgggga aacctcaaca cccgcctccg gaagctggat  720
gagctgcagg aattcagtgc catcgtcctg gctgtggctg gctacagcg catgggctgg  780
cagaaccggg tgggccagat tttgcaccca gaagaatgca tgtatgctgt gggtcaggga  840
gccctagccg tggaagtccg agccaaggac caggatatct tggacctagt gagtgtgttg  900
```

```
cacgatcctg aaactctgct tcgctgcatt gctgaaaggg cttttctgag gcacctggaa    960
ggaggctgca gcgtgcccgt agcagtgcat acagtgatga aagatgggca actgtacctg   1020
actggtggag tctggagtct agatggctca gatagcatgc aagagactat gcaggccacc   1080
atccaggtcc ctgttcagca agaagatggt ccagaagatg acccacaact ggttggaatc   1140
actgcccgta acattccaag aggagcccag ctagctgctg agaacctggg catcagcctg   1200
gccagcttgc tgctcaacaa aggagccaag aacatcctgg atgttgcacg gcagcttaat   1260
gatgtgcgct aactggtctg tagggcacag gaaccctggc tgccactcca ctgcctactt   1320
ctggcttcca agtgccctgt gctccatccc tagggatgtg attatcccag gaaattgaac   1380
cacggggttg ttgagacttc cactttggaa gatatgcctc accttggggc ctccatatct   1440
gcctttccct cagtagttgg gggcttcatc tcttttagaga aagtccatgc caatcttttga   1500
atgtaaccaa taccactaat aaaccagttt agaatgtggt tcttctgata gagttgggga   1560
agatatgaat aaacccaaag ccctttttaaa cttgaaaaaa aaaaaaaaaaa a          1611
```

```
SEQ ID NO: 7              moltype = DNA   length = 947
FEATURE                   Location/Qualifiers
source                    1..947
                          mol_type = other DNA
                          organism = Mus musculus
SEQUENCE: 7
agacagcctt agtgtcttct cagctgggga ttcaacacag gagaaacagc cattcacttt     60
gcctgagccc cagtctgaac ctgacccatc cctgctgggc accggagtca gaacacaatt    120
ccagctgcct tggctcctca gccgctcgct tgccagggcg tctcccgaac ggagcgcagc    180
cctgatggaa tggatgagat ctagagttgg gaccctggga ctgtgggtcc gactgctgct    240
ggctgtcttc ctgctggggg tctaccaagc ataccccatc cctgactcca gcccctcct    300
ccagtttggg ggtcaagtcc ggcagaggta cctctacaca gatgacgacc aagacactga    360
agcccacctg gagatcaggg aggatggaac agtggtaggc gcagcacacc gcagtccaga    420
aagtctcctg gagctcaaag ccttgaagcc aggggtcatt caaatcctgg gtgtcaaagc    480
ctctaggttt ctttgccaac agccagatgg agctctctat ggatcgcctc actttgatcc    540
tgaggcctgc agcttcagag aactgctgct ggaggacggt tacaatgtgt accagtctga    600
agcccatggc ctgcccctgc gtctgcctca gaaggactcc ccaaaccagg atgcaacatc    660
ctggggacct gtgcgcttcc tgcccatgcc aggcctgctc cacgagcccc aagaccaagc    720
aggattcctg cccccagagc ccccagatgt gggctcctct gacccctga gcatggtaga    780
gcctttacag ggccgaagcc ccagctatgc gtcctgactc ttcctgaatc tagggctgtt    840
tcttttttggg tttccactta tttattacgg gtatttatct tatttattta ttttagtttt    900
ttttttcttac ttggaataat aaagagtctg aaagaaaaat gtgtgtt               947
```

```
SEQ ID NO: 8              moltype =   length =
SEQUENCE: 8
000
```

```
SEQ ID NO: 9              moltype =   length =
SEQUENCE: 9
000
```

```
SEQ ID NO: 10             moltype =   length =
SEQUENCE: 10
000
```

```
SEQ ID NO: 11             moltype = RNA   length = 10
FEATURE                   Location/Qualifiers
source                    1..10
                          mol_type = other RNA
                          organism = synthetic construct
SEQUENCE: 11
ggactggact                                                            10
```

```
SEQ ID NO: 12             moltype = RNA   length = 13
FEATURE                   Location/Qualifiers
source                    1..13
                          mol_type = other RNA
                          organism = synthetic construct
SEQUENCE: 12
acggacttgg act                                                        13
```

```
SEQ ID NO: 13             moltype = RNA   length = 10
FEATURE                   Location/Qualifiers
source                    1..10
                          mol_type = other RNA
                          organism = synthetic construct
SEQUENCE: 13
aaactaaact                                                            10
```

```
SEQ ID NO: 14             moltype =   length =
SEQUENCE: 14
000
```

```
SEQ ID NO: 15             moltype = RNA   length = 10
FEATURE                   Location/Qualifiers
source                    1..10
```

-continued

```
                         mol_type = other RNA
                         organism = synthetic construct
SEQUENCE: 15
aaaaaaaaaa                                                              10

SEQ ID NO: 16           moltype = RNA  length = 17
FEATURE                 Location/Qualifiers
source                  1..17
                        mol_type = other RNA
                        organism = synthetic construct
modified_base           1
                        mod_base = OTHER
                        note = 2'-O-methyl adenosine
modified_base           2
                        mod_base = OTHER
                        note = 2'-O-methyl adenosine
modified_base           3
                        mod_base = OTHER
                        note = 2'-O-methyl cytidine
modified_base           4
                        mod_base = OTHER
                        note = 2'-O-methyl cytidine
modified_base           5
                        mod_base = OTHER
                        note = 2'-O-methyl adenosine
modified_base           6
                        mod_base = OTHER
                        note = 2'-O-methyl cytidine
modified_base           7
                        mod_base = OTHER
                        note = 2'-O-methyl adenosine
modified_base           8
                        mod_base = OTHER
                        note = 2'-O-methyl guanosine
modified_base           9
                        mod_base = OTHER
                        note = 2'-O-methyl adenosine
modified_base           10
                        mod_base = OTHER
                        note = 2'-O-methyl adenosine
modified_base           11
                        mod_base = OTHER
                        note = 2'-O-methyl adenosine
modified_base           12
                        mod_base = OTHER
                        note = 2'-O-methyl cytidine
modified_base           13
                        mod_base = OTHER
                        note = 2'-O-methyl uridine
modified_base           14
                        mod_base = OTHER
                        note = 2'-O-methyl adenosine
modified_base           15
                        mod_base = OTHER
                        note = 2'-O-methyl cytidine
modified_base           16
                        mod_base = OTHER
                        note = 2'-O-methyl cytidine
modified_base           17
                        mod_base = OTHER
                        note = 2'-O-methyl adenosine
SEQUENCE: 16
aaccacagaa actacca                                                     17

SEQ ID NO: 17           moltype = RNA  length = 22
FEATURE                 Location/Qualifiers
source                  1..22
                        mol_type = other RNA
                        organism = synthetic construct
modified_base           1
                        mod_base = OTHER
                        note = 2'-O-methyl guanosine
modified_base           2
                        mod_base = OTHER
                        note = 2'-O-methyl guanosine
modified_base           3
                        mod_base = OTHER
                        note = 2'-O-methyl adenosine
modified_base           4
```

```
                         mod_base = OTHER
                         note = 2'-O-methyl cytidine
modified_base            5
                         mod_base = OTHER
                         note = 2'-O-methyl uridine
modified_base            6
                         mod_base = OTHER
                         note = 2'-O-methyl adenosine
modified_base            7
                         mod_base = OTHER
                         note = 2'-O-methyl adenosine
modified_base            8
                         mod_base = OTHER
                         note = 2'-O-methyl cytidine
modified_base            9
                         mod_base = OTHER
                         note = 2'-O-methyl cytidine
modified_base            10
                         mod_base = OTHER
                         note = 2'-O-methyl adenosine
modified_base            11
                         mod_base = OTHER
                         note = 2'-O-methyl cytidine
modified_base            12
                         mod_base = OTHER
                         note = 2'-O-methyl adenosine
modified_base            13
                         mod_base = OTHER
                         note = 2'-O-methyl guanosine
modified_base            14
                         mod_base = OTHER
                         note = 2'-O-methyl adenosine
modified_base            15
                         mod_base = OTHER
                         note = 2'-O-methyl adenosine
modified_base            16
                         mod_base = OTHER
                         note = 2'-O-methyl adenosine
modified_base            17
                         mod_base = OTHER
                         note = 2'-O-methyl cytidine
modified_base            18
                         mod_base = OTHER
                         note = 2'-O-methyl uridine
modified_base            19
                         mod_base = OTHER
                         note = 2'-O-methyl adenosine
modified_base            20
                         mod_base = OTHER
                         note = 2'-O-methyl cytidine
modified_base            21
                         mod_base = OTHER
                         note = 2'-O-methyl cytidine
modified_base            22
                         mod_base = OTHER
                         note = 2'-O-methyl adenosine
SEQUENCE: 17
ggactaacca cagaaactac ca                                        22

SEQ ID NO: 18          moltype = RNA   length = 26
FEATURE                Location/Qualifiers
source                 1..26
                       mol_type = other RNA
                       organism = synthetic construct
modified_base          1
                       mod_base = OTHER
                       note = 2'-O-methyl guanosine
modified_base          2
                       mod_base = OTHER
                       note = 2'-O-methyl guanosine
modified_base          3
                       mod_base = OTHER
                       note = 2'-O-methyl adenosine
modified_base          4
                       mod_base = OTHER
                       note = 2'-O-methyl cytidine
modified_base          5
                       mod_base = OTHER
                       note = 2'-O-methyl uridine
```

-continued

```
modified_base         6
                      mod_base = OTHER
                      note = 2'-O-methyl guanosine
modified_base         7
                      mod_base = OTHER
                      note = 2'-O-methyl guanosine
modified_base         8
                      mod_base = OTHER
                      note = 2'-O-methyl adenosine
modified_base         9
                      mod_base = OTHER
                      note = 2'-O-methyl cytidine
modified_base         10
                      mod_base = OTHER
                      note = 2'-O-methyl adenosine
modified_base         11
                      mod_base = OTHER
                      note = 2'-O-methyl adenosine
modified_base         12
                      mod_base = OTHER
                      note = 2'-O-methyl cytidine
modified_base         13
                      mod_base = OTHER
                      note = 2'-O-methyl cytidine
modified_base         14
                      mod_base = OTHER
                      note = 2'-O-methyl adenosine
modified_base         15
                      mod_base = OTHER
                      note = 2'-O-methyl cytidine
modified_base         16
                      mod_base = OTHER
                      note = 2'-O-methyl adenosine
modified_base         17
                      mod_base = OTHER
                      note = 2'-O-methyl guanosine
modified_base         18
                      mod_base = OTHER
                      note = 2'-O-methyl adenosine
modified_base         19
                      mod_base = OTHER
                      note = 2'-O-methyl adenosine
modified_base         20
                      mod_base = OTHER
                      note = 2'-O-methyl adenosine
modified_base         21
                      mod_base = OTHER
                      note = 2'-O-methyl cytidine
modified_base         22
                      mod_base = OTHER
                      note = 2'-O-methyl uridine
modified_base         23
                      mod_base = OTHER
                      note = 2'-O-methyl adenosine
modified_base         24
                      mod_base = OTHER
                      note = 2'-O-methyl cytidine
modified_base         25
                      mod_base = OTHER
                      note = 2'-O-methyl cytidine
modified_base         26
                      mod_base = OTHER
                      note = 2'-O-methyl adenosine
SEQUENCE: 18
ggactggaca accacagaaa ctacca                                         26

SEQ ID NO: 19        moltype = RNA  length = 26
FEATURE              Location/Qualifiers
source               1..26
                     mol_type = other RNA
                     organism = synthetic construct
modified_base        1
                     mod_base = OTHER
                     note = 2'-O-methyl adenosine
modified_base        2
                     mod_base = OTHER
                     note = 2'-O-methyl adenosine
modified_base        3
                     mod_base = OTHER
```

-continued

```
                         note = 2'-O-methyl cytidine
modified_base            4
                         mod_base = OTHER
                         note = 2'-O-methyl cytidine
modified_base            5
                         mod_base = OTHER
                         note = 2'-O-methyl adenosine
modified_base            6
                         mod_base = OTHER
                         note = 2'-O-methyl cytidine
modified_base            7
                         mod_base = OTHER
                         note = 2'-O-methyl adenosine
modified_base            8
                         mod_base = OTHER
                         note = 2'-O-methyl guanosine
modified_base            9
                         mod_base = OTHER
                         note = 2'-O-methyl adenosine
modified_base            10
                         mod_base = OTHER
                         note = 2'-O-methyl adenosine
modified_base            11
                         mod_base = OTHER
                         note = 2'-O-methyl adenosine
modified_base            12
                         mod_base = OTHER
                         note = 2'-O-methyl cytidine
modified_base            13
                         mod_base = OTHER
                         note = 2'-O-methyl uridine
modified_base            14
                         mod_base = OTHER
                         note = 2'-O-methyl adenosine
modified_base            15
                         mod_base = OTHER
                         note = 2'-O-methyl cytidine
modified_base            16
                         mod_base = OTHER
                         note = 2'-O-methyl cytidine
modified_base            17
                         mod_base = OTHER
                         note = 2'-O-methyl adenosine
modified_base            18
                         mod_base = OTHER
                         note = 2'-O-methyl guanosine
modified_base            19
                         mod_base = OTHER
                         note = 2'-O-methyl guanosine
modified_base            20
                         mod_base = OTHER
                         note = 2'-O-methyl adenosine
modified_base            21
                         mod_base = OTHER
                         note = 2'-O-methyl cytidine
modified_base            22
                         mod_base = OTHER
                         note = 2'-O-methyl uridine
modified_base            23
                         mod_base = OTHER
                         note = 2'-O-methyl guanosine
modified_base            24
                         mod_base = OTHER
                         note = 2'-O-methyl guanosine
modified_base            25
                         mod_base = OTHER
                         note = 2'-O-methyl adenosine
modified_base            26
                         mod_base = OTHER
                         note = 2'-O-methyl cytidine
SEQUENCE: 19
aaccacagaa actaccagga ctggac                                26

SEQ ID NO: 20         moltype = RNA  length = 29
FEATURE               Location/Qualifiers
source                1..29
                      mol_type = other RNA
                      organism = synthetic construct
modified_base         1
```

-continued

```
                    mod_base = OTHER
                    note = 2'-O-methyl guanosine
modified_base       2
                    mod_base = OTHER
                    note = 2'-O-methyl guanosine
modified_base       3
                    mod_base = OTHER
                    note = 2'-O-methyl adenosine
modified_base       4
                    mod_base = OTHER
                    note = 2'-O-methyl cytidine
modified_base       5
                    mod_base = OTHER
                    note = 2'-O-methyl uridine
modified_base       6
                    mod_base = OTHER
                    note = 2'-O-methyl guanosine
modified_base       7
                    mod_base = OTHER
                    note = 2'-O-methyl guanosine
modified_base       8
                    mod_base = OTHER
                    note = 2'-O-methyl adenosine
modified_base       9
                    mod_base = OTHER
                    note = 2'-O-methyl cytidine
modified_base       10
                    mod_base = OTHER
                    note = 2'-O-methyl uridine
modified_base       11
                    mod_base = OTHER
                    note = 2'-O-methyl guanosine
modified_base       12
                    mod_base = OTHER
                    note = 2'-O-methyl uridine
modified_base       13
                    mod_base = OTHER
                    note = 2'-O-methyl uridine
modified_base       14
                    mod_base = OTHER
                    note = 2'-O-methyl uridine
modified_base       15
                    mod_base = OTHER
                    note = 2'-O-methyl adenosine
modified_base       16
                    mod_base = OTHER
                    note = 2'-O-methyl adenosine
modified_base       17
                    mod_base = OTHER
                    note = 2'-O-methyl adenosine
modified_base       18
                    mod_base = OTHER
                    note = 2'-O-methyl guanosine
modified_base       19
                    mod_base = OTHER
                    note = 2'-O-methyl adenosine
modified_base       20
                    mod_base = OTHER
                    note = 2'-O-methyl adenosine
modified_base       21
                    mod_base = OTHER
                    note = 2'-O-methyl cytidine
modified_base       22
                    mod_base = OTHER
                    note = 2'-O-methyl uridine
modified_base       23
                    mod_base = OTHER
                    note = 2'-O-methyl adenosine
modified_base       24
                    mod_base = OTHER
                    note = 2'-O-methyl cytidine
modified_base       25
                    mod_base = OTHER
                    note = 2'-O-methyl adenosine
modified_base       26
                    mod_base = OTHER
                    note = 2'-O-methyl adenosine
modified_base       27
                    mod_base = OTHER
```

-continued

```
                         note = 2'-O-methyl guanosine
modified_base            28
                         mod_base = OTHER
                         note = 2'-O-methyl cytidine
modified_base            29
                         mod_base = OTHER
                         note = 2'-O-methyl cytidine
SEQUENCE: 20
ggactggact gtttaaagaa ctacaagcc                                        29

SEQ ID NO: 21           moltype = RNA  length = 27
FEATURE                 Location/Qualifiers
source                  1..27
                        mol_type = other RNA
                        organism = synthetic construct
modified_base           1
                        mod_base = OTHER
                        note = 2'-O-methyl guanosine
modified_base           2
                        mod_base = OTHER
                        note = 2'-O-methyl guanosine
modified_base           3
                        mod_base = OTHER
                        note = 2'-O-methyl adenosine
modified_base           4
                        mod_base = OTHER
                        note = 2'-O-methyl cytidine
modified_base           5
                        mod_base = OTHER
                        note = 2'-O-methyl uridine
modified_base           6
                        mod_base = OTHER
                        note = 2'-O-methyl guanosine
modified_base           7
                        mod_base = OTHER
                        note = 2'-O-methyl guanosine
modified_base           8
                        mod_base = OTHER
                        note = 2'-O-methyl adenosine
modified_base           9
                        mod_base = OTHER
                        note = 2'-O-methyl cytidine
modified_base           10
                        mod_base = OTHER
                        note = 2'-O-methyl uridine
modified_base           11
                        mod_base = OTHER
                        note = 2'-O-methyl guanosine
modified_base           12
                        mod_base = OTHER
                        note = 2'-O-methyl guanosine
modified_base           13
                        mod_base = OTHER
                        note = 2'-O-methyl adenosine
modified_base           14
                        mod_base = OTHER
                        note = 2'-O-methyl uridine
modified_base           15
                        mod_base = OTHER
                        note = 2'-O-methyl uridine
modified_base           16
                        mod_base = OTHER
                        note = 2'-O-methyl cytidine
modified_base           17
                        mod_base = OTHER
                        note = 2'-O-methyl uridine
modified_base           18
                        mod_base = OTHER
                        note = 2'-O-methyl adenosine
modified_base           19
                        mod_base = OTHER
                        note = 2'-O-methyl adenosine
modified_base           20
                        mod_base = OTHER
                        note = 2'-O-methyl guanosine
modified_base           21
                        mod_base = OTHER
                        note = 2'-O-methyl uridine
modified_base           22
```

```
                              mod_base = OTHER
                              note = 2'-O-methyl cytidine
modified_base                 23
                              mod_base = OTHER
                              note = 2'-O-methyl adenosine
modified_base                 24
                              mod_base = OTHER
                              note = 2'-O-methyl guanosine
modified_base                 25
                              mod_base = OTHER
                              note = 2'-O-methyl cytidine
modified_base                 26
                              mod_base = OTHER
                              note = 2'-O-methyl adenosine
modified_base                 27
                              mod_base = OTHER
                              note = 2'-O-methyl adenosine
SEQUENCE: 21
ggactggact ggattctaag tcagcaa                                               27

SEQ ID NO: 22                 moltype = RNA  length = 28
FEATURE                       Location/Qualifiers
source                        1..28
                              mol_type = other RNA
                              organism = synthetic construct
modified_base                 1
                              mod_base = OTHER
                              note = 2'-O-methyl guanosine
modified_base                 2
                              mod_base = OTHER
                              note = 2'-O-methyl guanosine
modified_base                 3
                              mod_base = OTHER
                              note = 2'-O-methyl adenosine
modified_base                 4
                              mod_base = OTHER
                              note = 2'-O-methyl cytidine
modified_base                 5
                              mod_base = OTHER
                              note = 2'-O-methyl uridine
modified_base                 6
                              mod_base = OTHER
                              note = 2'-O-methyl guanosine
modified_base                 7
                              mod_base = OTHER
                              note = 2'-O-methyl guanosine
modified_base                 8
                              mod_base = OTHER
                              note = 2'-O-methyl adenosine
modified_base                 9
                              mod_base = OTHER
                              note = 2'-O-methyl cytidine
modified_base                 10
                              mod_base = OTHER
                              note = 2'-O-methyl uridine
modified_base                 11
                              mod_base = OTHER
                              note = 2'-O-methyl uridine
modified_base                 12
                              mod_base = OTHER
                              note = 2'-O-methyl guanosine
modified_base                 13
                              mod_base = OTHER
                              note = 2'-O-methyl cytidine
modified_base                 14
                              mod_base = OTHER
                              note = 2'-O-methyl uridine
modified_base                 15
                              mod_base = OTHER
                              note = 2'-O-methyl guanosine
modified_base                 16
                              mod_base = OTHER
                              note = 2'-O-methyl uridine
modified_base                 17
                              mod_base = OTHER
                              note = 2'-O-methyl guanosine
modified_base                 18
                              mod_base = OTHER
                              note = 2'-O-methyl guanosine
```

```
modified_base      19
                   mod_base = OTHER
                   note = 2'-O-methyl uridine
modified_base      20
                   mod_base = OTHER
                   note = 2'-O-methyl uridine
modified_base      21
                   mod_base = OTHER
                   note = 2'-O-methyl cytidine
modified_base      22
                   mod_base = OTHER
                   note = 2'-O-methyl uridine
modified_base      23
                   mod_base = OTHER
                   note = 2'-O-methyl guanosine
modified_base      24
                   mod_base = OTHER
                   note = 2'-O-methyl adenosine
modified_base      25
                   mod_base = OTHER
                   note = 2'-O-methyl guanosine
modified_base      26
                   mod_base = OTHER
                   note = 2'-O-methyl cytidine
modified_base      27
                   mod_base = OTHER
                   note = 2'-O-methyl uridine
modified_base      28
                   mod_base = OTHER
                   note = 2'-O-methyl guanosine
SEQUENCE: 22
ggactggact tgctgtggtt ctgagctg                                    28

SEQ ID NO: 23      moltype = RNA  length = 28
FEATURE            Location/Qualifiers
source             1..28
                   mol_type = other RNA
                   organism = synthetic construct
modified_base      1
                   mod_base = OTHER
                   note = 2'-O-methyl guanosine
modified_base      2
                   mod_base = OTHER
                   note = 2'-O-methyl guanosine
modified_base      3
                   mod_base = OTHER
                   note = 2'-O-methyl adenosine
modified_base      4
                   mod_base = OTHER
                   note = 2'-O-methyl cytidine
modified_base      5
                   mod_base = OTHER
                   note = 2'-O-methyl uridine
modified_base      6
                   mod_base = OTHER
                   note = 2'-O-methyl guanosine
modified_base      7
                   mod_base = OTHER
                   note = 2'-O-methyl guanosine
modified_base      8
                   mod_base = OTHER
                   note = 2'-O-methyl adenosine
modified_base      9
                   mod_base = OTHER
                   note = 2'-O-methyl cytidine
modified_base      10
                   mod_base = OTHER
                   note = 2'-O-methyl uridine
modified_base      11
                   mod_base = OTHER
                   note = 2'-O-methyl cytidine
modified_base      12
                   mod_base = OTHER
                   note = 2'-O-methyl uridine
modified_base      13
                   mod_base = OTHER
                   note = 2'-O-methyl guanosine
modified_base      14
                   mod_base = OTHER
```

-continued

```
                        note = 2'-O-methyl cytidine
modified_base           15
                        mod_base = OTHER
                        note = 2'-O-methyl adenosine
modified_base           16
                        mod_base = OTHER
                        note = 2'-O-methyl guanosine
modified_base           17
                        mod_base = OTHER
                        note = 2'-O-methyl cytidine
modified_base           18
                        mod_base = OTHER
                        note = 2'-O-methyl adenosine
modified_base           19
                        mod_base = OTHER
                        note = 2'-O-methyl guanosine
modified_base           20
                        mod_base = OTHER
                        note = 2'-O-methyl adenosine
modified_base           21
                        mod_base = OTHER
                        note = 2'-O-methyl uridine
modified_base           22
                        mod_base = OTHER
                        note = 2'-O-methyl cytidine
modified_base           23
                        mod_base = OTHER
                        note = 2'-O-methyl adenosine
modified_base           24
                        mod_base = OTHER
                        note = 2'-O-methyl cytidine
modified_base           25
                        mod_base = OTHER
                        note = 2'-O-methyl cytidine
modified_base           26
                        mod_base = OTHER
                        note = 2'-O-methyl uridine
modified_base           27
                        mod_base = OTHER
                        note = 2'-O-methyl guanosine
modified_base           28
                        mod_base = OTHER
                        note = 2'-O-methyl cytidine
SEQUENCE: 23
ggactggact ctgcagcaga tcacctgc                                                     28

SEQ ID NO: 24           moltype = RNA  length = 27
FEATURE                 Location/Qualifiers
source                  1..27
                        mol_type = other RNA
                        organism = synthetic construct
modified_base           1
                        mod_base = OTHER
                        note = 2'-O-methyl guanosine
modified_base           2
                        mod_base = OTHER
                        note = 2'-O-methyl guanosine 5'-thiophosphate
modified_base           3
                        mod_base = OTHER
                        note = 2'-O-methyl adenosine 5'-thiophosphate
modified_base           4
                        mod_base = OTHER
                        note = 2'-O-methyl cytidine
modified_base           5
                        mod_base = OTHER
                        note = 2'-O-methyl uridine
modified_base           6
                        mod_base = OTHER
                        note = 2'-O-methyl guanosine
modified_base           7
                        mod_base = OTHER
                        note = 2'-O-methyl guanosine
modified_base           8
                        mod_base = OTHER
                        note = 2'-O-methyl adenosine
modified_base           9
                        mod_base = OTHER
                        note = 2'-O-methyl cytidine
modified_base           10
```

```
                        mod_base = OTHER
                        note = 2'-O-methyl uridine
modified_base           11
                        mod_base = OTHER
                        note = 2'-O-(2-methoxyethyl) adenosine
modified_base           12
                        mod_base = OTHER
                        note = 2'-O-(2-methoxyethyl) adenosine 5'-thiophosphate
modified_base           13
                        mod_base = OTHER
                        note = 2'-O-(2-methoxyethyl) 5-methyl cytidine
                         5'-thiophosphate
modified_base           14
                        mod_base = OTHER
                        note = 2'-O-(2-methoxyethyl) 5-methyl cytidine
                         5'-thiophosphate
modified_base           15
                        mod_base = OTHER
                        note = 2'-O-(2-methoxyethyl) adenosine 5'-thiophosphate
modified_base           16
                        mod_base = OTHER
                        note = 2'-O-(2-methoxyethyl) 5-methyl cytidine
                         5'-thiophosphate
modified_base           17
                        mod_base = OTHER
                        note = 2'-O-(2-methoxyethyl) adenosine 5'-thiophosphate
modified_base           18
                        mod_base = OTHER
                        note = 2'-O-(2-methoxyethyl) guanosine 5'-thiophosphate
modified_base           19
                        mod_base = OTHER
                        note = 2'-O-(2-methoxyethyl) adenosine 5'-thiophosphate
modified_base           20
                        mod_base = OTHER
                        note = 2'-O-(2-methoxyethyl) adenosine 5'-thiophosphate
modified_base           21
                        mod_base = OTHER
                        note = 2'-O-(2-methoxyethyl) adenosine 5'-thiophosphate
modified_base           22
                        mod_base = OTHER
                        note = 2'-O-(2-methoxyethyl) 5-methyl cytidine
                         5'-thiophosphate
modified_base           23
                        mod_base = OTHER
                        note = 2'-O-(2-methoxyethyl) thymidine 5'-thiophosphate
modified_base           24
                        mod_base = OTHER
                        note = 2'-O-(2-methoxyethyl) adenosine 5'-thiophosphate
modified_base           25
                        mod_base = OTHER
                        note = 2'-O-(2-methoxyethyl) 5-methyl cytidine
                         5'-thiophosphate
modified_base           26
                        mod_base = OTHER
                        note = 2'-O-(2-methoxyethyl) 5-methyl cytidine
                         5'-thiophosphate
modified_base           27
                        mod_base = OTHER
                        note = 2'-O-(2-methoxyethyl) adenosine 5'-thiophosphate
SEQUENCE: 24
ggactggact aaccacagaa actacca                                               27

SEQ ID NO: 25           moltype = RNA   length = 27
FEATURE                 Location/Qualifiers
source                  1..27
                        mol_type = other RNA
                        organism = synthetic construct
modified_base           1
                        mod_base = OTHER
                        note = 2'-O-methyl guanosine
modified_base           2
                        mod_base = OTHER
                        note = 2'-O-methyl guanosine 5'-thiophosphate
modified_base           3
                        mod_base = OTHER
                        note = 2'-O-methyl adenosine 5'-thiophosphate
modified_base           4
                        mod_base = OTHER
                        note = 2'-O-methyl cytidine
```

| | | |
|---|---|---|
| modified_base | 5 | |
| | mod_base = OTHER | |
| | note = 2'-O-methyl uridine | |
| modified_base | 6 | |
| | mod_base = OTHER | |
| | note = 2'-O-methyl guanosine | |
| modified_base | 7 | |
| | mod_base = OTHER | |
| | note = 2'-O-methyl guanosine | |
| modified_base | 8 | |
| | mod_base = OTHER | |
| | note = 2'-O-methyl adenosine | |
| modified_base | 9 | |
| | mod_base = OTHER | |
| | note = 2'-O-methyl cytidine | |
| modified_base | 10 | |
| | mod_base = OTHER | |
| | note = 2'-O-methyl uridine | |
| modified_base | 11 | |
| | mod_base = OTHER | |
| | note = 2'-O-(2-methoxyethyl) adenosine | |
| modified_base | 12 | |
| | mod_base = OTHER | |
| | note = 2'-O-(2-methoxyethyl) adenosine | |
| modified_base | 13 | |
| | mod_base = OTHER | |
| | note = 2'-O-(2-methoxyethyl) 5-methyl cytidine | |
| modified_base | 14 | |
| | mod_base = OTHER | |
| | note = 2'-O-(2-methoxyethyl) 5-methyl cytidine | |
| | 5'-thiophosphate | |
| modified_base | 15 | |
| | mod_base = OTHER | |
| | note = 2'-O-(2-methoxyethyl) adenosine 5'-thiophosphate | |
| modified_base | 16 | |
| | mod_base = OTHER | |
| | note = 2'-O-(2-methoxyethyl) 5-methyl cytidine | |
| | 5'-thiophosphate | |
| modified_base | 17 | |
| | mod_base = OTHER | |
| | note = 2'-O-(2-methoxyethyl) adenosine 5'-thiophosphate | |
| modified_base | 18 | |
| | mod_base = OTHER | |
| | note = 2'-O-(2-methoxyethyl) guanosine 5'-thiophosphate | |
| modified_base | 19 | |
| | mod_base = OTHER | |
| | note = 2'-O-(2-methoxyethyl) adenosine 5'-thiophosphate | |
| modified_base | 20 | |
| | mod_base = OTHER | |
| | note = 2'-O-(2-methoxyethyl) adenosine 5'-thiophosphate | |
| modified_base | 21 | |
| | mod_base = OTHER | |
| | note = 2'-O-(2-methoxyethyl) adenosine 5'-thiophosphate | |
| modified_base | 22 | |
| | mod_base = OTHER | |
| | note = 2'-O-(2-methoxyethyl) 5-methyl cytidine | |
| | 5'-thiophosphate | |
| modified_base | 23 | |
| | mod_base = OTHER | |
| | note = 2'-O-(2-methoxyethyl) thymidine 5'-thiophosphate | |
| modified_base | 24 | |
| | mod_base = OTHER | |
| | note = 2'-O-(2-methoxyethyl) adenosine 5'-thiophosphate | |
| modified_base | 25 | |
| | mod_base = OTHER | |
| | note = 2'-O-(2-methoxyethyl) 5-methyl cytidine | |
| | 5'-thiophosphate | |
| modified_base | 26 | |
| | mod_base = OTHER | |
| | note = 2'-O-(2-methoxyethyl) 5-methyl cytidine | |
| | 5'-thiophosphate | |
| modified_base | 27 | |
| | mod_base = OTHER | |
| | note = 2'-O-(2-methoxyethyl) adenosine 5'-thiophosphate | |

SEQUENCE: 25
ggactggact aaccacagaa actacca                                                                    27

SEQ ID NO: 26          moltype = RNA   length = 29
FEATURE                Location/Qualifiers -continued

```
source            1..29
                  mol_type = other RNA
                  organism = synthetic construct
modified_base     1
                  mod_base = OTHER
                  note = 2'-O-methyl adenosine
modified_base     2
                  mod_base = OTHER
                  note = 2'-O-methyl cytidine 5'-thiophosphate
modified_base     3
                  mod_base = OTHER
                  note = 2'-O-methyl guanosine 5'-thiophosphate
modified_base     4
                  mod_base = OTHER
                  note = 2'-O-methyl guanosine
modified_base     5
                  mod_base = OTHER
                  note = 2'-O-methyl adenosine
modified_base     6
                  mod_base = OTHER
                  note = 2'-O-methyl cytidine
modified_base     7
                  mod_base = OTHER
                  note = 2'-O-methyl uridine
modified_base     8
                  mod_base = OTHER
                  note = 2'-O-methyl uridine
modified_base     9
                  mod_base = OTHER
                  note = 2'-O-methyl guanosine
modified_base     10
                  mod_base = OTHER
                  note = 2'-O-methyl guanosine
modified_base     11
                  mod_base = OTHER
                  note = 2'-O-methyl adenosine
modified_base     12
                  mod_base = OTHER
                  note = 2'-O-methyl cytidine
modified_base     13
                  mod_base = OTHER
                  note = 2'-O-methyl uridine
modified_base     14
                  mod_base = OTHER
                  note = 2'-O-methyl cytidine
modified_base     15
                  mod_base = OTHER
                  note = 2'-O-methyl uridine
modified_base     16
                  mod_base = OTHER
                  note = 2'-O-methyl guanosine
modified_base     17
                  mod_base = OTHER
                  note = 2'-O-methyl cytidine
modified_base     18
                  mod_base = OTHER
                  note = 2'-O-methyl uridine
modified_base     19
                  mod_base = OTHER
                  note = 2'-O-methyl guanosine
modified_base     20
                  mod_base = OTHER
                  note = 2'-O-methyl cytidine
modified_base     21
                  mod_base = OTHER
                  note = 2'-O-methyl adenosine
modified_base     22
                  mod_base = OTHER
                  note = 2'-O-methyl adenosine
modified_base     23
                  mod_base = OTHER
                  note = 2'-O-methyl adenosine
modified_base     24
                  mod_base = OTHER
                  note = 2'-O-methyl cytidine
modified_base     25
                  mod_base = OTHER
                  note = 2'-O-methyl guanosine
modified_base     26
```

```
                         mod_base = OTHER
                         note = 2'-O-methyl cytidine
modified_base            27
                         mod_base = OTHER
                         note = 2'-O-methyl uridine
modified_base            28
                         mod_base = OTHER
                         note = 2'-O-methyl adenosine 5'-thiophosphate
modified_base            29
                         mod_base = OTHER
                         note = 2'-O-methyl adenosine 5'-thiophosphate
SEQUENCE: 26
acggacttgg actctgctgc aaacgctaa                                             29

SEQ ID NO: 27            moltype = RNA  length = 29
FEATURE                  Location/Qualifiers
source                   1..29
                         mol_type = other RNA
                         organism = synthetic construct
modified_base            1
                         mod_base = OTHER
                         note = 2'-O-methyl adenosine
modified_base            2
                         mod_base = OTHER
                         note = 2'-O-methyl cytidine 5'-thiophosphate
modified_base            3
                         mod_base = OTHER
                         note = 2'-O-methyl guanosine 5'-thiophosphate
modified_base            4
                         mod_base = OTHER
                         note = 2'-O-methyl guanosine
modified_base            5
                         mod_base = OTHER
                         note = 2'-O-methyl adenosine
modified_base            6
                         mod_base = OTHER
                         note = 2'-O-methyl cytidine
modified_base            7
                         mod_base = OTHER
                         note = 2'-O-methyl uridine
modified_base            8
                         mod_base = OTHER
                         note = 2'-O-methyl uridine
modified_base            9
                         mod_base = OTHER
                         note = 2'-O-methyl guanosine
modified_base            10
                         mod_base = OTHER
                         note = 2'-O-methyl guanosine
modified_base            11
                         mod_base = OTHER
                         note = 2'-O-methyl adenosine
modified_base            12
                         mod_base = OTHER
                         note = 2'-O-methyl cytidine
modified_base            13
                         mod_base = OTHER
                         note = 2'-O-methyl uridine
modified_base            14
                         mod_base = OTHER
                         note = 2'-O-methyl cytidine
modified_base            15
                         mod_base = OTHER
                         note = 2'-O-methyl adenosine
modified_base            16
                         mod_base = OTHER
                         note = 2'-O-methyl adenosine
modified_base            17
                         mod_base = OTHER
                         note = 2'-O-methyl uridine
modified_base            18
                         mod_base = OTHER
                         note = 2'-O-methyl guanosine
modified_base            19
                         mod_base = OTHER
                         note = 2'-O-methyl guanosine
modified_base            20
                         mod_base = OTHER
                         note = 2'-O-methyl uridine
```

-continued

```
modified_base          21
                       mod_base = OTHER
                       note = 2'-O-methyl cytidine
modified_base          22
                       mod_base = OTHER
                       note = 2'-O-methyl cytidine
modified_base          23
                       mod_base = OTHER
                       note = 2'-O-methyl uridine
modified_base          24
                       mod_base = OTHER
                       note = 2'-O-methyl adenosine
modified_base          25
                       mod_base = OTHER
                       note = 2'-O-methyl cytidine
modified_base          26
                       mod_base = OTHER
                       note = 2'-O-methyl cytidine
modified_base          27
                       mod_base = OTHER
                       note = 2'-O-methyl uridine
modified_base          28
                       mod_base = OTHER
                       note = 2'-O-methyl guanosine 5'-thiophosphate
modified_base          29
                       mod_base = OTHER
                       note = 2'-O-methyl cytidine 5'-thiophosphate
SEQUENCE: 27
acggacttgg actcaatggt cctacctgc                                      29

SEQ ID NO: 28          moltype = RNA   length = 26
FEATURE                Location/Qualifiers
source                 1..26
                       mol_type = other RNA
                       organism = synthetic construct
modified_base          1
                       mod_base = OTHER
                       note = 2'-O-methyl guanosine
modified_base          2
                       mod_base = OTHER
                       note = 2'-O-methyl guanosine 5'-thiophosphate
modified_base          3
                       mod_base = OTHER
                       note = 2'-O-methyl adenosine 5'-thiophosphate
modified_base          4
                       mod_base = OTHER
                       note = 2'-O-methyl cytidine
modified_base          5
                       mod_base = OTHER
                       note = 2'-O-methyl uridine
modified_base          6
                       mod_base = OTHER
                       note = 2'-O-methyl guanosine
modified_base          7
                       mod_base = OTHER
                       note = 2'-O-methyl guanosine
modified_base          8
                       mod_base = OTHER
                       note = 2'-O-methyl adenosine
modified_base          9
                       mod_base = OTHER
                       note = 2'-O-methyl cytidine
modified_base          10
                       mod_base = OTHER
                       note = 2'-O-methyl uridine
modified_base          11
                       mod_base = OTHER
                       note = 2'-O-methyl cytidine 5'-thiophosphate
modified_base          12
                       mod_base = OTHER
                       note = 2'-O-methyl uridine 5'-thiophosphate
modified_base          13
                       mod_base = OTHER
                       note = 2'-O-methyl adenosine 5'-thiophosphate
modified_base          14
                       mod_base = OTHER
                       note = 2'-O-methyl adenosine 5'-thiophosphate
modified_base          15
                       mod_base = OTHER
```

```
                          note = 2'-O-methyl adenosine 5'-thiophosphate
modified_base             16
                          mod_base = OTHER
                          note = 2'-O-methyl guanosine 5'-thiophosphate
modified_base             17
                          mod_base = OTHER
                          note = 2'-O-methyl adenosine 5'-thiophosphate
modified_base             18
                          mod_base = OTHER
                          note = 2'-O-methyl guanosine 5'-thiophosphate
modified_base             19
                          mod_base = OTHER
                          note = 2'-O-methyl adenosine 5'-thiophosphate
modified_base             20
                          mod_base = OTHER
                          note = 2'-O-methyl uridine 5'-thiophosphate
modified_base             21
                          mod_base = OTHER
                          note = 2'-O-methyl guanosine 5'-thiophosphate
modified_base             22
                          mod_base = OTHER
                          note = 2'-O-methyl adenosine 5'-thiophosphate
modified_base             23
                          mod_base = OTHER
                          note = 2'-O-methyl adenosine 5'-thiophosphate
modified_base             24
                          mod_base = OTHER
                          note = 2'-O-methyl guanosine 5'-thiophosphate
modified_base             25
                          mod_base = OTHER
                          note = 2'-O-methyl cytidine 5'-thiophosphate
modified_base             26
                          mod_base = OTHER
                          note = 2'-O-methyl cytidine 5'-thiophosphate
SEQUENCE: 28
ggactggact ctaaagagat gaagcc                                            26

SEQ ID NO: 29             moltype = RNA  length = 27
FEATURE                   Location/Qualifiers
source                    1..27
                          mol_type = other RNA
                          organism = synthetic construct
modified_base             1
                          mod_base = OTHER
                          note = 2'-O-methyl guanosine
modified_base             2
                          mod_base = OTHER
                          note = 2'-O-methyl guanosine 5'-thiophosphate
modified_base             3
                          mod_base = OTHER
                          note = 2'-O-methyl adenosine 5'-thiophosphate
modified_base             4
                          mod_base = OTHER
                          note = 2'-O-methyl cytidine
modified_base             5
                          mod_base = OTHER
                          note = 2'-O-methyl uridine
modified_base             6
                          mod_base = OTHER
                          note = 2'-O-methyl guanosine
modified_base             7
                          mod_base = OTHER
                          note = 2'-O-methyl guanosine
modified_base             8
                          mod_base = OTHER
                          note = 2'-O-methyl adenosine
modified_base             9
                          mod_base = OTHER
                          note = 2'-O-methyl cytidine
modified_base             10
                          mod_base = OTHER
                          note = 2'-O-methyl uridine
modified_base             11
                          mod_base = OTHER
                          note = 2'-O-methyl adenosine
modified_base             12
                          mod_base = OTHER
                          note = 2'-O-methyl guanosine 5'-thiophosphate
modified_base             13
```

```
                        mod_base = OTHER
                        note = 2'-O-methyl guanosine 5'-thiophosphate
modified_base           14
                        mod_base = OTHER
                        note = 2'-O-methyl cytidine 5'-thiophosphate
modified_base           15
                        mod_base = OTHER
                        note = 2'-O-methyl cytidine 5'-thiophosphate
modified_base           16
                        mod_base = OTHER
                        note = 2'-O-methyl cytidine 5'-thiophosphate
modified_base           17
                        mod_base = OTHER
                        note = 2'-O-methyl cytidine 5'-thiophosphate
modified_base           18
                        mod_base = OTHER
                        note = 2'-O-methyl adenosine 5'-thiophosphate
modified_base           19
                        mod_base = OTHER
                        note = 2'-O-methyl adenosine 5'-thiophosphate
modified_base           20
                        mod_base = OTHER
                        note = 2'-O-methyl guanosine 5'-thiophosphate
modified_base           21
                        mod_base = OTHER
                        note = 2'-O-methyl guanosine 5'-thiophosphate
modified_base           22
                        mod_base = OTHER
                        note = 2'-O-methyl uridine 5'-thiophosphate
modified_base           23
                        mod_base = OTHER
                        note = 2'-O-methylene-4'-bridged (LNA) guanosine
                         5'-thiophosphate
modified_base           24
                        mod_base = OTHER
                        note = 2'-O-methyl adenosine 5'-thiophosphate
modified_base           25
                        mod_base = OTHER
                        note = 2'-O-methylene-4'-bridged (LNA) guanosine
                         5'-thiophosphate
modified_base           26
                        mod_base = OTHER
                        note = 2'-O-methyl guanosine 5'-thiophosphate
modified_base           27
                        mod_base = OTHER
                        note = 2'-O-methylene-4'-bridged (LNA) 5-methyl cytidine
                         5'-thiophosphate
misc_feature            27
                        note = 3'-O attached to a GalNAc-comprising compound via a
                         linker
SEQUENCE: 29
ggactggact aggccccaag gtgaggc                                              27

SEQ ID NO: 30           moltype = RNA  length = 28
FEATURE                 Location/Qualifiers
source                  1..28
                        mol_type = other RNA
                        organism = synthetic construct
modified_base           1
                        mod_base = OTHER
                        note = 2'-O-methyl guanosine
modified_base           2
                        mod_base = OTHER
                        note = 2'-O-methyl guanosine 5'-thiophosphate
modified_base           3
                        mod_base = OTHER
                        note = 2'-O-methyl adenosine 5'-thiophosphate
modified_base           4
                        mod_base = OTHER
                        note = 2'-O-methyl cytidine
modified_base           5
                        mod_base = OTHER
                        note = 2'-O-methyl uridine
modified_base           6
                        mod_base = OTHER
                        note = 2'-O-methyl guanosine
modified_base           7
                        mod_base = OTHER
                        note = 2'-O-methyl guanosine
```

-continued

```
modified_base        8
                     mod_base = OTHER
                     note = 2'-O-methyl adenosine
modified_base        9
                     mod_base = OTHER
                     note = 2'-O-methyl cytidine
modified_base        10
                     mod_base = OTHER
                     note = 2'-O-methyl uridine
modified_base        11
                     mod_base = OTHER
                     note = 2'-O-methyl cytidine
modified_base        12
                     mod_base = OTHER
                     note = 2'-O-methyl cytidine 5'-thiophosphate
modified_base        13
                     mod_base = OTHER
                     note = 2'-O-methyl cytidine 5'-thiophosphate
modified_base        14
                     mod_base = OTHER
                     note = 2'-O-methyl adenosine 5'-thiophosphate
modified_base        15
                     mod_base = OTHER
                     note = 2'-O-methyl adenosine 5'-thiophosphate
modified_base        16
                     mod_base = OTHER
                     note = 2'-O-methyl guanosine 5'-thiophosphate
modified_base        17
                     mod_base = OTHER
                     note = 2'-O-methyl guanosine 5'-thiophosphate
modified_base        18
                     mod_base = OTHER
                     note = 2'-O-methyl uridine 5'-thiophosphate
modified_base        19
                     mod_base = OTHER
                     note = 2'-O-methyl guanosine 5'-thiophosphate
modified_base        20
                     mod_base = OTHER
                     note = 2'-O-methyl adenosine 5'-thiophosphate
modified_base        21
                     mod_base = OTHER
                     note = 2'-O-methyl guanosine 5'-thiophosphate
modified_base        22
                     mod_base = OTHER
                     note = 2'-O-methyl guanosine 5'-thiophosphate
modified_base        23
                     mod_base = OTHER
                     note = 2'-O-methyl cytidine 5'-thiophosphate
modified_base        24
                     mod_base = OTHER
                     note = 2'-O-methyl adenosine 5'-thiophosphate
modified_base        25
                     mod_base = OTHER
                     note = 2'-O-methyl uridine 5'-thiophosphate
modified_base        26
                     mod_base = OTHER
                     note = 2'-O-methyl adenosine 5'-thiophosphate
modified_base        27
                     mod_base = OTHER
                     note = 2'-O-methyl uridine 5'-thiophosphate
modified_base        28
                     mod_base = OTHER
                     note = 2'-O-methyl cytidine 5'-thiophosphate
misc_feature         28
                     note = 3'-O attached to a GalNAc-comprising compound via a
                      linker
SEQUENCE: 30
ggactggact cccaaggtga ggcatatc                                        28

SEQ ID NO: 31        moltype = RNA  length = 26
FEATURE              Location/Qualifiers
source               1..26
                     mol_type = other RNA
                     organism = synthetic construct
modified_base        1
                     mod_base = OTHER
                     note = 2'-O-methyl guanosine
modified_base        2
                     mod_base = OTHER
```

-continued

```
                       note = 2'-O-methyl guanosine 5'-thiophosphate
modified_base          3
                       mod_base = OTHER
                       note = 2'-O-methyl adenosine 5'-thiophosphate
modified_base          4
                       mod_base = OTHER
                       note = 2'-O-methyl cytidine
modified_base          5
                       mod_base = OTHER
                       note = 2'-O-methyl uridine
modified_base          6
                       mod_base = OTHER
                       note = 2'-O-methyl guanosine
modified_base          7
                       mod_base = OTHER
                       note = 2'-O-methyl guanosine
modified_base          8
                       mod_base = OTHER
                       note = 2'-O-methyl adenosine
modified_base          9
                       mod_base = OTHER
                       note = 2'-O-methyl cytidine
modified_base          10
                       mod_base = OTHER
                       note = 2'-O-methyl uridine
modified_base          11
                       mod_base = OTHER
                       note = 2'-O-methyl cytidine
modified_base          12
                       mod_base = OTHER
                       note = 2'-O-methyl adenosine 5'-thiophosphate
modified_base          13
                       mod_base = OTHER
                       note = 2'-O-methyl adenosine 5'-thiophosphate
modified_base          14
                       mod_base = OTHER
                       note = 2'-O-methyl guanosine 5'-thiophosphate
modified_base          15
                       mod_base = OTHER
                       note = 2'-O-methyl guanosine 5'-thiophosphate
modified_base          16
                       mod_base = OTHER
                       note = 2'-O-methyl uridine 5'-thiophosphate
modified_base          17
                       mod_base = OTHER
                       note = 2'-O-methyl guanosine 5'-thiophosphate
modified_base          18
                       mod_base = OTHER
                       note = 2'-O-methyl adenosine 5'-thiophosphate
modified_base          19
                       mod_base = OTHER
                       note = 2'-O-methyl guanosine 5'-thiophosphate
modified_base          20
                       mod_base = OTHER
                       note = 2'-O-methyl guanosine 5'-thiophosphate
modified_base          21
                       mod_base = OTHER
                       note = 2'-O-methyl cytidine 5'-thiophosphate
modified_base          22
                       mod_base = OTHER
                       note = 2'-O-methyl adenosine 5'-thiophosphate
modified_base          23
                       mod_base = OTHER
                       note = 2'-O-methyl uridine 5'-thiophosphate
modified_base          24
                       mod_base = OTHER
                       note = 2'-O-methyl adenosine 5'-thiophosphate
modified_base          25
                       mod_base = OTHER
                       note = 2'-O-methyl uridine 5'-thiophosphate
modified_base          26
                       mod_base = OTHER
                       note = 2'-O-methyl cytidine 5'-thiophosphate
misc_feature           26
                       note = 3'-O attached to a GalNAc-comprising compound via a
                       linker
SEQUENCE: 31
ggactggact caaggtgagg catatc                                       26
```

```
SEQ ID NO: 32          moltype = RNA  length = 28
FEATURE                Location/Qualifiers
source                 1..28
                       mol_type = other RNA
                       organism = synthetic construct
modified_base          1
                       mod_base = OTHER
                       note = 2'-O-methyl guanosine
modified_base          2
                       mod_base = OTHER
                       note = 2'-O-methyl guanosine 5'-thiophosphate
modified_base          3
                       mod_base = OTHER
                       note = 2'-O-methyl adenosine 5'-thiophosphate
modified_base          4
                       mod_base = OTHER
                       note = 2'-O-methyl cytidine
modified_base          5
                       mod_base = OTHER
                       note = 2'-O-methyl uridine
modified_base          6
                       mod_base = OTHER
                       note = 2'-O-methyl guanosine
modified_base          7
                       mod_base = OTHER
                       note = 2'-O-methyl guanosine
modified_base          8
                       mod_base = OTHER
                       note = 2'-O-methyl adenosine
modified_base          9
                       mod_base = OTHER
                       note = 2'-O-methyl cytidine
modified_base          10
                       mod_base = OTHER
                       note = 2'-O-methyl uridine
modified_base          11
                       mod_base = OTHER
                       note = 2'-O-(2-methoxyethyl) adenosine
modified_base          12
                       mod_base = OTHER
                       note = 2'-O-(2-methoxyethyl) 5-methyl cytidine
                        5'-thiophosphate
modified_base          13
                       mod_base = OTHER
                       note = 2'-O-(2-methoxyethyl) thymidine 5'-thiophosphate
modified_base          14
                       mod_base = OTHER
                       note = 2'-O-(2-methoxyethyl) 5-methyl cytidine
                        5'-thiophosphate
modified_base          15
                       mod_base = OTHER
                       note = 2'-O-(2-methoxyethyl) thymidine 5'-thiophosphate
modified_base          16
                       mod_base = OTHER
                       note = 2'-O-(2-methoxyethyl) thymidine 5'-thiophosphate
modified_base          17
                       mod_base = OTHER
                       note = 2'-O-(2-methoxyethyl) thymidine 5'-thiophosphate
modified_base          18
                       mod_base = OTHER
                       note = 2'-O-(2-methoxyethyl) adenosine 5'-thiophosphate
modified_base          19
                       mod_base = OTHER
                       note = 2'-O-(2-methoxyethyl) thymidine 5'-thiophosphate
modified_base          20
                       mod_base = OTHER
                       note = 2'-O-(2-methoxyethyl) thymidine 5'-thiophosphate
modified_base          21
                       mod_base = OTHER
                       note = 2'-O-(2-methoxyethyl) adenosine 5'-thiophosphate
modified_base          22
                       mod_base = OTHER
                       note = 2'-O-(2-methoxyethyl) thymidine 5'-thiophosphate
modified_base          23
                       mod_base = OTHER
                       note = 2'-O-(2-methoxyethyl) 5-methyl cytidine
                        5'-thiophosphate
modified_base          24
                       mod_base = OTHER
```

-continued

```
                            note = 2'-O-(2-methoxyethyl) thymidine 5'-thiophosphate
modified_base               25
                            mod_base = OTHER
                            note = 2'-O-(2-methoxyethyl) 5-methyl cytidine
                             5'-thiophosphate
modified_base               26
                            mod_base = OTHER
                            note = 2'-O-(2-methoxyethyl) adenosine 5'-thiophosphate
modified_base               27
                            mod_base = OTHER
                            note = 2'-O-(2-methoxyethyl) adenosine 5'-thiophosphate
modified_base               28
                            mod_base = OTHER
                            note = 2'-O-(2-methoxyethyl) guanosine 5'-thiophosphate
SEQUENCE: 32
ggactggact actctttatt atctcaag                                         28

SEQ ID NO: 33              moltype = RNA   length = 28
FEATURE                   Location/Qualifiers
source                    1..28
                          mol_type = other RNA
                          organism = synthetic construct
modified_base             1
                          mod_base = OTHER
                          note = 2'-O-methyl guanosine
modified_base             2
                          mod_base = OTHER
                          note = 2'-O-methyl guanosine 5'-thiophosphate
modified_base             3
                          mod_base = OTHER
                          note = 2'-O-methyl adenosine 5'-thiophosphate
modified_base             4
                          mod_base = OTHER
                          note = 2'-O-methyl cytidine
modified_base             5
                          mod_base = OTHER
                          note = 2'-O-methyl uridine
modified_base             6
                          mod_base = OTHER
                          note = 2'-O-methyl guanosine
modified_base             7
                          mod_base = OTHER
                          note = 2'-O-methyl guanosine
modified_base             8
                          mod_base = OTHER
                          note = 2'-O-methyl adenosine
modified_base             9
                          mod_base = OTHER
                          note = 2'-O-methyl cytidine
modified_base             10
                          mod_base = OTHER
                          note = 2'-O-methyl uridine
modified_base             11
                          mod_base = OTHER
                          note = 2'-O-(2-methoxyethyl) adenosine
modified_base             12
                          mod_base = OTHER
                          note = 2'-O-(2-methoxyethyl) 5-methyl cytidine
                           5'-thiophosphate
modified_base             13
                          mod_base = OTHER
                          note = 2'-O-(2-methoxyethyl) thymidine 5'-thiophosphate
modified_base             14
                          mod_base = OTHER
                          note = 2'-O-(2-methoxyethyl) 5-methyl cytidine
                           5'-thiophosphate
modified_base             15
                          mod_base = OTHER
                          note = 2'-O-(2-methoxyethyl) thymidine 5'-thiophosphate
modified_base             16
                          mod_base = OTHER
                          note = 2'-O-(2-methoxyethyl) thymidine 5'-thiophosphate
modified_base             17
                          mod_base = OTHER
                          note = 2'-O-(2-methoxyethyl) thymidine 5'-thiophosphate
modified_base             18
                          mod_base = OTHER
                          note = 2'-O-(2-methoxyethyl) adenosine 5'-thiophosphate
modified_base             19
```

```
                              mod_base = OTHER
                              note = 2'-O-(2-methoxyethyl) thymidine 5'-thiophosphate
modified_base                 20
                              mod_base = OTHER
                              note = 2'-O-(2-methoxyethyl) thymidine 5'-thiophosphate
modified_base                 21
                              mod_base = OTHER
                              note = 2'-O-(2-methoxyethyl) adenosine 5'-thiophosphate
modified_base                 22
                              mod_base = OTHER
                              note = 2'-O-(2-methoxyethyl) thymidine 5'-thiophosphate
modified_base                 23
                              mod_base = OTHER
                              note = 2'-O-(2-methoxyethyl) thymidine 5'-thiophosphate
modified_base                 24
                              mod_base = OTHER
                              note = 2'-O-(2-methoxyethyl) 5-methyl cytidine
                               5'-thiophosphate
modified_base                 25
                              mod_base = OTHER
                              note = 2'-O-(2-methoxyethyl) 5-methyl cytidine
                               5'-thiophosphate
modified_base                 26
                              mod_base = OTHER
                              note = 2'-O-(2-methoxyethyl) adenosine 5'-thiophosphate
modified_base                 27
                              mod_base = OTHER
                              note = 2'-O-(2-methoxyethyl) adenosine 5'-thiophosphate
modified_base                 28
                              mod_base = OTHER
                              note = 2'-O-(2-methoxyethyl) guanosine 5'-thiophosphate
misc_feature                  28
                              note = 3'-O attached to a GalNAc-comprising compound via a
                               linker
SEQUENCE: 33
ggactggact actctttatt attccaag                                              28

SEQ ID NO: 34                 moltype = RNA  length = 28
FEATURE                       Location/Qualifiers
source                        1..28
                              mol_type = other RNA
                              organism = synthetic construct
modified_base                 1
                              mod_base = OTHER
                              note = 2'-O-methyl guanosine
modified_base                 2
                              mod_base = OTHER
                              note = 2'-O-methyl guanosine 5'-thiophosphate
modified_base                 3
                              mod_base = OTHER
                              note = 2'-O-methyl adenosine 5'-thiophosphate
modified_base                 4
                              mod_base = OTHER
                              note = 2'-O-methyl cytidine
modified_base                 5
                              mod_base = OTHER
                              note = 2'-O-methyl uridine
modified_base                 6
                              mod_base = OTHER
                              note = 2'-O-methyl guanosine
modified_base                 7
                              mod_base = OTHER
                              note = 2'-O-methyl guanosine
modified_base                 8
                              mod_base = OTHER
                              note = 2'-O-methyl adenosine
modified_base                 9
                              mod_base = OTHER
                              note = 2'-O-methyl cytidine
modified_base                 10
                              mod_base = OTHER
                              note = 2'-O-methyl uridine
modified_base                 11
                              mod_base = OTHER
                              note = 2'-O-(2-methoxyethyl) adenosine
modified_base                 12
                              mod_base = OTHER
                              note = 2'-O-(2-methoxyethyl) adenosine 5'-thiophosphate
modified_base                 13
```

-continued

```
                          mod_base = OTHER
                          note = 2'-O-(2-methoxyethyl) adenosine 5'-thiophosphate
modified_base             14
                          mod_base = OTHER
                          note = 2'-O-(2-methoxyethyl) thymidine 5'-thiophosphate
modified_base             15
                          mod_base = OTHER
                          note = 2'-O-(2-methoxyethyl) adenosine 5'-thiophosphate
modified_base             16
                          mod_base = OTHER
                          note = 2'-O-(2-methoxyethyl) adenosine 5'-thiophosphate
modified_base             17
                          mod_base = OTHER
                          note = 2'-O-(2-methoxyethyl) adenosine 5'-thiophosphate
modified_base             18
                          mod_base = OTHER
                          note = 2'-O-(2-methoxyethyl) thymidine 5'-thiophosphate
modified_base             19
                          mod_base = OTHER
                          note = 2'-O-(2-methoxyethyl) adenosine 5'-thiophosphate
modified_base             20
                          mod_base = OTHER
                          note = 2'-O-(2-methoxyethyl) adenosine 5'-thiophosphate
modified_base             21
                          mod_base = OTHER
                          note = 2'-O-(2-methoxyethyl) guanosine 5'-thiophosphate
modified_base             22
                          mod_base = OTHER
                          note = 2'-O-(2-methoxyethyl) adenosine 5'-thiophosphate
modified_base             23
                          mod_base = OTHER
                          note = 2'-O-(2-methoxyethyl) thymidine 5'-thiophosphate
modified_base             24
                          mod_base = OTHER
                          note = 2'-O-(2-methoxyethyl) adenosine 5'-thiophosphate
modified_base             25
                          mod_base = OTHER
                          note = 2'-O-(2-methoxyethyl) adenosine 5'-thiophosphate
modified_base             26
                          mod_base = OTHER
                          note = 2'-O-(2-methoxyethyl) adenosine 5'-thiophosphate
modified_base             27
                          mod_base = OTHER
                          note = 2'-O-(2-methoxyethyl) thymidine 5'-thiophosphate
modified_base             28
                          mod_base = OTHER
                          note = 2'-O-(2-methoxyethyl) adenosine 5'-thiophosphate
misc_feature              28
                          note = 3'-O attached to a GalNAc-comprising compound via a
                          linker
SEQUENCE: 34
ggactggact aaataaataa gataaata                                            28

SEQ ID NO: 35             moltype = RNA  length = 17
FEATURE                   Location/Qualifiers
source                    1..17
                          mol_type = other RNA
                          organism = synthetic construct
modified_base             1
                          mod_base = OTHER
                          note = 2'-O-methyl uridine
modified_base             2
                          mod_base = OTHER
                          note = 2'-O-methyl guanosine
modified_base             3
                          mod_base = OTHER
                          note = 2'-O-methyl guanosine
modified_base             4
                          mod_base = OTHER
                          note = 2'-O-methyl uridine
modified_base             5
                          mod_base = OTHER
                          note = 2'-O-methyl adenosine
modified_base             6
                          mod_base = OTHER
                          note = 2'-O-methyl guanosine
modified_base             7
                          mod_base = OTHER
                          note = 2'-O-methyl uridine
```

```
modified_base          8
                       mod_base = OTHER
                       note = 2'-O-methyl uridine
modified_base          9
                       mod_base = OTHER
                       note = 2'-O-methyl uridine
modified_base          10
                       mod_base = OTHER
                       note = 2'-O-methyl cytidine
modified_base          11
                       mod_base = OTHER
                       note = 2'-O-methyl uridine
modified_base          12
                       mod_base = OTHER
                       note = 2'-O-methyl guanosine
modified_base          13
                       mod_base = OTHER
                       note = 2'-O-methyl uridine
modified_base          14
                       mod_base = OTHER
                       note = 2'-O-methyl guanosine
modified_base          15
                       mod_base = OTHER
                       note = 2'-O-methyl guanosine
modified_base          16
                       mod_base = OTHER
                       note = 2'-O-methyl uridine
modified_base          17
                       mod_base = OTHER
                       note = 2'-O-methyl uridine
misc_feature           1
                       note = 5'-biotin attached
SEQUENCE: 35
tggtagtttc tgtggtt                                                             17

SEQ ID NO: 36          moltype = RNA  length = 27
FEATURE                Location/Qualifiers
source                 1..27
                       mol_type = other RNA
                       organism = synthetic construct
modified_base          1
                       mod_base = OTHER
                       note = 2'-O-methyl guanosine
modified_base          2
                       mod_base = OTHER
                       note = 2'-O-methyl guanosine 5'-thiophosphate
modified_base          3
                       mod_base = OTHER
                       note = 2'-O-methyl adenosine 5'-thiophosphate
modified_base          4
                       mod_base = OTHER
                       note = 2'-O-methyl cytidine
modified_base          5
                       mod_base = OTHER
                       note = 2'-O-methyl uridine
modified_base          6
                       mod_base = OTHER
                       note = 2'-O-methyl guanosine
modified_base          7
                       mod_base = OTHER
                       note = 2'-O-methyl guanosine
modified_base          8
                       mod_base = OTHER
                       note = 2'-O-methyl adenosine
modified_base          9
                       mod_base = OTHER
                       note = 2'-O-methyl cytidine
modified_base          10
                       mod_base = OTHER
                       note = 2'-O-methyl uridine
modified_base          11
                       mod_base = OTHER
                       note = 2'-O-(2-methoxyethyl) adenosine
modified_base          12
                       mod_base = OTHER
                       note = 2'-O-(2-methoxyethyl) adenosine 5'-thiophosphate
modified_base          13
                       mod_base = OTHER
                       note = 2'-O-(2-methoxyethyl) 5-methyl cytidine
```

```
                            5'-thiophosphate
modified_base               14
                            mod_base = OTHER
                            note = 2'-O-(2-methoxyethyl) 5-methyl cytidine
                             5'-thiophosphate
modified_base               15
                            mod_base = OTHER
                            note = 2'-O-(2-methoxyethyl) adenosine 5'-thiophosphate
modified_base               16
                            mod_base = OTHER
                            note = 2'-O-(2-methoxyethyl) 5-methyl cytidine
                             5'-thiophosphate
modified_base               17
                            mod_base = OTHER
                            note = 2'-O-(2-methoxyethyl) adenosine 5'-thiophosphate
modified_base               18
                            mod_base = OTHER
                            note = 2'-O-(2-methoxyethyl) guanosine 5'-thiophosphate
modified_base               19
                            mod_base = OTHER
                            note = 2'-O-(2-methoxyethyl) adenosine 5'-thiophosphate
modified_base               20
                            mod_base = OTHER
                            note = 2'-O-(2-methoxyethyl) adenosine 5'-thiophosphate
modified_base               21
                            mod_base = OTHER
                            note = 2'-O-(2-methoxyethyl) adenosine 5'-thiophosphate
modified_base               22
                            mod_base = OTHER
                            note = 2'-O-(2-methoxyethyl) 5-methyl cytidine
                             5'-thiophosphate
modified_base               23
                            mod_base = OTHER
                            note = 2'-O-(2-methoxyethyl) thymidine 5'-thiophosphate
modified_base               24
                            mod_base = OTHER
                            note = 2'-O-(2-methoxyethyl) adenosine 5'-thiophosphate
modified_base               25
                            mod_base = OTHER
                            note = 2'-O-(2-methoxyethyl) 5-methyl cytidine
                             5'-thiophosphate
modified_base               26
                            mod_base = OTHER
                            note = 2'-O-(2-methoxyethyl) 5-methyl cytidine
                             5'-thiophosphate
modified_base               27
                            mod_base = OTHER
                            note = 2'-O-(2-methoxyethyl) adenosine 5'-thiophosphate
misc_feature                27
                            note = 3'-O attached to a GalNAc-comprising compound via a
                             linker
SEQUENCE: 36
ggactggact aaccacagaa actacca                                               27

SEQ ID NO: 37           moltype = RNA  length = 27
FEATURE                 Location/Qualifiers
source                  1..27
                        mol_type = other RNA
                        organism = synthetic construct
modified_base           1
                        mod_base = OTHER
                        note = 2'-O-methyl adenosine
modified_base           2
                        mod_base = OTHER
                        note = 2'-O-methyl adenosine 5'-thiophosphate
modified_base           3
                        mod_base = OTHER
                        note = 2'-O-methyl adenosine 5'-thiophosphate
modified_base           4
                        mod_base = OTHER
                        note = 2'-O-methyl cytidine
modified_base           5
                        mod_base = OTHER
                        note = 2'-O-methyl uridine
modified_base           6
                        mod_base = OTHER
                        note = 2'-O-methyl adenosine
modified_base           7
                        mod_base = OTHER
```

```
                           note = 2'-O-methyl adenosine
modified_base              8
                           mod_base = OTHER
                           note = 2'-O-methyl adenosine
modified_base              9
                           mod_base = OTHER
                           note = 2'-O-methyl cytidine
modified_base              10
                           mod_base = OTHER
                           note = 2'-O-methyl uridine
modified_base              11
                           mod_base = OTHER
                           note = 2'-O-(2-methoxyethyl) adenosine
modified_base              12
                           mod_base = OTHER
                           note = 2'-O-(2-methoxyethyl) adenosine 5'-thiophosphate
modified_base              13
                           mod_base = OTHER
                           note = 2'-O-(2-methoxyethyl) 5-methyl cytidine
                            5'-thiophosphate
modified_base              14
                           mod_base = OTHER
                           note = 2'-O-(2-methoxyethyl) 5-methyl cytidine
                            5'-thiophosphate
modified_base              15
                           mod_base = OTHER
                           note = 2'-O-(2-methoxyethyl) adenosine 5'-thiophosphate
modified_base              16
                           mod_base = OTHER
                           note = 2'-O-(2-methoxyethyl) 5-methyl cytidine
                            5'-thiophosphate
modified_base              17
                           mod_base = OTHER
                           note = 2'-O-(2-methoxyethyl) adenosine 5'-thiophosphate
modified_base              18
                           mod_base = OTHER
                           note = 2'-O-(2-methoxyethyl) guanosine 5'-thiophosphate
modified_base              19
                           mod_base = OTHER
                           note = 2'-O-(2-methoxyethyl) adenosine 5'-thiophosphate
modified_base              20
                           mod_base = OTHER
                           note = 2'-O-(2-methoxyethyl) adenosine 5'-thiophosphate
modified_base              21
                           mod_base = OTHER
                           note = 2'-O-(2-methoxyethyl) adenosine 5'-thiophosphate
modified_base              22
                           mod_base = OTHER
                           note = 2'-O-(2-methoxyethyl) 5-methyl cytidine
                            5'-thiophosphate
modified_base              23
                           mod_base = OTHER
                           note = 2'-O-(2-methoxyethyl) thymidine 5'-thiophosphate
modified_base              24
                           mod_base = OTHER
                           note = 2'-O-(2-methoxyethyl) adenosine 5'-thiophosphate
modified_base              25
                           mod_base = OTHER
                           note = 2'-O-(2-methoxyethyl) 5-methyl cytidine
                            5'-thiophosphate
modified_base              26
                           mod_base = OTHER
                           note = 2'-O-(2-methoxyethyl) 5-methyl cytidine
                            5'-thiophosphate
modified_base              27
                           mod_base = OTHER
                           note = 2'-O-(2-methoxyethyl) adenosine 5'-thiophosphate
misc_feature               27
                           note = 3'-O attached to a GalNAc-comprising compound via a
                            linker
SEQUENCE: 37
aaactaaact aaccacagaa actacca                                      27

SEQ ID NO: 38             moltype = RNA  length = 27
FEATURE                   Location/Qualifiers
source                    1..27
                          mol_type = other RNA
                          organism = synthetic construct
modified_base             1
```

-continued

```
                             mod_base = OTHER
                             note = 2'-O-methyl adenosine
modified_base                2
                             mod_base = OTHER
                             note = 2'-O-methyl adenosine 5'-thiophosphate
modified_base                3
                             mod_base = OTHER
                             note = 2'-O-methyl adenosine 5'-thiophosphate
modified_base                4
                             mod_base = OTHER
                             note = 2'-O-methyl adenosine
modified_base                5
                             mod_base = OTHER
                             note = 2'-O-methyl adenosine
modified_base                6
                             mod_base = OTHER
                             note = 2'-O-methyl adenosine
modified_base                7
                             mod_base = OTHER
                             note = 2'-O-methyl adenosine
modified_base                8
                             mod_base = OTHER
                             note = 2'-O-methyl adenosine
modified_base                9
                             mod_base = OTHER
                             note = 2'-O-methyl adenosine
modified_base                10
                             mod_base = OTHER
                             note = 2'-O-methyl adenosine
modified_base                11
                             mod_base = OTHER
                             note = 2'-O-(2-methoxyethyl) adenosine
modified_base                12
                             mod_base = OTHER
                             note = 2'-O-(2-methoxyethyl) adenosine 5'-thiophosphate
modified_base                13
                             mod_base = OTHER
                             note = 2'-O-(2-methoxyethyl) 5-methyl cytidine
                              5'-thiophosphate
modified_base                14
                             mod_base = OTHER
                             note = 2'-O-(2-methoxyethyl) 5-methyl cytidine
                              5'-thiophosphate
modified_base                15
                             mod_base = OTHER
                             note = 2'-O-(2-methoxyethyl) adenosine 5'-thiophosphate
modified_base                16
                             mod_base = OTHER
                             note = 2'-O-(2-methoxyethyl) 5-methyl cytidine
                              5'-thiophosphate
modified_base                17
                             mod_base = OTHER
                             note = 2'-O-(2-methoxyethyl) adenosine 5'-thiophosphate
modified_base                18
                             mod_base = OTHER
                             note = 2'-O-(2-methoxyethyl) guanosine 5'-thiophosphate
modified_base                19
                             mod_base = OTHER
                             note = 2'-O-(2-methoxyethyl) adenosine 5'-thiophosphate
modified_base                20
                             mod_base = OTHER
                             note = 2'-O-(2-methoxyethyl) adenosine 5'-thiophosphate
modified_base                21
                             mod_base = OTHER
                             note = 2'-O-(2-methoxyethyl) adenosine 5'-thiophosphate
modified_base                22
                             mod_base = OTHER
                             note = 2'-O-(2-methoxyethyl) 5-methyl cytidine
                              5'-thiophosphate
modified_base                23
                             mod_base = OTHER
                             note = 2'-O-(2-methoxyethyl) thymidine 5'-thiophosphate
modified_base                24
                             mod_base = OTHER
                             note = 2'-O-(2-methoxyethyl) adenosine 5'-thiophosphate
modified_base                25
                             mod_base = OTHER
                             note = 2'-O-(2-methoxyethyl) 5-methyl cytidine
                              5'-thiophosphate
```

-continued

```
modified_base           26
                        mod_base = OTHER
                        note = 2'-O-(2-methoxyethyl) 5-methyl cytidine
                         5'-thiophosphate
modified_base           27
                        mod_base = OTHER
                        note = 2'-O-(2-methoxyethyl) adenosine 5'-thiophosphate
misc_feature            27
                        note = 3'-O attached to a GalNAc-comprising compound via a
                         linker
SEQUENCE: 38
aaaaaaaaaa aaccacagaa actacca                                              27

SEQ ID NO: 39           moltype = RNA  length = 25
FEATURE                 Location/Qualifiers
source                  1..25
                        mol_type = other RNA
                        organism = synthetic construct
modified_base           1
                        mod_base = OTHER
                        note = 2'-O-methyl adenosine
modified_base           2
                        mod_base = OTHER
                        note = 2'-O-methyl adenosine 5'-thiophosphate
modified_base           3
                        mod_base = OTHER
                        note = 2'-O-methyl adenosine 5'-thiophosphate
modified_base           4
                        mod_base = OTHER
                        note = 2'-O-methyl adenosine
modified_base           5
                        mod_base = OTHER
                        note = 2'-O-methyl adenosine
modified_base           6
                        mod_base = OTHER
                        note = 2'-O-methyl adenosine
modified_base           7
                        mod_base = OTHER
                        note = 2'-O-methyl adenosine
modified_base           8
                        mod_base = OTHER
                        note = 2'-O-methyl adenosine
modified_base           9
                        mod_base = OTHER
                        note = 2'-O-(2-methoxyethyl) adenosine
modified_base           10
                        mod_base = OTHER
                        note = 2'-O-(2-methoxyethyl) adenosine 5'-thiophosphate
modified_base           11
                        mod_base = OTHER
                        note = 2'-O-(2-methoxyethyl) 5-methyl cytidine
                         5'-thiophosphate
modified_base           12
                        mod_base = OTHER
                        note = 2'-O-(2-methoxyethyl) 5-methyl cytidine
                         5'-thiophosphate
modified_base           13
                        mod_base = OTHER
                        note = 2'-O-(2-methoxyethyl) adenosine 5'-thiophosphate
modified_base           14
                        mod_base = OTHER
                        note = 2'-O-(2-methoxyethyl) 5-methyl cytidine
                         5'-thiophosphate
modified_base           15
                        mod_base = OTHER
                        note = 2'-O-(2-methoxyethyl) adenosine 5'-thiophosphate
modified_base           16
                        mod_base = OTHER
                        note = 2'-O-(2-methoxyethyl) guanosine 5'-thiophosphate
modified_base           17
                        mod_base = OTHER
                        note = 2'-O-(2-methoxyethyl) adenosine 5'-thiophosphate
modified_base           18
                        mod_base = OTHER
                        note = 2'-O-(2-methoxyethyl) adenosine 5'-thiophosphate
modified_base           19
                        mod_base = OTHER
                        note = 2'-O-(2-methoxyethyl) adenosine 5'-thiophosphate
modified_base           20
```

-continued

```
                           mod_base = OTHER
                           note = 2'-O-(2-methoxyethyl) 5-methyl cytidine
                            5'-thiophosphate
modified_base              21
                           mod_base = OTHER
                           note = 2'-O-(2-methoxyethyl) thymidine 5'-thiophosphate
modified_base              22
                           mod_base = OTHER
                           note = 2'-O-(2-methoxyethyl) adenosine 5'-thiophosphate
modified_base              23
                           mod_base = OTHER
                           note = 2'-O-(2-methoxyethyl) 5-methyl cytidine
                            5'-thiophosphate
modified_base              24
                           mod_base = OTHER
                           note = 2'-O-(2-methoxyethyl) 5-methyl cytidine
                            5'-thiophosphate
modified_base              25
                           mod_base = OTHER
                           note = 2'-O-(2-methoxyethyl) adenosine 5'-thiophosphate
misc_feature               25
                           note = 3'-O attached to a GalNAc-comprising compound via a
                            linker
SEQUENCE: 39
aaaaaaaaaa ccacagaaac tacca                                          25

SEQ ID NO: 40              moltype = RNA  length = 24
FEATURE                    Location/Qualifiers
source                     1..24
                           mol_type = other RNA
                           organism = synthetic construct
modified_base              1
                           mod_base = OTHER
                           note = 2'-O-methyl guanosine
modified_base              2
                           mod_base = OTHER
                           note = 2'-O-methyl guanosine 5'-thiophosphate
modified_base              3
                           mod_base = OTHER
                           note = 2'-O-methyl adenosine 5'-thiophosphate
modified_base              4
                           mod_base = OTHER
                           note = 2'-O-methyl cytidine
modified_base              5
                           mod_base = OTHER
                           note = 2'-O-methyl uridine
modified_base              6
                           mod_base = OTHER
                           note = 2'-O-methyl guanosine
modified_base              7
                           mod_base = OTHER
                           note = 2'-O-methyl guanosine
modified_base              8
                           mod_base = OTHER
                           note = 2'-O-methyl adenosine
modified_base              9
                           mod_base = OTHER
                           note = 2'-O-methyl cytidine
modified_base              10
                           mod_base = OTHER
                           note = 2'-O-methyl uridine
modified_base              11
                           mod_base = OTHER
                           note = 2'-O-(2-methoxyethyl) adenosine
modified_base              12
                           mod_base = OTHER
                           note = 2'-O-(2-methoxyethyl) adenosine 5'-thiophosphate
modified_base              13
                           mod_base = OTHER
                           note = 2'-O-(2-methoxyethyl) 5-methyl cytidine
                            5'-thiophosphate
modified_base              14
                           mod_base = OTHER
                           note = 2'-O-(2-methoxyethyl) 5-methyl cytidine
                            5'-thiophosphate
modified_base              15
                           mod_base = OTHER
                           note = 2'-O-(2-methoxyethyl) adenosine 5'-thiophosphate
modified_base              16
```

```
                          mod_base = OTHER
                          note = 2'-O-(2-methoxyethyl) 5-methyl cytidine
                          5'-thiophosphate
modified_base             17
                          mod_base = OTHER
                          note = 2'-O-(2-methoxyethyl) adenosine 5'-thiophosphate
modified_base             18
                          mod_base = OTHER
                          note = 2'-O-(2-methoxyethyl) guanosine 5'-thiophosphate
modified_base             19
                          mod_base = OTHER
                          note = 2'-O-(2-methoxyethyl) adenosine 5'-thiophosphate
modified_base             20
                          mod_base = OTHER
                          note = 2'-O-(2-methoxyethyl) adenosine 5'-thiophosphate
modified_base             21
                          mod_base = OTHER
                          note = 2'-O-(2-methoxyethyl) adenosine 5'-thiophosphate
modified_base             22
                          mod_base = OTHER
                          note = 2'-O-(2-methoxyethyl) 5-methyl cytidine
                          5'-thiophosphate
modified_base             23
                          mod_base = OTHER
                          note = 2'-O-(2-methoxyethyl) 5-methyl cytidine
                          5'-thiophosphate
modified_base             24
                          mod_base = OTHER
                          note = 2'-O-(2-methoxyethyl) adenosine 5'-thiophosphate
misc_feature              24
                          note = 3'-O attached to a GalNAc-comprising compound via a
                          linker
SEQUENCE: 40
ggactggact aaccacagaa acca                                              24

SEQ ID NO: 41             moltype =  length =
SEQUENCE: 41
000

SEQ ID NO: 42             moltype =  length =
SEQUENCE: 42
000

SEQ ID NO: 43             moltype =  length =
SEQUENCE: 43
000

SEQ ID NO: 44             moltype =  length =
SEQUENCE: 44
000

SEQ ID NO: 45             moltype = DNA   length = 6460
FEATURE                   Location/Qualifiers
source                    1..6460
                          mol_type = other DNA
                          organism = Homo sapiens
SEQUENCE: 45
agatcttccc agaggacggt ttgaaaggaa ggcagagagg gcactgggag gaggcagtgg     60
gagggcggag ggcggggggcc ttcggggtgg gcgcccaggg tagggcaggt ggccgcgggcg   120
tggaggcagg gagaatgcga ctctccaaaa ccctcgtcga catggacatg gccgactaca    180
gtgctgcact ggacccagcc tacaccaccc tggaatttga gaatgtgcag gtgttgacga    240
tgggcaatga cacgtcccca tcagaaggca ccaacctcaa cgcgcccaac agcctggggtg   300
tcagcgccct gtgtgccatc tgcgggggacc gggccacggg caaacactac ggtgcctcga    360
gctgtgacgg ctgcaagggc ttcttccgga ggagcgtgcg gaagaaccac atgtactcct    420
gcagatttag ccggcagtgc gtggtggaca aagacaagag gaaccagtgc cgctactgca    480
ggctcaagaa atgcttccgg gctggcatga agaaggaagc cgtccagaat gagcgggacc    540
ggatcagcac tcgaaggtca agctatgagg acagcagcct gccctccatc aatgcgctcc    600
tgcaggcgga ggtcctgtcc cgacagatca cctcccccgt ctccgggatc aacggcgaca    660
ttcgggcgaa gaagattgcc agcatcgcag atgtgtgtga gtccatgaag gagcagctgc    720
tggttctcgt tgagtgggcc aagtacatcc agcttttctg cgagctcccc ctggacgacc    780
aggtggccct gctcagagcc catgctggcg agcacctgct gctcggagcc accaagagat    840
ccatggtgtt caaggacgtg ctgctcctag gcaatgacta cattgtccct cggcactgcc    900
cggagctggc ggagatgagc cgggtgtcca tacgcatcct tgacgagctg gtgctgccct    960
tccaggagct gcagatcgat gacaatgagt atgcctacct caaagccatc atcttctttg   1020
acccagatgc caaggggctg agcgatccag ggaagatcaa gcggctgcgt tccaggtgc    1080
aggtgagctt ggaggactac atcaacgacc gccagtatga ctcgcgtggc cgctttggag   1140
agctgctgct gctgctgccc accttgcaga gcatcacctg gcagatgatc gagcagatcc   1200
agttcatcaa gctcttcggc atggccaaga ttgacaacct gttgcaggag atgctgctgg   1260
gagggtcccc cagcgatgca ccccatgccc accaccccct gcaccctcac ctgatgcagg   1320
```

-continued

```
aacatatggg aaccaacgtc atcgttgcca acacaatgcc cactcacctc agcaacggac   1380
agatgtccac ccctgagacc ccacagccct caccgccagg tggctcaggg tctgagccct   1440
ataagctcct gccgggagcc gtcgccacaa tcgtcaagcc cctctctgcc atcccccagc   1500
cgaccatcac caagcaggaa gttatctagc aagccgctgg ggcttggggg ctccactggc   1560
tcccccagc cccctaagag agcacctggt gatcacgtgg tcacggcaaa ggaagacgtg   1620
atgccaggac cagtcccaga gcaggaatgg gaaggatgaa gggcccgaga acatggccta   1680
agggccacat cccactgcca cccttgacgc cctgctctgg ataacaagac tttgacttgg   1740
ggagacctct actgccttgg acaacttttc tcatgttgaa gccactgcct tcaccttcac   1800
cttcatccat gtccaacccc cgacttcatc ccaaaggaca gccgcctgga gatgacttga   1860
ggccttactt aaaacccagct cccttcttcc ctagcctggt gcttctcctc tcctagcccc   1920
tgtcatggtg tccagacaga gccctgtgag gctgggtcca attgtggcac ttggggcacc   1980
ttgctcctcc ttctgctgct gcccccacct ctgctgcctc cctctgctgt caccttgctc   2040
agccatcccg tcttctccaa caccacctct ccagaggcca aggaggcctt ggaaacgatt   2100
cccccagtca ttctgggaac atgttgtaag cactgactgg gaccaggcac caggcaggt   2160
ctagaaggct gtggtgaggg aagacgcctt tctcctccaa cccaacctca tcctccttct   2220
tcagggactt gggtgggtac ttgggtgagg atccctgaag gccttcaacc cgagaaaaca   2280
aacccaggtt ggcgactgca acaggaactt ggagtgtgaga ggaaaagcat cagaaagag   2340
cagaccatcc accaggcctt tgagaaaggg tagaattctg gctggtagag caggtgagat   2400
gggacattcc aaagaacagc ctgagccaag gcctagtggt agtaagaatc tagcaagaat   2460
tgaggaagaa tggtgtggga gagggatgat gaagagagag agggcctgct ggagagcata   2520
gggtctggaa caccaggctg aggtcctgat cagcttcaag gagtatgcag ggagctgggc   2580
ttccagaaaa tgaacacagc agttctgcag aggacgggag gctggaagct gggaggtcag   2640
gtgggggtgga tgatataatg cgggtgagag taatgaggct tggggctgga gaggacaaga   2700
tgggtaaacc ctcacatcag agtgacatcc aggaggaata agctcccagg gcctgtctca   2760
agctcttcct tactcccagg cactgtctta aggcatctga catgcatcat ctcatttaat   2820
cctcccttcc tccctattaa cctagagatt gtttttgttt tttattctcc tcctccctcc   2880
ccgccctcac ccgcccccact ccctcctaac ctagagattg ttacagaagc tgaaattgcg   2940
ttctaagagg tgaagtgatt tttttctga aactcacaca actaggaagt ggctgagtca   3000
ggacttgaac ccaggtctcc ctggatcaga acaggagctc ttaactacag tggctgaata   3060
gcttctccaa aggctccctg tgttctcacc gtgatcaagt tgaggggctt ccggctccct   3120
tctacagcct cagaaaccag actcgttctt ctgggaaccc tgcccactcc caggaccaag   3180
attggcctga ggctgcacta aaattcactt agggtcgagc atcctgtttg ctgataaata   3240
ttaaggagaa ttcatgactc ttgacagctt ttctctcttc actccccaag tcaaggggag   3300
gggtggcagg ggtctgtttc ctggaagtca ggctcatctg gcctgttggc atggggggtgg   3360
gacagtgtgc acagtgtggg ggcaggggag ggctaagcag gcctgggttt gagggctgct   3420
ccggagaccg tcactccagg tgcattctgg aagcattaga ccccaggatg gagcgaccag   3480
catgtcatcc atgtggaatc ttggtggctt tgaggacatt ctggaaaatg ccactgacca   3540
gtgtgaacaa aagggatgtg ttatgggggct ggaggtgtga ttaggtagga gggaaactgt   3600
tggaccgact cctgcccect gctcaacact gacccctcg agtggttgga ggcagtgccc   3660
cagtgcccag aaatcccacc attagtgatt gttttttatg agaaagaggc gtggagaagt   3720
attggggcaa tgtgtcaggg aggaatcacc acatccctac ggcagtccca gccaagcccc   3780
caatcccagc ggagactgtg ccctgctcag agctcccaag ccttcccccca ccacctcact   3840
caagtgcccc tgaaatccct gccagacggc tcagcctggt ctgcggtaag gcagggaggc   3900
tggaaccatt tctgggcatt gtggtcattc ccactgtgtt cctccacctc ctccctccag   3960
cgttgctcag acctctgtct tgggagaaag gttgagataa gaatgtccca tggagtgccg   4020
tgggcaacag tggcccttca tgggaacaat ctgttggagc aggggggtcag ttctctgctg   4080
ggaatctaac cctttctgga ggagaaaccc atttccacctt aataacttta ttgtaatgtg   4140
agaaacacaa aacaaagttt acttttttga ctctaagctg acatgatatt agaaaatctc   4200
tcgctctctt tttttttttt tttttttttt ttggctactt gagttgtggt cctaaaacat   4260
aaaatctgat ggacaaacag agggttgctg gggggacaag cgtgggcaca atttccccac   4320
caagacaccc tgatcttcag gcggggtctca ggagcttcta aaaatccgca tggctctcct   4380
gagagtggac agaggagagg agagggtcag aaatgaacgc tcttctattt cttgtcatta   4440
ccaagccaat tactttttgcc aaatttttct gtgatctgcc ctgattaaga tgaattgtga   4500
aatttacatc aagcaattat caaagcgggc tgggtcccat cagaacgacc cacatctttc   4560
tgtgggtgtg aatgtcatta ggtcttgcgc tgacccctga gcccccatca ctgccgcctg   4620
atggggcaaa gaaacaaaaa acatttctta ctcttctgtg ttttaacaaa agtttataaa   4680
acaaaataaa tggcgcatat gttttctaag tccttggata agtatctttt ctttcaggta   4740
tcagaaataa gactgaatct tctggttcta cttggggggtt aaaaaatttt ttttaaagga   4800
agaatgagaa tagtttttata gttctttgtg atgtgcagaa tgttttttgtg tccattataa   4860
tttttcagtc ttcacatcaa gaggtaagca gttagacatg attactccca ctttccagat   4920
gaggagactg aggcttgggg gaagtgactt ctccttggaag gcagaggtgg acatctaacc   4980
ctggtctctt gattccaagt acttagtata tcgagagagt gaaagttgat ccccccttctt   5040
gaagagggga gtgatgaggg gagagtgcaa tggcaagatc tggaagaatg gcaagagggt   5100
ccaaggtgtct gtcatcctcc accaaggttc aagacagaac cttttgctgg gtcacctcaa   5160
tctgccagca atggaagatg agtagctgtg gggacatttc ataaaagcaa gtggtttttt   5220
tgtttttgttt tgtttttgttt tttgtttttt tttctagaac aaggctgtgc acagtggctc   5280
acctctgtaa tcccagcact ttgggaggct gaggcgggag gatcacttga gctcaggagt   5340
tcgagaccag ccagagcaat ataaggagac cccatctcta caaaaaattt aaaaattagc   5400
caggtatagt ggtgtgtgcc tatagtacca gctactctga aggctgaggt gggaagattg   5460
cttcagccca ggagttcgag gatgcagtga gctatgaatg caacactgca ctacagcctg   5520
gatgaaagaa caagactctg tctcaaaaca taaataataa gtaaaaagaa taaaagcaag   5580
agatgcactt gagaatctcc agccagatct gtagccactg ggcttctctc caaggctaaa   5640
ctattacagg agggtggcct tgtgtctcgg tcaccacaga ccacagcgtt ccattcactc   5700
gggggttgtgc tggagctggc ttgtgagaac tgactgttag cttctcttcc caactccatg   5760
tttgccagtg ccacactgat agcttgaaat tggttattgc cggagtgttt acaccacaag   5820
gactagcaaa ctctacaaat ccgggctttt gttcctggag agcccgttgt taacattcac   5880
cagcacacca cagcattcgg caatggctgg accatgggat gctacatat ggggacatcc   5940
tccttgggga tgagggtaga gcaggggcgat cctttcacct cttccttaag ggaggggaca   6000
aaagttctgg tctgggaagc acacgttttg ctgatcagcg taaccttggg caggtcactc   6060
```

```
caccactccg agcctcatct gtaaagtggg aatgatatct ccctccaggg cagatgtcag  6120
gattcaatgg aatgagatca cagtaactgt gagagctccc gttacatgag gagtacaagt  6180
gaactcttca tgcgcccctt tttagcgaga agttaaccat taaactctcc aggcttcaga  6240
gcacccattc gctgtctacc tgatccctag ggccgctccc gccttcccct gtgccttccc  6300
tccactagtc agcaccagga aatgtttcg ataacgttgc aacggaggcc ttgttcatgc  6360
tgccgccatc ggggacaagc gcggggggg ggggtggag gccagaggag actatttcag  6420
tcctaaattg tgcttaataa acccatatca aaaccataaa                         6460

SEQ ID NO: 46            moltype = DNA  length = 5014
FEATURE                  Location/Qualifiers
source                   1..5014
                         mol_type = other DNA
                         organism = Homo sapiens
SEQUENCE: 46
gcctggctcc cgcgcagcat gcccgccagc gccccgccgc gccgcccgcg gccgccgccg  60
ccgtcgctgt cgctgctgct ggtgctgctg ggcctgggcg gccgccgcct gcgtgcggag  120
ccgggcgacg gcgcgcagac ctgggcccgt ttctcgcggc ctcctgcccc cgaggccgcg  180
ggcctcttcc agggcacctt ccccgacggc ttcctctggg ccgtgggcag ggccgcctac  240
cagaccgagg gcggctggca gcagcacggc aaggtgcgt ccatctggga tacgttcacc  300
caccaccccc tggcacccc gggagactcc cggaacgcca gtctgccgtt gggcgcccg  360
tcgccgctgc agcccgccac cggggacgta gccagcgaca gctacaacaa cgtcttccgc  420
gacacggagg cgctgcgcga gctcggggtc actcactacc gcttctccat ctcgtgggcg  480
cgagtgctcc ccaatggcag cgcgggcgtc cccaaccgcg aggggctgcg ctactaccgg  540
cgcctgctgg agcggctgcg ggagctgggc gtgcagcccg tggtcaccct gtaccactgg  600
gacctgcccc agcgcctgca ggacgcctac ggcggctggg ccaaccgcgc cctggccgac  660
cacttcaggg attacgcgga gctctgcttc cgccacttcg gcggtcaggt caagtactgg  720
atcaccatcg acaaccccta cgtggtggcc tggcacggct acgccaccgg gcgcctggcc  780
cccggcatcc ggggcagccc gcggctcggg tacctggtgg cgcacaacct cctcctggct  840
catgccaaag tctggcatct ctacaatact tctttccgtc ccactcaggg aggtcaggtg  900
tccattgccc taagctctca ctggatcaat cctcgaagaa tgaccgacca cagcatcaaa  960
gaatgtcaaa aatctctgga ctttgtacta ggttggtttg ccaaacccgt atttattgat  1020
ggtgactatc ccgagagcat gaagaataac ctttcatcta ttctgcctga ttttactgaa  1080
tctgagaaaa agttcatcaa aggaactgct gactttttg ctctttgctt tggacccacc  1140
ttgagttttc aactttttgga ccctcacatg aagttccgcc aattggaatc tcccaacctg  1200
aggcaactgc tttcctggat tgaccttgaa tttaaccatc ctcaaatatt tattgtggaa  1260
aatggctggt ttgtctcagg gaccaccaag agagatgatg ccaaatatat gtattacctc  1320
aaaaagttca tcatggaaac cttaaaagcc atcaagctgg atggggtgga tgtcatcggg  1380
tataccgcat ggtccctcat ggatggtttc gagtggcaca gaggttacag catccaggcgt  1440
ggactcttct atgttgactt tctaagccag gacaagatgt tgttgccaaa gtcttcagcc  1500
ttgttctacc aaaagctgat agagaaaaat ggcttccctc ctttacctga aaatcagccc  1560
ctagaaggga catttccctg tgactttgct tggggagttg ttgacaacta cattcaagta  1620
gataccactc tgtctcagtt taccgacctg aatgtttacc tgtgggatgt ccaccacagt  1680
aaaaggctta ttaaagtgga tggggttgtg accaagaaga ggaaatccta ctgtgttgac  1740
tttgctgcca tccagcccca gatcgcttta ctccaggaaa tgcacgttac acattttcgc  1800
ttctccctgg actgggccct gattctccct ctgggtaacc agtcccaggt gaaccacacc  1860
atcctgcagt actatcgctg catggccagc gagcttgtcc gtgtcaacat caccccagtg  1920
gtggccctgt ggcagcctat ggccccgaac caaggactgc cgcgcctcct ggccaggcag  1980
ggcgcctggg agaaccccta cactgccctg gcctttgcag agtatgcccg actgtgcttt  2040
caagagctcg gccatcacgt caagctttgg ataacgatga atgagccgta tacaaggaat  2100
atgacataca gtgctggcca caaccttctg aaggcccatg ccctggcttg gcatgtgtac  2160
aatgaaaagt ttaggcatgc tcagaatggg aaaatatcca tagccttgca ggctgattgg  2220
atagaacctg cctgcccttt ctcccaaaag gacaaagagg tggctgagag agttttggaa  2280
tttgacattg gctggctggc tgagcccatt ttcggctctg gagattatcc atgggtgatg  2340
agggactggc tgaaccaaag aaacaatttt cttcttcctt atttcactga agatgaaaaa  2400
aagctaatcc agggtacctt tgactttttg gctttaagcc attataccac catccttgta  2460
gactcagaaa aagaagatcc aataaaatac aatgattacc tagaagtgca agaaatgacc  2520
gacatcacgt ggctcaactc ccccagtcag gtggcggtag tgcccctgggg gttgcgcaaa  2580
gtgctgaact ggctgaagtt caagtacgga gacctcccca tgtacataat atccaatgga  2640
atcgatgacg ggctgcatgc tgaggacgac cagctgaggg tgtattatat gcagaattac  2700
ataaacgaag ctctcaaagc ccacatactg gatggtatca atctttgcgg atactttgct  2760
tattcgttta acgaccgcac agctccgagg tttggcctct atcgttatgc tgcagatcag  2820
tttgagccca aggcatccat gaaacattac aggaaaatta ttgacagcaa tggtttcccg  2880
ggcccagaaa ctctggaaag attttgtcca gaagaattca ccgtgtgtac tgagtgcagt  2940
tttttcaca cccgaaagtc tttactggct ttcatagctt ttctattttt tgcttctatt  3000
atttctctct cccttatatt ttactactcg aagaaaggca gaagaagtta caaatagttc  3060
tgaacatttt tctattcatt cattttgaaa taattatgca gacacatcag ctgttaacca  3120
tttgcacctc taagtgttgt gaaactgtaa atttcataca tttgacttct agaaaacatt  3180
tttgtggctt atgacagagg ttttgaaatg ggcataggta atcgtaaaat attgaataat  3240
gcgaatagtg cctgaatttg ttctcttttt gggtgattaa aaaactgaca ggcactataa  3300
tttctgtaac acactaacaa aagcatgaaa aataggaacc acaccaatgc aacatttgtg  3360
cagaaatttg aatgacaaga ttaggaatat tttcttctgc acccacttct aaatttaatg  3420
tttttctgga agtagtaatt gcaagagttc gaatagaaag ttatgtacca agtaaccatt  3480
tctcagctgc cataataatg cctagtggct tcccctctgt caaatctagt ttcctatgga  3540
aaagaagatg gcagatacag gagagacgac agagggtgaa aggctggaat gttccttttcg  3600
aaagcaatgc ttctatcaaa tactagtatt aatttatgta tctggttaat gacatacttg  3660
gagagcaaat tatggaaatg tgtattttat atgatttttg aggtcctgtc taaaccctgt  3720
gtccctgagg gatctgtctc actggcatct tgttgagggc cttgcacata ggaaactttt  3780
gataagtatc tgcggaaaaa caaacatgaa tcctgtgata ttgggctctt caggaagcat  3840
aaagcaattg tgaaatacag tataccgcag tggctctagg tggaggaaag gaggaaaaag  3900
```

```
tgcttattat gtgcaacatt atgattaatc tgattataca ccatttttga gcagatcttg   3960
gaatgaatga catgaccttt ccctagagaa taaggatgaa ataatcactc attctatgaa   4020
cagtgacact actttctatt ctttagctgt actgtaattt ctttgagttg atagtttac    4080
aaattcttaa taggttcaaa agcaatctgg tctgaataac actggatttg tttctgtgat    4140
ctctgaggtc tattttatgt ttttgctgct acttctgtgg aagtagcttt gaactagttt    4200
tactttgaac tttcacgctg aaacatgcta gtgatatcta gaaagggcta attaggtctc    4260
atcctttaat gccccttaaa taagtcttgc tgattttcag acagggaagt ctctctatta    4320
cactggagct gtttttataga taagtcaata ttgtatcagg caagataaac caatgtcata    4380
acaggcattg ccaacctcac tgacacaggg tcatagtgta taataatata ctgtactata    4440
taatatatca tctttagagg tatgattttt tcatgaaaga taagcttttg gtaatattca    4500
ttttaaagtg gacttattaa aattggatgc tagagaatca agtttatttt atgtatatat    4560
ttttctgatt ataagagtaa tatatgttca ttgtaaaaat ttttaaaaca cagaaactat    4620
atgcaaagaa aaaataaaaa ttatctataa tctcagaacc cagaaatagc cactattaac    4680
atttcctacg tattttattt tacatagatc atattgtata tagttagtat ctttattaat    4740
ttttattatg aaactttcct ttgtcattat tagtcttcaa aagcatgatt tttaatagtt    4800
gttgagtatt ccaccacagg aatgtatcac aacttaaccg ttcccgtttg ttagactagt    4860
ttcttattaa tgttgatgaa tgttgtttaa aaataatttt gttgctacat ttactttaat    4920
ttccttgact gtaaagagaa gtaattttgc tccttgataa agtattatat taataataaa    4980
tctgcctgca actttttgcc ttctttcata atca                                5014
```

```
SEQ ID NO: 47          moltype = DNA  length = 6264
FEATURE                Location/Qualifiers
source                 1..6264
                       mol_type = other DNA
                       organism = Homo sapiens
SEQUENCE: 47
aggctcttgc ggaagtccat gcgccattgg gagggcctcg gccgcggctc tgtgcccttg    60
ctgctgaggg ccacttcctg ggtcattcct ggaccgggag ccgggctggg gctcacacgg    120
gggctcccgc gtggccgtct cggcgcctgc gtgacctccc cgccggcggg atgtggcgac    180
tacgtcgggc cgctgtgtgcc tgtgaggtct gccagtcttt agtgaaacac agctctggaa    240
taaaaggaag tttaccacta caaaaactac atctggtttc acgaagcatt tatcattcac    300
atcatcctac cttaaagctt caacgacccc aattaaggac atcctttcag cagttctctt    360
ctctgacaaa ccttccttta cgtaaactga aattctctcc aattaaatat ggctaccagc    420
ctcgcaggaa tttttggcca gcaagattag ctacgagact cttaaaactt cgctatctca    480
tactaggatc ggctgttggg ggtggctaca cagccaaaaa gacttttgat cagtggaaag    540
atatgatacc ggaccttagt gaatataaat ggattgtgcc tgacattgtg tgggaaattg    600
atgagtatat cgattttgag aaaattagaa aagcccttcc tagttcagaa gaccttgtaa    660
agttagcacc agactttgac aagattgttg aaagccttag cttattgaag gactttttta    720
cctcaggttc tccggaagaa acggcgttta gagcaacaga tcgtggatct gaaagtgaca    780
agcattttag aaaggtgtca gacaaagaga aaattgacca acttcaggaa gaacttctgc    840
acactcagtt gaagtatcag agaatcttgg aacgattaga aaaggagaac aaagaattga    900
gaaaattagt attgcagaaa gatgacaaag gcattcatca tagaaagctt aagaaatctt    960
tgattgacat gtattctgaa gttcttgatg ttctctctga ttatgatgcc agttataata   1020
cgcaagatca tctgccacgg gttgttgtgg ttggagatca gagtgctgga aagactagtg   1080
tgttggaaat gattgcccaa gctcgaatat tcccaagagg atctgggag atgatgacac     1140
gttctccagt taaggtgact ctgagtgaag gtcctcacca tgtggcccta tttaaagata   1200
gttctcggga gtttgatctt accaaagaag aagatcttgc agcattaaga catgaaatag   1260
aacttcgaat gaggaaaaat gtgaaagaag gctgtaccgt tagccctgag accatatcct   1320
taaatgtaaa aggccctgga ctacagagga tggtgcttgt tgacttacca ggtgtgatta   1380
atactgtgac atcaggcatg gctcctgaca caaaggaaac tattttcagt atcagcaaag   1440
cttacatgca gaatcctaat gccatcatac tgtgtattca agatggatct gtggatgctg   1500
aacgcagtat tgttacagac ttggtcagtc aaatggaccc tcatggaagg agaaccatat   1560
tcgttttgac caaagtagac ctggcagaga aaaatgtagc cagtccaagc aggattcagc   1620
agataattga aggaaagctc ttcccaatga agctttagg ttattttgct gttgtaacag    1680
gaaaagggaa cagctctgaa agcattgaag ctataagaga atatgaagaa gagtttttttc   1740
agaattcaaa gctcctaaag acaagcatgc taaaggcaca ccaagtgact acaagaaatt   1800
taagccttgc agtatcagac tgctttttgga aaatggtacg agagtctgtt gaacaacagg   1860
ctgatagttt caaagcaaca cgtttttaacc ttgaaactga atggaagaat aactatcctc   1920
gcctgcggga acttgaccgg aatgaactat ttgaaaaagc taaaaatgaa atccttgatg   1980
aagttatcag tctgagccag gttacaccaa aacattggga ggaaatcctt caacaatctt   2040
tgtgggaaag agtatcaact catgtgattg aaaaacatcta ccttccagct gcgcagacca   2100
tgaattcagg aactttttaac accacagtgg atatcaagct taaacagtgg actgataaac   2160
aacttcctaa taaagcagta gaggttgctt gggagaccct acaagaagaa ttttcccgct   2220
ttatgacaga accgaaaggg aaagagcatg atgacatatt tgataacctt aaagaggctg   2280
ttaaggaaga aagtattaaa cgacacaagt ggaatgactt tgcggaggac agcttgaggg   2340
ttattcaaca caatgctttg gaagaccgat ccatatctga taaacagcaa tgggatgcag   2400
ctatttattt tatggaagag gctctgcagg ctcgtctcaa ggatactgaa aatgcaattg   2460
aaaacatggt gggtccagac tggaaaaaga ggtggttata ctggaagaat cggacccaag   2520
aacagtgtgt tcacaatgaa accaagaatg aattggagga gatgttgaaa tgtaatgagg   2580
agcacccagc ttatcttgca agtgatgaaa taaccacagt ccggaagaac cttgaatccc   2640
gaggagtaga agtagatcca agcttgatta aggatacttg gcatcaagtt tatagaagac   2700
atttttaaa aacagctcta aaccattgta acctttgtcg aagaggtttt tattactacc   2760
aaaggcattt tgtagattct gagttggaat gcaatgatgt ggtcttgttt tggcgtatac   2820
agcgcatgct tgctatcacc gcaaatactt taaggcaaca acttacaaat actgaagtta   2880
ggcgattaga gaaaaatgtt aaagaggtat tggaagattt tgctgaagat ggtgagaaga   2940
agattaaatt gcttactggt aaacgcgttc aactggcgga agacctcaag aaaagttagag   3000
aaattcaaga aaaacttgat gctttcattg aagctcttca tcaggagaaa taaattaaaa   3060
tcgtactcat aatcagctct gcatacatct gaagaacaaa aacatcaacg tcttttgtcc   3120
agcctctttt tcttctgctg ttccacctttt ctaaacatac aataaagtca tgggataaaa   3180
```

```
ataatcgatg tatgttacgg gcgctttaac catcagctgc ctctcgaatg gaagaacagt   3240
ggtaatggat taacatccta ttttgttgta ctaaagtgac aaatcggaat aatataattg   3300
gtatggccat taggttcagt ccttgaagat aagaaacttg ttctctgttt gttgtcttat   3360
ttgtggtggc actcgtttaa tggattaact gaggttgctc aatgttcagt ttcttttcca   3420
gaaatacaat gctaggtgtt ttgaaataaa acttatatag caattgttta aagttatcaa   3480
ttgtatataa aatcacagta gcctgctaaa tcattgtatg tgtctgtagt attctattcc   3540
cagaaactat ttgaccatga taattcagtt tatattcacc acatgaaaga aaaatgggta   3600
acagaagaac ccttaaaaca ggttaatttg gattgtaacg ttcagtgaaa gaaatttcaa   3660
cccttcatag ccagcgaaga aatttgcctt ggaagccaag tcagtaccag cttacctatt   3720
tgattcagtt gctgttttct cactctctat atccatttga aattgattta ttttagatgt   3780
tgtatactta cgttaggctt tctgttaata gtggttttc tcctgttgac agagccaccg   3840
gattatgaca caggatgagg aagattaagg ataatcaatt gactaatttc atttagaata   3900
ttatcaaaca tttcaactag gtatcagaaa aaggctttct ttcataagac tattttaaat   3960
agaaattatt tcaacaatta aagtaatgtt gaccatcccc ctctcagctg aataaagaaa   4020
aatttagttc aatttattgc aatttaatta caatactacc ttcacaacat tttcatgtgt   4080
tttaaataaa tatttttttaa ttggctaaag gacattcaag caaagaaatg ctttctttac   4140
ttaaaatgtc tatctcattt gctgcctttt cactaagcct ttactttgtt aataaaagtg   4200
tccattgtgt gatgtttttg attttacagt ttgctaaatc ttattttctt ggagttgctt   4260
tttggtaaca gccccattgc tactccccat tttattgttt tacatcaatg catgcttcgt   4320
tgtgatccct caagatgtaa cacttggtat gctcggttga ggatatgaaa aaatacttcc   4380
gaaaccagga attcaatgta tgtttgtttt atactgtttg ataagaaaag taggtccagc   4440
cttaagcagc acagatgcgc tggtagatgc atagtcaaga acttttttta tttcttttag   4500
gtctagggac aggagtgaat agaaaggagg gagagctcta ttatgttcta tacacagatt   4560
aggagatgac cttactgggt acaccccctct aaccagtgct tacaggttaa tgcatgttaa   4620
tgaatatttt tgcagttgta aagcataaca attacaacta cacatctatt tctaaagaat   4680
aaaacaggac catatttatt tacttctgtc aactatagaa agaaagacct tcagctgtat   4740
ttccacagat ttctcccaag gaaaaggcta atattagtca ctactgttat cacatccctt   4800
tgtataagtt ttaaaaagag atggagggag atcttcattt ctttgaggag atcagtattg   4860
taacgtatgt gaatagatga taacaattaa tattactaaa agtcccacat gagagtcctg   4920
acgccctctc catgccccac agtaatgtgg cttctttcat gggttttttt ttcttctttt   4980
tagctgatct catcctaagc atgctttatt tttccttgaa agctaggtat ttatcaactg   5040
cagatgttat tgaaagaaaa taaaattcag tctcaagagt aaaccctgtg tcttgtgtct   5100
gtagttcaaa agtcagaaat gattctaatt taaacaaaaa gatactaaat atacagaagt   5160
taaattcgaa ctagccacag aatcatttgt ttttatgtca gaatttgcaa agagtggagt   5220
ggacaaagct ctgtatggaa gactgaacaa ctgtaaatag atgatatcca aacttaattt   5280
ggctaggact tcaattttaa aaatcagtgt acctaggcag tgcacagcac gaaataagtg   5340
gcccttgcag cttccccgtt taacccactg tgctatagtt gcgggtggaa cagtcaacct   5400
ttctagtagt ttatgatatt gccctctttg tattcccatt ttctacagtt ttttccgcag   5460
acttctttct gcaaattatt cagcctccaa atgcaaatga atgatataaa aataagtagg   5520
gaacatggca gagagtggtg cttcccagcc tcacaatgtg ggaatttgac ataggatgag   5580
agtcagagta taggtttaaa agataaaatc tttagttaat aattttgtat ttatttattc   5640
tagatgtatg tatctgagga aagaaatctg gtattttttgc tttccaataa aggggatcaa   5700
agtaatggtt tttctctcag ttctctaagc tggtctatgt tatagctcta gcagtatgga   5760
aatgtgcttt aaaatatgct tacctttttga atgatcatgg ctatatgttg ttgagatatt   5820
tgaaacttac cttgtttttca cttgtgcact gtgaatgaac tttgtattat ttttttaaaa   5880
ccttcacatt acgtgtagat attattgcaa cttatatttt gcctgagctt gatcaaaggt   5940
catttgtgta gatgagtaat taaaaaatat ttaaatcaca ttataattct attattggag   6000
agcatctttt aaattttttt ctgttttaac gagggaaaga gaaacctgta tacctagggt   6060
cattatttga ccccatagta taaccagatt catggtctaa caagctctca gtgtggcttt   6120
tctctgaatg cttgaatttc acatgccttg catttcacag ttgtactcca tggtcaaccg   6180
gtgctttttt tcacatcgtg gtacttgtca aaacattttg ttattttcct tggtaaaata   6240
tataaaaaag gttttctaat ttca                                          6264
```

```
SEQ ID NO: 48              moltype = DNA  length = 14140
FEATURE                    Location/Qualifiers
source                     1..14140
                           mol_type = other DNA
                           organism = Homo sapiens
SEQUENCE: 48
gcactgcagc gccagcgtcc gagcgggcgg ccgagctccc ggagcggcct ggccccgagc   60
cccgagcggg cgtcgctcag cagcaggtcg cggccgcagc cccatccagc cccgcgcccg   120
ccatgccgtc cgcgggcccc gcctgagctg cggcctccgc gcgcgggcgg gcctggggac   180
ggcggggcca tgcgcgcgct gccctaacga tgccgcccgc cgcgcccgcc cgcctggcgc   240
tggccctggg cctgggcctg tggctcgggg cgctggcggg gggccccggg ggcggctgcg   300
ggccctgcga gcccccctgc ctctgcggcc cagcgcccgg cgccgcctgc cgcgtcaact   360
gctcgggccg cgggctgcgg acgctcggtc ccgcgctgcg catccccgcg gacgccacag   420
cgctagacgt ctcccacaac ctgctccggg cgctggacgt tgggctcctg gcgaacctct   480
cggcgctggc agagctggat ataagcaaca acaagatttc tacgttagaa gaaggaatat   540
ttgctaattt atttaattta agtgaaataa acctgagtgg gaacccgttt gagtgtgact   600
gtggcctggc gtggctgccg cgatgggcgg aggagcagca ggtgcgggtg gtgcagcccg   660
aggcagccac gtgtgctggg cctggctccc tggctggcca gcctctgctt ggcatccct   720
tgctggacag tggctgtggt gaggagtatg tcgcctgcct ccctgacaac agctcaggca   780
ccgtggcagc agtgtccttt tcagctgccc acgaaggcct gctcagcca gaggcctgca   840
gcgccttctg cttctccacc ggccagggcc tcgcagccct ctcggagcag ggctggtgcc   900
tgtgtggggc ggcccagccc tccagtgcct cctttgcctg cctgtccctc tgctccggcc   960
ccccgccacc tcctgccccc acctgtaggg gccccaccct cctccagcac gtcttcctg   1020
cctcccagg ggcaccctg gtggggcccc acgacctct ggcctctggc cagctagcag   1080
ccttccacat cgctgccccg ctccctgtca ctgccacacg ctgggacttc ggagacggct   1140
ccgccgaggt ggatgccgct gggccggctg cctcgcatcg ctatgtgctg cctgggcgct   1200
```

-continued

```
atcacgtgac ggccgtgctg gccctggggg ccggctcagc cctgctgggg acagacgtgc 1260
aggtggaagc ggcacctgcc gccctggagc tcgtgtgccc gtcctcggtg cagagtgacg 1320
agagcctcga cctcagcatc cagaaccgcg gtggttcagg cctggaggcc gcctacagca 1380
tcgtggccct gggcgaggag ccggcccgag cggtgcaccc gctctgcccc tcggacacgg 1440
agatcttccc tggcaacggg cactgctacc gcctggtggt ggagaaggcg gcctggctgc 1500
aggcgcagga gcagtgtcag gcctgggccg gggccgccct ggcaatggtg gacagtcccg 1560
ccgtgcagcg cttcctggtc tcccgggtca ccaggagcct agacgtgtgg atcggcttct 1620
cgactgtgca gggggtggag gtgggcccag cgccgcaggg cgaggccttc agcctggaga 1680
gctgccagaa ctggctgccc ggggagccac acccagccac agccgagcac tgcgtccggc 1740
tcgggcccac cgggtggtgt aacaccgacc tgtgctcagc gccgcacagc tacgtctgcg 1800
agctgcagcc cggaggccca gtgcaggatg ccgagaacct cctcgtggga gcgcccagtg 1860
gggacctgca gggacccctg acgcctctgg cacagcagga cggcctctca gccccgcacg 1920
agcccgtgga ggtcatggta ttcccgggcc tgcgtctgag ccgtgaagcc ttcctcacca 1980
cggccgaatt tgggacccag gagctccggc ggccgccgtg gctgccggctg caggtgtacc 2040
ggctcctcag cacagcaggg accccggaga acggcagcga gcctgagagc aggtccccgg 2100
acaacaggac ccagctggcc cccgcgtgca tgccagggg acgctggtgc cctggagcca 2160
acatctgctt gccgctggac gcctcctgcc accccaggc ctgcgccaat ggctgcacgt 2220
cagggccagg gctacccggg gcccctatg cgctatggag agagttcctc ttctccgttc 2280
ccgcgggggcc ccccgcgcag tactcggtca ccctccacgg ccaggatgtc ctcatgctcc 2340
ctggtgacct cgttggcttg cagcacgacg ctggccctgg cgcctcctg cactgctcgc 2400
cggctcccgg ccaccctggt ccccgggccc cgtacctctc cgccaacgcc tcgtcatggc 2460
tgccccactt gccagcccag ctggaggga cttgggcctg ccctgcctgt gccctgcggc 2520
tgcttgcagc cacggaacag ctcaccgtgc tgctgggctt gaggcccaac cctggactgc 2580
ggctgcctgg gcgctatgag gtccgggcag aggtgggcaa tggcgtgtcc aggcacaacc 2640
tctcctgcag ctttgacgtg gtctccccag tggctgggct gcgggtcatc taccctgccc 2700
cccgcagccg gcgcctctac gtgcccacca acggctcagc cttggtgctc caggtggact 2760
ctggtgccaa cgccacggcc acggctcgct ggcctggggg cagtgtcagc gcccgctttg 2820
agaatgtctg ccctgccctg gtggccacct tcgtgcccgg ctgcccctgg gagaccaacg 2880
ataccctgtt ctcagtggta gcactgccgt ggctcagtga gggggagcac gtggtggacg 2940
tggtggtgga aaacagcgcc agccgggcca acctcagcct ggggtgacg gcggaggagc 3000
ccatctgtgg cctccgcgcc acgcccagcc ccgaggcccg tgtactgcag ggagtcctag 3060
tgaggtacag ccccgtggtg gaggccggct cggacatggt cttccggtgg accatcaacg 3120
acaagcagtc cctgaccttc cagaacgtgg tcttcaatgt catttatcag agcgcggcgg 3180
tcttcaagct ctcactgacg gcctccaacc acgtgagcaa cgtcaccgtg aactacaacg 3240
taaccgtgga gcggatgaac aggatgcagg gtctgcaggt ctccacagtg ccggccgtgc 3300
tgtcccccaa tgccacgcta gcactgacgg cgggcgtgct ggtggactcg gccgtggagg 3360
tggccttcct gtgggacctt ggggatgggg agcaggcct ccaccagttc cagcctccgt 3420
acaacgagtc cttcccggtt ccagaccct cggtggccca ggtgctggtg gagcacaatg 3480
tcatgcacac ctacgctgcc ccaggtgagt acctcctgac cgtgctggca tctaatgcct 3540
tcgagaacct gacgcagcag gtgcctgtga gcgtgcgcgc ctccctgccc tccgtggctg 3600
tgggtgtgag tgacggcgtc ctggtggccg gccggcccgt caccttctac ccgcacccgc 3660
tgccctcgcc tgggggtgtt ctttacacgt gggacttcgg ggacggctcc cctgtcctga 3720
cccagagcca gccggctgcc aaccacacct atgcctccag gggcacctac cacgtgcgcc 3780
tggaggtcaa caacacggtg agcggtgcgg cggcccaggc ggatgtgcgc gtctttgagg 3840
agctccgcgg actcagcgtg gacatgagcc tggccgtgga gcaggcgcc cccgtggtgg 3900
tcagcgccgc ggtgcagacg ggcgacaaca tcacgtggac cttcgacatg ggggacggca 3960
ccgtgctgtc gggccggag gcaacagtgg agcatgtgta cctgcgggca cagaactgca 4020
cagtgaccgt gggtgcggcc agccccgccg gccacctgtg ccggagcctg cacgtgctga 4080
tcttcgtcct ggaggtgctg cgcgttgaac ccgccgcctg catccccacg cagcctgacg 4140
cgcggctcac ggcctacgtc accgggaacc cggcccacta cctcttcgac tggaccttcg 4200
gggatggtct ctcaaacacg accgtgcggg ggtgcccgac ggtgacacac aacttcacgc 4260
ggagcggcac gttccccctg gcgctggtgc tgtccagccg cgtgaacagg gcgcattact 4320
tcaccagcat ctgcgtggag ccagaggtgg gcaacgtcac cctgcagcca gagaggcagt 4380
ttgtgcagct cggggacgag gcctggctgg tggcatgtgc ctggcccccg ttccctacc 4440
gctacacctg ggactttggc accgagaag ccgcccccac ccgtgccagg ggccctgagg 4500
tgacgttcat ctaccgagac ccaggctcct atcttgtgca agtcaccgcg tccaacaaca 4560
tctctgctgc caatgactca gccctggtgg aggtgcagga gcccgtgctg gtcaccagca 4620
tcaaggtcaa tggctcctt gggctggagc tgcagcagcc gtaccgtgttc tctgctgtgg 4680
gccgtggggcg ccccgccagc tacctgtggg atctgggga cggtgggtgg ctcgagggtc 4740
cggaggtcac ccacgcttac aacagcacag gtgacttcac cgttagggtg gccggctgga 4800
atgaggtgag ccgcagcgag gcctggctca atgtgacggt gaagcggcgc gtgcgggggc 4860
tcgtcgtcaa tgcaagccgc acggtggtgc ccctgaatgg gagcgtgagc ttcagcacgt 4920
cgctggaggc cggcagtgat gtgcgctatt cctgggtgct ctgtgaccgc tgcacgcccca 4980
tccctgggag tcctaccatc tcttacacct tccgctcccg gggcaccttc aatatcatcg 5040
tcacggctga gaacgaggtg ggctccgccc aggacagcat cttcgtctat gtcctgcagc 5100
tcatagaggg gctgcaggtg gtgggcggt gccgctactt ccccaccaac cacacggtac 5160
agctgcaggc cgtggttagg gatggcacca acgtctccta cagctggact gcctggaggg 5220
acaggggccc ggccctggcc ggcagcggca aaggcttctc gctcaccgtg ctcgaggccg 5280
gcacctacca tgtgcagctg cgggccacca acatgctgga gcagcctggg gccgactgca 5340
ccatggactt cgtggagcct gtggggtggc tgatggtggc cgcctccccg aacccagctg 5400
ccgtcaacac aagcgtcacc ctcagtgccg agctggctgg tggcagtggt gtcgtataca 5460
cttggtcctt ggaggagggg ctgagctggg agacctccga gccatttacc acccatagct 5520
tccccacacc cggcctgcac ttggtcacca tgacggcagg gaaccccgctg ggctcagcca 5580
acgccaccgt ggaagtggat gtgcaggtgc ctgtgagtgg cctcagcatc agggccaacg 5640
agcccgagg cagcttcgtg gcggccgggt cctctgtgcc cttttgggg cagctggcca 5700
cgggcaccaa tgtgagctgg tgctgggctg tgccggcgg cagcagcaag cgtgccctc 5760
atgtcaccat ggtcttcccg gatgctgca ccttctccat ccggctcaat gcctccaacg 5820
cagtcagctg ggtctcagcc acgtacaacc tcacggcgga ggagcccatc gtgggcctgg 5880
tgctgtgggc cagcagcaag gtggtggcgc ccgggcagct ggtccatttt cagatcctgc 5940
```

-continued

```
tggctgccgg ctcagctgtc accttccgcc tgcaggtcgg cggggccaac cccgaggtgc  6000
tccccgggcc ccgtttctcc cacagcttcc cccgcgtcgg agaccacgtg gtgagcgtgc  6060
ggggcaaaaa ccacgtgagc tgggcccagg cgcaggtgcg catcgtggtg ctggaggccg  6120
tgagtgggct gcaggtgccc aactgctgcg agcctggcat cgccacgggc actgagagga  6180
acttcacagc ccgcgtgcag cgcggctctc gggtcgccta ggcctggtac ttctcgctgc  6240
agaaggtcca gggcgactcg ctggtcatcc tgtcgggccg cgacgtcacc tacacgcccg  6300
tggccgcggg gctgttggag atccaggtgc gcgccttcaa cgccctgggc agtgagaacc  6360
gcacgctggt gctggaggtt caggacgccg tccagtatgt ggccctgcag agcggcccct  6420
gcttcaccaa ccgctcggcg cagtttgagg ccgccaccag ccccagcccc cggcgtgtgg  6480
cctaccactg ggactttggg gatgggtcgc cagggcagga cacagatgag cccagggccg  6540
agcactccta cctgaggcct ggggactacc gcgtgcaggt gaacgcctcc aacctggtga  6600
gcttcttcgt ggcgcaggcc acggtgaccg tccaggtgct ggcctgccgg gagccggagg  6660
tggacgtggt cctgcccctg caggtgctga tgcggcgatc acagcgcaac tacttggagg  6720
cccacgttga cctgcgcgac tgcgtcacct accagactga gtaccgctgg gaggtgtatc  6780
gcaccgccag ctgccagcgg ccggggcgcc cagcgcgtgt ggccctgccc ggcgtggacg  6840
tgagccggcc tcggctggtg ctgccgcggc tggcgctgcc tgtggggcac tactgctttg  6900
tgtttgtcgt gtcatttggg gacacgccac tgacacagag catccaggcc aatgtgacgg  6960
tggccccga gcgcctggtg cccatcattg agggtggctc ataccgcgtg tggtcagaca  7020
cacgggacct ggtgctggat gggagcgagt cctacgaccc caacctggag gacggcgacc  7080
agacgccgct cagtttccac tgggcctgtg tggcttcgac acagagggag gctggcgggt  7140
gtgcgctgaa ctttgggccc cgcgggagca gcacggtcac cattccacgg gagcggctgg  7200
cggctggcgt ggagtacacc ttcagcctga ccgtgtggaa ggccggccgc aaggaggagg  7260
ccaccaacca gacggtgctg atccggagtg gccgggtgcc cattgtgtcc ttggagtgtg  7320
tgtcctgcaa ggcacaggcc gtgtacgaag tgagccgcag ctcctacgtg tacttggagg  7380
gccgctgcct caattgcagc agcggctcca agcgagggcg gtgggctgca cgtacgttca  7440
gcaacaagac gctggtgctg gatgagacca ccacatccac gggcagtgca ggcatgcgac  7500
tggtgctgcg gcggggcgtg ctgcgggacg gcgaggggta caccttcacg ctcacggtgc  7560
tgggccgctc tggcgaggag gagggctgcg cctccatccg cctgtccccc aaccgcccgc  7620
cgctggggggg ctcttgccgc ctcttccacc tgggcgctgt gcacgccctc accaccaagg  7680
tgcacttcga atgcacgggc tggcatgacg cggaggatgc tggcgccccg ctggtgtacg  7740
ccctgctgct gcgcgcgctgt cgccagggcc actgcgagga gttctgtgtc tacaagggca  7800
gcctctccag ctacggagcc gtgctgcccc cgggtttcag gccacacttc gaggtgggcc  7860
tggccgtggt ggtgcaggac cagctgggag ccgctgtggt cgccctcaac aggtctttgg  7920
ccatcaccct cccagagccc aacggcagcg caacggggct cacagtctgg ctgcacgggc  7980
tcaccgctag tgtgctccca gggctgctgc ggcaggccga tccccagcac gtcatcgagt  8040
actcgttggc cctggtcacc gtgctgaacg agtacgagcg ggccctggac gtggcggcag  8100
agcccaagca cgagcggcag caccgagccc agatacgcaa gaacatcacg gagactctgg  8160
tgtccctgag ggtccacact gtggatgaca tccagcagat cgctgctgcg ctggcccagt  8220
gcatggggcc cagcagggag ctcgtatgcc gctcgtgcct gaagcagacg ctgcacaagc  8280
tggaggccat gatgctcatc ctgcaggcag agaccaccgc gggcaccgtg acgcccaccg  8340
ccatcggaga cagcatcctc aacatcacag gagacctcat ccacctggcc agctcggacg  8400
tgcgggcacc acagccctca gagctgggag ccgagtcacc atctcggatg gtggcgtccc  8460
aggcctacaa cctgacctct gccctcatgc gcatcctcat gcgctcccgc tgctcaacg  8520
aggagccct gacgctggcg ggcgaggaga tcgtggccca gggcaagcgc tcggaccgc  8580
ggagcctgct gtgctatggc ggcgccccag ggctggctg ccacttctcc atccccgagg  8640
ctttttcagcgg ggccctggcc aacctcagtg acgtggtgca gctcatcttt ctggtggact  8700
ccaatccctt tcccttggc tatatcagca actacaccgt ctccaccaag gtggcctcga  8760
tggcattcca gacacaggcc ggcgcccaga tccccatcga gcggctggcc tcagagcgcg  8820
ccatcaccgt gaaggtgccc aacaactcgg actgggctgc ccggggccac cgcagctccg  8880
ccaactccgc caactccgtt gtggtccagc cccaggcctc cgtcggtgct gtggtcaccc  8940
tggacagcag caaccctgcg gccggggctgc atctgcagct caactatacg ctgctggacg  9000
gccactacct gtctgaggaa cctgagccct acctggcagt ctacctacac tcggagcccc  9060
ggcccaatga gcacaactgc tcggctagca ggaggatccg cccagagtca ctccagggtg  9120
ctgaccaccg gccctacacc ttcttcattt ccccgggggag cagagaccca gcggggagtt  9180
accatctgaa cctctccagc cacttccgct ggtcggcgct gcaggtgtcc gtgggcctgt  9240
acacgtccct gtgccagtac ttcagcgagg aggacatggt gtggcggaca gaggggctgc  9300
tgccctggga ggagacctcg ccccgccagg ccgtctgcct cacccgccac ctcaccgcct  9360
tcggcgccag cctcttcgtg cccccaagcc atgtccgctt tgtgtttcct gagccgacag  9420
cggatgtaaa ctacatcgtc atgctgacat gtgctgtgtg cctggtgacc tacatggtca  9480
tggccgccat cctgcacaag ctggaccagt tggatgccag ccgggccgc gccatccctt  9540
tctgtgggca gcggggccgc ttcaagtacg agatcctcgt caagacaggc tggggccggg  9600
gctcaggtac cacggcccac gtgggcatca tgctgtatgg ggtggacagc cggagcggcc  9660
accggcacct ggacggcgac agagccttcc accgcaacag cctggacatc ttccggatcg  9720
ccacccgcgca cagcctgggt agcgtgtgga agatccgcat gtggccacac aacaaaggcc  9780
tcagccctgc ctggttcctg cagcacgtca tcgtcaggga cctgcagacg gcacgcagcg  9840
ccttcttcct ggtcaatgac tggctttcgg tggagacgga ggccaacggg ggcctggtgg  9900
agaaggaggt gctggccgcg agcgacgcag cccttttgcg cttccggcgc ctgctggtgg  9960
ctgagctgca gcgtggcttc tttgacaaagc acatctggct ctccatatgg gaccggccgc  10020
ctcgtagccg tttcactcgc atccagaggg ccacctgctg cgttctcctc atctgcctct  10080
tcctgggcgc caacgccgtg tggtacgggg ctgttggcga ctctgcctac agcacggggc  10140
atgtgtccag gctgagcccg ctgagcgtcg acacagtcgc tgttggcctg gtgtccagcg  10200
tggttgtcta tcccgtctac ctggccatcc ttttttctctt ccggatgtcc cggagcaagg  10260
tggctgggag cccgagcccc acacctgccg ggcagcaggt gctggacatc gacagctgcc  10320
tggactcgtc cgtgctggac agctccttcc tcacgttctc aggcctccac aggtgagcag  10380
cctttgttgg acagatgaag agtgacttgt ttctggatga ttctaagagt ctggtgtgct  10440
ggcccctccgg cgagggaacg ctcagttggc cggacctgct cagtgacccg tccattgtgg  10500
gtagcaatct gcgcgcagctg gcacggggcc aggcgggcca tgggctgggc ccagaggagg  10560
acggcttctc cctggccagc ccctactcgc ctgccaaatc cttctcagca tcagatgaag  10620
acctgatcca gcaggtcctt gccgagggg tcagcagccc agccctacc caagacaccc  10680
```

-continued

```
acatggaaac ggacctgctc agcagcctgt ccagcactcc tggggagaag acagagacgc   10740
tggcgctgca gaggctgggg gagctggggc cacccagccc aggcctgaac tgggaacagc   10800
cccaggcagc gaggctgtcc aggacaggac tggtggaggg tctgcggaag cgcctgctgc   10860
cggcctggtg tgcctccctg gcccacgggc tcagcctgct cctggtggct gtggctgtgg   10920
ctgtctcagg gtgggtgggt gcgagcttcc ccccgggcgt gagtgttgcg tggctcctgt   10980
ccagcagcgc cagcttcctg gcctcattcc tcggctggga gccactgaag gtcttgctgg   11040
aagccctgta cttctcactg gtggccaagc ggctgcaccc ggatgaagat gacaccctgg   11100
tagagagccc ggctgtgacg cctgtgagcg cacgtgtgcc ccgcgtacgg ccaccccacg   11160
gctttgcact cttcctggcc aaggaagaag cccgcaaggt caagaggcta catggcatgc   11220
tgcggagcct cctggtgtac atgcttttc tgctggtgac cctgctggcc agctatgggg   11280
atgcctcatg ccatgggcac gcctaccgtc tgcaaagcgc catcaagcag gagctgcaca   11340
gccgggcctt cctggccatc acgcggtctg aggagctctg gccatggatg gcccacgtgc   11400
tgctgcccta cgtccacggg aaccagtcca gcccagagct ggggcccca cggctgcggc   11460
aggtgcggct gcaggaagca ctctacccag accctcccgg ccccagggtc cacacgtgt   11520
cggccgcagg aggcttcagc accagcgatt acgacgttgg ctgggagagt cctcacaatg   11580
gctcggggac gtgggcctat tcagcgccgg atctgctggg ggcatggtcc tggggctcct   11640
gtgccgtgta tgacagcggg ggctacgtgc aggagctggg cctgagcctg gaggagagcc   11700
gcgaccggct gcgcttcctg cagctgcaca actggctgga caacaggagc cgcgctgtgt   11760
tcctggagct cacgcgctac agcccggccg tggggctgca cgccgccgtc acgctgcgcg   11820
tcgagttccc ggcggccggc cgcgcccg ccgccctcag cgtccgcccc tttgcgctgc   11880
gccgcctcag cgcgggcctc tcgctgcctc tgctcacctc ggtgtgcctg ctgctgttcg   11940
ccgtgcactt cgccgtggcc gaggcccgta cttggcacag ggaagggcgc tggcgcgtgc   12000
tgcggctcgg agcctgggcg cggtggctgc tggtggcgct gacggcggcc acggcactgg   12060
tacgcctcgc ccagctgggt gccgctgacc gccagtggac ccgtttcgtg cgcggccgcc   12120
cgcgccgctt cactagcttc gaccaggtgg cgcagctgag ctccgcagcc cgtggcctgg   12180
cggcctcgct gctcttcctg cttttggtca aggctgccca gcagctacgc ttcgtgcgtc   12240
agtggtccgt ctttggcaag acattatgcc gagctctgcc agagctcctg ggggtcacct   12300
tgggcctggt ggtgctcggg gtagcctacg cccagctggc catcctgctc gtgtcttcct   12360
gtgtggactc cctctggagc gtggcccagg ccctgttggt gctgtgccct gggactgggc   12420
tctctaccct gtgtcctgcc gagtcctggc acctgtcacc cctgctgtgt gtggggctct   12480
gggcactgcg gctgtggggc gccctacggc tgggggctgt tattctccgc tggcgctacc   12540
acgccttgcg tggagagctg taccggccgg cctgggagcc ccaggactac gagatggtgg   12600
agttgttcct gcgcaggctg cgcctctgga tgggcctcag caaggtcaag gagttccgcc   12660
acaaagtccg ctttgaaggg atggagccgc tgccctctcg ctcctccagg ggctccaagg   12720
tatccccgga tgtgcccca cccagcgctg gctccgatgc ctcgcacccc tccacctcct   12780
ccagccagct ggatgggctg agcgtgagcc tgggccggct ggggacaagg tgtgagcctg   12840
agccctcccg cctccaagcc gtgttcgagg ccctgctcac ccagtttgac cgactcaacc   12900
aggccacaga ggacgtctac cagctggagc agcagctgca cagcctgcaa ggccgcagga   12960
gcagccgggc gcccgccgga tcttcccgtg gcccatcccc gggcctgcgg ccagcactgc   13020
ccagccgcct tgcccgggcc agtcggggtg tggacctggc cactggcccc agcaggacac   13080
cccttcgggc caagaacaag gtccacccca gcagcactta gtcctccttc ctggcggggg   13140
tgggccgtgg agtcggagtg gacaccgctc agtattactt tctgccgctg tcaaggccga   13200
gggccaggca gaatggctgc acgtaggttc cccagagagc aggcaggggc atctgtctgt   13260
ctgtgggctt cagcacttta aagaggctgt gtggccaacc aggacccagg gtccctccc   13320
cagctccctt gggaaggaca cagcagtatt ggacggtttc tagcctctga gatgctaatt   13380
tatttccccg agtcctcagg tacagcgggc tgtgcccggc cccacccct gggcagatgt   13440
ccccactgc taaggctgct ggcttcaggg agggttagcc tgcaccgccg ccaccctgcc   13500
cctaagttat tacctctcca gttcctaccg tactcccgc accgtctcac tgtgtgtctc   13560
gtgtcagtaa tttatatggt gttaaaatgt gtatatttt gtatgtcact attttcacta   13620
gggctgaggg gcctgcgccc agagctggcc tcccccaaca cctgctgcgc ttggtaggtg   13680
tggtggcgtt atggcagccc ggctgctgct tggatgcgag cttggccttg ggccggtgct   13740
gggggcacag ctgtctgcca ggcactctca tcaccccaga ggccttgtca tcctcccttg   13800
ccccaggcca ggtagcaaga gagcagcgcc caggcctgct ggcatcaggt ctgggcaagt   13860
agcaggacta ggcatgtcag aggaccccag ggtggttaga ggaaaagact cctcctgggg   13920
gctggctccc agggtggagg aaggtgactg tgtgtgtgtg tgtgtgcgcg cgcgcacgcg   13980
cgagtgtgct gtatggccca agcagcctca aggccctcgg agctggctgt gcctgcttct   14040
gtgtaccact tctgtgggca tggccgcttc tagagcctcg acaccccccc aaccccgca   14100
ccaagcagac aaagtcaata aaagagctgt ctgactgcaa                         14140
```

SEQ ID NO: 49          moltype = DNA   length = 5089
FEATURE                Location/Qualifiers
source                 1..5089
                       mol_type = other DNA
                       organism = Homo sapiens

SEQUENCE: 49

```
aggcggcggc gggcgccggg aagaaaggaa catggctcct gaggcgcaca gcgccgagcg   60
cggcgccgcg cacccgcgcg ccggacgcca gtgaccgcga tggtgaactc cagtcgcgtg   120
cagcctcagc agcccgggga cgccaagcgg ccgcccgcgc cccgcgcggg ggaccgggc   180
cggctgatgg ctggctgcgc gccgtgggc gccagcctcg ccgcccggcc ggcctctgc   240
gagcagcggg gcctggagat cgagatgcag cgcatccggc aggcggccgc gcgggacccc   300
ccggccggag ccgcggcctc cccttctcct ccgctctcgt cgtgctcccg gcaggcgtgg   360
agccgcgata accccggctt cgaggccgag gaggaggag aggaggtgga aggggaagaa   420
ggcggaatgg tggtggagat ggacgtagag tggcgcccgg gcagccggag gtcggccgcc   480
tcctcgtcgt tgagctccgt gggcgcgcgg agccgggggc ttggggggcta ccacggcgcg   540
ggccacccga gcgggaggcg gcgcggcga gaggaccagg gccgccgtg ccccagccca   600
gtcggcggcg gggaccgct gcatcgccac ctcccctgg aagggcagcc gccccgagtg   660
gcctgggcgg agaggctggt tcgcgggctg cgaggtctct ggggaacaag actcatggag   720
gaaagcagca ctaaccgaga gaaatacctt aaaagtgttt tacgggaact ggtcacatac   780
ctccttttc tcatagtctt gtgcatcttg acctacggca tgatgagctc caatgtgtac   840
```

```
tactacacccc ggatgatgtc acagctcttc ctagacaccc ccgtgtccaa aacggagaaa    900
actaacttta aaactctgtc ttccatggaa gacttctgga agttcacaga aggctcctta    960
ttggatgggc tgtactggaa gatgcagccc agcaaccaga ctgaagctga caaccgaagt   1020
ttcatcttct atgagaacct gctgttaggg gttccacgaa tacggcaact ccgagtcaga   1080
aatggatcct gctctatccc ccaggacttg agagatgaaa ttaaagagtg ctatgatgtc   1140
tactctgtca gtagtgaaga tagggctccc tttgggcccc gaaatggaac cgcttggatc   1200
tacacaagtg aaaaagactt gaatggtagt agccactggg gaatcattgc aacttatagt   1260
ggagctggct attatctgga tttgtcaaga acaagagagg aaacagctgc acaagttgct   1320
agcctcaaga aaaatgtctg gctggaccga ggaaccaggg caacttttat tgacttctca   1380
gtgtacaacg ccaacattaa cctgttctgt gtggtcaggt tattggttga attcccagca   1440
acaggtggtg tgattccatc ttggcaattt cagcctttaa agctgatccg atatgtcaca   1500
actttttgatt tcttcctggc agcctgtgag attatctttt gtttctttat cttttactat   1560
gtggtggaag agatattgga aattcgcatt cacaaactac actatttcag gagtttctgg   1620
aattgtctcgg atgttgtgat cgttgtgctg tcagtggtag ctataggaat taacatatac   1680
agaacatcaa atgtggaggt gctactacag tttctggaag atcaaaatac tttccccaac   1740
tttgagcatc tggcatattg gcagatacag ttcaacaata tagctgctgt cacagtattt   1800
tttgtctgga ttaagctctt caaattcatc aattttaaca ggaccatgag ccagctctcg   1860
acaaccatgt ctcgatgtgc caaagacctg tttggctttg ctattatgtt cttcattatt   1920
ttcctagcgt atgctcagtt ggcatacctt gtctttggca ctcaggtcga tgacttcagt   1980
actttccaag agtgtatctt cactcaattc cgtatcattt tgggcgatat caactttgca   2040
gagattgagg aagctaatcg agtttttggga ccaatttatt tcactacatt tgtgttcttt   2100
atgttcttca ttcttttgaa tatgtttttg gctatcatca atgatactta ctctgaagtg   2160
aaatctgact tggcacagca gaaagctgaa atggaactct cagatcttat cagaaagggc   2220
taccataaag ctttggtcaa actaaaactg aaaaaaaata ccgtggatga catttcagag   2280
agtctgcggc aaggaggagg caagttaaac tttgacgaac ttcgacaaga tctcaaaggg   2340
aagggccata ctgatgcaga gattgaggca atattccaa agtacgacca agatggagac   2400
caagaactga ccgaacatga acatcagcag atgagagacg acttggagaa agagagggag   2460
gacctggatt tggatcacag ttctttacca cgtcccatga gcagccgaag tttccctcga   2520
agcctggatg actctgagga ggatgacgat gaagatagcg gacatagctc cagaaggagg   2580
ggaagcattt ctagtggcgt ttcttacgaa gagtttcaag tcctggtgag acgagtggac   2640
cggatggagc attccatcgg cagcatagtg tccaagattg acgccgtgat cgtgaagcta   2700
gagattatgg agcgagccaa actgaagagg agggaggtgc tgggaaggct gttggatggg   2760
gtggccgagg atgaaaggct gggtcgtgac agtgaaatcc ataggggaaca gatggaacgg   2820
ctagtacgtg aagagttgga acgctgggaa tccgatgatg cagcttccca gatcagtcat   2880
ggtttaggca cgccagtggg actaaatggt caacctcgcc ccagaagctc ccgcccatct   2940
tcctcccaat ctacagaagg catggaaggt gcaggtggaa atgggagttc taatgtccac   3000
gtatgatatg tgtgtttcag tatgtgtgtt tctaataagt gaggaagtgg ctgtcctgaa   3060
ttgctgtaac aagcacacta tttatatgcc ctgaccacca taggatgcta gtctttgtga   3120
ccgattgcta atcttctgca cttaattta ttttatataa actttaccca tggttcaaag   3180
atttttttttt ctttttctca tataagaaat ctaggtgtaa atattgagta cagaaaaaaa   3240
atcttcatga tgtgtattga gcggtacgcc cagttgccac catgactgag tcttctcagt   3300
tgacaatgaa gtagcctttt aaagctagaa aactgtcaaa gggcttctga gtttcatttc   3360
cagtcacaaa aatcagtatt gttatttttt tccaagagtg tgaaggaaaa tggggcattc   3420
ctttccactc tggcatagtt catgagctta atacatagct ttcttttaag aaaggagcct   3480
ttttttttcaa ctagcttcct ggggtaaact tttctaaaag ataaaatgga aaggaactcc   3540
aaactatgat agaatctgtg tgaatggtta agatgaatgt taaatactat gctttttttgt   3600
aagttgatcg tatctgatgt ctgtgggact aactgtatca cttaattttt accttatttt   3660
ggctctaatt tgaataagct gagtaaaaacc accaaagatc agttatagga taaaatggca   3720
tctctaacca taacacagga gaattggaag gagccctaag ttgtcactca gtttaatttc   3780
ttttaatggt tagtttagcc taaagattta tctgcatatt cttttttccca tgtggctcta   3840
ctcatttgca actgaattta atgttataac tcatctagtg agaccaactt actaaatttt   3900
tagtatgcac tgaaagtttt tatccaacaa ttatgttcat tttaagcaaa attttaagaa   3960
agttttgaaa ttcataaagc atttggtttt aaactatttt aagaatatag tactcggtca   4020
ggtatgacgg ctcacgcctg taatcccagc actttgggag gccgaaacag gcgaatcact   4080
tgagcccagg agttcaagac caacatgggc aatgtggcga aactccatct ctacaaaaaa   4140
tgcaaaaata aaaaatatag tactcaagta ttcttgatcc tgtgtttcaa aactagaatt   4200
tgtaatgcaa atggagctca gtctaataaa aaagaggttt tggtattaaa agttcataca   4260
ttagacagta tcagccaaaa tttgagttag caacactgtt ttctttacga gagggtctca   4320
cccaaattta tggggagaaa tctatttctc aaaaaaaaaa atcttctttt acagaaatgt   4380
tgagtaaggt gacattttga gcgctaataa gcaaaagagc atgcagtgct gttgaataac   4440
cctcacttgg agaaccaaga gaatcctgtc gtttaatgct atattttaat ttcacaagtt   4500
gttcatttaa ctggtagaat gtcagtccaa tctccaatga gaacatgagc aaaatagacct   4560
ttccaggttg aaagtgaaac atactgggtt tctgtaagtt tttcctcatg gcttcatctc   4620
tatctttact ttctcttgaa tatgctacac aaagttcttt attactacat actaaagttt   4680
gcattccagg gatattgact gtacatattt atgtatatgt accatgttgt tacatgtaaa   4740
caaacttcaa tttgaagtgc agctattatg tggtatccat gtgtatcgac catgtgccat   4800
atatcaatta tggtcactag aaagtctctt tatgatactt tttattgtac tgtttttcat   4860
ttcacttgca aaattttgca gaattcctcc tttctaccca taaattacat atatttttct   4920
tctttagtca tggagaactc cccccctcat ctcttcccta ttatctttcc ctgtgtactg   4980
gtattattaa aaagacatta catacgcaag tctttctcga caatcaagaa tgttattaat   5040
gtgtaaatact gagcacttta cttcttaata aaaacttgat atagtagca          5089
```

SEQ ID NO: 50       moltype = DNA   length = 628
FEATURE            Location/Qualifiers
source             1..628
                     mol_type = other DNA
                     organism = Homo sapiens
SEQUENCE: 50

```
acatttgctt ctgacacaac tgtgttcact agcaacctca aacagacacc atggtgcatc    60
```

```
tgactcctga ggagaagtct gccgttactg ccctgtgggg caaggtgaac gtggatgaag    120
ttggtggtga ggccctgggc aggctgctgg tggtctaccc ttggacccag aggttctttg    180
agtcctttgg ggatctgtcc actcctgatg ctgttatggg caaccctaag gtgaaggctc    240
atggcaagaa agtgctcggt gcctttagtg atggcctggc tcacctggac aacctcaagg    300
gcacctttgc cacactgagt gagctgcact gtgacaagct gcacgtggat cctgagaact    360
tcaggctcct gggcaacgtg ctggtctgtg tgctggccca tcactttggc aaagaattca    420
ccccaccagt gcaggctgcc tatcagaaag tggtggctgg tgtggctaat gccctggccc    480
acaagtatca ctaagctcgc tttcttgctg tccaatttct attaaaggtt cctttgttcc    540
ctaagtccaa ctactaaact gggggatatt atgaagggcc ttgagcatct ggattctgcc    600
taataaaaaa catttatttt cattgcaa                                       628
```

SEQ ID NO: 51          moltype = DNA   length = 2130
FEATURE                Location/Qualifiers
source                 1..2130
                       mol_type = other DNA
                       organism = Homo sapiens
SEQUENCE: 51

```
gctgctgccc aaggaccgcg gagtcggacg caggcagacc atgtggaccc tggtgagctg     60
ggtggcctta acagcagggc tggtggctgg aacgcggtgc ccagatggtc agttctgccc    120
tgtggcctgc tgcctggacc ccggaggagc cagctacagc tgctgccgtc cccttctgga    180
caaatggccc acaacactga gcaggcatct gggtggcccc tgccaggttg atgcccactg    240
ctctgccggc cactcctgca tctttaccgt ctcagggact tccagttgct gcccttccc    300
agaggccgtg gcatgcgggg atggccatca ctgctgccca cggggcttcc actgcagtgc    360
agacgggcga tcctgcttcc aaagatcagg taacaactcc gtgggtgcca tccagtgccc    420
tgatagtcag ttcgaatgcc cggacttctc cacgtgctgt gttatggtcg atggctcctg    480
ggggtgctgc cccatgcccc aggcttcctg ctgtgaagac agggtgcact gctgtccgca    540
cggtgccttc tgcgacctgg ttcacacccg ctgcatcaca cccacgggca cccaccccct    600
ggcaaagaag ctccctgccc agaggactaa caggcagtg gccttgtcca gctcggtcat    660
gtgtccggac gcacggtccc ggtgccctga tggttctacc tgctgtgagc tgcccagtgg    720
gaagtatggc tgctgcccaa tgcccaacgc cacctgctgc tccgatcaac tgcactgctg    780
cccccaagac actgtgtgtg acctgatcca gagtaagtgc ctctccaagg agaacgctac    840
cacggacctc ctcactaagc tgcctgcgca cacagtgggg gatgtgaaat gtgacatgga    900
ggtgagctgc ccagatggct atacctgctg ccgtctacag tcggggggcct ggggctgctg    960
ccctttacc caggctgtgt gctgtgagga ccacatcacc tgctgtcccg cggggtttac   1020
gtgtgacacg cagaagggta cctgtgaaca ggggcccac caggtgccct ggatgggagaa   1080
ggccccagct cacctcagcc tgccagaccc acaagccttg aagagagatg tccctgtga   1140
taatgtcagc agctgtccct cctccgatac ctgctgccaa ctcacgtctg gggagtgggg   1200
ctgctgtcca atcccagagg ctgtctgctg ctcggaccac cagcactgct gcccccaggg   1260
ctacacgtgt gtagctgagg ggcagtgtca gcgaggaagc gagatcgtgg ctggactgga   1320
gaagatgcct gcccgccggg cttccttatc ccaccccaga gacatcggct gtgaccagca   1380
caccagctgc ccggtggggc agacctgctg cccgagcctg ggtgggagct gggcctgctg   1440
ccagttgccc catgctgtgt gctgcgagga tcgccagcac tgctgcccgg ctggctacac   1500
ctgcaacgtg aaggctcgat cctgcagaa ggaagtgctc tctgcccagc ctgccacctt   1560
cctggcccgt agccctcacg tgggtgtgaa ggacgtggag tgtgggggaag gacacttctg   1620
ccatgataac cagacctgct gccgagacaa ccgacagggc tgggcctgct gtccctaccg   1680
ccagggcgtc tgttgtgctg atcggcgcca ctgctgtcct gctggcttcc gctgcgcagc   1740
caggggtacc aagtgtttgc gcagggaggc ccgcgctgtg gacgcccctt tgagggaccc   1800
agccttgaga cagctgctgt gagggacagt actgaagact ctgcagccct cgggacccca   1860
ctcggaggt gccctctgct caggcctccc tagcacctcc ccctaaccaa attctccctg   1920
gaccccattc tgagctcccc atcaccatgg gaggtgggc ctcaatctaa ggccttccct   1980
gtcagaaggg ggttgtggca aaagccacat tacaagctgc catcccctcc ccgtttcagt   2040
ggaccctgtg gccaggtgct tttccctatc cacagggggt tttgtgtgtg tgcgcgtgtg   2100
cgtttcaata aagtttgtac actttcttaa                                    2130
```

SEQ ID NO: 52          moltype = DNA   length = 11940
FEATURE                Location/Qualifiers
source                 1..11940
                       mol_type = other DNA
                       organism = Homo sapiens
SEQUENCE: 52

```
accatagagt gaggcgagga tgaagccgag aggatactgc agaggtctct ggtgcatgtg     60
tgtatgtgtg cgtttgtgtg tgtttgtgtg tctgtgtgtt ctgccccagt gagactgcag    120
cccttgtaaa tactttgaca ccttttgcaa gaaggaatct gaacaattgc aactgaaggc    180
acattgttat catctcgtct ttgggtgatg ctgttcctca ctgcagatgg ataattttcc    240
ttttaatcag aacagcataa gaattatttc tgagtggagg tgaggcttgt ccaaatgtct    300
ttgctatcat ggatttcctg actcctacct gtttgaggtt tgggcaatta tgaataaggc    360
tgctgtatac atccgtgtgc aggattttgt gtggacataa gttttcaact cctttggtta    420
aatcctaagg aatttcatat gcagaataaa tggtaattaa aatgtgcagg atgacaagat    480
ggagcaaaca gtgcttgtac caccaggacc tgacagcttc aacttcttca ccagagaatc    540
tcttgcggct attgaaagac gcattgcaga agaaaaggca aagaatccca aaccagacaa    600
aaaagatgac gacgaaaatg gcccaaagcc aaatagtgac ttggaagctg gaaagaacct    660
tccatttatt tatggagaca ttcctccaga gatggtgtca gagccctgg aggacctgga    720
ccctactat atcaataaga aaactttat agtattgaat aaagggaagg ccatcttccg    780
gttcagtgcc acctcctgcc tgtacatttt aactccctc aatcctctta ggaaaatagc    840
tattaagatt ttggtacatt cattattcag catgctcaatt atgtgcacta ttttgacaaa    900
ctgtgtgttt atgacaatga gtaaccctcc tgattggaca aagaatgtag aatacacctt    960
cacaggaata tatactttg aatcacttat aaaaattatt gcaaggggat tctgtttaga   1020
agattttact ttccttcggg atccatggaa ctggctcgat ttcactgtca ttacatttgc   1080
gtacgtcaca gagtttgtgg acctgggcaa tgtctcggca ttgagaacat tcagagttct   1140
```

-continued

```
ccgagcattg aagacgattt cagtcattcc aggcctgaaa accattgtgg gagccctgat   1200
ccagtctgtg aagaagctct cagatgtaat gatcctgact gtgttctgtc tgagcgtatt   1260
tgctctaatt gggctgcagc tgttcatggg caacctgagg aataaatgta tacaatggcc   1320
tcccaccaat gcttccttgg aggaacatag tatagaaaag aatataactg tgaattataa   1380
tggtacactt ataaatgaaa ctgtctttga gtttgactgg aagtcatata ttcaagattc   1440
aagatatcat tatttcctgg agggtttttt agatgcacta ctatgtggaa atagctctga   1500
tgcaggccaa tgtccagagg gatatatgtg tgtgaaagct ggtagaaatc ccaattatgg   1560
ctacacaagc tttgatacct tcagttgggc tttttttgtcc ttgtttcgac taatgactca   1620
ggacttctgg gaaaatcttt atcaactgac attacgtgct gctgggaaaa cgtacatgat   1680
attttttgta ttggtcattt tcttgggctc attctaccta ataaatttga tcctggctgt   1740
ggtggccatg gcctacgagg aacagaatca ggccaccttg gaagaagcag aacagaaaga   1800
ggccgaattt cagcagatga ttgaacagct taaaaagcaa caggaggcag ctcagcaggc   1860
agcaacggca actgcctcag aacattccag agagcccagt gcagcaggca ggctctcaga   1920
cagctcatct gaagcctcta agttgagttc caagagtgct aaggaaagaa gaaatcggag   1980
gaagaaaaga aaacagaaag agcagtctgg tggggaagaa aaagatgagg atgaattcca   2040
aaaatctgaa tctgaggaca gcatcaggag gaaaggtttt cgcttctcca ttgaagggaa   2100
ccgattgaca tatgaaaaga ggtactcctc cccacaccag tctttgttga gcatccgtgg   2160
ctccctattt tcaccaaggc gaaatagcag aacaagcctt ttcagcttta gagggcgagc   2220
aaaggatgtg ggatctgaga acgacttcgc agatgatgac cacagcacct ttgaggataa   2280
cgagagccgt agagattcct tgtttgtgcc ccgacgacac ggagagagac gcaacagcaa   2340
cctgagtcag accagtaggt catcccggat gctggcagtg tttccagcga atgggaagat   2400
gcacagcact gtggattgca atggtgtggt ttccttggtt ggtggacctt cagttcctac   2460
atcgcctgtt ggacagcttc tgccagaggt gataatagat aagccagcta ctgatgacaa   2520
tggaacaacc actgaaactg aaatgagaaa gagaaggtca agttctttcc acgtttccat   2580
ggactttcta gaagatcctt cccaaaggca acgagcaatg agtatagcca gcattctaac   2640
aaatacagta gaagaacttg aagaatccag gcagaaatgc ccaccctgtt ggtataaatt   2700
ttccaacata ttcttaatct gggactgttc tccatattgg ttaaaagtga aacatgttgt   2760
caacctggtt gtgatggacc catttgttga cctggccatc accatctgta ttgtcttaaa   2820
tactctttc atggccatgg agcactatcc aatgacggac catttcaata atgtgcttac   2880
agtaggaaac ttggttttca ctgggatctt tacagcagag atgtttctga aaattattgc   2940
catggatcct tactattatt tccaagaagg ctggaatatc tttgacggtt ttattgtgac   3000
gcttagcctg gtagaacttg gactcgccaa tgtggaagga ttatctgttc tccgttcatt   3060
tcgattgctg cgagttttca agttggcaaa atcttggcca acgttaaata tgctaataaa   3120
gatcatcggc aattccgtgg gggctctggg aaatttaacc ctcgtcttgg ccatcatcgt   3180
cttcattttt gccgtggtcg gcatgcagct ctttggtaaa agctacaaag attgtgtctg   3240
caagatcgcc agtgattgtc aactcccacg ctggcacatg aatgacttct tccactcctt   3300
cctgattgtg ttccgcgtgc tgtgtgggga gtggatagag accatgtggg actgtatgga   3360
ggttgctggt caagccatgt gccttactgt cttcatgatg gtcatggtga ttggaaacct   3420
agtggtccta aatctctttc tggccttgct tctgagctca tttagtgcag acaaccttgc   3480
agccactgat gatgataatg aaatgaataa tctccaaatt gctgtggata ggatgcacaa   3540
aggagtagct tatgtgaaaa gaaaaatata tgaatttatt caacagtcct tcattaggaa   3600
acaaaagatt ttagatgaaa ttaaaccact tgatgatcta aacaacaaga aagacagttg   3660
tatgtccaat catacagcag aaattgggaa agatcttgac tatcttaaag atgtaaatgg   3720
aactacaagt ggtataggaa ctggcagcag tgttgaaaaa tacattattg atgaaagtga   3780
ttacatgtca ttcataaaca accccagtct tactgtgact gtaccaattg ctgtaggaga   3840
atctgacttt gaaaatttaa acacggaaga ctttagtagt gaatcggatc tggaagaaag   3900
caaagagaaa ctgaatgaaa gcagtagctc atcagaaagt agcactgttg acatcggcgc   3960
acctgtagaa gaacagcccg tagtggaacc tgaagaaact cttgaaccag aagcttgttt   4020
cactgaaggc tgtgtacaaa gattcaagtg ttgtcaaatc aatgtggaag aaggcagagg   4080
aaaacaatgg tggaacctga aaggacgtg tttccgaata gttgaacata actggtttga   4140
gaccttcatt gttttcatga ttctccttag tagtggtgct ctggcatttg aagatatata   4200
tattgatcag cgaaagacga ttaagacgat gttggaatat gctgacaagg ttttcactta   4260
catttttcatt ctggaaatgc ttctaaaatg ggtggcatat ggctatcaaa catatttcac   4320
caatgcctgc tgttggctgg acttcttaat tgttgatgtt tcattggtca gtttaacagc   4380
aaatgccttg ggttactcag aacttggagc catcaaatct ctcaggacac taagagctct   4440
gagacctcta agagccttat ctcgatttga agggatgagg gtggttgtga tgcccttttt   4500
aggagcaatt ccatccatca tgaatgtgct tctggttttgt cttatattct ggctaatttt   4560
cagcatcatg ggcgtaaatt tgtttgctgg caaattctac cactgtatta acaccacaac   4620
tggtgacagg tttgacatcg aagacgtgaa taatcatact gattgcctaa aactaataga   4680
aagaaatgag actgctcgat ggaaaaatgt gaaagtaaac tttgataatg taggatttgg   4740
gtatctctct ttgcttcaag ttgccacatt caaaggatgg atggatataa tgtatgcagc   4800
agttgattcc agaaatgtgg aactccagcc taagtatgaa gaaagtctgt acatgtatct   4860
ttactttgtt attttcatca tctttgggtc cttcttcacc ttgaacctgt ttattggtgt   4920
catcatagat aatttcaacc agcagaaaaa gaagtttgga ggtcaagaca tctttatgac   4980
agaagaacag aagaaatact ataatgcaat gaaaaaatta ggatcgaaaa aaccgcaaaa   5040
gcctatacct cgaccaggaa acaaatttca aggaatggtc tttgacttcg taaccagaca   5100
agtttttgac ataagcatca tgattctcat ctgtcttaac atggtcacaa tgatggtgga   5160
aacagatgac cagagtgaat atgtgactac catttttgtca cgcatcaatc tggtgttcat   5220
tgtgctattt actggagagt gtgtactgaa actcatctct acgccatt attattttac   5280
cattggatgg aatatttttg attttgtggt tgtcattctc tccattgtag gtatgtttct   5340
tgccgagctg atagaaaagt atttcgtgtc ccctaccctg ttccgagtga tccgtcttgc   5400
taggattggc cgaatcctac gtctgatcaa aggagcaaag gggatccgca cgctgctctt   5460
tgctttgatg atgtcccttc ctgcgttgtt taacatcggc ctcctactct tcctagtcat   5520
gttcatctac gccatctttg ggatgtccaa ctttgcctat gttaagaggg aagttgggat   5580
cgatgacatg ttcaactttg agacctttgg caacagcatg atctgcctat tccaaattac   5640
aacctctgct ggctgggatg gattgctagc acccattctc aacagtaagc cacccgactg   5700
tgaccctaat aaagttaacc ctggaagctc agttaaggga gactgtggga acccatctgt   5760
tggaattttttc ttttttgtca gttacatcat catatccttc ctggttgtgg tgaacatgta   5820
catcgcggtc atcctggaga acttcagtgt tgctactgaa gaaagtgcag agcctctgag   5880
```

```
tgaggatgac tttgagatgt tctatgaggt ttgggagaag tttgatcccg atgcaactca   5940
gttcatggaa tttgaaaaat tatctccagtt tgcagctgcg cttgaaccgc ctctcaatct   6000
gccacaacca aacaaactcc agctcattgc catggatttg cccatggtga gtggtgaccg   6060
gatccactgt cttgatatct tatttgcttt tacaaagcgg gttctaggag agagtggaga   6120
gatggatgct ctacgaatac agatggaaga gcgattcatg gcttccaatc cttccaaggt   6180
ctcctatcag ccaatcacta ctactttaaa acgaaaacaa gaggaagtat ctgctgtcat   6240
tattcagcgt gcttacagac gccacctttt aaagcgaact gtaaaacaag cttcctttac   6300
gtacaataaa aacaaaatca aaggtggggc taatcttctt ataaaagaag acatgataat   6360
tgacagaata aatgaaaact ctattacaga aaaaactgat ctgaccatgt ccactgcagc   6420
ttgtccacct tcctatgacc gggtgacaaa gccaattgtg gaaaaacatg agcaagaagg   6480
caaagatgaa aaagccaaag ggaaataaat gaaaataaat aaaaataatt gggtgacaaa   6540
ttgtttacag cctgtgaagg tgatgtattt ttatcaacag gactcctta ggaggtcaat    6600
gccaaactga ctgtttttac acaaatctcc ttaaggtcag tgcctacaat aagacagtga   6660
cccccttgtca gcaaactgtg actctgtgta aaggggagat gaccttgaca ggaggttact   6720
gttctcacta ccagctgaca ctgctgaaga taagatgcac aatggctagt cagactgtag   6780
ggaccagttt caaggggtgc aaacctgtga tttgggggt gtttaacatg aaacacttta     6840
gtgtagtaat tgtatccact gtttgcattt caactgccac atttgtcaca ttttatgga     6900
atctgttagt ggattcatct tttgttaat ccatgtgttt attatatgtg actattttg      6960
taaacgaagt ttctgttgag aaataggcta aggacctcta taacaggtat gccacctggg    7020
gggtatggca accacatggc cctcccagct acacaaagtc gtggtttgca tgagggcatg     7080
ctgcacttag agatcatgca tgagaaaaag tcacaagaaa aacaaattct taaatttcac     7140
catatttctg ggaggggtaa ttgggtgata agtggaggtg ctttgttgat cttgttttgc     7200
gaaatccagc ccctagacca agtagattat ttgtgggtag gccagtaaat cttagcaggt     7260
gcaaacttca ttcaaatgtt tggagtcata aatgttatgt ttcttttgt tgtattaaaa      7320
aaaaaacctg aatagtgaat attgcccctc accctccacc gccagaagac tgaattgacc     7380
aaaattactc tttataaatt tctgcttttt cctgcacttt gtttagccat cttcggctct     7440
cagcaaggtt gacactgtat atgttaatga aatgctattt attatgtaaa tagtcatttt      7500
accctgtggt gcacgtttga gcaaacaaat aatgacctaa gcacagtatt tattgcatca     7560
aatatgtacc acaagaaatg tagagtgcaa gctttacaca ggtaataaaa tgtattctgt      7620
accatttata gatagtttgg atgctatcaa tgcatgttta tattaccatg ctgctgtatc     7680
tggtttctct cactgctcag aatctcattt atgagaaacc atatgtcagt ggtaaagtca     7740
aggaaattgt tcaacagatc tcatttattt aagtcattaa gcaatagttt gcagcacttt     7800
aacagctttt tggttatttt tacattttaa gtggataaca tatggtatat agccagactg     7860
tacagacatg tttaaaaaaa cacactgctt aacctattaa atatgtgttt agaattttat     7920
aagcaaatat aaatactgta aaaagtcact ttattttatt tttcagcatt atgtacataa     7980
atatgaagag gaaattatct tcaggttgat atcacaatca cttttcttac tttctgtcca     8040
tagtacttttt tcatgaaaga aatttgctaa ataagacatg aaaacaagac tgggtagttg     8100
tagatttctg cttttttaaat tacatttgct aatttttagat tatttcacaa ttttaaggag     8160
caaaataggt tcacgattca tatccaaatt atgctttgca attggaaaag ggtttaaaat     8220
tttatttata tttctggtag tacctgcact aactgaattg aaggtagtgc ttatgttatt     8280
tttgttcttt ttttctgact tcggtttatg ttttcatttc tttggagtaa tgctgctcta     8340
gattgttcta aatagaatgt gggcttcata atttttttttt ccacaaaaac agagtagtca     8400
acttatatag tcaattacat caggacattt tgtgtttctt acagaagcaa accataggct     8460
cctctttttcc ttaaaactac ttagataaac tgtattcgtg aactgcatgc tggaaaatgc     8520
tactattatg ctaaataatg ctaaccaaca tttaaaatgt gcaaaactaa taaagattac     8580
attttttattt ttattgtttg cccagtcact ttttgttaac agaatattct aatgatatgg     8640
agatttttta cattacaaat tggggggagaa ggggagcgcg cgcgcacaca cacacacaca    8700
cacacacaca cacacacaca cacagaggca taccacgtt gacaacaaaa cctagggtag      8760
atatgtcact ggaggtaggg ggtaatgacc tcccagaatt acaagcagca ggtgtgttct     8820
ctgttaggag gaagaactgg tgtcagagga tagctagtga ttctaggagg aagagaagta     8880
tggaagccag agtgatggtg gatgacccct tgagctatga aaagaaaccc ttaaatcatc     8940
atttaaaaat ttagaattgc catgtgtgta ggatactgtg tttgctcctc cagagccact     9000
ctctctgctt ctgcatcatt ctgtgtgtcc cagaagggtg acttctacac attgcaaaaa     9060
tgggctctcc tacctttgag ctcccaattg gtttggccaa tgagaagcac cagtgggaaa     9120
gcaccagaga gagaagattg acataggaat atttcttctc caattccttc tttgctgggt     9180
tggcactgga ctcattcctc cccgaaaagt catactccaa tcagactgcc cctcatacaa     9240
ctgaagctac tttctctggg gtcaggtaat cactcctccc cttgctcctt caggtctgct     9300
gctgcattga gagtgctttt gtattccttg tagctttctc ctaacattgc tgacactttt     9360
gtaaatgtcc ccttcatgaa attcttctat atgcctcatt tcagcatgcc atctgtctcc     9420
tgcctggctg acacaaggtg attcaacagc tcatgaaagt cagcaggaag caaagatgtg    9480
ccttgcttca gcttgggggtc ttaatcttgc taacttttgc agataaagaa aaacagtaac     9540
tggggggaacc acagtgaagt ccagtgcaga attcacagat atcatggaaa ggttactcgg    9600
gtggtccaga tagtaaaatt aacagtctaa attaatctat ctaaatttct gaggaacgag      9660
aagccttccc ttgtcatcag gtgaagccag aagagggagt atagcctcaa ccagaaaagg     9720
gacagtaatt aaaaggcttt tcccatcctt gtacaatgga ctgactttgc ctcttcataa      9780
catcacaatc ctaaagcaac acaacaatta attctgatat attagtagct gaaaaaaatt     9840
cccatttcca actaaggtag gtcagaatta taggataaac cctgcagact tttttatacta    9900
cccatccacg ccattactca ctgttacctt tccaaataca aagagaagaa ctggtaaaac     9960
ataatcatat aaatctccat attcattttg aaatatttgg catgatattt tctgtgctaa    10020
aaagtaatta ttcttcaaag aatgatgagg tcatgtcagt aagacacagg aaccaactag    10080
aagggggcttc ccactggcca aatctggggc aagttgagca tcaaaataaa tgatagtaaa    10140
agattataat tcattgaata agaatcagca aatacatact gatgtaagta aataaggaaa    10200
agtacaaatc tgtttcttgc agttgaatgt taattaacaa ttgtagaaga aataacggag    10260
ttagaaaaat cactatttgg caatcaccct aatgacaatt gattcatca agaatcatca     10320
atgagtatta aaactcatgg gtgaaagttt gatgaggaat agggtattta tagcatctta    10380
aagtatctct tctctattaa gtagaaaatt taaacagaag aaagtatact ttggagaaat    10440
acagcagaca atacctttcaa agatatcatc aattatgaga ccaactgata ctatgtgcct    10500
cctgataaga tatactgaaa gggccacatt acttcttggt acacagtcaa aattttaaaa    10560
ccagaatcta actacaagga aaatcaaatt gaggacactc tataaaataa gtggactgaa    10620
```

-continued

```
ctccttaaaa atgtcaatgt catgaaagac aaagaaaggc taaagaattc catgaggtca  10680
aagaactatg acaactaaac acaattctgg atggaatatc aaattaaaaa ataacagata  10740
aataatatta ttgggaaagt tgaataaatt tgaatatgga ctgtttatta gttattagta  10800
ttataatagt gttaatttc ctaattttgt taagactagt gtgcctgttc catgaaaata  10860
gaaaatgttc ttattctctg aaaatgcatg ctaaagtatt taggggtgaa tgcaacaatg  10920
tctgcagctc attcttgaat cagttcaaag aaaaatgagt tacatttata tatatatgta  10980
tgtatgtaaa cagacataga taaaagtata gatgtgtgtg tgtctttaga aaggggagga  11040
tttttttttt tttttttgctg tgtgttactg aagtgcctat gtctgcgtgt tcacactatc  11100
atattttgta tgccctggac tttataattt ctaccttcaa aattagatct actgttggta  11160
attaattcaa tatatactgg tttttttaact actattctca tttcctagca gtaatcttcc  11220
tgaaaagtca cagaaatgat tacattcctt gttcttcata ataatcactg tttaattaaa  11280
ataagaatat tttagaaaag atctgcggca tagtggttaa gaccccagta tttgatgcta  11340
aacagatctg atttggataa cagaaggtgg cactttgctg tttaagctgg ggaccagaca  11400
ctgtgggtat aaatagtaat tccaaacaca gctccacaga gcagcaccct tatgacaagg  11460
ttttcatatg tctatagtta agccagaaaa ttaagaataa tgccataaat atttataaag  11520
ctgaacatat ccaagttaaa gacctttatc ctgaaattgt atctttttaga ttattttcta  11580
aagactaata ccatttaatg tttaaatgtt ctttggaaat gatggtgaga atacgtgata  11640
atgggtcatt ggtttttaata tttttatttag ccaagtggaa aattggcaac ctggtgtcgg  11700
tcctcccatt tgtattttac tggtgcatga aatccaaaag tctagtaacc attgggacag  11760
acaactctac tgcataagtt tgtatgtttg tatatctgta tcacaaagcc cagacactcg  11820
aactatataa acttgtcgca ctaaagacag caaatatgtc tggtaattgc atattcttca  11880
tgtgtgcact ggaatttctt attatataag aaaataaatg tgtttctaaa ccaccatgaa  11940
```

```
SEQ ID NO: 53              moltype = RNA   length = 28
FEATURE                    Location/Qualifiers
source                     1..28
                           mol_type = other RNA
                           organism = synthetic construct
modified_base              1
                           mod_base = OTHER
                           note = 2'-O-methyl guanosine
modified_base              2
                           mod_base = OTHER
                           note = 2'-O-methyl guanosine 5'-thiophosphate
modified_base              3
                           mod_base = OTHER
                           note = 2'-O-methyl adenosine 5'-thiophosphate
modified_base              4
                           mod_base = OTHER
                           note = 2'-O-methyl cytidine
modified_base              5
                           mod_base = OTHER
                           note = 2'-O-methyl uridine
modified_base              6
                           mod_base = OTHER
                           note = 2'-O-methyl guanosine
modified_base              7
                           mod_base = OTHER
                           note = 2'-O-methyl guanosine
modified_base              8
                           mod_base = OTHER
                           note = 2'-O-methyl adenosine
modified_base              9
                           mod_base = OTHER
                           note = 2'-O-methyl cytidine
modified_base              10
                           mod_base = OTHER
                           note = 2'-O-methyl uridine
modified_base              11
                           mod_base = OTHER
                           note = 2'-O-methyl cytidine
modified_base              12
                           mod_base = OTHER
                           note = 2'-O-methyl cytidine
modified_base              13
                           mod_base = OTHER
                           note = 2'-O-methyl uridine
modified_base              14
                           mod_base = OTHER
                           note = 2'-O-methyl uridine
modified_base              15
                           mod_base = OTHER
                           note = 2'-O-methyl uridine
modified_base              16
                           mod_base = OTHER
                           note = 2'-O-methyl guanosine
modified_base              17
                           mod_base = OTHER
                           note = 2'-O-methyl cytidine
```

-continued

```
modified_base      18
                   mod_base = OTHER
                   note = 2'-O-methyl cytidine
modified_base      19
                   mod_base = OTHER
                   note = 2'-O-methyl guanosine
modified_base      20
                   mod_base = OTHER
                   note = 2'-O-methyl uridine
modified_base      21
                   mod_base = OTHER
                   note = 2'-O-methyl guanosine
modified_base      22
                   mod_base = OTHER
                   note = 2'-O-methyl adenosine
modified_base      23
                   mod_base = OTHER
                   note = 2'-O-methyl cytidine
modified_base      24
                   mod_base = OTHER
                   note = 2'-O-methyl cytidine
modified_base      25
                   mod_base = OTHER
                   note = 2'-O-methyl adenosine
modified_base      26
                   mod_base = OTHER
                   note = 2'-O-methyl cytidine
modified_base      27
                   mod_base = OTHER
                   note = 2'-O-methyl guanosine 5'-thiophosphate
modified_base      28
                   mod_base = OTHER
                   note = 2'-O-methyl uridine 5'-thiophosphate
SEQUENCE: 53
ggactggact cctttgccgt gaccacgt                                            28

SEQ ID NO: 54      moltype = RNA  length = 28
FEATURE            Location/Qualifiers
source             1..28
                   mol_type = other RNA
                   organism = synthetic construct
modified_base      1
                   mod_base = OTHER
                   note = 2'-O-methyl guanosine
modified_base      2
                   mod_base = OTHER
                   note = 2'-O-methyl guanosine 5'-thiophosphate
modified_base      3
                   mod_base = OTHER
                   note = 2'-O-methyl adenosine 5'-thiophosphate
modified_base      4
                   mod_base = OTHER
                   note = 2'-O-methyl cytidine
modified_base      5
                   mod_base = OTHER
                   note = 2'-O-methyl uridine
modified_base      6
                   mod_base = OTHER
                   note = 2'-O-methyl guanosine
modified_base      7
                   mod_base = OTHER
                   note = 2'-O-methyl guanosine
modified_base      8
                   mod_base = OTHER
                   note = 2'-O-methyl adenosine
modified_base      9
                   mod_base = OTHER
                   note = 2'-O-methyl cytidine
modified_base      10
                   mod_base = OTHER
                   note = 2'-O-methyl uridine
modified_base      11
                   mod_base = OTHER
                   note = 2'-O-methyl cytidine
modified_base      12
                   mod_base = OTHER
                   note = 2'-O-methyl uridine
modified_base      13
                   mod_base = OTHER
```

-continued

```
                             note = 2'-O-methyl guanosine
modified_base                14
                             mod_base = OTHER
                             note = 2'-O-methyl cytidine
modified_base                15
                             mod_base = OTHER
                             note = 2'-O-methyl uridine
modified_base                16
                             mod_base = OTHER
                             note = 2'-O-methyl cytidine
modified_base                17
                             mod_base = OTHER
                             note = 2'-O-methyl uridine
modified_base                18
                             mod_base = OTHER
                             note = 2'-O-methyl guanosine
modified_base                19
                             mod_base = OTHER
                             note = 2'-O-methyl guanosine
modified_base                20
                             mod_base = OTHER
                             note = 2'-O-methyl guanosine
modified_base                21
                             mod_base = OTHER
                             note = 2'-O-methyl adenosine
modified_base                22
                             mod_base = OTHER
                             note = 2'-O-methyl cytidine
modified_base                23
                             mod_base = OTHER
                             note = 2'-O-methyl uridine
modified_base                24
                             mod_base = OTHER
                             note = 2'-O-methyl guanosine
modified_base                25
                             mod_base = OTHER
                             note = 2'-O-methyl guanosine
modified_base                26
                             mod_base = OTHER
                             note = 2'-O-methyl uridine
modified_base                27
                             mod_base = OTHER
                             note = 2'-O-methyl cytidine 5'-thiophosphate
modified_base                28
                             mod_base = OTHER
                             note = 2'-O-methyl cytidine 5'-thiophosphate
SEQUENCE: 54
ggactggact ctgctctggg actggtcc                                          28

SEQ ID NO: 55               moltype = RNA  length = 28
FEATURE                     Location/Qualifiers
source                      1..28
                            mol_type = other RNA
                            organism = synthetic construct
modified_base               1
                            mod_base = OTHER
                            note = 2'-O-methyl guanosine
modified_base               2
                            mod_base = OTHER
                            note = 2'-O-methyl guanosine 5'-thiophosphate
modified_base               3
                            mod_base = OTHER
                            note = 2'-O-methyl adenosine 5'-thiophosphate
modified_base               4
                            mod_base = OTHER
                            note = 2'-O-methyl cytidine
modified_base               5
                            mod_base = OTHER
                            note = 2'-O-methyl uridine
modified_base               6
                            mod_base = OTHER
                            note = 2'-O-methyl guanosine
modified_base               7
                            mod_base = OTHER
                            note = 2'-O-methyl guanosine
modified_base               8
                            mod_base = OTHER
                            note = 2'-O-methyl adenosine
modified_base               9
```

-continued

```
                        mod_base = OTHER
                        note = 2'-O-methyl cytidine
modified_base           10
                        mod_base = OTHER
                        note = 2'-O-methyl uridine
modified_base           11
                        mod_base = OTHER
                        note = 2'-O-methyl cytidine
modified_base           12
                        mod_base = OTHER
                        note = 2'-O-methyl cytidine
modified_base           13
                        mod_base = OTHER
                        note = 2'-O-methyl uridine
modified_base           14
                        mod_base = OTHER
                        note = 2'-O-methyl uridine
modified_base           15
                        mod_base = OTHER
                        note = 2'-O-methyl adenosine
modified_base           16
                        mod_base = OTHER
                        note = 2'-O-methyl guanosine
modified_base           17
                        mod_base = OTHER
                        note = 2'-O-methyl guanosine
modified_base           18
                        mod_base = OTHER
                        note = 2'-O-methyl cytidine
modified_base           19
                        mod_base = OTHER
                        note = 2'-O-methyl cytidine
modified_base           20
                        mod_base = OTHER
                        note = 2'-O-methyl adenosine
modified_base           21
                        mod_base = OTHER
                        note = 2'-O-methyl uridine
modified_base           22
                        mod_base = OTHER
                        note = 2'-O-methyl guanosine
modified_base           23
                        mod_base = OTHER
                        note = 2'-O-methyl uridine
modified_base           24
                        mod_base = OTHER
                        note = 2'-O-methyl uridine
modified_base           25
                        mod_base = OTHER
                        note = 2'-O-methyl cytidine
modified_base           26
                        mod_base = OTHER
                        note = 2'-O-methyl uridine
modified_base           27
                        mod_base = OTHER
                        note = 2'-O-methyl cytidine 5'-thiophosphate
modified_base           28
                        mod_base = OTHER
                        note = 2'-O-methyl guanosine 5'-thiophosphate
SEQUENCE: 55
ggactggact ccttaggcca tgttctcg                                     28

SEQ ID NO: 56           moltype = RNA  length = 27
FEATURE                 Location/Qualifiers
source                  1..27
                        mol_type = other RNA
                        organism = synthetic construct
modified_base           1
                        mod_base = OTHER
                        note = 2'-O-methyl guanosine
modified_base           2
                        mod_base = OTHER
                        note = 2'-O-methyl guanosine 5'-thiophosphate
modified_base           3
                        mod_base = OTHER
                        note = 2'-O-methyl adenosine 5'-thiophosphate
modified_base           4
                        mod_base = OTHER
                        note = 2'-O-methyl cytidine
```

-continued

```
modified_base       5
                    mod_base = OTHER
                    note = 2'-O-methyl uridine
modified_base       6
                    mod_base = OTHER
                    note = 2'-O-methyl guanosine
modified_base       7
                    mod_base = OTHER
                    note = 2'-O-methyl guanosine
modified_base       8
                    mod_base = OTHER
                    note = 2'-O-methyl adenosine
modified_base       9
                    mod_base = OTHER
                    note = 2'-O-methyl cytidine
modified_base       10
                    mod_base = OTHER
                    note = 2'-O-methyl uridine
modified_base       11
                    mod_base = OTHER
                    note = 2'-O-methyl guanosine
modified_base       12
                    mod_base = OTHER
                    note = 2'-O-methyl uridine
modified_base       13
                    mod_base = OTHER
                    note = 2'-O-methyl guanosine
modified_base       14
                    mod_base = OTHER
                    note = 2'-O-methyl guanosine
modified_base       15
                    mod_base = OTHER
                    note = 2'-O-methyl cytidine
modified_base       16
                    mod_base = OTHER
                    note = 2'-O-methyl uridine
modified_base       17
                    mod_base = OTHER
                    note = 2'-O-methyl uridine
modified_base       18
                    mod_base = OTHER
                    note = 2'-O-methyl cytidine
modified_base       19
                    mod_base = OTHER
                    note = 2'-O-methyl adenosine
modified_base       20
                    mod_base = OTHER
                    note = 2'-O-methyl adenosine
modified_base       21
                    mod_base = OTHER
                    note = 2'-O-methyl cytidine
modified_base       22
                    mod_base = OTHER
                    note = 2'-O-methyl adenosine
modified_base       23
                    mod_base = OTHER
                    note = 2'-O-methyl uridine
modified_base       24
                    mod_base = OTHER
                    note = 2'-O-methyl guanosine
modified_base       25
                    mod_base = OTHER
                    note = 2'-O-methyl adenosine
modified_base       26
                    mod_base = OTHER
                    note = 2'-O-methyl guanosine 5'-thiophosphate
modified_base       27
                    mod_base = OTHER
                    note = 2'-O-methyl adenosine 5'-thiophosphate
SEQUENCE: 56
ggactggact gtggcttcaa catgaga                                      27

SEQ ID NO: 57       moltype = RNA  length = 24
FEATURE             Location/Qualifiers
source              1..24
                    mol_type = other RNA
                    organism = synthetic construct
modified_base       1
                    mod_base = OTHER
```

-continued

```
                           note = 2'-O-methyl guanosine
modified_base              2
                           mod_base = OTHER
                           note = 2'-O-methyl guanosine 5'-thiophosphate
modified_base              3
                           mod_base = OTHER
                           note = 2'-O-methyl adenosine 5'-thiophosphate
modified_base              4
                           mod_base = OTHER
                           note = 2'-O-methyl cytidine
modified_base              5
                           mod_base = OTHER
                           note = 2'-O-methyl uridine
modified_base              6
                           mod_base = OTHER
                           note = 2'-O-methyl guanosine
modified_base              7
                           mod_base = OTHER
                           note = 2'-O-methyl guanosine
modified_base              8
                           mod_base = OTHER
                           note = 2'-O-methyl adenosine
modified_base              9
                           mod_base = OTHER
                           note = 2'-O-methyl cytidine
modified_base              10
                           mod_base = OTHER
                           note = 2'-O-methyl uridine
modified_base              11
                           mod_base = OTHER
                           note = 2'-O-(2-methoxyethyl) adenosine
modified_base              12
                           mod_base = OTHER
                           note = 2'-O-(2-methoxyethyl) adenosine 5'-thiophosphate
modified_base              13
                           mod_base = OTHER
                           note = 2'-O-(2-methoxyethyl) 5-methyl cytidine
                            5'-thiophosphate
modified_base              14
                           mod_base = OTHER
                           note = 2'-O-(2-methoxyethyl) 5-methyl cytidine
                            5'-thiophosphate
modified_base              15
                           mod_base = OTHER
                           note = 2'-O-(2-methoxyethyl) adenosine 5'-thiophosphate
modified_base              16
                           mod_base = OTHER
                           note = 2'-O-(2-methoxyethyl) 5-methyl cytidine
                            5'-thiophosphate
modified_base              17
                           mod_base = OTHER
                           note = 2'-O-(2-methoxyethyl) adenosine 5'-thiophosphate
modified_base              18
                           mod_base = OTHER
                           note = 2'-O-(2-methoxyethyl) guanosine 5'-thiophosphate
modified_base              19
                           mod_base = OTHER
                           note = 2'-O-(2-methoxyethyl) adenosine 5'-thiophosphate
modified_base              20
                           mod_base = OTHER
                           note = 2'-O-(2-methoxyethyl) adenosine 5'-thiophosphate
modified_base              21
                           mod_base = OTHER
                           note = 2'-O-(2-methoxyethyl) adenosine 5'-thiophosphate
modified_base              22
                           mod_base = OTHER
                           note = 2'-O-(2-methoxyethyl) 5-methyl cytidine
                            5'-thiophosphate
modified_base              23
                           mod_base = OTHER
                           note = 2'-O-(2-methoxyethyl) 5-methyl cytidine
                            5'-thiophosphate
modified_base              24
                           mod_base = OTHER
                           note = 2'-O-(2-methoxyethyl) adenosine 5'-thiophosphate
SEQUENCE: 57
ggactggact aaccacagaa acca                                          24

SEQ ID NO: 58             moltype = RNA   length = 29
```

-continued

```
FEATURE          Location/Qualifiers
source           1..29
                 mol_type = other RNA
                 organism = synthetic construct
modified_base    1
                 mod_base = OTHER
                 note = 2'-O-methyl guanosine
modified_base    2
                 mod_base = OTHER
                 note = 2'-O-methyl guanosine 5'-thiophosphate
modified_base    3
                 mod_base = OTHER
                 note = 2'-O-methyl adenosine 5'-thiophosphate
modified_base    4
                 mod_base = OTHER
                 note = 2'-O-methyl cytidine
modified_base    5
                 mod_base = OTHER
                 note = 2'-O-methyl uridine
modified_base    6
                 mod_base = OTHER
                 note = 2'-O-methyl guanosine
modified_base    7
                 mod_base = OTHER
                 note = 2'-O-methyl guanosine
modified_base    8
                 mod_base = OTHER
                 note = 2'-O-methyl adenosine
modified_base    9
                 mod_base = OTHER
                 note = 2'-O-methyl cytidine
modified_base    10
                 mod_base = OTHER
                 note = 2'-O-methyl uridine
modified_base    11
                 mod_base = OTHER
                 note = 2'-O-(2-methoxyethyl) guanosine
modified_base    12
                 mod_base = OTHER
                 note = 2'-O-(2-methoxyethyl) thymidine 5'-thiophosphate
modified_base    13
                 mod_base = OTHER
                 note = 2'-O-(2-methoxyethyl) thymidine 5'-thiophosphate
modified_base    14
                 mod_base = OTHER
                 note = 2'-O-(2-methoxyethyl) thymidine 5'-thiophosphate
modified_base    15
                 mod_base = OTHER
                 note = 2'-O-(2-methoxyethyl) adenosine 5'-thiophosphate
modified_base    16
                 mod_base = OTHER
                 note = 2'-O-(2-methoxyethyl) adenosine 5'-thiophosphate
modified_base    17
                 mod_base = OTHER
                 note = 2'-O-(2-methoxyethyl) adenosine 5'-thiophosphate
modified_base    18
                 mod_base = OTHER
                 note = 2'-O-(2-methoxyethyl) guanosine 5'-thiophosphate
modified_base    19
                 mod_base = OTHER
                 note = 2'-O-(2-methoxyethyl) adenosine 5'-thiophosphate
modified_base    20
                 mod_base = OTHER
                 note = 2'-O-(2-methoxyethyl) adenosine 5'-thiophosphate
modified_base    21
                 mod_base = OTHER
                 note = 2'-O-(2-methoxyethyl) 5-methyl cytidine
                  5'-thiophosphate
modified_base    22
                 mod_base = OTHER
                 note = 2'-O-(2-methoxyethyl) thymidine 5'-thiophosphate
modified_base    23
                 mod_base = OTHER
                 note = 2'-O-(2-methoxyethyl) adenosine 5'-thiophosphate
modified_base    24
                 mod_base = OTHER
                 note = 2'-O-(2-methoxyethyl) 5-methyl cytidine
                  5'-thiophosphate
modified_base    25
```

-continued

```
                          mod_base = OTHER
                          note = 2'-O-(2-methoxyethyl) adenosine 5'-thiophosphate
modified_base             26
                          mod_base = OTHER
                          note = 2'-O-(2-methoxyethyl) adenosine 5'-thiophosphate
modified_base             27
                          mod_base = OTHER
                          note = 2'-O-(2-methoxyethyl) guanosine 5'-thiophosphate
modified_base             28
                          mod_base = OTHER
                          note = 2'-O-(2-methoxyethyl) 5-methyl cytidine
                           5'-thiophosphate
modified_base             29
                          mod_base = OTHER
                          note = 2'-O-(2-methoxyethyl) 5-methyl cytidine
                           5'-thiophosphate
misc_feature              29
                          note = 3'-O attached to a GalNAc-comprising compound via a
                           linker
SEQUENCE: 58
ggactggact gtttaaagaa ctacaagcc                                           29

SEQ ID NO: 59             moltype = RNA  length = 29
FEATURE                   Location/Qualifiers
source                    1..29
                          mol_type = other RNA
                          organism = synthetic construct
modified_base             1
                          mod_base = OTHER
                          note = 2'-O-methyl guanosine
modified_base             2
                          mod_base = OTHER
                          note = 2'-O-methyl guanosine 5'-thiophosphate
modified_base             3
                          mod_base = OTHER
                          note = 2'-O-methyl adenosine 5'-thiophosphate
modified_base             4
                          mod_base = OTHER
                          note = 2'-O-methyl cytidine
modified_base             5
                          mod_base = OTHER
                          note = 2'-O-methyl uridine
modified_base             6
                          mod_base = OTHER
                          note = 2'-O-methyl guanosine
modified_base             7
                          mod_base = OTHER
                          note = 2'-O-methyl guanosine
modified_base             8
                          mod_base = OTHER
                          note = 2'-O-methyl adenosine
modified_base             9
                          mod_base = OTHER
                          note = 2'-O-methyl cytidine
modified_base             10
                          mod_base = OTHER
                          note = 2'-O-methyl uridine
modified_base             11
                          mod_base = OTHER
                          note = 2'-O-(2-methoxyethyl) guanosine
modified_base             12
                          mod_base = OTHER
                          note = 2'-O-(2-methoxyethyl) thymidine 5'-thiophosphate
modified_base             13
                          mod_base = OTHER
                          note = 2'-O-(2-methoxyethyl) thymidine 5'-thiophosphate
modified_base             14
                          mod_base = OTHER
                          note = 2'-O-(2-methoxyethyl) thymidine 5'-thiophosphate
modified_base             15
                          mod_base = OTHER
                          note = 2'-O-(2-methoxyethyl) adenosine 5'-thiophosphate
modified_base             16
                          mod_base = OTHER
                          note = 2'-O-(2-methoxyethyl) adenosine 5'-thiophosphate
modified_base             17
                          mod_base = OTHER
                          note = 2'-O-(2-methoxyethyl) adenosine 5'-thiophosphate
modified_base             18
```

```
                         mod_base = OTHER
                         note = 2'-O-(2-methoxyethyl) guanosine 5'-thiophosphate
modified_base            19
                         mod_base = OTHER
                         note = 2'-O-(2-methoxyethyl) adenosine 5'-thiophosphate
modified_base            20
                         mod_base = OTHER
                         note = 2'-O-(2-methoxyethyl) adenosine 5'-thiophosphate
modified_base            21
                         mod_base = OTHER
                         note = 2'-O-(2-methoxyethyl) 5-methyl cytidine
                          5'-thiophosphate
modified_base            22
                         mod_base = OTHER
                         note = 2'-O-(2-methoxyethyl) thymidine 5'-thiophosphate
modified_base            23
                         mod_base = OTHER
                         note = 2'-O-(2-methoxyethyl) adenosine 5'-thiophosphate
modified_base            24
                         mod_base = OTHER
                         note = 2'-O-(2-methoxyethyl) 5-methyl cytidine
                          5'-thiophosphate
modified_base            25
                         mod_base = OTHER
                         note = 2'-O-(2-methoxyethyl) adenosine 5'-thiophosphate
modified_base            26
                         mod_base = OTHER
                         note = 2'-O-(2-methoxyethyl) adenosine 5'-thiophosphate
modified_base            27
                         mod_base = OTHER
                         note = 2'-O-(2-methoxyethyl) guanosine 5'-thiophosphate
modified_base            28
                         mod_base = OTHER
                         note = 2'-O-(2-methoxyethyl) 5-methyl cytidine
                          5'-thiophosphate
modified_base            29
                         mod_base = OTHER
                         note = 2'-O-(2-methoxyethyl) 5-methyl cytidine
                          5'-thiophosphate
SEQUENCE: 59
ggactggact gtttaaagaa ctacaagcc                                          29

SEQ ID NO: 60            moltype = RNA  length = 18
FEATURE                  Location/Qualifiers
source                   1..18
                         mol_type = other RNA
                         organism = synthetic construct
modified_base            1
                         mod_base = OTHER
                         note = 2'-O-(2-methoxyethyl) thymidine
modified_base            2
                         mod_base = OTHER
                         note = 2'-O-(2-methoxyethyl) guanosine 5'-thiophosphate
modified_base            3
                         mod_base = OTHER
                         note = 2'-O-(2-methoxyethyl) 5-methyl cytidine
                          5'-thiophosphate
modified_base            4
                         mod_base = OTHER
                         note = 2'-O-(2-methoxyethyl) adenosine 5'-thiophosphate
modified_base            5
                         mod_base = OTHER
                         note = 2'-O-(2-methoxyethyl) 5-methyl cytidine
                          5'-thiophosphate
modified_base            6
                         mod_base = OTHER
                         note = 2'-O-(2-methoxyethyl) thymidine 5'-thiophosphate
modified_base            7
                         mod_base = OTHER
                         note = 2'-O-(2-methoxyethyl) guanosine 5'-thiophosphate
modified_base            8
                         mod_base = OTHER
                         note = 2'-O-(2-methoxyethyl) adenosine 5'-thiophosphate
modified_base            9
                         mod_base = OTHER
                         note = 2'-O-(2-methoxyethyl) 5-methyl cytidine
                          5'-thiophosphate
modified_base            10
                         mod_base = OTHER
```

-continued

```
                       note = 2'-O-(2-methoxyethyl) guanosine 5'-thiophosphate
modified_base          11
                       mod_base = OTHER
                       note = 2'-O-(2-methoxyethyl) guanosine 5'-thiophosphate
modified_base          12
                       mod_base = OTHER
                       note = 2'-O-(2-methoxyethyl) adenosine 5'-thiophosphate
modified_base          13
                       mod_base = OTHER
                       note = 2'-O-(2-methoxyethyl) adenosine 5'-thiophosphate
modified_base          14
                       mod_base = OTHER
                       note = 2'-O-(2-methoxyethyl) thymidine 5'-thiophosphate
modified_base          15
                       mod_base = OTHER
                       note = 2'-O-(2-methoxyethyl) adenosine 5'-thiophosphate
modified_base          16
                       mod_base = OTHER
                       note = 2'-O-(2-methoxyethyl) 5-methyl cytidine
                        5'-thiophosphate
modified_base          17
                       mod_base = OTHER
                       note = 2'-O-(2-methoxyethyl) adenosine 5'-thiophosphate
modified_base          18
                       mod_base = OTHER
                       note = 2'-O-(2-methoxyethyl) adenosine 5'-thiophosphate
misc_feature           18
                       note = 3'-O attached to a GalNAc-comprising compound via a
                        linker
SEQUENCE: 60
tgcactgacg gaatacaa                                                            18

SEQ ID NO: 61          moltype = RNA  length = 18
FEATURE                Location/Qualifiers
source                 1..18
                       mol_type = other RNA
                       organism = synthetic construct
modified_base          1
                       mod_base = OTHER
                       note = 2'-O-(2-methoxyethyl) thymidine
modified_base          2
                       mod_base = OTHER
                       note = 2'-O-(2-methoxyethyl) guanosine 5'-thiophosphate
modified_base          3
                       mod_base = OTHER
                       note = 2'-O-(2-methoxyethyl) 5-methyl cytidine
                        5'-thiophosphate
modified_base          4
                       mod_base = OTHER
                       note = 2'-O-(2-methoxyethyl) adenosine 5'-thiophosphate
modified_base          5
                       mod_base = OTHER
                       note = 2'-O-(2-methoxyethyl) 5-methyl cytidine
                        5'-thiophosphate
modified_base          6
                       mod_base = OTHER
                       note = 2'-O-(2-methoxyethyl) guanosine 5'-thiophosphate
modified_base          7
                       mod_base = OTHER
                       note = 2'-O-(2-methoxyethyl) adenosine 5'-thiophosphate
modified_base          8
                       mod_base = OTHER
                       note = 2'-O-(2-methoxyethyl) 5-methyl cytidine
                        5'-thiophosphate
modified_base          9
                       mod_base = OTHER
                       note = 2'-O-(2-methoxyethyl) thymidine 5'-thiophosphate
modified_base          10
                       mod_base = OTHER
                       note = 2'-O-(2-methoxyethyl) guanosine 5'-thiophosphate
modified_base          11
                       mod_base = OTHER
                       note = 2'-O-(2-methoxyethyl) guanosine 5'-thiophosphate
modified_base          12
                       mod_base = OTHER
                       note = 2'-O-(2-methoxyethyl) adenosine 5'-thiophosphate
modified_base          13
                       mod_base = OTHER
                       note = 2'-O-(2-methoxyethyl) adenosine 5'-thiophosphate
```

```
modified_base          14
                       mod_base = OTHER
                       note = 2'-O-(2-methoxyethyl) adenosine 5'-thiophosphate
modified_base          15
                       mod_base = OTHER
                       note = 2'-O-(2-methoxyethyl) adenosine 5'-thiophosphate
modified_base          16
                       mod_base = OTHER
                       note = 2'-O-(2-methoxyethyl) 5-methyl cytidine
                        5'-thiophosphate
modified_base          17
                       mod_base = OTHER
                       note = 2'-O-(2-methoxyethyl) adenosine 5'-thiophosphate
modified_base          18
                       mod_base = OTHER
                       note = 2'-O-(2-methoxyethyl) adenosine 5'-thiophosphate
misc_feature           18
                       note = 3'-O attached to a GalNAc-comprising compound via a
                        linker
SEQUENCE: 61
tgcacgactg gaaaacaa                                                    18

SEQ ID NO: 62          moltype = RNA  length = 27
FEATURE                Location/Qualifiers
source                 1..27
                       mol_type = other RNA
                       organism = synthetic construct
modified_base          1
                       mod_base = OTHER
                       note = 2'-O-methyl guanosine
modified_base          2
                       mod_base = OTHER
                       note = 2'-O-methyl guanosine 5'-thiophosphate
modified_base          3
                       mod_base = OTHER
                       note = 2'-O-methyl adenosine 5'-thiophosphate
modified_base          4
                       mod_base = OTHER
                       note = 2'-O-methyl cytidine 5'-thiophosphate
modified_base          5
                       mod_base = OTHER
                       note = 2'-O-methyl uridine 5'-thiophosphate
modified_base          6
                       mod_base = OTHER
                       note = 2'-O-methyl guanosine 5'-thiophosphate
modified_base          7
                       mod_base = OTHER
                       note = 2'-O-methyl guanosine 5'-thiophosphate
modified_base          8
                       mod_base = OTHER
                       note = 2'-O-methyl adenosine 5'-thiophosphate
modified_base          9
                       mod_base = OTHER
                       note = 2'-O-methyl cytidine 5'-thiophosphate
modified_base          10
                       mod_base = OTHER
                       note = 2'-O-methyl uridine 5'-thiophosphate
modified_base          11
                       mod_base = OTHER
                       note = 2'-O-(2-methoxyethyl) adenosine 5'-thiophosphate
modified_base          12
                       mod_base = OTHER
                       note = 2'-O-(2-methoxyethyl) adenosine 5'-thiophosphate
modified_base          13
                       mod_base = OTHER
                       note = 2'-O-(2-methoxyethyl) 5-methyl cytidine
                        5'-thiophosphate
modified_base          14
                       mod_base = OTHER
                       note = 2'-O-(2-methoxyethyl) 5-methyl cytidine
                        5'-thiophosphate
modified_base          15
                       mod_base = OTHER
                       note = 2'-O-(2-methoxyethyl) adenosine 5'-thiophosphate
modified_base          16
                       mod_base = OTHER
                       note = 2'-O-(2-methoxyethyl) 5-methyl cytidine
                        5'-thiophosphate
modified_base          17
```

```
                            mod_base = OTHER
                            note = 2'-O-(2-methoxyethyl) adenosine 5'-thiophosphate
modified_base               18
                            mod_base = OTHER
                            note = 2'-O-(2-methoxyethyl) guanosine 5'-thiophosphate
modified_base               19
                            mod_base = OTHER
                            note = 2'-O-(2-methoxyethyl) adenosine 5'-thiophosphate
modified_base               20
                            mod_base = OTHER
                            note = 2'-O-(2-methoxyethyl) adenosine 5'-thiophosphate
modified_base               21
                            mod_base = OTHER
                            note = 2'-O-(2-methoxyethyl) adenosine 5'-thiophosphate
modified_base               22
                            mod_base = OTHER
                            note = 2'-O-(2-methoxyethyl) 5-methyl cytidine
                             5'-thiophosphate
modified_base               23
                            mod_base = OTHER
                            note = 2'-O-(2-methoxyethyl) thymidine 5'-thiophosphate
modified_base               24
                            mod_base = OTHER
                            note = 2'-O-(2-methoxyethyl) adenosine 5'-thiophosphate
modified_base               25
                            mod_base = OTHER
                            note = 2'-O-(2-methoxyethyl) 5-methyl cytidine
                             5'-thiophosphate
modified_base               26
                            mod_base = OTHER
                            note = 2'-O-(2-methoxyethyl) 5-methyl cytidine
                             5'-thiophosphate
modified_base               27
                            mod_base = OTHER
                            note = 2'-O-(2-methoxyethyl) adenosine 5'-thiophosphate
misc_feature                27
                            note = 3'-O attached to a GalNAc-comprising compound via a
                             linker
SEQUENCE: 62
ggactggact aaccacagaa actacca                                              27

SEQ ID NO: 63               moltype = RNA  length = 27
FEATURE                     Location/Qualifiers
source                      1..27
                            mol_type = other RNA
                            organism = synthetic construct
modified_base               1
                            mod_base = OTHER
                            note = 2'-O-methyl guanosine
modified_base               2
                            mod_base = OTHER
                            note = 2'-O-methyl guanosine 5'-thiophosphate
modified_base               3
                            mod_base = OTHER
                            note = 2'-O-methyl adenosine 5'-thiophosphate
modified_base               4
                            mod_base = OTHER
                            note = 2'-O-methyl cytidine
modified_base               5
                            mod_base = OTHER
                            note = 2'-O-methyl uridine
modified_base               6
                            mod_base = OTHER
                            note = 2'-O-methyl guanosine
modified_base               7
                            mod_base = OTHER
                            note = 2'-O-methyl guanosine 5'-thiophosphate
modified_base               8
                            mod_base = OTHER
                            note = 2'-O-methyl adenosine 5'-thiophosphate
modified_base               9
                            mod_base = OTHER
                            note = 2'-O-methyl cytidine
modified_base               10
                            mod_base = OTHER
                            note = 2'-O-methyl uridine
modified_base               11
                            mod_base = OTHER
                            note = 2'-O-(2-methoxyethyl) adenosine 5'-thiophosphate
```

-continued

```
modified_base      12
                   mod_base = OTHER
                   note = 2'-O-(2-methoxyethyl) adenosine 5'-thiophosphate
modified_base      13
                   mod_base = OTHER
                   note = 2'-O-(2-methoxyethyl) 5-methyl cytidine
                    5'-thiophosphate
modified_base      14
                   mod_base = OTHER
                   note = 2'-O-(2-methoxyethyl) 5-methyl cytidine
                    5'-thiophosphate
modified_base      15
                   mod_base = OTHER
                   note = 2'-O-(2-methoxyethyl) adenosine 5'-thiophosphate
modified_base      16
                   mod_base = OTHER
                   note = 2'-O-(2-methoxyethyl) 5-methyl cytidine
                    5'-thiophosphate
modified_base      17
                   mod_base = OTHER
                   note = 2'-O-(2-methoxyethyl) adenosine 5'-thiophosphate
modified_base      18
                   mod_base = OTHER
                   note = 2'-O-(2-methoxyethyl) guanosine 5'-thiophosphate
modified_base      19
                   mod_base = OTHER
                   note = 2'-O-(2-methoxyethyl) adenosine 5'-thiophosphate
modified_base      20
                   mod_base = OTHER
                   note = 2'-O-(2-methoxyethyl) adenosine 5'-thiophosphate
modified_base      21
                   mod_base = OTHER
                   note = 2'-O-(2-methoxyethyl) adenosine 5'-thiophosphate
modified_base      22
                   mod_base = OTHER
                   note = 2'-O-(2-methoxyethyl) 5-methyl cytidine
                    5'-thiophosphate
modified_base      23
                   mod_base = OTHER
                   note = 2'-O-(2-methoxyethyl) thymidine 5'-thiophosphate
modified_base      24
                   mod_base = OTHER
                   note = 2'-O-(2-methoxyethyl) adenosine 5'-thiophosphate
modified_base      25
                   mod_base = OTHER
                   note = 2'-O-(2-methoxyethyl) 5-methyl cytidine
                    5'-thiophosphate
modified_base      26
                   mod_base = OTHER
                   note = 2'-O-(2-methoxyethyl) 5-methyl cytidine
                    5'-thiophosphate
modified_base      27
                   mod_base = OTHER
                   note = 2'-O-(2-methoxyethyl) adenosine 5'-thiophosphate
misc_feature       27
                   note = 3'-O attached to a GalNAc-comprising compound via a
                    linker SEQUENCE: 63
ggactggact aaccacagaa actacca                                           27

SEQ ID NO: 64      moltype = RNA   length = 23
FEATURE            Location/Qualifiers
source             1..23
                   mol_type = other RNA
                   organism = synthetic construct
modified_base      1
                   mod_base = OTHER
                   note = 2'-O-(2-methoxyethyl) adenosine
modified_base      2
                   mod_base = OTHER
                   note = 2'-O-(2-methoxyethyl) thymidine 5'-thiophosphate
modified_base      3
                   mod_base = OTHER
                   note = 2'-O-(2-methoxyethyl) adenosine 5'-thiophosphate
modified_base      4
                   mod_base = OTHER
                   note = 2'-O-(2-methoxyethyl) adenosine 5'-thiophosphate
modified_base      5
                   mod_base = OTHER
```

-continued

```
                        note = 2'-O-(2-methoxyethyl) guanosine 5'-thiophosphate
modified_base           6
                        mod_base = OTHER
                        note = 2'-O-(2-methoxyethyl) adenosine 5'-thiophosphate
modified_base           7
                        mod_base = OTHER
                        note = 2'-O-(2-methoxyethyl) thymidine 5'-thiophosphate
modified_base           8
                        mod_base = OTHER
                        note = 2'-O-(2-methoxyethyl) adenosine 5'-thiophosphate
modified_base           9
                        mod_base = OTHER
                        note = 2'-O-(2-methoxyethyl) adenosine 5'-thiophosphate
modified_base           10
                        mod_base = OTHER
                        note = 2'-O-(2-methoxyethyl) adenosine 5'-thiophosphate
modified_base           11
                        mod_base = OTHER
                        note = 2'-O-(2-methoxyethyl) thymidine 5'-thiophosphate
modified_base           12
                        mod_base = OTHER
                        note = 2'-O-(2-methoxyethyl) adenosine 5'-thiophosphate
modified_base           13
                        mod_base = OTHER
                        note = 2'-O-(2-methoxyethyl) adenosine 5'-thiophosphate
modified_base           14
                        mod_base = OTHER
                        note = 2'-O-(2-methoxyethyl) 5-methyl cytidine
                         5'-thiophosphate
modified_base           15
                        mod_base = OTHER
                        note = 2'-O-(2-methoxyethyl) 5-methyl cytidine
                         5'-thiophosphate
modified_base           16
                        mod_base = OTHER
                        note = 2'-O-(2-methoxyethyl) thymidine 5'-thiophosphate
modified_base           17
                        mod_base = OTHER
                        note = 2'-O-(2-methoxyethyl) adenosine 5'-thiophosphate
modified_base           18
                        mod_base = OTHER
                        note = 2'-O-methylene-4'-bridged (LNA) adenosine
                         5'-thiophosphate
modified_base           19
                        mod_base = OTHER
                        note = 2'-O-(2-methoxyethyl) thymidine 5'-thiophosphate
modified_base           20
                        mod_base = OTHER
                        note = 2'-O-methylene-4'-bridged (LNA) adenosine
                         5'-thiophosphate
modified_base           21
                        mod_base = OTHER
                        note = 2'-O-(2-methoxyethyl) adenosine 5'-thiophosphate
modified_base           22
                        mod_base = OTHER
                        note = 2'-O-methylene-4'-bridged (LNA) adenosine
                         5'-thiophosphate
modified_base           23
                        mod_base = OTHER
                        note = 2'-O-(2-methoxyethyl) thymidine 5'-thiophosphate
SEQUENCE: 64
ataagataaa taacctaata aat                                              23

SEQ ID NO: 65           moltype = RNA  length = 23
FEATURE                 Location/Qualifiers
source                  1..23
                        mol_type = other RNA
                        organism = synthetic construct
modified_base           1
                        mod_base = OTHER
                        note = 2'-O-(2-methoxyethyl) adenosine
modified_base           2
                        mod_base = OTHER
                        note = 2'-O-(2-methoxyethyl) thymidine 5'-thiophosphate
modified_base           3
                        mod_base = OTHER
                        note = 2'-O-(2-methoxyethyl) adenosine 5'-thiophosphate
modified_base           4
                        mod_base = OTHER
```

-continued

```
                          note = 2'-O-(2-methoxyethyl) adenosine
modified_base             5
                          mod_base = OTHER
                          note = 2'-O-(2-methoxyethyl) guanosine
modified_base             6
                          mod_base = OTHER
                          note = 2'-O-(2-methoxyethyl) adenosine
modified_base             7
                          mod_base = OTHER
                          note = 2'-O-(2-methoxyethyl) thymidine
modified_base             8
                          mod_base = OTHER
                          note = 2'-O-(2-methoxyethyl) adenosine
modified_base             9
                          mod_base = OTHER
                          note = 2'-O-(2-methoxyethyl) adenosine
modified_base             10
                          mod_base = OTHER
                          note = 2'-O-(2-methoxyethyl) adenosine
modified_base             11
                          mod_base = OTHER
                          note = 2'-O-(2-methoxyethyl) thymidine
modified_base             12
                          mod_base = OTHER
                          note = 2'-O-(2-methoxyethyl) adenosine
modified_base             13
                          mod_base = OTHER
                          note = 2'-O-(2-methoxyethyl) adenosine
modified_base             14
                          mod_base = OTHER
                          note = 2'-O-(2-methoxyethyl) 5-methyl cytidine
modified_base             15
                          mod_base = OTHER
                          note = 2'-O-(2-methoxyethyl) 5-methyl cytidine
modified_base             16
                          mod_base = OTHER
                          note = 2'-O-(2-methoxyethyl) thymidine
modified_base             17
                          mod_base = OTHER
                          note = 2'-O-(2-methoxyethyl) adenosine
modified_base             18
                          mod_base = OTHER
                          note = 2'-O-(2-methoxyethyl) adenosine
modified_base             19
                          mod_base = OTHER
                          note = 2'-O-(2-methoxyethyl) thymidine
modified_base             20
                          mod_base = OTHER
                          note = 2'-O-(2-methoxyethyl) adenosine
modified_base             21
                          mod_base = OTHER
                          note = 2'-O-(2-methoxyethyl) adenosine 5'-thiophosphate
modified_base             22
                          mod_base = OTHER
                          note = 2'-O-(2-methoxyethyl) adenosine 5'-thiophosphate
modified_base             23
                          mod_base = OTHER
                          note = 2'-O-(2-methoxyethyl) thymidine 5'-thiophosphate
SEQUENCE: 65
ataagataaa taacctaata aat                                             23

SEQ ID NO: 66             moltype = RNA  length = 21
FEATURE                   Location/Qualifiers
source                    1..21
                          mol_type = other RNA
                          organism = synthetic construct
modified_base             1
                          mod_base = OTHER
                          note = 2'-O-(2-methoxyethyl) thymidine
modified_base             2
                          mod_base = OTHER
                          note = 2'-O-(2-methoxyethyl) adenosine 5'-thiophosphate
modified_base             3
                          mod_base = OTHER
                          note = 2'-O-(2-methoxyethyl) adenosine 5'-thiophosphate
modified_base             4
                          mod_base = OTHER
                          note = 2'-O-(2-methoxyethyl) guanosine 5'-thiophosphate
modified_base             5
```

```
                              mod_base = OTHER
                              note = 2'-O-(2-methoxyethyl) adenosine
modified_base                 6
                              mod_base = OTHER
                              note = 2'-O-(2-methoxyethyl) thymidine
modified_base                 7
                              mod_base = OTHER
                              note = 2'-O-(2-methoxyethyl) adenosine
modified_base                 8
                              mod_base = OTHER
                              note = 2'-O-(2-methoxyethyl) adenosine
modified_base                 9
                              mod_base = OTHER
                              note = 2'-O-(2-methoxyethyl) adenosine
modified_base                 10
                              mod_base = OTHER
                              note = 2'-O-(2-methoxyethyl) thymidine
modified_base                 11
                              mod_base = OTHER
                              note = 2'-O-(2-methoxyethyl) adenosine
modified_base                 12
                              mod_base = OTHER
                              note = 2'-O-(2-methoxyethyl) adenosine
modified_base                 13
                              mod_base = OTHER
                              note = 2'-O-(2-methoxyethyl) 5-methyl cytidine
modified_base                 14
                              mod_base = OTHER
                              note = 2'-O-(2-methoxyethyl) 5-methyl cytidine
modified_base                 15
                              mod_base = OTHER
                              note = 2'-O-(2-methoxyethyl) thymidine
modified_base                 16
                              mod_base = OTHER
                              note = 2'-O-(2-methoxyethyl) adenosine
modified_base                 17
                              mod_base = OTHER
                              note = 2'-O-(2-methoxyethyl) adenosine
modified_base                 18
                              mod_base = OTHER
                              note = 2'-O-(2-methoxyethyl) thymidine
modified_base                 19
                              mod_base = OTHER
                              note = 2'-O-(2-methoxyethyl) adenosine 5'-thiophosphate
modified_base                 20
                              mod_base = OTHER
                              note = 2'-O-(2-methoxyethyl) adenosine 5'-thiophosphate
modified_base                 21
                              mod_base = OTHER
                              note = 2'-O-(2-methoxyethyl) adenosine 5'-thiophosphate
SEQUENCE: 66
taagataaat aacctaataa a                                                    21

SEQ ID NO: 67                 moltype = RNA  length = 20
FEATURE                       Location/Qualifiers
source                        1..20
                              mol_type = other RNA
                              organism = synthetic construct
modified_base                 1
                              mod_base = OTHER
                              note = 2'-O-(2-methoxyethyl) adenosine
modified_base                 2
                              mod_base = OTHER
                              note = 2'-O-(2-methoxyethyl) adenosine 5'-thiophosphate
modified_base                 3
                              mod_base = OTHER
                              note = 2'-O-(2-methoxyethyl) thymidine 5'-thiophosphate
modified_base                 4
                              mod_base = OTHER
                              note = 2'-O-(2-methoxyethyl) adenosine 5'-thiophosphate
modified_base                 5
                              mod_base = OTHER
                              note = 2'-O-(2-methoxyethyl) adenosine
modified_base                 6
                              mod_base = OTHER
                              note = 2'-O-(2-methoxyethyl) adenosine
modified_base                 7
                              mod_base = OTHER
                              note = 2'-O-(2-methoxyethyl) thymidine
```

-continued

```
modified_base        8
                     mod_base = OTHER
                     note = 2'-O-(2-methoxyethyl) adenosine
modified_base        9
                     mod_base = OTHER
                     note = 2'-O-(2-methoxyethyl) adenosine
modified_base        10
                     mod_base = OTHER
                     note = 2'-O-(2-methoxyethyl) guanosine
modified_base        11
                     mod_base = OTHER
                     note = 2'-O-(2-methoxyethyl) adenosine
modified_base        12
                     mod_base = OTHER
                     note = 2'-O-(2-methoxyethyl) thymidine
modified_base        13
                     mod_base = OTHER
                     note = 2'-O-(2-methoxyethyl) adenosine
modified_base        14
                     mod_base = OTHER
                     note = 2'-O-(2-methoxyethyl) adenosine
modified_base        15
                     mod_base = OTHER
                     note = 2'-O-(2-methoxyethyl) adenosine
modified_base        16
                     mod_base = OTHER
                     note = 2'-O-(2-methoxyethyl) thymidine
modified_base        17
                     mod_base = OTHER
                     note = 2'-O-(2-methoxyethyl) adenosine
modified_base        18
                     mod_base = OTHER
                     note = 2'-O-(2-methoxyethyl) adenosine 5'-thiophosphate
modified_base        19
                     mod_base = OTHER
                     note = 2'-O-(2-methoxyethyl) 5-methyl cytidine
                      5'-thiophosphate
modified_base        20
                     mod_base = OTHER
                     note = 2'-O-(2-methoxyethyl) 5-methyl cytidine
                      5'-thiophosphate
SEQUENCE: 67
aataaataag ataaataacc                                            20

SEQ ID NO: 68        moltype = RNA   length = 33
FEATURE              Location/Qualifiers
source               1..33
                     mol_type = other RNA
                     organism = synthetic construct
modified_base        1
                     mod_base = OTHER
                     note = 2'-O-methyl guanosine
modified_base        2
                     mod_base = OTHER
                     note = 2'-O-methyl guanosine 5'-thiophosphate
modified_base        3
                     mod_base = OTHER
                     note = 2'-O-methyl adenosine 5'-thiophosphate
modified_base        4
                     mod_base = OTHER
                     note = 2'-O-methyl cytidine
modified_base        5
                     mod_base = OTHER
                     note = 2'-O-methyl uridine
modified_base        6
                     mod_base = OTHER
                     note = 2'-O-methyl guanosine
modified_base        7
                     mod_base = OTHER
                     note = 2'-O-methyl guanosine
modified_base        8
                     mod_base = OTHER
                     note = 2'-O-methyl adenosine
modified_base        9
                     mod_base = OTHER
                     note = 2'-O-methyl cytidine
modified_base        10
                     mod_base = OTHER
                     note = 2'-O-methyl uridine
```

```
modified_base        11
                     mod_base = OTHER
                     note = 2'-O-(2-methoxyethyl) adenosine
modified_base        12
                     mod_base = OTHER
                     note = 2'-O-(2-methoxyethyl) thymidine 5'-thiophosphate
modified_base        13
                     mod_base = OTHER
                     note = 2'-O-(2-methoxyethyl) adenosine 5'-thiophosphate
modified_base        14
                     mod_base = OTHER
                     note = 2'-O-(2-methoxyethyl) adenosine
modified_base        15
                     mod_base = OTHER
                     note = 2'-O-(2-methoxyethyl) guanosine
modified_base        16
                     mod_base = OTHER
                     note = 2'-O-(2-methoxyethyl) adenosine
modified_base        17
                     mod_base = OTHER
                     note = 2'-O-(2-methoxyethyl) thymidine
modified_base        18
                     mod_base = OTHER
                     note = 2'-O-(2-methoxyethyl) adenosine
modified_base        19
                     mod_base = OTHER
                     note = 2'-O-(2-methoxyethyl) adenosine
modified_base        20
                     mod_base = OTHER
                     note = 2'-O-(2-methoxyethyl) adenosine
modified_base        21
                     mod_base = OTHER
                     note = 2'-O-(2-methoxyethyl) thymidine
modified_base        22
                     mod_base = OTHER
                     note = 2'-O-(2-methoxyethyl) adenosine
modified_base        23
                     mod_base = OTHER
                     note = 2'-O-(2-methoxyethyl) adenosine
modified_base        24
                     mod_base = OTHER
                     note = 2'-O-(2-methoxyethyl) 5-methyl cytidine
modified_base        25
                     mod_base = OTHER
                     note = 2'-O-(2-methoxyethyl) 5-methyl cytidine
modified_base        26
                     mod_base = OTHER
                     note = 2'-O-(2-methoxyethyl) thymidine
modified_base        27
                     mod_base = OTHER
                     note = 2'-O-(2-methoxyethyl) adenosine
modified_base        28
                     mod_base = OTHER
                     note = 2'-O-(2-methoxyethyl) adenosine
modified_base        29
                     mod_base = OTHER
                     note = 2'-O-(2-methoxyethyl) thymidine
modified_base        30
                     mod_base = OTHER
                     note = 2'-O-(2-methoxyethyl) adenosine
modified_base        31
                     mod_base = OTHER
                     note = 2'-O-(2-methoxyethyl) adenosine 5'-thiophosphate
modified_base        32
                     mod_base = OTHER
                     note = 2'-O-(2-methoxyethyl) adenosine 5'-thiophosphate
modified_base        33
                     mod_base = OTHER
                     note = 2'-O-(2-methoxyethyl) thymidine 5'-thiophosphate
SEQUENCE: 68
ggactggact ataagataaa taacctaata aat                             33

SEQ ID NO: 69        moltype = RNA  length = 23
FEATURE              Location/Qualifiers
source               1..23
                     mol_type = other RNA
                     organism = synthetic construct
modified_base        1
                     mod_base = OTHER
```

-continued

```
                          note = 2'-O-(2-methoxyethyl) adenosine
modified_base             2
                          mod_base = OTHER
                          note = 2'-O-(2-methoxyethyl) thymidine 5'-thiophosphate
modified_base             3
                          mod_base = OTHER
                          note = 2'-O-(2-methoxyethyl) adenosine 5'-thiophosphate
modified_base             4
                          mod_base = OTHER
                          note = 2'-O-(2-methoxyethyl) adenosine 5'-thiophosphate
modified_base             5
                          mod_base = OTHER
                          note = 2'-O-(2-methoxyethyl) guanosine 5'-thiophosphate
modified_base             6
                          mod_base = OTHER
                          note = 2'-O-(2-methoxyethyl) adenosine 5'-thiophosphate
modified_base             7
                          mod_base = OTHER
                          note = 2'-O-(2-methoxyethyl) thymidine 5'-thiophosphate
modified_base             8
                          mod_base = OTHER
                          note = 2'-O-(2-methoxyethyl) adenosine 5'-thiophosphate
modified_base             9
                          mod_base = OTHER
                          note = 2'-O-(2-methoxyethyl) adenosine 5'-thiophosphate
modified_base             10
                          mod_base = OTHER
                          note = 2'-O-(2-methoxyethyl) adenosine 5'-thiophosphate
modified_base             11
                          mod_base = OTHER
                          note = 2'-O-(2-methoxyethyl) thymidine 5'-thiophosphate
modified_base             12
                          mod_base = OTHER
                          note = 2'-O-(2-methoxyethyl) adenosine 5'-thiophosphate
modified_base             13
                          mod_base = OTHER
                          note = 2'-O-(2-methoxyethyl) adenosine 5'-thiophosphate
modified_base             14
                          mod_base = OTHER
                          note = 2'-O-(2-methoxyethyl) 5-methyl cytidine
                           5'-thiophosphate
modified_base             15
                          mod_base = OTHER
                          note = 2'-O-(2-methoxyethyl) 5-methyl cytidine
                           5'-thiophosphate
modified_base             16
                          mod_base = OTHER
                          note = 2'-O-(2-methoxyethyl) thymidine 5'-thiophosphate
modified_base             17
                          mod_base = OTHER
                          note = 2'-O-(2-methoxyethyl) adenosine 5'-thiophosphate
modified_base             18
                          mod_base = OTHER
                          note = 2'-O-(2-methoxyethyl) adenosine 5'-thiophosphate
modified_base             19
                          mod_base = OTHER
                          note = 2'-O-(2-methoxyethyl) thymidine 5'-thiophosphate
modified_base             20
                          mod_base = OTHER
                          note = 2'-O-(2-methoxyethyl) adenosine 5'-thiophosphate
modified_base             21
                          mod_base = OTHER
                          note = 2'-O-(2-methoxyethyl) adenosine 5'-thiophosphate
modified_base             22
                          mod_base = OTHER
                          note = 2'-O-(2-methoxyethyl) adenosine 5'-thiophosphate
modified_base             23
                          mod_base = OTHER
                          note = 2'-O-(2-methoxyethyl) thymidine 5'-thiophosphate
misc_feature              23
                          note = 3'-O attached to a GalNAc-comprising compound via a
                           linker
SEQUENCE: 69
ataagataaa taacctaata aat                                                    23

SEQ ID NO: 70            moltype = RNA  length = 33
FEATURE                  Location/Qualifiers
source                   1..33
                         mol_type = other RNA
```

-continued

```
                      organism = synthetic construct
modified_base         1
                      mod_base = OTHER
                      note = 2'-O-methyl guanosine
modified_base         2
                      mod_base = OTHER
                      note = 2'-O-methyl guanosine 5'-thiophosphate
modified_base         3
                      mod_base = OTHER
                      note = 2'-O-methyl adenosine 5'-thiophosphate
modified_base         4
                      mod_base = OTHER
                      note = 2'-O-methyl cytidine
modified_base         5
                      mod_base = OTHER
                      note = 2'-O-methyl uridine
modified_base         6
                      mod_base = OTHER
                      note = 2'-O-methyl guanosine
modified_base         7
                      mod_base = OTHER
                      note = 2'-O-methyl guanosine
modified_base         8
                      mod_base = OTHER
                      note = 2'-O-methyl adenosine
modified_base         9
                      mod_base = OTHER
                      note = 2'-O-methyl cytidine
modified_base         10
                      mod_base = OTHER
                      note = 2'-O-methyl uridine
modified_base         11
                      mod_base = OTHER
                      note = 2'-O-(2-methoxyethyl) adenosine
modified_base         12
                      mod_base = OTHER
                      note = 2'-O-(2-methoxyethyl) thymidine 5'-thiophosphate
modified_base         13
                      mod_base = OTHER
                      note = 2'-O-(2-methoxyethyl) adenosine 5'-thiophosphate
modified_base         14
                      mod_base = OTHER
                      note = 2'-O-(2-methoxyethyl) adenosine 5'-thiophosphate
modified_base         15
                      mod_base = OTHER
                      note = 2'-O-(2-methoxyethyl) guanosine 5'-thiophosphate
modified_base         16
                      mod_base = OTHER
                      note = 2'-O-(2-methoxyethyl) adenosine 5'-thiophosphate
modified_base         17
                      mod_base = OTHER
                      note = 2'-O-(2-methoxyethyl) thymidine 5'-thiophosphate
modified_base         18
                      mod_base = OTHER
                      note = 2'-O-(2-methoxyethyl) adenosine 5'-thiophosphate
modified_base         19
                      mod_base = OTHER
                      note = 2'-O-(2-methoxyethyl) adenosine 5'-thiophosphate
modified_base         20
                      mod_base = OTHER
                      note = 2'-O-(2-methoxyethyl) adenosine 5'-thiophosphate
modified_base         21
                      mod_base = OTHER
                      note = 2'-O-(2-methoxyethyl) thymidine 5'-thiophosphate
modified_base         22
                      mod_base = OTHER
                      note = 2'-O-(2-methoxyethyl) adenosine 5'-thiophosphate
modified_base         23
                      mod_base = OTHER
                      note = 2'-O-(2-methoxyethyl) adenosine 5'-thiophosphate
modified_base         24
                      mod_base = OTHER
                      note = 2'-O-(2-methoxyethyl) 5-methyl cytidine
                       5'-thiophosphate
modified_base         25
                      mod_base = OTHER
                      note = 2'-O-(2-methoxyethyl) 5-methyl cytidine
                       5'-thiophosphate
modified_base         26
```

-continued

```
                        mod_base = OTHER
                        note = 2'-O-(2-methoxyethyl) thymidine 5'-thiophosphate
modified_base           27
                        mod_base = OTHER
                        note = 2'-O-(2-methoxyethyl) adenosine 5'-thiophosphate
modified_base           28
                        mod_base = OTHER
                        note = 2'-O-(2-methoxyethyl) adenosine 5'-thiophosphate
modified_base           29
                        mod_base = OTHER
                        note = 2'-O-(2-methoxyethyl) thymidine 5'-thiophosphate
modified_base           30
                        mod_base = OTHER
                        note = 2'-O-(2-methoxyethyl) adenosine 5'-thiophosphate
modified_base           31
                        mod_base = OTHER
                        note = 2'-O-(2-methoxyethyl) adenosine 5'-thiophosphate
modified_base           32
                        mod_base = OTHER
                        note = 2'-O-(2-methoxyethyl) adenosine 5'-thiophosphate
modified_base           33
                        mod_base = OTHER
                        note = 2'-O-(2-methoxyethyl) thymidine 5'-thiophosphate
misc_feature            33
                        note = 3'-O attached to a GalNAc-comprising compound via a
                        linker
SEQUENCE: 70
ggactggact ataagataaa taacctaata aat                                        33

SEQ ID NO: 71           moltype = RNA  length = 27
FEATURE                 Location/Qualifiers
source                  1..27
                        mol_type = other RNA
                        organism = synthetic construct
modified_base           1
                        mod_base = OTHER
                        note = 2'-O-methyl cytidine
modified_base           2
                        mod_base = OTHER
                        note = 2'-O-methyl cytidine 5'-thiophosphate
modified_base           3
                        mod_base = OTHER
                        note = 2'-O-methyl cytidine 5'-thiophosphate
modified_base           4
                        mod_base = OTHER
                        note = 2'-O-methyl cytidine
modified_base           5
                        mod_base = OTHER
                        note = 2'-O-methyl cytidine
modified_base           6
                        mod_base = OTHER
                        note = 2'-O-methyl cytidine
modified_base           7
                        mod_base = OTHER
                        note = 2'-O-methyl cytidine
modified_base           8
                        mod_base = OTHER
                        note = 2'-O-methyl cytidine
modified_base           9
                        mod_base = OTHER
                        note = 2'-O-methyl cytidine
modified_base           10
                        mod_base = OTHER
                        note = 2'-O-methyl cytidine
modified_base           11
                        mod_base = OTHER
                        note = 2'-O-(2-methoxyethyl) adenosine
modified_base           12
                        mod_base = OTHER
                        note = 2'-O-(2-methoxyethyl) adenosine 5'-thiophosphate
modified_base           13
                        mod_base = OTHER
                        note = 2'-O-(2-methoxyethyl) 5-methyl cytidine
                        5'-thiophosphate
modified_base           14
                        mod_base = OTHER
                        note = 2'-O-(2-methoxyethyl) 5-methyl cytidine
                        5'-thiophosphate
modified_base           15
```

```
                         mod_base = OTHER
                         note = 2'-O-(2-methoxyethyl) adenosine 5'-thiophosphate
modified_base            16
                         mod_base = OTHER
                         note = 2'-O-(2-methoxyethyl) 5-methyl cytidine
                          5'-thiophosphate
modified_base            17
                         mod_base = OTHER
                         note = 2'-O-(2-methoxyethyl) adenosine 5'-thiophosphate
modified_base            18
                         mod_base = OTHER
                         note = 2'-O-(2-methoxyethyl) guanosine 5'-thiophosphate
modified_base            19
                         mod_base = OTHER
                         note = 2'-O-(2-methoxyethyl) adenosine 5'-thiophosphate
modified_base            20
                         mod_base = OTHER
                         note = 2'-O-(2-methoxyethyl) adenosine 5'-thiophosphate
modified_base            21
                         mod_base = OTHER
                         note = 2'-O-(2-methoxyethyl) adenosine 5'-thiophosphate
modified_base            22
                         mod_base = OTHER
                         note = 2'-O-(2-methoxyethyl) 5-methyl cytidine
                          5'-thiophosphate
modified_base            23
                         mod_base = OTHER
                         note = 2'-O-(2-methoxyethyl) thymidine 5'-thiophosphate
modified_base            24
                         mod_base = OTHER
                         note = 2'-O-(2-methoxyethyl) adenosine 5'-thiophosphate
modified_base            25
                         mod_base = OTHER
                         note = 2'-O-(2-methoxyethyl) 5-methyl cytidine
                          5'-thiophosphate
modified_base            26
                         mod_base = OTHER
                         note = 2'-O-(2-methoxyethyl) 5-methyl cytidine
                          5'-thiophosphate
modified_base            27
                         mod_base = OTHER
                         note = 2'-O-(2-methoxyethyl) adenosine 5'-thiophosphate
SEQUENCE: 71
cccccccccc aaccacagaa actacca                                               27

SEQ ID NO: 72            moltype = RNA  length = 27
FEATURE                  Location/Qualifiers
source                   1..27
                         mol_type = other RNA
                         organism = synthetic construct
modified_base            1
                         mod_base = OTHER
                         note = 2'-O-methyl uridine
modified_base            2
                         mod_base = OTHER
                         note = 2'-O-methyl uridine 5'-thiophosphate
modified_base            3
                         mod_base = OTHER
                         note = 2'-O-methyl uridine 5'-thiophosphate
modified_base            4
                         mod_base = OTHER
                         note = 2'-O-methyl uridine
modified_base            5
                         mod_base = OTHER
                         note = 2'-O-methyl uridine
modified_base            6
                         mod_base = OTHER
                         note = 2'-O-methyl uridine
modified_base            7
                         mod_base = OTHER
                         note = 2'-O-methyl uridine
modified_base            8
                         mod_base = OTHER
                         note = 2'-O-methyl uridine
modified_base            9
                         mod_base = OTHER
                         note = 2'-O-methyl uridine
modified_base            10
                         mod_base = OTHER
```

-continued

```
                              note = 2'-O-methyl uridine
modified_base                 11
                              mod_base = OTHER
                              note = 2'-O-(2-methoxyethyl) adenosine
modified_base                 12
                              mod_base = OTHER
                              note = 2'-O-(2-methoxyethyl) adenosine 5'-thiophosphate
modified_base                 13
                              mod_base = OTHER
                              note = 2'-O-(2-methoxyethyl) 5-methyl cytidine
                               5'-thiophosphate
modified_base                 14
                              mod_base = OTHER
                              note = 2'-O-(2-methoxyethyl) 5-methyl cytidine
                               5'-thiophosphate
modified_base                 15
                              mod_base = OTHER
                              note = 2'-O-(2-methoxyethyl) adenosine 5'-thiophosphate
modified_base                 16
                              mod_base = OTHER
                              note = 2'-O-(2-methoxyethyl) 5-methyl cytidine
                               5'-thiophosphate
modified_base                 17
                              mod_base = OTHER
                              note = 2'-O-(2-methoxyethyl) adenosine 5'-thiophosphate
modified_base                 18
                              mod_base = OTHER
                              note = 2'-O-(2-methoxyethyl) guanosine 5'-thiophosphate
modified_base                 19
                              mod_base = OTHER
                              note = 2'-O-(2-methoxyethyl) adenosine 5'-thiophosphate
modified_base                 20
                              mod_base = OTHER
                              note = 2'-O-(2-methoxyethyl) adenosine 5'-thiophosphate
modified_base                 21
                              mod_base = OTHER
                              note = 2'-O-(2-methoxyethyl) adenosine 5'-thiophosphate
modified_base                 22
                              mod_base = OTHER
                              note = 2'-O-(2-methoxyethyl) 5-methyl cytidine
                               5'-thiophosphate
modified_base                 23
                              mod_base = OTHER
                              note = 2'-O-(2-methoxyethyl) thymidine 5'-thiophosphate
modified_base                 24
                              mod_base = OTHER
                              note = 2'-O-(2-methoxyethyl) adenosine 5'-thiophosphate
modified_base                 25
                              mod_base = OTHER
                              note = 2'-O-(2-methoxyethyl) 5-methyl cytidine
                               5'-thiophosphate
modified_base                 26
                              mod_base = OTHER
                              note = 2'-O-(2-methoxyethyl) 5-methyl cytidine
                               5'-thiophosphate
modified_base                 27
                              mod_base = OTHER
                              note = 2'-O-(2-methoxyethyl) adenosine 5'-thiophosphate
SEQUENCE: 72
tttttttttt aaccacagaa actacca                                              27

SEQ ID NO: 73                 moltype = RNA  length = 27
FEATURE                       Location/Qualifiers
source                        1..27
                              mol_type = other RNA
                              organism = synthetic construct
modified_base                 1
                              mod_base = OTHER
                              note = 2'-O-methyl adenosine
modified_base                 2
                              mod_base = OTHER
                              note = 2'-O-methyl cytidine 5'-thiophosphate
modified_base                 3
                              mod_base = OTHER
                              note = 2'-O-methyl adenosine 5'-thiophosphate
modified_base                 4
                              mod_base = OTHER
                              note = 2'-O-methyl cytidine
modified_base                 5
```

```
                        mod_base = OTHER
                        note = 2'-O-methyl adenosine
modified_base           6
                        mod_base = OTHER
                        note = 2'-O-methyl cytidine
modified_base           7
                        mod_base = OTHER
                        note = 2'-O-methyl adenosine
modified_base           8
                        mod_base = OTHER
                        note = 2'-O-methyl cytidine
modified_base           9
                        mod_base = OTHER
                        note = 2'-O-methyl adenosine
modified_base           10
                        mod_base = OTHER
                        note = 2'-O-methyl cytidine
modified_base           11
                        mod_base = OTHER
                        note = 2'-O-(2-methoxyethyl) adenosine
modified_base           12
                        mod_base = OTHER
                        note = 2'-O-(2-methoxyethyl) adenosine 5'-thiophosphate
modified_base           13
                        mod_base = OTHER
                        note = 2'-O-(2-methoxyethyl) 5-methyl cytidine
                         5'-thiophosphate
modified_base           14
                        mod_base = OTHER
                        note = 2'-O-(2-methoxyethyl) 5-methyl cytidine
                         5'-thiophosphate
modified_base           15
                        mod_base = OTHER
                        note = 2'-O-(2-methoxyethyl) adenosine 5'-thiophosphate
modified_base           16
                        mod_base = OTHER
                        note = 2'-O-(2-methoxyethyl) 5-methyl cytidine
                         5'-thiophosphate
modified_base           17
                        mod_base = OTHER
                        note = 2'-O-(2-methoxyethyl) adenosine 5'-thiophosphate
modified_base           18
                        mod_base = OTHER
                        note = 2'-O-(2-methoxyethyl) guanosine 5'-thiophosphate
modified_base           19
                        mod_base = OTHER
                        note = 2'-O-(2-methoxyethyl) adenosine 5'-thiophosphate
modified_base           20
                        mod_base = OTHER
                        note = 2'-O-(2-methoxyethyl) adenosine 5'-thiophosphate
modified_base           21
                        mod_base = OTHER
                        note = 2'-O-(2-methoxyethyl) adenosine 5'-thiophosphate
modified_base           22
                        mod_base = OTHER
                        note = 2'-O-(2-methoxyethyl) 5-methyl cytidine
                         5'-thiophosphate
modified_base           23
                        mod_base = OTHER
                        note = 2'-O-(2-methoxyethyl) thymidine 5'-thiophosphate
modified_base           24
                        mod_base = OTHER
                        note = 2'-O-(2-methoxyethyl) adenosine 5'-thiophosphate
modified_base           25
                        mod_base = OTHER
                        note = 2'-O-(2-methoxyethyl) 5-methyl cytidine
                         5'-thiophosphate
modified_base           26
                        mod_base = OTHER
                        note = 2'-O-(2-methoxyethyl) 5-methyl cytidine
                         5'-thiophosphate
modified_base           27
                        mod_base = OTHER
                        note = 2'-O-(2-methoxyethyl) adenosine 5'-thiophosphate
SEQUENCE: 73
acacacacac aaccacagaa actacca                                                 27

SEQ ID NO: 74           moltype = RNA  length = 27
FEATURE                 Location/Qualifiers
```

```
source              1..27
                    mol_type = other RNA
                    organism = synthetic construct
modified_base       1
                    mod_base = OTHER
                    note = 2'-O-methyl adenosine
modified_base       2
                    mod_base = OTHER
                    note = 2'-O-methyl guanosine 5'-thiophosphate
modified_base       3
                    mod_base = OTHER
                    note = 2'-O-methyl adenosine 5'-thiophosphate
modified_base       4
                    mod_base = OTHER
                    note = 2'-O-methyl guanosine
modified_base       5
                    mod_base = OTHER
                    note = 2'-O-methyl adenosine
modified_base       6
                    mod_base = OTHER
                    note = 2'-O-methyl guanosine
modified_base       7
                    mod_base = OTHER
                    note = 2'-O-methyl adenosine
modified_base       8
                    mod_base = OTHER
                    note = 2'-O-methyl guanosine
modified_base       9
                    mod_base = OTHER
                    note = 2'-O-methyl adenosine
modified_base       10
                    mod_base = OTHER
                    note = 2'-O-methyl guanosine
modified_base       11
                    mod_base = OTHER
                    note = 2'-O-(2-methoxyethyl) adenosine
modified_base       12
                    mod_base = OTHER
                    note = 2'-O-(2-methoxyethyl) adenosine 5'-thiophosphate
modified_base       13
                    mod_base = OTHER
                    note = 2'-O-(2-methoxyethyl) 5-methyl cytidine
                    5'-thiophosphate
modified_base       14
                    mod_base = OTHER
                    note = 2'-O-(2-methoxyethyl) 5-methyl cytidine
                    5'-thiophosphate
modified_base       15
                    mod_base = OTHER
                    note = 2'-O-(2-methoxyethyl) adenosine 5'-thiophosphate
modified_base       16
                    mod_base = OTHER
                    note = 2'-O-(2-methoxyethyl) 5-methyl cytidine
                    5'-thiophosphate
modified_base       17
                    mod_base = OTHER
                    note = 2'-O-(2-methoxyethyl) adenosine 5'-thiophosphate
modified_base       18
                    mod_base = OTHER
                    note = 2'-O-(2-methoxyethyl) guanosine 5'-thiophosphate
modified_base       19
                    mod_base = OTHER
                    note = 2'-O-(2-methoxyethyl) adenosine 5'-thiophosphate
modified_base       20
                    mod_base = OTHER
                    note = 2'-O-(2-methoxyethyl) adenosine 5'-thiophosphate
modified_base       21
                    mod_base = OTHER
                    note = 2'-O-(2-methoxyethyl) adenosine 5'-thiophosphate
modified_base       22
                    mod_base = OTHER
                    note = 2'-O-(2-methoxyethyl) 5-methyl cytidine
                    5'-thiophosphate
modified_base       23
                    mod_base = OTHER
                    note = 2'-O-(2-methoxyethyl) thymidine 5'-thiophosphate
modified_base       24
                    mod_base = OTHER
                    note = 2'-O-(2-methoxyethyl) adenosine 5'-thiophosphate
```

-continued

```
modified_base        25
                     mod_base = OTHER
                     note = 2'-O-(2-methoxyethyl) 5-methyl cytidine
                      5'-thiophosphate
modified_base        26
                     mod_base = OTHER
                     note = 2'-O-(2-methoxyethyl) 5-methyl cytidine
                      5'-thiophosphate
modified_base        27
                     mod_base = OTHER
                     note = 2'-O-(2-methoxyethyl) adenosine 5'-thiophosphate
SEQUENCE: 74
agagagagag aaccacagaa actacca                                         27

SEQ ID NO: 75        moltype = RNA  length = 27
FEATURE              Location/Qualifiers
source               1..27
                     mol_type = other RNA
                     organism = synthetic construct
modified_base        1
                     mod_base = OTHER
                     note = 2'-O-methyl cytidine
modified_base        2
                     mod_base = OTHER
                     note = 2'-O-methyl uridine 5'-thiophosphate
modified_base        3
                     mod_base = OTHER
                     note = 2'-O-methyl cytidine 5'-thiophosphate
modified_base        4
                     mod_base = OTHER
                     note = 2'-O-methyl uridine
modified_base        5
                     mod_base = OTHER
                     note = 2'-O-methyl cytidine
modified_base        6
                     mod_base = OTHER
                     note = 2'-O-methyl uridine
modified_base        7
                     mod_base = OTHER
                     note = 2'-O-methyl cytidine
modified_base        8
                     mod_base = OTHER
                     note = 2'-O-methyl uridine
modified_base        9
                     mod_base = OTHER
                     note = 2'-O-methyl cytidine
modified_base        10
                     mod_base = OTHER
                     note = 2'-O-methyl uridine
modified_base        11
                     mod_base = OTHER
                     note = 2'-O-(2-methoxyethyl) adenosine
modified_base        12
                     mod_base = OTHER
                     note = 2'-O-(2-methoxyethyl) adenosine 5'-thiophosphate
modified_base        13
                     mod_base = OTHER
                     note = 2'-O-(2-methoxyethyl) 5-methyl cytidine
                      5'-thiophosphate
modified_base        14
                     mod_base = OTHER
                     note = 2'-O-(2-methoxyethyl) 5-methyl cytidine
                      5'-thiophosphate
modified_base        15
                     mod_base = OTHER
                     note = 2'-O-(2-methoxyethyl) adenosine 5'-thiophosphate
modified_base        16
                     mod_base = OTHER
                     note = 2'-O-(2-methoxyethyl) 5-methyl cytidine
                      5'-thiophosphate
modified_base        17
                     mod_base = OTHER
                     note = 2'-O-(2-methoxyethyl) adenosine 5'-thiophosphate
modified_base        18
                     mod_base = OTHER
                     note = 2'-O-(2-methoxyethyl) guanosine 5'-thiophosphate
modified_base        19
                     mod_base = OTHER
                     note = 2'-O-(2-methoxyethyl) adenosine 5'-thiophosphate
```

```
modified_base            20
                         mod_base = OTHER
                         note = 2'-O-(2-methoxyethyl) adenosine 5'-thiophosphate
modified_base            21
                         mod_base = OTHER
                         note = 2'-O-(2-methoxyethyl) adenosine 5'-thiophosphate
modified_base            22
                         mod_base = OTHER
                         note = 2'-O-(2-methoxyethyl) 5-methyl cytidine
                          5'-thiophosphate
modified_base            23
                         mod_base = OTHER
                         note = 2'-O-(2-methoxyethyl) thymidine 5'-thiophosphate
modified_base            24
                         mod_base = OTHER
                         note = 2'-O-(2-methoxyethyl) adenosine 5'-thiophosphate
modified_base            25
                         mod_base = OTHER
                         note = 2'-O-(2-methoxyethyl) 5-methyl cytidine
                          5'-thiophosphate
modified_base            26
                         mod_base = OTHER
                         note = 2'-O-(2-methoxyethyl) 5-methyl cytidine
                          5'-thiophosphate
modified_base            27
                         mod_base = OTHER
                         note = 2'-O-(2-methoxyethyl) adenosine 5'-thiophosphate
SEQUENCE: 75
ctctctctct aaccacagaa actacca                                         27

SEQ ID NO: 76           moltype = RNA  length = 27
FEATURE                 Location/Qualifiers
source                  1..27
                        mol_type = other RNA
                        organism = synthetic construct
modified_base            1
                         mod_base = OTHER
                         note = 2'-O-methyl guanosine
modified_base            2
                         mod_base = OTHER
                         note = 2'-O-methyl uridine 5'-thiophosphate
modified_base            3
                         mod_base = OTHER
                         note = 2'-O-methyl guanosine 5'-thiophosphate
modified_base            4
                         mod_base = OTHER
                         note = 2'-O-methyl uridine
modified_base            5
                         mod_base = OTHER
                         note = 2'-O-methyl guanosine
modified_base            6
                         mod_base = OTHER
                         note = 2'-O-methyl uridine
modified_base            7
                         mod_base = OTHER
                         note = 2'-O-methyl guanosine
modified_base            8
                         mod_base = OTHER
                         note = 2'-O-methyl uridine
modified_base            9
                         mod_base = OTHER
                         note = 2'-O-methyl guanosine
modified_base            10
                         mod_base = OTHER
                         note = 2'-O-methyl uridine
modified_base            11
                         mod_base = OTHER
                         note = 2'-O-(2-methoxyethyl) adenosine
modified_base            12
                         mod_base = OTHER
                         note = 2'-O-(2-methoxyethyl) adenosine 5'-thiophosphate
modified_base            13
                         mod_base = OTHER
                         note = 2'-O-(2-methoxyethyl) 5-methyl cytidine
                          5'-thiophosphate
modified_base            14
                         mod_base = OTHER
                         note = 2'-O-(2-methoxyethyl) 5-methyl cytidine
                          5'-thiophosphate
```

```
modified_base      15
                   mod_base = OTHER
                   note = 2'-O-(2-methoxyethyl) adenosine 5'-thiophosphate
modified_base      16
                   mod_base = OTHER
                   note = 2'-O-(2-methoxyethyl) 5-methyl cytidine
                    5'-thiophosphate
modified_base      17
                   mod_base = OTHER
                   note = 2'-O-(2-methoxyethyl) adenosine 5'-thiophosphate
modified_base      18
                   mod_base = OTHER
                   note = 2'-O-(2-methoxyethyl) guanosine 5'-thiophosphate
modified_base      19
                   mod_base = OTHER
                   note = 2'-O-(2-methoxyethyl) adenosine 5'-thiophosphate
modified_base      20
                   mod_base = OTHER
                   note = 2'-O-(2-methoxyethyl) adenosine 5'-thiophosphate
modified_base      21
                   mod_base = OTHER
                   note = 2'-O-(2-methoxyethyl) adenosine 5'-thiophosphate
modified_base      22
                   mod_base = OTHER
                   note = 2'-O-(2-methoxyethyl) 5-methyl cytidine
                    5'-thiophosphate
modified_base      23
                   mod_base = OTHER
                   note = 2'-O-(2-methoxyethyl) thymidine 5'-thiophosphate
modified_base      24
                   mod_base = OTHER
                   note = 2'-O-(2-methoxyethyl) adenosine 5'-thiophosphate
modified_base      25
                   mod_base = OTHER
                   note = 2'-O-(2-methoxyethyl) 5-methyl cytidine
                    5'-thiophosphate
modified_base      26
                   mod_base = OTHER
                   note = 2'-O-(2-methoxyethyl) 5-methyl cytidine
                    5'-thiophosphate
modified_base      27
                   mod_base = OTHER
                   note = 2'-O-(2-methoxyethyl) adenosine 5'-thiophosphate
SEQUENCE: 76
gtgtgtgtgt aaccacagaa actacca                                          27

SEQ ID NO: 77         moltype = RNA  length = 27
FEATURE               Location/Qualifiers
source                1..27
                      mol_type = other RNA
                      organism = synthetic construct
modified_base         1
                      mod_base = OTHER
                      note = 2'-O-methyl adenosine
modified_base         2
                      mod_base = OTHER
                      note = 2'-O-methyl adenosine 5'-thiophosphate
modified_base         3
                      mod_base = OTHER
                      note = 2'-O-methyl adenosine 5'-thiophosphate
modified_base         4
                      mod_base = OTHER
                      note = 2'-O-methyl cytidine
modified_base         5
                      mod_base = OTHER
                      note = 2'-O-methyl adenosine
modified_base         6
                      mod_base = OTHER
                      note = 2'-O-methyl adenosine
modified_base         7
                      mod_base = OTHER
                      note = 2'-O-methyl adenosine
modified_base         8
                      mod_base = OTHER
                      note = 2'-O-methyl adenosine
modified_base         9
                      mod_base = OTHER
                      note = 2'-O-methyl cytidine
modified_base         10
```

-continued

```
                        mod_base = OTHER
                        note = 2'-O-methyl adenosine
modified_base           11
                        mod_base = OTHER
                        note = 2'-O-(2-methoxyethyl) adenosine
modified_base           12
                        mod_base = OTHER
                        note = 2'-O-(2-methoxyethyl) adenosine 5'-thiophosphate
modified_base           13
                        mod_base = OTHER
                        note = 2'-O-(2-methoxyethyl) 5-methyl cytidine
                         5'-thiophosphate
modified_base           14
                        mod_base = OTHER
                        note = 2'-O-(2-methoxyethyl) 5-methyl cytidine
                         5'-thiophosphate
modified_base           15
                        mod_base = OTHER
                        note = 2'-O-(2-methoxyethyl) adenosine 5'-thiophosphate
modified_base           16
                        mod_base = OTHER
                        note = 2'-O-(2-methoxyethyl) 5-methyl cytidine
                         5'-thiophosphate
modified_base           17
                        mod_base = OTHER
                        note = 2'-O-(2-methoxyethyl) adenosine 5'-thiophosphate
modified_base           18
                        mod_base = OTHER
                        note = 2'-O-(2-methoxyethyl) guanosine 5'-thiophosphate
modified_base           19
                        mod_base = OTHER
                        note = 2'-O-(2-methoxyethyl) adenosine 5'-thiophosphate
modified_base           20
                        mod_base = OTHER
                        note = 2'-O-(2-methoxyethyl) adenosine 5'-thiophosphate
modified_base           21
                        mod_base = OTHER
                        note = 2'-O-(2-methoxyethyl) adenosine 5'-thiophosphate
modified_base           22
                        mod_base = OTHER
                        note = 2'-O-(2-methoxyethyl) 5-methyl cytidine
                         5'-thiophosphate
modified_base           23
                        mod_base = OTHER
                        note = 2'-O-(2-methoxyethyl) thymidine 5'-thiophosphate
modified_base           24
                        mod_base = OTHER
                        note = 2'-O-(2-methoxyethyl) adenosine 5'-thiophosphate
modified_base           25
                        mod_base = OTHER
                        note = 2'-O-(2-methoxyethyl) 5-methyl cytidine
                         5'-thiophosphate
modified_base           26
                        mod_base = OTHER
                        note = 2'-O-(2-methoxyethyl) 5-methyl cytidine
                         5'-thiophosphate
modified_base           27
                        mod_base = OTHER
                        note = 2'-O-(2-methoxyethyl) adenosine 5'-thiophosphate
SEQUENCE: 77
aaacaaaaca aaccacagaa actacca                                        27

SEQ ID NO: 78          moltype = RNA  length = 27
FEATURE                Location/Qualifiers
source                 1..27
                        mol_type = other RNA
                        organism = synthetic construct
modified_base           1
                        mod_base = OTHER
                        note = 2'-O-methyl adenosine
modified_base           2
                        mod_base = OTHER
                        note = 2'-O-methyl uridine 5'-thiophosphate
modified_base           3
                        mod_base = OTHER
                        note = 2'-O-methyl uridine 5'-thiophosphate
modified_base           4
                        mod_base = OTHER
                        note = 2'-O-methyl adenosine
```

-continued

| | | |
|---|---|---|
| modified_base | 5 | |
| | mod_base = OTHER | |
| | note = 2'-O-methyl uridine | |
| modified_base | 6 | |
| | mod_base = OTHER | |
| | note = 2'-O-methyl uridine | |
| modified_base | 7 | |
| | mod_base = OTHER | |
| | note = 2'-O-methyl adenosine | |
| modified_base | 8 | |
| | mod_base = OTHER | |
| | note = 2'-O-methyl uridine | |
| modified_base | 9 | |
| | mod_base = OTHER | |
| | note = 2'-O-methyl uridine | |
| modified_base | 10 | |
| | mod_base = OTHER | |
| | note = 2'-O-methyl adenosine | |
| modified_base | 11 | |
| | mod_base = OTHER | |
| | note = 2'-O-(2-methoxyethyl) adenosine | |
| modified_base | 12 | |
| | mod_base = OTHER | |
| | note = 2'-O-(2-methoxyethyl) adenosine 5'-thiophosphate | |
| modified_base | 13 | |
| | mod_base = OTHER | |
| | note = 2'-O-(2-methoxyethyl) 5-methyl cytidine 5'-thiophosphate | |
| modified_base | 14 | |
| | mod_base = OTHER | |
| | note = 2'-O-(2-methoxyethyl) 5-methyl cytidine 5'-thiophosphate | |
| modified_base | 15 | |
| | mod_base = OTHER | |
| | note = 2'-O-(2-methoxyethyl) adenosine 5'-thiophosphate | |
| modified_base | 16 | |
| | mod_base = OTHER | |
| | note = 2'-O-(2-methoxyethyl) 5-methyl cytidine 5'-thiophosphate | |
| modified_base | 17 | |
| | mod_base = OTHER | |
| | note = 2'-O-(2-methoxyethyl) adenosine 5'-thiophosphate | |
| modified_base | 18 | |
| | mod_base = OTHER | |
| | note = 2'-O-(2-methoxyethyl) guanosine 5'-thiophosphate | |
| modified_base | 19 | |
| | mod_base = OTHER | |
| | note = 2'-O-(2-methoxyethyl) adenosine 5'-thiophosphate | |
| modified_base | 20 | |
| | mod_base = OTHER | |
| | note = 2'-O-(2-methoxyethyl) adenosine 5'-thiophosphate | |
| modified_base | 21 | |
| | mod_base = OTHER | |
| | note = 2'-O-(2-methoxyethyl) adenosine 5'-thiophosphate | |
| modified_base | 22 | |
| | mod_base = OTHER | |
| | note = 2'-O-(2-methoxyethyl) 5-methyl cytidine 5'-thiophosphate | |
| modified_base | 23 | |
| | mod_base = OTHER | |
| | note = 2'-O-(2-methoxyethyl) thymidine 5'-thiophosphate | |
| modified_base | 24 | |
| | mod_base = OTHER | |
| | note = 2'-O-(2-methoxyethyl) adenosine 5'-thiophosphate | |
| modified_base | 25 | |
| | mod_base = OTHER | |
| | note = 2'-O-(2-methoxyethyl) 5-methyl cytidine 5'-thiophosphate | |
| modified_base | 26 | |
| | mod_base = OTHER | |
| | note = 2'-O-(2-methoxyethyl) 5-methyl cytidine 5'-thiophosphate | |
| modified_base | 27 | |
| | mod_base = OTHER | |
| | note = 2'-O-(2-methoxyethyl) adenosine 5'-thiophosphate | |

SEQUENCE: 78
attattatta aaccacagaa actacca                                        27

SEQ ID NO: 79          moltype = RNA   length = 32

-continued

```
FEATURE                Location/Qualifiers
source                 1..32
                       mol_type = other RNA
                       organism = synthetic construct
modified_base          1
                       mod_base = OTHER
                       note = 2'-O-methyl guanosine
modified_base          2
                       mod_base = OTHER
                       note = 2'-O-methyl guanosine 5'-thiophosphate
modified_base          3
                       mod_base = OTHER
                       note = 2'-O-methyl adenosine 5'-thiophosphate
modified_base          4
                       mod_base = OTHER
                       note = 2'-O-methyl cytidine
modified_base          5
                       mod_base = OTHER
                       note = 2'-O-methyl uridine
modified_base          6
                       mod_base = OTHER
                       note = 2'-O-methyl guanosine
modified_base          7
                       mod_base = OTHER
                       note = 2'-O-methyl guanosine
modified_base          8
                       mod_base = OTHER
                       note = 2'-O-methyl adenosine
modified_base          9
                       mod_base = OTHER
                       note = 2'-O-methyl cytidine
modified_base          10
                       mod_base = OTHER
                       note = 2'-O-methyl uridine
modified_base          11
                       mod_base = OTHER
                       note = 2'-O-methyl guanosine
modified_base          12
                       mod_base = OTHER
                       note = 2'-O-methyl guanosine
modified_base          13
                       mod_base = OTHER
                       note = 2'-O-methyl adenosine
modified_base          14
                       mod_base = OTHER
                       note = 2'-O-methyl cytidine
modified_base          15
                       mod_base = OTHER
                       note = 2'-O-methyl uridine
modified_base          16
                       mod_base = OTHER
                       note = 2'-O-(2-methoxyethyl) adenosine
modified_base          17
                       mod_base = OTHER
                       note = 2'-O-(2-methoxyethyl) adenosine 5'-thiophosphate
modified_base          18
                       mod_base = OTHER
                       note = 2'-O-(2-methoxyethyl) 5-methyl cytidine
                        5'-thiophosphate
modified_base          19
                       mod_base = OTHER
                       note = 2'-O-(2-methoxyethyl) 5-methyl cytidine
                        5'-thiophosphate
modified_base          20
                       mod_base = OTHER
                       note = 2'-O-(2-methoxyethyl) adenosine 5'-thiophosphate
modified_base          21
                       mod_base = OTHER
                       note = 2'-O-(2-methoxyethyl) 5-methyl cytidine
                        5'-thiophosphate
modified_base          22
                       mod_base = OTHER
                       note = 2'-O-(2-methoxyethyl) adenosine 5'-thiophosphate
modified_base          23
                       mod_base = OTHER
                       note = 2'-O-(2-methoxyethyl) guanosine 5'-thiophosphate
modified_base          24
                       mod_base = OTHER
                       note = 2'-O-(2-methoxyethyl) adenosine 5'-thiophosphate
```

-continued

```
modified_base          25
                       mod_base = OTHER
                       note = 2'-O-(2-methoxyethyl) adenosine 5'-thiophosphate
modified_base          26
                       mod_base = OTHER
                       note = 2'-O-(2-methoxyethyl) adenosine 5'-thiophosphate
modified_base          27
                       mod_base = OTHER
                       note = 2'-O-(2-methoxyethyl) 5-methyl cytidine
                        5'-thiophosphate
modified_base          28
                       mod_base = OTHER
                       note = 2'-O-(2-methoxyethyl) thymidine 5'-thiophosphate
modified_base          29
                       mod_base = OTHER
                       note = 2'-O-(2-methoxyethyl) adenosine 5'-thiophosphate
modified_base          30
                       mod_base = OTHER
                       note = 2'-O-(2-methoxyethyl) 5-methyl cytidine
                        5'-thiophosphate
modified_base          31
                       mod_base = OTHER
                       note = 2'-O-(2-methoxyethyl) 5-methyl cytidine
                        5'-thiophosphate
modified_base          32
                       mod_base = OTHER
                       note = 2'-O-(2-methoxyethyl) adenosine 5'-thiophosphate
SEQUENCE: 79
ggactggact ggactaacca cagaaactac ca                              32

SEQ ID NO: 80          moltype = RNA  length = 29
FEATURE                Location/Qualifiers
source                 1..29
                       mol_type = other RNA
                       organism = synthetic construct
modified_base          1
                       mod_base = OTHER
                       note = 2'-O-methyl adenosine
modified_base          2
                       mod_base = OTHER
                       note = 2'-O-methyl adenosine 5'-thiophosphate
modified_base          3
                       mod_base = OTHER
                       note = 2'-O-methyl adenosine 5'-thiophosphate
modified_base          4
                       mod_base = OTHER
                       note = 2'-O-methyl adenosine
modified_base          5
                       mod_base = OTHER
                       note = 2'-O-methyl adenosine
modified_base          6
                       mod_base = OTHER
                       note = 2'-O-methyl adenosine
modified_base          7
                       mod_base = OTHER
                       note = 2'-O-methyl adenosine
modified_base          8
                       mod_base = OTHER
                       note = 2'-O-methyl adenosine
modified_base          9
                       mod_base = OTHER
                       note = 2'-O-methyl adenosine
modified_base          10
                       mod_base = OTHER
                       note = 2'-O-methyl adenosine
modified_base          11
                       mod_base = OTHER
                       note = 2'-O-methyl adenosine
modified_base          12
                       mod_base = OTHER
                       note = 2'-O-methyl adenosine
modified_base          13
                       mod_base = OTHER
                       note = 2'-O-(2-methoxyethyl) adenosine
modified_base          14
                       mod_base = OTHER
                       note = 2'-O-(2-methoxyethyl) adenosine 5'-thiophosphate
modified_base          15
                       mod_base = OTHER
```

-continued

```
                       note = 2'-O-(2-methoxyethyl) 5-methyl cytidine
                        5'-thiophosphate
modified_base          16
                       mod_base = OTHER
                       note = 2'-O-(2-methoxyethyl) 5-methyl cytidine
                        5'-thiophosphate
modified_base          17
                       mod_base = OTHER
                       note = 2'-O-(2-methoxyethyl) adenosine 5'-thiophosphate
modified_base          18
                       mod_base = OTHER
                       note = 2'-O-(2-methoxyethyl) 5-methyl cytidine
                        5'-thiophosphate
modified_base          19
                       mod_base = OTHER
                       note = 2'-O-(2-methoxyethyl) adenosine 5'-thiophosphate
modified_base          20
                       mod_base = OTHER
                       note = 2'-O-(2-methoxyethyl) guanosine 5'-thiophosphate
modified_base          21
                       mod_base = OTHER
                       note = 2'-O-(2-methoxyethyl) adenosine 5'-thiophosphate
modified_base          22
                       mod_base = OTHER
                       note = 2'-O-(2-methoxyethyl) adenosine 5'-thiophosphate
modified_base          23
                       mod_base = OTHER
                       note = 2'-O-(2-methoxyethyl) adenosine 5'-thiophosphate
modified_base          24
                       mod_base = OTHER
                       note = 2'-O-(2-methoxyethyl) 5-methyl cytidine
                        5'-thiophosphate
modified_base          25
                       mod_base = OTHER
                       note = 2'-O-(2-methoxyethyl) thymidine 5'-thiophosphate
modified_base          26
                       mod_base = OTHER
                       note = 2'-O-(2-methoxyethyl) adenosine 5'-thiophosphate
modified_base          27
                       mod_base = OTHER
                       note = 2'-O-(2-methoxyethyl) 5-methyl cytidine
                        5'-thiophosphate
modified_base          28
                       mod_base = OTHER
                       note = 2'-O-(2-methoxyethyl) 5-methyl cytidine
                        5'-thiophosphate
modified_base          29
                       mod_base = OTHER
                       note = 2'-O-(2-methoxyethyl) adenosine 5'-thiophosphate
SEQUENCE: 80
aaaaaaaaaa aaaaccacag aaactacca                                 29

SEQ ID NO: 81          moltype = RNA  length = 33
FEATURE                Location/Qualifiers
source                 1..33
                       mol_type = other RNA
                       organism = synthetic construct
modified_base          1
                       mod_base = OTHER
                       note = 2'-O-methyl guanosine
modified_base          2
                       mod_base = OTHER
                       note = 2'-O-methyl guanosine 5'-thiophosphate
modified_base          3
                       mod_base = OTHER
                       note = 2'-O-methyl adenosine 5'-thiophosphate
modified_base          4
                       mod_base = OTHER
                       note = 2'-O-methyl cytidine
modified_base          5
                       mod_base = OTHER
                       note = 2'-O-methyl uridine
modified_base          6
                       mod_base = OTHER
                       note = 2'-O-methyl guanosine
modified_base          7
                       mod_base = OTHER
                       note = 2'-O-methyl guanosine
modified_base          8
```

```
                            mod_base = OTHER
                            note = 2'-O-methyl adenosine
modified_base               9
                            mod_base = OTHER
                            note = 2'-O-methyl cytidine
modified_base               10
                            mod_base = OTHER
                            note = 2'-O-methyl uridine
modified_base               11
                            mod_base = OTHER
                            note = 2'-O-(2-methoxyethyl) adenosine 5'-thiophosphate
modified_base               12
                            mod_base = OTHER
                            note = 2'-O-(2-methoxyethyl) thymidine 5'-thiophosphate
modified_base               13
                            mod_base = OTHER
                            note = 2'-O-(2-methoxyethyl) adenosine 5'-thiophosphate
modified_base               14
                            mod_base = OTHER
                            note = 2'-O-(2-methoxyethyl) adenosine 5'-thiophosphate
modified_base               15
                            mod_base = OTHER
                            note = 2'-O-(2-methoxyethyl) guanosine 5'-thiophosphate
modified_base               16
                            mod_base = OTHER
                            note = 2'-O-(2-methoxyethyl) adenosine 5'-thiophosphate
modified_base               17
                            mod_base = OTHER
                            note = 2'-O-(2-methoxyethyl) thymidine 5'-thiophosphate
modified_base               18
                            mod_base = OTHER
                            note = 2'-O-(2-methoxyethyl) adenosine 5'-thiophosphate
modified_base               19
                            mod_base = OTHER
                            note = 2'-O-(2-methoxyethyl) adenosine 5'-thiophosphate
modified_base               20
                            mod_base = OTHER
                            note = 2'-O-(2-methoxyethyl) adenosine 5'-thiophosphate
modified_base               21
                            mod_base = OTHER
                            note = 2'-O-(2-methoxyethyl) thymidine 5'-thiophosphate
modified_base               22
                            mod_base = OTHER
                            note = 2'-O-(2-methoxyethyl) adenosine 5'-thiophosphate
modified_base               23
                            mod_base = OTHER
                            note = 2'-O-(2-methoxyethyl) adenosine 5'-thiophosphate
modified_base               24
                            mod_base = OTHER
                            note = 2'-O-(2-methoxyethyl) 5-methyl cytidine
                             5'-thiophosphate
modified_base               25
                            mod_base = OTHER
                            note = 2'-O-(2-methoxyethyl) 5-methyl cytidine
                             5'-thiophosphate
modified_base               26
                            mod_base = OTHER
                            note = 2'-O-(2-methoxyethyl) thymidine 5'-thiophosphate
modified_base               27
                            mod_base = OTHER
                            note = 2'-O-(2-methoxyethyl) adenosine 5'-thiophosphate
modified_base               28
                            mod_base = OTHER
                            note = 2'-O-(2-methoxyethyl) adenosine 5'-thiophosphate
modified_base               29
                            mod_base = OTHER
                            note = 2'-O-(2-methoxyethyl) thymidine 5'-thiophosphate
modified_base               30
                            mod_base = OTHER
                            note = 2'-O-(2-methoxyethyl) adenosine 5'-thiophosphate
modified_base               31
                            mod_base = OTHER
                            note = 2'-O-(2-methoxyethyl) adenosine 5'-thiophosphate
modified_base               32
                            mod_base = OTHER
                            note = 2'-O-(2-methoxyethyl) adenosine 5'-thiophosphate
modified_base               33
                            mod_base = OTHER
                            note = 2'-O-(2-methoxyethyl) thymidine 5'-thiophosphate
```

-continued

```
SEQUENCE: 81
ggactggact ataagataaa taacctaata aat                                        33

SEQ ID NO: 82              moltype = RNA  length = 33
FEATURE                   Location/Qualifiers
source                    1..33
                          mol_type = other RNA
                          organism = synthetic construct
modified_base             1
                          mod_base = OTHER
                          note = 2'-O-methyl guanosine
modified_base             2
                          mod_base = OTHER
                          note = 2'-O-methyl guanosine 5'-thiophosphate
modified_base             3
                          mod_base = OTHER
                          note = 2'-O-methyl adenosine 5'-thiophosphate
modified_base             4
                          mod_base = OTHER
                          note = 2'-O-methyl cytidine
modified_base             5
                          mod_base = OTHER
                          note = 2'-O-methyl uridine
modified_base             6
                          mod_base = OTHER
                          note = 2'-O-methyl guanosine
modified_base             7
                          mod_base = OTHER
                          note = 2'-O-methyl guanosine 5'-thiophosphate
modified_base             8
                          mod_base = OTHER
                          note = 2'-O-methyl adenosine 5'-thiophosphate
modified_base             9
                          mod_base = OTHER
                          note = 2'-O-methyl cytidine
modified_base             10
                          mod_base = OTHER
                          note = 2'-O-methyl uridine
modified_base             11
                          mod_base = OTHER
                          note = 2'-O-(2-methoxyethyl) adenosine 5'-thiophosphate
modified_base             12
                          mod_base = OTHER
                          note = 2'-O-(2-methoxyethyl) thymidine 5'-thiophosphate
modified_base             13
                          mod_base = OTHER
                          note = 2'-O-(2-methoxyethyl) adenosine 5'-thiophosphate
modified_base             14
                          mod_base = OTHER
                          note = 2'-O-(2-methoxyethyl) adenosine 5'-thiophosphate
modified_base             15
                          mod_base = OTHER
                          note = 2'-O-(2-methoxyethyl) guanosine 5'-thiophosphate
modified_base             16
                          mod_base = OTHER
                          note = 2'-O-(2-methoxyethyl) adenosine 5'-thiophosphate
modified_base             17
                          mod_base = OTHER
                          note = 2'-O-(2-methoxyethyl) thymidine 5'-thiophosphate
modified_base             18
                          mod_base = OTHER
                          note = 2'-O-(2-methoxyethyl) adenosine 5'-thiophosphate
modified_base             19
                          mod_base = OTHER
                          note = 2'-O-(2-methoxyethyl) adenosine 5'-thiophosphate
modified_base             20
                          mod_base = OTHER
                          note = 2'-O-(2-methoxyethyl) adenosine 5'-thiophosphate
modified_base             21
                          mod_base = OTHER
                          note = 2'-O-(2-methoxyethyl) thymidine 5'-thiophosphate
modified_base             22
                          mod_base = OTHER
                          note = 2'-O-(2-methoxyethyl) adenosine 5'-thiophosphate
modified_base             23
                          mod_base = OTHER
                          note = 2'-O-(2-methoxyethyl) adenosine 5'-thiophosphate
modified_base             24
                          mod_base = OTHER
```

```
                        note = 2'-O-(2-methoxyethyl) 5-methyl cytidine
                         5'-thiophosphate
modified_base           25
                        mod_base = OTHER
                        note = 2'-O-(2-methoxyethyl) 5-methyl cytidine
                         5'-thiophosphate
modified_base           26
                        mod_base = OTHER
                        note = 2'-O-(2-methoxyethyl) thymidine 5'-thiophosphate
modified_base           27
                        mod_base = OTHER
                        note = 2'-O-(2-methoxyethyl) adenosine 5'-thiophosphate
modified_base           28
                        mod_base = OTHER
                        note = 2'-O-(2-methoxyethyl) adenosine 5'-thiophosphate
modified_base           29
                        mod_base = OTHER
                        note = 2'-O-(2-methoxyethyl) thymidine 5'-thiophosphate
modified_base           30
                        mod_base = OTHER
                        note = 2'-O-(2-methoxyethyl) adenosine 5'-thiophosphate
modified_base           31
                        mod_base = OTHER
                        note = 2'-O-(2-methoxyethyl) adenosine 5'-thiophosphate
modified_base           32
                        mod_base = OTHER
                        note = 2'-O-(2-methoxyethyl) adenosine 5'-thiophosphate
modified_base           33
                        mod_base = OTHER
                        note = 2'-O-(2-methoxyethyl) thymidine 5'-thiophosphate
SEQUENCE: 82
ggactggact ataagataaa taacctaata aat                                    33

SEQ ID NO: 83           moltype = RNA  length = 33
FEATURE                 Location/Qualifiers
source                  1..33
                        mol_type = other RNA
                        organism = synthetic construct
modified_base           1
                        mod_base = OTHER
                        note = 2'-O-methyl guanosine
modified_base           2
                        mod_base = OTHER
                        note = 2'-O-methyl guanosine 5'-thiophosphate
modified_base           3
                        mod_base = OTHER
                        note = 2'-O-methyl adenosine 5'-thiophosphate
modified_base           4
                        mod_base = OTHER
                        note = 2'-O-methyl cytidine
modified_base           5
                        mod_base = OTHER
                        note = 2'-O-methyl uridine
modified_base           6
                        mod_base = OTHER
                        note = 2'-O-methyl guanosine
modified_base           7
                        mod_base = OTHER
                        note = 2'-O-methyl guanosine 5'-thiophosphate
modified_base           8
                        mod_base = OTHER
                        note = 2'-O-methyl adenosine 5'-thiophosphate
modified_base           9
                        mod_base = OTHER
                        note = 2'-O-methyl cytidine
modified_base           10
                        mod_base = OTHER
                        note = 2'-O-methyl uridine
modified_base           11
                        mod_base = OTHER
                        note = 2'-O-(2-methoxyethyl) adenosine
modified_base           12
                        mod_base = OTHER
                        note = 2'-O-(2-methoxyethyl) thymidine 5'-thiophosphate
modified_base           13
                        mod_base = OTHER
                        note = 2'-O-(2-methoxyethyl) adenosine 5'-thiophosphate
modified_base           14
                        mod_base = OTHER
```

```
                           note = 2'-O-(2-methoxyethyl) adenosine 5'-thiophosphate
modified_base              15
                           mod_base = OTHER
                           note = 2'-O-(2-methoxyethyl) guanosine 5'-thiophosphate
modified_base              16
                           mod_base = OTHER
                           note = 2'-O-(2-methoxyethyl) adenosine 5'-thiophosphate
modified_base              17
                           mod_base = OTHER
                           note = 2'-O-(2-methoxyethyl) thymidine 5'-thiophosphate
modified_base              18
                           mod_base = OTHER
                           note = 2'-O-(2-methoxyethyl) adenosine 5'-thiophosphate
modified_base              19
                           mod_base = OTHER
                           note = 2'-O-(2-methoxyethyl) adenosine 5'-thiophosphate
modified_base              20
                           mod_base = OTHER
                           note = 2'-O-(2-methoxyethyl) adenosine 5'-thiophosphate
modified_base              21
                           mod_base = OTHER
                           note = 2'-O-(2-methoxyethyl) thymidine 5'-thiophosphate
modified_base              22
                           mod_base = OTHER
                           note = 2'-O-(2-methoxyethyl) adenosine 5'-thiophosphate
modified_base              23
                           mod_base = OTHER
                           note = 2'-O-(2-methoxyethyl) adenosine 5'-thiophosphate
modified_base              24
                           mod_base = OTHER
                           note = 2'-O-(2-methoxyethyl) 5-methyl cytidine
                            5'-thiophosphate
modified_base              25
                           mod_base = OTHER
                           note = 2'-O-(2-methoxyethyl) 5-methyl cytidine
                            5'-thiophosphate
modified_base              26
                           mod_base = OTHER
                           note = 2'-O-(2-methoxyethyl) thymidine 5'-thiophosphate
modified_base              27
                           mod_base = OTHER
                           note = 2'-O-(2-methoxyethyl) adenosine 5'-thiophosphate
modified_base              28
                           mod_base = OTHER
                           note = 2'-O-(2-methoxyethyl) adenosine 5'-thiophosphate
modified_base              29
                           mod_base = OTHER
                           note = 2'-O-(2-methoxyethyl) thymidine 5'-thiophosphate
modified_base              30
                           mod_base = OTHER
                           note = 2'-O-(2-methoxyethyl) adenosine 5'-thiophosphate
modified_base              31
                           mod_base = OTHER
                           note = 2'-O-(2-methoxyethyl) adenosine 5'-thiophosphate
modified_base              32
                           mod_base = OTHER
                           note = 2'-O-(2-methoxyethyl) adenosine 5'-thiophosphate
modified_base              33
                           mod_base = OTHER
                           note = 2'-O-(2-methoxyethyl) thymidine 5'-thiophosphate
SEQUENCE: 83
ggactggact ataagataaa taacctaata aat                                  33

SEQ ID NO: 84              moltype = RNA   length = 33
FEATURE                   Location/Qualifiers
source                    1..33
                          mol_type = other RNA
                          organism = synthetic construct
modified_base             1
                          mod_base = OTHER
                          note = 2'-O-methyl guanosine
modified_base             2
                          mod_base = OTHER
                          note = 2'-O-methyl guanosine 5'-thiophosphate
modified_base             3
                          mod_base = OTHER
                          note = 2'-O-methyl adenosine 5'-thiophosphate
modified_base             4
                          mod_base = OTHER
```

```
                        note = 2'-O-methyl cytidine
modified_base           5
                        mod_base = OTHER
                        note = 2'-O-methyl uridine
modified_base           6
                        mod_base = OTHER
                        note = 2'-O-methyl guanosine
modified_base           7
                        mod_base = OTHER
                        note = 2'-O-methyl guanosine 5'-thiophosphate
modified_base           8
                        mod_base = OTHER
                        note = 2'-O-methyl adenosine
modified_base           9
                        mod_base = OTHER
                        note = 2'-O-methyl cytidine 5'-thiophosphate
modified_base           10
                        mod_base = OTHER
                        note = 2'-O-methyl uridine 5'-thiophosphate
modified_base           11
                        mod_base = OTHER
                        note = 2'-O-(2-methoxyethyl) adenosine 5'-thiophosphate
modified_base           12
                        mod_base = OTHER
                        note = 2'-O-(2-methoxyethyl) thymidine 5'-thiophosphate
modified_base           13
                        mod_base = OTHER
                        note = 2'-O-(2-methoxyethyl) adenosine 5'-thiophosphate
modified_base           14
                        mod_base = OTHER
                        note = 2'-O-(2-methoxyethyl) adenosine 5'-thiophosphate
modified_base           15
                        mod_base = OTHER
                        note = 2'-O-(2-methoxyethyl) guanosine 5'-thiophosphate
modified_base           16
                        mod_base = OTHER
                        note = 2'-O-(2-methoxyethyl) adenosine 5'-thiophosphate
modified_base           17
                        mod_base = OTHER
                        note = 2'-O-(2-methoxyethyl) thymidine 5'-thiophosphate
modified_base           18
                        mod_base = OTHER
                        note = 2'-O-(2-methoxyethyl) adenosine 5'-thiophosphate
modified_base           19
                        mod_base = OTHER
                        note = 2'-O-(2-methoxyethyl) adenosine 5'-thiophosphate
modified_base           20
                        mod_base = OTHER
                        note = 2'-O-(2-methoxyethyl) adenosine 5'-thiophosphate
modified_base           21
                        mod_base = OTHER
                        note = 2'-O-(2-methoxyethyl) thymidine 5'-thiophosphate
modified_base           22
                        mod_base = OTHER
                        note = 2'-O-(2-methoxyethyl) adenosine 5'-thiophosphate
modified_base           23
                        mod_base = OTHER
                        note = 2'-O-(2-methoxyethyl) adenosine 5'-thiophosphate
modified_base           24
                        mod_base = OTHER
                        note = 2'-O-(2-methoxyethyl) 5-methyl cytidine
                         5'-thiophosphate
modified_base           25
                        mod_base = OTHER
                        note = 2'-O-(2-methoxyethyl) 5-methyl cytidine
                         5'-thiophosphate
modified_base           26
                        mod_base = OTHER
                        note = 2'-O-(2-methoxyethyl) thymidine 5'-thiophosphate
modified_base           27
                        mod_base = OTHER
                        note = 2'-O-(2-methoxyethyl) adenosine 5'-thiophosphate
modified_base           28
                        mod_base = OTHER
                        note = 2'-O-(2-methoxyethyl) adenosine 5'-thiophosphate
modified_base           29
                        mod_base = OTHER
                        note = 2'-O-(2-methoxyethyl) thymidine 5'-thiophosphate
modified_base           30
```

-continued

```
                        mod_base = OTHER
                        note = 2'-O-(2-methoxyethyl) adenosine 5'-thiophosphate
modified_base           31
                        mod_base = OTHER
                        note = 2'-O-(2-methoxyethyl) adenosine 5'-thiophosphate
modified_base           32
                        mod_base = OTHER
                        note = 2'-O-(2-methoxyethyl) adenosine 5'-thiophosphate
modified_base           33
                        mod_base = OTHER
                        note = 2'-O-(2-methoxyethyl) thymidine 5'-thiophosphate
SEQUENCE: 84
ggactggact ataagataaa taacctaata aat                                33

SEQ ID NO: 85           moltype = RNA  length = 33
FEATURE                 Location/Qualifiers
source                  1..33
                        mol_type = other RNA
                        organism = synthetic construct
modified_base           1
                        mod_base = OTHER
                        note = 2'-O-methyl guanosine
modified_base           2
                        mod_base = OTHER
                        note = 2'-O-methyl guanosine 5'-thiophosphate
modified_base           3
                        mod_base = OTHER
                        note = 2'-O-methyl adenosine 5'-thiophosphate
modified_base           4
                        mod_base = OTHER
                        note = 2'-O-methyl cytidine
modified_base           5
                        mod_base = OTHER
                        note = 2'-O-methyl uridine
modified_base           6
                        mod_base = OTHER
                        note = 2'-O-methyl guanosine
modified_base           7
                        mod_base = OTHER
                        note = 2'-O-methyl guanosine 5'-thiophosphate
modified_base           8
                        mod_base = OTHER
                        note = 2'-O-methyl adenosine 5'-thiophosphate
modified_base           9
                        mod_base = OTHER
                        note = 2'-O-methyl cytidine 5'-thiophosphate
modified_base           10
                        mod_base = OTHER
                        note = 2'-O-methyl uridine 5'-thiophosphate
modified_base           11
                        mod_base = OTHER
                        note = 2'-O-(2-methoxyethyl) adenosine 5'-thiophosphate
modified_base           12
                        mod_base = OTHER
                        note = 2'-O-(2-methoxyethyl) thymidine 5'-thiophosphate
modified_base           13
                        mod_base = OTHER
                        note = 2'-O-(2-methoxyethyl) adenosine 5'-thiophosphate
modified_base           14
                        mod_base = OTHER
                        note = 2'-O-(2-methoxyethyl) adenosine 5'-thiophosphate
modified_base           15
                        mod_base = OTHER
                        note = 2'-O-(2-methoxyethyl) guanosine 5'-thiophosphate
modified_base           16
                        mod_base = OTHER
                        note = 2'-O-(2-methoxyethyl) adenosine 5'-thiophosphate
modified_base           17
                        mod_base = OTHER
                        note = 2'-O-(2-methoxyethyl) thymidine 5'-thiophosphate
modified_base           18
                        mod_base = OTHER
                        note = 2'-O-(2-methoxyethyl) adenosine 5'-thiophosphate
modified_base           19
                        mod_base = OTHER
                        note = 2'-O-(2-methoxyethyl) adenosine 5'-thiophosphate
modified_base           20
                        mod_base = OTHER
                        note = 2'-O-(2-methoxyethyl) adenosine 5'-thiophosphate
```

-continued

```
modified_base       21
                    mod_base = OTHER
                    note = 2'-O-(2-methoxyethyl) thymidine 5'-thiophosphate
modified_base       22
                    mod_base = OTHER
                    note = 2'-O-(2-methoxyethyl) adenosine 5'-thiophosphate
modified_base       23
                    mod_base = OTHER
                    note = 2'-O-(2-methoxyethyl) adenosine 5'-thiophosphate
modified_base       24
                    mod_base = OTHER
                    note = 2'-O-(2-methoxyethyl) 5-methyl cytidine
                     5'-thiophosphate
modified_base       25
                    mod_base = OTHER
                    note = 2'-O-(2-methoxyethyl) 5-methyl cytidine
                     5'-thiophosphate
modified_base       26
                    mod_base = OTHER
                    note = 2'-O-(2-methoxyethyl) thymidine 5'-thiophosphate
modified_base       27
                    mod_base = OTHER
                    note = 2'-O-(2-methoxyethyl) adenosine 5'-thiophosphate
modified_base       28
                    mod_base = OTHER
                    note = 2'-O-(2-methoxyethyl) adenosine 5'-thiophosphate
modified_base       29
                    mod_base = OTHER
                    note = 2'-O-(2-methoxyethyl) thymidine 5'-thiophosphate
modified_base       30
                    mod_base = OTHER
                    note = 2'-O-(2-methoxyethyl) adenosine 5'-thiophosphate
modified_base       31
                    mod_base = OTHER
                    note = 2'-O-(2-methoxyethyl) adenosine 5'-thiophosphate
modified_base       32
                    mod_base = OTHER
                    note = 2'-O-(2-methoxyethyl) adenosine 5'-thiophosphate
modified_base       33
                    mod_base = OTHER
                    note = 2'-O-(2-methoxyethyl) thymidine 5'-thiophosphate
SEQUENCE: 85
ggactggact ataagataaa taacctaata aat                          33

SEQ ID NO: 86       moltype = RNA  length = 32
FEATURE             Location/Qualifiers
source              1..32
                    mol_type = other RNA
                    organism = synthetic construct
modified_base       1
                    mod_base = OTHER
                    note = 2'-O-methyl guanosine
modified_base       2
                    mod_base = OTHER
                    note = 2'-O-methyl guanosine 5'-thiophosphate
modified_base       3
                    mod_base = OTHER
                    note = 2'-O-methyl adenosine 5'-thiophosphate
modified_base       4
                    mod_base = OTHER
                    note = 2'-O-methyl cytidine
modified_base       5
                    mod_base = OTHER
                    note = 2'-O-methyl uridine
modified_base       6
                    mod_base = OTHER
                    note = 2'-O-methyl guanosine
modified_base       7
                    mod_base = OTHER
                    note = 2'-O-methyl guanosine 5'-thiophosphate
modified_base       8
                    mod_base = OTHER
                    note = 2'-O-methyl adenosine
modified_base       9
                    mod_base = OTHER
                    note = 2'-O-methyl cytidine 5'-thiophosphate
modified_base       10
                    mod_base = OTHER
                    note = 2'-O-(2-methoxyethyl) adenosine 5'-thiophosphate
```

-continued

```
modified_base    11
                 mod_base = OTHER
                 note = 2'-O-(2-methoxyethyl) thymidine 5'-thiophosphate
modified_base    12
                 mod_base = OTHER
                 note = 2'-O-(2-methoxyethyl) adenosine 5'-thiophosphate
modified_base    13
                 mod_base = OTHER
                 note = 2'-O-(2-methoxyethyl) adenosine 5'-thiophosphate
modified_base    14
                 mod_base = OTHER
                 note = 2'-O-(2-methoxyethyl) guanosine 5'-thiophosphate
modified_base    15
                 mod_base = OTHER
                 note = 2'-O-(2-methoxyethyl) adenosine 5'-thiophosphate
modified_base    16
                 mod_base = OTHER
                 note = 2'-O-(2-methoxyethyl) thymidine 5'-thiophosphate
modified_base    17
                 mod_base = OTHER
                 note = 2'-O-(2-methoxyethyl) adenosine 5'-thiophosphate
modified_base    18
                 mod_base = OTHER
                 note = 2'-O-(2-methoxyethyl) adenosine 5'-thiophosphate
modified_base    19
                 mod_base = OTHER
                 note = 2'-O-(2-methoxyethyl) adenosine 5'-thiophosphate
modified_base    20
                 mod_base = OTHER
                 note = 2'-O-(2-methoxyethyl) thymidine 5'-thiophosphate
modified_base    21
                 mod_base = OTHER
                 note = 2'-O-(2-methoxyethyl) adenosine 5'-thiophosphate
modified_base    22
                 mod_base = OTHER
                 note = 2'-O-(2-methoxyethyl) adenosine 5'-thiophosphate
modified_base    23
                 mod_base = OTHER
                 note = 2'-O-(2-methoxyethyl) 5-methyl cytidine
                 5'-thiophosphate
modified_base    24
                 mod_base = OTHER
                 note = 2'-O-(2-methoxyethyl) 5-methyl cytidine
                 5'-thiophosphate
modified_base    25
                 mod_base = OTHER
                 note = 2'-O-(2-methoxyethyl) thymidine 5'-thiophosphate
modified_base    26
                 mod_base = OTHER
                 note = 2'-O-(2-methoxyethyl) adenosine 5'-thiophosphate
modified_base    27
                 mod_base = OTHER
                 note = 2'-O-(2-methoxyethyl) adenosine 5'-thiophosphate
modified_base    28
                 mod_base = OTHER
                 note = 2'-O-(2-methoxyethyl) thymidine 5'-thiophosphate
modified_base    29
                 mod_base = OTHER
                 note = 2'-O-(2-methoxyethyl) adenosine 5'-thiophosphate
modified_base    30
                 mod_base = OTHER
                 note = 2'-O-(2-methoxyethyl) adenosine 5'-thiophosphate
modified_base    31
                 mod_base = OTHER
                 note = 2'-O-(2-methoxyethyl) adenosine 5'-thiophosphate
modified_base    32
                 mod_base = OTHER
                 note = 2'-O-(2-methoxyethyl) thymidine 5'-thiophosphate
SEQUENCE: 86
ggactggaca taagataaat aacctaataa at                              32

SEQ ID NO: 87    moltype = RNA  length = 33
FEATURE          Location/Qualifiers
source           1..33
                 mol_type = other RNA
                 organism = synthetic construct
modified_base    1
                 mod_base = OTHER
                 note = 2'-O-methyl guanosine
```

-continued

```
modified_base      2
                   mod_base = OTHER
                   note = 2'-O-methyl guanosine 5'-thiophosphate
modified_base      3
                   mod_base = OTHER
                   note = 2'-O-methyl adenosine 5'-thiophosphate
modified_base      4
                   mod_base = OTHER
                   note = 2'-O-methyl cytidine
modified_base      5
                   mod_base = OTHER
                   note = 2'-O-methyl uridine
modified_base      6
                   mod_base = OTHER
                   note = 2'-O-methyl guanosine
modified_base      7
                   mod_base = OTHER
                   note = 2'-O-methyl guanosine
modified_base      8
                   mod_base = OTHER
                   note = 2'-O-methyl adenosine
modified_base      9
                   mod_base = OTHER
                   note = 2'-O-methyl cytidine
modified_base      10
                   mod_base = OTHER
                   note = 2'-O-methyl uridine
modified_base      11
                   mod_base = OTHER
                   note = 2'-O-methyl adenosine
modified_base      12
                   mod_base = OTHER
                   note = 2'-O-methyl uridine 5'-thiophosphate
modified_base      13
                   mod_base = OTHER
                   note = 2'-O-methyl adenosine 5'-thiophosphate
modified_base      14
                   mod_base = OTHER
                   note = 2'-O-methyl adenosine 5'-thiophosphate
modified_base      15
                   mod_base = OTHER
                   note = 2'-O-methyl guanosine 5'-thiophosphate
modified_base      16
                   mod_base = OTHER
                   note = 2'-O-methyl adenosine 5'-thiophosphate
modified_base      17
                   mod_base = OTHER
                   note = 2'-O-methyl uridine 5'-thiophosphate
modified_base      18
                   mod_base = OTHER
                   note = 2'-O-methyl adenosine 5'-thiophosphate
modified_base      19
                   mod_base = OTHER
                   note = 2'-O-methyl adenosine 5'-thiophosphate
modified_base      20
                   mod_base = OTHER
                   note = 2'-O-methyl adenosine 5'-thiophosphate
modified_base      21
                   mod_base = OTHER
                   note = 2'-O-methyl uridine 5'-thiophosphate
modified_base      22
                   mod_base = OTHER
                   note = 2'-O-methyl adenosine 5'-thiophosphate
modified_base      23
                   mod_base = OTHER
                   note = 2'-O-methyl adenosine 5'-thiophosphate
modified_base      24
                   mod_base = OTHER
                   note = 2'-O-methyl cytidine 5'-thiophosphate
modified_base      25
                   mod_base = OTHER
                   note = 2'-O-methyl cytidine 5'-thiophosphate
modified_base      26
                   mod_base = OTHER
                   note = 2'-O-methyl uridine 5'-thiophosphate
modified_base      27
                   mod_base = OTHER
                   note = 2'-O-methyl adenosine 5'-thiophosphate
modified_base      28
```

```
                          mod_base = OTHER
                          note = 2'-O-methyl adenosine 5'-thiophosphate
modified_base             29
                          mod_base = OTHER
                          note = 2'-O-methyl uridine 5'-thiophosphate
modified_base             30
                          mod_base = OTHER
                          note = 2'-O-methyl adenosine 5'-thiophosphate
modified_base             31
                          mod_base = OTHER
                          note = 2'-O-methyl adenosine 5'-thiophosphate
modified_base             32
                          mod_base = OTHER
                          note = 2'-O-methyl adenosine 5'-thiophosphate
modified_base             33
                          mod_base = OTHER
                          note = 2'-O-methyl uridine 5'-thiophosphate
SEQUENCE: 87
ggactggact ataagataaa taacctaata aat                                    33

SEQ ID NO: 88             moltype = RNA  length = 28
FEATURE                   Location/Qualifiers
source                    1..28
                          mol_type = other RNA
                          organism = synthetic construct
modified_base             1
                          mod_base = OTHER
                          note = 2'-O-methyl guanosine
modified_base             2
                          mod_base = OTHER
                          note = 2'-O-methyl guanosine 5'-thiophosphate
modified_base             3
                          mod_base = OTHER
                          note = 2'-O-methyl adenosine 5'-thiophosphate
modified_base             4
                          mod_base = OTHER
                          note = 2'-O-methyl cytidine 5'-thiophosphate
modified_base             5
                          mod_base = OTHER
                          note = 2'-O-methyl uridine 5'-thiophosphate
modified_base             6
                          mod_base = OTHER
                          note = 2'-O-(2-methoxyethyl) adenosine 5'-thiophosphate
modified_base             7
                          mod_base = OTHER
                          note = 2'-O-(2-methoxyethyl) thymidine 5'-thiophosphate
modified_base             8
                          mod_base = OTHER
                          note = 2'-O-(2-methoxyethyl) adenosine 5'-thiophosphate
modified_base             9
                          mod_base = OTHER
                          note = 2'-O-(2-methoxyethyl) adenosine 5'-thiophosphate
modified_base             10
                          mod_base = OTHER
                          note = 2'-O-(2-methoxyethyl) guanosine 5'-thiophosphate
modified_base             11
                          mod_base = OTHER
                          note = 2'-O-(2-methoxyethyl) adenosine 5'-thiophosphate
modified_base             12
                          mod_base = OTHER
                          note = 2'-O-(2-methoxyethyl) thymidine 5'-thiophosphate
modified_base             13
                          mod_base = OTHER
                          note = 2'-O-(2-methoxyethyl) adenosine 5'-thiophosphate
modified_base             14
                          mod_base = OTHER
                          note = 2'-O-(2-methoxyethyl) adenosine 5'-thiophosphate
modified_base             15
                          mod_base = OTHER
                          note = 2'-O-(2-methoxyethyl) adenosine 5'-thiophosphate
modified_base             16
                          mod_base = OTHER
                          note = 2'-O-(2-methoxyethyl) thymidine 5'-thiophosphate
modified_base             17
                          mod_base = OTHER
                          note = 2'-O-(2-methoxyethyl) adenosine 5'-thiophosphate
modified_base             18
                          mod_base = OTHER
                          note = 2'-O-(2-methoxyethyl) adenosine 5'-thiophosphate
```

-continued

```
modified_base          19
                       mod_base = OTHER
                       note = 2'-O-(2-methoxyethyl) 5-methyl cytidine
                        5'-thiophosphate
modified_base          20
                       mod_base = OTHER
                       note = 2'-O-(2-methoxyethyl) 5-methyl cytidine
                        5'-thiophosphate
modified_base          21
                       mod_base = OTHER
                       note = 2'-O-(2-methoxyethyl) thymidine 5'-thiophosphate
modified_base          22
                       mod_base = OTHER
                       note = 2'-O-(2-methoxyethyl) adenosine 5'-thiophosphate
modified_base          23
                       mod_base = OTHER
                       note = 2'-O-(2-methoxyethyl) adenosine 5'-thiophosphate
modified_base          24
                       mod_base = OTHER
                       note = 2'-O-(2-methoxyethyl) thymidine 5'-thiophosphate
modified_base          25
                       mod_base = OTHER
                       note = 2'-O-(2-methoxyethyl) adenosine 5'-thiophosphate
modified_base          26
                       mod_base = OTHER
                       note = 2'-O-(2-methoxyethyl) adenosine 5'-thiophosphate
modified_base          27
                       mod_base = OTHER
                       note = 2'-O-(2-methoxyethyl) adenosine 5'-thiophosphate
modified_base          28
                       mod_base = OTHER
                       note = 2'-O-(2-methoxyethyl) thymidine 5'-thiophosphate
SEQUENCE: 88
ggactataag ataaataacc taataaat                                    28

SEQ ID NO: 89          moltype = RNA  length = 28
FEATURE                Location/Qualifiers
source                 1..28
                       mol_type = other RNA
                       organism = synthetic construct
modified_base          1
                       mod_base = OTHER
                       note = 2'-O-methyl guanosine
modified_base          2
                       mod_base = OTHER
                       note = 2'-O-methyl guanosine 5'-thiophosphate
modified_base          3
                       mod_base = OTHER
                       note = 2'-O-methyl adenosine 5'-thiophosphate
modified_base          4
                       mod_base = OTHER
                       note = 2'-O-methyl cytidine
modified_base          5
                       mod_base = OTHER
                       note = 2'-O-methyl uridine
modified_base          6
                       mod_base = OTHER
                       note = 2'-O-(2-methoxyethyl) adenosine 5'-thiophosphate
modified_base          7
                       mod_base = OTHER
                       note = 2'-O-(2-methoxyethyl) thymidine 5'-thiophosphate
modified_base          8
                       mod_base = OTHER
                       note = 2'-O-(2-methoxyethyl) adenosine 5'-thiophosphate
modified_base          9
                       mod_base = OTHER
                       note = 2'-O-(2-methoxyethyl) adenosine 5'-thiophosphate
modified_base          10
                       mod_base = OTHER
                       note = 2'-O-(2-methoxyethyl) guanosine 5'-thiophosphate
modified_base          11
                       mod_base = OTHER
                       note = 2'-O-(2-methoxyethyl) adenosine 5'-thiophosphate
modified_base          12
                       mod_base = OTHER
                       note = 2'-O-(2-methoxyethyl) thymidine 5'-thiophosphate
modified_base          13
                       mod_base = OTHER
                       note = 2'-O-(2-methoxyethyl) adenosine 5'-thiophosphate
```

-continued

```
modified_base        14
                     mod_base = OTHER
                     note = 2'-O-(2-methoxyethyl) adenosine 5'-thiophosphate
modified_base        15
                     mod_base = OTHER
                     note = 2'-O-(2-methoxyethyl) adenosine 5'-thiophosphate
modified_base        16
                     mod_base = OTHER
                     note = 2'-O-(2-methoxyethyl) thymidine 5'-thiophosphate
modified_base        17
                     mod_base = OTHER
                     note = 2'-O-(2-methoxyethyl) adenosine 5'-thiophosphate
modified_base        18
                     mod_base = OTHER
                     note = 2'-O-(2-methoxyethyl) adenosine 5'-thiophosphate
modified_base        19
                     mod_base = OTHER
                     note = 2'-O-(2-methoxyethyl) 5-methyl cytidine
                      5'-thiophosphate
modified_base        20
                     mod_base = OTHER
                     note = 2'-O-(2-methoxyethyl) 5-methyl cytidine
                      5'-thiophosphate
modified_base        21
                     mod_base = OTHER
                     note = 2'-O-(2-methoxyethyl) thymidine 5'-thiophosphate
modified_base        22
                     mod_base = OTHER
                     note = 2'-O-(2-methoxyethyl) adenosine 5'-thiophosphate
modified_base        23
                     mod_base = OTHER
                     note = 2'-O-(2-methoxyethyl) adenosine 5'-thiophosphate
modified_base        24
                     mod_base = OTHER
                     note = 2'-O-(2-methoxyethyl) thymidine 5'-thiophosphate
modified_base        25
                     mod_base = OTHER
                     note = 2'-O-(2-methoxyethyl) adenosine 5'-thiophosphate
modified_base        26
                     mod_base = OTHER
                     note = 2'-O-(2-methoxyethyl) adenosine 5'-thiophosphate
modified_base        27
                     mod_base = OTHER
                     note = 2'-O-(2-methoxyethyl) adenosine 5'-thiophosphate
modified_base        28
                     mod_base = OTHER
                     note = 2'-O-(2-methoxyethyl) thymidine 5'-thiophosphate
SEQUENCE: 89
ggactataag ataaataacc taataaat                                    28

SEQ ID NO: 90        moltype = RNA  length = 28
FEATURE              Location/Qualifiers
source               1..28
                     mol_type = other RNA
                     organism = synthetic construct
modified_base        1
                     mod_base = OTHER
                     note = 2'-O-methyl guanosine
modified_base        2
                     mod_base = OTHER
                     note = 2'-O-methyl guanosine 5'-thiophosphate
modified_base        3
                     mod_base = OTHER
                     note = 2'-O-methyl adenosine 5'-thiophosphate
modified_base        4
                     mod_base = OTHER
                     note = 2'-O-methyl cytidine
modified_base        5
                     mod_base = OTHER
                     note = 2'-O-methyl uridine
modified_base        6
                     mod_base = OTHER
                     note = 2'-O-(2-methoxyethyl) adenosine
modified_base        7
                     mod_base = OTHER
                     note = 2'-O-(2-methoxyethyl) thymidine 5'-thiophosphate
modified_base        8
                     mod_base = OTHER
                     note = 2'-O-(2-methoxyethyl) adenosine 5'-thiophosphate
```

-continued

```
modified_base          9
                       mod_base = OTHER
                       note = 2'-O-(2-methoxyethyl) adenosine 5'-thiophosphate
modified_base          10
                       mod_base = OTHER
                       note = 2'-O-(2-methoxyethyl) guanosine 5'-thiophosphate
modified_base          11
                       mod_base = OTHER
                       note = 2'-O-(2-methoxyethyl) adenosine 5'-thiophosphate
modified_base          12
                       mod_base = OTHER
                       note = 2'-O-(2-methoxyethyl) thymidine 5'-thiophosphate
modified_base          13
                       mod_base = OTHER
                       note = 2'-O-(2-methoxyethyl) adenosine 5'-thiophosphate
modified_base          14
                       mod_base = OTHER
                       note = 2'-O-(2-methoxyethyl) adenosine 5'-thiophosphate
modified_base          15
                       mod_base = OTHER
                       note = 2'-O-(2-methoxyethyl) adenosine 5'-thiophosphate
modified_base          16
                       mod_base = OTHER
                       note = 2'-O-(2-methoxyethyl) thymidine 5'-thiophosphate
modified_base          17
                       mod_base = OTHER
                       note = 2'-O-(2-methoxyethyl) adenosine 5'-thiophosphate
modified_base          18
                       mod_base = OTHER
                       note = 2'-O-(2-methoxyethyl) adenosine 5'-thiophosphate
modified_base          19
                       mod_base = OTHER
                       note = 2'-O-(2-methoxyethyl) 5-methyl cytidine
                         5'-thiophosphate
modified_base          20
                       mod_base = OTHER
                       note = 2'-O-(2-methoxyethyl) 5-methyl cytidine
                         5'-thiophosphate
modified_base          21
                       mod_base = OTHER
                       note = 2'-O-(2-methoxyethyl) thymidine 5'-thiophosphate
modified_base          22
                       mod_base = OTHER
                       note = 2'-O-(2-methoxyethyl) adenosine 5'-thiophosphate
modified_base          23
                       mod_base = OTHER
                       note = 2'-O-(2-methoxyethyl) adenosine 5'-thiophosphate
modified_base          24
                       mod_base = OTHER
                       note = 2'-O-(2-methoxyethyl) thymidine 5'-thiophosphate
modified_base          25
                       mod_base = OTHER
                       note = 2'-O-(2-methoxyethyl) adenosine 5'-thiophosphate
modified_base          26
                       mod_base = OTHER
                       note = 2'-O-(2-methoxyethyl) adenosine 5'-thiophosphate
modified_base          27
                       mod_base = OTHER
                       note = 2'-O-(2-methoxyethyl) adenosine 5'-thiophosphate
modified_base          28
                       mod_base = OTHER
                       note = 2'-O-(2-methoxyethyl) thymidine 5'-thiophosphate
SEQUENCE: 90
ggactataag ataaataacc taataaat                                        28

SEQ ID NO: 91          moltype = RNA  length = 26
FEATURE                Location/Qualifiers
source                 1..26
                       mol_type = other RNA
                       organism = synthetic construct
modified_base          1
                       mod_base = OTHER
                       note = 2'-O-methyl guanosine
modified_base          2
                       mod_base = OTHER
                       note = 2'-O-methyl guanosine 5'-thiophosphate
modified_base          3
                       mod_base = OTHER
                       note = 2'-O-methyl adenosine 5'-thiophosphate
```

-continued

| modified_base | 4 |
| | mod_base = OTHER |
| | note = 2'-O-methyl cytidine |
| modified_base | 5 |
| | mod_base = OTHER |
| | note = 2'-O-methyl uridine |
| modified_base | 6 |
| | mod_base = OTHER |
| | note = 2'-O-methyl guanosine |
| modified_base | 7 |
| | mod_base = OTHER |
| | note = 2'-O-methyl guanosine |
| modified_base | 8 |
| | mod_base = OTHER |
| | note = 2'-O-methyl adenosine |
| modified_base | 9 |
| | mod_base = OTHER |
| | note = 2'-O-methyl cytidine |
| modified_base | 10 |
| | mod_base = OTHER |
| | note = 2'-O-methyl uridine |
| modified_base | 11 |
| | mod_base = OTHER |
| | note = 2'-O-(2-methoxyethyl) 5-methyl cytidine |
| modified_base | 12 |
| | mod_base = OTHER |
| | note = 2'-O-(2-methoxyethyl) thymidine 5'-thiophosphate |
| modified_base | 13 |
| | mod_base = OTHER |
| | note = 2'-O-(2-methoxyethyl) guanosine 5'-thiophosphate |
| modified_base | 14 |
| | mod_base = OTHER |
| | note = 2'-O-(2-methoxyethyl) 5-methyl cytidine 5'-thiophosphate |
| modified_base | 15 |
| | mod_base = OTHER |
| | note = 2'-O-(2-methoxyethyl) thymidine 5'-thiophosphate |
| modified_base | 16 |
| | mod_base = OTHER |
| | note = 2'-O-(2-methoxyethyl) 5-methyl cytidine 5'-thiophosphate |
| modified_base | 17 |
| | mod_base = OTHER |
| | note = 2'-O-(2-methoxyethyl) thymidine 5'-thiophosphate |
| modified_base | 18 |
| | mod_base = OTHER |
| | note = 2'-O-(2-methoxyethyl) guanosine 5'-thiophosphate |
| modified_base | 19 |
| | mod_base = OTHER |
| | note = 2'-O-(2-methoxyethyl) guanosine 5'-thiophosphate |
| modified_base | 20 |
| | mod_base = OTHER |
| | note = 2'-O-(2-methoxyethyl) guanosine 5'-thiophosphate |
| modified_base | 21 |
| | mod_base = OTHER |
| | note = 2'-O-(2-methoxyethyl) adenosine 5'-thiophosphate |
| modified_base | 22 |
| | mod_base = OTHER |
| | note = 2'-O-(2-methoxyethyl) 5-methyl cytidine 5'-thiophosphate |
| modified_base | 23 |
| | mod_base = OTHER |
| | note = 2'-O-(2-methoxyethyl) thymidine 5'-thiophosphate |
| modified_base | 24 |
| | mod_base = OTHER |
| | note = 2'-O-(2-methoxyethyl) guanosine 5'-thiophosphate |
| modified_base | 25 |
| | mod_base = OTHER |
| | note = 2'-O-(2-methoxyethyl) guanosine 5'-thiophosphate |
| modified_base | 26 |
| | mod_base = OTHER |
| | note = 2'-O-(2-methoxyethyl) thymidine 5'-thiophosphate |
| misc_feature | 26 |
| | note = 3'-O attached to a GalNAc-comprising compound via a linker |

SEQUENCE: 91
ggactggact ctgctctggg actggt                                             26

SEQ ID NO: 92          moltype = RNA   length = 26

-continued

```
FEATURE            Location/Qualifiers
source             1..26
                   mol_type = other RNA
                   organism = synthetic construct
modified_base      1
                   mod_base = OTHER
                   note = 2'-O-methyl guanosine
modified_base      2
                   mod_base = OTHER
                   note = 2'-O-methyl guanosine 5'-thiophosphate
modified_base      3
                   mod_base = OTHER
                   note = 2'-O-methyl adenosine 5'-thiophosphate
modified_base      4
                   mod_base = OTHER
                   note = 2'-O-methyl cytidine
modified_base      5
                   mod_base = OTHER
                   note = 2'-O-methyl uridine
modified_base      6
                   mod_base = OTHER
                   note = 2'-O-methyl guanosine
modified_base      7
                   mod_base = OTHER
                   note = 2'-O-methyl guanosine
modified_base      8
                   mod_base = OTHER
                   note = 2'-O-methyl adenosine
modified_base      9
                   mod_base = OTHER
                   note = 2'-O-methyl cytidine
modified_base      10
                   mod_base = OTHER
                   note = 2'-O-methyl uridine
modified_base      11
                   mod_base = OTHER
                   note = 2'-O-(2-methoxyethyl) guanosine
modified_base      12
                   mod_base = OTHER
                   note = 2'-O-(2-methoxyethyl) 5-methyl cytidine
                    5'-thiophosphate
modified_base      13
                   mod_base = OTHER
                   note = 2'-O-(2-methoxyethyl) thymidine 5'-thiophosphate
modified_base      14
                   mod_base = OTHER
                   note = 2'-O-(2-methoxyethyl) 5-methyl cytidine
                    5'-thiophosphate
modified_base      15
                   mod_base = OTHER
                   note = 2'-O-(2-methoxyethyl) thymidine 5'-thiophosphate
modified_base      16
                   mod_base = OTHER
                   note = 2'-O-(2-methoxyethyl) guanosine 5'-thiophosphate
modified_base      17
                   mod_base = OTHER
                   note = 2'-O-(2-methoxyethyl) guanosine 5'-thiophosphate
modified_base      18
                   mod_base = OTHER
                   note = 2'-O-(2-methoxyethyl) guanosine 5'-thiophosphate
modified_base      19
                   mod_base = OTHER
                   note = 2'-O-(2-methoxyethyl) adenosine 5'-thiophosphate
modified_base      20
                   mod_base = OTHER
                   note = 2'-O-(2-methoxyethyl) 5-methyl cytidine
                    5'-thiophosphate
modified_base      21
                   mod_base = OTHER
                   note = 2'-O-(2-methoxyethyl) thymidine 5'-thiophosphate
modified_base      22
                   mod_base = OTHER
                   note = 2'-O-(2-methoxyethyl) guanosine 5'-thiophosphate
modified_base      23
                   mod_base = OTHER
                   note = 2'-O-(2-methoxyethyl) guanosine 5'-thiophosphate
modified_base      24
                   mod_base = OTHER
                   note = 2'-O-(2-methoxyethyl) thymidine 5'-thiophosphate
```

-continued

```
modified_base          25
                       mod_base = OTHER
                       note = 2'-O-(2-methoxyethyl) 5-methyl cytidine
                        5'-thiophosphate
modified_base          26
                       mod_base = OTHER
                       note = 2'-O-(2-methoxyethyl) 5-methyl cytidine
                        5'-thiophosphate
misc_feature           26
                       note = 3'-O attached to a GalNAc-comprising compound via a
                        linker
SEQUENCE: 92
ggactggact gctctgggac tggtcc                                                26

SEQ ID NO: 93          moltype = RNA   length = 10
FEATURE                Location/Qualifiers
source                 1..10
                       mol_type = other RNA
                       organism = synthetic construct
SEQUENCE: 93
cccccccccc                                                                  10

SEQ ID NO: 94          moltype = RNA   length = 10
FEATURE                Location/Qualifiers
source                 1..10
                       mol_type = other RNA
                       organism = synthetic construct
SEQUENCE: 94
tttttttttt                                                                  10

SEQ ID NO: 95          moltype = RNA   length = 10
FEATURE                Location/Qualifiers
source                 1..10
                       mol_type = other RNA
                       organism = synthetic construct
SEQUENCE: 95
acacacacac                                                                  10

SEQ ID NO: 96          moltype = RNA   length = 10
FEATURE                Location/Qualifiers
source                 1..10
                       mol_type = other RNA
                       organism = synthetic construct
SEQUENCE: 96
agagagagag                                                                  10

SEQ ID NO: 97          moltype = RNA   length = 10
FEATURE                Location/Qualifiers
source                 1..10
                       mol_type = other RNA
                       organism = synthetic construct
SEQUENCE: 97
ctctctctct                                                                  10

SEQ ID NO: 98          moltype = RNA   length = 10
FEATURE                Location/Qualifiers
source                 1..10
                       mol_type = other RNA
                       organism = synthetic construct
SEQUENCE: 98
gtgtgtgtgt                                                                  10

SEQ ID NO: 99          moltype = RNA   length = 10
FEATURE                Location/Qualifiers
source                 1..10
                       mol_type = other RNA
                       organism = synthetic construct
SEQUENCE: 99
aaacaaaaca                                                                  10

SEQ ID NO: 100         moltype = RNA   length = 10
FEATURE                Location/Qualifiers
source                 1..10
                       mol_type = other RNA
                       organism = synthetic construct
SEQUENCE: 100
attattatta                                                                  10

SEQ ID NO: 101         moltype = RNA   length = 15
```

-continued

```
FEATURE                    Location/Qualifiers
source                     1..15
                           mol_type = other RNA
                           organism = synthetic construct
SEQUENCE: 101
ggactggact ggact                                                              15

SEQ ID NO: 102             moltype = RNA   length = 12
FEATURE                    Location/Qualifiers
source                     1..12
                           mol_type = other RNA
                           organism = synthetic construct
SEQUENCE: 102
aaaaaaaaaa aa                                                                 12

SEQ ID NO: 103             moltype = RNA   length = 17
FEATURE                    Location/Qualifiers
source                     1..17
                           mol_type = other RNA
                           organism = synthetic construct
SEQUENCE: 103
aaccacagaa actacca                                                           17

SEQ ID NO: 104             moltype = RNA   length = 22
FEATURE                    Location/Qualifiers
source                     1..22
                           mol_type = other RNA
                           organism = synthetic construct
SEQUENCE: 104
ggactaacca cagaaactac ca                                                      22

SEQ ID NO: 105             moltype = RNA   length = 26
FEATURE                    Location/Qualifiers
source                     1..26
                           mol_type = other RNA
                           organism = synthetic construct
SEQUENCE: 105
ggactggaca accacagaaa ctacca                                                  26

SEQ ID NO: 106             moltype = RNA   length = 26
FEATURE                    Location/Qualifiers
source                     1..26
                           mol_type = other RNA
                           organism = synthetic construct
SEQUENCE: 106
aaccacagaa actaccagga ctggac                                                  26

SEQ ID NO: 107             moltype = RNA   length = 29
FEATURE                    Location/Qualifiers
source                     1..29
                           mol_type = other RNA
                           organism = synthetic construct
SEQUENCE: 107
ggactggact gtttaaagaa ctacaagcc                                               29

SEQ ID NO: 108             moltype = RNA   length = 27
FEATURE                    Location/Qualifiers
source                     1..27
                           mol_type = other RNA
                           organism = synthetic construct
SEQUENCE: 108
ggactggact ggattctaag tcagcaa                                                 27

SEQ ID NO: 109             moltype = RNA   length = 28
FEATURE                    Location/Qualifiers
source                     1..28
                           mol_type = other RNA
                           organism = synthetic construct
SEQUENCE: 109
ggactggact tgctgtggtt ctgagctg                                                28

SEQ ID NO: 110             moltype = RNA   length = 28
FEATURE                    Location/Qualifiers
source                     1..28
                           mol_type = other RNA
                           organism = synthetic construct
SEQUENCE: 110
ggactggact ctgcagcaga tcacctgc                                                28
```

-continued

```
SEQ ID NO: 111            moltype = RNA   length = 27
FEATURE                   Location/Qualifiers
source                    1..27
                          mol_type = other RNA
                          organism = synthetic construct
modified_base             23
                          mod_base = OTHER
                          note = 2'-deoxy thymidine
SEQUENCE: 111
ggactggact aaccacagaa actacca                                            27

SEQ ID NO: 112            moltype = RNA   length = 29
FEATURE                   Location/Qualifiers
source                    1..29
                          mol_type = other RNA
                          organism = synthetic construct
SEQUENCE: 112
acggacttgg actctgctgc aaacgctaa                                         29

SEQ ID NO: 113            moltype = RNA   length = 29
FEATURE                   Location/Qualifiers
source                    1..29
                          mol_type = other RNA
                          organism = synthetic construct
SEQUENCE: 113
acggacttgg actcaatggt cctacctgc                                         29

SEQ ID NO: 114            moltype = RNA   length = 26
FEATURE                   Location/Qualifiers
source                    1..26
                          mol_type = other RNA
                          organism = synthetic construct
SEQUENCE: 114
ggactggact ctaaagagat gaagcc                                            26

SEQ ID NO: 115            moltype = RNA   length = 27
FEATURE                   Location/Qualifiers
source                    1..27
                          mol_type = other RNA
                          organism = synthetic construct
SEQUENCE: 115
ggactggact aggccccaag gtgaggc                                           27

SEQ ID NO: 116            moltype = RNA   length = 28
FEATURE                   Location/Qualifiers
source                    1..28
                          mol_type = other RNA
                          organism = synthetic construct
SEQUENCE: 116
ggactggact cccaaggtga ggcatatc                                          28

SEQ ID NO: 117            moltype = RNA   length = 26
FEATURE                   Location/Qualifiers
source                    1..26
                          mol_type = other RNA
                          organism = synthetic construct
SEQUENCE: 117
ggactggact caaggtgagg catatc                                            26

SEQ ID NO: 118            moltype = RNA   length = 28
FEATURE                   Location/Qualifiers
source                    1..28
                          mol_type = other RNA
                          organism = synthetic construct
modified_base             13
                          mod_base = OTHER
                          note = 2'-deoxy thymidine
modified_base             15
                          mod_base = OTHER
                          note = 2'-deoxy thymidine
modified_base             16
                          mod_base = OTHER
                          note = 2'-deoxy thymidine
modified_base             17
                          mod_base = OTHER
                          note = 2'-deoxy thymidine
modified_base             19
                          mod_base = OTHER
                          note = 2'-deoxy thymidine
```

-continued

```
modified_base          20
                       mod_base = OTHER
                       note = 2'-deoxy thymidine
modified_base          22
                       mod_base = OTHER
                       note = 2'-deoxy thymidine
modified_base          24
                       mod_base = OTHER
                       note = 2'-deoxy thymidine
SEQUENCE: 118
ggactggact actctttatt atctcaag                                      28

SEQ ID NO: 119        moltype = RNA  length = 28
FEATURE               Location/Qualifiers
source                1..28
                      mol_type = other RNA
                      organism = synthetic construct
modified_base          13
                       mod_base = OTHER
                       note = 2'-deoxy thymidine
modified_base          15
                       mod_base = OTHER
                       note = 2'-deoxy thymidine
modified_base          16
                       mod_base = OTHER
                       note = 2'-deoxy thymidine
modified_base          17
                       mod_base = OTHER
                       note = 2'-deoxy thymidine
modified_base          19
                       mod_base = OTHER
                       note = 2'-deoxy thymidine
modified_base          20
                       mod_base = OTHER
                       note = 2'-deoxy thymidine
modified_base          22
                       mod_base = OTHER
                       note = 2'-deoxy thymidine
modified_base          23
                       mod_base = OTHER
                       note = 2'-deoxy thymidine
SEQUENCE: 119
ggactggact actctttatt attccaag                                      28

SEQ ID NO: 120        moltype = RNA  length = 28
FEATURE               Location/Qualifiers
source                1..28
                      mol_type = other RNA
                      organism = synthetic construct
modified_base          14
                       mod_base = OTHER
                       note = 2'-deoxy thymidine
modified_base          18
                       mod_base = OTHER
                       note = 2'-deoxy thymidine
modified_base          23
                       mod_base = OTHER
                       note = 2'-deoxy thymidine
modified_base          27
                       mod_base = OTHER
                       note = 2'-deoxy thymidine
SEQUENCE: 120
ggactggact aaataaataa gataaata                                      28

SEQ ID NO: 121        moltype = RNA  length = 17
FEATURE               Location/Qualifiers
source                1..17
                      mol_type = other RNA
                      organism = synthetic construct
SEQUENCE: 121
tggtagtttc tgtggtt                                                  17

SEQ ID NO: 122        moltype = RNA  length = 27
FEATURE               Location/Qualifiers
source                1..27
                      mol_type = other RNA
                      organism = synthetic construct
modified_base          23
                       mod_base = OTHER
```

-continued

```
                       note = 2'-deoxy thymidine
SEQUENCE: 122
aaactaaact aaccacagaa actacca                                        27

SEQ ID NO: 123         moltype = RNA  length = 27
FEATURE                Location/Qualifiers
source                 1..27
                       mol_type = other RNA
                       organism = synthetic construct
modified_base          23
                       mod_base = OTHER
                       note = 2'-deoxy thymidine
SEQUENCE: 123
aaaaaaaaaa aaccacagaa actacca                                        27

SEQ ID NO: 124         moltype = RNA  length = 25
FEATURE                Location/Qualifiers
source                 1..25
                       mol_type = other RNA
                       organism = synthetic construct
modified_base          21
                       mod_base = OTHER
                       note = 2'-deoxy thymidine
SEQUENCE: 124
aaaaaaaaaa ccacagaaac tacca                                          25

SEQ ID NO: 125         moltype = RNA  length = 24
FEATURE                Location/Qualifiers
source                 1..24
                       mol_type = other RNA
                       organism = synthetic construct
SEQUENCE: 125
ggactggact aaccacagaa acca                                           24

SEQ ID NO: 126         moltype = RNA  length = 28
FEATURE                Location/Qualifiers
source                 1..28
                       mol_type = other RNA
                       organism = synthetic construct
SEQUENCE: 126
ggactggact cctttgccgt gaccacgt                                       28

SEQ ID NO: 127         moltype = RNA  length = 28
FEATURE                Location/Qualifiers
source                 1..28
                       mol_type = other RNA
                       organism = synthetic construct
SEQUENCE: 127
ggactggact ctgctctggg actggtcc                                       28

SEQ ID NO: 128         moltype = RNA  length = 28
FEATURE                Location/Qualifiers
source                 1..28
                       mol_type = other RNA
                       organism = synthetic construct
SEQUENCE: 128
ggactggact ccttaggcca tgttctcg                                       28

SEQ ID NO: 129         moltype = RNA  length = 27
FEATURE                Location/Qualifiers
source                 1..27
                       mol_type = other RNA
                       organism = synthetic construct
SEQUENCE: 129
ggactggact gtggcttcaa catgaga                                        27

SEQ ID NO: 130         moltype = RNA  length = 29
FEATURE                Location/Qualifiers
source                 1..29
                       mol_type = other RNA
                       organism = synthetic construct
modified_base          12
                       mod_base = OTHER
                       note = 2'-deoxy thymidine
modified_base          13
                       mod_base = OTHER
                       note = 2'-deoxy thymidine
modified_base          14
                       mod_base = OTHER
```

-continued

```
                           note = 2'-deoxy thymidine
modified_base              22
                           mod_base = OTHER
                           note = 2'-deoxy thymidine
SEQUENCE: 130
ggactggact gtttaaagaa ctacaagcc                                          29

SEQ ID NO: 131            moltype = RNA  length = 18
FEATURE                   Location/Qualifiers
source                    1..18
                           mol_type = other RNA
                           organism = synthetic construct
modified_base              1
                           mod_base = OTHER
                           note = 2'-deoxy thymidine
modified_base              6
                           mod_base = OTHER
                           note = 2'-deoxy thymidine
modified_base              14
                           mod_base = OTHER
                           note = 2'-deoxy thymidine
SEQUENCE: 131
tgcactgacg gaatacaa                                                      18

SEQ ID NO: 132            moltype = RNA  length = 18
FEATURE                   Location/Qualifiers
source                    1..18
                           mol_type = other RNA
                           organism = synthetic construct
modified_base              1
                           mod_base = OTHER
                           note = 2'-deoxy thymidine
modified_base              9
                           mod_base = OTHER
                           note = 2'-deoxy thymidine
SEQUENCE: 132
tgcacgactg gaaaacaa                                                      18

SEQ ID NO: 133            moltype = RNA  length = 23
FEATURE                   Location/Qualifiers
source                    1..23
                           mol_type = other RNA
                           organism = synthetic construct
modified_base              2
                           mod_base = OTHER
                           note = 2'-deoxy thymidine
modified_base              7
                           mod_base = OTHER
                           note = 2'-deoxy thymidine
modified_base              11
                           mod_base = OTHER
                           note = 2'-deoxy thymidine
modified_base              16
                           mod_base = OTHER
                           note = 2'-deoxy thymidine
modified_base              19
                           mod_base = OTHER
                           note = 2'-deoxy thymidine
modified_base              23
                           mod_base = OTHER
                           note = 2'-deoxy thymidine
SEQUENCE: 133
ataagataaa taacctaata aat                                                23

SEQ ID NO: 134            moltype = RNA  length = 21
FEATURE                   Location/Qualifiers
source                    1..21
                           mol_type = other RNA
                           organism = synthetic construct
modified_base              1
                           mod_base = OTHER
                           note = 2'-deoxy thymidine
modified_base              6
                           mod_base = OTHER
                           note = 2'-deoxy thymidine
modified_base              10
                           mod_base = OTHER
                           note = 2'-deoxy thymidine
modified_base              15
```

-continued

```
                              mod_base = OTHER
                              note = 2'-deoxy thymidine
modified_base                 18
                              mod_base = OTHER
                              note = 2'-deoxy thymidine
SEQUENCE: 134
taagataaat aacctaataa a                                      21

SEQ ID NO: 135               moltype = RNA  length = 20
FEATURE                      Location/Qualifiers
source                       1..20
                              mol_type = other RNA
                              organism = synthetic construct
modified_base                3
                              mod_base = OTHER
                              note = 2'-deoxy thymidine
modified_base                7
                              mod_base = OTHER
                              note = 2'-deoxy thymidine
modified_base                12
                              mod_base = OTHER
                              note = 2'-deoxy thymidine
modified_base                16
                              mod_base = OTHER
                              note = 2'-deoxy thymidine
SEQUENCE: 135
aataaataag ataaataacc                                        20

SEQ ID NO: 136               moltype = RNA  length = 33
FEATURE                      Location/Qualifiers
source                       1..33
                              mol_type = other RNA
                              organism = synthetic construct
modified_base                12
                              mod_base = OTHER
                              note = 2'-deoxy thymidine
modified_base                17
                              mod_base = OTHER
                              note = 2'-deoxy thymidine
modified_base                21
                              mod_base = OTHER
                              note = 2'-deoxy thymidine
modified_base                26
                              mod_base = OTHER
                              note = 2'-deoxy thymidine
modified_base                29
                              mod_base = OTHER
                              note = 2'-deoxy thymidine
modified_base                33
                              mod_base = OTHER
                              note = 2'-deoxy thymidine
SEQUENCE: 136
ggactggact ataagataaa taacctaata aat                         33

SEQ ID NO: 137               moltype = RNA  length = 27
FEATURE                      Location/Qualifiers
source                       1..27
                              mol_type = other RNA
                              organism = synthetic construct
modified_base                23
                              mod_base = OTHER
                              note = 2'-deoxy thymidine
SEQUENCE: 137
cccccccccc aaccacagaa actacca                                27

SEQ ID NO: 138               moltype = RNA  length = 27
FEATURE                      Location/Qualifiers
source                       1..27
                              mol_type = other RNA
                              organism = synthetic construct
modified_base                23
                              mod_base = OTHER
                              note = 2'-deoxy thymidine
SEQUENCE: 138
tttttttttt aaccacagaa actacca                                27

SEQ ID NO: 139               moltype = RNA  length = 27
FEATURE                      Location/Qualifiers
source                       1..27
```

-continued

```
                            mol_type = other RNA
                            organism = synthetic construct
modified_base               23
                            mod_base = OTHER
                            note = 2'-deoxy thymidine
SEQUENCE: 139
acacacacac aaccacagaa actacca                                            27

SEQ ID NO: 140              moltype = RNA   length = 27
FEATURE                     Location/Qualifiers
source                      1..27
                            mol_type = other RNA
                            organism = synthetic construct
modified_base               23
                            mod_base = OTHER
                            note = 2'-deoxy thymidine
SEQUENCE: 140
agagagagag aaccacagaa actacca                                            27

SEQ ID NO: 141              moltype = RNA   length = 27
FEATURE                     Location/Qualifiers
source                      1..27
                            mol_type = other RNA
                            organism = synthetic construct
modified_base               23
                            mod_base = OTHER
                            note = 2'-deoxy thymidine
SEQUENCE: 141
ctctctctct aaccacagaa actacca                                            27

SEQ ID NO: 142              moltype = RNA   length = 27
FEATURE                     Location/Qualifiers
source                      1..27
                            mol_type = other RNA
                            organism = synthetic construct
modified_base               23
                            mod_base = OTHER
                            note = 2'-deoxy thymidine
SEQUENCE: 142
gtgtgtgtgt aaccacagaa actacca                                            27

SEQ ID NO: 143              moltype = RNA   length = 27
FEATURE                     Location/Qualifiers
source                      1..27
                            mol_type = other RNA
                            organism = synthetic construct
modified_base               23
                            mod_base = OTHER
                            note = 2'-deoxy thymidine
SEQUENCE: 143
aaacaaaaca aaccacagaa actacca                                            27

SEQ ID NO: 144              moltype = RNA   length = 27
FEATURE                     Location/Qualifiers
source                      1..27
                            mol_type = other RNA
                            organism = synthetic construct
modified_base               23
                            mod_base = OTHER
                            note = 2'-deoxy thymidine
SEQUENCE: 144
attattatta aaccacagaa actacca                                            27

SEQ ID NO: 145              moltype = RNA   length = 32
FEATURE                     Location/Qualifiers
source                      1..32
                            mol_type = other RNA
                            organism = synthetic construct
modified_base               28
                            mod_base = OTHER
                            note = 2'-deoxy thymidine
SEQUENCE: 145
ggactggact ggactaacca cagaaactac ca                                      32

SEQ ID NO: 146              moltype = RNA   length = 29
FEATURE                     Location/Qualifiers
source                      1..29
                            mol_type = other RNA
                            organism = synthetic construct
```

-continued

```
modified_base           25
                        mod_base = OTHER
                        note = 2'-deoxy thymidine
SEQUENCE: 146
aaaaaaaaaa aaaaccacag aaactacca                              29

SEQ ID NO: 147          moltype = RNA  length = 32
FEATURE                 Location/Qualifiers
source                  1..32
                        mol_type = other RNA
                        organism = synthetic construct
modified_base           11
                        mod_base = OTHER
                        note = 2'-deoxy thymidine
modified_base           16
                        mod_base = OTHER
                        note = 2'-deoxy thymidine
modified_base           20
                        mod_base = OTHER
                        note = 2'-deoxy thymidine
modified_base           25
                        mod_base = OTHER
                        note = 2'-deoxy thymidine
modified_base           28
                        mod_base = OTHER
                        note = 2'-deoxy thymidine
modified_base           32
                        mod_base = OTHER
                        note = 2'-deoxy thymidine
SEQUENCE: 147
ggactggaca taagataaat aacctaataa at                          32

SEQ ID NO: 148          moltype = RNA  length = 33
FEATURE                 Location/Qualifiers
source                  1..33
                        mol_type = other RNA
                        organism = synthetic construct
SEQUENCE: 148
ggactggact ataagataaa taacctaata aat                         33

SEQ ID NO: 149          moltype = RNA  length = 28
FEATURE                 Location/Qualifiers
source                  1..28
                        mol_type = other RNA
                        organism = synthetic construct
modified_base           7
                        mod_base = OTHER
                        note = 2'-deoxy thymidine
modified_base           12
                        mod_base = OTHER
                        note = 2'-deoxy thymidine
modified_base           16
                        mod_base = OTHER
                        note = 2'-deoxy thymidine
modified_base           21
                        mod_base = OTHER
                        note = 2'-deoxy thymidine
modified_base           24
                        mod_base = OTHER
                        note = 2'-deoxy thymidine
modified_base           28
                        mod_base = OTHER
                        note = 2'-deoxy thymidine
SEQUENCE: 149
ggactataag ataaataacc taataaat                               28

SEQ ID NO: 150          moltype = RNA  length = 26
FEATURE                 Location/Qualifiers
source                  1..26
                        mol_type = other RNA
                        organism = synthetic construct
modified_base           12
                        mod_base = OTHER
                        note = 2'-deoxy thymidine
modified_base           15
                        mod_base = OTHER
                        note = 2'-deoxy thymidine
modified_base           17
                        mod_base = OTHER
```

-continued

```
                            note = 2'-deoxy thymidine
modified_base               23
                            mod_base = OTHER
                            note = 2'-deoxy thymidine
modified_base               26
                            mod_base = OTHER
                            note = 2'-deoxy thymidine
SEQUENCE: 150
ggactggact ctgctctggg actggt                                    26

SEQ ID NO: 151              moltype = RNA  length = 26
FEATURE                     Location/Qualifiers
source                      1..26
                            mol_type = other RNA
                            organism = synthetic construct
modified_base               13
                            mod_base = OTHER
                            note = 2'-deoxy thymidine
modified_base               15
                            mod_base = OTHER
                            note = 2'-deoxy thymidine
modified_base               21
                            mod_base = OTHER
                            note = 2'-deoxy thymidine
modified_base               24
                            mod_base = OTHER
                            note = 2'-deoxy thymidine
SEQUENCE: 151
ggactggact gctctgggac tggtcc                                    26

SEQ ID NO: 152              moltype = RNA  length = 10
FEATURE                     Location/Qualifiers
source                      1..10
                            mol_type = other RNA
                            organism = synthetic construct
SEQUENCE: 152
gggggggggg                                                      10

SEQ ID NO: 153              moltype = RNA  length = 10
FEATURE                     Location/Qualifiers
source                      1..10
                            mol_type = other RNA
                            organism = synthetic construct
modified_base               1
                            mod_base = OTHER
                            note = 2'-deoxy thymidine
modified_base               2
                            mod_base = OTHER
                            note = 2'-deoxy thymidine
modified_base               3
                            mod_base = OTHER
                            note = 2'-deoxy thymidine
modified_base               4
                            mod_base = OTHER
                            note = 2'-deoxy thymidine
modified_base               5
                            mod_base = OTHER
                            note = 2'-deoxy thymidine
modified_base               6
                            mod_base = OTHER
                            note = 2'-deoxy thymidine
modified_base               7
                            mod_base = OTHER
                            note = 2'-deoxy thymidine
modified_base               8
                            mod_base = OTHER
                            note = 2'-deoxy thymidine
```

-continued

```
modified_base        9
                     mod_base = OTHER
                     note = 2'-deoxy thymidine
modified_base        10
                     mod_base = OTHER
                     note = 2'-deoxy thymidine
SEQUENCE: 153
tttttttttt                                                    10

SEQ ID NO: 154       moltype =    length =
SEQUENCE: 154
000
```